United States Patent
Uchida et al.

(10) Patent No.: US 11,629,152 B2
(45) Date of Patent: Apr. 18, 2023

(54) COMPOUND WITH ANTICANCER ACTIVITY

(71) Applicant: KYOWA KIRIN CO., LTD., Chiyoda-ku (JP)

(72) Inventors: Kenji Uchida, Chiyoda-ku (JP); Ryohei Kawai, Chiyoda-ku (JP); Keisuke Yamamoto, Chiyoda-ku (JP); Toshimi Kanai, Chiyoda-ku (JP); Hideo Ikota, Chiyoda-ku (JP); Takashi Imaeda, Chiyoda-ku (JP); Kei Yoshida, Chiyoda-ku (JP)

(73) Assignee: KYOWA KIRIN CO., LTD., Chiyoda-ku (JP)

( * ) Notice: Subject to any disclaimer, the term of this patent is extended or adjusted under 35 U.S.C. 154(b) by 0 days.

(21) Appl. No.: 17/043,348

(22) PCT Filed: Mar. 29, 2019

(86) PCT No.: PCT/JP2019/014042
§ 371 (c)(1),
(2) Date: Sep. 29, 2020

(87) PCT Pub. No.: WO2019/189778
PCT Pub. Date: Oct. 3, 2019

(65) Prior Publication Data
US 2021/0024540 A1 Jan. 28, 2021

(30) Foreign Application Priority Data
Mar. 30, 2018 (JP) .............................. JP2018-068816

(51) Int. Cl.
| | | |
|---|---|---|
| C07D 215/44 | (2006.01) | |
| C07D 215/46 | (2006.01) | |
| C07D 401/12 | (2006.01) | |
| C07D 487/04 | (2006.01) | |
| C07D 487/08 | (2006.01) | |
| C07D 495/14 | (2006.01) | |
| C07D 519/00 | (2006.01) | |
| A61K 31/4709 | (2006.01) | |
| A61K 31/4985 | (2006.01) | |
| A61K 31/551 | (2006.01) | |
| A61P 35/00 | (2006.01) | |
| C07D 209/08 | (2006.01) | |
| C07D 261/08 | (2006.01) | |

(52) U.S. Cl.
CPC ......... *C07D 495/14* (2013.01); *C07D 209/08* (2013.01); *C07D 215/46* (2013.01); *C07D 261/08* (2013.01)

(58) Field of Classification Search
CPC ............ C07D 215/44; C07D 215/46; C07D 401/12; C07D 487/04; C07D 487/08; C07D 495/14; C07D 519/00; A61K 31/4709; A61K 31/4985; A61K 31/551; A61P 35/00
See application file for complete search history.

(56) References Cited

U.S. PATENT DOCUMENTS

| | | |
|---|---|---|
| 2014/0066459 A1 | 3/2014 | Amans et al. |
| 2016/0016908 A1 | 1/2016 | Amans et al. |
| 2017/0189401 A1 | 7/2017 | Amans et al. |
| 2017/0360760 A1 | 12/2017 | Kharenko et al. |
| 2018/0303831 A1 | 10/2018 | Amans et al. |
| 2021/0046073 A1 | 2/2021 | Amans et al. |

FOREIGN PATENT DOCUMENTS

| | | |
|---|---|---|
| EA | 026894 | 5/2017 |
| WO | WO 2012/150234 A1 | 11/2012 |
| WO | WO 2013/033268 A2 | 3/2013 |
| WO | WO 2013/184876 | 12/2013 |
| WO | WO 2014/140076 A1 | 9/2014 |
| WO | WO 2015/081284 A1 | 6/2015 |
| WO | WO 2016/097863 A1 | 6/2016 |
| WO | WO 2017/091673 A2 | 6/2017 |
| WO | WO 2017/197056 A1 | 11/2017 |

OTHER PUBLICATIONS

Extended European Search Report dated Nov. 19, 2021 in corresponding European Patent Application No. 19774768.6, 8 pages.
International Search Report and Written Opinion dated Jun. 25, 2019 in PCT/JP2019/014042 (with English translation of Search Report only), 12 pages.
International Preliminary Report on Patentability and Written Opinion dated Oct. 15, 2020 in PCT/JP2019/014042 (submitting English translation only), 7 pages.
Chan, K,-H., et al., Impact of Target Warhead and Linkage Vector on Inducing Protein Degradation: Comparison of Bromodomain and Extra-Terminal (BET) Degraders Derived from Triazolodiazepine (JQ1) and Tetrahydroquinoline (I-BET726) BET Inhibitor Scaffolds, Journal of Medical Chemistry, Jun. 8, 2017, vol. 61, pp. 504-513.

(Continued)

*Primary Examiner* — Bruck Kifle
(74) *Attorney, Agent, or Firm* — Oblon, McClelland, Maier & Neustadt, L.L.P.

(57) ABSTRACT

A compound having anticancer activity, or a pharmaceutically acceptable salt thereof is provided. Used is a compound represented by the following formula (I) or a pharmaceutically acceptable salt thereof:

(I)

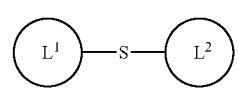

(wherein, $L^1$ and $L^2$ are the same or different and each represents a group represented by one formula selected from the group consisting of formulas (A) to (F), and S represents a group represented by one formula selected from the group consisting of formulas (S1) to (S18)).

19 Claims, No Drawings

(56) References Cited

OTHER PUBLICATIONS

Zuber, J., et al., "RNAi screen identifies BRD4 as a therapeutic target in acute myeloid leukaemia", Nature, 2011, vol. 478, pp. 524-528.
Delmore, J.E., et al., "BET Bromodomain Inhibition as a Therapeutic Strategy to Target c-Myc", Cell, 2011, vol. 146, pp. 904-917.
Nicodeme, E., et al., "Suppression of inflammation by a synthetic histone mimic", Nature, 2010, vol. 468, pp. 1119-1123.
French, C.A., et al., "BRD4-NUT Fusion Oncogene: A Novel Mechanism in Aggressive Carcinoma", Cancer Research, Jan. 15, 2003, vol. 63, pp. 304-307 (with cover page).
Lovén, J., et al., "Selective Inhibition of Tumor Oncogenes by Disruption of Super-Enhancers", Cell, 2013, vol. 153, pp. 320-334.
Picaud, S., et al., "RVX-208, an inhibitor of BET transcriptional regulators with selectivity for the second bromodomain", Proceeding of the National Academy of Science, 2013, vol. 110, No. 49, pp. 19754-19759.
Mirguet, O., et al., "Discovery of Epigenetic Regulator I-BET762: Lead Optimization to Afford a Clinical Candidate Inhibitor of the BET Bromodomains", Journal of Medicinal Chemistry, 2013, vol. 56, p. 7501-7515.
Coudé, M.-M., et al., "BET inhibitor OTX015 targets BRD2 and BRD4 and decreases c-MYC in acute leukemia cells", Oncotarget, 2015, vol. 6, p. 17698-17712.
Siu, PhD., K.T., et al., "Effect of the BET inhibitor, Cpi-0610, Alone and in Combination with Lenalidomide in Multiple Myeloma", Blood, 2015, vol. 126, pp. 4255-4255 (submitting English abstract only).
Shapiro, G.I., et al., "Abstract A49: Clinically efficacy of the BET bromodomain inhibitor TEN-010 in an open-label substudy with patients with documented NUT-midline carcinoma (NMC)", Molecular Cancer Therapeutech, 2015, vol. 14, A49.
Sarthy, A., et al., "Abstract 4718: ABBV-075, a novel BET family bromodomain inhibitor, represents a promising therapeutic agent for a broad spectrum of cancer indications", Cancer Research, 2016, vol. 76, pp. 4718-4718.
Tanaka, M., et al., "Design and characterization of bivalent BET inhibitors", Nature Chemical Biology, 2016, vol. 112, pp. 1089-1096.
Office Action issued in corresponding Russian Application No. 2020134995 dated Sep. 27, 2022. (with English Translation).
Office Acion issued in corresponding Taiwan Application No. 108111333 dated Feb. 6, 2023 with English translation.
Office Action issued in corresponding Chinese Application No. 201980023780.2 dated Jan. 19, 2023 with English translation.

COMPOUND WITH ANTICANCER ACTIVITY

CROSS-REFERENCE TO RELATED APPLICATION

The present patent application claims priority to Japanese Patent Application No. 2018-68816 filed on Mar. 30, 2018, and the entire disclosure of which is incorporated herein by reference.

TECHNICAL FIELD

The present invention relates to a compound with anticancer activity, or a pharmaceutically acceptable salt thereof and the like.

BACKGROUND ART

In humans, 46 bromodomain proteins that recognize the acetylated lysine in histone proteins are known. The BET (bromodomain and extra-terminal domain) family has been reported as one of the families, and recognizes acetyllysine in histones H3 and H4. BRD (bromodomain containing protein) 2, BRD3, BRD4 and BRDT (bromodomain testis specific protein) are known as the BET family. BET family proteins have two bromo domains (BD1, BD2) at the N-terminus, and the sequences are strongly conserved between the families. Further, it has been reported that the BET protein is involved in cancer growth [see non-patent documents 1 and 2] and progression of inflammation [see non-patent document 3].

BRD4 enhances expression of genes that promote growth by recruiting P-TEBb on mitotic chromosomes. In NUT-midline carcinoma (NMC), increased expression of c-MYC protein has been confirmed by the BRD4-NUT fusion protein [see non-patent document 4]. It has also been reported that the degree of decrease in expression of the MYC gene is the most significant level in the human multiple myeloma-derived MM1.S cells, among the genes whose expression is decreased by the BET inhibitor JQ-1 treatment [See non-patent document 5].

As typical BET inhibitors, clinical trials of RVX-208/Apabetalone [see non-patent document 6], I-BET762/GSK-525762A [see non-patent document 7], OTX-015/MK8628 [see non-patent document 8], CPI-0610 [see non-patent document 9], TEN-010 [see non-patent document 10], and ABBV-075 [see non-patent document 11] are in progress. Among these drugs, all but RVX-208 are being developed as cancer treatment drugs.

In addition, in recent years, a compound, as a bivalent BET inhibitor, having a stronger BET inhibitory activity by simultaneously inhibiting the BD1 and BD2 domains has also been reported (see non-patent document 12). As the divalent BET inhibitor described above, for example, compounds represented by the following formulas (P1) to (P5) are known (see non-patent document 12, patent documents 1, 2 and 3).

[Chemical Formula 1]

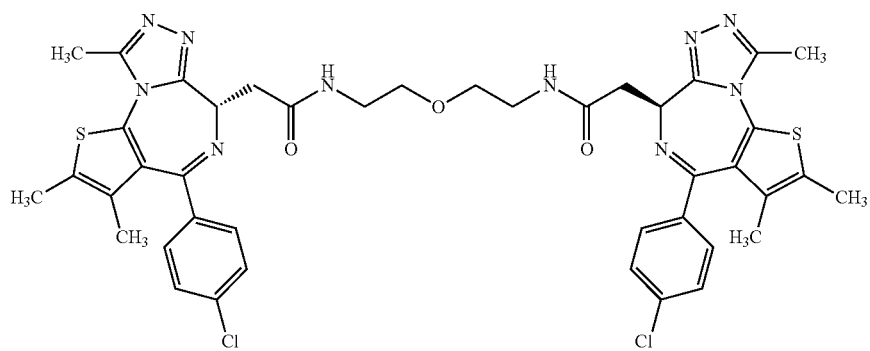

(P1)

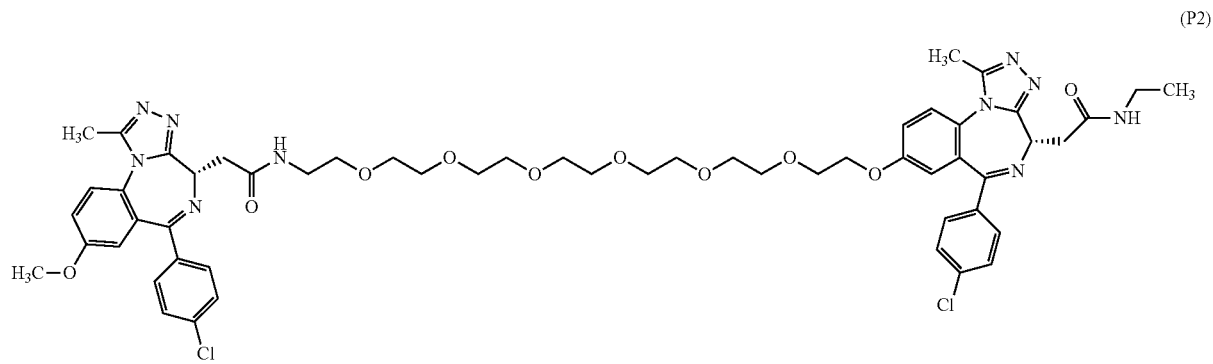

(P2)

(P3)

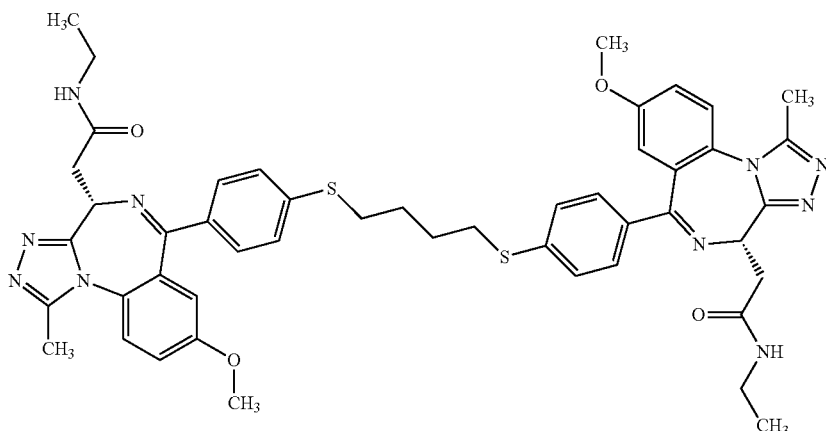

(P4)

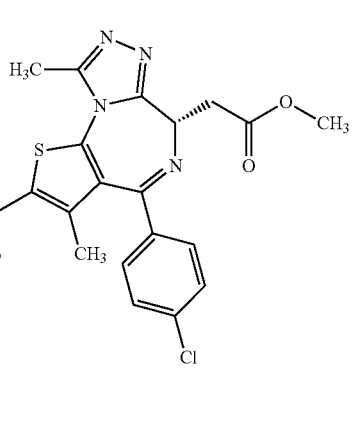

(P5)

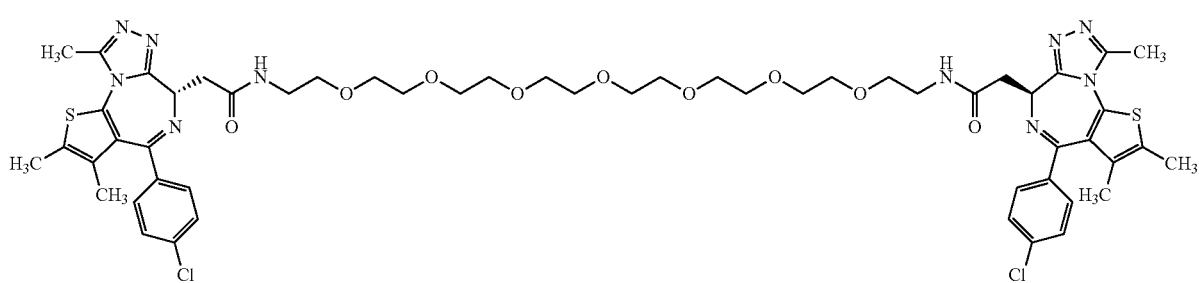

PRIOR ART DOCUMENTS

Patent Documents

[Patent Document 1] WO 2013/033268
[Patent Document 2] WO 2015/081284
[Patent Document 3] WO 2017/091673

NON-PATENT DOCUMENTS

[Non-patent Document 1] Nature, 2011, Vol. 478, p. 524-528
[Non-patent Document 2] Cell, 2011, Vol. 146, p. 904-917
[Non-patent Document 3] Nature, 2010, Vol. 468, p. 1119-1123
[Non-patent Document 4] Cancer Research, 2003, Vol. 63, p. 304-307
[Non-patent Document 5] Cell, 2013, Vol. 153, p. 320-334
[Non-patent Document 6] Proceeding of the National Academy of Science, 2013, Vol. 110, p. 19754-19759
[Non-patent Document 7] Journal of Medicinal Chemistry, 2013, Vol. 56, p. 7501-7515
[Non-patent Document 8] Oncotarget, 2015, Vol. 6, p. 17698-17712
[Non-patent Document 9] Blood, 2015, Vol. 126, p. 4255-4255
[Non-patent Document 10] Molecular Cancer Therapeutics, 2015, Vol. 14, A49
[Non-patent Document 11] Cancer Research, 2016, Vol. 76, Abstract 4718
[Non-Patent Document 12] Nature Chemical Biology, 2016, Vol. 12, P. 1089-1096

SUMMARY OF INVENTION

The present invention provides a compound having anti-cancer activity, a pharmaceutically acceptable salt thereof, or the like.

In recent years, as a bivalent BET inhibitor, a compound that simultaneously inhibits the BD1 and BD2 domains and thereby exhibits stronger BET inhibitory activity as compared with a normal BET inhibitor has been reported. However, its pharmacological activity is still insufficient, and a compound having a stronger pharmacological action is desired.

In the present invention, a compound having a strong BET inhibitory action, a pharmaceutically acceptable salt thereof, or the like has been found by binding two BET inhibitors, which become ligands, at specific bonding positions by a spacer having a specific structure.

The present invention relates to the following (1) to (56).

(1) A compound represented by the following formula (I) or a pharmaceutically acceptable salt thereof:

[Chemical formula 2]

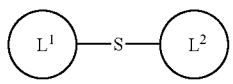

(I)

(wherein, $L^1$ and $L^2$ are the same or different and each represents a group represented by one formula selected from the group consisting of the following formulas (A) to (F), and S represents a group represented by one formula selected from the group consisting of the following formulas (S1) to (S18):

[Chemical formula 3]

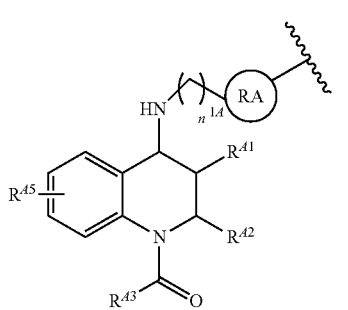

(A)

(B)

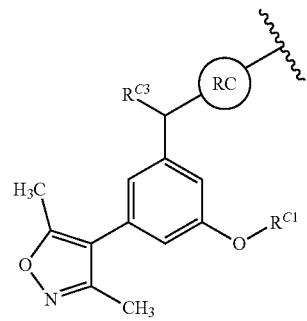

(C)

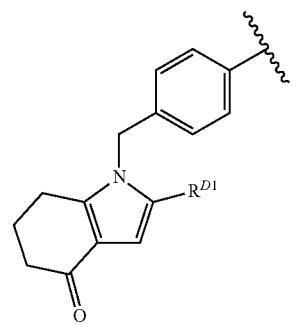

(D)

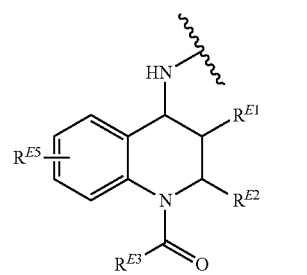

(E)

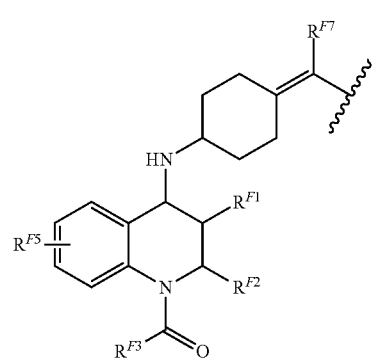

(F)

($R^{A1}$, $R^{A2}$, and $R^{A3}$ are the same or different and each represents a hydrogen atom or lower alkyl, $R^{A5}$ represents a hydrogen atom, a halogen, optionally substituted lower alkyl, optionally substituted lower alkenyl, optionally substituted tetrahydropyridinyl, optionally substituted dihydro-1H-pyrrolyl, or optionally substituted tetrahydro-1H-azepinyl, ring RA represents benzenediyl, cycloalkanediyl, pyridinediyl, piperidinediyl, azetidinediyl, pyrrolidinediyl, or homopiperidinediyl, $n^{1A}$ represents 0 or 1, $R^{B1}$ represents a hydrogen atom, optionally substituted lower alkoxycarbonylmethyl, optionally substituted cycloalkyloxycarbonylmethyl, or —$CH_2CONR^{B5}R^{B6}$ (wherein, $R^{B5}$ and $R^{B6}$ are the same or different and each represents a hydrogen atom or optionally substituted lower alkyl, or they represent an optionally substituted nitrogen-containing aliphatic heterocyclic group together with an adjacent nitrogen atom), $R^{B2}$ represents optionally substituted lower alkyl, $R^{B3}$ and $R^{B4}$ are the same or different and each represents a halogen or optionally substituted lower alkyl, $R^{C1}$ represents a hydrogen atom, lower alkyl, or lower alkanoyl, $R^{C3}$ represents a hydrogen atom or hydroxy, ring RC represents benzenediyl, piperidinediyl, azetidinediyl, pyrrolidinediyl, or homopiperidinediyl, $R^{D1}$ represents optionally substituted lower alkyl or optionally substituted lower alkoxycarbonyl, $R^{E1}$ and $R^{F1}$ have the same definition as $R^{A1}$, $R^{E2}$ and $R^{F2}$ have the same definition as $R^{A2}$, $R^{E3}$ and $R^{F3}$ have the same definition as $R^{A3}$, $R^{E5}$ and $R^{F5}$ have the same definition as $R^{A5}$, and $R^{F7}$ represents a hydrogen atom or a halogen);

[Chemical formula 4]

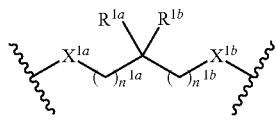

(S1)

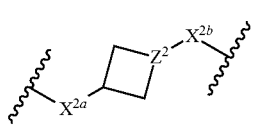

(S2)

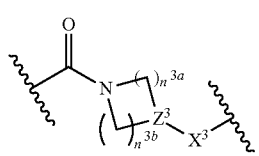

(S3)

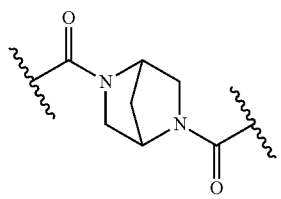

(S4)

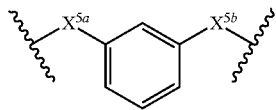

(S5)

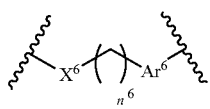

(S6)

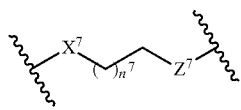

(S7)

-continued

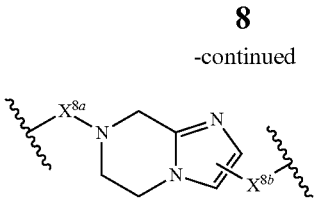

(S8)

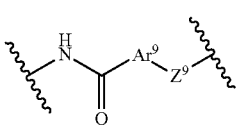

(S9)

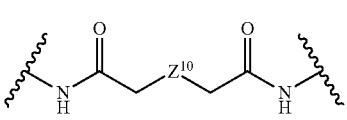

(S10)

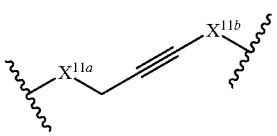

(S11)

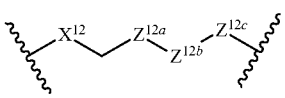

(S12)

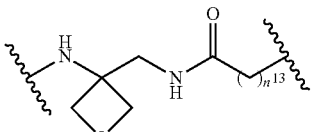

(S13)

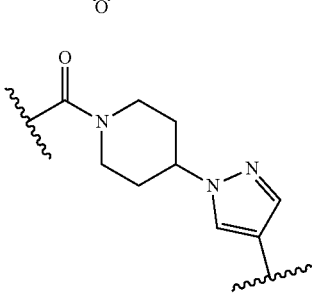

(S14)

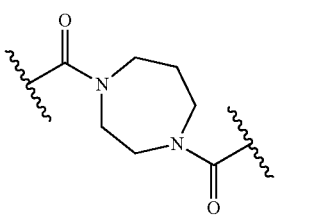

(S15)

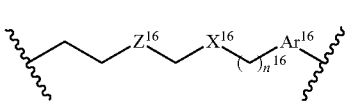

(S16)

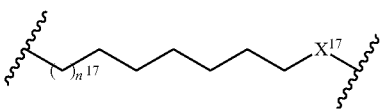

(S17)

-continued (S18)

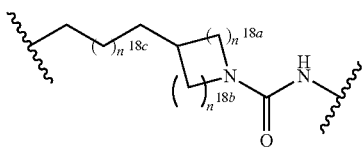

(wherein, the wavy line represents a bonding site to $L^1$ or $L^2$, $n^{1a}$ and $n^{1b}$ are the same or different and each represents 0 or 1, $X^{1a}$ and $X^{1b}$ are the same or different and each represents —C(=O)—NH—, —NH—C(=O)—, —SO$_2$—NH—, —NH—SO$_2$—, —O—C(=S)—NH—, —O—C(=O)—NH—, —NH—C(=O)—O—, or —NH—C(=O)—NH—, $R^{1a}$ represents a hydrogen atom and $R^{1b}$ represents a hydrogen atom or lower alkyl, or $R^{1a}$ and $R^{1b}$ together represent carbonyl, $X^{2a}$ represents —C(=O)—NH—, —NH—C(=O)—, —SO$_2$—NH—, or —NH—SO$_2$—, $X^{2b}$ represents —C(=O)—NH—, —NH—C(=O)—, —SO$_2$—NH—, —NH—SO$_2$—, or —CH$_2$—, $Z^2$ represents CH or N, $n^{3a}$ and $n^{3b}$ are the same or different and each represents 1 or 2, $X^3$ represents —C(=O)—NH—, —NH—C(=O)—, —SO$_2$—NH—, —NH—SO$_2$—, —NH—C(=O)—NH—, or —NH—CH$_2$—, $Z^3$ represents CH or N, $X^{5a}$ and $X^{5b}$ are the same or different and each represents —C(=O)—NH—, —NH—C(=O)—, —SO$_2$—NH—, or —NH—SO$_2$—, $n^6$ represents 1 or 2, $Ar^6$ represents triazolediyl, oxadiazolediyl, pyrazolediyl, thiophenediyl, or tetrahydropyridinediyl, $X^6$ represents —C(=O)—NH—, —NH—C(=O)—, —SO$_2$—NH—, —NH—SO$_2$—, —CH$_2$—NH—, —NH—CH$_2$—, or —NH—C(=O)—NH—, $X^7$ represents —C(=O)—NH—, —NH—C(=O)—, —SO$_2$—NH—, or —NH—C(=O)—NH—, $n^7$ represents 1, 2, or 3, $Z^7$ represents S, SO, or SO$_2$, $X^{8a}$ represents —C(=O)—, —CH$_2$—, or —NH—C(=O)—, $X^{8b}$ represents a bond, —C(=O)—, —CH$_2$—, or —CH(OH)—, $Ar^9$ represents triazolediyl or oxazolediyl, $Z^9$ represents CH$_2$ or NH, $Z^{10}$ represents O or NH, $X^{11a}$ represents —C(=O)—NH—, —NH—C(=O)—, —SO$_2$—NH—, —NH—SO$_2$—, or —NH—C(=O)—NH—, $X^{11a'}$ represents —C(=O)—NH—, —NH—C(=O)—, or —C(=O)—, $X^{12}$ represents —C(=O)—NH—, —NH—C(=O)—, —SO$_2$—NH—, —NH—SO$_2$—, or —NH—C(=O)—NH—, $Z^{12a}$ represents CH$_2$ or NH, $Z^{12b}$ represents CH$_2$ or O, $Z^{12c}$ represents a bond, CH$_2$, or O, $n^{13}$ represents 0, 1, or 2, n16 represents 1 or 2, $Z^{16}$ represents a bond, CH$_2$, or O, $X^{16}$ represents —CH$_2$—O—, —C(=O)—NH—, —NH—C(=O)—, or —NH—C(=O)—NH—, $Ar^{16}$ represents triazolediyl, oxadiazolediyl, or pyrazolediyl, $n^{17}$ represents 1 or 2, $X^{17}$ represents —C(=O)—NH—, —NH—C(=O)—, —NH—SO$_2$—, or —NH—C(=O)—NH—, and $n^{18a}$, $n^{18b}$, and $n^{18c}$ are the same or different and each represents 1 or 2)).

(2) A compound represented by the following formula (I) or a pharmaceutically acceptable salt thereof:

[Chemical formula 5]

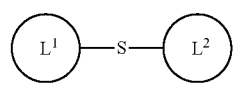

(I)

(wherein, $L^1$ and $L^2$ are the same or different and each represents a group represented by one formula selected from the group consisting of the following formulas (A) to (F), and S represents a group represented by one formula selected from the group consisting of the following formulas (S1) to (S18):

[Chemical formula 6]

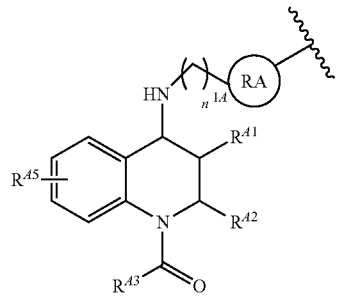

(A)

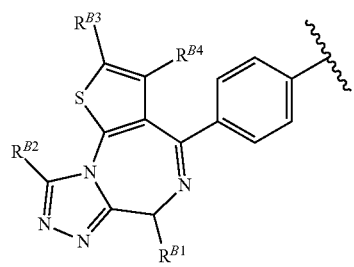

(B)

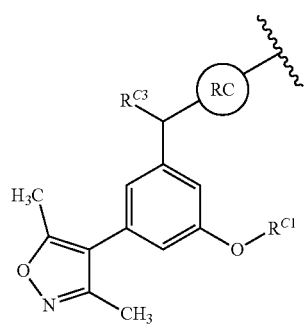

(C)

-continued (D)

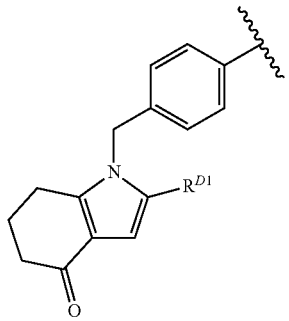

(E)

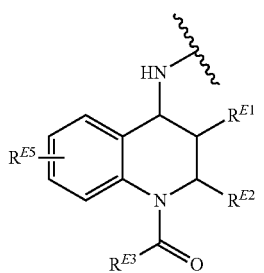

(F)

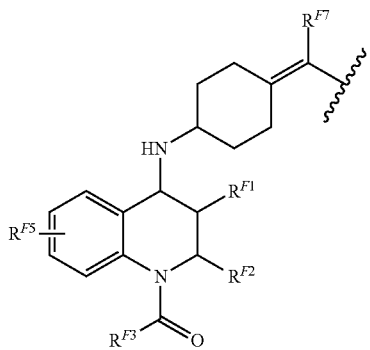

(wherein,
the wavy line represents a bonding site to S,
$R^{A1}$, $R^{A2}$, and $R^{A3}$ are the same or different and each represents a hydrogen atom or lower alkyl,
$R^{A5}$ represents a hydrogen atom, a halogen, optionally substituted lower alkyl, optionally substituted lower alkenyl, optionally substituted tetrahydropyridinyl, optionally substituted dihydro-1H-pyrrolyl, or optionally substituted tetrahydro-1H-azepinyl,
ring RA represents benzenediyl, cycloalkanediyl, pyridinediyl, piperidinediyl, azetidinediyl, pyrrolidinediyl, or homopiperidinediyl,
$n^{1A}$ represents 0 or 1,
$R^{B1}$ represents a hydrogen atom, optionally substituted lower alkoxycarbonylmethyl, optionally substituted cycloalkyloxycarbonylmethyl, or —CH$_2$CONR$^{B5}$R$^{B6}$ (wherein, $R^{B5}$ and $R^{B6}$ are the same or different and each represents a hydrogen atom or optionally substituted lower alkyl, or they represent an optionally substituted nitrogen-containing aliphatic heterocyclic group together with an adjacent nitrogen atom),
$R^{B2}$ represents optionally substituted lower alkyl,
$R^{B3}$ and $R^{B4}$ are the same or different and each represents a halogen or optionally substituted lower alkyl,
$R^{C1}$ represents a hydrogen atom, lower alkyl, or lower alkanoyl,
$R^{C3}$ represents a hydrogen atom or hydroxy, ring RC represents benzenediyl, piperidinediyl, azetidinediyl, pyrrolidinediyl, or homopiperidinediyl,
$R^{D1}$ represents optionally substituted lower alkyl or optionally substituted lower alkoxycarbonyl,
$R^{E1}$ and $R^{F1}$ have the same definition as $R^{A1}$,
$R^{E2}$ and $R^{F2}$ have the same definition as $R^{A2}$,
$R^{E3}$ and $R^{F3}$ have the same definition as $R^{A3}$,
$R^{E5}$ and $R^{F5}$ have the same definition as $R^{A5}$, and
$R^{F7}$ represents a hydrogen atom or a halogen);

[Chemical formula 7]

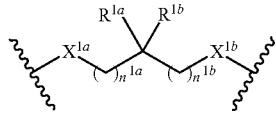

(S1)

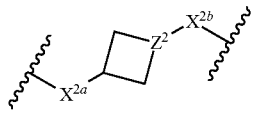

(S2)

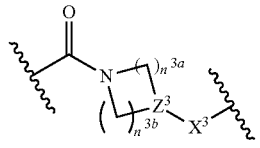

(S3)

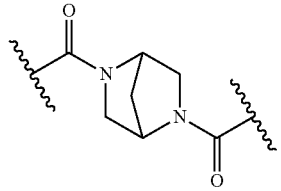 [SMILES: *C(=O)N1C[C@H]2C[C@@H]1CN2C(*)=O]

(S4)

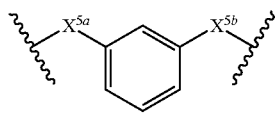

(S5)

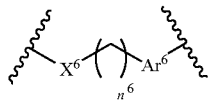

(S6)

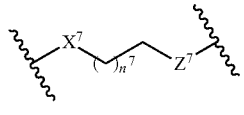

(S7)

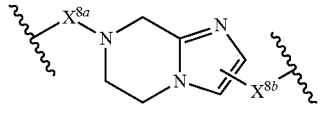

(S8)

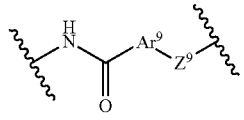

(S9)

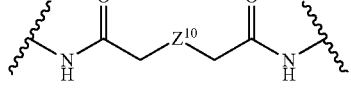

(S10)

-continued

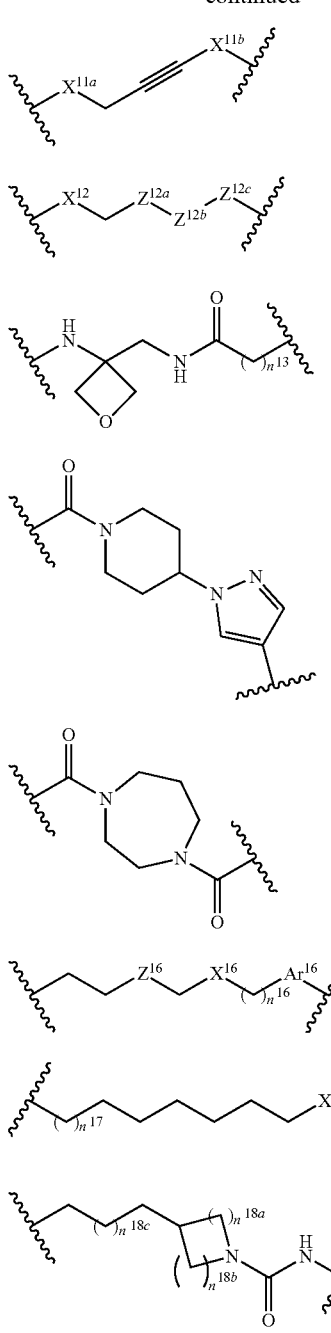

(S11)

(S12)

(S13)

(S14)

(S15)

(S16)

(S17)

(S18)

(wherein, the wavy line represents a bonding site to $L^1$ or $L^2$, $n^{1a}$ and $n^{1b}$ are the same or different and each represents 0 or 1, $X^{1a}$ and $X^{1b}$ are the same or different and each represents —C(=O)—NH—, —NH—C(=O)—, —SO$_2$—NH—, —NH—SO$_2$—, —O—C(=S)—NH—, —O—C(=O)—NH—, —NH—C(=O)—O—, or —NH—C(=O)—NH— (except for the cases where (i) $X^{1a}$ is —NH—SO$_2$—, and $X^{1b}$ is —SO$_2$—NH—, (ii) $n^{1a}$ and $n^{1b}$ are 0, $X^{1a}$ is —C(=O)—NH—, —SO$_2$—NH—, —O—C(=S)—NH—, —O—C(=O)—NH—, or —NH—C(=O)—NH—, and $X^{1b}$ is —NH—C(=O)—, —NH—SO$_2$—, —NH—C(=O)—O—, or —NH—C(=O)—NH—, and (iii) $X^{1a}$ is —O—C(=S)—NH—, —O—C(=O)—NH—, —NH—C(=O)—O—, or —NH—C(=O)—NH— and $X^{1b}$ is —O—C(=S)—NH—, —O—C(=O)—NH—, —NH—C(=O)—O—, or —NH—C(=O)—NH—), $R^{1a}$ represents a hydrogen atom and $R^{1b}$ represents a hydrogen atom or lower alkyl, or $R^{1a}$ and $R^{1b}$ together represent carbonyl, $X^2a$ represents —C(=O)—NH—, —NH—C(=O)—, —SO$_2$—NH—, or —NH—SO$_2$—, $X^{2b}$ represents —C(=O)—NH—, —NH—C(=O)—, —SO$_2$—NH—, —NH—SO$_2$—, or —CH$_2$— (except for the case where $X^{2a}$ is —NH—SO$_2$— and $X^{2b}$ is —SO$_2$—NH—), $Z^2$ represents CH or N (except for the cases where (i) $Z^2$ is N and $X^{2b}$ is —NH—C(=O)—, —SO$_2$—NH—, or —NH—SO$_2$— and (ii) $Z^2$ is CH and $X^{2b}$ is —CH$_2$—), $n^{3a}$ and $n^{3b}$ are the same or different and each represents 1 or 2, $X^3$ represents —C(=O)—NH—, —NH—C(=O)—, —SO$_2$—NH—, —NH—SO$_2$—, —NH—C(=O)—NH—, or —NH—CH$_2$—, $Z^3$ represents CH or N (except for the cases where (i) $Z^3$ is N and $X^3$ is —NH—C(=O)—, —SO$_2$—NH—, —NH—SO$_2$—, —NH—C(=O)—NH—, or —NH—CH$_2$— and (ii) $Z^3$ is N and $n^{3a}$ or $n^{3b}$ is 1), $X^{5a}$ and $X^{5b}$ are the same or different and each represents —C(=O)—NH—, —NH—C(=O)—, —SO$_2$—NH—, or —NH—SO$_2$— (except for the case where $X^{5a}$ is —NH—SO$_2$— and $X^{5b}$ is —SO$_2$—NH—), $n^6$ represents 1 or 2, $Ar^6$ represents triazolediyl, oxadiazolediyl, pyrazolediyl, thiophenediyl, or tetrahydropyridinediyl, $X^6$ represents —C(=O)—NH—, —NH—C(=O)—, —SO$_2$—NH—, —NH—SO$_2$—, —CH$_2$—NH— or —NH—C(=O)—NH— (except for the cases where (i) $Ar^6$ is oxadiazolediyl, pyrazolediyl, thiophenediyl, or tetrahydropyridinediyl and $X^6$ is —NH—SO$_2$— and (ii) $n^6$ is 1, $Ar^6$ is pyrazolediyl or tetrahydropyridinediyl, and $X^6$ is —C(=O)—NH—, —SO$_2$—NH—, —CH$_2$—NH—, or —NH—C(=O)—NH—), $X^7$ represents —C(=O)—NH—, —NH—C(=O)—, —SO$_2$—NH—, or —NH—C(=O)—NH—, $n^7$ represents 1, 2, or 3, $Z^7$ represents S, SO, or SO$_2$, $X^{8a}$ represents —C(=O)—, —CH$_2$—, or —NH—C(=O)—, $X^{8b}$ represents a bond, —C(=O)—, —CH$_2$—, or —CH(OH)—, $Ar^9$ represents triazolediyl or oxazolediyl, $Z^9$ represents CH$_2$ or NH (except for the cases where (i) $Ar^9$ is triazolediyl and $Z^9$ is NH and (ii) $Ar^9$ is oxazolediyl and $Z^9$ is CH$_2$), $Z^{10}$ represents O or NH, $X^{11a}$ represents —C(=O)—NH—, —SO$_2$—NH—, or —NH—C(=O)—NH—, $X^{11b}$ represents —C(=O)—NH— or —C(=O)—, $X^{12}$ represents —C(=O)—NH—, —NH—C(=O)—, —SO$_2$—NH—, or —NH—C(=O)—NH—, $Z^{12a}$ represents CH$_2$ or NH (except for the case where $X^{12}$ is —C(=O)—NH—, —SO$_2$—NH—, or —NH—C(=O)—NH— and $Z^{12}a$ is NH), $Z^{12b}$ represents CH$_2$ or O (except for the case where $Z^{12a}$ is NH and $Z^{12b}$ is O), $Z^{12c}$ represents a bond, CH$_2$, or O (except for the cases where (i) $Z^{12b}$ is O and $Z^{12c}$ is O and (ii) $Z^{12a}$ is NH and $Z^{12c}$ is CH$_2$ or O), $n^{13}$ represents 0, 1 or 2, $n^{16}$ represents 1 or 2, $Z^{16}$ represents a bond, $CH_2$, or O, $X^{16}$ represents —$CH_2$—O—, —C(=O)—NH—, —NH—C(=O)—, or —NH—C(=O)—NH— (except for the case where $Z^{16}$ is O and $X^{16}$ is —NH—C(=O)— or —NH—C(=O)—NH—), $Ar^{16}$ represents triazolediyl, oxadiazolediyl or pyrazolediyl (except for the cases where (i) $X^{16}$ is —$CH_2$—O— and $Ar^{16}$ is oxadiazolediyl or pyrazolediyl and (ii) $n^{16}$ is 1, $X^{16}$ is —C(=O)—NH— or —NH—C(=O)—NH—, and $Ar^{16}$ is pyrazolediyl), $n^{17}$ represents 1 or 2, $X^{17}$ represents —C(=O)—NH—, —NH—C(=O)—, —NH—$SO_2$—, or —NH—C(=O)—NH—, and $n^{18a}$, $n^{18b}$, and $n^{18c}$ are the same or different and each represents 1 or 2).

(3) The compound according to (1) or (2) or a pharmaceutically acceptable salt thereof, wherein $L^1$ represents a group represented by formula (A), (B), (C), (D), or (F), $L^2$ represents a group represented by formula (A), (B), (C), or (D), and S is a group represented by formula (S1).

(4) The compound according to (1) or (2) or a pharmaceutically acceptable salt thereof, wherein $L^1$ represents a group represented by formula (A), $L^2$ represents a group represented by formula (A), and S is a group represented by formula (S2).

(5) The compound according to (1) or (2) or a pharmaceutically acceptable salt thereof, wherein $L^1$ represents a group represented by formula (A), (B), or (C), $L^2$ represents a group represented by formula (A) or (B), and S is a group represented by formula (S3).

(6) The compound according to (1) or (2) or a pharmaceutically acceptable salt thereof, wherein $L^1$ represents a group represented by formula (A), $L^2$ represents a group represented by formula (A), and S is a group represented by formula (S4) or (S5).

(7) The compound according to (1) or (2) or a pharmaceutically acceptable salt thereof, wherein $L^1$ represents a group represented by formula (A), (B), (C), or (D), $L^2$ represents a group represented by formula (A), (B), or (D), and S is a group represented by formula (S6).

(8) The compound according to (1) or (2) or a pharmaceutically acceptable salt thereof, wherein $L^1$ represents a group represented by formula (A) or (B), $L^2$ represents a group represented by formula (A), and S is a group represented by formula (S7).

(9) The compound according to (1) or (2) or a pharmaceutically acceptable salt thereof, wherein $L^1$ represents a group represented by formula (A) or (B), $L^2$ represents a group represented by formula (A), and S is a group represented by formula (S8).

(10) The compound according to (1) or (2) or a pharmaceutically acceptable salt thereof, wherein $L^1$ represents a group represented by formula (A), $L^2$ represents a group represented by formula (A), and S is a group represented by formula (S9).

(11) The compound according to (1) or (2) or a pharmaceutically acceptable salt thereof, wherein $L^1$ represents a group represented by formula (A) or (B), $L^2$ represents a group represented by formula (A), and S is a group represented by formula (S10).

(12) The compound according to (1) or (2) or a pharmaceutically acceptable salt thereof, wherein $L^1$ represents a group represented by formula (A) or (B), $L^2$ represents a group represented by formula (A) or (B), and S is a group represented by formula (S11).

(13) The compound according to (1) or (2) or a pharmaceutically acceptable salt thereof, wherein $L^1$ represents a group represented by formula (A), $L^2$ represents a group represented by formula (A), and S is a group represented by formula (S12), (S13), (S14), or (S15).

(14) The compound according to (1) or (2) or a pharmaceutically acceptable salt thereof, wherein $L^1$ represents a group represented by formula (E), $L^2$ represents a group represented by formula (A), and S is a group represented by formula (S16), (S17), or (S18).

(15) The compound according to any one of (1) to (14) or a pharmaceutically acceptable salt thereof, wherein formula (A) is the following formula (A)-1:

[Chemical formula 8]

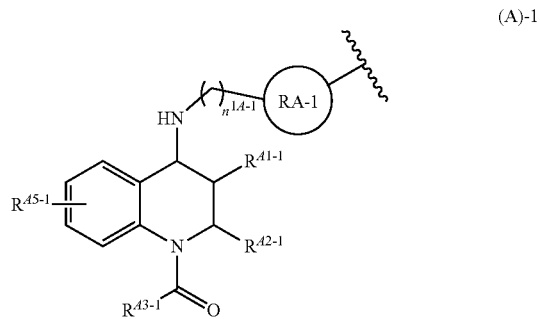

(A)-1

(wherein, the wavy line represents the bonding site to S, $R^{A1-1}$ represents a hydrogen atom, $R^{A2-1}$ and $R^{A3-1}$ are the same or different and each represents alkyl having 1 to 5 carbon atoms, $R^{A5-1}$ represents a hydrogen atom, a fluorine atom, optionally substituted alkyl having 1 to 5 carbon atoms, optionally substituted alkenyl having 2 to 6 carbon atoms, or optionally substituted tetrahydropyridinyl, ring RA-1 represents benzenediyl, cycloalkanediyl, pyridinediyl, or piperidinediyl, and $n^{14-1}$ represents 0 or 1).

(16) The compound according to any one of (1) to (3), (5), (7) to (9), (11), and (12) or a pharmaceutically acceptable salt thereof, wherein formula (B) is the following formula (B)-1:

[Chemical formula 9]

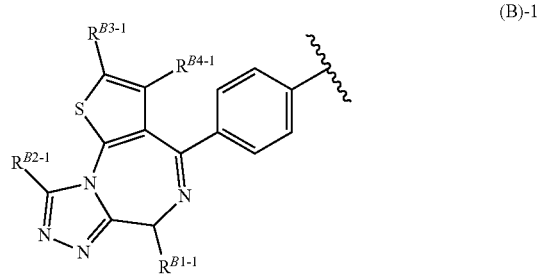

(B)-1

(wherein, the wavy line represents the bonding site to S, $R^{B1-1}$ represents a hydrogen atom, optionally substituted alkoxycarbonylmethyl having 1 to 5 carbon atoms, optionally substituted cycloalkyloxycarbonylmethyl, or —CH$_2$CONR$^{B5-1}$R$^{B6-1}$ (wherein, R$^{B5-1}$ and R$^{B6-1}$ are the same or different and each represents a hydrogen atom or alkyl having 1 to 5 carbon atoms, or they represent an optionally substituted nitrogen-containing aliphatic heterocyclic group together with an adjacent nitrogen atom), R$^{B2-1}$ represents optionally substituted alkyl having 1 to 5 carbon atoms, and R$^{B3-1}$ and R$^{B4-1}$ represent optionally substituted alkyl having 1 to 5 carbon atoms).

(17) The compound according to any one of (1), (2), (3), (5), and (7) or a pharmaceutically acceptable salt thereof, wherein formula (C) is the following formula (C)-1:

[Chemical formula 10]

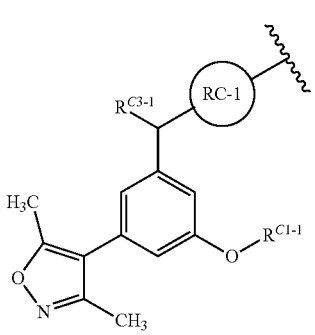

(C)-1

(wherein,
the wavy line represents the bonding site to S,
R$^{C1-1}$ represents a hydrogen atom,
R$^{C3-1}$ represents a hydrogen atom or hydroxy, and
ring RC-1 represents benzenediyl or piperidinediyl).

(18) The compound according to any one of (1) to (3) and (7) or a pharmaceutically acceptable salt thereof, wherein formula (D) is the following formula (D)-1:

[Chemical formula 11]

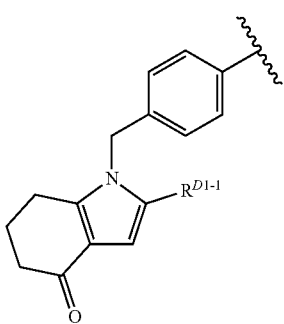

(D)-1

(wherein,
the wavy line represents the bonding site to S, and
R$^{D1-1}$ represents optionally substituted alkyl having 1 to 5 carbon atoms or optionally substituted alkoxycarbonyl having 1 to 5 carbon atoms).

(19) The compound according to any one of (1), (2), and (14) or a pharmaceutically acceptable salt thereof, wherein formula (E) is the following formula (E)-1:

[Chemical formula 12]

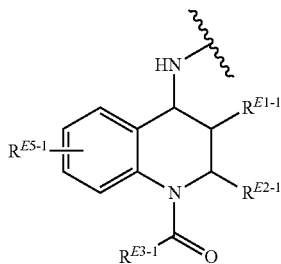

(E)-1

(wherein,
the wavy line represents the bonding site to S,
R$^{E1-1}$ represents a hydrogen atom,
R$^{E2-1}$ and R$^{E3-1}$ are the same or different and each represents alkyl having 1 to 5 carbon atoms, and
R$^{E5-1}$ represents a hydrogen atom).

(20) The compound according to any one of (1) to (3) or a pharmaceutically acceptable salt thereof, wherein formula (F) is the following formula (F)-1:

[Chemical formula 13]

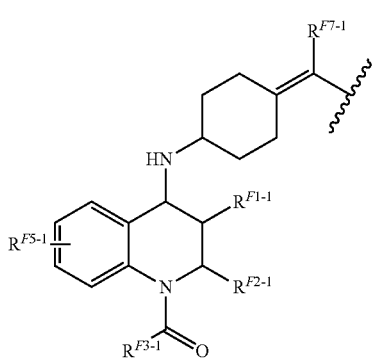

(F)-1

(wherein,
the wavy line represents the bonding site to S,
R$^{F1-1}$ represents a hydrogen atom,
R$^{F2-1}$ and R$^{F3-1}$ are the same or different and each represents alkyl having 1 to 5 carbon atoms,
R$^{F5-1}$ represents a hydrogen atom, and
R$^{F7-1}$ represents a hydrogen atom or a fluorine atom).

(21) The compound according to any one of (1) to (3) or a pharmaceutically acceptable salt thereof, wherein S is the following formula (S1)-1:

[Chemical formula 14]

(S1)-1

(wherein,
the wavy line represents the bonding site to L$^1$ or L$^2$,
n$^{1a-1}$ and n$^{1b-1}$ are the same or different and each represents 0 or 1,
X$^{1a-1}$ and X$^{1b-1}$ are the same or different and each represents —C(=O)—NH—, —NH—C(=O)—, —SO$_2$—

NH—, —NH—SO$_2$—, —O—C(=S)—NH—, —O—C(=O)—NH—, —NH—C(=O)—O—, or —NH—C(=O)—NH— (except for the cases where (i) $X^{1a-1}$ is —NH—SO$_2$— and $X^{1b-1}$ is —SO$_2$—NH—, (ii) $n^{1a-1}$ and $n^{1b-1}$ are 0, $X^{1a-1}$ is —C(=O)—NH—, —SO$_2$—NH—, —O—C(=S)—NH—, —O—C(=O)—NH—, or —NH—C(=O)—NH—, and $X^{1b-1}$ is —NH—C(=O)—, —NH—SO$_2$—, —NH—C(=O)—O—, or —NH—C(=O)—NH—, and (iii) $X^{1a-1}$ is —O—C(=S)—NH—, —O—C(=O)—NH—, —NH—C(=O)—O—, or —NH—C(=O)—NH— and $X^{1b-1}$ is —O—C(=S)—NH—, —O—C(=O)—NH—, —NH—C(=O)—O—, or —NH—C(=O)—NH—), and $R^{1a-1}$ represents a hydrogen atom and $R^{1b-1}$ represents a hydrogen atom or an alkyl having 1 to 5 carbon atoms, or $R^{1a-1}$ and $R^{1b-1}$ together represent carbonyl).

(22) The compound according to any one of (1), (2), and (4) or a pharmaceutically acceptable salt thereof, wherein S is the following formula (S2)-1:

[Chemical formula 15]

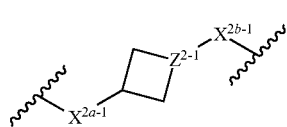

(S2)-1

(wherein,
the wavy line represents the bonding site to $L^1$ or $L^2$,
$X^{2a-1}$ represents —C(=O)—NH— or —NH—C(=O)—,
$X^{2b-1}$ represents —C(=O)—NH—, —NH—C(=O)—, or —CH$_2$—, and
$Z^{2-1}$ represents CH or N (except for the cases where (i) $Z^{2-1}$ is N and $X^{2b-1}$ is —NH—C(=O)— and (ii) $Z^{2-1}$ is CH and $X^{2b-1}$ is —CH$_2$—)).

(23) The compound according to any one of (1), (2), and (5) or a pharmaceutically acceptable salt thereof, wherein S is the following formula (S3)-1:

[Chemical formula 16]

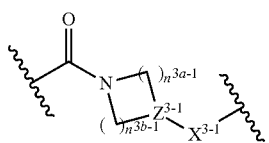

(S3)-1

(wherein,
the wavy line represents the bonding site to $L^1$ or $L^2$,
$n^{3a-1}$ and $n^{3b-1}$ are the same or different and each represents 1 or 2,
$X^{3-1}$ represents —C(=O)—NH—, —NH—C(=O)—, —NH—C(=O)—NH—, or —NH—CH$_2$—, and
$Z^{3-1}$ represents CH or N (except for the cases where (i) $Z^{3-1}$ is N and $X^{3-1}$ is —NH—C(=O)—, —NH—C(=O)—NH—, or —NH—CH$_2$— and (ii) $Z^{3-1}$ is N and $n^{3a-1}$ or $n^{3b-1}$ is 1)).

(24) The compound according to any one of (1), (2), and (6) or a pharmaceutically acceptable salt thereof, wherein S is the following formula (S5)-1:

[Chemical formula 17]

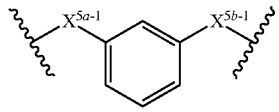

(S5)-1

(wherein,
the wavy line represents the bonding site to $L^1$ or $L^2$ and $X^{5a-1}$ and $X^{5b-1}$ are the same or different and each represents —C(=O)—NH—, —NH—C(=O)—, or —NH—SO$_2$—).

(25) The compound according to any one of (1), (2), and (7) or a pharmaceutically acceptable salt thereof, wherein S is the following formula (S6)-1:

[Chemical formula 18]

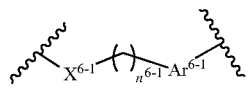

(S6)-1

(wherein,
the wavy line represents the bonding site to $L^1$ or $L^2$,
$n^{6-1}$ represents 1 or 2,
$Ar^{6-1}$ represents triazolediyl, oxadiazolediyl, pyrazolediyl, thiophenediyl, or tetrahydropyridinediyl, and
$X^{6-1}$ represents —C(=O)—NH—, —NH—C(=O)—, or —CH$_2$—NH— (except for the case where $n^{6-1}$ is 1, $Ar^{6-1}$ is pyrazolediyl or tetrahydropyridinediyl, and $X^{6-1}$ is —C(=O)—NH— or —CH$_2$—NH—)).

(26) The compound according to any one of (1), (2), and (8) or a pharmaceutically acceptable salt thereof, wherein S is the following formula (S7)-1:

[Chemical formula 19]

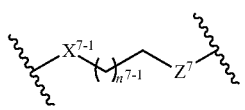

(S7)-1

(wherein,
the wavy line represents the bonding site to $L^1$ or $L^2$,
$X^{7-1}$ represents —C(=O)—NH— or —NH—C(=O)—,
$n^{7-1}$ represents 1, and
$Z^{7-1}$ represents S, SO, or SO$_2$).

(27) The compound according to any one of (1), (2), and (9) or a pharmaceutically acceptable salt thereof, wherein S is the following formula (S8)-1:

[Chemical formula 20]

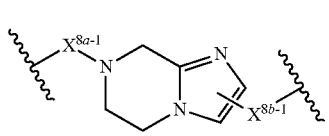

(S8)-1

(wherein, the wavy line represents the bonding site to $L^1$ or $L^2$, $X^{8a-1}$ represents —C(=O)— or —CH$_2$—, and $X^{8b-1}$ represents a bond, —C(=O)—, —CH$_2$—, or —CH(OH)—).

(28) The compound according to any one of (1), (2), and (10) or a pharmaceutically acceptable salt thereof, wherein S is the following formula (S9)-1:

[Chemical formula 21]

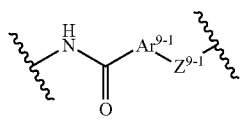

(S9)-1

(wherein, the wavy line represents the bonding site to $L^1$ or $L^2$, $Ar^{9-1}$ represents triazolediyl or oxazolediyl, and $Z^{9-1}$ represents CH$_2$ or NH (except for the cases where (i) $Ar^{9-1}$ is triazolediyl and $Z^{9-1}$ is NH and (ii) $Ar^{9-1}$ is oxazolediyl and $Z^{9-1}$ is CH$_2$)).

(29) The compound according to any one of (1), (2), and (11) or a pharmaceutically acceptable salt thereof, wherein S is the following formula (S10)-1:

[Chemical formula 22]

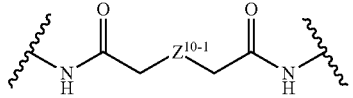

(S10)-1

(wherein, the wavy line represents the bonding site to $L^1$ or $L^2$ and $Z^{10-1}$ represents O or NH).

(30) The compound according to any one of (1), (2), and (12) or a pharmaceutically acceptable salt thereof, wherein S is the following formula (S11)-1:

[Chemical formula 23]

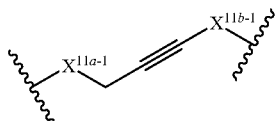

(S11)-1

(wherein, the wavy line represents the bonding site to $L^1$ or $L^2$, $X^{11a-1}$ represents —C(=O)—NH—, and $X^{11b-1}$ represents —C(=O)—NH— or —C(=O)—).

(31) The compound according to any one of (1), (2), and (13) or a pharmaceutically acceptable salt thereof, wherein S is the following formula (S12)-1:

[Chemical formula 24]

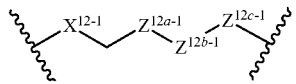

(S12)-1

(wherein, the wavy line represents the bonding site to $L^1$ or $L^2$, $X^{12-1}$ represents —C(=O)—NH— or —NH—C(=O)—, $Z^{12a-1}$ represents CH$_2$ or NH (except for the case where $X^{12-1}$ is —C(=O)—NH— and $Z^{12a-1}$ is NH), $Z^{12b-1}$ represents CH$_2$ or O (except for the case where $Z^{12a-1}$ is NH and $Z^{12b-1}$ is O), and $Z^{12c-1}$ represents a bond or O (except for the cases where (i) $Z^{12b-1}$ is O and $Z^{12c-1}$ is O and (ii) $Z^{12a-1}$ is NH and $Z^{12c-1}$ is O)).

(32) The compound according to any one of (1), (2), and (13) or a pharmaceutically acceptable salt thereof, wherein S is the following formula (S13)-1:

[Chemical formula 25]

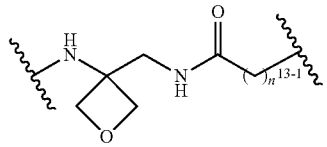

(S13)-1

(wherein, the wavy line represents the bonding site to $L^1$ or $L^2$ and $n^{13-1}$ represents 0 or 2).

(33) The compound according to any one of (1), (2), and (14) or a pharmaceutically acceptable salt thereof, wherein S is the following formula (S16)-1:

[Chemical formula 26]

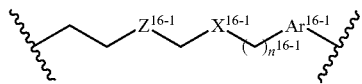

(S16)-1

(wherein, the wavy line represents the bonding site to $L^1$ or $L^2$, $n^{16-1}$ represents 1 or 2, $Z^{16-1}$ represents a bond, CH$_2$, or O, $X^{16-1}$ represents —CH$_2$—O— or —C(=O)—NH—, and $Ar^{16-1}$ represents triazolediyl, oxadiazolediyl, or pyrazolediyl (except for the cases where (i) $X^{16-1}$ is —CH$_2$—O— and $Ar^{16-1}$ is oxadiazolediyl or pyrazolediyl and (ii) $n^{16-1}$ is 1, $X^{16-1}$ is —C(=O)—NH—, and $Ar^{16-1}$ is pyrazolediyl)).

(34) The compound according to any one of (1), (2), and (14) or a pharmaceutically acceptable salt thereof, wherein S is the following formula (S17)-1:

[Chemical formula 27]

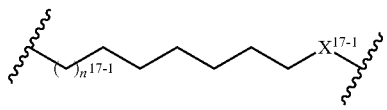

(S17)-1

(wherein,
the wavy line represents the bonding site to $L^1$ or $L^2$,
$n^{17-1}$ represents 1 or 2, and
$X^{17-1}$ represents —C(=O)—NH—).

(35) The compound according to any one of (1), (2), and (14) or a pharmaceutically acceptable salt thereof, wherein S is the following formula (S18)-1:

[Chemical formula 28]

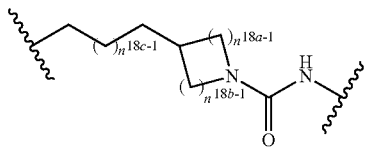

(S18)-1

(wherein,
the wavy line represents the bonding site to $L^1$ or $L^2$ and
$n^{18a-1}$ represents 2, $n^{18b-1}$ represents 2, and $n^{18c-1}$ represents 1).

(36) The compound according to (1) or (2) or a pharmaceutically acceptable salt thereof, wherein $L^1$ and $L^2$ represent a group represented by formula (A) and S is a group represented by formula (S1), wherein,
in the formula (A),
$R^{A1}$ represents a hydrogen atom, $R^{A2}$ and $R^{A3}$ are the same or different and each represents alkyl having 1 to 5 carbon atoms, $R^{A5}$ represents a hydrogen atom, ring RA represents benzenediyl, and $n^{1A}$ represents 0, and
in the formula (S1),
$n^{1a}$ and $n^{1b}$ represent 1, $X^{1a}$ and $X^{1b}$ are the same or different and each represents —C(=O)—NH— or —NH—C(=O)—, $R^{1a}$ represents a hydrogen atom, and $R^{1b}$ represents a hydrogen atom.

(37) The compound according to (1) or (2) or a pharmaceutically acceptable salt thereof, wherein $L^1$ and $L^2$ represent a group represented by formula (A) and S is a group represented by formula (51), wherein,
in the formula (A),
$R^{A1}$ represents a hydrogen atom, $R^{A2}$ and $R^{A3}$ are the same or different and each represents alkyl having 1 to 5 carbon atoms, $R^{A5}$ represents a hydrogen atom, ring RA represents benzenediyl or cycloalkanediyl, and $n^{1A}$ represents 0, and
in the formula (S1),
$n^{1a}$ and $n^{1b}$ represent 0,
$X^{1a}$ and $X^{1b}$ are the same or different and each represents —C(=O)—NH—, —NH—C(=O)—, or —NH—C(=O)—NH— (except for the case where $X^{1a}$ is —C(=O)—NH— or —NH—C(=O)—NH— and $X^{1b}$ is —NH—C(=O)— or —NH—C(=O)—NH—),
$R^{1a}$ represents a hydrogen atom, and $R^{1b}$ represents a hydrogen atom.

(38) The compound according to (1) or (2) or a pharmaceutically acceptable salt thereof, wherein $L^1$ and $L^2$ represent a group represented by formula (A) and S is a group represented by formula (S1), wherein,
in the formula (A),
$R^{A1}$ represents a hydrogen atom, $R^{A2}$ and $R^{A3}$ are the same or different and each represents alkyl having 1 to 5 carbon atoms, $R^{A5}$ represents a hydrogen atom, ring RA represents benzenediyl or pyridinediyl, and $n^{1A}$ represents 0, and in the formula (S1),
$n^{1a}$ and $n^{1b}$ represent 1,
$X^{1a}$ and $X^{1b}$ are the same or different and each represents —C(=O)—NH— or —NH—C(=O)—,
$R^{1a}$ represents a hydrogen atom, and $R^{1b}$ represents a hydrogen atom.

(39) The compound according to (1) or (2) or a pharmaceutically acceptable salt thereof, wherein $L^1$ and $L^2$ represent a group represented by formula (A) and S is a group represented by formula (S3), wherein,
in the formula (A),
$R^{A1}$ represents a hydrogen atom, $R^{A2}$ and $R^{A3}$ are the same or different and each represents alkyl having 1 to 5 carbon atoms, $R^{A5}$ represents a hydrogen atom, ring RA represents benzenediyl or cycloalkanediyl, and $n^{1A}$ represents 0, and
in the formula (S3),
$n^{3a}$ and $n^{3b}$ represent 2, $X^3$ represents —C(=O)—NH—, and $Z^3$ represents N.

(40) The compound according to (1) or (2) or a pharmaceutically acceptable salt thereof, wherein $L^1$ and $L^2$ represent a group represented by formula (A) and S is a group represented by formula (S3), wherein,
in the formula (A),
$R^{A1}$ represents a hydrogen atom, $R^{A2}$ and $R^{A3}$ are the same or different and each represents alkyl having 1 to 5 carbon atoms, $R^{A5}$ represents a hydrogen atom, ring RA represents benzenediyl or cycloalkanediyl, and $n^{1A}$ represents 0, and
in the formula (S3),
$n^{3a}$ and $n^{3b}$ represent 1, $X^3$ represents —C(=O)—NH—, and $Z^3$ represents CH.

(41) The compound according to (1) or (2) or a pharmaceutically acceptable salt thereof, wherein $L^1$ and $L^2$ represent a group represented by formula (A) and S is a group represented by formula (S6), wherein,
in the formula (A),
$R^{A1}$ represents a hydrogen atom, $R^{A2}$ and $R^{A3}$ are the same or different and each represents alkyl having 1 to 5 carbon atoms, $R^{A5}$ represents a hydrogen atom, ring RA represents benzenediyl, and $n^{1A}$ represents 0, and
in the formula (S6),
$n^6$ represents 1, $Ar^6$ represents oxadiazolediyl, and $X^6$ represents —CH$_2$—NH—.

(42) The compound according to (1) or (2) or a pharmaceutically acceptable salt thereof, wherein $L^1$ and $L^2$ represent a group represented by formula (A) and S is a group represented by formula (S6), wherein,
in the formula (A),
$R^{A1}$ represents a hydrogen atom, $R^{A2}$ and $R^{A3}$ are the same or different and each represents alkyl having 1 to 5 carbon atoms, $R^{A5}$ represents a hydrogen atom, ring RA represents benzenediyl, and $n^{1A}$ represents 0, and
in the formula (S6),
$n^6$ represents 1, $Ar^6$ represents triazolediyl, and $X^6$ represents —CH$_2$—NH—.

(43) The compound according to (1) or (2) or a pharmaceutically acceptable salt thereof, wherein $L^1$ and $L^2$ represent a group represented by formula (A) and S is a group represented by formula (S6), wherein,
in the formula (A),
$R^{A1}$ represents a hydrogen atom, $R^{A2}$ and $R^{A3}$ are the same or different and each represents alkyl having 1 to 5 carbon atoms, $R^{A5}$ represents a hydrogen atom, ring RA represents benzenediyl or cycloalkanediyl, and $n^{1A}$ represents 0, and in the formula (S6), $n^6$ represents 1, $Ar^6$ represents oxadiazolediyl, and $X^6$ represents —C(=O)—NH—.

(44) The compound according to (1) or (2) or a pharmaceutically acceptable salt thereof, wherein $L^1$ and $L^2$ represent a group represented by formula (A) and S is a group represented by formula (S6), wherein, in the formula (A), $R^{41}$ represents a hydrogen atom, $R^{42}$ and $R^{43}$ are the same or different and each represents alkyl having 1 to 5 carbon atoms, $R^{45}$ represents a hydrogen atom, ring RA represents benzenediyl or cycloalkanediyl, and $n^{1A}$ represents 0, and in the formula (S6), $n^6$ represents 2, $Ar^6$ represents triazolediyl, and $X^6$ represents —C(=O)—NH—.

(45) A pharmaceutical composition comprising the compound according to any one of (1) to (44) or a pharmaceutically acceptable salt thereof.

(46) The pharmaceutical composition according to (45), further comprising a carrier.

(47) The pharmaceutical composition according to (45) or (46) for inhibiting BET.

(48) The pharmaceutical composition according to (45) or (46) for the treatment of cancer.

(49) A method for the treatment or prevention comprising administration of the compound according to any one of (1) to (44) or a pharmaceutically acceptable salt thereof to a subject.

(50) The method for the treatment or prevention according to (49), which is a method for the treatment or prevention of cancer.

(51) The compound according to any one of (1) to (44) or a pharmaceutically acceptable salt thereof for use as a medicine.

(52) The compound according to any one of (1) to (44) or a pharmaceutically acceptable salt thereof for use in the treatment or prevention of cancer.

(53) Use of the compound according to any one of (1) to (44) or a pharmaceutically acceptable salt thereof for the manufacture of a medicament for treating or preventing cancer.

(54) Use of the compound according to any one of (1) to (44) or a pharmaceutically acceptable salt thereof for the treatment or prevention of cancer.

(55) A medicine comprising the compound according to any one of (1) to (44) or a pharmaceutically acceptable salt thereof as an active ingredient.

(56) A prophylactic or therapeutic agent for cancer, comprising the compound according to any one of (1) to (44) or a pharmaceutically acceptable salt thereof as an active ingredient.

The present invention provides a compound having anticancer activity, a pharmaceutically acceptable salt thereof, or the like.

The compound of the present invention shows a strong BET inhibitory action by, as described in (1) to (56) above, binding two specific BET inhibitors, which become ligands, at specific bonding positions via a spacer having a specific structure.

DETAILED DESCRIPTION OF THE INVENTION

According to the present invention, there is provided a compound represented by the following formula (I) or a pharmaceutically acceptable salt thereof:

[Chemical formula 29]

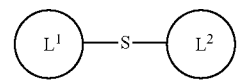

(I)

(wherein, $L^1$ and $L^2$ are the same or different and each represents a group represented by one formula selected from the group consisting of the following formulas (A) to (F), and S is a group represented by one formula selected from the group consisting of the following formulas (S1) to (S18):

[Chemical formula 30]

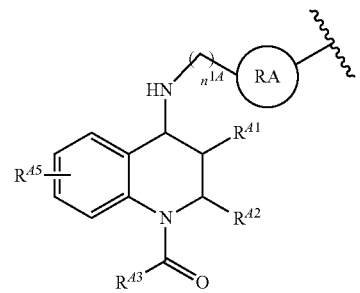

(A)

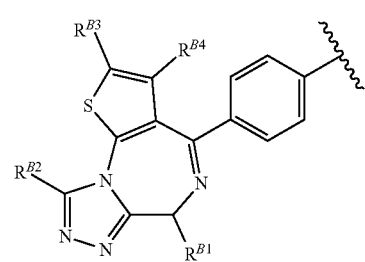

(B)

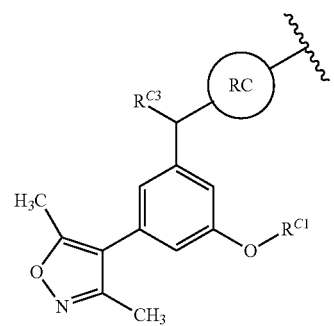

(C)

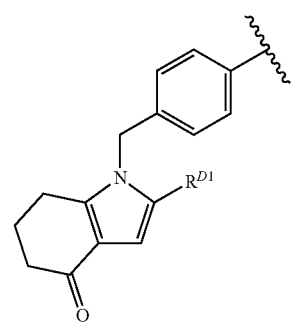

(D)

-continued

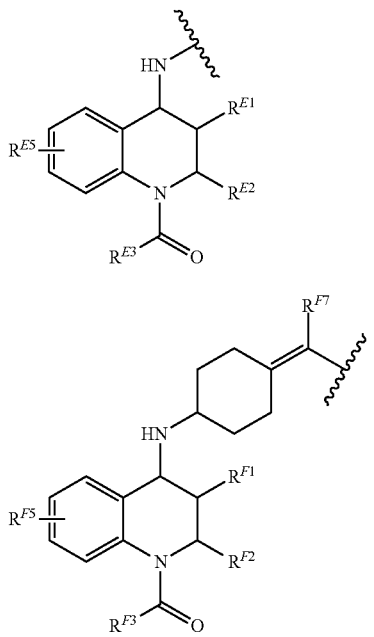

(E)

(F)

(wherein, the wavy line represents the bonding site to S, $R^{A1}$, $R^{A2}$, and $R^{A3}$ are the same or different and each represents a hydrogen atom or lower alkyl, $R^{A5}$ represents a hydrogen atom, a halogen, optionally substituted lower alkyl, optionally substituted lower alkenyl, optionally substituted tetrahydropyridinyl, optionally substituted dihydro-1H-pyrrolyl, or optionally substituted tetrahydro-1H-azepinyl, ring RA represents benzenediyl, cycloalkanediyl, pyridinediyl, piperidinediyl, azetidinediyl, pyrrolidinediyl, or homopiperidinediyl, $n^{1A}$ represents 0 or 1, $R^{B1}$ represents a hydrogen atom, optionally substituted lower alkoxycarbonylmethyl, optionally substituted cycloalkyloxycarbonylmethyl, or —CH$_2$CONR$^{B5}$R$^{B6}$ (wherein, $R^{B5}$ and $R^{B6}$ are the same or different and each represents a hydrogen atom or optionally substituted lower alkyl, or they represent an optionally substituted nitrogen-containing aliphatic heterocyclic group together with an adjacent nitrogen atom), $R^{B2}$ represents optionally substituted lower alkyl, $R^{B3}$ and $R^{B4}$ are the same or different and each represents a halogen or optionally substituted lower alkyl, $R^{C1}$ represents a hydrogen atom, lower alkyl, or lower alkanoyl, $R^{C3}$ represents a hydrogen atom or hydroxy, ring RC represents benzenediyl, piperidinediyl, azetidinediyl, pyrrolidinediyl, or homopiperidinediyl, $R^{D1}$ represents optionally substituted lower alkyl or optionally substituted lower alkoxycarbonyl, $R^{E1}$ and $R^{F1}$ have the same definition as $R^{A1}$, $R^{E2}$ and $R^{F2}$ have the same definition as $R^{A2}$, $R^{E3}$ and $R^{F3}$ have the same definition as $R^{A3}$, $R^{E5}$ and $R^{F5}$ have the same definition as $R^{A5}$, and $R^{F7}$ represents a hydrogen atom or a halogen);

[Chemical formula 31]

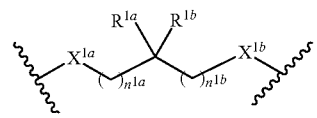

(S1)

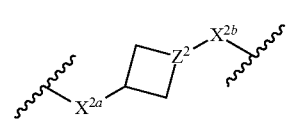

(S2)

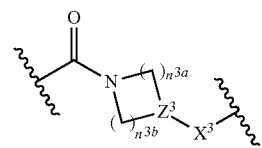

(S3)

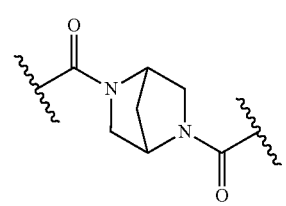

(S4)

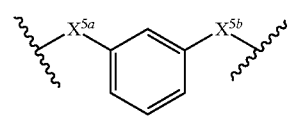

(S5)

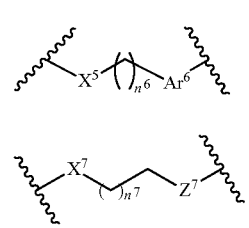

(S6)

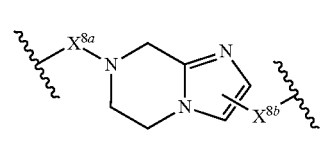

(S7)

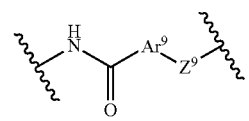

(S8)

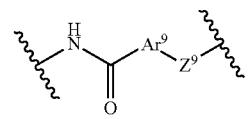

(S9)

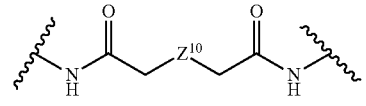

(S10)

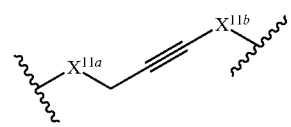

(S11)

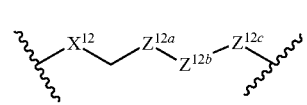

(S12)

29
-continued

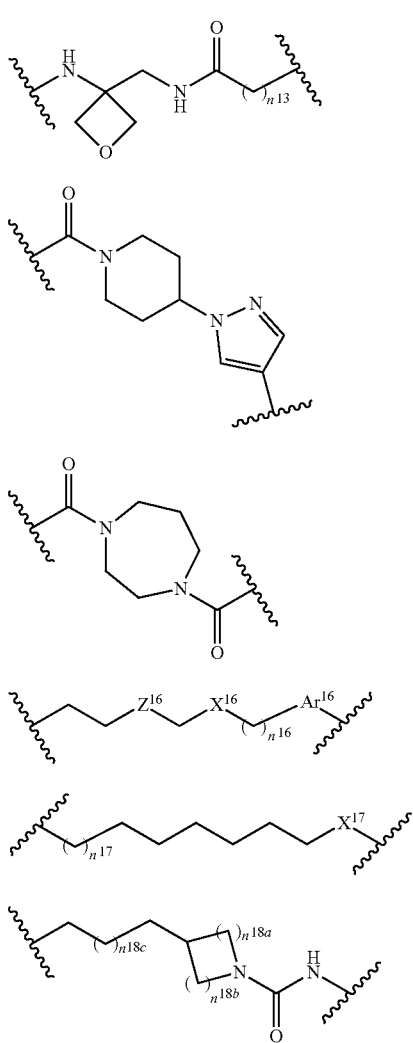

(S13)
(S14)
(S15)
(S16)
(S17)
(S18)

(wherein, the wavy line represents the bonding site to $L^1$ or $L^2$, $n^{1a}$ and $n^{1b}$ are the same or different and each represents 0 or 1, $X^{1a}$ and $X^{1b}$ are the same or different and each represents —C(=O)—NH—, —NH—C(=O)—, —SO$_2$—NH—, —NH—SO$_2$—, —O—C(=S)—NH—, —O—C(=O)—NH—, —NH—C(=O)—O—, or —NH—C(=O)—NH—, $R^{1a}$ represents a hydrogen atom and $R^{1b}$ represents a hydrogen atom or lower alkyl, or $R^{1a}$ and $R^{1b}$ together represent carbonyl, $X^{2a}$ represents —C(=O)—NH—, —NH—C(=O)—, —SO$_2$—NH—, or —NH—SO$_2$—, $X^{2b}$ represents —C(=O)—NH—, —NH—C(=O)—, —SO$_2$—NH—, —NH—SO$_2$—, or —CH$_2$—, $Z^2$ represents CH or N, $n^{3a}$ and $n^{3b}$ are the same or different and each represents 1 or 2, $X^3$ represents —C(=O)—NH—, —NH—C(=O)—, —SO$_2$—NH—, —NH—SO$_2$—, —NH—C(=O)—NH—, or —NH—CH$_2$—, $Z^3$ represents CH or N, $X^{5a}$ and $X^{5b}$ are the same or different and each represents —C(=O)—NH—, —NH—C(=O)—, —SO$_2$—NH—, or —NH—SO$_2$—,

30

$n^6$ represents 1 or 2, $Ar^6$ represents triazolediyl, oxadiazolediyl, pyrazolediyl, thiophenediyl or tetrahydropyridinediyl, $X^6$ represents —C(=O)—NH—, —NH—C(=O)—, —SO$_2$—NH—, —NH—SO$_2$—, —CH$_2$—NH—, —NH—CH$_2$—, or —NH—C(=O)—NH—, $X^7$ represents —C(=O)—NH—, —NH—C(=O)—, —SO$_2$—NH—, or —NH—C(=O)—NH—, $n^7$ represents 1, 2, or 3, $Z^7$ represents S, SO, or SO$_2$, $X^{8a}$ represents —C(=O)—, —CH$_2$—, or —NH—C(=O)—, $X^{8b}$ represents a bond, —C(=O)—, —CH$_2$—, or —CH(OH)—, $Ar^9$ represents triazolediyl or oxazolediyl, $Z^9$ represents CH$_2$ or NH, $Z^{10}$ represents O or NH, $X^{11a}$ represents —C(=O)—NH—, —NH—C(=O)—, —SO$_2$—NH—, —NH—SO$_2$—, or —NH—C(=O)—NH—, $X^{11b}$ represents —C(=O)—NH—, —NH—C(=O)—, or —C(=O)—, $X^{12}$ represents —C(=O)—NH—, —NH—C(=O)—, —SO$_2$—NH—, —NH—SO$_2$—, or —NH—C(=O)—NH—, $Z^{12a}$ represents CH$_2$ or NH, $Z^{12b}$ represents CH$_2$ or O, $Z^{12c}$ represents a bond, CH$_2$, or O, $n^{13}$ represents 0, 1, or 2, $n^{16}$ represents 1 or 2, $Z^{16}$ represents a bond, CH$_2$, or O, $X^{16}$ represents —CH$_2$—O—, —C(=O)—NH—, —NH—C(=O)—, or —NH—C(=O)—NH—, $Ar^{16}$ represents triazolediyl, oxadiazolediyl, or pyrazolediyl, $n^{17}$ represents 1 or 2, $X^{17}$ represents —C(=O)—NH—, —NH—C(=O)—, —NH—SO$_2$—, or —NH—C(=O)—NH—, and $n^{18a}$, $n^{18b}$, and $n^{18c}$ are the same or different and each represents 1 or 2)).

According to a preferred embodiment of the present invention, there is provided a compound represented by the following formula (I) or a pharmaceutically acceptable salt thereof:

[Chemical formula 32]

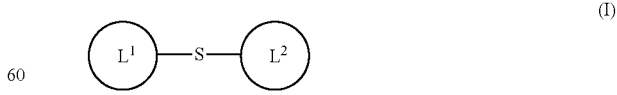

(I)

(wherein, $L^1$ and $L^2$ are the same or different and each represents a group represented by one formula selected from the group consisting of the following formulas (A) to (F), and S is a group represented by one formula selected from the group consisting of the following formulas (S1) to (S18):

[Chemical formula 33]

(A) 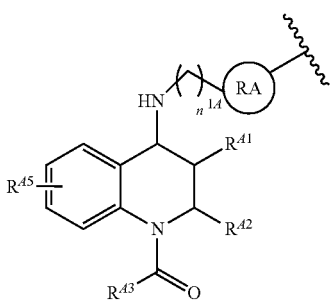

(B) 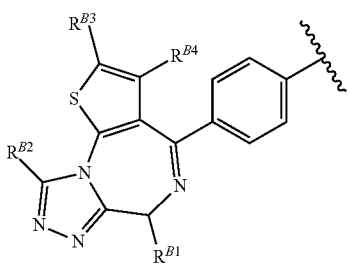

(C) 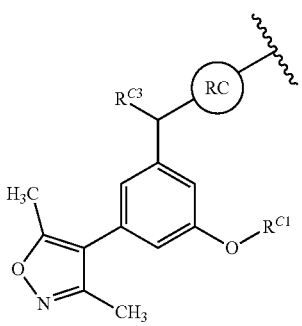

(D) 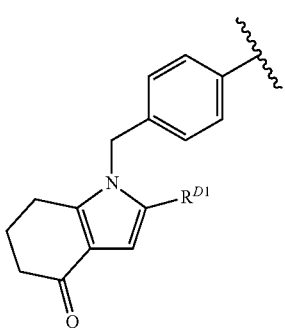

(E) 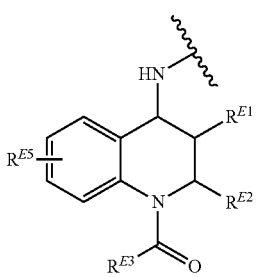

(F) 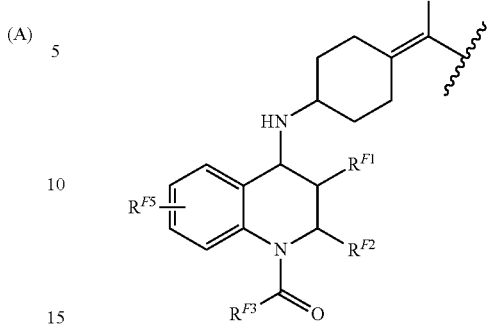

(wherein, the wavy line represents the bonding site to S, $R^{A1}$, $R^{A2}$, and $R^{A3}$ are the same or different and each represents a hydrogen atom or lower alkyl, $R^{A5}$ represents a hydrogen atom, a halogen, optionally substituted lower alkyl, optionally substituted lower alkenyl, optionally substituted tetrahydropyridinyl, optionally substituted dihydro-1H-pyrrolyl, or optionally substituted tetrahydro-1H-azepinyl, ring RA represents benzenediyl, cycloalkanediyl, pyridinediyl, piperidinediyl, azetidinediyl, pyrrolidinediyl or homopiperidinediyl, $n^{1A}$ represents 0 or 1, $R^{B1}$ represents a hydrogen atom, optionally substituted lower alkoxycarbonylmethyl, optionally substituted cycloalkyloxycarbonylmethyl, or —CH$_2$CONR$^{B5}$R$^{B6}$ (wherein, $R^{B5}$ and $R^{B6}$ are the same or different and each represents a hydrogen atom or optionally substituted lower alkyl, or they represent an optionally substituted nitrogen-containing aliphatic heterocyclic group together with an adjacent nitrogen atom), $R^{B2}$ represents optionally substituted lower alkyl, $R^{B3}$ and $R^{B4}$ are the same or different and each represents a halogen or optionally substituted lower alkyl, $R^{C1}$ represents a hydrogen atom, lower alkyl, or lower alkanoyl, $R^{C3}$ represents a hydrogen atom or hydroxy, ring RC represents benzenediyl, piperidinediyl, azetidinediyl, pyrrolidinediyl, or homopiperidinediyl, $R^{D1}$ represents optionally substituted lower alkyl or optionally substituted lower alkoxycarbonyl, $R^{E1}$ and $R^{F1}$ have the same definition as $R^{A1}$,
$R^{E2}$ and $R^{F2}$ have the same definition as $R^{A2}$,
$R^{E3}$ and $R^{F3}$ have the same definition as $R^{A3}$,
$R^{E5}$ and $R^{F5}$ have the same definition as $R^{A5}$, and
$R^{F7}$ represents a hydrogen atom or a halogen);

[Chemical formula 34]

(S1) 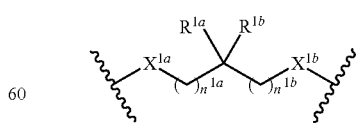

(S2) 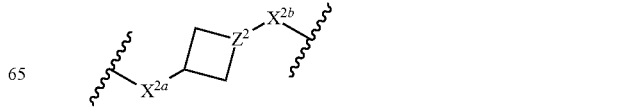

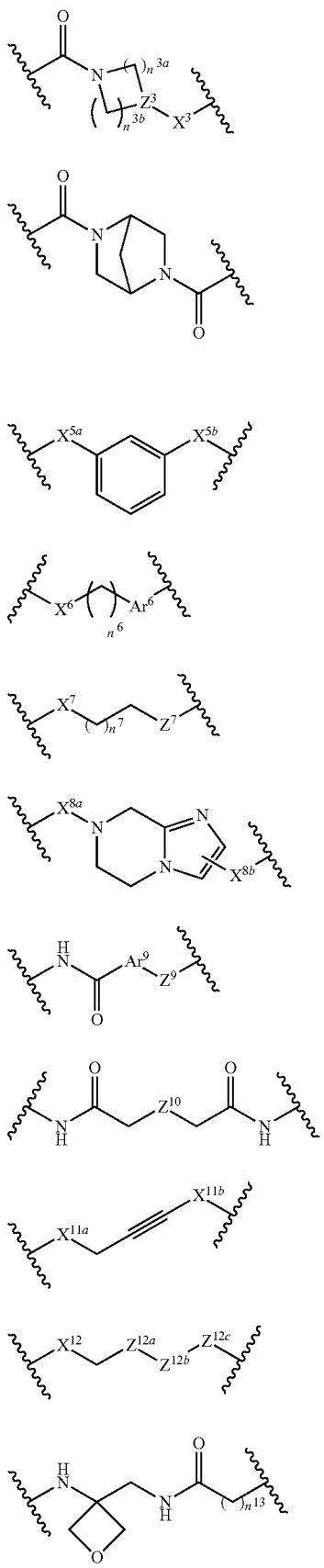

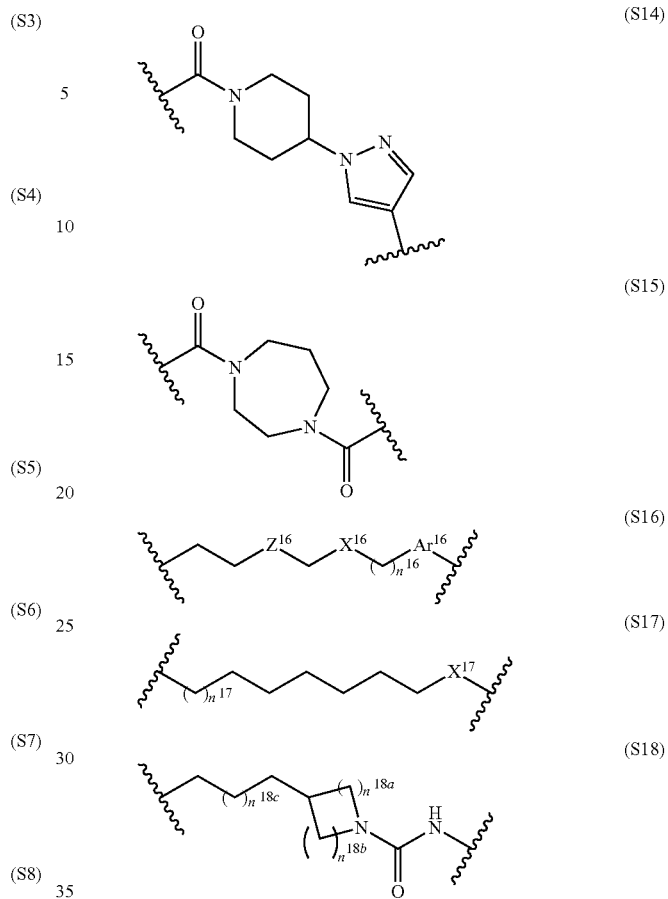

(wherein,
the wavy line represents the bonding site to $L^1$ or $L^2$,
$n^{1a}$ and $n^{2b}$ are the same or different and each represents 0 or 1,
$X^{1a}$ and $X^{1b}$ are the same or different and each represents —C(=O)—NH—, —NH—C(=O)—, —SO$_2$—NH—, —NH—SO$_2$—, —O—C(=S)—NH—, —O—C(=O)—NH—, —NH—C(=O)—O—, or —NH—C(=O)—NH— (except for the cases where (i) $X^{1a}$ is —NH—SO$_2$— and $X^{1b}$ is —SO$_2$—NH—, (ii) $n^{1a}$ and $n^{1b}$ are 0, $X^{1a}$ is —C(=O)—NH—, —SO$_2$—NH—, —O—C(=S)—NH—, —O—C(=O)—NH—, or —NH—C(=O)—NH—, and $X^{1b}$ is —NH—C(=O)—, —NH—SO$_2$—, —NH—C(=O)—O—, or —NH—C(=O)—NH—, and (iii) $X^{1a}$ is —O—C(=S)—NH—, —O—C(=O)—NH—, —NH—C(=O)—O—, or —NH—C(=O)—NH— and $X^{1b}$ is —O—C(=S)—NH—, —O—C(=O)—NH—, —NH—C(=O)—O—, or —NH—C(=O)—NH—), $R^{1a}$ represents a hydrogen atom and $R^{1b}$ represents a hydrogen atom or lower alkyl, or $R^{1a}$ and $R^{1b}$ together represent carbonyl, $X^{2a}$ represents —C(=O)—NH—, —NH—C(=O)—, —SO$_2$—NH—, or —NH—SO$_2$—, $X^{2b}$ represents —C(=O)—NH—, —NH—C(=O)—, —SO$_2$—NH—, —NH—SO$_2$—, or —CH$_2$— (except for the case where $X^2$a is —NH—SO$_2$— and $X^{2b}$ is —SO$_2$—NH—), $Z^2$ represents CH or N (except for the cases where (i) $Z^2$ is N and $X^{2b}$ is —NH—C(=O)—, —SO$_2$—NH—, or —NH—SO$_2$— and (ii) $Z^2$ is CH and $X^{2b}$ is —CH$_2$—), $n^{3a}$ and $n^{3b}$ are the same or different and each represents 1 or 2, $X^3$ represents —C(=O)—NH—, —NH—C(=O)—, —SO$_2$—NH—, —NH—SO$_2$—, —NH—C(=O)—NH—, or —NH—CH$_2$—, $Z^3$ represents CH or N (except for the cases where (i) $Z^3$ is N and $X^3$ is —NH—C(=O)—, —SO$_2$—NH—, —NH—SO$_2$—, —NH—C(=O)—NH—, or —NH—CH$_2$— and (ii) $Z^3$ is N and $n^{3a}$ or $n^{3b}$ is 1), $X^{5a}$ and $X^{5b}$ are the same or different and each represents —C(=O)—NH—, —NH—C(=O)—, —SO$_2$—NH—, or —NH—SO$_2$— (except for the case where $X^{5a}$ is —NH—SO$_2$— and $X^{5b}$ is —SO$_2$—NH—), $n^6$ represents 1 or 2, $Ar^6$ represents triazolediyl, oxadiazolediyl, pyrazolediyl, thiophenediyl, or tetrahydropyridinediyl, $X^6$ is —C(=O)—NH—, —NH—C(=O)—, —SO$_2$—NH—, —NH—SO$_2$—, —CH$_2$—NH—, or —NH—C(=O)—NH— (except for the cases where (i) $Ar^6$ is oxadiazolediyl, pyrazolediyl, thiophenediyl, or tetrahydropyridinediyl and $X^6$ is —NH—SO$_2$— and (ii) $n^6$ is 1, $Ar^6$ is pyrazolediyl or tetrahydropyridinediyl, and $X^6$ is —C(=O)—NH—, —SO$_2$—NH—, —CH$_2$—NH—, or —NH—C(=O)—NH—), $X^7$ represents —C(=O)—NH—, —NH—C(=O)—, —SO$_2$—NH—, or —NH—C(=O)—NH—, $n^7$ represents 1, 2, or 3, $Z^7$ represents S, SO, or SO$_2$, $X^{8a}$ represents —C(=O)—, —CH$_2$—, or —NH—C(=O)—, $X^{8b}$ represents a bond, —C(=O)—, —CH$_2$—, or —CH(OH)—, $Ar^9$ represents triazolediyl or oxazolediyl, $Z^9$ represents CH$_2$ or NH (except for the cases where (i) $Ar^9$ is triazolediyl and $Z^9$ is NH and (ii) $Ar^9$ is oxazolediyl and $Z^9$ is CH$_2$), $Z^{10}$ represents O or NH, $X^{11a}$ represents —C(=O)—NH—, —SO$_2$—NH—, or —NH—C(=O)—NH—, $X^{11b}$ represents —C(=O)—NH— or —C(=O)—, $X^{12}$ represents —C(=O)—NH—, —NH—C(=O)—, —SO$_2$—NH—, or —NH—C(=O)—NH—, $Z^{12a}$ represents CH$_2$ or NH (except for the case where $X^{12}$ is —C(=O)—NH—, —SO$_2$—NH—, or —NH—C(=O)—NH— and $Z^{12}a$ is NH), $Z^{12b}$ represents CH$_2$ or O (except for the case where $Z^{12a}$ is NH and $Z^{12b}$ is O), $Z^{12c}$ represents a bond, CH$_2$, or O (except for the cases where (i) $Z^{12b}$ is O and $Z^{12c}$ is O and (ii) $Z^{12a}$ is NH and $Z^{12c}$ is CH$_2$ or O), $n^{13}$ represents 0, 1, or 2, $n^{16}$ represents 1 or 2, $Z^{16}$ represents a bond, CH$_2$, or O, $X^{16}$ represents —CH$_2$—O—, —C(=O)—NH—, —NH—C(=O)—, or —NH—C(=O)—NH— (except for the case where $Z^{16}$ is O and $X^{16}$ is —NH—C(=O)— or —NH—C(=O)—NH—), $Ar^{16}$ represents triazolediyl, oxadiazolediyl, or pyrazolediyl (except for the cases where (i) $X^{16}$ is —CH$_2$—O— and $Ar^{16}$ is oxadiazolediyl or pyrazolediyl and (ii) $n^{16}$ is 1, $X^{16}$ is —C(=O)—NH— or —NH—C(=O)—NH—, and $Ar^{16}$ is pyrazolediyl), $n^{17}$ represents 1 or 2, $X^{17}$ represents —C(=O)—NH—, —NH—C(=O)—, —NH—SO$_2$—, or —NH—C(=O)—NH—, and $n^{18a}$, $n^{18b}$, and $n^{18c}$ are the same or different and each represents 1 or 2)).

Hereinafter, the compound represented by the general formula (I) is referred to as the compound (I). The same applies to compounds having other formula numbers.

In the present specification, examples of the lower alkyl include linear or branched alkyl having 1 to 10 carbon atoms, and more specifically include methyl, ethyl, propyl, isopropyl, butyl, isobutyl, sec-butyl, tert-butyl, pentyl, isopentyl, neopentyl, hexyl, heptyl, octyl, nonyl, decyl, and the like.

In the present specification, examples of the lower alkoxycarbonylmethyl include $C_{1-10}$ alkoxycarbonylmethyl, and more specifically include methoxycarbonylmethyl, ethoxycarbonylmethyl, propoxycarbonylmethyl, iso propoxycarbonylmethyl, butoxycarbonylmethyl, isobutoxycarbonylmethyl, sec-butoxycarbonylmethyl, tert-butoxycarbonylmethyl, pentoxycarbonylmethyl, isopentoxycarbonylmethyl, neopentoxycarbonylmethyl, hexyloxycarbonylmethyl, heptoxycarbonylmethyl, octoxycarbonylmethyl, nonyloxycarbonylmethyl, docyloxycarbonylmethyl, and the like, wherein preferable is tert-butoxycarbonylmethyl.

In the present specification, the halogen means each atom of fluorine, chlorine, bromine, and iodine.

In the present specification, examples of the lower alkanoyl include $C_{2-11}$ alkanoyl.

The lower alkyl in $R^{A1}$, $R^{A2}$, and $R^{A3}$ is preferably alkyl having 1 to 5 carbon atoms, more preferably alkyl having 1 to 3 carbon atoms, and further preferably methyl or ethyl.

The lower alkyl in $R^{A5}$ is preferably alkyl having 1 to 5 carbon atoms, more preferably alkyl having 1 to 3 carbon atoms, and further preferably propyl.

The lower alkenyl in $R^{A5}$ is preferably alkenyl having 2 to 6 carbon atoms, more preferably alkenyl having 2 to 4 carbon atoms, and further preferably propenyl.

The alkyl having 1 to 5 carbon atoms in $R^{A2-1}$ and $R^{A3-1}$ is preferably alkyl having 1 to 3 carbon atoms and more preferably methyl or ethyl.

The alkyl having 1 to 5 carbon atoms in $R^{A5-1}$ is preferably alkyl having 1 to 3 carbon atoms and further preferably propyl.

The alkenyl having 2 to 6 carbon atoms in $R^{A5-1}$ is preferably alkenyl having 2 to 4 carbon atoms and more preferably propenyl.

The cycloalkanediyl in ring RA and ring RA-1 is preferably cycloalkanediyl having 3 to 8 carbon atoms and more preferably cyclobutanediyl or cyclohexanediyl.

The lower alkoxycarbonylmethyl in $R^{B1}$ is preferably alkoxycarbonylmethyl having 1 to 10 carbon atoms and more preferably ethoxycarbonylmethyl, propoxycarbonylmethyl, or butoxycarbonylmethyl (preferably tert-butoxycarbonylmethyl).

The cycloalkyloxycarbonylmethyl in $R^{B1}$ and $R^{B1-1}$ is preferably cycloalkyloxycarbonylmethyl having 3 to 8 carbon atoms and more preferably cyclohexyloxycarbonylmethyl.

The alkoxycarbonylmethyl having 1 to 5 carbon atoms in $R^{B1-1}$ is preferably ethoxycarbonylmethyl, propoxycarbonylmethyl, or butoxycarbonylmethyl (preferably tert-butoxycarbonylmethyl).

The lower alkyl in $R^{B5}$ and $R^{B6}$ is preferably alkyl having 1 to 5 carbon atoms, more preferably alkyl having 1 to 5 carbon atoms, and further preferably ethyl.

The lower alkyl in $R^{B5-1}$ and $R^{B6-1}$ is, 1 to 5 carbon atoms is preferably alkyl having 1 to 5 carbon atoms and more preferably ethyl.

The nitrogen-containing aliphatic heterocyclic group in that $R^{B5}$ and $R^{B6}$ as well as $R^{B5-1}$ and $R^{B6-1}$ "representing an optionally substituted nitrogen-containing aliphatic heterocyclic group together with the adjacent nitrogen atom" is preferably a nitrogen-containing aliphatic heterocyclic group having 4 to 6 carbon atoms, more preferably azetidine, pyrrolidine, piperidine, piperazine, or morpholine, and further preferably piperazine.

The lower alkyl in $R^{B2}$ is preferably alkyl having 1 to 5 carbon atoms, more preferably alkyl having 1 to 3 carbon atoms, and further preferably methyl.

The alkyl having 1 to 5 carbon atoms in $R^{B2-1}$ is preferably alkyl having 1 to 3 carbon atoms and more preferably methyl.

The halogen in $R^{B3}$ and $R^{B4}$ is preferably a fluorine atom or a chlorine atom.

The lower alkyl in $R^{B3}$ and $R^{B4}$ is preferably alkyl having 1 to 5 carbon atoms, more preferably alkyl having 1 to 3 carbon atoms, and further preferably methyl.

The alkyl having 1 to 5 carbon atoms in $R^{B3-1}$ and $R^{B4-1}$ is preferably alkyl having 1 to 3 carbon atoms and more preferably methyl.

The lower alkyl in $R^{C1}$ is preferably alkyl having 1 to 5 carbon atoms, more preferably alkyl having 1 to 3 carbon atoms, and further preferably methyl or ethyl.

The lower alkanoyl in $R^{C1}$ is preferably alkanoyl having 2 to 11 carbon atoms, more preferably alkanoyl having 2 to 5 carbon atoms, and further preferably acetyl.

The lower alkyl in $R^{D1}$ is preferably alkyl having 1 to 5 carbon atoms, more preferably alkyl having 1 to 3 carbon atoms, and further preferably ethyl.

The alkyl having 1 to 5 carbon atoms in $R^{D1-1}$ is more preferably alkyl having 1 to 3 carbon atoms and more preferably ethyl.

The lower alkoxycarbonyl in $R^{D1}$ is preferably alkoxycarbonyl having 1 to 5 carbon atoms, more preferably alkoxycarbonyl having 1 to 3 carbon atoms, and further preferably ethoxycarbonyl or methoxycarbonyl.

The alkoxycarbonyl having 1 to 5 carbon atoms in $R^{D1-1}$ is preferably alkoxycarbonyl having 1 to 3 carbon atoms and more preferably ethoxycarbonyl or methoxycarbonyl.

The halogen in $R^{F7}$ is preferably a fluorine atom.

The lower alkyl in $R^{1b}$ is preferably alkyl having 1 to 5 carbon atoms, more preferably alkyl having 1 to 3 carbon atoms, and further preferably methyl or propyl (preferably isopropyl).

Examples of substituents in the "optionally substituted lower alkyl" and the "optionally substituted alkyl having 1 to 5 carbon atoms" of $R^{A5}$ and $R^{A5-1}$ include one or more substituents selected from the group consisting of a halogen, hydroxy, methoxy, ethoxy, nitro, cyano, carboxy, methoxycarbonyl, ethoxycarbonyl, amino, methylamino, ethylamino, dimethylamino, diethylamino, carbamoyl, methylcarbamoyl, ethylcarbamoyl, dimethylcarbamoyl, diethylcarbamoyl, cyclopropyl, cyclobutyl, cyclopentyl, cyclohexyl, phenyl, furyl, thiophenyl, pyrrolyl, pyrazolyl, imidazolyl, oxazolyl, thiazolyl, triazolyl, oxadiazolyl, tetrazolyl, pyridyl, pyridazinyl, pyrimidinyl, pyrazinyl, and the like, wherein preferable is amino.

Examples of substituents in the "optionally substituted lower alkenyl" and the "optionally substituted alkenyl having 2 to 6 carbon atoms" of $R^{A5}$ and $R^{A5-1}$ include one or more substituents selected from the group consisting of a halogen, hydroxy, methoxy, ethoxy, nitro, cyano, carboxy, methoxycarbonyl, ethoxycarbonyl, amino, methylamino, ethylamino, dimethylamino, diethylamino, carbamoyl, methylcarbamoyl, ethylcarbamoyl, dimethylcarbamoyl, diethylcarbamoyl, cyclopropyl, cyclobutyl, cyclopentyl, cyclohexyl, phenyl, furyl, thiophenyl, pyrrolyl, pyrazolyl, imidazolyl, oxazolyl, thiazolyl, triazolyl, oxadiazolyl, tetrazolyl, pyridyl, pyridazinyl, pyrimidinyl, pyrazinyl, and the like, wherein preferable is amino.

Examples of substituents in the "optionally substituted tetrahydropyridinyl" of $R^{A5}$ and $R^{A5-1}$ include a halogen, methyl, ethyl, hydroxy, methoxy, ethoxy, nitro, cyano, carboxy, methoxycarbonyl, ethoxycarbonyl, amino, methylamino, ethylamino, dimethylamino, diethylamino, carbamoyl, methylcarbamoyl, ethylcarbamoyl, dimethylcarbamoyl, diethylcarbamoyl, and the like, but preferably the tetrahydropyridinyl is unsubstituted.

Examples of substituents in the "optionally substituted dihydro-1H-pyrrolyl" of $R^{A5}$ include a halogen, methyl, ethyl, hydroxy, methoxy, ethoxy, nitro, cyano, carboxy, methoxycarbonyl, ethoxycarbonyl, amino, methylamino, ethylamino, dimethylamino, diethylamino, carbamoyl, methylcarbamoyl, ethylcarbamoyl, dimethylcarbamoyl, diethylcarbamoyl, and the like, but preferably the dihydro-1H-pyrrolyl is unsubstituted.

Examples of substituents in the "optionally substituted tetrahydro-1H-azepinyl" of $R^{A5}$ include a halogen, methyl, ethyl, hydroxy, methoxy, ethoxy, nitro, cyano, carboxy, methoxycarbonyl, ethoxycarbonyl, amino, methylamino, ethylamino, dimethylamino, diethylamino, carbamoyl, methylcarbamoyl, ethylcarbamoyl, dimethylcarbamoyl, diethylcarbamoyl, and the like, but preferably the tetrahydro-1H-azepinyl is unsubstituted.

Examples of substituents in the "optionally substituted lower alkoxycarbonylmethyl" and the "optionally substituted alkoxycarbonylmethyl having 1 to 5 carbon atoms" of $R^{B1}$ and $R^{B1-1}$ include one or more substituents selected from the group consisting of a halogen, hydroxy, methoxy, ethoxy, nitro, cyano, carboxy, methoxycarbonyl, ethoxycarbonyl, amino, methylamino, ethylamino, dimethylamino, diethylamino, carbamoyl, methylcarbamoyl, ethylcarbamoyl, dimethylcarbamoyl, diethylcarbamoyl, cyclopropyl, cyclobutyl, cyclopentyl, cyclohexyl, phenyl, furyl, thiophenyl, pyrrolyl, pyrazolyl, imidazolyl, oxazolyl, thiazolyl, triazolyl, oxadiazolyl, tetrazolyl, pyridyl, pyridazinyl, pyrimidinyl, and pyrazinyl, wherein preferable is hydroxy, methoxy, or dimethylamino but unsubstituted cases are also preferable.

Examples of substituents in the "optionally substituted cycloalkyloxycarbonylmethyl" of $R^{B1}$ and $R^{B1-1}$ include one or more substituents selected from the group consisting of a halogen, methyl, ethyl, hydroxy, methoxy, ethoxy, nitro, cyano, carboxy, methoxycarbonyl, ethoxycarbonyl, amino, methylamino, ethylamino, dimethylamino, diethylamino, carbamoyl, methylcarbamoyl, ethylcarbamoyl, dimethylcarbamoyl, diethylcarbamoyl, and the like, wherein preferable is hydroxy.

Examples of substituents in $R^{B5}$ and $R^{B6}$ as well as $R^{B5-1}$ and $R^{B6-1}$ "representing an optionally substituted nitrogen-containing aliphatic heterocyclic group together with the adjacent nitrogen atom" include one or more substituents selected from the group consisting of a halogen, methyl, ethyl, hydroxy, methoxy, ethoxy, nitro, cyano, carboxy, methoxycarbonyl, ethoxycarbonyl, amino, methylamino, ethylamino, dimethylamino, diethylamino, carbamoyl, methylcarbamoyl, ethylcarbamoyl, dimethylcarbamoyl, diethylcarbamoyl, hydroxymethyl, hydroxyethyl, hydroxypropyl, and the like, wherein preferable is hydroxyethyl.

Examples of substituents in the "optionally substituted lower alkyl" and the "optionally substituted alkyl having 1 to 5 carbon atoms" of $R^{B2}$ and $R^{B2-1}$ include a halogen, hydroxy, methoxy, ethoxy, nitro, cyano, carboxy, methoxycarbonyl, ethoxycarbonyl, amino, methylamino, ethylamino, dimethylamino, diethylamino, carbamoyl, methylcarbamoyl, ethylcarbamoyl, dimethylcarbamoyl, diethylcarbamoyl, cyclopropyl, cyclobutyl, cyclopentyl, cyclohexyl, phenyl, furyl, thiophenyl, pyrrolyl, pyrazolyl, imidazolyl, oxazolyl, thiazolyl, triazolyl, oxadiazolyl, tetrazolyl, pyridyl, pyridazinyl, pyrimidinyl, pyrazinyl, and the like, but preferably the lower alkyl and the alkyl having 1 to 5 carbon atoms are unsubstituted.

Examples of substituents in the "optionally substituted lower alkyl" and the "optionally substituted alkyl having 1 to 5 carbon atoms" of $R^{B3}$ and $R^{B4}$ as well as $R^{B3-1}$ and $R^{B4-1}$ include one or more substituents selected from the group consisting of a halogen, hydroxy, methoxy, ethoxy, nitro, cyano, carboxy, methoxycarbonyl, ethoxycarbonyl, amino, methylamino, ethylamino, dimethylamino, diethylamino, carbamoyl, methylcarbamoyl, ethylcarbamoyl, dimethylcarbamoyl, diethylcarbamoyl, cyclopropyl, cyclobutyl, cyclopentyl, cyclohexyl, phenyl, furyl, thiophenyl, pyrrolyl, pyrazolyl, imidazolyl, oxazolyl, thiazolyl, triazolyl, oxadiazolyl, tetrazolyl, pyridyl, pyridazinyl, pyrimidinyl, pyrazinyl, and the like, wherein preferable is a fluorine atom or cyano. Examples of the "optionally substituted lower alkyl" and "optionally substituted alkyl having 1 to 5 carbon atoms" of $R^{B3}$ and $R^{B4}$ as well as $R^{B3-1}$ and $R^{B4-1}$ are particularly preferably unsubstituted lower alkyl and unsubstituted alkyl having 1 to 5 carbon atoms, respectively.

Examples of substituents in the "optionally substituted lower alkyl" and "optionally substituted alkyl having 1 to 5 carbon atoms" of $R^{D1}$ and $R^{D1-1}$ include a halogen, hydroxy, methoxy, ethoxy, nitro, cyano, carboxy, methoxycarbonyl, ethoxycarbonyl, amino, methylamino, ethylamino, dimethylamino, diethylamino, carbamoyl, methylcarbamoyl, ethylcarbamoyl, dimethylcarbamoyl, diethylcarbamoyl, cyclopropyl, cyclobutyl, cyclopentyl, cyclohexyl, phenyl, furyl, thiophenyl, pyrrolyl, pyrazolyl, imidazolyl, oxazolyl, thiazolyl, triazolyl, oxadiazolyl, tetrazolyl, pyridyl, pyridazinyl, pyrimidinyl, pyrazinyl, and the like, but preferably the lower alkyl and the alkyl having 1 to 5 carbon atoms are unsubstituted.

Examples of substituents in the "optionally substituted lower alkoxycarbonyl" and "optionally substituted alkoxycarbonyl having 1 to 5 carbon atoms" of $R^{D1}$ and $R^{D1-1}$ include one or more substituents selected from the group consisting of a halogen, hydroxy, methoxy, ethoxy, nitro, cyano, carboxy, methoxycarbonyl, ethoxycarbonyl, amino, methylamino, ethylamino, dimethylamino, diethylamino, carbamoyl, methylcarbamoyl, ethylcarbamoyl, dimethylcarbamoyl, diethylcarbamoyl, cyclopropyl, cyclobutyl, cyclopentyl, cyclohexyl, phenyl, furyl, thiophenyl, pyrrolyl, pyrazolyl, imidazolyl, oxazolyl, thiazolyl, triazolyl, oxadiazolyl, tetrazolyl, pyridyl, pyridazinyl, pyrimidinyl, pyrazinyl, and the like, wherein preferable is hydroxy or dimethylamino but unsubstituted cases are also preferable.

In the formula (S1), $X^{1a}$ and $X^{1b}$ are the same or different and each represents —C(=O)—NH—, —NH—C(=O)—, —SO$_2$—NH—, —NH—SO$_2$—, —O—C(=S)—NH—, —O—C(=O)—NH—, —NH—C(=O)—O—, or —NH—C(=O)—NH—, preferably except for the cases where (i) $X^{1a}$ is —NH—SO$_2$— and $X^{1b}$ is —SO$_2$—NH—, (ii) $n^{1a}$ and $n^{1b}$ are 0, $X^{1a}$ is —C(=O)—NH—, —SO$_2$—NH—, —O—C(=S)—NH—, —O—C(=O)—NH—, or —NH—C(=O)—NH—, and $X^{1b}$ is —NH—C(=O)—, —NH—SO$_2$—, —NH—C(=O)—O—, or —NH—C(=O)—NH—, and (iii) $X^{1a}$ is —O—C(=S)—NH—, —O—C(=O)—NH—, —NH—C(=O)—O—, or —NH—C(=O)—NH— and $X^{1b}$ is —O—C(=S)—NH—, —O—C(=O)—NH—, —NH—C(=O)—O—, or —NH—C(=O)—NH—.

Here, the left bonding hand of $X^{1a}$ bonds to $L^1$ and the right bonding hand of $X^{1b}$ bonds to $L^2$. For example, Compound No. 1a in the following Table 1 is a compound formed by bonding of $L^1$ and the left bonding hand of $X^{1a}$ (—C(=O)—NH—) to become $L^1$-C(=O)—NH— and bonding of $L^2$ and the right bonding hand of $X^{1b}$ (—NH—C(=O)—) to become —NH—C(=O)-$L^2$. The same applies to the following.

In the formula (S2), $X^{2a}$ represents —C(=O)—NH—, —NH—C(=O)—, —SO$_2$—NH—, or —NH—SO$_2$— and $X^{2b}$ represents —C(=O)—NH—, —NH—C(=O)—, —SO$_2$—NH—, —NH—SO$_2$—, or —CH$_2$—, preferably except for the case where $X^{2a}$ is —NH—SO$_2$— and $X^{2b}$ is —SO$_2$—NH—. Similar to the above, the left bonding hand of $X^{2a}$ bonds to $L^1$ and the right bonding hand of $X^{2b}$ bonds to $L^2$.

In the formula (S3), $X^3$ represents —C(=O)—NH—, —NH—C(=O)—, —SO$_2$—NH—, —NH—SO$_2$—, —NH—C(=O)—NH—, or —NH—CH$_2$—. Similar to the above, the right bonding hand of $X^3$ bonds to $L^2$.

In the formula (S5), $X^{5a}$ and $X^{5b}$ are the same or different and each represents —C(=O)—NH—, —NH—C(=O)—, —SO$_2$—NH—, or —NH—SO$_2$—, preferably except for the case where $X^{5a}$ is —NH—SO$_2$— and $X^{5b}$ is —SO$_2$—NH—. Similar to the above, the left bonding hand of $X^{5a}$ bonds to $L^1$ and the right bonding hand of $X^{5b}$ bonds to $L^2$.

In the formula (S6), $X^6$ is —C(=O)—NH—, —NH—C(=O)—, —SO$_2$—NH—, —NH—SO$_2$—, —CH$_2$—NH, or —NH—C(=O)—NH—, preferably except for the cases where (i) Ar$^6$ is oxadiazolediyl, pyrazolediyl, thiophenediyl, or tetrahydropyridinediyl and $X^6$ is —NH—SO$_2$— and (ii) $n^6$ is 1, Ar$^6$ is pyrazolediyl or tetrahydropyridinediyl, and $X^6$ is —C(=O)—NH—, —SO$_2$—NH—, —CH$_2$—NH—, or —NH—C(=O)—NH—. Similar to the above, the left bonding hand of $X^6$ bonds to $L^1$.

In the formula (S7), $X^7$ represents —C(=O)—NH—, —NH—C(=O)—, —SO$_2$—NH—, or —NH—C(=O)—NH—. Similar to the above, the left bonding hand of $X^7$ bonds to $L^1$.

In the formula (S8), $X^{8a}$ represents —C(=O)—, —CH$_2$—, or —NH—C(=O)— and $X^{8b}$ is a bond, —C(=O)—, —CH$_2$—, or —CH(OH)—. Similar to the above, the left bonding hand of $X^{8a}$ bonds to $L^1$ and the right bonding hand of $X^{8b}$ bonds to $L^2$.

In the formula (S11), $X^{11a}$ represents —C(=O)—NH—, —SO$_2$—NH—, or —NH—C(=O)—NH— and $X^{11b}$ represents —C(=O)—NH— or —C(=O)—. Similar to the above, the left bonding hand of $X^{11a}$ bonds to $L^1$ and the right bonding hand of $X^{11b}$ bonds to $L^2$.

In the above formula (S12), $X^{12}$ represents —C(=O)—NH—, —NH—C(=O)—, —SO$_2$—NH—, or —NH—C(=O)—NH—. Similar to the above, the left bonding hand of $X^{11a}$ bonds to $L^1$.

In the formula (S16), $X^{16}$ represents —CH$_2$—O—, —C(=O)—NH—, —NH—C(=O)—, or —NH—C(=O)—NH—, preferably except for the case where $Z^{16}$ is O and $X^{16}$ is —NH—C(=O)— or —NH—C(=O)—NH—. Similar to the above, the left bonding hand of $X^{16}$ bonds to $L^1$ via $Z^{16}$ or the like.

In the formula (S17), $X^{17}$ represents —C(=O)—NH—, —NH—C(=O)—, —NH—SO$_2$—, or —NH—C(=O)—NH—. Similar to the above, the right bonding hand of $X^{17}$ bonds to $L^2$.

In general formula (I), $L^1$ and $L^2$ are the same or different and each represents a group represented by one formula selected from the group consisting of formulas (A) to (F), wherein preferably at least either one of $L^1$ and $L^2$ is a group represented by formula (A) or (B), and more preferably at least either one of $L^1$ and $L^2$ is a group represented by formula (A).

According to a preferred embodiment of the present invention, in general formula (I), when $L^1$ and $L^2$ are the same or different and each is a group represented by formula (A), (B), (C), or (D), S is preferably a group represented by one formula selected from the group consisting of formulas (S1) to (S15).

According to a preferred embodiment of the present invention, in general formula (I), when $L^1$ or $L^2$ is a group represented by formula (E), S is preferably a group represented by formula (S16), (S17), or (S18).

According to a preferred embodiment of the present invention, in general formula (I), when $L^1$ is a group represented by formula (F), S is preferably a group represented by any of the following:
 a group represented by formula (S1), wherein $X^{1a}$ is —C(=O)—NH—,
 a group represented by formula (S2), wherein $X^2a$ is —C(=O)—NH—,
 a group represented by formula (S3),
 a group represented by formula (S4),
 a group represented by formula (S5), wherein $X^{5a}$ is —C(=O)—NH—,
 a group represented by formula (S6), wherein $X^6$ is —C(=O)—NH—,
 a group represented by formula (S7), wherein $X^7$ is —C(=O)—NH—,
 a group represented by formula (S8), wherein $X^8a$ is —C(=O)—,
 a group represented by formula (S11), wherein $X^{11}a$ is —C(=O)—NH—,
 a group represented by formula (S12), wherein $X^{12}$ is —C(=O)—NH—,
 a group represented by formula (S14), or
 a group represented by formula (S15).

According to another preferred embodiment of the present invention, in general formula (I), when $L^2$ is a group represented by formula (F), S is a group represented by any of the following:
 a group represented by formula (S1), wherein $X^1b$ is —NH—C(=O)—,
 a group represented by formula (S2) wherein $X^{2b}$ is —NH—C(=O)—,
 a group represented by formula (S3), wherein $X^3$ is —NH—C(=O)—,
 a group represented by formula (S4),
 a group represented by formula (S5), wherein $X^{5b}$ is —NH—C(=O)—,
 a group represented by formula (S13), wherein $n^{13}$ is 0,
 a group represented by formula (S15), or
 a group represented by formula (S17), wherein $X^{17}$ is —NH—C(=O)—.

According to a preferred embodiment of the present invention, there is provided a compound or a pharmaceutically acceptable salt thereof, wherein in the formula (I), $L^1$ represents a group represented by formula (A), (B), (C), (D), or (F), $L^2$ represents a group represented by formula (A), (B), (C), or (D), and S is a group represented by formula (S1).

According to a preferred embodiment of the present invention, there is provided a compound or a pharmaceutically acceptable salt thereof, wherein in the formula (I), $L^1$ represents a group represented by formula (A) (preferably formula (A1), formula (A5), or formula (A15)), $L^2$ represents a group represented by formula (A) (preferably formula (A1)), and S is a group represented by formula (S1).

According to a preferred embodiment of the present invention, there is provided a compound or a pharmaceutically acceptable salt thereof, wherein in the formula (I), $L^1$ represents a group represented by formula (A), $L^2$ represents a group represented by formula (A), and S is a group represented by formula (S2).

According to a preferred embodiment of the present invention, there is provided a compound or a pharmaceutically acceptable salt thereof, wherein in the formula (I), $L^1$ represents a group represented by formula (A), (B), or (C), $L^2$ represents a group represented by formula (A) or (B), and S is a group represented by formula (S3).

According to a preferred embodiment of the present invention, there is provided a compound or a pharmaceutically acceptable salt thereof, wherein in the formula (I), $L^1$ represents a group represented by formula (A) (preferably formula (A1) or formula (A5)), $L^2$ represents a group represented by formula (A) (preferably formula (A1) or formula (A5)), and S is a group represented by formula (S3).

According to a preferred embodiment of the present invention, there is provided a compound or a pharmaceutically acceptable salt thereof, wherein in the formula (I), $L^1$ represents a group represented by formula (A), $L^2$ represents a group represented by formula (A), and S is a group represented by formula (S4) or (S5).

According to a preferred embodiment of the present invention, there is provided a compound or a pharmaceutically acceptable salt thereof, wherein in the formula (I), $L^1$ represents a group represented by formula (A), (B), (C), or (D), $L^2$ represents formula (A), (B), or (D), and S is a group represented by formula (S6).

According to a preferred embodiment of the present invention, there is provided a compound or a pharmaceutically acceptable salt thereof, wherein in the formula (I), $L^1$ represents a group represented by formula (A) (preferably formula (A1) or formula (A5)), $L^2$ represents a group represented by formula (A) (preferably a group represented by formula (A1) or formula (A5)), and S is a group represented by formula (S6).

According to a preferred embodiment of the present invention, there is provided a compound or a pharmaceutically acceptable salt thereof, wherein in the formula (I), $L^1$ represents a group represented by formula (A) or (B), $L^2$ represents a group represented by formula (A), and S is a group represented by formula (S7).

According to a preferred embodiment of the present invention, there is provided a compound or a pharmaceutically acceptable salt thereof, wherein in the formula (I), $L^1$ represents a group represented by formula (A) or (B), $L^2$ represents a group represented by formula (A), and S is a group represented by formula (S8).

According to a preferred embodiment of the present invention, there is provided a compound or a pharmaceutically acceptable salt thereof, wherein in the formula (I), $L^1$ represents a group represented by formula (A), $L^2$ represents a group represented by formula (A), and S is a group represented by formula (S9).

According to a preferred embodiment of the present invention, there is provided a compound or a pharmaceutically acceptable salt thereof, wherein in the formula (I), $L^1$ represents a group represented by formula (A) or (B), $L^2$ represents a group represented by formula (A), and S is a group represented by formula (S10).

According to a preferred embodiment of the present invention, there is provided a compound or a pharmaceutically acceptable salt thereof, wherein in the formula (I), $L^1$ represents a group represented by the formula (A) or (B), $L^2$ represents a group represented by formula (A) or (B), and S is a group represented by formula (S11). According to a more preferred embodiment of the present invention, there is provided a compound or a pharmaceutically acceptable salt thereof, wherein in the formula (I), $L^1$ represents a group represented by formula (A) or (B), $L^2$ represents a group represented by formula (A), and S is a group represented by formula (S11), wherein the group represented by said formula (S11) is a group where $X^{11b}$ is —C(=O)—, and the group represented by said formula (A) in $L^2$ is a group where ring RA is piperidinediyl, azetidinediyl, pyrrolidinediyl, or homopiperidinediyl.

According to a preferred embodiment of the present invention, there is provided a compound or a pharmaceutically acceptable salt thereof, wherein in the formula (I), $L^1$ represents a group represented by formula (A), $L^2$ represents a group represented by formula (A), and S is a group represented by formula (S12), (S13), (S14), or (S15).

According to a preferred embodiment of the present invention, there is provided a compound or a pharmaceutically acceptable salt thereof, wherein in the formula (I), $L^1$ represents a group represented by formula (E), $L^2$ represents a group represented by formula (A), and S is a group represented by formula (S16), (S17), or (S18).

According to a preferred embodiment of the present invention, there is provided a compound or a pharmaceutically acceptable salt thereof, wherein in the formula (I), formula (A) is the following formula (A)-1:

[Chemical formula 35]

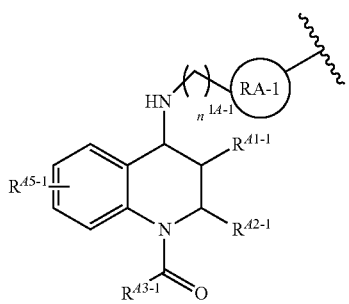

(A)-1

(wherein,
the wavy line represents the bonding site to S,
$R^{A1-1}$ represents a hydrogen atom,
$R^{A2-1}$ and $R^{A3-1}$ are the same or different and each represents alkyl having 1 to 5 carbon atoms (preferably, $R^{A2-1}$ represents methyl and $R^{A3-1}$ represents ethyl),
$R^{A5-1}$ represents a hydrogen atom, a fluorine atom, optionally substituted alkyl having 1 to 5 carbon atoms (preferably alkyl having 1 to 3 carbon atoms which may be substituted with amino and more preferably propyl substituted with amino), optionally substituted alkenyl having 2 to 6 carbon atoms (preferably propenyl optionally substituted with amino and more preferably, propenyl substituted with amino), or optionally substituted tetrahydropyridinyl (preferably tetrahydropyridinyl), ring RA-1 represents benzenediyl, cycloalkanediyl (preferably cyclobutanediyl or cyclohexanediyl), pyridinediyl, or piperidinediyl, and
$n^{1,A-1}$ represents 0 or 1 (preferably 0)).

According to a more preferred embodiment of the present invention, there is provided a compound or a pharmaceutically acceptable salt thereof, wherein in the formula (I), formula (A) is the formula (A)-1, wherein in the formula (A)-1,
the wavy line represents the bonding site to S,
$R^{A1-1}$ represents a hydrogen atom,
$R^{A2-1}$ and $R^{A3-1}$ are the same or different and each represents alkyl having 1 to 5 carbon atoms (preferably, $R^{A2-1}$ represents methyl and $R^{A3-1}$ represents ethyl),
$R^{A5-1}$ represents a hydrogen atom,
ring RA-1 represents benzenediyl, cyclohexanediyl, or pyridinediyl, and
$n^{1,A-1}$ represents 0 or 1 (preferably 0).

According to a preferred embodiment of the present invention, there is provided a compound or a pharmaceutically acceptable salt thereof, wherein in the formula (I), formula (B) is the following formula (B)-1:

[Chemical formula 36]

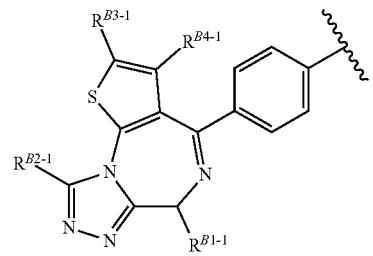

(B)-1

(wherein,
the wavy line represents the bonding site to S,
$R^{B1-1}$ represents a hydrogen atom, optionally substituted alkoxycarbonylmethyl having 1 to 5 carbon atoms (preferably optionally substituted ethoxycarbonylmethyl (more preferably hydroxy-substituted ethoxycarbonyl, methoxy-substituted ethoxycarbonyl, or dimethylamino-substituted ethoxycarbonyl), optionally substituted propoxycarbonylmethyl (more preferably methoxy-substituted propoxycarbonylmethyl), or butoxycarbonylmethyl (more preferably tert-butoxycarbonylmethyl)), optionally substituted cycloalkyloxycarbonylmethyl (preferably optionally substituted cyclohexyloxycarbonylmethyl (more preferably hydroxy-substituted cyclohexylmethyl), or —CH$_2$CONR$^{B5-1}$R$^{B6-1}$ (wherein, R$^{B5-1}$ and R$^{B6-1}$ are the same or different and each represents a hydrogen atom or alkyl having 1 to 5 carbon atoms (preferably, R$^{B5-1}$ represents a hydrogen atom and R$^{B5-1}$ represents ethyl), or represents an optionally substituted nitrogen-containing aliphatic heterocyclic group (preferably piperazine) together with an adjacent nitrogen atom),
$R^{B2-1}$ represents optionally substituted alkyl having 1 to 5 carbon atoms (preferably methyl), and
$R^{B3-1}$ and $R^{B4-1}$ represent optionally substituted alkyl (preferably methyl) having 1 to 5 carbon atoms).

According to a more preferred embodiment of the present invention, there is provided a compound or a pharmaceutically acceptable salt thereof, wherein in the formula (I), formula (B) is the formula (B)-1, wherein in the formula (B)-1, the wavy line represents the bonding site to S, $R^{B1-1}$ represents tert-butoxycarbonylmethyl, $R^{B2-1}$ represents optionally substituted alkyl having 1 to 5 carbon atoms (preferably methyl), and $R^{B3-1}$ and $R^{B4-1}$ represent optionally substituted alkyl having 1 to 5 carbon atoms (preferably methyl).

According to a preferred embodiment of the present invention, there is provided a compound or a pharmaceutically acceptable salt thereof, wherein in the formula (I), formula (C) is the following formula (C)-1:

[Chemical formula 37]

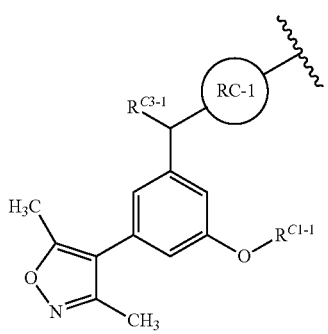

(C)-1

(wherein, the wavy line represents the bonding site to S, $R^{C1-1}$ represents a hydrogen atom, $R^{C3-1}$ represents a hydrogen atom or hydroxy, and ring RC-1 represents benzenediyl or piperidinediyl (preferably, ring RC-1 is piperidinediyl when $R^{C3-1}$ is a hydrogen atom, and ring RC-1 is benzenediyl when $R^{C3-1}$ is hydroxy)).

According to a preferred embodiment of the present invention, there is provided a compound or a pharmaceutically acceptable salt thereof, wherein in the formula (I), formula (D) is the following formula (D)-1:

[Chemical formula 38]

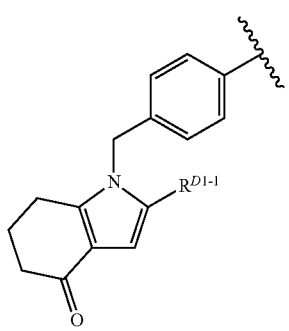

(D)-1

(wherein, the wavy line represents the bonding site to S, $R^{D1-1}$ represents optionally substituted alkyl having 1 to 5 carbon atoms (preferably ethyl) or optionally substituted alkoxycarbonyl having 1 to 5 carbon atoms (preferably hydroxyl-substituted ethoxycarbonyl, diethylamino-substituted ethoxycarbonyl, or unsubstituted methoxycarbonyl)).

According to a preferred embodiment of the present invention, there is provided a compound or a pharmaceutically acceptable salt thereof, wherein in the formula (I), formula (E) is the following formula (E)-1:

[Chemical formula 39]

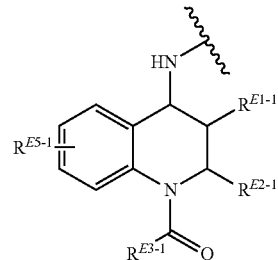

(E)-1

(wherein, the wavy line represents the bonding site to S, $R^{E1-1}$ represents a hydrogen atom, $R^{E2-1}$ and $R^{E3-1}$ are the same or different and each represents alkyl having 1 to 5 carbon atoms (preferably, $R^{E2-1}$ represents methyl and $R^{E3-1}$ represents ethyl), and $R^{E5-1}$ represents a hydrogen atom).

According to a preferred embodiment of the present invention, there is provided a compound or a pharmaceutically acceptable salt thereof, wherein in the formula (I), formula (F) is the following formula (F)-1:

[Chemical formula 40]

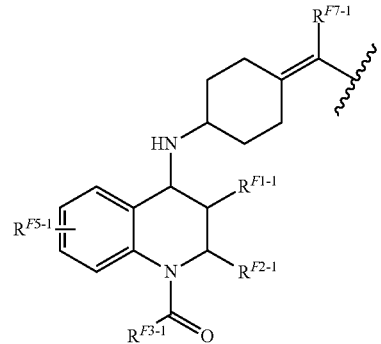

(F)-1

(wherein, the wavy line represents the bonding site to S, $R^{F1-1}$ represents a hydrogen atom, $R^{F2-1}$ and $R^{F3-1}$ are the same or different and each represents alkyl having 1 to 5 carbon atoms (preferably, $R^{F2-1}$ represents methyl and $R^{F3-1}$ represents ethyl), $R^{F5-1}$ represents a hydrogen atom, and $R^{F7-1}$ represents a hydrogen atom or a fluorine atom).

According to a preferred embodiment of the present invention, there is provided a compound or a pharmaceutically acceptable salt thereof, wherein in the formula (I), formula (S) is the following formula (S1)-1:

[Chemical formula 41]

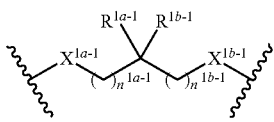

(S1)-1

(wherein, the wavy line represents the bonding site to $L^1$ or $L^2$, $n^{1a-1}$ and $n^{1b-1}$ are the same or different and each represents 0 or 1, $X^{1-a1}$ and $X^{1b-1}$ are the same or different and each represents —C(=O)—NH—, —NH—C(=O)—, —SO$_2$—NH—, —NH—SO$_2$—, —O—C(=S)—NH—, —O—C(=O)—NH—, —NH—C(=O)—O—, or —NH—C(=O)—NH— (except for the cases where (i) $X^{1a-1}$ is —NH—SO$_2$— and $X^{1b-1}$ is —SO$_2$—NH—, (ii) $n^{1a-1}$ and $n^{1b-1}$ are 0, $X^{1a-1}$ is —C(=O)—NH—, —SO$_2$—NH—, —O—C(=S)—NH—, —O—C(=O)—NH—, or —NH—C(=O)—NH—, and $X^{1b-1}$ is —NH—C(=O)—, —NH—SO$_2$—, —NH—C(=O)—O—, or —NH—C(=O)—NH—, and (iii) $X^{1a-1}$ is —O—C(=S)—NH—, —O—C(=O)—NH—, —NH—C(=O)—O—, or —NH—C(=O)—NH— and $X^{1b-1}$ is —O—C(=S)—NH—, —O—C(=O)—NH—, —NH—C(=O)—O—, or —NH—C(=O)—NH—), wherein preferably $X^{1a-1}$ and $X^{1b-1}$ are the same or different and each represents —C(=O)—NH—, —NH—C(=O)—, or —NH—C(=O)—NH— (except for the cases where (i) $X^{1a}$ is —NH—C(=O)—NH— and $X^{1b}$ is —NH—C(=O)—NH— and (ii) $n^{1a}$ and $n^{1b}$ are 0, $X^{1a}$ is —C(=O)—NH— or —NH—C(=O)—NH—, and $X^{1b}$ is —NH—C(=O)—), and more preferably $X^{1a}$ represents —NH—C(=O)— or —NH—C(=O)—NH— and $X^{1b}$ represents —C(=O)—NH—, and $R^{1a-1}$ represents a hydrogen atom, $R^{1b-1}$ represents a hydrogen atom or alkyl having 1 to 5 carbon atoms (preferably methyl or isopropyl), or $R^{1a-1}$ and $R^{1b-1}$ together represent carbonyl).

According to a more preferred embodiment of the present invention, there is provided a compound or a pharmaceutically acceptable salt thereof, wherein in the formula (I), S is the formula (S1)-1, wherein in the formula (S1)-1, the wavy line represents the bonding site to $L^1$ or $L^2$, $n^{1a-1}$ and $n^{1b-1}$ are the same or different and each represents 0 or 1, $X^{1a-1}$ and $X^{1b-1}$ are the same or different and each represents —C(=O)—NH—, —NH—C(=O)—, —SO$_2$—NH—, —NH—SO$_2$—, —O—C(=S)—NH—, —O—C(=O)—NH—, —NH—C(=O)—O—, or —NH—C(=O)—NH— (except for the cases where (i) $X^{1a-1}$ is —NH—SO$_2$— and $X^{1b-1}$ is —SO$_2$—NH—, (ii) $n^{1a-1}$ and $n^{1b-1}$ are 0, $X^{1a-1}$ is —C(=O)—NH—, —SO$_2$—NH—, —O—C(=S)—NH—, —O—C(=O)—NH—, or —NH—C(=O)—NH—, and $X^{1b-1}$ is —NH—C(=O)—, —NH—SO$_2$—, —NH—C(=O)—O—, or —NH—C(=O)—NH—, and (iii) $X^{1a-1}$ is —O—C(=S)—NH—, —O—C(=O)—NH—, —NH—C(=O)—O—, or —NH—C(=O)—NH— and $X^{1b-1}$ is —O—C(=S)—NH—, —O—C(=O)—NH—, —NH—C(=O)—O—, or —NH—C(=O)—NH—), wherein preferably $X^{1a-1}$ and $X^{1b-1}$ are the same or different and each represents —C(=O)—NH—, —NH—C(=O)—, or —NH—C(=O)—NH— (except for the cases where (i) $X^{1a}$ is —NH—C(=O)—NH— and $X^{1b}$ is —NH—C(=O)—NH— and (ii) $n^{1a}$ and $n^{1b}$ are 0, $X^{1a}$ is —C(=O)—NH— or —NH—C(=O)—NH—, and $X^{1b}$ is —NH—C(=O)—), and more preferably $X^{1a}$ represents —NH—C(=O)— or —NH—C(=O)—NH— and $X^{1b}$ represents —C(=O)—NH—, and $R^{1a-1}$ represents a hydrogen atom and $R^{1b-1}$ represents a hydrogen atom.

According to a preferred embodiment of the present invention, there is provided a compound or a pharmaceutically acceptable salt thereof, wherein in the formula (I), S is the following formula (S2)-1:

[Chemical formula 42]

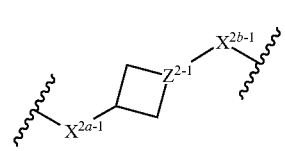

(S2)-1

(wherein, the wavy line represents the bonding site to $L^1$ or $L^2$, $X^{2a-1}$ represents —C(=O)—NH— or —NH—C(=O)—, $X^{2b-1}$ represents —C(=O)—NH—, —NH—C(=O)—, or —CH$_2$—, and $Z^{2-1}$ represents CH or N (except for the cases where (i) $Z^{2-1}$ is N and $X^{2b-1}$ is —NH—C(=O)— and (ii) $Z^{2-1}$ is CH and $X^{2b-1}$ is —CH$_2$—)).

According to a preferred embodiment of the present invention, there is provided a compound or a pharmaceutically acceptable salt thereof, wherein in the formula (I), S is the following formula (S3)-1:

[Chemical formula 43]

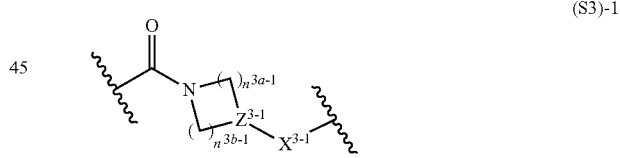

(S3)-1

(wherein, the wavy line represents the bonding site to $L^1$ or $L^2$, $n^{3a-1}$ and $n^{3b-1}$ are the same or different and each represents 1 or 2, $X^{3-1}$ represents —C(=O)—NH—, —NH—C(=O)—, —NH—C(=O)—NH—, or —NH—CH$_2$— (preferably —C(=O)—NH—), and $Z^{3-1}$ represents CH or N (except for the cases where (i) $Z^{3-1}$ is N and $X^{3-1}$ is —NH—C(=O)—, —NH—C(=O)—NH—, or —NH—CH$_2$— and (ii) $Z^{3-1}$ is N and $n^{3a-1}$ or $n^{3b-1}$ is 1)).

According to a preferred embodiment of the present invention, there is provided a compound or a pharmaceutically acceptable salt thereof, wherein in the formula (I), S is the following formula (S5)-1:

[Chemical formula 44]

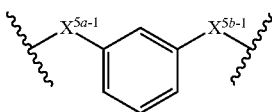

(S5)-1

(wherein,
the wavy line represents the bonding site to $L^1$ or $L^2$, and
$X^{5a-1}$ and $X^{5b-1}$ are the same or different and each represents —C(=O)—NH—, —NH—C(=O)—, or —NH—SO$_2$— (preferably, $X^{5a}$ is —C(=O)—NH— or —NH—SO$_2$— and $X^{5b}$ represents —C(=O)—NH— or —NH—C(=O)—)).

According to a preferred embodiment of the present invention, there is provided a compound or a pharmaceutically acceptable salt thereof, wherein in the formula (I), S is the following formula (S6)-1:

[Chemical formula 45]

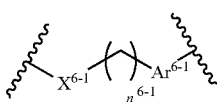

(S6)-1

(wherein,
the wavy line represents the bonding site to $L^1$ or $L^2$,
$n^{6-1}$ represents 1 or 2,
$Ar^{6-1}$ represents triazolediyl, oxadiazolediyl, pyrazolediyl, thiophenediyl, or tetrahydropyridinediyl, and
$X^{6-1}$ represents —C(=O)—NH—, —NH—C(=O)—, or —CH$_2$—NH— (except for the case where (i) $n^{6-1}$ is 1, $Ar^{6-1}$ is pyrazolediyl or tetrahydropyridinediyl, and $X^{6-1}$ is —C(=O)—NH— or —CH$_2$—NH—)).

According to a preferred embodiment of the present invention, there is provided a compound or a pharmaceutically acceptable salt thereof, wherein in the formula (I), S is the following formula (S7)-1:

[Chemical formula 46]

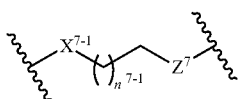

(S7)-1

(wherein,
the wavy line represents the bonding site to $L^1$ or $L^2$,
$X^{7-1}$ represents —C(=O)—NH— or —NH—C(=O)—,
$n^{7-1}$ represents 1, and
$Z^{7-1}$ represents S, SO, or SO$_2$).

According to a preferred embodiment of the present invention, there is provided a compound or a pharmaceutically acceptable salt thereof, wherein in the formula (I), S is the following formula (S8)-1:

[Chemical formula 47]

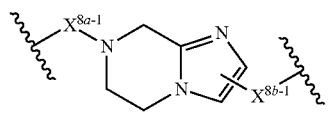

(S8)-1

(wherein,
the wavy line represents the bonding site to $L^1$ or $L^2$,
$X^{8a-1}$ represents —C(=O)— or —CH$_2$—, and
$X^{8b-1}$ represents a bond, —C(=O)—, —CH$_2$—, or —CH(OH)—).

According to a preferred embodiment of the present invention, there is provided a compound or a pharmaceutically acceptable salt thereof, wherein in the formula (I), S is the following formula (S9)-1:

[Chemical formula 48]

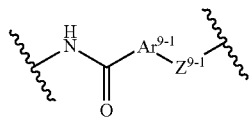

(S9)-1

(wherein,
the wavy line represents the bonding site to $L^1$ or $L^2$,
$Ar^{9-1}$ represents triazolediyl or oxazolediyl, and
$Z^{9-1}$ represents CH$_2$ or NH (except for the cases where (i) $Ar^{9-1}$ is triazolediyl and $Z^{9-1}$ is NH and (ii) $Ar^{9-1}$ is oxazolediyl and $Z^{9-1}$ is CH$_2$)).

According to a preferred embodiment of the present invention, there is provided a compound or a pharmaceutically acceptable salt thereof, wherein in the formula (I), S is the following formula (S10)-1:

[Chemical formula 49]

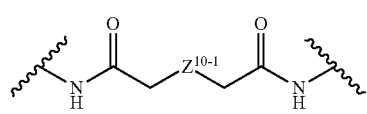

(S10)-1

(wherein,
the wavy line represents the bonding site to $L^1$ or $L^2$, and
$Z^{10-1}$ represents O or NH).

According to a preferred embodiment of the present invention, there is provided a compound or a pharmaceutically acceptable salt thereof, wherein in the formula (I), S is the following formula (S11)-1:

[Chemical formula 50]

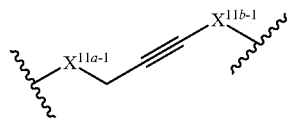

(S11)-1

(wherein,
the wavy line represents the bonding site to $L^1$ or $L^2$,
$X^{11a-1}$ represents —C(=O)—NH—, and
$X^{11b-1}$ represents —C(=O)—NH— or —C(=O)—).

According to a preferred embodiment of the present invention, there is provided a compound or a pharmaceutically acceptable salt thereof, wherein in the formula (I), S is the following formula (S12)-1:

[Chemical formula 51]

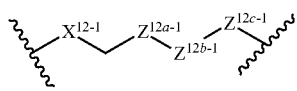

(S12)-1

(wherein,
the wavy line represents the bonding site to $L^1$ or $L^2$,
$X^{12-1}$ represents —C(=O)—NH— or —NH—C(=O)—,
$Z^{12a-1}$ represents $CH_2$ or NH (except for the case where $X^{12-1}$ is —C(=O)—NH— and $Z^{12a-1}$ is NH),
$Z^{12b-1}$ represents $CH_2$ or O (except for the case where $Z^{12a-1}$ is NH and $Z^{12b-1}$ is O), and
$Z^{12c-1}$ represents a bond or O (except for the cases where (i) $Z^{12b-1}$ is O and $Z^{12c-1}$ is O and (ii) $Z^{12a-1}$ is NH and $Z^{12c-1}$ is O)).

According to a preferred embodiment of the present invention, there is provided a compound or a pharmaceutically acceptable salt thereof, wherein in the formula (I), S is the following formula (S13)-1:

[Chemical formula 52]

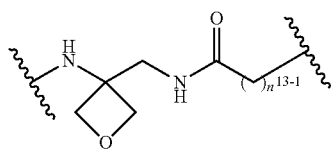

(S13)-1

(wherein,
the wavy line represents the bonding site to $L^1$ or $L^2$, and
$n^{13-1}$ represents 0 or 2).

According to a preferred embodiment of the present invention, there is provided a compound or a pharmaceutically acceptable salt thereof, wherein in the formula (I), S is the following formula (S16)-1:

[Chemical formula 53]

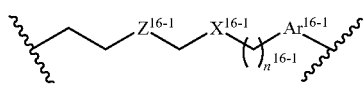

(S16)-1

(wherein,
the wavy line represents the bonding site to $L^1$ or $L^2$,
$n^{16-1}$ represents 1 or 2,
$Z^{16-1}$ represents a bond, $CH_2$, or O,
$X^{16-1}$ represents —$CH_2$—O— or —C(=O)—NH—, and
$Ar^{16-1}$ represents triazolediyl, oxadiazolediyl, or pyrazolediyl (except for the cases where (i) $X^{16-1}$ is —$CH_2$—O— and $Ar^{16-1}$ is oxadiazolediyl or pyrazolediyl and (ii) $n^{16-1}$ is 1, $X^{16-1}$ is —C(=O)—NH—, and $Ar^{16-1}$ is pyrazolediyl)).

According to a preferred embodiment of the present invention, there is provided a compound or a pharmaceutically acceptable salt thereof, wherein in the formula (I), S is the following formula (S17)-1:

[Chemical formula 54]

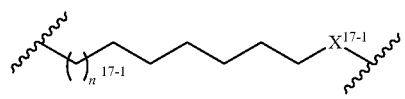

(S17)-1

(wherein,
the wavy line represents the bonding site to $L^1$ or $L^2$,
$n^{17-1}$ represents 1 or 2, and
$X^{17-1}$ represents —C(=O)—NH—).

According to a preferred embodiment of the present invention, there is provided a compound or a pharmaceutically acceptable salt thereof, wherein in the formula (I), S is the following formula (S18)-1:

[Chemical formula 55]

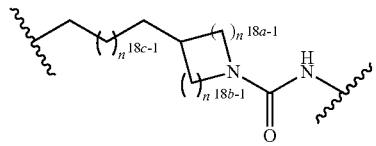

(S18)-1

(wherein,
the wavy line represents the bonding site to $L^1$ or $L^2$, and
$n^{18a-1}$ represents 2, $n^{18b-1}$ represents 2, and $n^{18c-1}$ represents 1).

According to a more preferred embodiment of the present invention, there is provided a compound or a pharmaceutically acceptable salt thereof, wherein in the formula (I), $L^1$ and $L^2$ represent a group represented by formula (A) (preferably formula (A1)) and S is a group represented by formula (S1), wherein
in the formula (A),
$R^{A1}$ represents a hydrogen atom, $R^{A2}$ and $R^{A3}$ are the same or different and each represents alkyl having 1 to 5 carbon atoms (preferably, $R^{A2}$ represents methyl and $R^{A3}$ represents ethyl), $R^{A5}$ represents a hydrogen atom, ring RA represents benzenediyl, and $n^{A4}$ represents 0, and
in the formula (S1),
$n^{1a}$ and $n^{1b}$ represent 1, $X^{1a}$ and $X^{1b}$ are the same or different and each represents —C(=O)—NH— or —NH—C(=O)—, $R^{1a}$ represents a hydrogen atom, and $R^{1b}$ represents a hydrogen atom.

According to a more preferred embodiment of the present invention, there is provided a compound or a pharmaceutically acceptable salt thereof, wherein in the formula (I), $L^1$ and $L^2$ represent a group represented by formula (A) (preferably formula (A1) or (A5)) and S is a group represented by formula (S1), wherein
in the formula (A),
$R^{A1}$ represents a hydrogen atom, $R^{A2}$ and $R^{A3}$ are the same or different and each represents alkyl having 1 to 5 carbon atoms (preferably, $R^{A2}$ represents methyl and $R^{A3}$ represents ethyl), $R^{45}$ represents a hydrogen atom, ring RA represents benzenediyl or cycloalkanediyl, and $n^{1A}$ represents O, and in the formula (S1), $n^{1a}$ and $n^{1b}$ represent 0, $X^{1a}$ and $X^{1b}$ are the same or different and each represents —C(=O)—NH—, —NH—C(=O)—, or —NH—C(=O)—NH— (preferably —NH—C(=O)— or —NH—C(=O)—NH—) (except for the case where $X^{1a}$ is —C(=O)—NH— or —NH—C(=O)—NH— and $X^{1b}$ is —NH—C(=O)— or —NH—C(=O)—NH—), and $R^{1a}$ represents a hydrogen atom and $R^{1b}$ represents a hydrogen atom.

According to a more preferred embodiment of the present invention, there is provided a compound or a pharmaceutically acceptable salt thereof, wherein in the formula (I), $L^1$ and $L^2$ represent a group represented by formula (A) (preferably formula (A1) or (A15)) and S is a group represented by the formula (S1), wherein in the formula (A), $R^{41}$ represents a hydrogen atom, $R^{42}$ and $R^{43}$ are the same or different and each represents alkyl having 1 to 5 carbon atoms (preferably, $R^{42}$ represents methyl and $R^{43}$ represents ethyl), $R^{45}$ represents a hydrogen atom, ring RA represents benzenediyl or pyridinediyl, and $n^{1A}$ represents 0, and in the formula (S1), $n^{1a}$ and $n^{1b}$ represent 1, $X^{1a}$ and $X^{1b}$ are the same or different and each represents —C(=O)—NH— or —NH—C(=O)—, and $R^{1a}$ represents a hydrogen atom and $R^{1b}$ represents a hydrogen atom.

According to a more preferred embodiment of the present invention, there is provided a compound or a pharmaceutically acceptable salt thereof, wherein in the formula (I), $L^1$ and $L^2$ represent a group represented by formula (A) (preferably formula (A1) or (A5)) and S is a group represented by formula (S3), wherein in the formula (A), $R^{41}$ represents a hydrogen atom, $R^{42}$ and $R^{43}$ are the same or different and each represents alkyl having 1 to 5 carbon atoms (preferably, $R^{42}$ represents methyl and $R^{43}$ represents ethyl), $R^{45}$ represents a hydrogen atom, ring RA represents benzenediyl or cycloalkanediyl, and $n^{1A}$ represents 0, and in the formula (S3), $n^{3a}$ and nab represent 2, $X^3$ represents —C(=O)—NH—, and $Z^3$ represents N.

According to a more preferred embodiment of the present invention, there is provided a compound or a pharmaceutically acceptable salt thereof, wherein in the formula (I), $L^1$ and $L^2$ represent a group represented by formula (A) (preferably formula (A1) or (A5)) and S is a group represented by formula (S3), wherein in the formula (A), $R^{41}$ represents a hydrogen atom, $R^{42}$ and $R^{43}$ are the same or different and each represents alkyl having 1 to 5 carbon atoms (preferably, $R^{42}$ represents methyl and $R^{43}$ represents ethyl), $R^{45}$ represents a hydrogen atom, ring RA represents benzenediyl or cycloalkanediyl, and $n^{1A}$ represents 0, and in the formula (S3), $n^{3a}$ and $n^{3b}$ represent 1, $X^3$ represents —C(=O)—NH—, and $Z^3$ represents CH.

According to a more preferred embodiment of the present invention, there is provided a compound or a pharmaceutically acceptable salt thereof, wherein in the formula (I), $L^1$ and $L^2$ represent a group represented by formula (A) (preferably formula (A1)) and S is a group represented by formula (S6), wherein in the formula (A), $R^{41}$ represents a hydrogen atom, $R^{42}$ and $R^{43}$ are the same or different and each represents alkyl having 1 to 5 carbon atoms (preferably, $R^{42}$ represents methyl and $R^{43}$ represents ethyl), $R^{45}$ represents a hydrogen atom, ring RA represents benzenediyl, and $n^{1A}$ represents 0, and in the formula (S6), $n^6$ represents 1, $Ar^6$ represents oxadiazolediyl, and $X^6$ represents —CH$_2$—NH—.

According to a more preferred embodiment of the present invention, there is provided a compound or a pharmaceutically acceptable salt thereof, wherein in the formula (I), $L^1$ and $L^2$ represent a group represented by formula (A) (preferably formula (A1)) and S is a group represented by formula (S6), wherein in the formula (A), $R^{41}$ represents a hydrogen atom, $R^{42}$ and $R^{43}$ are the same or different and each represents alkyl having 1 to 5 carbon atoms (preferably, $R^{42}$ represents methyl and $R^{43}$ represents ethyl), $R^{45}$ represents a hydrogen atom, ring RA represents benzenediyl, and $n^{1A}$ represents 0, and in the formula (S6), $n^6$ represents 1, $Ar^6$ represents triazolediyl, and $X^6$ represents —CH$_2$—NH—.

According to a more preferred embodiment of the present invention, there is provided a compound or a pharmaceutically acceptable salt thereof, wherein in the formula (I), $L^1$ and $L^2$ represent a group represented by formula (A) (preferably formula (A1) or (A5)) and S is a group represented by formula (S6), wherein in the formula (A), $R^{41}$ represents a hydrogen atom, $R^{42}$ and $R^{43}$ are the same or different and each represents alkyl having 1 to 5 carbon atoms (preferably, $R^{42}$ represents methyl and $R^{43}$ represents ethyl), $R^{45}$ represents a hydrogen atom, ring RA represents benzenediyl or cycloalkanediyl, and $n^{1A}$ represents 0, and in the formula (S6), $n^6$ represents 1, $Ar^6$ represents oxadiazolediyl, and $X^6$ represents —C(=O)—NH—.

According to a more preferred embodiment of the present invention, there is provided a compound or a pharmaceutically acceptable salt thereof, wherein in the formula (I), $L^1$ and $L^2$ represent a group represented by formula (A) (preferably formula (A1) or (A5)) and S is a group represented by formula (S6), wherein in the formula (A), $R^{41}$ represents a hydrogen atom, $R^{42}$ and $R^{43}$ are the same or different and each represents alkyl having 1 to 5 carbon atoms (preferably, $R^{42}$ represents methyl and $R^{43}$ represents ethyl), $R^{45}$ represents a hydrogen atom, ring RA represents benzenediyl or cycloalkanediyl, and $n^{1A}$ represents 0, and in the formula (S6), $n^6$ represents 2, $Ar^6$ represents triazolediyl, and $X^6$ represents —C(=O)—NH—.

The pharmaceutically acceptable salt of compound (I) includes, for example, pharmaceutically acceptable acid addition salt, metal salt, ammonium salt, organic amine addition salt, amino acid addition salt, and the like. Examples of the pharmaceutically acceptable acid addition salt of compound (I) include inorganic acid salt such as hydrochloride, hydrobromide, nitrate, sulfate, phosphate, and the like; and organic acid salt such as acetate, oxalate, maleate, fumarate, citrate, benzoate, methanesulfonate, and the like; and the like. Examples of the pharmaceutically acceptable metal salt include alkali metal salt such as sodium salt, potassium salt, and the like; alkaline earth metal salt such as magnesium salt, calcium salt, and the like; aluminum salt; zinc salt; and the like. Examples of the pharmaceutically acceptable ammonium salt include salt of such as ammonium, tetramethylammonium, and the like. Examples of the pharmaceutically acceptable organic amine addition salt include addition salt of such as morpholine, piperidine, and the like, and examples of the pharmaceutically acceptable amino acid addition salts include addition salts of such as lysine, glycine, phenylalanine, aspartic acid, glutamic acid, and the like.

The compound of the present invention means a compound that has desirable properties for one or more of various evaluation items required of a pharmaceutical composition or a therapeutic or prophylactic agent for cancer, the properties including not only pharmacological activity but also physical stability, stability under physiological conditions, safety for living body, and the like.

Method for the Manufacture of Compound (I)

Next, the method for the manufacture of compound (I) will be described.

Incidentally, in the manufacturing method described below, when the defined groups change under the conditions of the manufacturing method or are not appropriate to implement the manufacturing method, the target compounds can be manufactured by using a method of introducing and removing a protecting group commonly used in organic synthetic chemistry [e.g., a method described in Protective Groups in Organic Synthesis, 3rd Edition by T. W. Greene, John Wiley & Sons Inc. (1999) and the like]. Furthermore, depending on necessity, the order of reaction steps such as introduction of substituents and the like can also be changed.

First, among compound (I), the method for the manufacture of a compound having a chemical structure of $L^1$ or $L^2$ corresponding to a ligand will be described.

[Manufacturing Method 1]

Among compounds represented by formula (A), under the condition of having a chemical structure in which ring RA is ring RA1 and $n^{1.4}$ is 0, (i) compound (a-10) in which carboxy is bonded to the wavy line portion, (ii) compound (a-14) in which amino is bonded to the wavy line portion, and (iii) compound (a-12) in which a halogen is bonded to the wavy line portion can be manufactured according to the following steps:

[Chemical formula 56]

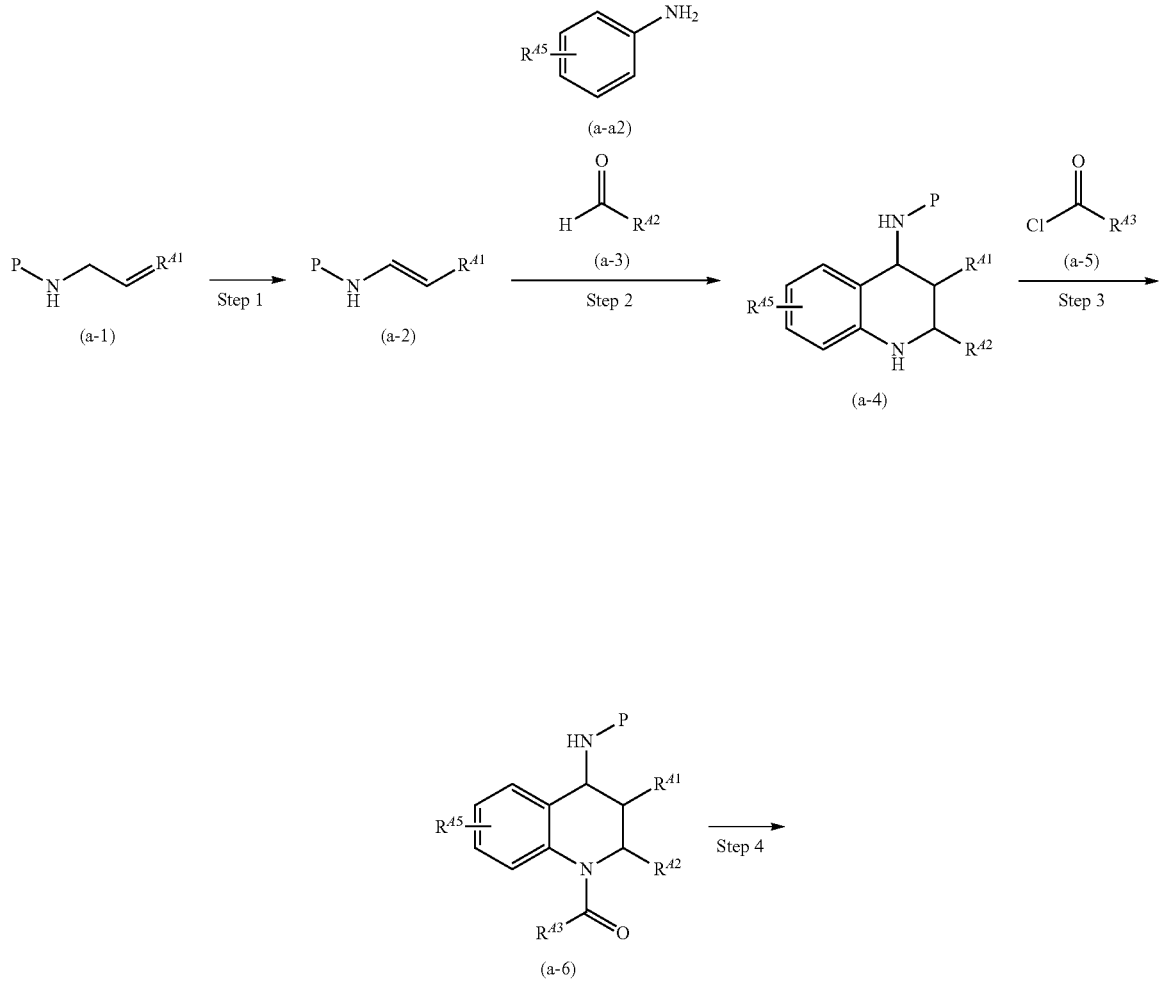

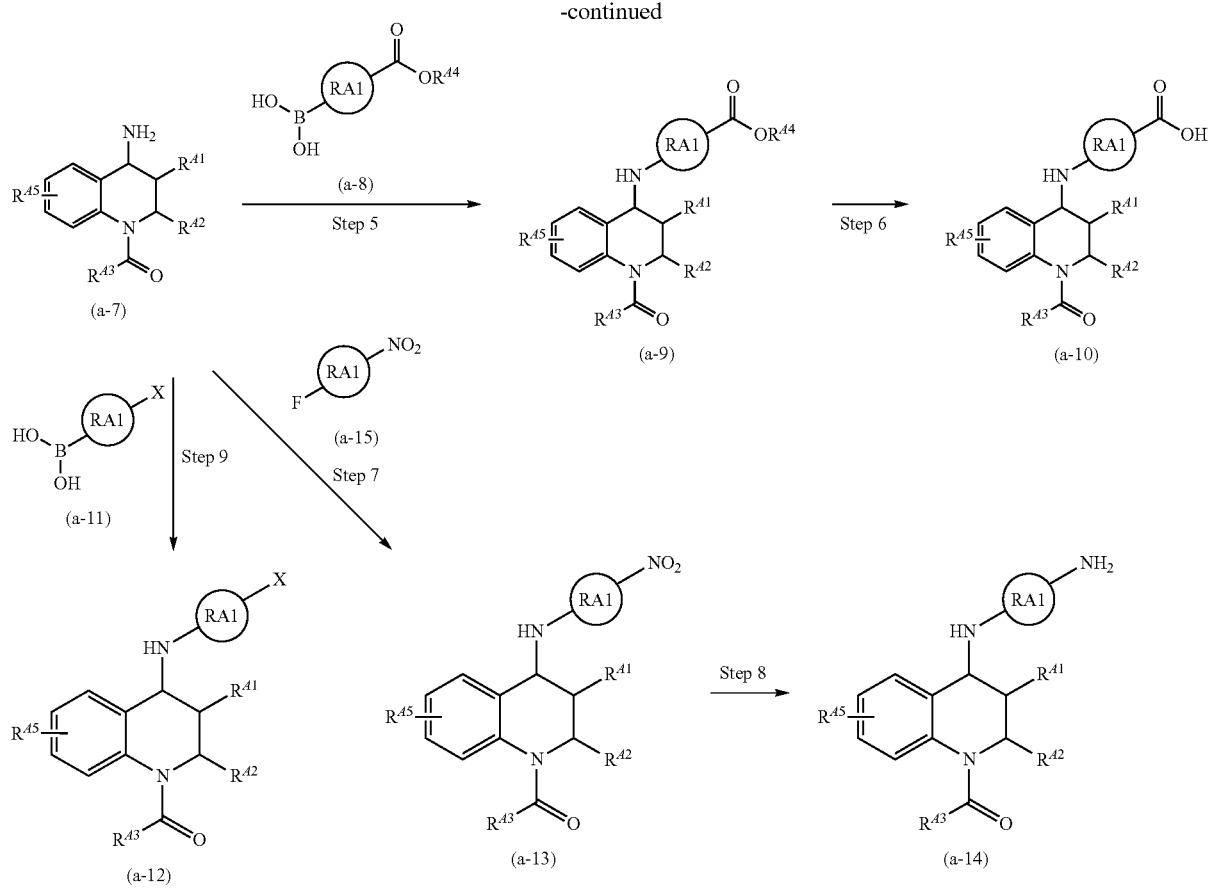

(wherein, $R^{A1}$, $R^{A2}$, $R^{A3}$, and $R^{A5}$ are as defined above, X represents a halogen, $R^{A4}$ represents lower alkyl, ring RA1 represents benzenediyl or pyridinediyl, and P represents an amine protecting group such as, for example, tert-butoxycarbonyl (Boc), benzyloxycarbonyl (Cbz), p-methoxybenzyl (PMB), and the like).

(Step 1)

Compound (a-2) can be manufactured by reacting compound (a-1) and 0.001 equivalent to 0.5 equivalent of rhodium catalyst in a solvent at a temperature between −20° C. and the boiling point of the solvent used for 5 minutes to 120 hours.

Examples of the rhodium catalyst include tris(triphenylphosphine)carbonyl rhodium hydride and the like.

Examples of the solvent include tetrahydrofuran (THF), acetonitrile, and the like, and these can be used alone or as a mixture.

Compound (a-1) can be obtained as a commercially available product, or can be obtained by known methods [e.g., Experimental Chemistry Lecture, 5th Edition, Volume 13, p. 118, Maruzen Co., Ltd. (2004) and the like] or methods based thereon.

(Step 2)

Compound (a-4) can be manufactured by reacting compound (a-a2), 1 equivalent to 5 equivalents of compound (a-2), and 1 equivalent to 5 equivalents of compound (a-3) in the presence of a catalytic amount of bismuth (III) chloride in a solvent at a temperature between −20° C. and the boiling point of the solvent used for 5 minutes to 120 hours.

Examples of the solvent include THF, acetonitrile, and the like, and these can be used alone or as a mixture.

Compound (a-3) can be obtained as a commercially available product, or can be obtained by known methods [e.g., Experimental Chemistry Lecture, 5th Edition, Volume 15, p. 1, Maruzen Co., Ltd. (2004) and the like] or methods based thereon.

Compound (a-a2) can be obtained as a commercially available product, or can be obtained by known methods [e.g., Experimental Chemistry Lecture, 5th edition, Volume 14, p. 351, Maruzen Co., Ltd. (2004) and the like] or methods based thereon.

(Step 3)

Compound (a-6) can be manufactured by reacting compound (a-4) and 1 equivalent to 5 equivalents of compound (a-5) in the presence of 1 equivalent to a large excess of base in a solvent at a temperature between −20° C. and the boiling point of the solvent used for 5 minutes to 120 hours.

Examples of the base include sodium hydride, potassium hydride, lithium diisopropylamide (LDA), lithium bis[trimethylsilyl]amide, sodium bis[trimethylsilyl]amide, sodium methoxide, potassium ethoxide, potassium tert-butoxide, potassium carbonate, sodium hydroxide, 1,8-diazabicyclo[5.4.0]-7-undecene (DBU), triethylamine, N,N-diisopropylethylamine, pyridine, 4-dimethylaminopyridine, and the like.

Examples of the solvent include chloroform, dichloromethane, dimethylformamide (DMF), dimethylacetamide (DMA), N-methylpyrrolidone (NMP), dimethylsulfoxide (DMSO), THF, acetonitrile, and the like, and these can be used alone or as a mixture.

Compound (a-5) can be obtained as a commercially available product, or can be obtained by known methods [e.g., Experimental Chemistry Lecture, 5th Edition, Volume 16, p. 101, Maruzen Co., Ltd. (2004) and the like] or methods based thereon.

(Step 4)

When P in compound (a-6) is, for example, Boc, compound (a-7) can be manufactured by reacting compound (a-6) in the presence of 1 equivalent to a large excess of acid in a solvent at a temperature between −20° C. and the boiling point of the solvent used for 5 minutes to 120 hours.

Examples of the acid include hydrochloric acid, sulfuric acid, trifluoroacetic acid, trifluoromethanesulfonic acid, bis(trifluoromethanesulfonyl)imide, and the like.

Examples of the solvent include chloroform, dichloromethane, toluene, THF, acetonitrile, and the like, and these can be used alone or as a mixture.

Further, when P in compound (a-6) is, for example, Cbz, compound (a-7) can be manufactured by reacting compound (a-6) in the presence of 0.001 equivalent to 0.5 equivalent of palladium catalyst under a hydrogen atmosphere in a solvent at a temperature between −20° C. and the boiling point of the solvent used for 5 minutes to 120 hours.

Examples of the palladium catalyst include palladium on carbon, palladium hydroxide, and the like.

Examples of the solvent include methanol, ethanol, ethyl acetate, THF, 1,4-dioxane, and the like, and these can be used alone or as a mixture.

Further, when P in compound (a-6) is, for example, PMB, compound (a-7) can be manufactured by reacting compound (a-6) in the presence of 1 equivalent to 5 equivalents of an oxidizing agent in a solvent at a temperature between −20° C. and the boiling point of the solvent used for 5 minutes to 120 hours. Compound (a-7) can also be manufactured by the same method as when P is Boc or Cbz.

Examples of the oxidizing agent include 2,3-dichloro-5,6-dicyano-p-benzoquinone (DDQ), ammonium cerium(IV) nitrate (CAN), and the like.

Examples of the solvent include chloroform, dichloromethane, dichloroethane, and the like, and these can be used alone or as a mixture.

(Step 5)

Compound (a-9) can be manufactured by reacting compound (a-7), 1 equivalent to 5 equivalents of compound (a-8), and 0.001 equivalent to 2 equivalents of copper(II) catalyst in the presence of 1 equivalent to a large excess of base under an oxygen atmosphere in a solvent at a temperature between −20° C. and the boiling point of the solvent used for 5 minutes to 120 hours.

Examples of the copper catalyst include copper(II) acetate, copper(II) chloride, copper(II) oxide, and copper sulfate pentahydrate, and the like.

Examples of the base include pyridine, 4-dimethylaminopyridine, DBU, triethylamine, N,N-diisopropylethylamine, and the like.

Examples of the solvent include chloroform, dichloromethane, THF, acetonitrile, and the like, and these can be used alone or as a mixture.

Compound (a-8) can be obtained as a commercially available product, or can be obtained by known methods [e.g., Experimental Chemistry Lecture, 5th Edition, Volume 18, p. 97, Maruzen Co., Ltd. (2004) and the like] or methods based thereon.

(Step 6)

Compound (a-10) can be manufactured by reacting compound (a-9) in the presence of 1 equivalent to a large excess of base in a solvent at a temperature between −20° C. and the boiling point of the solvent used for 5 minutes to 120 hours.

Examples of the base include sodium hydroxide, potassium hydroxide, lithium hydroxide, sodium carbonate, potassium carbonate, cesium carbonate, potassium phosphate, and the like.

Examples of the solvent include methanol, ethanol, DMF, DMA, NMP, DMSO, THF, acetonitrile, water, and the like, and these can be used alone or as a mixture.

(Step 7)

Compound (a-13) can be manufactured by reacting compound (a-7) and 1 equivalent to 5 equivalents of compound (a-15) in the presence of 1 equivalent to a large excess of base in a solvent at a temperature between −20° C. and the boiling point of the solvent used for 5 minutes to 120 hours.

Examples of the base include sodium hydride, potassium hydride, LDA, lithium bis[trimethylsilyl]amide, sodium bis[trimethylsilyl]amide, sodium methoxide, potassium ethoxide, potassium tert-butoxide, potassium carbonate, sodium hydroxide, DBU, triethylamine, N,N-diisopropylethylamine, and the like.

Examples of the solvent include DMF, DMA, NMP, DMSO, THF, acetonitrile, and the like, and these can be used alone or as a mixture.

Compound (a-15) can be obtained as a commercially available product, or can be obtained by known methods [e.g., Experimental Chemistry Lecture, 5th Edition, Volume 17, p. 396, Maruzen Co., Ltd. (2004) and the like] or methods based thereon.

(Step 8)

Compound (a-14) can be manufactured by reacting compound (a-13) in the presence of 0.001 equivalent to 0.5 equivalent of palladium catalyst under a hydrogen atmosphere in a solvent at a temperature between −20° C. and the boiling point of the solvent used for 5 minute to 120 hours.

Examples of the palladium catalyst include palladium on carbon, palladium hydroxide, and the like.

Examples of the solvent include methanol, ethanol, ethyl acetate, THF, 1,4-dioxane, and the like, and these can be used alone or as a mixture.

(Step 9)

Compound (a-12) can be manufactured by using compound (a-7) and 1 equivalent to 5 equivalents of compound (a-11) in the same manner as in step 5 of manufacturing method 1.

Compound (a-11) can be obtained as a commercially available product, or can be obtained by known methods [e.g., Experimental Chemistry Lecture, 5th Edition, Volume 18, p. 97, Maruzen Co., Ltd. (2004) and the like] or methods based thereon.

[Manufacturing Method 1-2]

Among compounds represented by formula (A), under the condition of having a chemical structure in which ring RA is ring RA1 and $n1^A$ is 1, (i) compound (a-18) in which carboxy is bonded to the wavy line portion, (ii) compound (a-21) in which amino is bonded to the wavy line portion, and (iii) compound (a-23) in which a halogen is bonded to the wavy portion can be manufactured according to the following steps:

[Chemical formula 57]

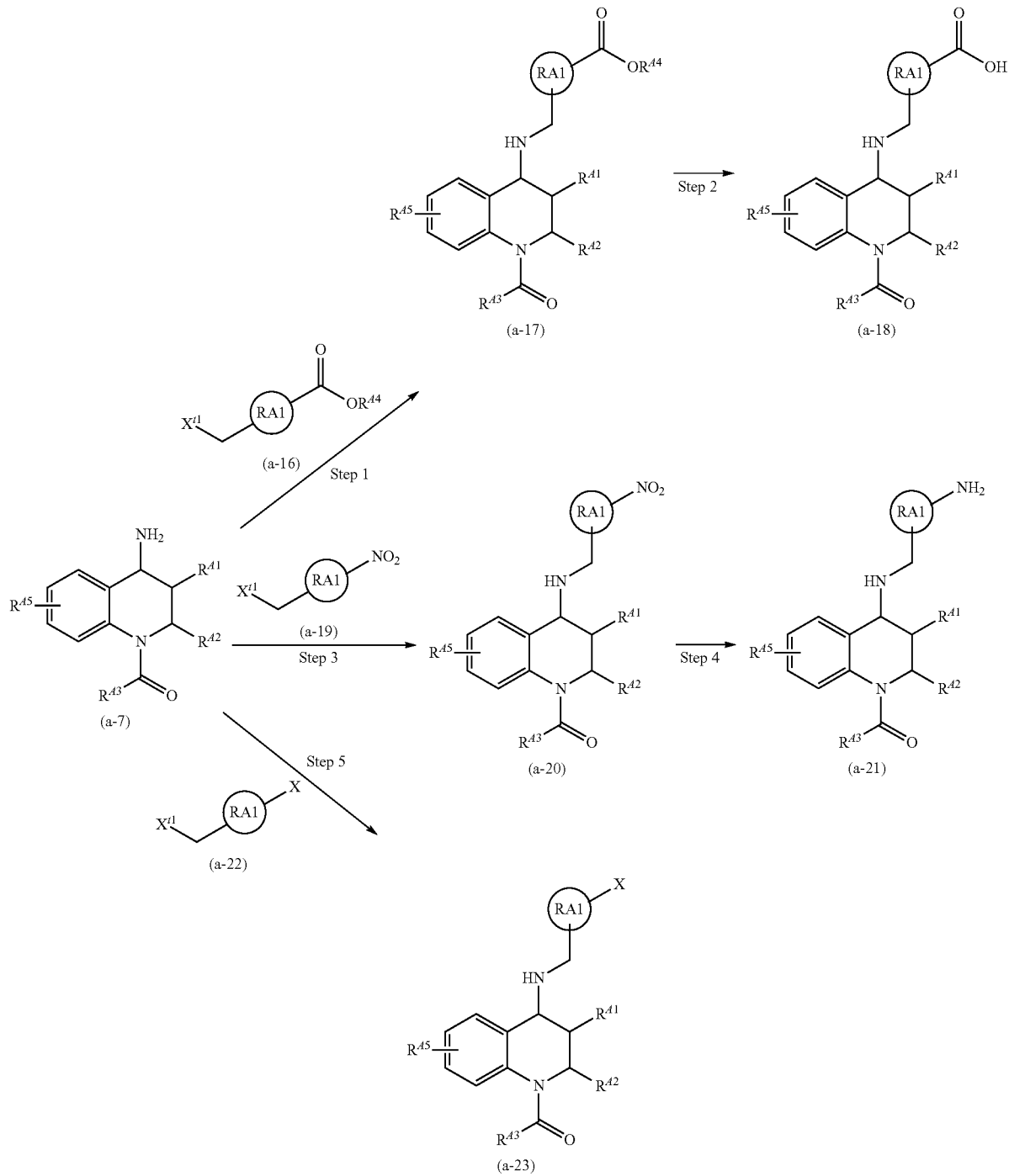

(wherein, $R^{A1}$, $R^{A2}$, $R^{A3}$, and $R^{A5}$ are as defined above, $R^{A4}$ represents lower alkyl, $X^{t1}$ represents a halogen, and ring RA1 represents benzenediyl or pyridinediyl).

(Step 1)

Compound (a-17) can be manufactured by reacting compound (a-7) and 1 equivalent to 5 equivalents of compound (a-16) in the presence of 1 equivalent to a large excess of base in a solvent at a temperature between −20° C. and the boiling point of the solvent used for 5 minutes to 120 hours.

Examples of the base include sodium hydride, potassium hydride, LDA, lithium bis[trimethylsilyl]amide, sodium bis[trimethylsilyl]amide, sodium methoxide, potassium ethoxide, potassium tert-butoxide, potassium carbonate, sodium hydroxide, DBU, triethylamine, N,N-diisopropylethylamine, and the like.

Examples of the solvent include DMF, DMA, NMP, DMSO, THF, acetonitrile, dichloromethane, chloroform, and the like, and these can be used alone or as a mixture.

Compound (a-16) can be obtained as a commercially available product, or can be obtained by known methods [e.g., Experimental Chemistry Lecture, 5th Edition, Volume 13, p. 377, Maruzen Co., Ltd. (2004) and the like] or methods based thereon.

(Step 2)

Compound (a-18) can be manufactured by using compound (a-17) in the same manner as in step 6 of manufacturing method 1.

(Step 3)

Compound (a-20) can be manufactured by using compound (a-7) and 1 equivalent to 5 equivalents of compound (a-19) in the same manner as in step 1 of manufacturing method 1-2.

Compound (a-19) can be obtained as a commercially available product, or can be obtained by known methods [e.g., Experimental Chemistry Lecture, 5th Edition, Volume 13, p. 377, Maruzen Co., Ltd. (2004) and the like] or methods based thereon.

(Step 4)

Compound (a-21) can be manufactured by using compound (a-20) in the same manner as in step 8 of manufacturing method 1.

(Step 5)

Compound (a-23) can be manufactured by using compound (a-7) and 1 equivalent to 5 equivalents of compound (a-22) in the same manner as in step 1 of manufacturing method 1-2.

Compound (a-22) can be obtained as a commercially available product, or can be obtained by known methods [e.g., Experimental Chemistry Lecture, 5th Edition, Volume 13, p. 377, Maruzen Co., Ltd. (2004) and the like] or methods based thereon.

[Manufacturing Method 1-3]

Among compounds represented by formula (A), under the condition of having a chemical structure in which ring RA is ring RA2 and $n1^A$ is 0, (i) compound (a-26) in which carboxy is bonded to the wavy line portion and (ii) compound (a-29) in which amino is bonded to the wavy line portion; and among compounds represented by formula (A), compound (a-32) in which ring RA is ring RA3 can be manufactured respectively according to the following steps:

[Chemical formula 58]

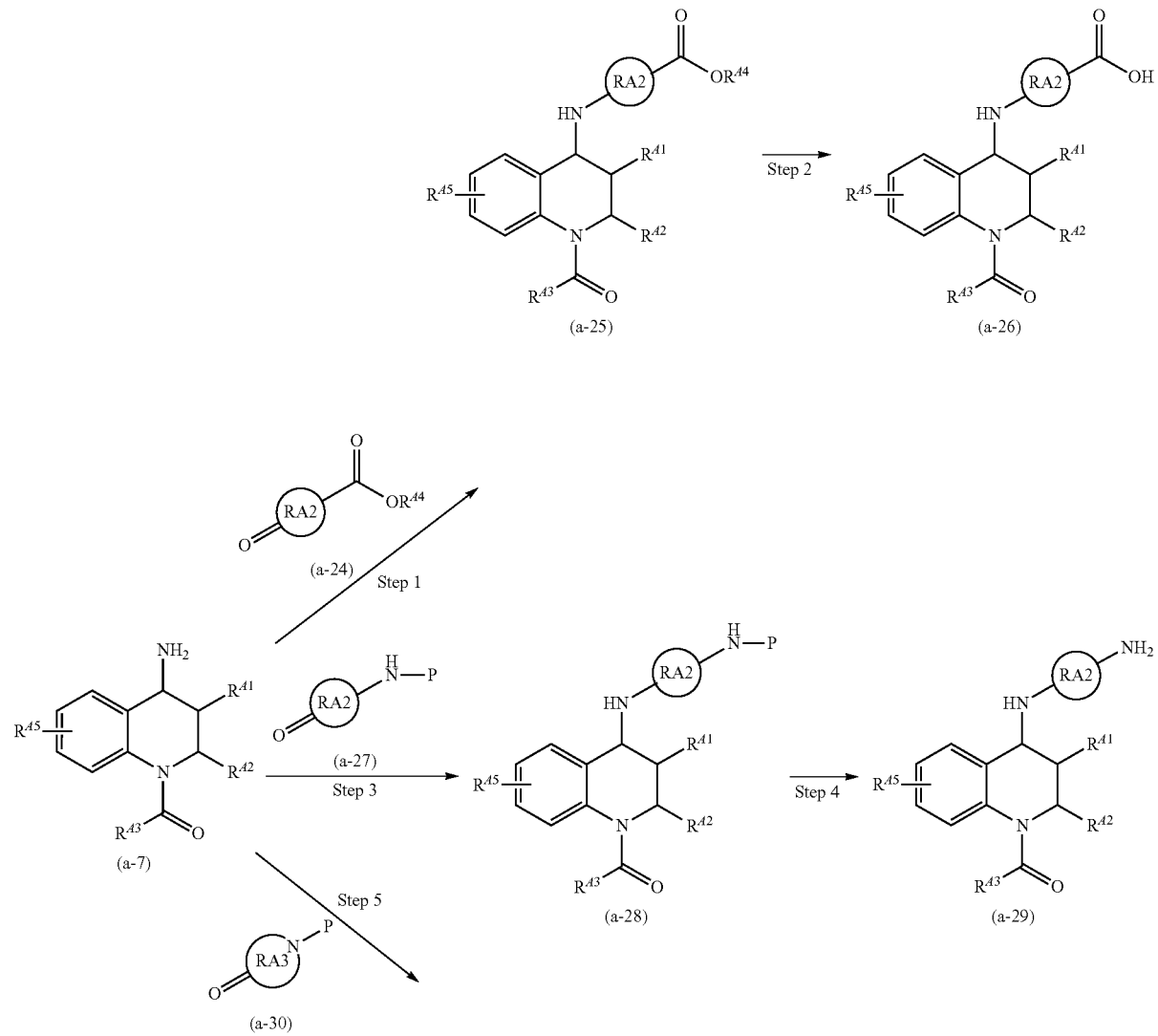

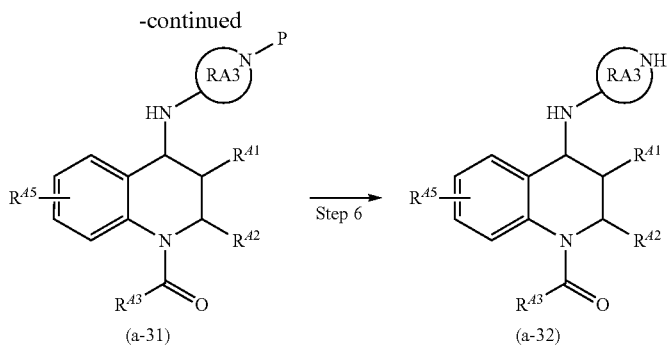

(wherein, $R^{A1}$, $R^{A2}$, $R^{A3}$, $R^{A5}$, and P are as defined above, $R^{A4}$ represents lower alkyl, ring RA2 represents cycloalkanediyl, and ring RA3 represents piperidinediyl, azetidinediyl, pyrrolidinediyl, or homopiperidinediyl).

(Step 1)

Compound (a-25) can be manufactured by reacting compound (a-7) and 1 equivalent to 5 equivalents of compound (a-24) in the presence of 1 equivalent to 5 equivalents of reducing agent and 1 equivalent to 5 equivalents of acid in a solvent at a temperature between $-20°$ C. and the boiling point of the solvent used for 5 minutes to 120 hours.

Examples of the reducing agent include sodium borohydride, sodium cyanoborohydride, sodium triacetoxyborohydride, and the like.

Examples of the acid include hydrochloric acid, trifluoroacetic acid, acetic acid, and the like.

Examples of the solvent include methanol, ethanol, and the like, and these can be used alone or as a mixture.

Compound (a-24) can be obtained as a commercially available product, or can be obtained by known methods [e.g., Experimental Chemistry Lecture, 5th Edition, Volume 15, p. 153, Maruzen Co., Ltd. (2004) and the like] or methods based thereon.

(Step 2)

Compound (a-26) can be manufactured by using compound (a-25) in the same manner as in step 6 of manufacturing method 1.

(Step 3)

Compound (a-28) can be manufactured by using compound (a-7) and 1 equivalent to 5 equivalents of compound (a-27) in the same manner as in step 1 of manufacturing method 1-3.

Compound (a-27) can be obtained as a commercially available product, or can be obtained by known methods [e.g., Experimental Chemistry Lecture, 5th Edition, Volume 15, p. 153, Maruzen Co., Ltd. (2004) and the like] or methods based thereon.

(Step 4)

Compound (a-29) can be manufactured by using compound (a-28) in the same manner as in step 4 of manufacturing method 1.

(Step 5)

Compound (a-31) can be manufactured by using compound (a-7) and 1 equivalent to 5 equivalents of compound (a-30) in the same manner as in step 1 of manufacturing method 1-3.

Compound (a-30) can be obtained as a commercially available product, or can be obtained by known methods [e.g., Experimental Chemistry Lecture, 5th Edition, Volume 15, p. 153, Maruzen Co., Ltd. (2004) and the like] or methods based thereon.

(Step 6)

Compound (a-32) can be manufactured by using compound (a-31) in the same manner as in step 4 of manufacturing method 1.

[Manufacturing Method 1-4]

Among compounds represented by formula (A), under the condition of having a chemical structure in which ring RA is ring RA2 and $n^{14}$ is 1, (i) compound (a-35) in which carboxy is bonded to the wavy line portion and (ii) compound (a-38) in which amino is bonded to the wavy line portion; and among compounds represented by formula (A), compound (a-41) in which ring RA is ring RA3 can be manufactured respectively according to the following steps:

[Chemical formula 59]

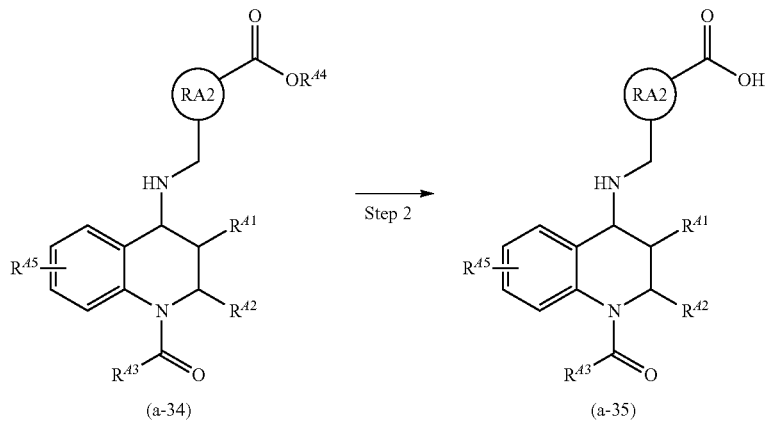

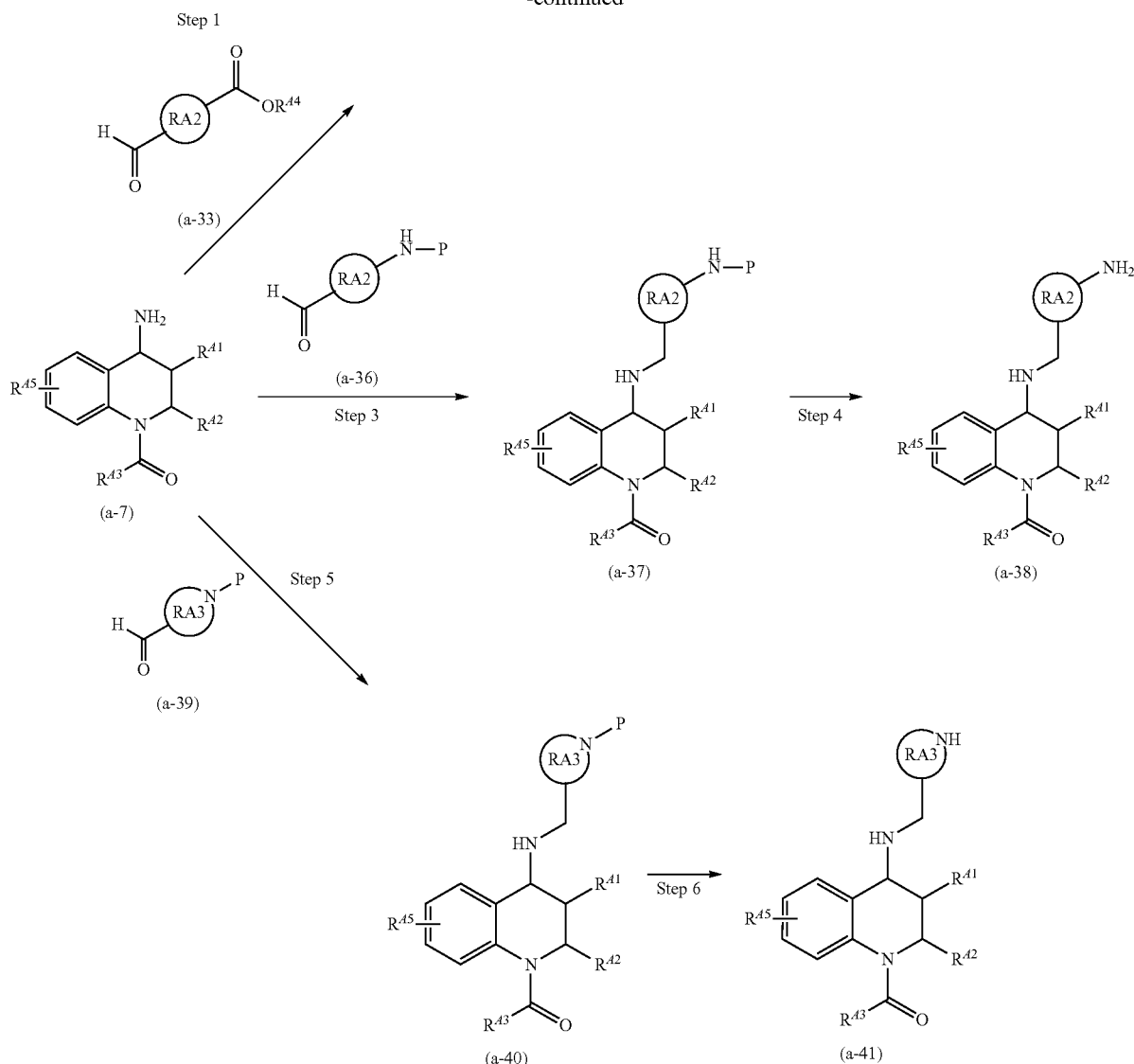

(wherein, $R^{A1}$, $R^{A2}$, $R^{A3}$, $R^{A5}$, and P are as defined above, $R^{A4}$ represents lower alkyl, ring RA2 represents cycloalkanediyl, and ring RA3 represents piperidinediyl, azetidinediyl, pyrrolidinediyl, or homopiperidinediyl).

(Step 1)

Compound (a-34) can be manufactured by using compound (a-7) and 1 equivalent to 5 equivalents of compound (a-33) in the same manner as in step 1 of manufacturing method 1-3.

Compound (a-33) can be obtained as a commercially available product, or can be obtained by known methods [e.g., Experimental Chemistry Lecture, 5th Edition, Volume 15, p. 1, Maruzen Co., Ltd. (2004) and the like] or methods based thereon.

(Step 2)

Compound (a-35) can be manufactured by using compound (a-34) in the same manner as in step 6 of manufacturing method 1.

(Step 3)

Compound (a-37) can be manufactured by using compound (a-7) and 1 equivalent to 5 equivalents of compound (a-36) in the same manner as in step 1 of manufacturing method 1-3.

Compound (a-36) can be obtained as a commercially available product, or can be obtained by known methods [e.g., Experimental Chemistry Lecture, 5th Edition, Volume 15, p. 1, Maruzen Co., Ltd. (2004) and the like] or methods based thereon.

(Step 4)

Compound (a-38) can be manufactured by using compound (a-37) in the same manner as in step 4 of manufacturing method 1.

(Step 5)

Compound (a-40) can be manufactured by using compound (a-7) and 1 equivalent to 5 equivalents of compound (a-39) in the same manner as in step 1 of manufacturing method 1-3.

Compound (a-39) can be obtained as a commercially available product, or can be obtained by known methods

[e.g., Experimental Chemistry Lecture, 5th Edition, Volume 15, p. 1, Maruzen Co., Ltd. (2004) and the like] or methods based thereon.

(Step 6)

Compound (a-41) can be manufactured by using compound (a-40) in the same manner as in step 4 of manufacturing method 1.

[Manufacturing Method 2]

Among compounds represented by formula (B), under the condition of having a chemical structure in which $R^{B1}$ is $R^{B7}$, (i) compound (b-9) in which bromine is bonded to the wavy portion, (ii) compound (b-10) in which carboxy is bonded to the wavy portion, and (iii) compound (b-11) in which amino is bonded to the wavy portion can be manufactured respectively according to the following steps:

[Chemical formula 60]

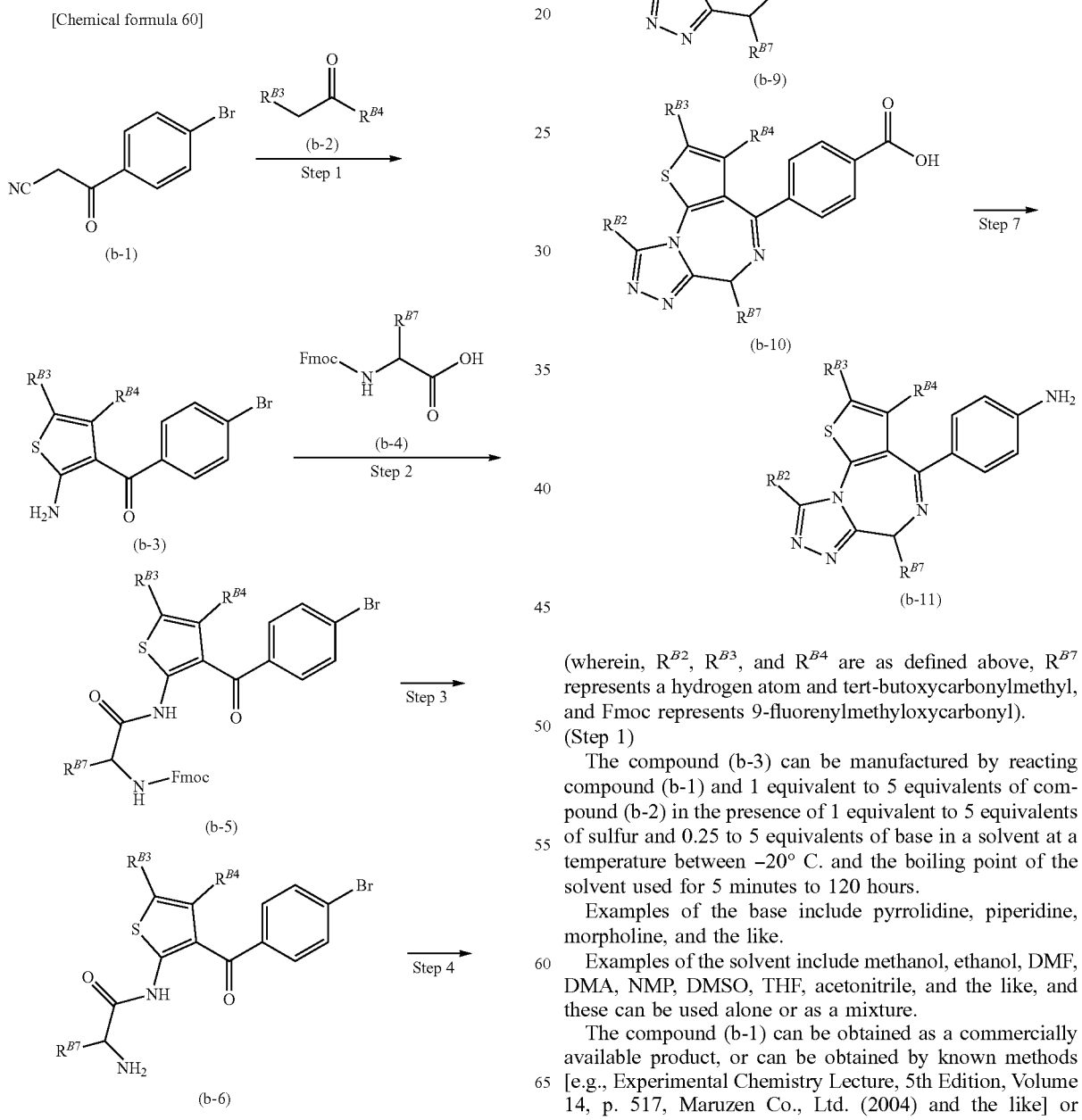

(wherein, $R^{B2}$, $R^{B3}$, and $R^{B4}$ are as defined above, $R^{B7}$ represents a hydrogen atom and tert-butoxycarbonylmethyl, and Fmoc represents 9-fluorenylmethyloxycarbonyl).

(Step 1)

The compound (b-3) can be manufactured by reacting compound (b-1) and 1 equivalent to 5 equivalents of compound (b-2) in the presence of 1 equivalent to 5 equivalents of sulfur and 0.25 to 5 equivalents of base in a solvent at a temperature between −20° C. and the boiling point of the solvent used for 5 minutes to 120 hours.

Examples of the base include pyrrolidine, piperidine, morpholine, and the like.

Examples of the solvent include methanol, ethanol, DMF, DMA, NMP, DMSO, THF, acetonitrile, and the like, and these can be used alone or as a mixture.

The compound (b-1) can be obtained as a commercially available product, or can be obtained by known methods [e.g., Experimental Chemistry Lecture, 5th Edition, Volume 14, p. 517, Maruzen Co., Ltd. (2004) and the like] or methods based thereon.

Compound (b-2) can be obtained as a commercially available product, or can be obtained by known methods [e.g., Experimental Chemistry Lecture, 5th Edition, Volume 15, p. 153, Maruzen Co., Ltd. (2004) and the like] or methods based thereon.

(Step 2)

Compound (b-5) can be manufactured by reacting compound (b-3) and 1 equivalent to 5 equivalents of compound (b-4) in the presence of 1 equivalent to a large excess of condensing agent and, according to necessity, in the presence of 1 equivalent to a large excess of additive in a solvent at a temperature between −20° C. and the boiling point of the solvent used for 5 minutes to 120 hours.

Examples of the condensing agent include dicyclohexylcarbodiimide (DCC), N-(3-dimethylaminopropyl)-N'-ethylcarbodimide hydrochloride (EDC), O-(7-azabenzotriazol-1-yl)-N,N,N',N'-tetramethyluronium hexafluorophosphate (HATU), (1-cyano-2-ethoxy-2-oxoethylideneaminooxy)dimethylamino-morpholino-carbenium hexafluorophosphate (COMU), and the like.

Examples of the additive include 1-hydroxybenzotriazole monohydrate (HOBt), triethylamine, N,N-diisopropylethylamine, and the like.

Examples of the solvent include chloroform, dichloromethane, DMF, DMA, THF, acetonitrile, and the like, and these can be used alone or as a mixture.

Compound (b-4) can be obtained as a commercially available product, or can be obtained by known methods [e.g., Experimental Chemistry Lecture, 5th Edition, Volume 16, p. 175, Maruzen Co., Ltd. (2004) and the like] or methods based thereon.

(Step 3)

Compound (b-6) can be manufactured by reacting compound (b-5) in the presence of 1 equivalent to a large excess of base in a solvent at a temperature between −20° C. and the boiling point of the solvent used for 5 minutes to 120 hours.

Examples of the base include pyrrolidine, piperidine, morpholine, and the like.

Examples of the solvent include methanol, ethanol, DMF, DMA, NMP, DMSO, THF, acetonitrile, and the like, and these can be used alone or as a mixture.

(Step 4)

Compound (b-7) can be manufactured by reacting compound (b-6) in the presence of 1 equivalent to a large excess of acid in a solvent at a temperature between −20° C. and the boiling point of the solvent used for 5 minutes to 120 hours.

Examples of the acid include acetic acid, formic acid, hydrochloric acid, magnesium sulfate, and the like.

Examples of the solvent include methanol, ethanol, toluene and the like, and these can be used alone or as a mixture.

(Step 5)

Compound (b-9) can be manufactured by reacting compound (b-7) and 1 equivalent to 5 equivalents of compound (b-8) in the presence of 1 equivalent to a large excess of base and 1 equivalent to 5 equivalents of phosphoric ester in a solvent at a temperature between −78° C. and the boiling point of the solvent used for 5 minutes to 120 hours.

Examples of the base include sodium hydride, potassium hydride, LDA, lithium bis[trimethylsilyl]amide, sodium bis[trimethylsilyl]amide, sodium methoxide, potassium ethoxide, potassium tert-butoxide, potassium carbonate, sodium hydroxide, DBU, triethylamine, N,N-diisopropylethylamine, and the like.

Examples of the phosphoric acid ester include diethyl chlorophosphate, dimethyl chlorophosphate, and the like.

Examples of the solvent include DMF, DMA, NMP, DMSO, THF, acetonitrile, and the like, and these can be used alone or as a mixture.

Compound (b-8) can be obtained as a commercially available product, or can be obtained by known methods [e.g., Experimental Chemistry Lecture, 5th Edition, Volume 14, p. 406, Maruzen Co., Ltd. (2004) and the like] or methods based thereon.

(Step 6)

Compound (b-10) can be manufactured by reacting compound (b-9) in the presence of 0.001 equivalent to 0.5 equivalent of palladium catalyst, 0.001 equivalent to 0.5 equivalent of phosphorus ligand, and 1 equivalent to a large excess of base under a carbon monoxide atmosphere in a solvent at a temperature between −20° C. and the boiling point of the solvent used for 5 minutes to 120 hours.

Examples of the palladium catalyst include palladium acetate, palladium chloride, tetrakis(triphenylphosphine)palladium (Pd(PPh$_3$)$_4$), bis(triphenylphosphine)palladium dichloride, [1,1'-bis(diphenylphosphino)ferrocene]palladium dichloride (Pd(dppf)Cl$_2$), tris(dibenzylideneacetone)dipalladium (Pd$_2$(dba)$_3$), and the like.

Examples of the phosphorus ligand include triphenylphosphine, tributylphosphine, bis(diphenylphosphino)propane, bis(diphenylphosphino)butane, bis(diphenylphosphino)ferrocene, and the like.

Examples of the base include sodium hydride, potassium hydride, LDA, lithium bis[trimethylsilyl]amide, sodium bis[trimethylsilyl]amide, sodium methoxide, potassium ethoxide, potassium tert-butoxide, potassium carbonate, sodium hydroxide, DBU, triethylamine, N,N-diisopropylethylamine, and the like.

Examples of the solvent include DMF, DMA, NMP, DMSO, THF, acetonitrile, 1,4-dioxane, toluene, water, and the like, and these can be used alone or as a mixture.

(Step 7)

Compound (b-11) can be manufactured by reacting compound (b-10) in the presence of 1 equivalent to 5 equivalents of diphenylphosphoryl azide and 1 equivalent to a large excess of base in a solvent at a temperature between −20° C. and the boiling point of the solvent used for 5 minutes to 120 hours.

Examples of the base include potassium carbonate, sodium carbonate, cesium carbonate, potassium phosphate, sodium hydroxide, potassium hydroxide, DBU, triethylamine, N,N-diisopropylethylamine, and the like.

Examples of the solvent include THF, acetonitrile, 1,4-dioxane, toluene, water, and the like, and these can be used alone or as a mixture.

[Manufacturing Method T2]

Among compounds represented by formula (B), under the condition of having a chemical structure in which $R^{B1}$ is $R^{B9}$, (i) compound (b-16) in which bromine is bonded to the wavy portion, (ii) compound (b-20) in which carboxy is bonded to the wavy portion, and (iii) compound (b-24) in which amino is bonded to the wavy portion can be manufactured respectively according to the following steps.

[Chemical formula 61]
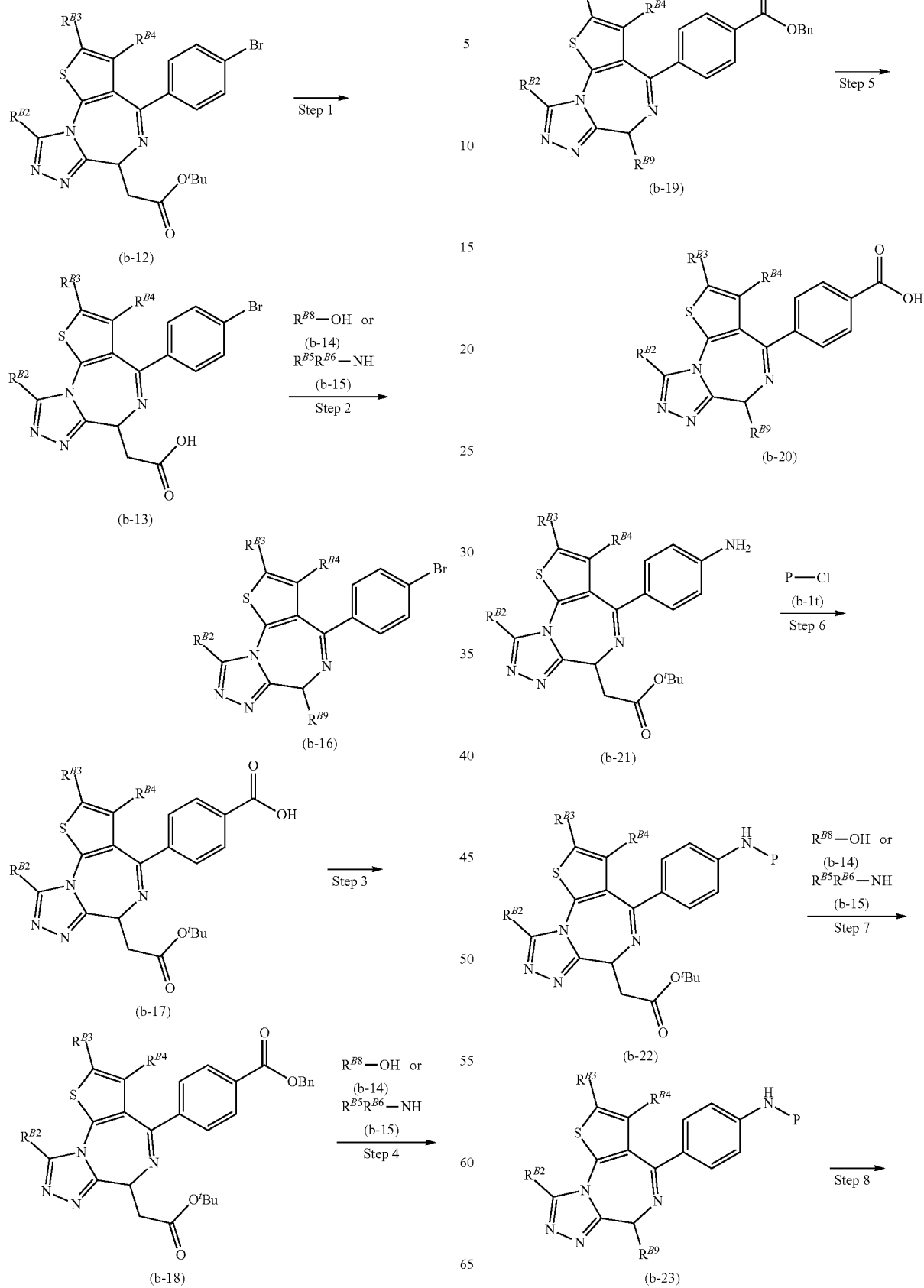

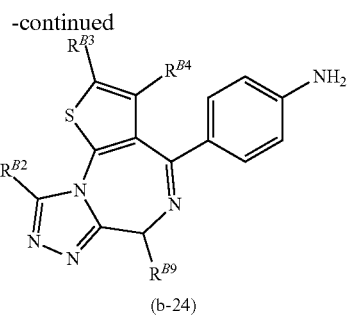

(b-24)

(wherein, $R^{B2}$, $R^{B3}$, $R^{B4}$, $R^{B5}$, and $R^{B6}$ are as defined above, $R^{B8}$ represents optionally substituted lower alkyl or optionally substituted cycloalkyl, $R^{B9}$ represents optionally substituted lower alkoxycarbonylmethyl, optionally substituted cycloalkyloxycarbonylmethyl, or —$CH_2CONR^{B5}R^{B6}$, $^tBu$ represents tert-butyl, Bn represents benzyl, and P represents an amine protecting group such as Cbz, Fmoc, and the like).

(Step 1)

Compound (b-13) can be manufactured by reacting compound (b-12) in the presence of 1 equivalent to a large excess of acid without solvent or in a solvent at a temperature between 0° C. and 150° C. for 5 minutes to 120 hours.

Compound (b-12) is, among compound (b-9) obtained in step 5 of manufacturing method 2, a compound in which $R^{B7}$ is tort-butoxycarbonylmethyl.

Examples of the acid include hydrochloric acid, sulfuric acid, formic acid, acetic acid, trifluoroacetic acid, p-toluenesulfonic acid, methanesulfonic acid, titanium tetrachloride, boron trifluoride, and the like, and these are used alone or as a mixture.

Examples of the solvent include methanol, ethanol, dichloromethane, chloroform, 1,2-dichloroethane, toluene, ethyl acetate, acetonitrile, diethyl ether, THF, 1,2-dimethoxyethane (DME), 1,4-dioxane, DMF, DMA, NMP, and the like, and these are used alone or as a mixture.

(Step 2)

Compound (b-16) can be manufactured by using compound (b-13) and 1 equivalent to 10 equivalents of compound (b-14) or compound (b-15) in the same manner as in step 2 of manufacturing method 2.

Compound (b-14) can be obtained as a commercially available product, or can be obtained by known methods [e.g., Experimental Chemistry Lecture, 5th Edition, Volume 14, p. 1, Maruzen Co., Ltd. (2004) and the like] or methods based thereon.

Compound (b-15) can be obtained as a commercially available product, or can be obtained by known methods [e.g., Experimental Chemistry Lecture, 5th Edition, Volume 14, p. 351, Maruzen Co., Ltd. (2004) and the like] or methods based thereon.

(Step 3)

Compound (b-18) can be manufactured by reacting compound (b-17) and 1 equivalent to 10 equivalents of benzyl bromide in the presence of 1 equivalent to 10 equivalents of base without solvent or in a solvent at a temperature between −20° C. and 150° C. for 5 minutes to 120 hours.

Compound (b-17) is, among compound (b-10) obtained in step 6 of manufacturing method 2, a compound in which $R^{B7}$ is tert-butoxycarbonylmethyl.

Examples of the base include potassium carbonate, potassium hydroxide, sodium hydroxide, sodium methoxide, potassium tert-butoxide, triethylamine, N,N-diisopropylethylamine, N-methylmorpholine, pyridine, DBU, and the like.

Examples of the solvent include methanol, ethanol, dichloromethane, chloroform, 1,2-dichloroethane, toluene, ethyl acetate, acetonitrile, THF, DME, 1,4-dioxane, DMF, DMA, NMP, pyridine, and the like, and these are used alone or as a mixture.

(Step 4)

Compound (b-19) can be manufactured by using compound (b-18) and 1 equivalent to 10 equivalents of compound (b-14) or compound (b-15) in the same manner as in step 1 and step 2.

(Step 5)

Compound (b-20) can be manufactured by reacting compound (b-19) in the presence of 0.001 equivalent to 0.5 equivalent of palladium catalyst under a hydrogen atmosphere in a solvent at a temperature between −20° C. and the boiling point of the solvent used for 5 minutes to 120 hours.

Examples of the palladium catalyst include palladium on carbon, palladium hydroxide, and the like.

Examples of the solvent include methanol, ethanol, ethyl acetate, THF, 1,4-dioxane, and the like, and these can be used alone or as a mixture.

(Step 6)

Compound (b-22) can be manufactured by reacting compound (b-21) and 1 equivalent to 10 equivalents of compound (b-1t) in the presence of 1 equivalent to 10 equivalents of base without solvent or in a solvent at a temperature between −20° C. and 150° C. for 5 minutes to 120 hours.

Compound (b-1t) can be obtained as a commercially available product, or can be obtained by known methods [e.g., Organic Syntheses, Coll. Vol. 3, p. 167 (1955) and the like] or methods based thereon.

Compound (b-21) is, among compound (b-11) obtained in step 7 of manufacturing method 2, a compound in which $R^{B7}$ is tert-butoxycarbonylmethyl.

Examples of the base include potassium carbonate, potassium hydroxide, sodium hydroxide, potassium tert-butoxide, triethylamine, N,N-diisopropylethylamine, N-methylmorpholine, pyridine, DBU, 4-dimethylaminopyridine, and the like.

Examples of the solvent include methanol, ethanol, dichloromethane, chloroform, 1,2-dichloroethane, toluene, ethyl acetate, acetonitrile, diethyl ether, THF, DME, 1,4-dioxane, DMF, DMA, NMP, pyridine, water, and the like, and these are used alone or as a mixture.

(Step 7)

Compound (b-23) can be manufactured by using compound (b-22) and 1 equivalent to 10 equivalents of compound (b-14) or compound (b-15) in the same manner as in step 1 and step 2.

(Step 8)

Compound (b-24) can be manufactured in the same manner as in step 5 when P in compound (b-23) is, for example, Cbz, and can be manufactured in the same manner as in step 3 of manufacturing method 2 when P in compound (b-23) is, for example, Fmoc.

[Manufacturing Method 3]

Among compounds represented by formula (C), compound (c-7) having a chemical structure in which $R^{C3}$ is hydroxy and ring RC is benzenediyl and having carboxy bonded to the wavy portion can be manufactured according to the following steps:

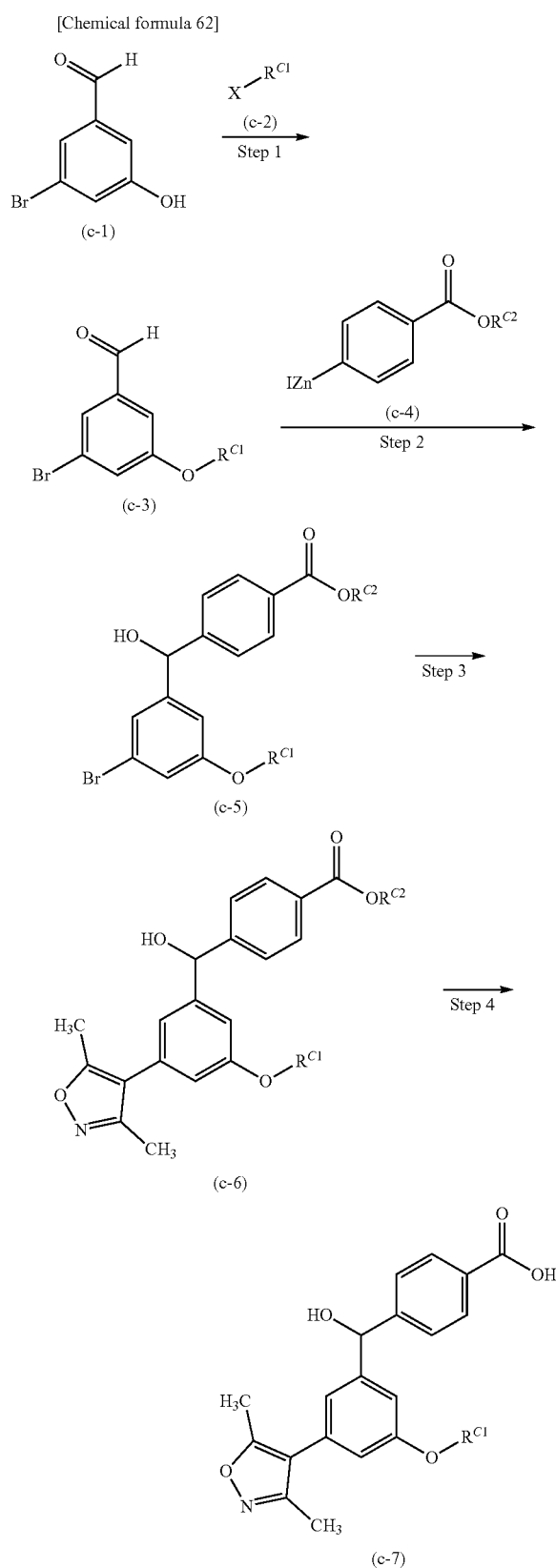

(wherein, $R^{C1}$ is as defined above, X represents a halogen, and $R^{C2}$ represents lower alkyl).

(Step 1)

Compound (c-3) can be manufactured by reacting compound (c-1) and 1 equivalent to 5 equivalents of compound (c-2) in the presence of 1 equivalent to a large excess of base in a solvent at a temperature between −20° C. and the boiling point of the solvent used for 5 minutes to 120 hours.

Examples of the base include sodium hydride, potassium hydride, butyllithium, LDA, lithium bis[trimethylsilyl]amide, sodium bis[trimethylsilyl]amide, sodium methoxide, potassium ethoxide, potassium tert-butoxide, potassium carbonate, sodium hydroxide, DBU, triethylamine, N,N-diisopropylethylamine, and the like.

Examples of the solvent include DMF, DMA, NMP, DMSO, THF, acetonitrile, and the like, and these can be used alone or as a mixture.

Compound (c-2) can be obtained as a commercially available product, or can be obtained by known methods [e.g., Experimental Chemistry Lecture, 5th Edition, Volume 13, p. 341, Maruzen Co., Ltd. (2004) and the like] or methods based thereon.

(Step 2)

Compound (c-5) can be manufactured by reacting compound (c-3) and 1 equivalent to 5 equivalents of compound (c-4) in a solvent at a temperature between −20° C. and the boiling point of the solvent used for 5 minutes to 120 hours.

Examples of the solvent include THF, 1,4-dioxane, diethyl ether, toluene, and the like, and these can be used alone or as a mixture.

Compound (c-4) can be obtained as a commercially available product, or can be obtained by known methods [e.g., Experimental Chemistry Lecture, 5th Edition, Volume 18, p. 78, Maruzen Co., Ltd. (2004) and the like] or methods based thereon.

(Step 3)

The compound (c-6) can be manufactured by reacting compound (c-5) and 1 equivalent to 5 equivalents of 3,5-dimethyl-4-(4,4,5,5-tetramethyl-1,3,2-dioxaboran-2-yl) isoxazole in the presence of 0.001 equivalent to 0.5 equivalent of palladium catalyst and 1 equivalent to a large excess of base in a solvent at a temperature between −20° C. and the boiling point of the solvent used for 5 minutes to 120 hours.

Examples of the palladium catalyst include palladium acetate, palladium chloride, Pd(PPh$_3$)$_4$, bis(triphenylphosphine)palladium dichloride, Pd(dppf)Cl$_2$, Pd$_2$(dba)$_3$, and the like.

Examples of the base include potassium carbonate, sodium carbonate, cesium carbonate, potassium phosphate, sodium hydroxide, potassium hydroxide, DBU, triethylamine, N,N-diisopropylethylamine, and the like.

Examples of the solvent include DMF, DMA, NMP, DMSO, THF, acetonitrile, 1,4-dioxane, toluene, water, and the like, and these can be used alone or as a mixture.

(Step 4)

Compound (c-7) can be manufactured by using compound (c-6) in the same manner as in step 6 of manufacturing method 1.

[Manufacturing Method Y4]

Among compounds represented by formula (C), under the condition of having a chemical structure in which $R^{C3}$ is a hydrogen atom and ring RC is ring RC1, (i) compound (c-11) in which carboxy is bonded to the wavy portion and (ii) compound (c-14) in which amino is bonded to the wavy portion can be manufactured respectively according to the following steps:

[Chemical formula 63]

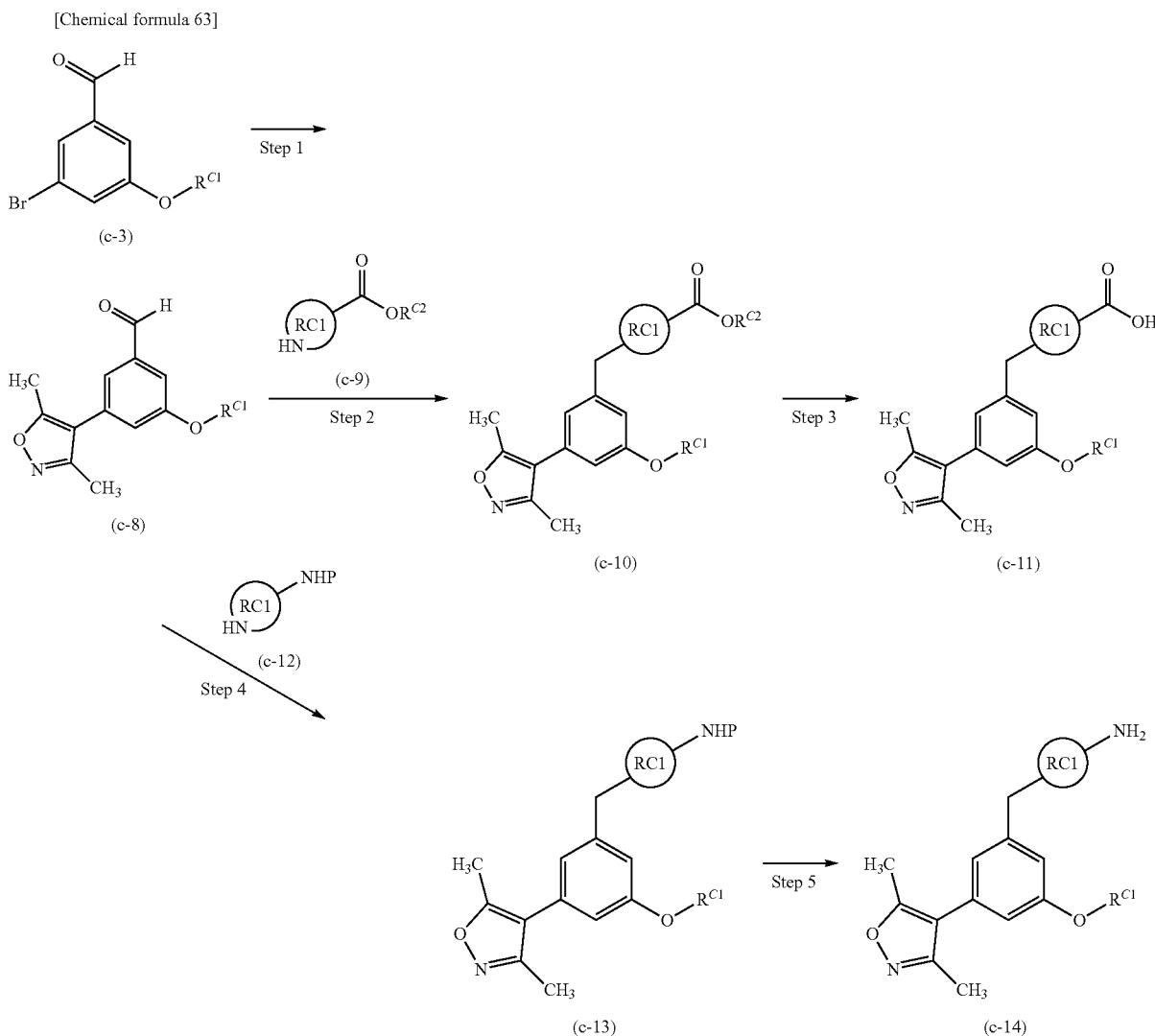

(wherein, $R^{C1}$ and $R^{C2}$ are as defined above, P represents an amine protecting group such as Boc, Cbz, PMB, and the like, and ring RC1 represents piperidinediyl, azetidinediyl, pyrrolidinediyl, or homopiperidinediyl. Incidentally, one secondary amine that forms the ring RC1 becomes a reaction point with compound (c-8)).

(Step 1)
Compound (c-8) can be manufactured by using compound (c-3) in the same manner as in step 3 of manufacturing method 3.

(Step 2)
Compound (c-10) can be manufactured by using compound (c-8) and 1 equivalent to 5 equivalents of (c-9) in the same manner as in step 1 of manufacturing method 1-3.

Compound (c-9) can be obtained as a commercially available product, or can be obtained by known methods [e.g., Experimental Chemistry Lecture, 5th Edition, Volume 14, p. 351, Maruzen Co., Ltd. (2004) and the like] or methods based thereon.

(Step 3)
Compound (c-11) can be manufactured by using compound (c-10) in the same manner as in step 6 of manufacturing method 1.

(Step 4)
Compound (c-13) can be manufactured by using compound (c-8) and 1 equivalent to 5 equivalents of compound (c-12) in the same manner as in step 1 of manufacturing method 1-3.

Compound (c-12) can be obtained as a commercially available product, or can be obtained by known methods [e.g., Experimental Chemistry Lecture, 5th Edition, Volume 14, p. 351, Maruzen Co., Ltd. (2004) and the like] or methods based thereon.

(Step 5)
Compound (c-14) can be manufactured by using compound (c-13) in the same manner as in step 4 of manufacturing method 1.

[Manufacturing Method 4]
Among compounds having a chemical structure represented by formula (D), (i) compound (d-6) in which carboxy is bonded to the wavy portion, (ii) compound (d-9) in which amino is bonded to the wavy portion, and (iii) compound (d-11) in which bromine is bonded to the wavy portion can be manufactured respectively according to the following steps:

[Chemical formula 64]

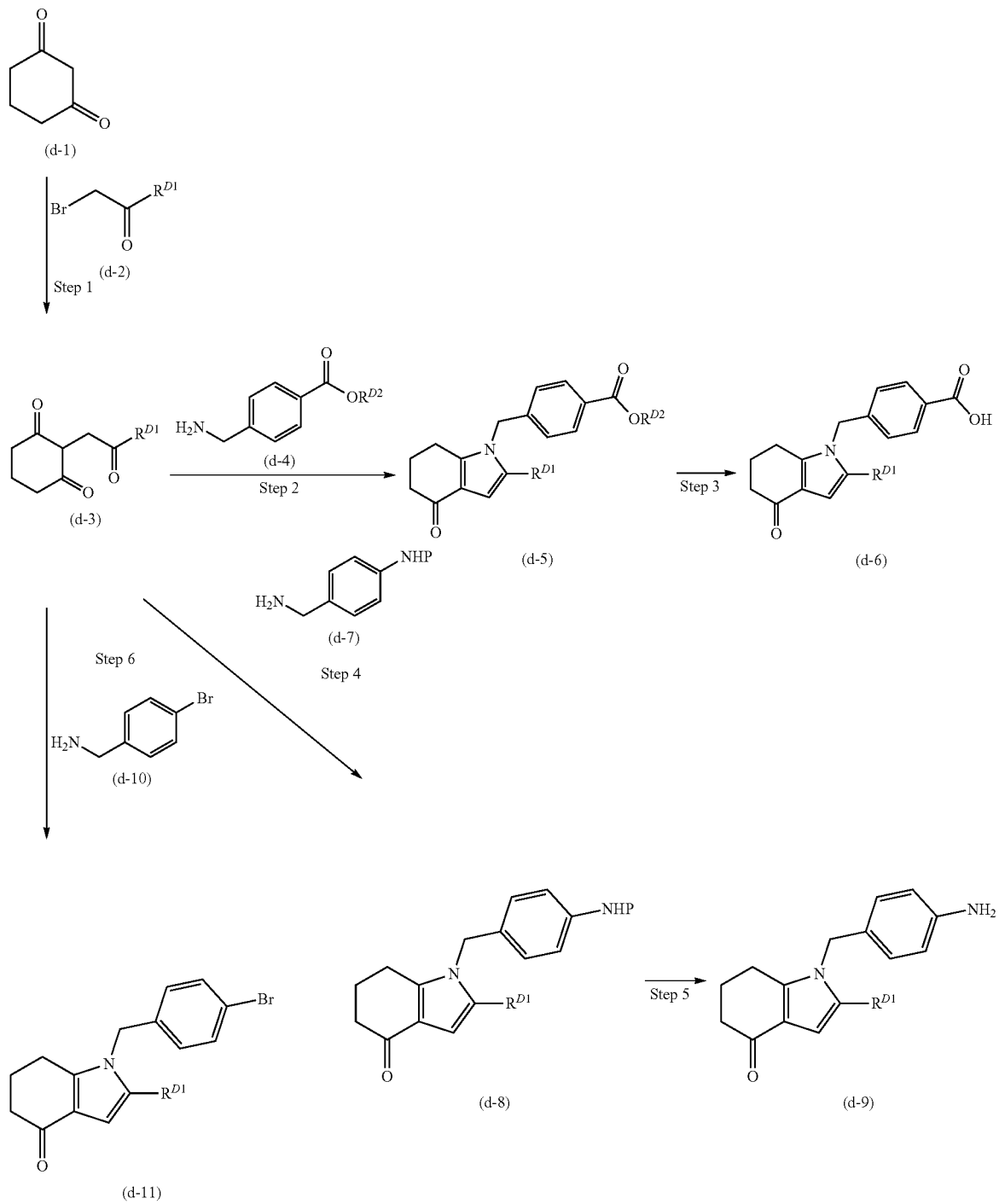

(wherein, $R^{D1}$ is as defined above, $R^{D2}$ represents lower alkyl, and P represents an amine protecting group such as Boc, Cbz, PMB, and the like).

(Step 1)

Compound (d-3) can be manufactured by reacting cyclohexane-1,3-dione and 1 equivalent to 5 equivalents of compound (d-2) in the presence of 1 equivalent to a large excess of base in a solvent at a temperature between −20° C. and the boiling point of the solvent used for 5 minutes to 120 hours.

Examples of the base include sodium hydride, potassium hydride, LDA, lithium bis[trimethylsilyl]amide, sodium bis[trimethylsilyl]amide, sodium methoxide, potassium ethoxide, potassium tert-butoxide, potassium carbonate, sodium hydroxide, DBU, triethylamine, N,N-diisopropylethylamine, and the like.

Examples of the solvent include DMF, DMA, NMP, DMSO, THF, acetonitrile, and the like, and these can be used alone or as a mixture.

Compound (d-2) can be obtained as a commercially available product, or can be obtained by known methods [e.g., Experimental Chemistry Lecture, 5th Edition, Volume 13, p. 374, Maruzen Co., Ltd. (2004) and the like] or methods based thereon.

(Step 2)

The compound (d-5) can be manufactured by reacting compound (d-3) and 1 equivalent to 5 equivalents of compound (d-4) in the presence of 1 equivalent to a large excess of base in a solvent at a temperature between −20° C. and the boiling point of the solvent used for 5 minutes to 120 hours.

Examples of the base include sodium hydride, potassium hydride, LDA, lithium bis[trimethylsilyl]amide, sodium bis[trimethylsilyl]amide, sodium methoxide, potassium ethoxide, potassium tert-butoxide, potassium carbonate, sodium hydroxide, DBU, triethylamine, N,N-diisopropylethylamine, and the like.

Examples of the solvent include toluene, DMF, DMA, NMP, DMSO, THF, acetonitrile, and the like, and these can be used alone or as a mixture.

Compound (d-4) can be obtained as a commercially available product, or can be obtained by known methods [e.g., Experimental Chemistry Lecture, 5th Edition, Volume 14, p. 351, Maruzen Co., Ltd. (2004) and the like] or methods based thereon.

(Step 3)

Compound (d-6) can be manufactured by using compound (d-5) in the same manner as in step 6 of manufacturing method 1.

(Step 4)

Compound (d-8) can be manufactured by using compound (d-3) and 1 equivalent to 5 equivalents of compound (d-7) in the same manner as in step 2.

Compound (d-7) can be obtained as a commercially available product, or can be obtained by known methods [e.g., Experimental Chemistry Lecture, 5th Edition, Volume 14, p. 351, Maruzen Co., Ltd. (2004) and the like] or methods based thereon.

(Step 5)

Compound (d-9) can be manufactured by using compound (d-8) in the same manner as in step 4 of manufacturing method 1.

(Step 6)

Compound (d-11) can be manufactured by using compound (d-3) and 1 equivalent to 5 equivalents of compound (d-10) in the same manner as in step 2.

Compound (d-10) can be obtained as a commercially available product, or can be obtained by known methods [e.g., Experimental Chemistry Lecture, 5th Edition, Volume 14, p. 351, Maruzen Co., Ltd. (2004) and the like] or methods based thereon.

[Manufacturing Method Y5]

Compound (e-1) having a chemical structure represented by formula (E) and having a hydrogen atom bonded to the wavy portion can be obtained in the same manner as in step 4 of manufacturing method 1.

[Manufacturing Method Y6]

Compound (f-5) having a chemical structure represented by formula (F) and having carboxy bonded to the wavy portion can be manufactured according to the following steps:

[Chemical formula 65]

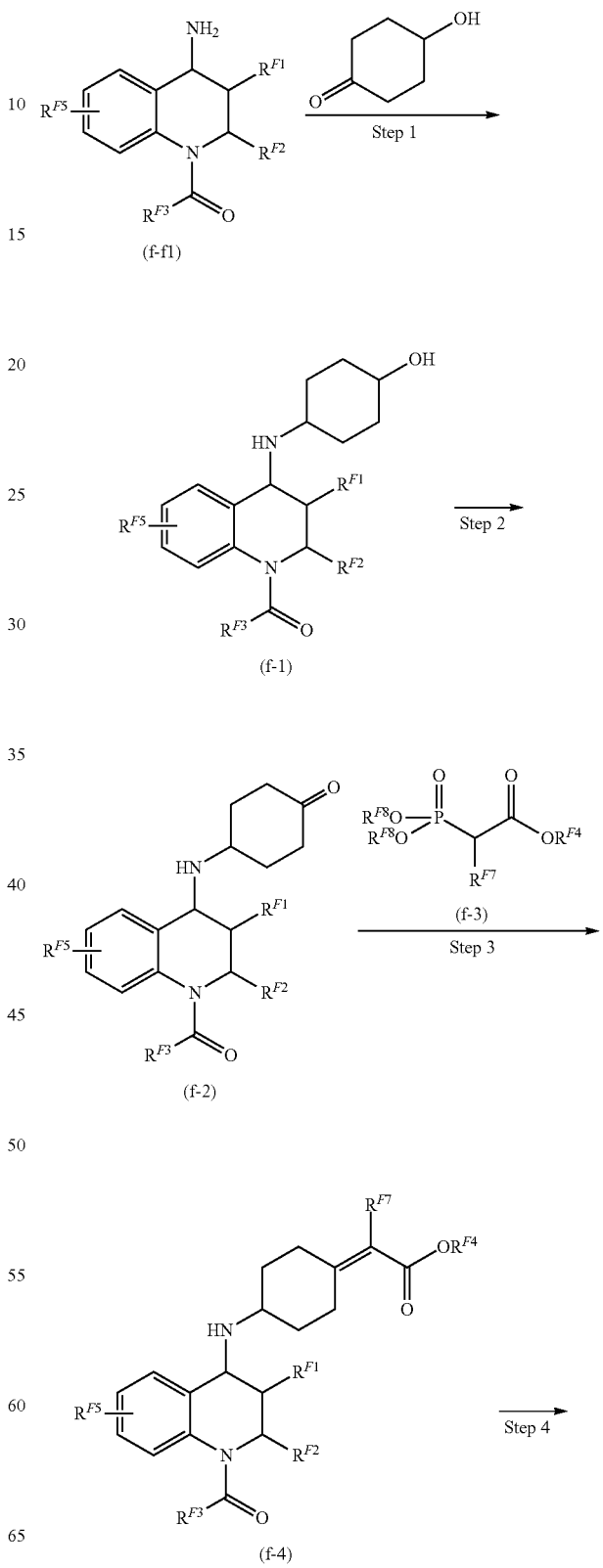

-continued

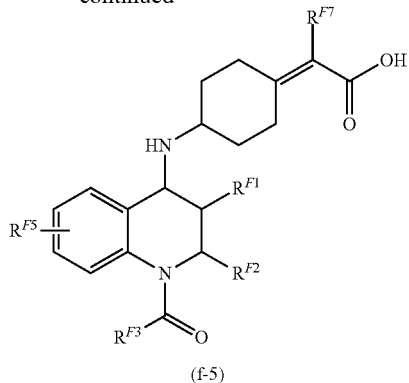

(f-5)

(wherein, $R^{F1}$, $R^{F2}$, $R^{F3}$, $R^{F5}$, and $R^{F7}$ are as defined above, and $R^{F4}$ and $R^{F8}$ each represent lower alkyl).

(Step 1)

Compound (f-1) can be manufactured by using compound (f-f1) and 1 equivalent to 10 equivalents of 4-hydroxycyclohexan-1-one in the same manner as in step 1 of manufacturing method 1-3.

Compound (f-f1) can be obtained in the same manner as in step 4 of manufacturing method 1.

(Step 2)

Compound (f-2) can be manufactured by reacting compound (f-1) in the presence of 1 equivalent to 5 equivalents of oxidizing agent in a solvent at a temperature between −20° C. and the boiling point of the solvent used for 5 minutes to 120 hours.

Examples of the oxidizing agent include Dess-Martin periodinane (DMP), DMSO/oxalyl chloride, sulfur trioxide-pyridine, and the like.

Examples of the solvent include dichloromethane, chloroform, 1,2-dichloroethane, toluene, ethyl acetate, acetonitrile, diethyl ether, THF, DME, 1,4-dioxane, DMF, DMA, NMP, DMSO, and the like, and these can be used alone or as a mixture.

(Step 3)

Compound (f-4) can be manufactured by reacting 1 equivalent to 5 equivalents of compound (f-3) and 1 equivalent to 5 equivalents of base in a solvent at a temperature between −78° C. and the boiling point of the solvent used for 5 minutes to 30 minutes and, subsequently, by adding compound (f-2) to the reaction mixture and reacting the mixture at a temperature between −78° C. and the boiling point of the solvent used for 5 minutes to 120 hours.

Examples of the base include sodium hydride, potassium tert-butoxide, LDA, lithium bis[trimethylsilyl]amide, sodium bis[trimethylsilyl]amide, DBU, and the like.

Examples of the solvent include THF, DME, hexamethylphosphoric triamide (HMPA), and the like, and these can be used alone or as a mixture.

Compound (f-3) can be obtained as a commercially available product, or can be obtained by known methods [e.g., Experimental Chemistry Lecture, 4th Edition, Volume 24, p. 243, Maruzen Co., Ltd. (1994) and the like] or methods based thereon.

(Step 4)

Compound (f-5) can be manufactured by using compound (f-4) in the same manner as in step 6 of manufacturing method 1.

Next, there will be described a manufacturing method of compound (I) by using compounds (a-10), (a-12), (a-14), (a-18), (a-21), (a-23), (a-26), (a-29), (a-32), (a-35), (a-38), (a-41), (b-9), (b-10), (b-11), (b-16), (b-20), (b-24), (c-7), (c-11), (c-14), (d-6), (d-9), (d-11), (e-1), (f-1), and/or (f-5), which are obtained by the above-mentioned manufacturing method 1, manufacturing method 1-2, manufacturing method 1-3, Manufacturing method 1-4, manufacturing method 2, manufacturing method T2, manufacturing method 3, Manufacturing method Y4, manufacturing method 4, or manufacturing method Y6.

Here, compounds (a-10), (a-18), (a-26), (a-35), (b-10), (b-20), (c-7), (c-11), (d-6), and (f-5) shall be collectively represented as L-$CO_2$H (I-1). Similarly, compounds (a-14), (a-21), (a-29), (a-38), (b-11), (b-24), (c-14), and (d-9) shall be represented as L-$NH_2$ (I-2), and a compound in which X represents bromo among compounds (a-12) and (a-23), and compound (b-9), (b-16), and (d-11) shall be represented as L-Br (I-3).

[Manufacturing Method 5]

Among compound (I) in which S is formula (S1), (i) compound (I-13) in which $X^{1b}$ is —NH—C(=O)— and (ii) compound (I-14) in which $X^{1b}$ is —NH—$SO_2$— can be manufactured respectively according to the following steps:

[Chemical formula 66]

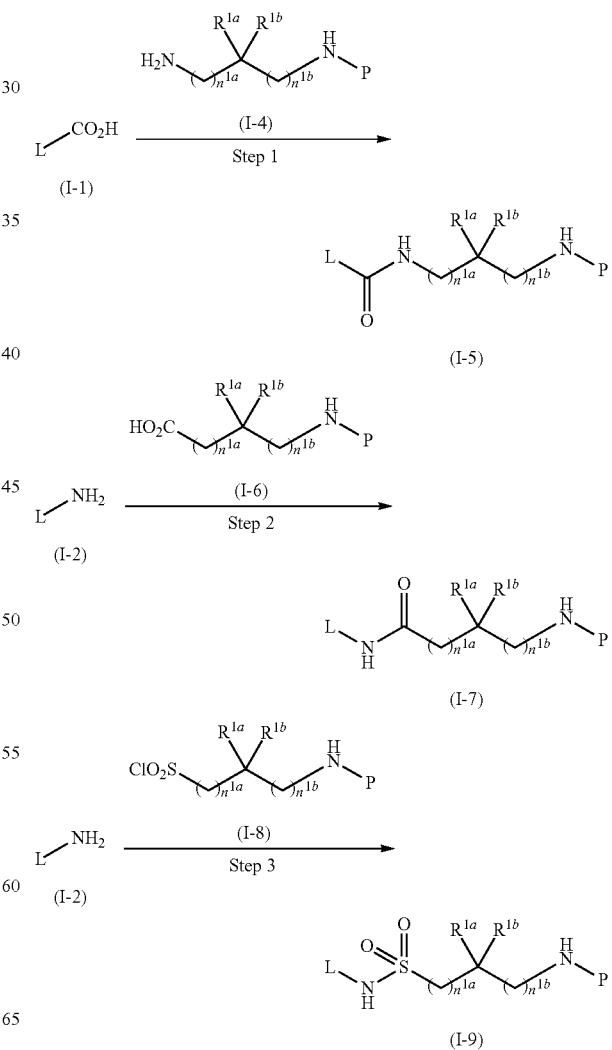

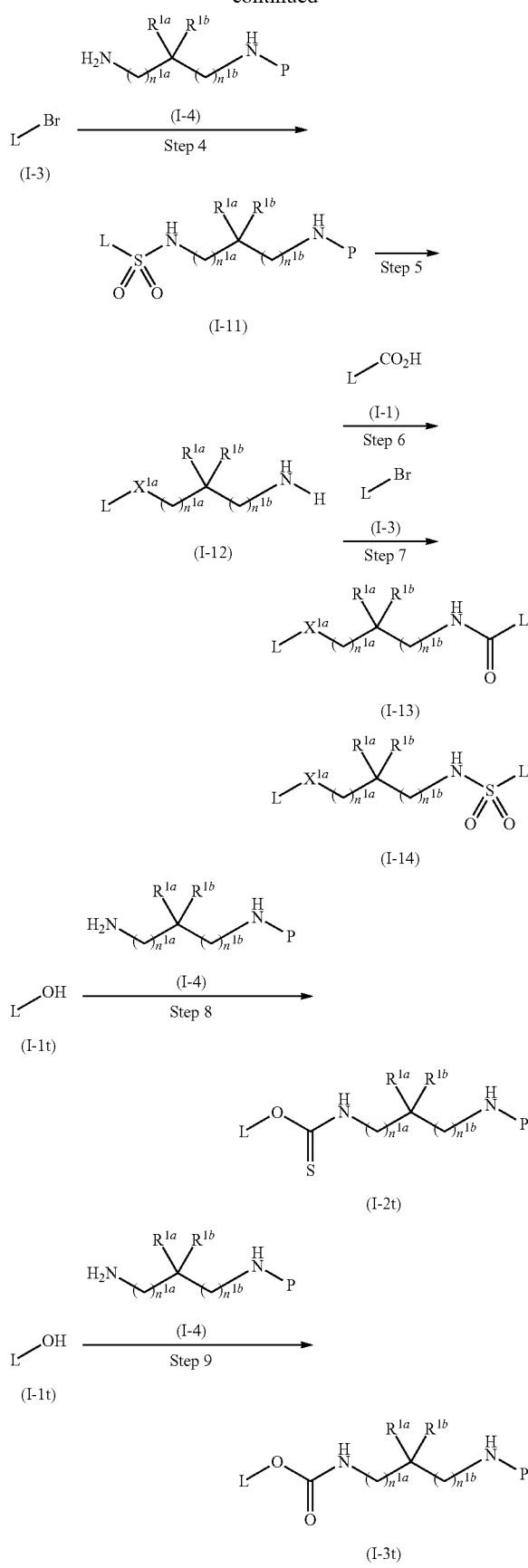

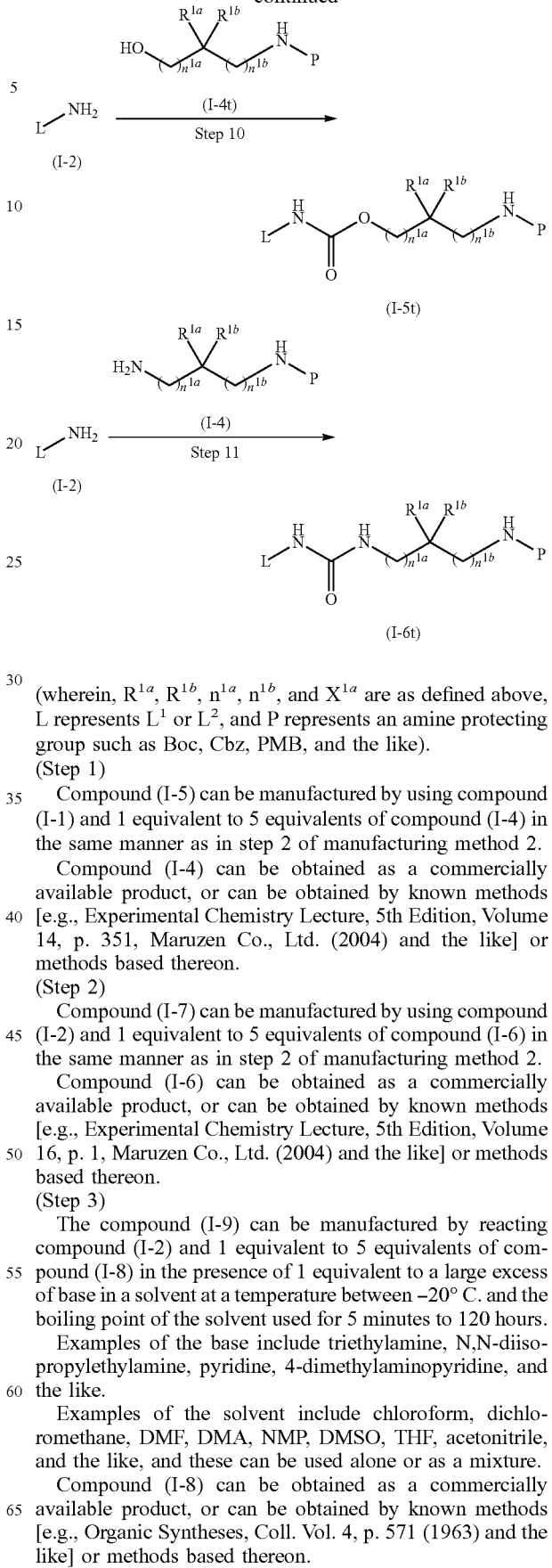

(wherein, $R^{1a}$, $R^{1b}$, $n^{1a}$, $n^{1b}$, and $X^{1a}$ are as defined above, L represents $L^1$ or $L^2$, and P represents an amine protecting group such as Boc, Cbz, PMB, and the like).

(Step 1)

Compound (I-5) can be manufactured by using compound (I-1) and 1 equivalent to 5 equivalents of compound (I-4) in the same manner as in step 2 of manufacturing method 2.

Compound (I-4) can be obtained as a commercially available product, or can be obtained by known methods [e.g., Experimental Chemistry Lecture, 5th Edition, Volume 14, p. 351, Maruzen Co., Ltd. (2004) and the like] or methods based thereon.

(Step 2)

Compound (I-7) can be manufactured by using compound (I-2) and 1 equivalent to 5 equivalents of compound (I-6) in the same manner as in step 2 of manufacturing method 2.

Compound (I-6) can be obtained as a commercially available product, or can be obtained by known methods [e.g., Experimental Chemistry Lecture, 5th Edition, Volume 16, p. 1, Maruzen Co., Ltd. (2004) and the like] or methods based thereon.

(Step 3)

The compound (I-9) can be manufactured by reacting compound (I-2) and 1 equivalent to 5 equivalents of compound (I-8) in the presence of 1 equivalent to a large excess of base in a solvent at a temperature between −20° C. and the boiling point of the solvent used for 5 minutes to 120 hours.

Examples of the base include triethylamine, N,N-diisopropylethylamine, pyridine, 4-dimethylaminopyridine, and the like.

Examples of the solvent include chloroform, dichloromethane, DMF, DMA, NMP, DMSO, THF, acetonitrile, and the like, and these can be used alone or as a mixture.

Compound (I-8) can be obtained as a commercially available product, or can be obtained by known methods [e.g., Organic Syntheses, Coll. Vol. 4, p. 571 (1963) and the like] or methods based thereon.

(Step 4)

Compound (I-11) can be manufactured by (i) reacting compound (I-3) in the presence of 1 equivalent to 5 equivalents of 4-methoxyphenylmethanethiol, 0.001 equivalent to 3 equivalents of palladium catalyst, 0.001 equivalent to 3 equivalents of phosphorus ligand, and 1 equivalent to a large excess of base in a solvent at a temperature between room temperature and the boiling point of the solvent used for 5 minutes to 120 hours, and then, (ii) reacting the obtained compound in the presence of 1 equivalent to 5 equivalents of trichloroisocyanuric acid and 1 equivalent to a large excess of compound (I-4) in a solvent at a temperature between −20° C. and room temperature for 5 minutes to 120 hours.

Examples of the palladium catalyst used in (i) include $Pd_2(dba)_3$ and the like.

Examples of the phosphorus ligand used in (i) include xantphos and the like.

Examples of the base used in (i) include triethylamine, N,N-diisopropylethylamine, pyridine, 4-dimethylaminopyridine, potassium tert-butoxide, sodium carbonate, potassium carbonate, and the like.

Examples of the solvent used in (i) include DMF, DMA, NMP, DMSO, THF, acetonitrile, 1,4-dioxane, and the like, and these can be used alone or as a mixture.

Examples of the solvent used in (ii) include acetonitrile, water, and the like, and these can be used alone or as a mixture.

(Step 5)

Compound (I-12) can be manufactured by using compound (I-5), (I-7), (I-9), (I-11), (I-2t), (I-3t), (I-5t), or (I-6t) in the same manner as in step 4 of manufacturing method 1.

(Step 6)

Compound (I-13) can be manufactured by using compound (I-12) and 1 equivalent to 5 equivalents of compound (I-1) in the same manner as in step 2 of manufacturing method 2.

(Step 7)

Compound (I-14) can be manufactured by using compound (I-12) and 1 equivalent to 5 equivalents of compound (I-3) in the same manner as in step 4 of manufacturing method 5.

(Step 8)

Compound (I-2t) can be manufactured by reacting compound (I-1t), 1 equivalent to 10 equivalents of compound (I-4), and 1 equivalent to 10 equivalents of thiocarbonyl reagent in the presence of 1 equivalent to 10 equivalents of base in a solvent at a temperature between −20° C. and the boiling point of the solvent used for 5 minutes to 120 hours.

Examples of the thiocarbonyl reagent include thiophosgene, 1,1-thiocarbonyldiimidazole, and the like.

Examples of the base include triethylamine, N,N-diisopropylethylamine, pyridine, 4-dimethylaminopyridine, and the like.

Examples of the solvent include dichloromethane, chloroform, 1,2-dichloroethane, toluene, ethyl acetate, acetonitrile, diethyl ether, THF, DMF, NMP, pyridine, and the like, and these are used alone or as a mixture.

As for compound (I-1t), compound (Iy-58) obtained in step 1 of manufacturing method YS12-1 and compound (f-1) obtained in step 1 of manufacturing method Y6 are collectively represented as compound (I-1t).

(Step 9)

Compound (I-3t) can be manufactured by reacting compound (I-1t), 1 equivalent to 10 equivalents of compound (I-4), and 1 equivalent to 10 equivalents of carbonyl reagent in the presence of 1 equivalent to 10 equivalents of base in a solvent at a temperature between −20° C. and the boiling point of the solvent used for 5 minutes to 120 hours.

Examples of the carbonyl reagent include phosgene, 1,1-carbonyldiimidazole (CDI), and the like.

Examples of the base include triethylamine, N,N-diisopropylethylamine, pyridine, 4-dimethylaminopyridine, and the like.

Examples of the solvent include dichloromethane, chloroform, 1,2-dichloroethane, toluene, ethyl acetate, acetonitrile, diethyl ether, THF, DMF, NMP, pyridine, and the like, and these are used alone or as a mixture.

(Step 10)

Compound (I-5t) can be manufactured by using compound (I-2) and 1 equivalent to 10 equivalents of compound (I-4t) in the same manner as in step 9.

Compound (I-4t) can be obtained as a commercially available product, or can be obtained by known methods [e.g., Experimental Chemistry Lecture, 5th Edition, Volume 14, p. 1, Maruzen Co., Ltd. (2004) and the like] or methods based thereon.

(Step 11)

Compound (I-6t) can be manufactured by using compound (I-2) and 1 equivalent to 10 equivalents of compound (I-4) in the same manner as in step 9.

[Manufacturing Method 6]

Among compound (I) in which S is formula (S1), compound (1-24) in which $X^{1b}$ is —C(=O)—NH— can be manufactured according to the following steps:

[Chemical formula 67]

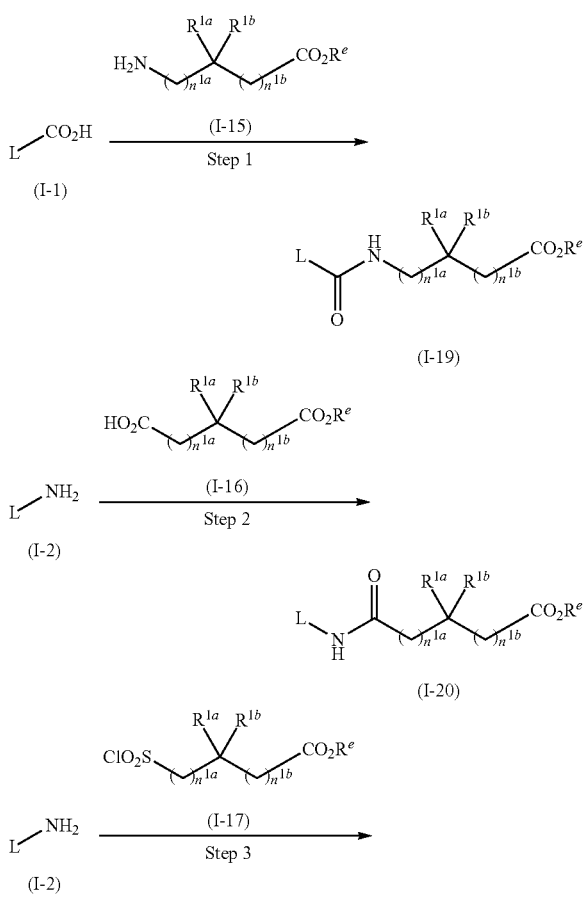

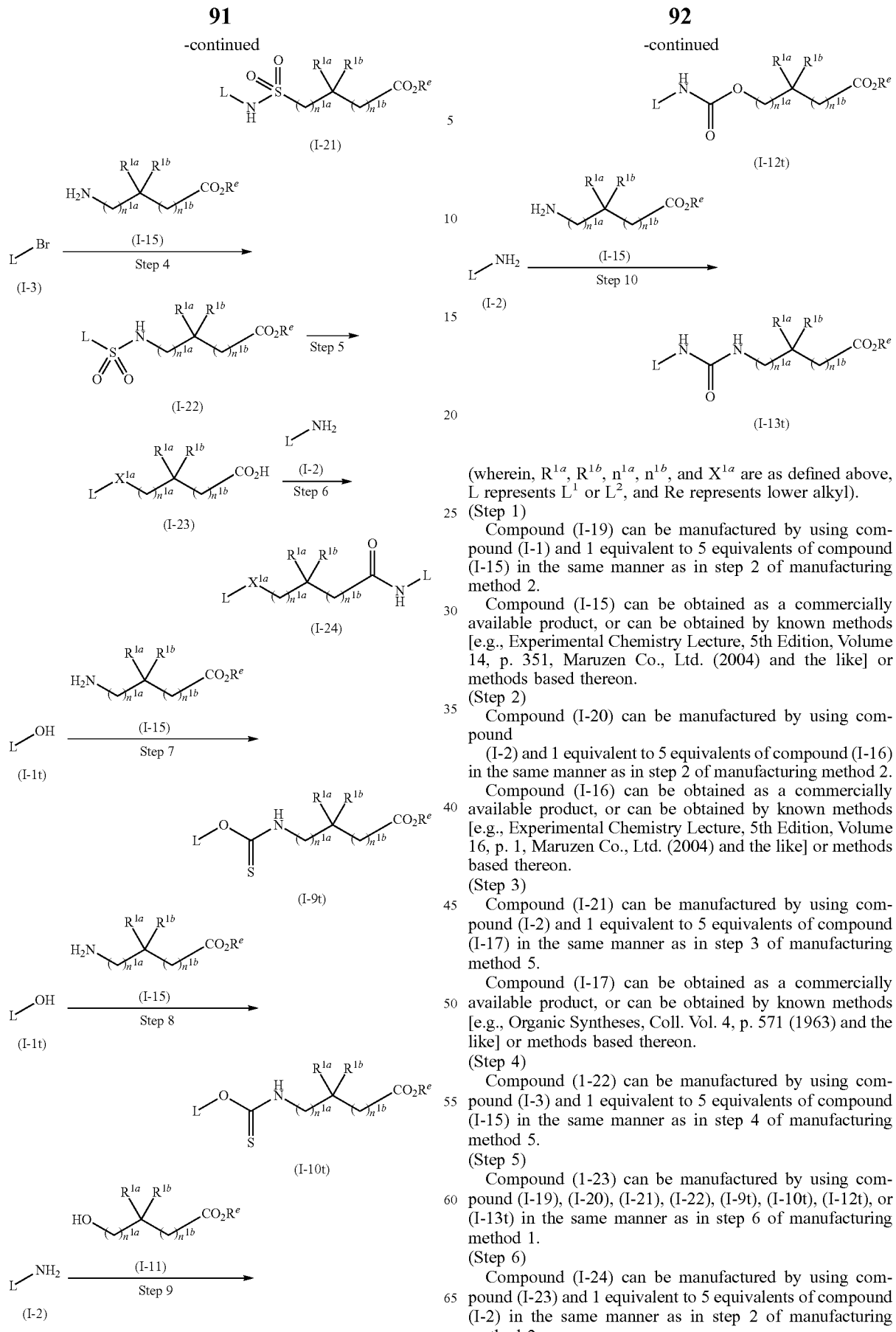

(wherein, $R^{1a}$, $R^{1b}$, $n^{1a}$, $n^{1b}$, and $X^{1a}$ are as defined above, L represents $L^1$ or $L^2$, and Re represents lower alkyl).

(Step 1)

Compound (I-19) can be manufactured by using compound (I-1) and 1 equivalent to 5 equivalents of compound (I-15) in the same manner as in step 2 of manufacturing method 2.

Compound (I-15) can be obtained as a commercially available product, or can be obtained by known methods [e.g., Experimental Chemistry Lecture, 5th Edition, Volume 14, p. 351, Maruzen Co., Ltd. (2004) and the like] or methods based thereon.

(Step 2)

Compound (I-20) can be manufactured by using compound (I-2) and 1 equivalent to 5 equivalents of compound (I-16) in the same manner as in step 2 of manufacturing method 2.

Compound (I-16) can be obtained as a commercially available product, or can be obtained by known methods [e.g., Experimental Chemistry Lecture, 5th Edition, Volume 16, p. 1, Maruzen Co., Ltd. (2004) and the like] or methods based thereon.

(Step 3)

Compound (I-21) can be manufactured by using compound (I-2) and 1 equivalent to 5 equivalents of compound (I-17) in the same manner as in step 3 of manufacturing method 5.

Compound (I-17) can be obtained as a commercially available product, or can be obtained by known methods [e.g., Organic Syntheses, Coll. Vol. 4, p. 571 (1963) and the like] or methods based thereon.

(Step 4)

Compound (1-22) can be manufactured by using compound (1-3) and 1 equivalent to 5 equivalents of compound (I-15) in the same manner as in step 4 of manufacturing method 5.

(Step 5)

Compound (1-23) can be manufactured by using compound (1-19), (I-20), (I-21), (I-22), (I-9t), (I-10t), (I-12t), or (I-13t) in the same manner as in step 6 of manufacturing method 1.

(Step 6)

Compound (I-24) can be manufactured by using compound (I-23) and 1 equivalent to 5 equivalents of compound (I-2) in the same manner as in step 2 of manufacturing method 2.

(Step 7)

Compound (I-9t) can be manufactured by using compound (I-1t) and 1 equivalent to 10 equivalents of compound (I-15) in the same manner as in step 8 of manufacturing method 5.

(Step 8)

Compound (I-10t) can be manufactured by using compound (I-2t) and 1 equivalent to 10 equivalents of compound (I-15) in the same manner as in step 9 of manufacturing method 5.

(Step 9)

Compound (I-12t) can be manufactured by using compound (I-2) and 1 equivalent to 10 equivalents of compound (I-11t) in the same manner as in step 9 of manufacturing method 5.

Compound (I-11t) can be obtained as a commercially available product, or can be obtained by known methods [e.g., Experimental Chemistry Lecture, 5th Edition, Volume 14, p. 1, Maruzen Co., Ltd. (2004) and the like] or methods based thereon.

(Step 10)

Compound (I-13t) can be manufactured by using compound (I-2) and 1 equivalent to 10 equivalents of compound (I-15) in the same manner as in step 9 of manufacturing method 5.

[Manufacturing Method 7]

Among compound (I) in which S is formula (S1), under the condition that $X^{1b}$ is —$SO_2$—NH—, (i) compound (I-16t) in which $X^{1a}$ is —C(=O)—NH—, (ii) compound (I-17t) in which $X^{1a}$ is —$SO_2$—NH—, (iii) compound (I-18t) in which $X^{1a}$ is —O—C(=S)—NH—, (iv) compound (I-19t) in which $X^{1a}$ is —O—C(=O)—NH—, (v) compound (I-20t) in which $X^{1a}$ is —NH—C(=O)—NH—, (vi) compound (I-21t) in which $X^{1a}$ is —NH—C(=O)—, and (vii) compound (I-22t) in which $X^{1a}$ is —NH—C(=O)—O— can be manufactured respectively according to the following steps:

[Chemical formula 68]

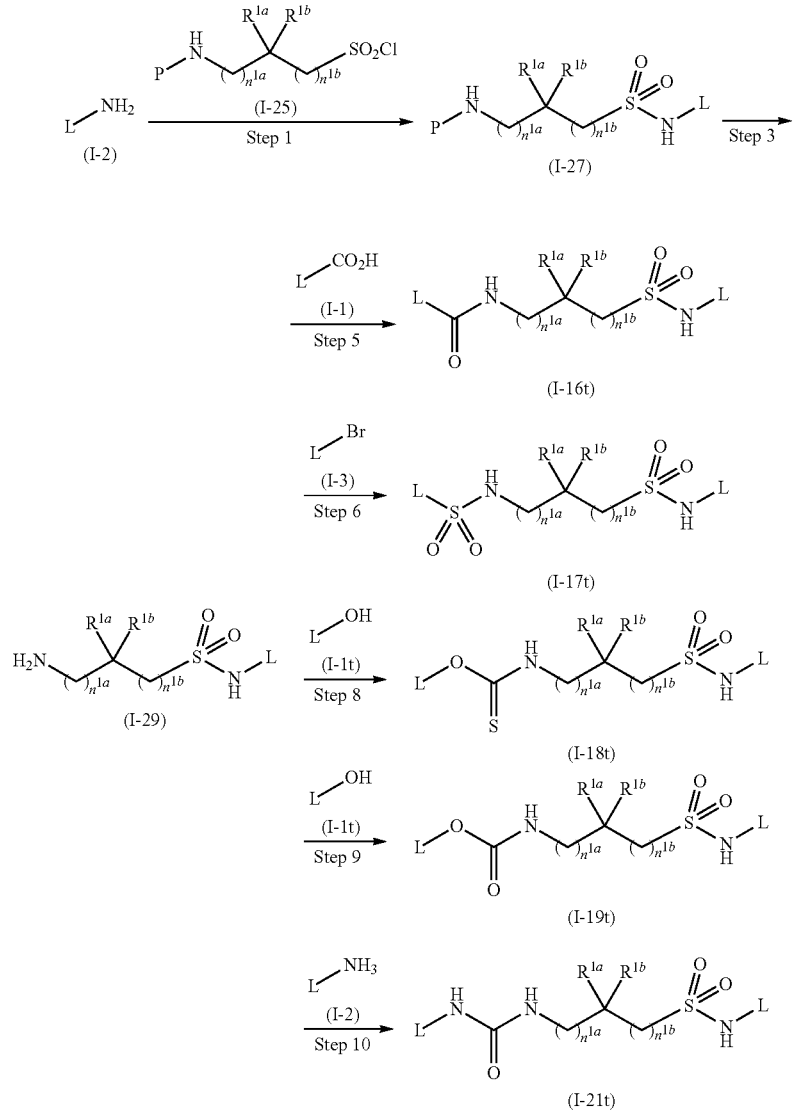

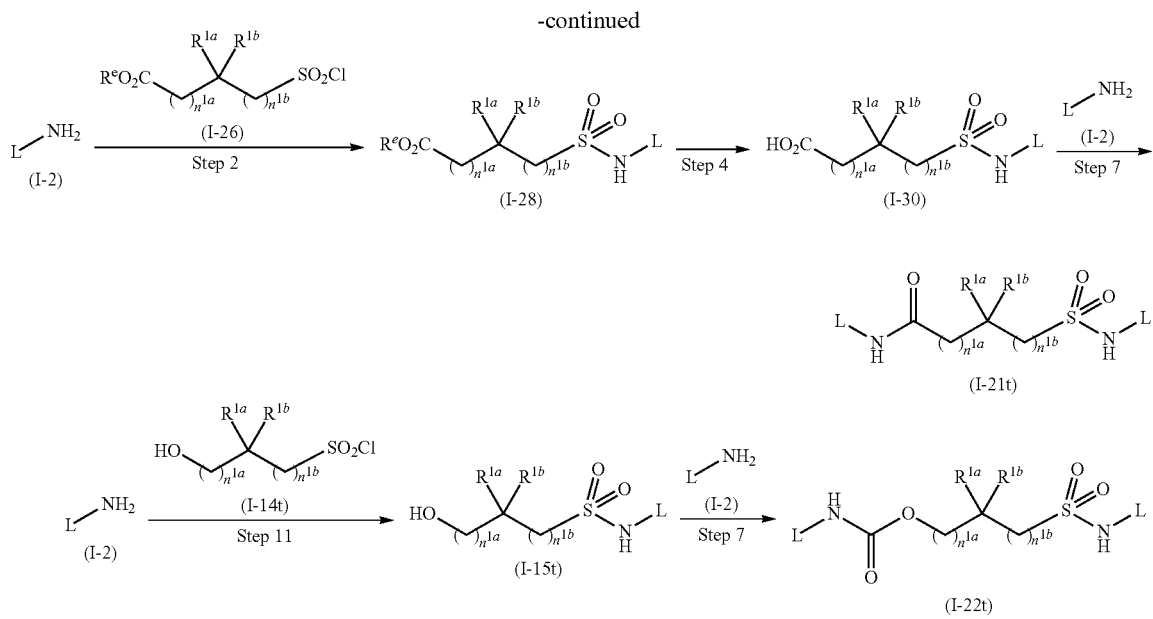

(wherein, $R^{1a}$, $R^{1b}$, $n^{1a}$, and $n^{1b}$ are as defined above, L represents $L^1$ or $L^2$, $R^e$ represents lower alkyl, and P represents an amine protecting group such as Boc, Cbz, PMB, and the like).

(Step 1)

Compound (I-27) can be manufactured by using compound (I-2) and 1 equivalent to 5 equivalents of compound (I-25) in the same manner as in step 3 of manufacturing method 5.

Compound (I-25) can be obtained as a commercially available product, or can be obtained by known methods [e.g., Organic Syntheses, Coll. Vol. 4, p. 571 (1963) and the like] or methods based thereon.

(Step 2)

Compound (I-28) can be manufactured by using compound (I-2) and 1 equivalent to 5 equivalents of compound (I-26) in the same manner as in step 3 of manufacturing method 5.

Compound (I-26) can be obtained as a commercially available product, or can be obtained by known methods [e.g., Organic Syntheses, Coll. Vol. 4, p. 571 (1963) and the like] or methods based thereon.

(Step 3)

Compound (I-29) can be manufactured by using compound (I-27) in the same manner as in step 4 of manufacturing method 1.

(Step 4)

Compound (I-30) can be manufactured by using compound (I-28) in the same manner as in step 6 of manufacturing method 1.

(Step 5)

Compound (I-16t) can be manufactured by using compound (I-29) and 1 equivalent to 5 equivalents of compound (I-1) in the same manner as in step 2 of manufacturing method 2.

(Step 6)

Compound (I-17t) can be manufactured by using compound (I-29) and 1 equivalent to 5 equivalents of compound (I-3) in the same manner as in step 4 of manufacturing method 5.

(Step 7)

Compound (I-21t) can be manufactured by using compound (I-30) and 1 equivalent to 5 equivalents of compound (I-2) in the same manner as in step 2 of manufacturing method 2.

(Step 8)

Compound (I-18t) can be manufactured by using compound (I-29) and 1 equivalent to 5 equivalents of compound (I-1t) in the same manner as in step 8 of manufacturing method 5.

(Step 9)

Compound (I-19t) can be manufactured by using compound (I-29) and 1 equivalent to 5 equivalents of compound (I-1t) in the same manner as in step 9 of manufacturing method 5.

(Step 10)

Compound (I-20t) can be manufactured by using compound (I-29) and 1 equivalent to 5 equivalents of compound (I-2) in the same manner as in step 9 of manufacturing method 5.

(Step 11)

Compound (I-15t) can be manufactured by using compound (I-2) and 1 equivalent to 5 equivalents of compound (I-14t) in the same manner as in step 3 of manufacturing method 5.

Compound (I-14t) can be obtained as a commercially available product, or can be obtained by known methods [e.g., Organic Syntheses, Coll. Vol. 4, p. 571 (1963) and the like] or methods based thereon.

(Step 12)

Compound (I-22t) can be manufactured by using compound (I-15t) and 1 equivalent to 5 equivalents of compound (I-2) in the same manner as in step 9 of manufacturing method 5.

[Manufacturing Method 8]

Among compound (I) in which S is formula (S2), under the condition that $Z^2$ is CH, (i) compound (I-41) in which $X^{2b}$ is —NH—C(=O)— and (ii) compound (I-42) in which $X^{2b}$ is —NH—SO₂— can be manufactured respectively according to the following steps:

[Chemical formula 69]

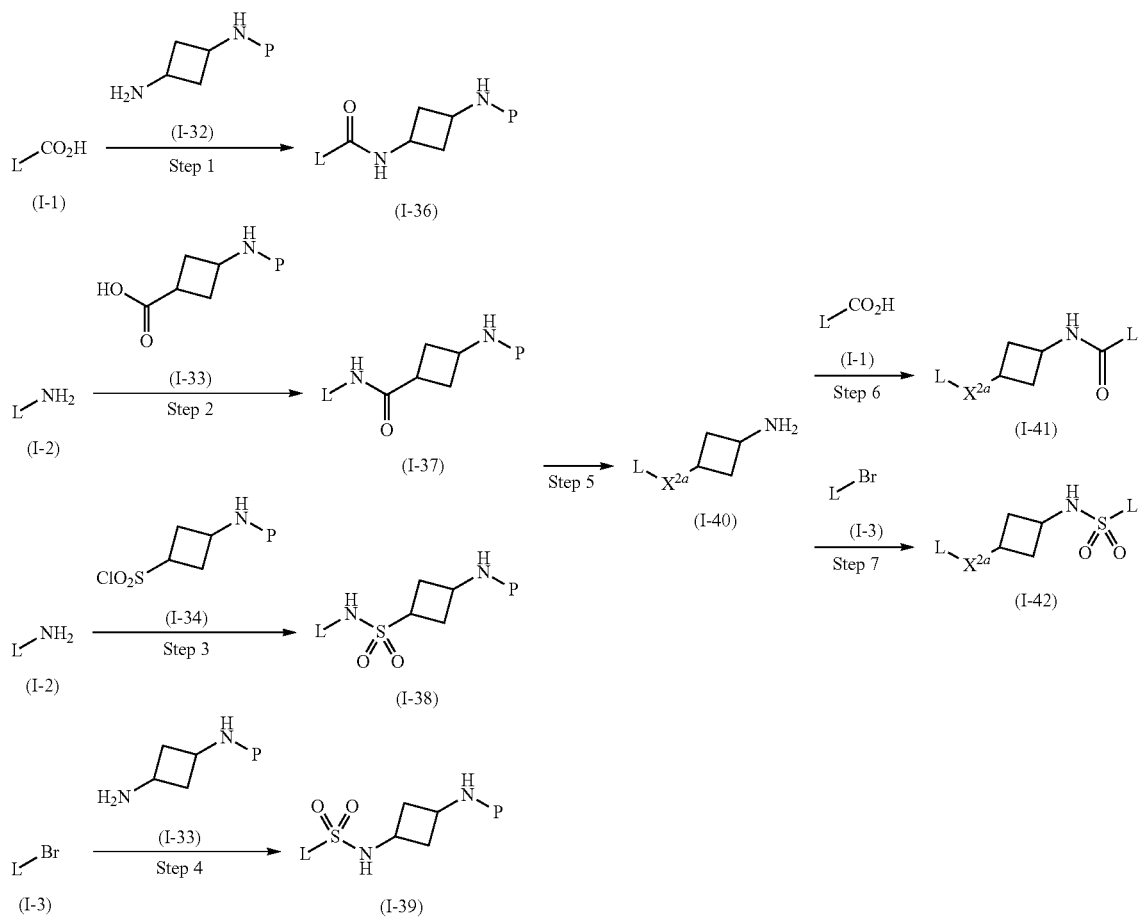

(wherein, $X^{2a}$ is as defined above, L represents $L^1$ or $L^2$, and P represents an amine protecting group such as Boc, Cbz, PMB, and the like).

(Step 1)

Compound (I-36) can be manufactured by using compound (I-1) and 1 equivalent to 5 equivalents of compound (I-32) in the same manner as in step 2 of manufacturing method 2.

Compound (I-32) can be obtained as a commercially available product, or can be obtained by known methods [e.g., Experimental Chemistry Lecture, 5th Edition, Volume 14, p. 351, Maruzen Co., Ltd. (2004) and the like] or methods based thereon.

(Step 2)

Compound (I-37) can be manufactured by using compound (I-2) and 1 equivalent to 5 equivalents of compound (I-33) in the same manner as in step 2 of manufacturing method 2.

Compound (I-33) can be obtained as a commercially available product, or can be obtained by known methods [e.g., Experimental Chemistry Lecture, 5th Edition, Volume 16, p. 1, Maruzen Co., Ltd. (2004) and the like] or methods based thereon.

(Step 3)

Compound (I-38) can be manufactured by using compound (I-2) and 1 equivalent to 5 equivalents of compound (I-34) in the same manner as in step 3 of manufacturing method 5.

Compound (I-34) can be obtained as a commercially available product, or can be obtained by known methods [e.g., Organic Syntheses, Coll. Vol. 4, p. 571 (1963) and the like] or methods based thereon.

(Step 4)

Compound (I-39) can be manufactured by using compound (I-3) and 1 equivalent to 5 equivalents of compound (I-32) in the same manner as in step 4 of manufacturing method 5.

(Step 5)

Compound (I-40) can be manufactured by using compound (I-36), (I-37), (I-38), or (I-39) in the same manner as in step 4 of manufacturing method 1.

(Step 6)

Compound (I-41) can be manufactured by using compound (I-40) and 1 equivalent to 5 equivalents of compound (I-1) in the same manner as in step 2 of manufacturing method 2.

(Step 7)

Compound (I-42) can be manufactured by using compound (I-40) and 1 equivalent to 5 equivalents of compound (I-3) in the same manner as in step 4 of manufacturing method 5.

[Manufacturing Method 9]

Among compound (I) in which S is formula (S2), compound (I-52) in which $Z^2$ is CH and $X^{2b}$ is —C(=O)—NH— can be manufactured according to the following steps:

[Chemical formula 70]

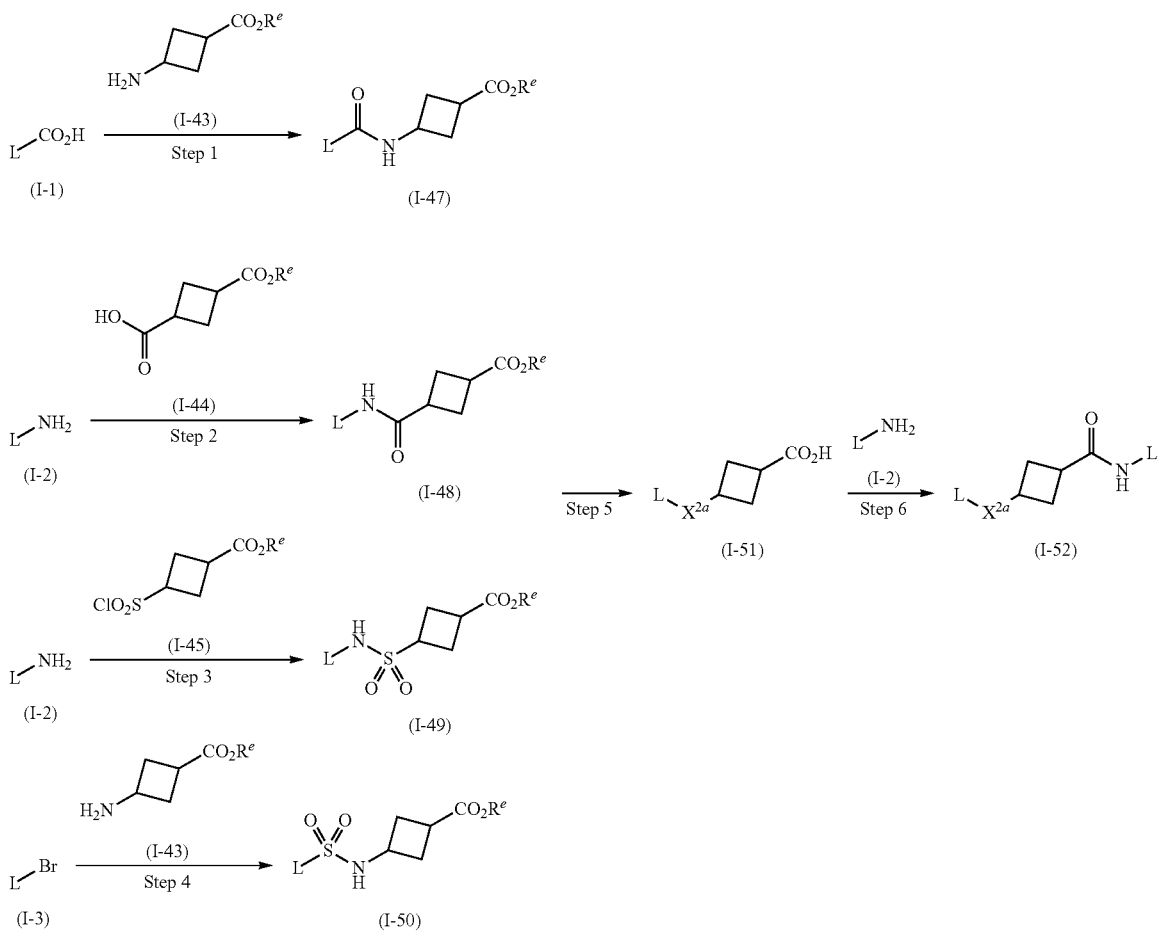

(wherein, $X^{2a}$ is as defined above, L represents $L^1$ or $L^2$, and $R^e$ represents lower alkyl).

(Step 1)

Compound (I-47) can be manufactured by using compound (I-1) and 1 equivalent to 5 equivalents of compound (I-43) in the same manner as in step 2 of manufacturing method 2.

Compound (I-43) can be obtained as a commercially available product, or can be obtained by known methods [e.g., Experimental Chemistry Lecture, 5th Edition, Volume 14, p. 351, Maruzen Co., Ltd. (2004) and the like] or methods based thereon.

(Step 2)

Compound (I-48) can be manufactured by using compound (I-2) and 1 equivalent to 5 equivalents of compound (I-44) in the same manner as in step 2 of manufacturing method 2.

Compound (I-44) can be obtained as a commercially available product, or can be obtained by known methods [e.g., Experimental Chemistry Lecture, 5th Edition, Volume 16, p. 1, Maruzen Co., Ltd. (2004) and the like] or methods based thereon.

(Step 3)

Compound (I-49) can be manufactured by using compound (I-2) and 1 equivalent to 5 equivalents of compound (I-45) in the same manner as in step 3 of manufacturing method 5.

Compound (I-45) can be obtained as a commercially available product, or can be obtained by known methods [e.g., Organic Syntheses, Coll. Vol. 4, p. 571 (1963) and the like] or methods based thereon.

(Step 4)

Compound (I-50) can be manufactured by using compound (I-3) and 1 equivalent to 5 equivalents of compound (I-43) in the same manner as in step 4 of manufacturing method 5.

(Step 5)

Compound (I-51) can be manufactured by using compound (I-47), (I-48), (I-49), or (I-50) in the same manner as in step 6 of manufacturing method 1.

(Step 6)

Compound (I-52) can be manufactured by using compound (I-51) and 1 equivalent to 5 equivalents of compound (I-2) in the same manner as in step 2 of manufacturing method 2.

[Manufacturing Method 10]

Among compound (I) in which S is formula (S2), compound (I-59) in which $Z^2$ is CH and $X^{2b}$ is —$SO_2$—NH— can be manufactured according to the following steps:

[Chemical formula 71]

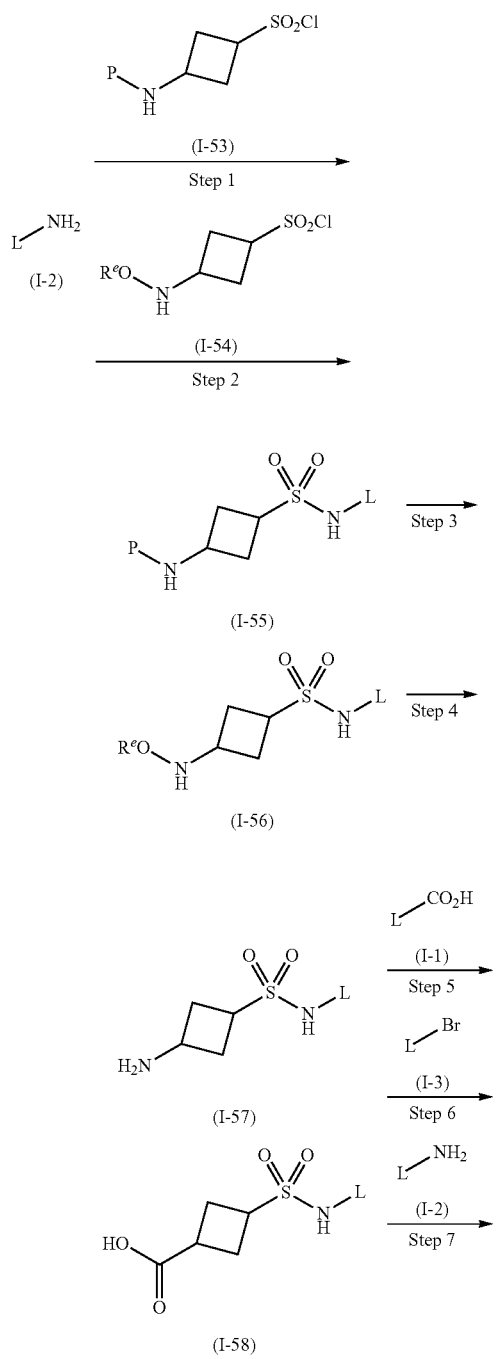

(wherein, $X^{2a}$ is as defined above, L represents $L^1$ or $L^2$, $R^e$ represents lower alkyl, and P represents an amine protecting group such as Boc, Cbz, PMB, and the like).

(Step 1)

Compound (I-55) can be manufactured by using compound (I-2) and 1 equivalent to 5 equivalents of compound (I-53) in the same manner as in step 3 of manufacturing method 5.

Compound (I-53) can be obtained as a commercially available product, or can be obtained by known methods [e.g., Organic Syntheses, Coll. Vol. 4, p. 571 (1963) and the like] or methods based thereon.

(Step 2)

Compound (I-56) can be manufactured by using compound (I-2) and 1 equivalent to 5 equivalents of compound (I-54) in the same manner as in step 3 of manufacturing method 5.

Compound (I-54) can be obtained as a commercially available product, or can be obtained by known methods [e.g., Organic Syntheses, Coll. Vol. 4, p. 571 (1963) and the like] or methods based thereon.

(Step 3)

Compound (I-57) can be manufactured by using compound (I-55) in the same manner as in step 4 of manufacturing method 1.

(Step 4)

Compound (I-58) can be manufactured by using compound (I-56) in the same manner as in step 6 of manufacturing method 1.

(Step 5)

Among compound (I-59), a compound in which $X^2a$ is —C(=O)—NH— can be manufactured by using compound (I-57) and 1 equivalent to 5 equivalents of compound (I-1) in the same manner as in step 2 of manufacturing method 2.

(Step 6)

Among compound (I-59), a compound in which $X^2a$ is —$SO_2$—NH— can be manufactured by using compound (I-57) and 1 equivalent to 5 equivalents of compound (I-3) in the same manner as in step 4 of manufacturing method 5.

(Step 7)

Among compound (I-59), a compound in which $X^2a$ is —NH—C(=O)— can be manufactured by using compound (I-58) and 1 equivalent to 5 equivalents of compound (I-2) in the same manner as in step 2 of manufacturing method 2.

[Manufacturing Method YS2]

In compound (I) in which S is formula (S2), under the condition that $Z^2$ is N, (i) compound (I-31t) in which $X^{2b}$ is —C(=O)—NH— and (ii) compound (I-32t) in which $X^{2b}$ is —$CH_2$— can be manufactured according to the following steps:

[Chemical formula 72]

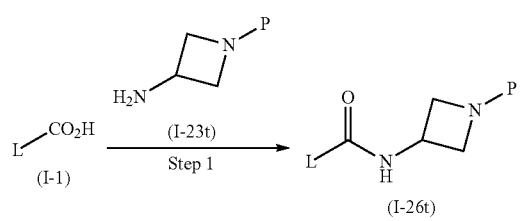

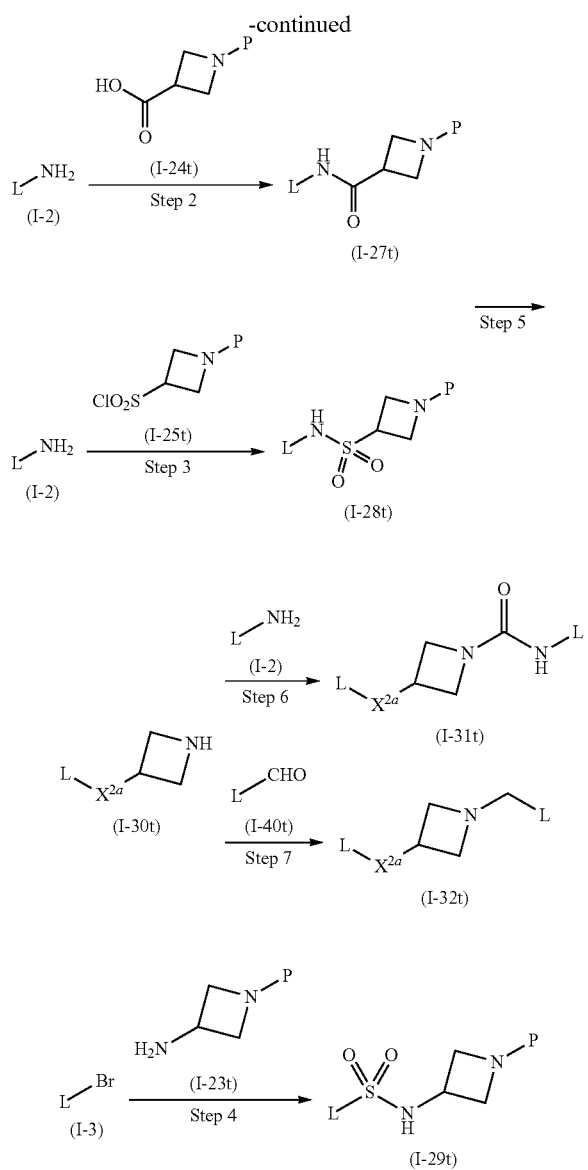

(wherein, $X^{2a}$ is as defined above, L represents $L^1$ or $L^2$, and P represents an amine protecting group such as Boc, Cbz, PMB, and the like).

(Step 1)

Compound (I-26t) can be manufactured by using compound (I-1) and 1 equivalent to 10 equivalents of compound (I-23t) in the same manner as in step 2 of manufacturing method 2.

Compound (I-23t) can be obtained as a commercially available product, or can be obtained by known methods [e.g., Experimental Chemistry Lecture, 5th Edition, Volume 14, p. 351, Maruzen Co., Ltd. (2004) and the like] or methods based thereon.

(Step 2)

Compound (I-27t) can be manufactured by using compound (I-2) and 1 equivalent to 10 equivalents of compound (I-24t) in the same manner as in step 2 of manufacturing method 2.

Compound (I-24t) can be obtained as a commercially available product, or can be obtained by known methods [e.g., Experimental Chemistry Lecture, 5th Edition, Volume 16, p. 1, Maruzen Co., Ltd. (2004) and the like] or methods based thereon.

(Step 3)

Compound (I-28t) can be manufactured by using compound (I-2) and 1 equivalent to 10 equivalents of compound (I-25t) in the same manner as in step 3 of manufacturing method 5.

Compound (I-25t) can be obtained as a commercially available product, or can be obtained by known methods [e.g., Organic Syntheses, Coll. Vol. 4, p. 571 (1963) and the like] or methods based thereon.

(Step 4)

Compound (I-29t) can be manufactured by using compound (I-3) and 1 equivalent to 10 equivalents of compound (I-23t) in the same manner as in step 4 of manufacturing method 5.

(Step 5)

Compound (I-30t) can be manufactured using compound (I-26t), compound (I-27t), compound (I-28t), or compound (I-29t) in the same manner as in step 4 of manufacturing method 1.

(Step 6)

Compound (I-31t) can be manufactured by using compound (I-30t) and 1 equivalent to 5 equivalents of compound (I-2) in the same manner as in step 9 of manufacturing method 5.

(Step 7)

Compound (I-32t) can be manufactured by using compound (I-30t) and 1 equivalent to 5 equivalents of compound (I-40t) in the same manner as in step 1 of manufacturing method 1-3.

Compound (I-40t) can be obtained according to step 10 of manufacturing method 17.

[Manufacturing Method 11]

Among compound (I) in which S is formula (S3), compound (I-63) in which $Z^3$ is CH and $X^3$ is $X^{3a}$ can be manufactured according to the following steps:

[Chemical formula 73]

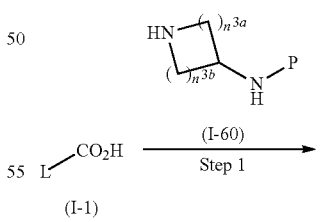

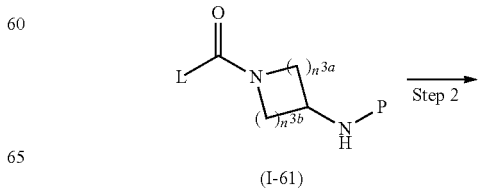

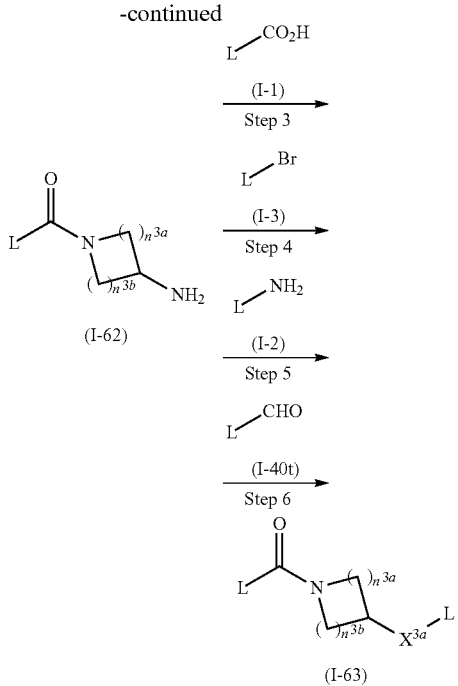

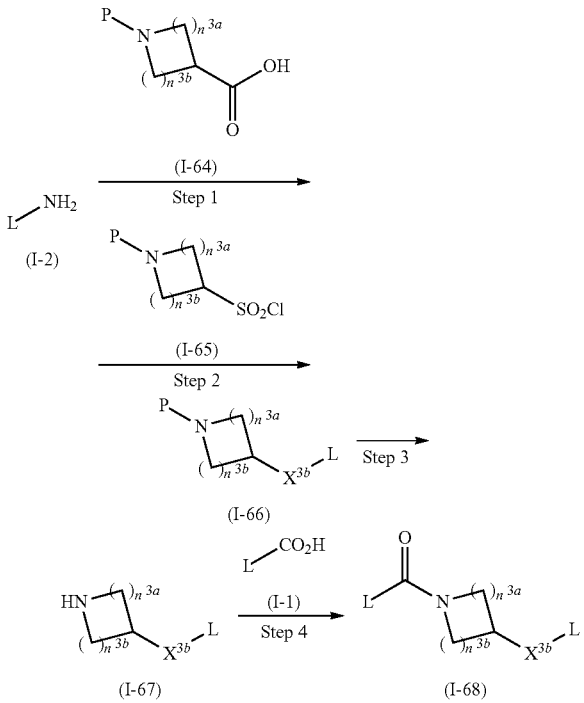

(wherein, $n^{3a}$ and $n^{3b}$ are as defined above, L represents $L^1$ or $L^2$, $X^{3a}$ represents —NH—C(=O)—, —NH—SO$_2$—, —NH—C(=O)—NH—, or —NHCH$_2$—, and P represents an amine protecting group such as Boc, Cbz, PMB, and the like).

(Step 1)

Compound (I-61) can be manufactured by using compound (I-1) and 1 equivalent to 5 equivalents of compound (I-60) in the same manner as in step 2 of manufacturing method 2.

Compound (I-60) can be obtained as a commercially available product, or can be obtained by known methods [e.g., Experimental Chemistry Lecture, 5th Edition, Volume 14, p. 351, Maruzen Co., Ltd. (2004) and the like] or methods based thereon.

(Step 2)

Compound (I-62) can be manufactured by using compound (I-61) in the same manner as in step 4 of manufacturing method 1.

(Step 3)

Among compound (I-63), a compound in which $X^3a$ is —NH—C(=O)— can be manufactured by using compound (I-62) and 1 equivalent to 5 equivalents of compound (I-1) in the same manner as in step 2 of manufacturing method 2.

(Step 4)

Among compound (I-63), a compound in which $X^{3a}$ is —NH—SO$_2$— can be manufactured by using compound (I-62) and 1 equivalent to 5 equivalents of compound (I-3) in the same manner as in step 4 of manufacturing method 5.

(Step 5)

Among compound (I-63), a compound in which $X^3a$ is —NH—C(=O)—NH— can be manufactured by using compound (I-62) and 1 equivalent to 5 equivalents of compound (I-2) in the same manner as in step 9 of manufacturing method 5.

(Step 6)

Among compound (I-63), a compound in which $X^3a$ is —NHCH$_2$— can be manufactured by using compound (I-62) and 1 equivalent to 5 equivalents of compound (I-40t) in the same manner as in step 1 of manufacturing method 1-3.

[Manufacturing Method 12]

Among compound (I) in which S is formula (S3), compound (I-68) in which $Z^3$ is CH and $X^3$ is $X^{3b}$ can be manufactured according to the following steps:

[Chemical formula 74]

(wherein, $n^{3a}$ and $n^{3b}$ are as defined above, L represents $L^1$ or $L^2$, $X^{3b}$ represents —C(=O)—NH— or —SO$_2$—NH—, and P represents an amine protecting group such as Boc, Cbz, PMB, and the like).

(Step 1)

Among compound (I-66), a compound in which $X^3b$ is —C(=O)—NH— can be manufactured by using compound (I-2) and 1 equivalent to 5 equivalents of compound (I-64) in the same manner as in step 2 of manufacturing method 2.

Compound (I-64) can be obtained as a commercially available product, or can be obtained by known methods [e.g., Experimental Chemistry Lecture, 5th Edition, Volume 16, p. 1, Maruzen Co., Ltd. (2004) and the like] or methods based thereon.

(Step 2)

Among compound (I-66), a compound in which $X^{3b}$ is —SO$_2$—NH— can be manufactured by using compound (I-2) and 1 equivalent to 5 equivalents of compound (I-65) in the same manner as in step 3 of manufacturing method 5.

Compound (I-65) can be obtained as a commercially available product, or can be obtained by known methods [e.g., Organic Syntheses, Coll. Vol. 4, p. 571 (1963) and the like] or methods based thereon.

(Step 3)

Compound (I-67) can be manufactured by using compound (I-66) in the same manner as in step 4 of manufacturing method 1.

(Step 4)

Compound (I-68) can be manufactured by using compound (I-67) and 1 equivalent to 5 equivalents of compound (I-1) in the same manner as in step 2 of manufacturing method 2.

[Manufacturing Method YS3]

Among compound (I) in which S is formula (S3), compound (I-35t) in which $Z^3$ is N, $X^3$ is —C(=O)—NH—, and $n^{3a}$ and $n^{3b}$ are 2 can be manufactured according to the following steps:

[Chemical formula 75]

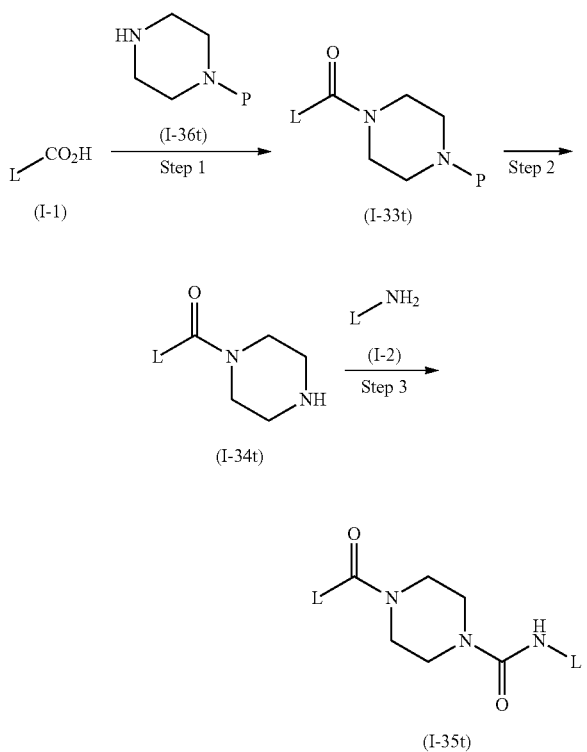

(wherein, L represents $L^1$ or $L^2$, and P represents an amine protecting group such as Boc, Cbz, PMB, and the like).

(Step 1)

Compound (I-33t) can be manufactured by using compound (I-1) and 1 equivalent to 10 equivalents of compound (I-36t) in the same manner as in step 2 of manufacturing method 2.

Compound (I-36t) can be obtained as a commercially available product, or can be obtained by known methods [e.g., Experimental Chemistry Lecture, 5th Edition, Volume 14, p. 351, Maruzen Co., Ltd. (2004) and the like] or methods based thereon.

(Step 2)

Compound (I-34t) can be manufactured by using compound (I-33t) in the same manner as in step 4 of manufacturing method 1.

(Step 3)

Compound (I-35t) can be manufactured by using compound (I-34t) and 1 equivalent to 5 equivalents of compound (I-2) in the same manner as in step 9 of manufacturing method 5.

[Manufacturing Method 13]

Compound (I) in which S is formula (S4) can be manufactured according to the following steps:

[Chemical formula 76]

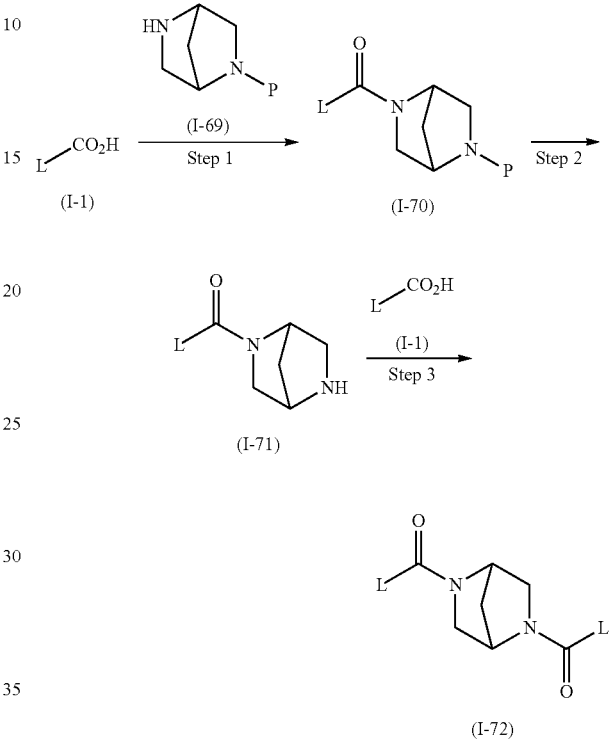

(wherein, L represents $L^1$ or $L^2$, and P represents an amine protecting group such as Boc, Cbz, PMB, and the like).

(Step 1)

Compound (I-70) can be manufactured by using compound (I-1) and 1 equivalent to 5 equivalents of compound (I-69) in the same manner as in step 2 of manufacturing method 2.

Compound (I-69) can be obtained as a commercially available product, or can be obtained by known methods [e.g., Experimental Chemistry Lecture, 5th Edition, Volume 14, p. 351, Maruzen Co., Ltd. (2004) and the like] or methods based thereon.

(Step 2)

Compound (I-71) can be manufactured by using compound (I-70) in the same manner as in step 4 of manufacturing method 1.

(Step 3)

Compound (I-72) can be manufactured by using compound (I-71) and 1 equivalent to 5 equivalents of compound (I-1) in the same manner as in step 2 of manufacturing method 2.

[Manufacturing Method 14]

Among compound (I) in which S is formula (S5), (i) compound (I-82) in which $X^{5b}$ is —NH—C(=O)— and (ii) compound (I-83) in which $X^{5b}$ is —NH—SO$_2$— can be manufactured respectively according to the following steps:

[Chemical formula 77]

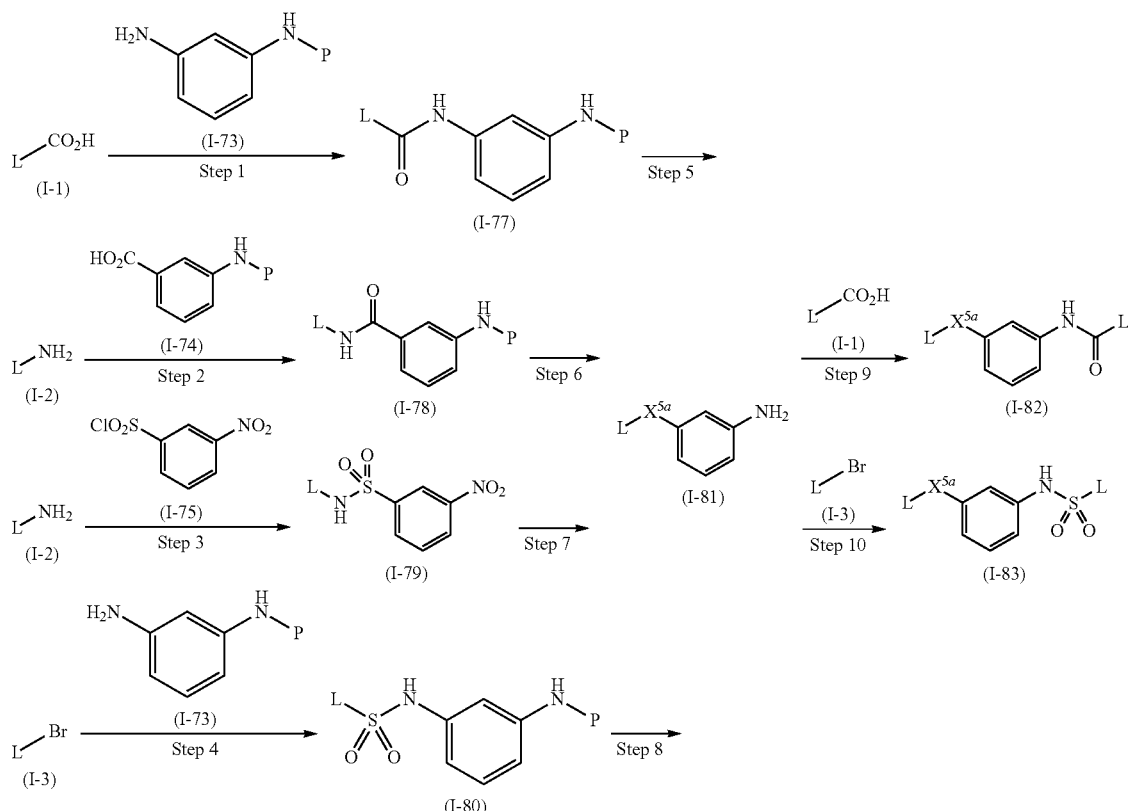

(wherein, $X^{5a}$ is as defined above, L represents $L^1$ or $L^2$, and P represents an amine protecting group such as Boc, Cbz, PMB, and the like).

(Step 1)

Compound (I-77) can be manufactured by using compound (I-1) and 1 equivalent to 5 equivalents of compound (I-73) in the same manner as in step 2 of manufacturing method 2.

Compound (I-73) can be obtained as a commercially available product, or can be obtained by known methods [e.g., Experimental Chemistry Lecture, 5th Edition, Volume 14, p. 351, Maruzen Co., Ltd. (2004) and the like] or methods based thereon.

(Step 2)

Compound (I-78) can be manufactured by using compound (I-2) and 1 equivalent to 5 equivalents of compound (I-74) in the same manner as in step 2 of manufacturing method 2.

Compound (I-74) can be obtained as a commercially available product, or can be obtained by known methods [e.g., Experimental Chemistry Lecture, 5th Edition, Volume 16, p. 1, Maruzen Co., Ltd. (2004) and the like] or methods based thereon.

(Step 3)

Compound (I-79) can be manufactured by using compound (I-2) and 1 equivalent to 5 equivalents of compound (I-75) in the same manner as in step 3 of manufacturing method 5.

Compound (I-75) can be obtained as a commercially available product, or can be obtained by known methods [e.g., Organic Syntheses, Coll. Vol. 4, p. 571 (1963) and the like] or methods based thereon.

(Step 4)

Compound (I-80) can be manufactured by using compound (I-3) and 1 equivalent to 5 equivalents of compound (I-73) in the same manner as in step 4 of manufacturing method 5.

(Step 5)

Among compound (I-81), a compound in which $X^{5a}$ is —C(=O)—NH— can be manufactured by using compound (I-77) in the same manner as in step 4 of manufacturing method 1.

(Step 6)

Among compound (I-81), a compound in which $X^{5a}$ is —NH—C(=O)— can be manufactured by using compound (I-78) in the same manner as in step 4 of manufacturing method 1.

(Step 7)

Among compound (I-81), a compound in which $X^{5a}$ is —NH—SO$_2$— can be manufactured by using compound (I-79) in the same manner as in step 8 of manufacturing method 1.

(Step 8)

Among compound (I-81), a compound in which $X^{5a}$ is —SO$_2$—NH— can be manufactured by using compound (I-80) in the same manner as in step 4 of manufacturing method 1.

(Step 9)

Compound (I-82) can be manufactured by using compound (I-81) and 1 equivalent to 5 equivalents of compound (I-1) in the same manner as in step 2 of manufacturing method 2.

(Step 10)

Compound (I-83) can be manufactured by using compound (I-81) and 1 equivalent to 5 equivalents of compound (I-3) in the same manner as in step 4 of manufacturing method 5.

[Manufacturing Method 15]

Among compound (I) in which S is formula (S5), compound (I-93) in which $X^{5b}$ is —C(=O)—NH— can be manufactured according to the following steps:

(Step 2)

Compound (I-89) can be manufactured by using compound (I-2) and 1 equivalent to 5 equivalents of compound (I-85) in the same manner as in step 2 of manufacturing method 2.

Compound (I-85) can be obtained as a commercially available product, or can be obtained by known methods [e.g., Experimental Chemistry Lecture, 5th Edition, Volume 16, p. 1, Maruzen Co., Ltd. (2004) and the like] or methods based thereon.

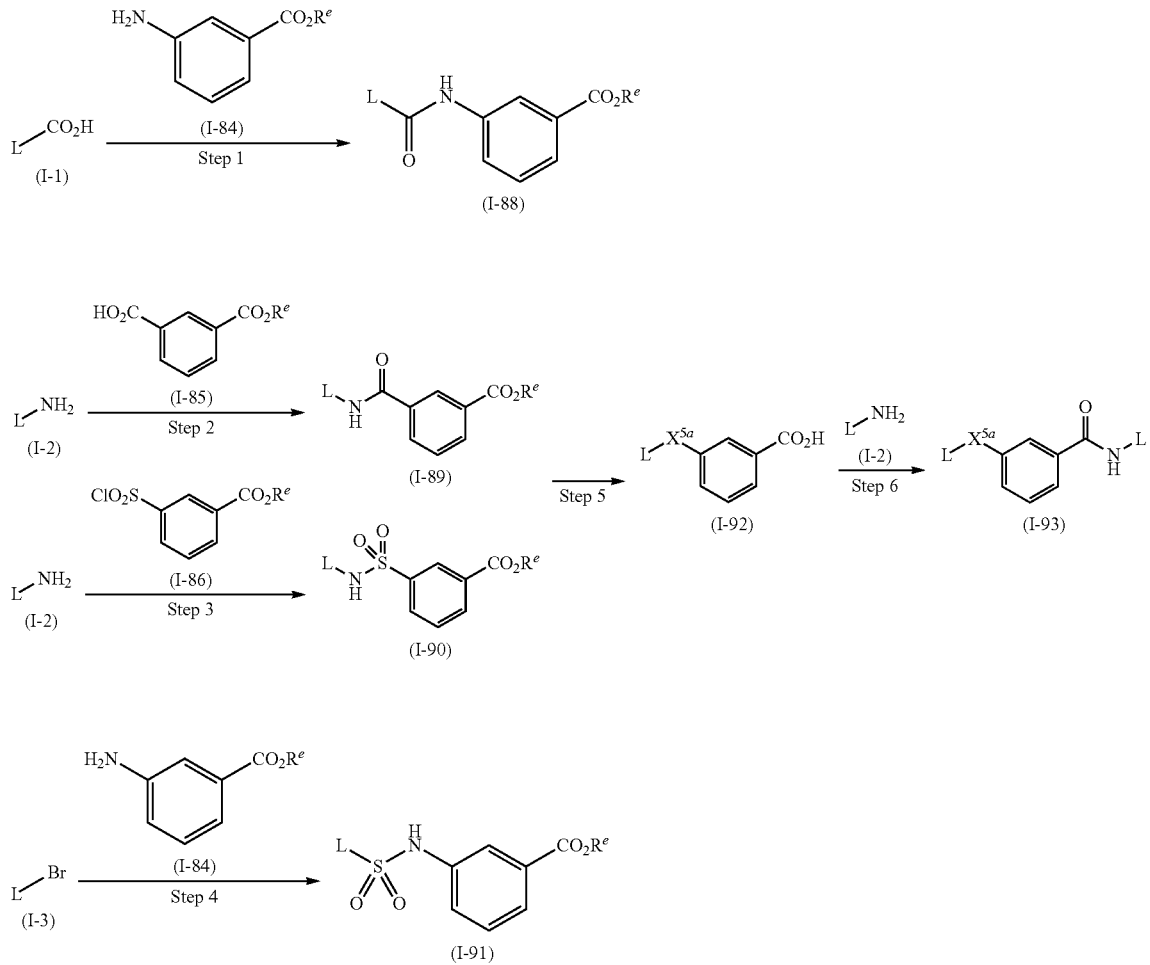

[Chemical formula 78]

(wherein, $X^{5a}$ is as defined above, L represents $L^1$ or $L^2$, and $R^e$ represents lower alkyl).

(Step 1)

Compound (I-88) can be manufactured by using compound (I-1) and 1 equivalent to 5 equivalents of compound (I-84) in the same manner as in step 2 of manufacturing method 2.

Compound (I-84) can be obtained as a commercially available product, or can be obtained by known methods [e.g., Experimental Chemistry Lecture, 5th Edition, Volume 14, p. 351, Maruzen Co., Ltd. (2004) and the like] or methods based thereon.

(Step 3)

Compound (I-90) can be manufactured by using compound (I-2) and 1 equivalent to 5 equivalents of compound (I-86) in the same manner as in step 3 of manufacturing method 5.

Compound (I-86) can be obtained as a commercially available product, or can be obtained by known methods [e.g., Organic Syntheses, Coll. Vol. 4, p. 571 (1963) and the like] or methods based thereon.

(Step 4)

Compound (I-91) can be manufactured by using compound (I-3) and 1 equivalent to 5 equivalents of compound (I-84) in the same manner as in step 4 of manufacturing method 5.

(Step 5)

Compound (I-92) can be manufactured by using compound (I-88), (I-89), (I-90), or (I-91) in the same manner as in step 6 of manufacturing method 1.

(Step 6)

Compound (I-93) can be manufactured by using compound (I-92) and 1 equivalent to 5 equivalents of compound (I-2) in the same manner as in step 2 of manufacturing method 2.

[Manufacturing Method 16]

Among compound (I) in which S is formula (S5), compound (I-100) in which $X^{5b}$ is —$SO_2$—NH— can be manufactured according to the following steps:

[Chemical formula 79]

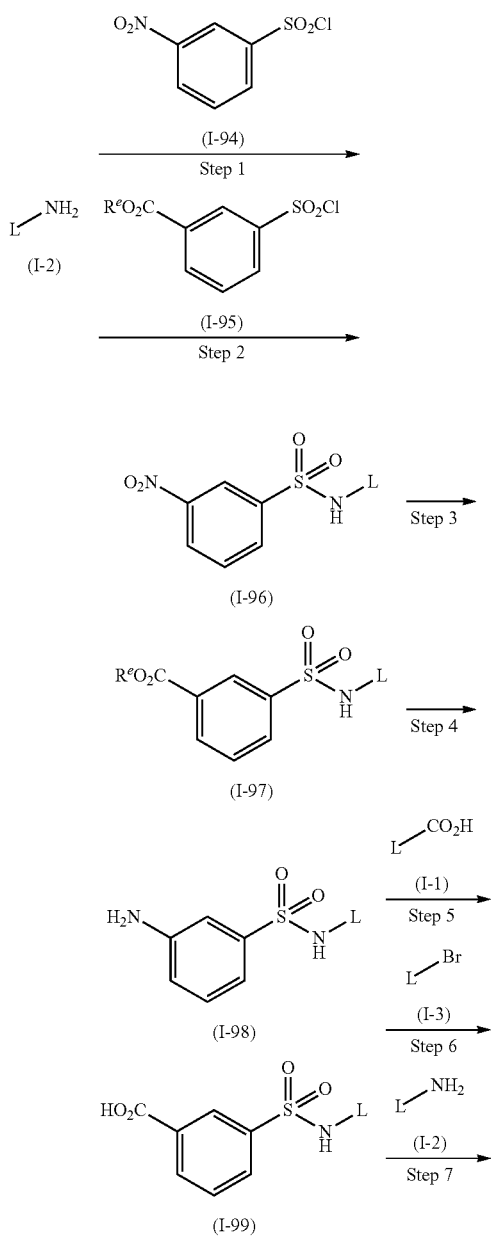

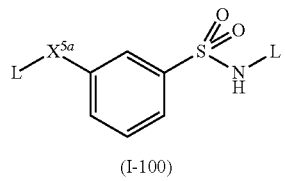

(wherein, $X^{5a}$ is as defined above, L represents $L^1$ or $L^2$, and $R^e$ represents lower alkyl).

(Step 1)

Compound (I-96) can be manufactured by using compound (I-2) and 1 equivalent to 5 equivalents of compound (I-94) in the same manner as in step 3 of manufacturing method 5.

Compound (I-94) can be obtained as a commercially available product, or can be obtained by known methods [e.g., Organic Syntheses, Coll. Vol. 4, p. 571 (1963) and the like] or methods based thereon.

(Step 2)

Compound (I-97) can be manufactured by using compound (I-2) and 1 equivalent to 5 equivalents of compound (I-95) in the same manner as in step 3 of manufacturing method 5.

Compound (I-95) can be obtained as a commercially available product, or can be obtained by known methods [e.g., Organic Syntheses, Coll. Vol. 4, p. 571 (1963) and the like] or methods based thereon.

(Step 3)

Compound (I-98) can be manufactured by using compound (I-96) in the same manner as in step 8 of manufacturing method 1.

(Step 4)

Compound (I-99) can be manufactured by using compound (I-97) in the same manner as in step 6 of manufacturing method 1.

(Step 5)

Among compound (I-100), a compound in which $X^{5a}$ is —C(=O)—NH— can be manufactured by using compound (I-98) and 1 equivalent to 5 equivalents of compound (I-1) in the same manner as in step 2 of manufacturing method 2.

(Step 6)

Among compound (I-100), a compound in which $X^{5a}$ is —$SO_2$—NH— can be manufactured by using compound (I-98) and 1 equivalent to 5 equivalents of compound (I-3) in the same manner as in step 4 of manufacturing method 5.

(Step 7)

Among compound (I-100), a compound in which $X^{5a}$ is —NH—C(=O)— can be manufactured by using compound (I-99) and 1 equivalent to 5 equivalents of compound (I-2) in the same manner as in step 2 of manufacturing method 2.

[Manufacturing Method 17]

Among compound (I) in which S is formula (S6), compound (I-103) in which $Ar^6$ is triazole can be manufactured according to the following steps:

[Chemical formula 80]

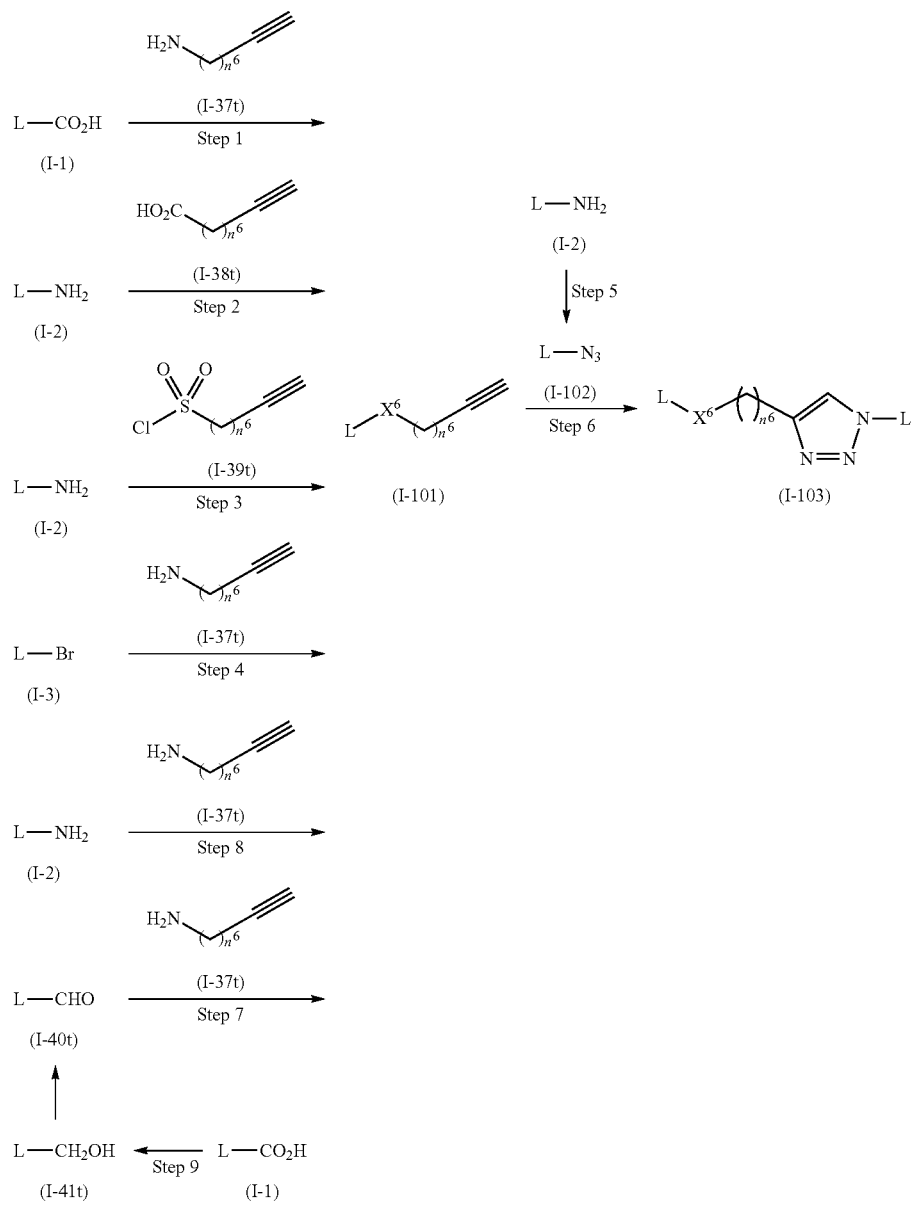

(wherein, $X^6$ and $n^6$ are as defined above, and L represents $L^1$ or $L^2$).

(Step 1)

Among Compound (I-101), a compound in which $X^6$ is —C(=O)—NH— can be manufactured by using compound (I-1) and 1 equivalent to 5 equivalents of compound (I-37t) in the same manner as in step 2 of manufacturing method 2.

Compound (I-37t) can be obtained as a commercially available product, or can be obtained by known methods [e.g., Experimental Chemistry Lecture, 5th Edition, Volume 14, p. 351, Maruzen Co., Ltd. (2004) and the like] or methods based thereon.

(Step 2)

Among compound (I-101), a compound in which $X^6$ is —NH—C(=O)— can be manufactured by using compound (I-2) and 1 equivalent to 5 equivalents of compound (I-38t) in the same manner as in step 2 of manufacturing method 2.

Compound (I-38t) can be obtained as a commercially available product, or can be obtained by known methods [e.g., Experimental Chemistry Lecture, 5th Edition, Volume 16, p. 1, Maruzen Co., Ltd. (2004) and the like] or methods based thereon.

(Step 3)

Among compound (I-101), a compound in which $X^6$ is —NH—SO$_2$— can be manufactured by using compound (I-2) and 1 equivalent to 5 equivalents of compound (I-39t) in the same manner as in step 3 of manufacturing method 5.

Compound (I-39t) can be obtained as a commercially available product, or can be obtained by known methods [e.g., Organic Syntheses, Coll. Vol. 4, p. 571 (1963) and the like] or methods based thereon.

(Step 4)

Among compound (I-101), a compound in which $X^6$ is —SO$_2$—NH— can be manufactured by using compound (I-3) and 1 equivalent to 5 equivalents of compound (I-37t) in the same manner as in step 4 of manufacturing method 5.
(Step 5)
Compound (I-102) can be manufactured by reacting compound (I-2) and 1 equivalent to 5 equivalents of an azidation agent in the presence of, according to necessity, 1 equivalent to 5 equivalents of an additive in a solvent at a temperature between room temperature and the boiling point of the solvent used for 5 minutes to 120 hours.

Examples of the azidation agent include 2-azido-1,3-dimethylimidazolinium hexafluorophosphate (ADMP) and the like.

Examples of the additive include 4-dimethylaminopyridine (DMAP), triethylamine, and the like.

Examples of the solvent include dichloromethane, acetonitrile, THF, and the like, and these can be used alone or as a mixture.
(Step 6)
Compound (I-103) can be manufactured by reacting compound (I-101) and 1 equivalent to 5 equivalents of compound (I-102) in the presence of 0.001 equivalent to 2 equivalents of copper catalyst and 0.001 equivalent to 2 equivalents of sodium L-ascorbate in a solvent at a temperature between room temperature and the boiling point of the solvent used for 5 minutes to 120 hours.

Examples of the copper catalyst include copper sulfate pentahydrate and the like.

Examples of the solvent include chloroform, dichloromethane, DMF, DMA, NMP, DMSO, THF, acetonitrile, water, 1,4-dioxane, s-butanol, and the like, and these can be used alone or as a mixture.
(Step 7)
Among compound (I-101), a compound in which $X^6$ is —$CH_2$—NH— can be manufactured by using compound (I-40t) and 1 equivalent to 5 equivalents of compound (I-37t) in the same manner as in step 1 of manufacturing method 1-3.

(Step 8)
Among compound (I-101), a compound in which $X^6$ is —NH—C(=O)—NH— can be manufactured by using compound (I-2) and 1 equivalent to 5 equivalents of compound (I-37t) in the same manner as in step 9 of manufacturing method 5.
(Step 9)
Compound (I-41t) can be manufactured by reacting compound (I-1) in the presence of 1 equivalent to 10 equivalents of reducing agent in a solvent at a temperature between −78° C. and the boiling point of the solvent used for 5 minutes to 120 minutes.

Examples of the reducing agent include lithium aluminum hydride, diisobutylaluminum hydride, sodium bis(2-methoxyethoxy)aluminum hydride, borane dimethyl sulfide complex, lithium borohydride, sodium borohydride, and the like.

Examples of the solvent include methanol, ethanol, dichloromethane, chloroform, 1,2-dichloroethane, toluene, acetonitrile, diethyl ether, THF, DME, 1,4-dioxane, DMF, DMA, NMP, and the like, and these are used alone or as a mixture.
(Step 10)
Compound (I-40t) can be manufactured by reacting compound (I-41t) in the presence of 1 equivalent to 10 equivalents of oxidizing agent in a solvent at a temperature between −20° C. and the boiling point of the solvent used for 5 minutes to 120 minutes.

Examples of the oxidizing agent include manganese dioxide, DMP, sulfur trioxide-pyridine, DMSO/oxalyl chloride, and the like.

Examples of the solvent include dichloromethane, THF, DME, 1,4-dioxane, DMF, DMA, NMP, DMSO, and the like, and these are used alone or as a mixture.
[Manufacturing Method 18]
Among compound (I) in which S is formula (S6), compound (I-112) in which $Ar^6$ is 1,3,4-oxadiazolediyl can be manufactured according to the following steps:

[Chemical formula 81]
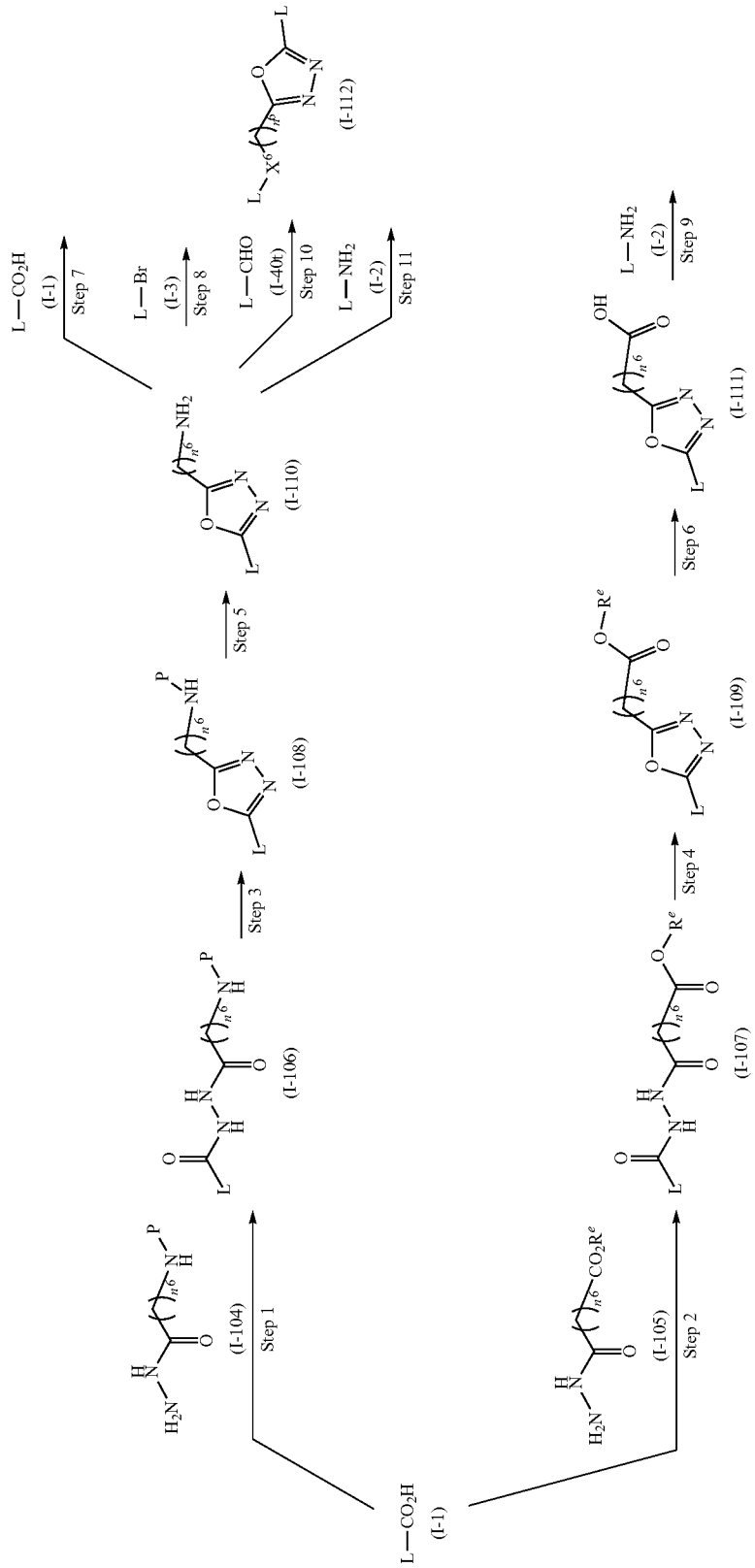

(wherein, $X^6$ and $n^6$ are as defined above, L represents $L^1$ or $L^2$, $R^e$ represents lower alkyl, and P represents an amine protecting group such as Boc, Cbz, PMB, and the like).

(Step 1)

Compound (I-106) can be manufactured by using compound (I-1) and 1 equivalent to 5 equivalents of compound (I-104) in the same manner as in step 2 of manufacturing method 2.

Compound (I-104) can be obtained as a commercially available product, or can be obtained by known methods [e.g., Experimental Chemistry Lecture, 5th Edition, Volume 14, p. 406, Maruzen Co., Ltd. (2004) and the like] or methods based thereon.

(Step 2)

Compound (I-107) can be manufactured by using compound (I-1) and 1 equivalent to 5 equivalents of compound (I-105) in the same manner as in step 2 of manufacturing method 2.

Compound (I-105) can be obtained as a commercially available product, or can be obtained by known methods [e.g., Experimental Chemistry Lecture, 5th Edition, Volume 14, p. 406, Maruzen Co., Ltd. (2004) and the like] or methods based thereon.

(Step 3)

Compound (I-108) can be manufactured by reacting compound (I-106) in the presence of 1 equivalent to 5 equivalents of triphenylphosphine, 1 equivalent to 5 equivalents of carbon tetrachloride, and 1 equivalent to a large excess of base in a solvent at a temperature between room temperature and the boiling point of the solvent used for 5 minutes to 120 hours.

Examples of the base include triethylamine, N,N-diisopropylethylamine, DBU, pyridine, and the like.

Examples of the solvent include chloroform, dichloromethane, DMF, DMA, NMP, THF, acetonitrile, 1,4-dioxane, and the like, and these can be used alone or as a mixture.

(Step 4)

Compound (I-109) can be manufactured by using compound (1-107) in the same manner as in step 3 of manufacturing method 18.

(Step 5)

Compound (I-110) can be manufactured by using compound (I-108) in the same manner as in step 4 of manufacturing method 1.

(Step 6)

Compound (I-111) can be manufactured by using compound (I-109) in the same manner as in step 6 of manufacturing method 1.

(Step 7)

Among compound (I-112), a compound in which $X^6$ is —C(=O)—NH— can be manufactured by using compound (I-110) and 1 equivalent to 5 equivalents of compound (I-1) in the same manner as in step 2 of manufacturing method 2.

(Step 8)

Among compound (I-112), a compound in which $X^6$ is —SO$_2$—NH— can be manufactured by using compound (I-110) and 1 equivalent to 5 equivalents of compound (I-3) in the same manner as in step 4 of manufacturing method 5.

(Step 9)

Among compound (I-112), a compound in which $X^6$ is —NH—C(=O)— can be manufactured by using compound (I-111) and 1 equivalent to 5 equivalents of compound (I-2) in the same manner as in step 2 of manufacturing method 2.

(Step 10)

Among compound (I-112), a compound in which $X^6$ is —CH$_2$—NH— can be manufactured by using compound (I-110) and 1 equivalent to 5 equivalents of compound (I-40t) in the same manner as in step 1 of manufacturing method 1-3.

(Step 11)

Among compound (I-112), a compound in which $X^6$ is —NH—C(=O)—NH— can be manufactured by using compound (I-110) and 1 equivalent to 5 equivalents of compound (I-2) in the same manner as in step 9 of manufacturing method 5.

[Manufacturing Method 19]

Among compound (I) in which S is formula (S6), compound (I-119) in which $Ar^6$ is 1,2,4-oxadiazolediyl can be manufactured according to the following steps:

[Chemical formula 82]

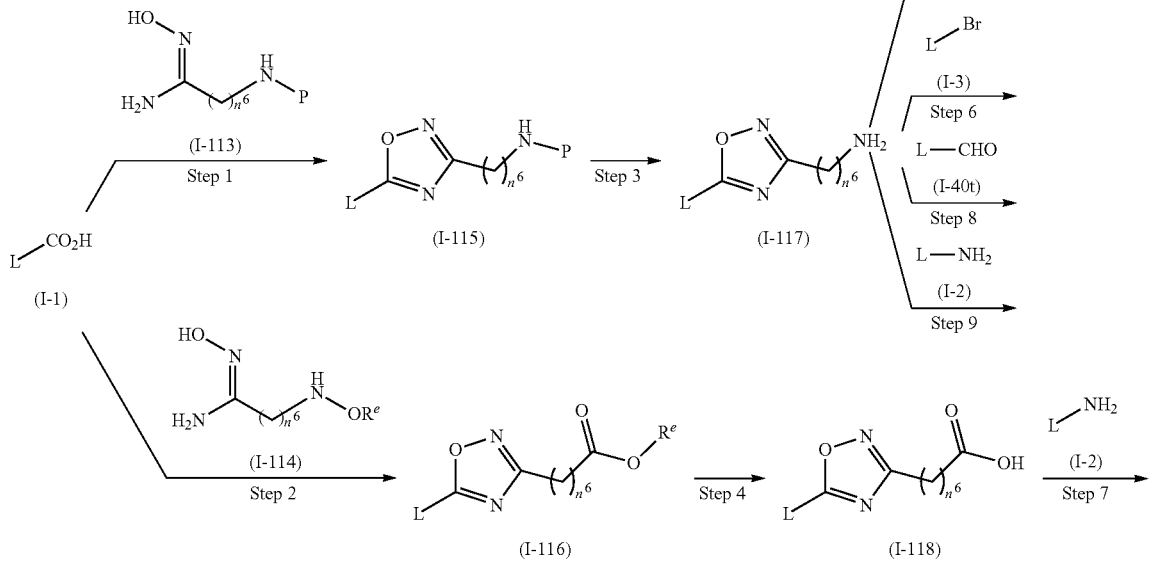

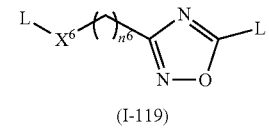

(I-119)

(wherein, $X^6$ and $n^6$ are as defined above, L represents $L^1$ or $L^2$, $R^e$ represents lower alkyl, and P represents an amine protecting group such as Boc, Cbz, PMB, and the like).

(Step 1)

Compound (I-115) can be manufactured by reacting compound (I-1) and 1 equivalent to 5 equivalents of compound (I-113) in the presence of 1 equivalent to a large excess of condensing agent and 1 equivalent to a large excess of base in a solvent at a temperature between 60° C. and the boiling point of the solvent used for 5 minutes to 120 hours.

Examples of the condensing agent include DCC, EDC, HATU, COMU, and the like.

Examples of the base include triethylamine, N,N-diisopropylethylamine, pyridine, 4-dimethylaminopyridine, and the like.

Examples of the solvent include chloroform, dichloromethane, DMF, DMA, NMP, DMSO, THF, acetonitrile, and the like, and these can be used alone or as a mixture.

Compound (I-113) can be obtained as a commercially available product, or can be obtained by known methods [e.g., Chemical Reviews, Volume 62, Issue 2, p. 155 (1962) and the like] or methods based thereon.

(Step 2)

Compound (I-116) can be manufactured by using compound (I-1) and 1 equivalent to 5 equivalents of compound (I-114) in the same manner as in step 1 of manufacturing method 19.

Compound (I-114) can be obtained as a commercially available product, or can be obtained by known methods [e.g., Chemical Reviews, Volume 62, Issue 2, p. 155 (1962) and the like] or methods based thereon.

(Step 3)

Compound (I-117) can be manufactured by using compound (I-115) in the same manner as in step 4 of manufacturing method 1.

(Step 4)

Compound (I-118) can be manufactured by using compound (I-116) in the same manner as in step 6 of manufacturing method 1.

(Step 5)

Among compound (I-119), a compound in which $X^6$ is —C(=O)—NH— can be manufactured by using compound (I-117) and 1 equivalent to 5 equivalents of compound (I-1) in the same manner as in step 2 of manufacturing method 2.

(Step 6)

Among compound (I-119), a compound in which $X^6$ is —SO$_2$—NH— can be manufactured by using compound (I-117) and 1 equivalent to 5 equivalents of compound (I-3) in the same manner as in step 4 of manufacturing method 5.

(Step 7)

Among compound (I-119), a compound in which $X^6$ is —NH—C(=O)— can be manufactured by using compound (I-118) and 1 equivalent to 5 equivalents of compound (I-2) in the same manner as in step 2 of manufacturing method 2.

(Step 8)

Among compound (I-119), a compound in which $X^6$ is —CH$_2$—NH— can be manufactured by using compound (I-117) and 1 equivalent to 5 equivalents of compound (I-40t) in the same manner as in step 1 of manufacturing method 1-3.

(Step 9)

Among compound (I-119), a compound in which $X^6$ is —NH—C(=O)—NH— can be manufactured by using compound (I-117) and 1 equivalent to 5 equivalents of compound (1-2) in the same manner as in step 9 of manufacturing method 5.

[Manufacturing Method YS6-1]

Among compound (I) in which S is formula (S6), under the condition that $Ar^6$ is pyrazolediyl, (i) compound (Iy-119) in which $X^6$ is —C(=O)—NH—, (ii) compound (Iy-120) in which $X^6$ is —SO$_2$—NH—, (iii) compound (Iy-121) in which $X^6$ is —CH$_2$—NH—, (iv) compound (Iy-122) in which $X^6$ is —NH—C(=O)—NH—, and (v) compound (Iy-123) in which $X^6$ is —NH—C(=O)— can be manufactured respectively according to the following steps:

[Chemical formula 83]

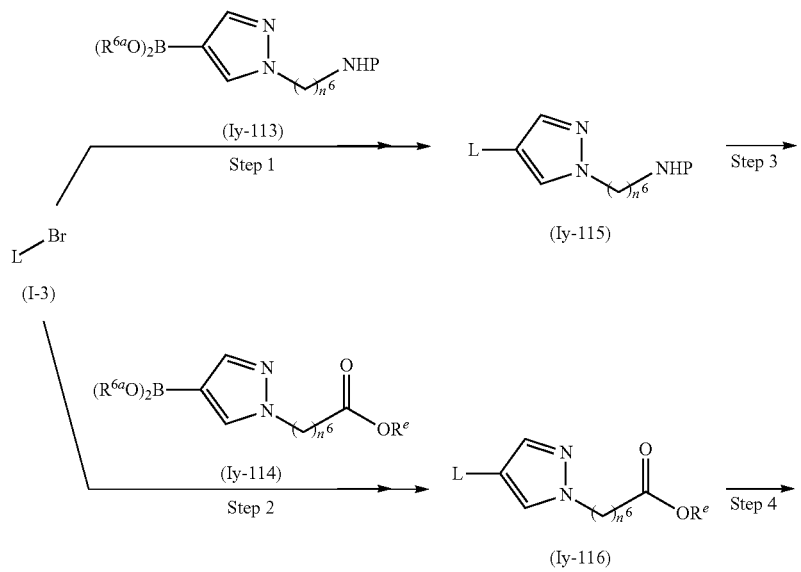

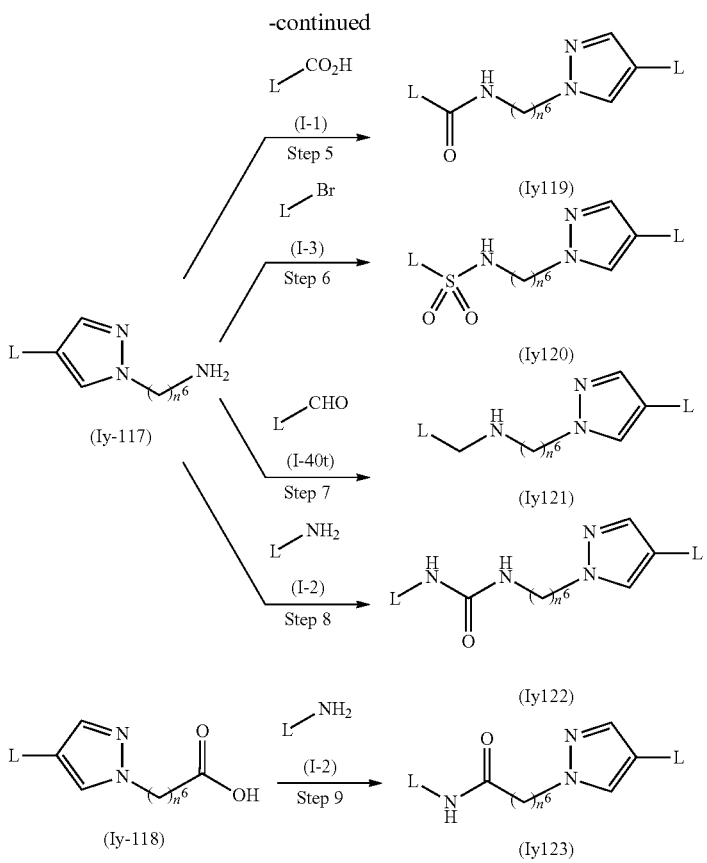

(wherein, $n^6$ is as defined above, L represents $L^1$ or $L^2$, $R^e$ represents lower alkyl, $R^{6a}$ represents a hydrogen atom or lower alkyl, and P represents an amine protecting group such as Boc, Cbz, PMB, and the like).

(Step 1)

Compound (Iy-115) can be manufactured by using compound (I-3) and 1 equivalent to 5 equivalents of compound (Iy-113) in the same manner as in step 3 of manufacturing method 3.

Compound (Iy-113) can be obtained as a commercially available product, or can be obtained by known methods [e.g., Experimental Chemistry Lecture, 5th Edition, Volume 18, p. 95, Maruzen Co., Ltd. (2004) and the like] or methods based thereon.

(Step 2)

Compound (Iy-116) can be manufactured by using compound (I-3) and 1 equivalent to 5 equivalents of compound (Iy-114) in the same manner as in step 3 of manufacturing method 3.

Compound (Iy-114) can be obtained as a commercially available product, or can be obtained by known methods [e.g., Experimental Chemistry Lecture, 5th Edition, Volume 18, p. 95, Maruzen Co., Ltd. (2004) and the like] or methods based thereon.

(Step 3)

Compound (Iy-117) can be manufactured by using compound (Iy-115) in the same manner as in step 4 of manufacturing method 1.

(Step 4)

Compound (Iy-118) can be manufactured by using compound (Iy-116) in the same manner as in step 6 of manufacturing method 1.

(Step 5)

Compound (Iy-119) can be manufactured by using compound (Iy-117) and 1 equivalent to 5 equivalents of compound (I-1) in the same manner as in step 2 of manufacturing method 2.

(Step 6)

Compound (Iy-120) can be manufactured by using compound (Iy-117) and 1 equivalent to 5 equivalents of compound (I-3) in the same manner as in step 4 of manufacturing method 5.

(Step 7)

Compound (Iy-121) can be manufactured by using compound (Iy-117) and 1 equivalent to 5 equivalents of compound (I-40t) in the same manner as in step 1 of manufacturing method 1-3.

(Step 8)

Compound (Iy-122) can be manufactured by using compound (Iy-117) and 1 equivalent to 5 equivalents of compound (I-2) in the same manner as in step 9 of manufacturing method 5.

(Step 9)

Compound (Iy-123) can be manufactured by using compound (Iy-118) and 1 equivalent to 5 equivalents of compound (I-2) in the same manner as in step 2 of manufacturing method 2.

[Manufacturing Method YS6-2]

Among compound (I) in which S is formula (S6), under the condition that $Ar^6$ is tetrahydropyridinyl, (i) compound (Iy-102a) in which $X^6$ is —C(=O)—NH—, (ii) compound (Iy-102b) in which $X^6$ is —$SO_2$—NH—, (iii) compound (Iy-102c) in which $X^6$ is —$CH_2$—NH—, (iv) compound (Iy-102d) in which $X^6$ is —NH—C(=O)—NH—, and (v)

compound (Iy-102e) in which $X^6$ is —NH—C(=O)— can be manufactured respectively according to the following steps:
[Chemical formula 84]
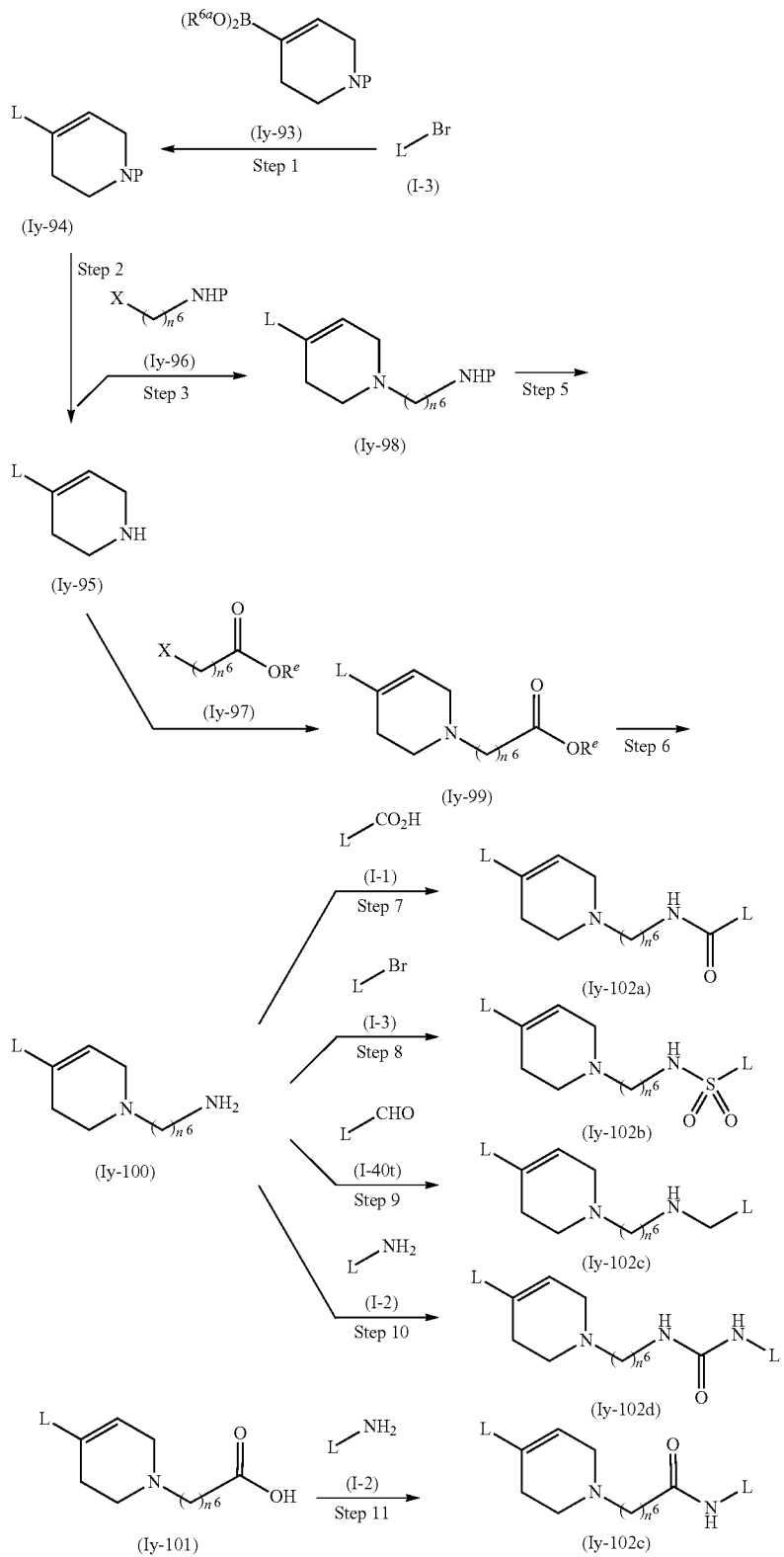

(wherein, $n^6$ is as defined above, L represents $L^1$ or $L^2$, $R^e$ represents lower alkyl, $R^{6a}$ represents a hydrogen atom or lower alkyl, X represents a halogen, and P represents an amine protecting group such as Boc, Cbz, PMB, and the like).

(Step 1)

Compound (Iy-94) can be manufactured by using compound (I-3) and 1 equivalent to 5 equivalents of compound (Iy-93) in the same manner as in step 3 of manufacturing method 3.

Compound (Iy-93) can be obtained as a commercially available product, or can be obtained by known methods [e.g., Experimental Chemistry Lecture, 5th Edition, Volume 18, p. 95, Maruzen Co., Ltd. (2004) and the like] or methods based thereon.

(Step 2)

Compound (Iy-95) can be manufactured by using compound (Iy-94) in the same manner as in step 4 of manufacturing method 1.

(Step 3)

Compound (Iy-98) can be manufactured by using compound (Iy-95) and 1 equivalent to 5 equivalents of compound (Iy-96) in the same manner as in step 1 of manufacturing method 1-2.

Compound (Iy-96) can be obtained as a commercially available product, or can be obtained by known methods [e.g., Experimental Chemistry Lecture, 5th Edition, Volume 13, p. 374, Maruzen Co., Ltd. (2004) and the like] or methods based thereon.

(Step 4)

Compound (Iy-99) can be manufactured by using compound (Iy-95) and 1 equivalent to 5 equivalents of compound (Iy-97) in the same manner as in step 1 of manufacturing method 1-2.

Compound (Iy-97) can be obtained as a commercially available product, or can be obtained by known methods [e.g., Experimental Chemistry Lecture, 5th Edition, Volume 13, p. 374, Maruzen Co., Ltd. (2004) and the like] or methods based thereon.

(Step 5)

Compound (Iy-100) can be manufactured by using compound (Iy-98) in the same manner as in step 4 of manufacturing method 1.

(Step 6)

Compound (Iy-101) can be manufactured by using compound (Iy-99) in the same manner as in step 6 of manufacturing method 1.

(Step 7)

Compound (Iy-102a) can be manufactured by using compound (Iy-100) and 1 equivalent to 5 equivalents of compound (I-1) in the same manner as in step 2 of manufacturing method 2.

(Step 8)

Compound (Iy-102b) can be manufactured by using compound (Iy-100) and 1 equivalent to 5 equivalents of compound (I-3) in the same manner as in step 4 of manufacturing method 5.

(Step 9)

Compound (Iy-102c) can be manufactured by using compound (Iy-100) and 1 equivalent to 5 equivalents of compound (I-40t) in the same manner as in step 1 of manufacturing method 1-3.

(Step 10)

Compound (Iy-102d) can be manufactured by using compound (Iy-100) and 1 equivalent to 5 equivalents of compound (I-2) in the same manner as in step 9 of manufacturing method 5.

(Step 11)

Compound (Iy-102e) can be manufactured by using compound (Iy-101) and 1 equivalent to 5 equivalents of compound (I-2) in the same manner as in step 2 of manufacturing method 2.

[Manufacturing Method YS6-3]

In compound (I) in which S is formula (S6), under the condition that $Ar^6$ is thiophenediyl, (i) compound (Iy-109) in which $X^6$ is —C(=O)—NH—, (ii) compound (Iy-110) in which $X^6$ is —SO$_2$—NH—, (iii) compound (Iy-111) in which $X^6$ is —CH$_2$—NH—, (iv) compound (Iy-112) in which $X^6$ is —NH—C(=O)—NH—, and (v) compound (Iy-112a) in which $X^6$ is —NH—C(=O)— can be manufactured respectively according to the following steps:

[Chemical formula 85]
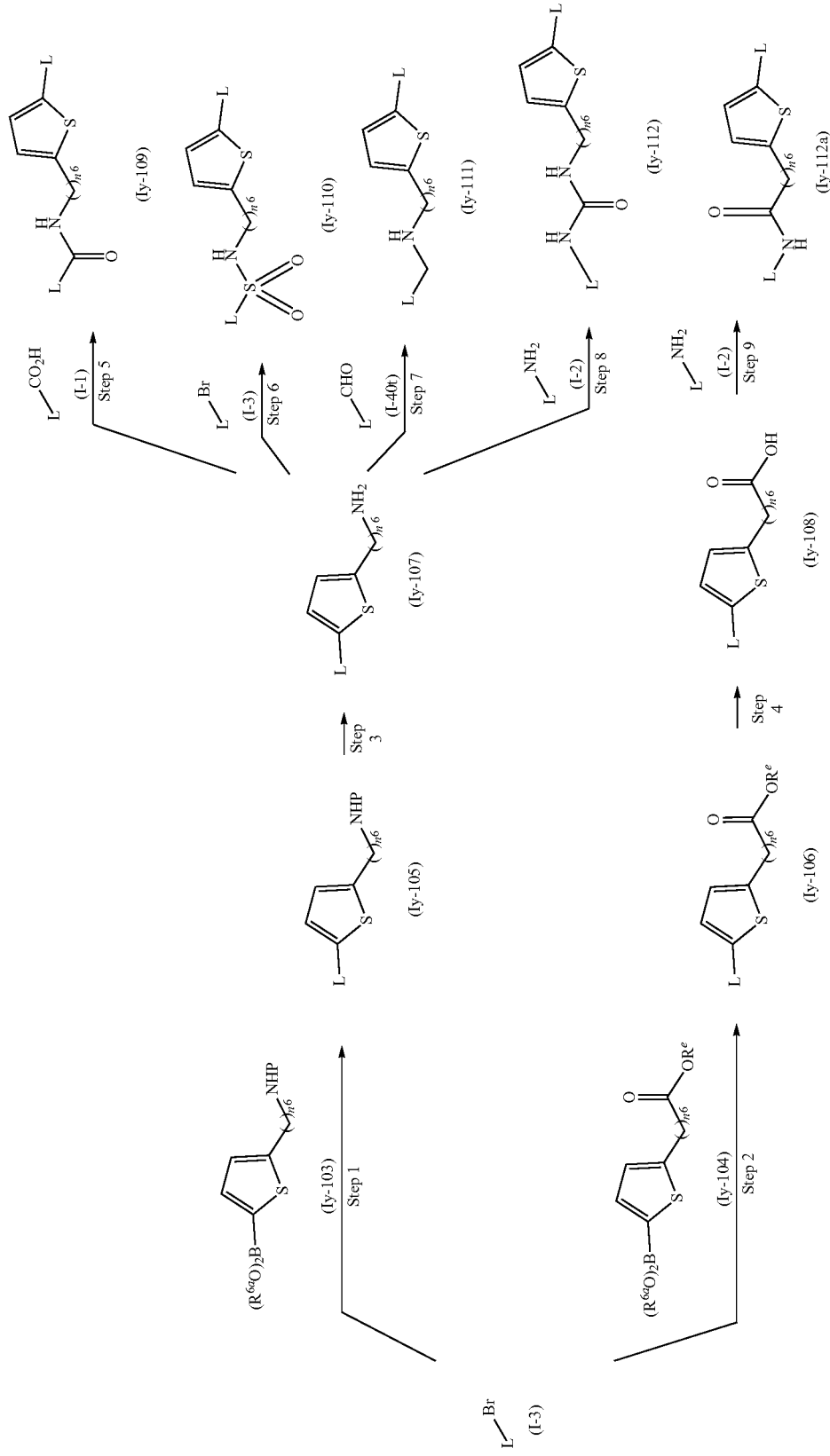

(wherein, $n^6$ is as defined above, L represents $L^1$ or $L^2$, $R^e$ represents lower alkyl, $R^{6a}$ represents a hydrogen atom or lower alkyl, and P represents an amine protecting group such as Boc, Cbz, PMB, and the like).

(Step 1)

Compound (Iy-105) can be manufactured by using compound (I-3) and 1 equivalent to 5 equivalents of compound (Iy-103) in the same manner as in step 3 of manufacturing method 3.

Compound (Iy-103) can be obtained as a commercially available product, or can be obtained by known methods [e.g., Experimental Chemistry Lecture, 5th Edition, Volume 18, p. 95, Maruzen Co., Ltd. (2004) and the like] or methods based thereon.

(Step 2)

Compound (Iy-106) can be manufactured by using compound (I-3) and 1 equivalent to 5 equivalents of compound (Iy-104) in the same manner as in step 3 of manufacturing method 3.

Compound (Iy-104) can be obtained as a commercially available product, or can be obtained by known methods [e.g., Experimental Chemistry Lecture, 5th Edition, Volume 18, p. 95, Maruzen Co., Ltd. (2004) and the like] or methods based thereon.

(Step 3)

Compound (Iy-107) can be manufactured by using compound (Iy-105) in the same manner as in step 4 of manufacturing method 1.

(Step 4)

Compound (Iy-108) can be manufactured by using compound (Iy-106) in the same manner as in step 6 of manufacturing method 1.

(Step 5)

Compound (Iy-109) can be manufactured by using compound (Iy-107) and 1 equivalent to 5 equivalents of compound (I-1) in the same manner as in step 2 of manufacturing method 2.

(Step 6)

Compound (Iy-110) can be manufactured by using compound (Iy-107) and 1 equivalent to 5 equivalents of compound (I-3) in the same manner as in step 4 of manufacturing method 5.

(Step 7)

Compound (Iy-111) can be manufactured by using compound (Iy-107) and 1 equivalent to 5 equivalents of compound (I-40t) in the same manner as in step 1 of manufacturing method 1-3.

(Step 8)

Compound (Iy-112) can be manufactured by using compound (Iy-107) and 1 equivalent to 5 equivalents of compound (I-2) in the same manner as in step 9 of manufacturing method 5.

(Step 9)

Compound (Iy-112a) can be manufactured by using compound (Iy-108) and 1 equivalent to 5 equivalents of compound (I-2) in the same manner as in step 2 of manufacturing method 2.

[Manufacturing Method 20]

Among compound (I), compound (I-126), compound (I-126a), and compound (I-126b), in which S is formula (S7), can be manufactured respectively according to the following steps:

[Chemical formula 86]
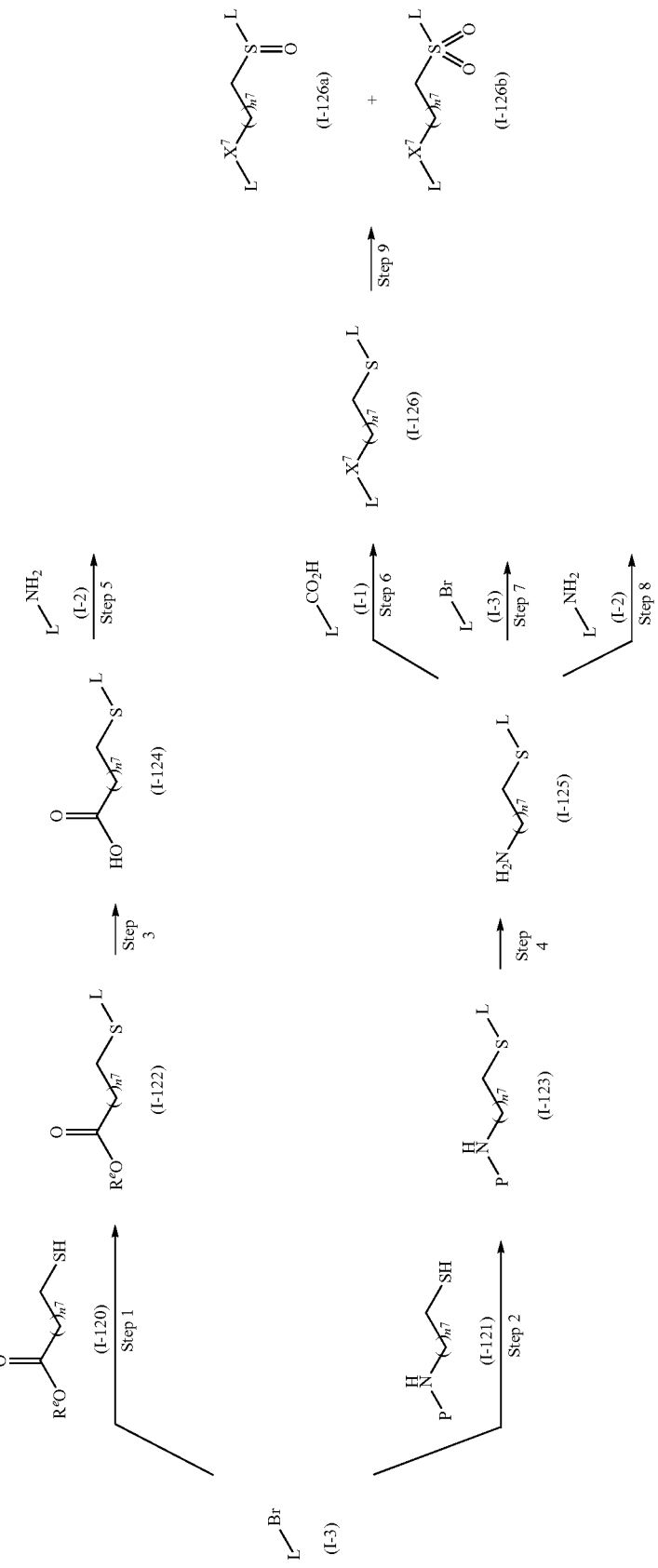

(wherein, $X^7$ and $n^7$ are as defined above, L represents $L^1$ or $L^2$, $R^e$ represents lower alkyl, and P represents an amine protecting group such as Boc, Cbz, PMB, and the like).
(Step 1)
Compound (I-122) can be manufactured by reacting compound (I-3) and 1 equivalent to 5 equivalents of compound (I-120) in the presence of 0.001 equivalent to 3 equivalents of palladium catalyst, 0.001 equivalent to 3 equivalents of phosphorus ligand, and 1 equivalent to a large excess of base in a solvent at a temperature between room temperature and the boiling point of the solvent used for 5 minutes to 120 hours.

Examples of the palladium catalyst include $Pd_2(dba)_3$ and the like.

Examples of the phosphorus ligand include xantphos and the like.

Examples of the base include triethylamine, N,N-diisopropylethylamine, pyridine, 4-dimethylaminopyridine, potassium tert-butoxide, sodium carbonate, potassium carbonate, and the like.

Examples of the solvent include chloroform, dichloromethane, DMF, DMA, NMP, DMSO, THF, acetonitrile, 1,4-dioxane, and the like, and these can be used alone or as a mixture.

Compound (I-120) can be obtained as a commercially available product, or can be obtained by known methods [e.g., Organic Syntheses, Coll. Vol. 3, p. 363 (1955) and the like] or methods based thereon.
(Step 2)
Compound (I-123) can be manufactured by using compound (1-3) and 1 equivalent to 5 equivalents of compound (I-121) in the same manner as in step 1 of manufacturing method 20.

Compound (I-121) can be obtained as a commercially available product, or can be obtained by known methods [e.g., Organic Syntheses, Coll. Vol. 3, p. 363 (1955) and the like] or methods based thereon.
(Step 3)
Compound (I-124) can be manufactured by using compound (I-122) in the same manner as in step 6 of manufacturing method 1.
(Step 4)
Compound (I-125) can be manufactured by using compound (I-123) in the same manner as in step 4 of manufacturing method 1.
(Step 5)
Among compound (I-126), a compound in which $X^7$ is —NH—C(=O)— can be manufactured by using compound (I-124) and 1 equivalent to 5 equivalents of compound (I-2) in the same manner as in step 2 of manufacturing method 2.
(Step 6)
Among compound (I-126), a compound in which $X^7$ is —C(=O)—NH— can be manufactured by using compound (I-125) and 1 equivalent to 5 equivalents of compound (I-1) in the same manner as in step 2 of manufacturing method 2.
(Step 7)
Among compound (I-126), a compound in which $X^7$ is —$SO_2$—NH— can be manufactured by using compound (I-125) and 1 equivalent to 5 equivalents of compound (I-3) in the same manner as in step 4 of manufacturing method 5.
(Step 8)
Among compound (I-126), a compound in which $X^7$ is —NH—C(=O)—NH— can be manufactured by using compound (I-125) and 1 equivalent to 5 equivalents of compound (I-2) in the same manner as in step 9 of manufacturing method 5.

(Step 9)
Compounds (I-126a) and (I-126b) can be manufactured by reacting compound (I-126) in the presence of 1 equivalent to 10 equivalents of oxidizing agent in a solvent at a temperature between −20° C. and the boiling point of the solvent used for 5 minutes to 120 hours.

Examples of the oxidizing agent include meta-chloroperbenzoic acid (m-CPBA), benzoyl peroxide, peracetic acid, aqueous hydrogen peroxide, sodium periodate, and the like.

Examples of the solvent include dichloromethane, 1,2-dichloroethane, toluene, and the like, and these are used alone or as a mixture.

In addition, either of compounds (I-126a) and (I-126b) can be obtained selectively or they are obtained as a mixture by adjusting the reaction conditions such as, for example, the number of equivalents of the oxidizing agent, temperature, and the like.
[Manufacturing Method YS-8-1]
Among compound (I) in which S is formula (S8), compound (Iy-85) in which $X^{8b}$ is a bond can be manufactured according to the following steps:

[Chemical formula 87]

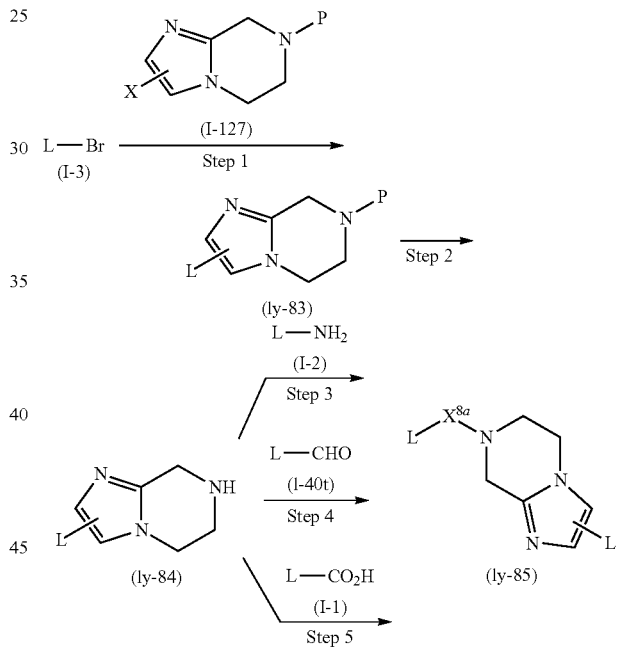

(wherein, $X^{8a}$ is as defined above, L represents $L^1$ or $L^2$, X represents a halogen, and P represents an amine protecting group such as Boc, Cbz, PMB, and the like).
(Step 1)
Compound (Iy-83) can be manufactured by (i) reacting compound (I-3) in the presence of 1 equivalent to 5 equivalents of bis(pinacolato)diboron, 0.001 equivalent to 3 equivalents of palladium catalyst, 0.001 equivalent to 3 equivalents of phosphorus ligand as necessary, and 1 equivalent to a large excess of base in a solvent at a temperature between room temperature and the boiling point of the solvent used for 5 minutes to 120 hours, and then (ii) reacting the obtained compound in the presence of 1 equivalent to 5 equivalents of compound (I-127), 0.001 equivalent to 3 equivalents of palladium catalyst, 0.001 equivalent to 3 equivalents of phosphorus ligand as necessary, and 1 equivalent to a large excess of base in a solvent at a temperature between room temperature and the boiling point of the solvent used for 5 minutes to 120 hours.

Examples of the palladium catalyst used in (i) include $Pd(dppf)Cl_2$, $Pd_2(dba)_3$, $Pd(PPh_3)_4$, and the like.

Examples of the phosphorus ligand used in (i) include tricyclohexylphosphine and the like.

Examples of the base used in (i) include potassium acetate, potassium carbonate, sodium carbonate, cesium carbonate, potassium phosphate, and the like.

Examples of the solvent used in (i) include chloroform, dichloromethane, DMF, DMA, NMP, DMSO, THF, acetonitrile, 1,4-dioxane, water, and the like, and these can be used alone or as a mixture.

Examples of the palladium catalyst used in (ii) include $Pd(dppf)Cl_2$, $Pd_2(dba)_3$, $Pd(PPh_3)_4$, and the like.

Examples of the phosphorus ligand used in (ii) include triphenylphosphine, tricyclohexylphosphine, and the like.

Examples of the base used in (ii) include potassium acetate, potassium carbonate, sodium carbonate, cesium carbonate, potassium phosphate, and the like.

Examples of the solvent used in (ii) include chloroform, dichloromethane, DMF, DMA, NMP, DMSO, THF, acetonitrile, 1,4-dioxane, water, and the like, and these can be used alone or as a mixture.

Compound (I-127) can be obtained as a commercially available product, or can be obtained by known methods [e.g., Experimental Chemistry Lecture, 5th Edition, Volume 13, p. 341, Maruzen Co., Ltd. (2004) and the like] or methods based thereon.

(Step 2)

Compound (Iy-84) can be manufactured by using compound (Iy-83) in the same manner as in step 4 of manufacturing method 1.

(Step 3)

Among compound (Iy-85), a compound in which $X^8a$ is —C(=O)— can be manufactured by using compound (Iy-84) and 1 equivalent to 5 equivalents of compound (I-1) in the same manner as in step 2 of manufacturing method 2.

(Step 4)

Among compound (Iy-85), a compound in which $X^8a$ is —$CH_2$—can be manufactured by using compound (Iy-84) and 1 equivalent to 5 equivalents of compound (I-40t) in the same manner as in step 1 of manufacturing method 1-3.

(Step 5)

Among compound (Iy-85), a compound in which $X^8a$ is —NH—C(=O)— can be manufactured by using compound (Iy-84) and 1 equivalent to 5 equivalents of compound (I-2) in the same manner as in step 9 of manufacturing method 5.

[Manufacturing Method YS-8-2]

Among compound (I) in which S is formula (S8), (i) compound (Iy-92) in which $X^{8b}$ is —C(=O)—, (ii) compound (Iy-91) in which $X^{8b}$ is —$CH_2$—, and (iii) compound (Iy-90) in which $X^{8b}$ is —CH(OH)— can be manufactured respectively according to the following steps:

[Chemical formula 88]
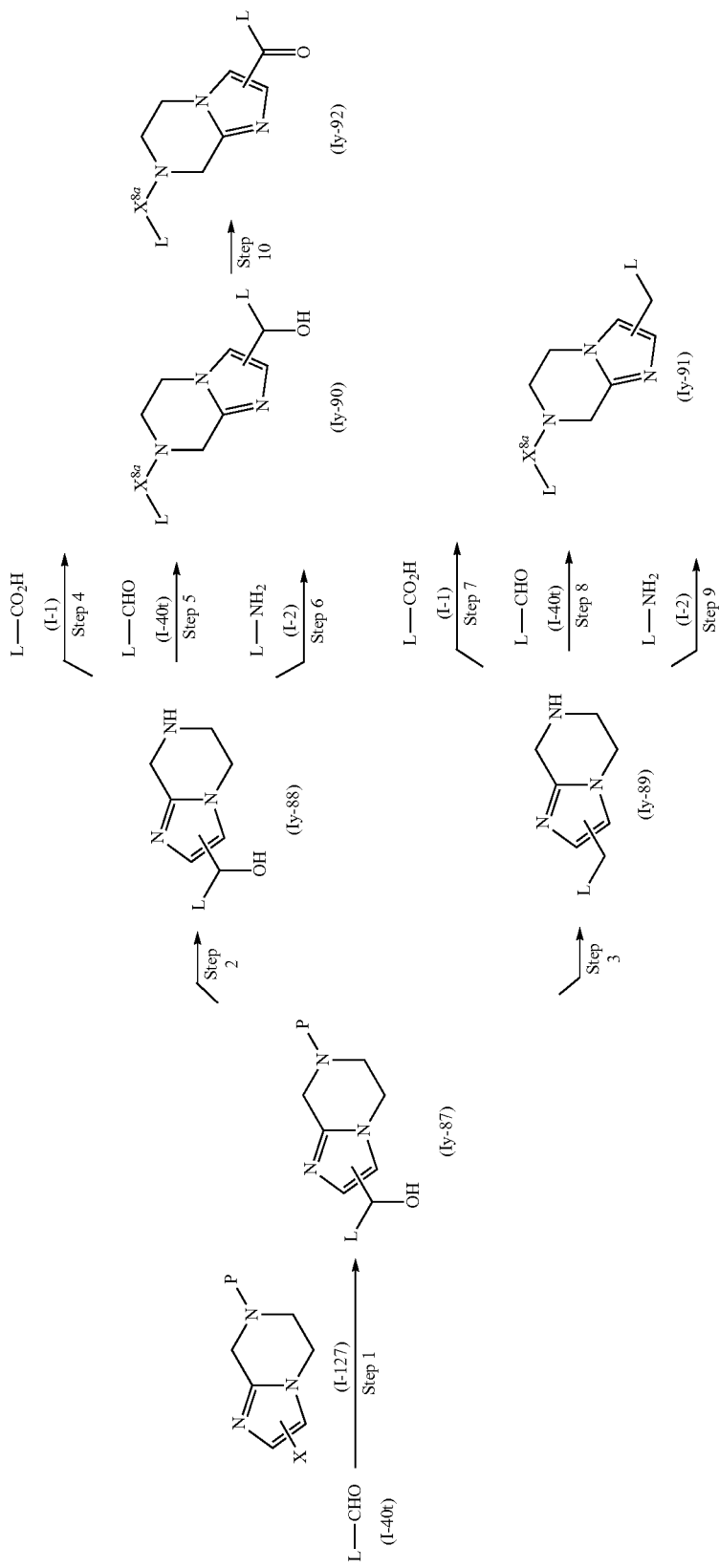

(wherein, $X^{8a}$ is as defined above, L represents $L^1$ or $L^2$, X represents a halogen, and P represents an amine protecting group such as Boc, Cbz, and the like).

(Step 1)

Compound (Iy-87) can be manufactured by reacting 1 equivalent to 10 equivalents of compound (I-127) and 1 equivalent to 10 equivalents of organometallic reagent in a solvent at a temperature between −78° C. and the boiling point of the solvent used for 5 minutes to 24 hours, and by subsequently adding compound (I-40t) to the reaction mixture and reacting the mixture at a temperature between −78° C. and the boiling point of the solvent used for 5 minutes to 120 hours.

Examples of the organometallic reagent include n-butyllithium, s-butyllithium, t-butyllithium, isopropylmagnesium chloride-lithium chloride, and the like. These organometallic reagents can be obtained as commercial products, or can be obtained by known methods [e.g., Experimental Chemistry Lecture, 5th Edition, Volume 18, p. 7 (Li) and p. 59 (Mg), Maruzen Co., Ltd. (2004) and the like] or methods based thereon.

Examples of the solvent include toluene, diethyl ether, THF, DME, 1,4-dioxane, hexane, and the like, and these are used alone or as a mixture.

(Step 2)

Compound (Iy-88) can be manufactured by using compound (Iy-87) in the same manner as in step 4 of manufacturing method 1.

(Step 3)

When P in compound (Iy-87) is, for example, Boc, compound (Iy-89) can be manufactured by reacting compound (Iy-87) in the presence of 1 equivalent to a large excess of acid and 1 equivalent to a large excess of reducing agent without a solvent or in a solvent at a temperature between room temperature and 150° C. for 5 minutes to 120 hours.

Examples of the acid include hydrochloric acid, sulfuric acid, formic acid, acetic acid, trifluoroacetic acid, p-toluenesulfonic acid, methanesulfonic acid, titanium tetrachloride, boron trifluoride, and the like.

Examples of the reducing agent include triethylsilane, diethylsilane, triphenylsilane, and the like.

Examples of the solvent include toluene, dichloromethane, THF, DME, 1,4-dioxane, dichloroethane, and the like, and these are used alone or as a mixture.

Further, when P in compound (Iy-87) is, for example, Cbz, compound (Iy-89) can be manufactured by reacting compound (Iy-87) in the presence of 0.001 equivalent to 0.5 equivalent of palladium catalyst and 1 equivalent to a large excess of acid under a hydrogen atmosphere in a solvent at a temperature between −20° C. and the boiling point of the solvent used for 5 minutes to 120 hours.

Examples of the palladium catalyst include palladium on carbon, palladium hydroxide, and the like.

Examples of the acid include hydrochloric acid, sulfuric acid, formic acid, acetic acid, trifluoroacetic acid, p-toluenesulfonic acid, methanesulfonic acid, and the like.

Examples of the solvent include methanol, ethanol, ethyl acetate, THF, 1,4-dioxane, and the like, and these can be used alone or as a mixture.

(Step 4)

Among compound (Iy-90), a compound in which $X^8a$ is —C(═O)— can be manufactured by using compound (Iy-88) and 1 equivalent to 5 equivalents of compound (I-1) in the same manner as in step 2 of manufacturing method 2.

(Step 5)

Among compound (Iy-90), a compound in which $X^8a$ is —CH$_2$— can be manufactured by using compound (Iy-88) and 1 equivalent to 5 equivalents of compound (I-40t) in the same manner as in step 1 of manufacturing method 1-3.

(Step 6)

Among compound (Iy-90), a compound in which $X^8a$ is —NH—C(═O)— can be manufactured by using compound (Iy-88) and 1 equivalent to 5 equivalents of compound (I-2) in the same manner as in step 9 of manufacturing method 5.

(Step 7)

Among compound (Iy-91), a compound in which $X^8a$ is —C(═O)— can be manufactured by using compound (Iy-89) and 1 equivalent to 5 equivalents of compound (I-1) in the same manner as in step 2 of manufacturing method 2.

(Step 8)

Among compound (Iy-91), a compound in which $X^{88}$ is —CH$_2$— can be manufactured by using compound (Iy-89) and 1 equivalent to 5 equivalents of compound (I-40t) in the same manner as in step 1 of manufacturing method 1-3.

(Step 9)

Among compound (Iy-91), a compound in which $X^8a$ is —NH—C(═O)— can be manufactured by using compound (Iy-89) and 1 equivalent to 5 equivalents of compound (I-2) in the same manner as in step 9 of manufacturing method 5.

(Step 10)

Compound (Iy-92) can be manufactured by using compound (Iy-90) in the same manner as in step 2 of manufacturing method Y6.

[Manufacturing Method YS9-1]

Among compound (I) in which S is formula (S9), compound (Iy-75) in which Arg is triazolediyl and $Z^9$ is —CH$_2$— can be manufactured according to the following steps:

[Chemical Formula 89]

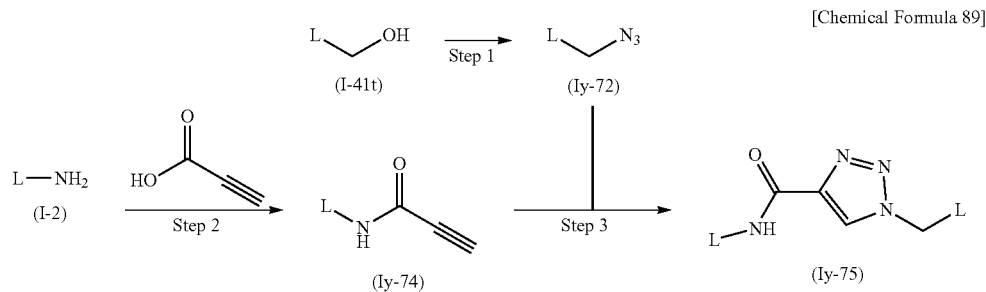

(wherein, L represents $L^1$ or $L^2$).

(Step 1)

Compound (Iy-72) can be manufactured by reacting compound (I-41t) in the presence of 1 equivalent to 10 equivalents of diphenylphosphoryl azide and a large excess of base in a solvent at a temperature between room temperature and the boiling point of the solvent used for 5 minutes to 120 hours.

Examples of the base include potassium tert-butoxide, potassium carbonate, sodium hydroxide, DBU, triethylamine, N,N-diisopropylethylamine, pyridine, 4-dimethylaminopyridine, and the like.

Examples of the solvent include toluene, dichloroethane, THF, 1,4-dioxane, and the like, and these can be used alone or as a mixture.

(Step 2)

Compound (Iy-74) can be manufactured by using compound (I-2) and 1 equivalent to 10 equivalents of propiolic acid in the same manner as in step 2 of manufacturing method 2.

(Step 3)

Compound (Iy-75) can be manufactured by using compound (Iy-74) and 1 equivalent to 5 equivalents of compound (Iy-72) in the same manner as in step 6 of manufacturing method 17.

[Manufacturing Method YS9-2]

Among compound (I) in which S is formula (S9), compound (Iy-81) in which Arg is oxazolediyl and $Z^9$ is —NH— can be manufactured according to the following steps:

[Chemical formula 90]

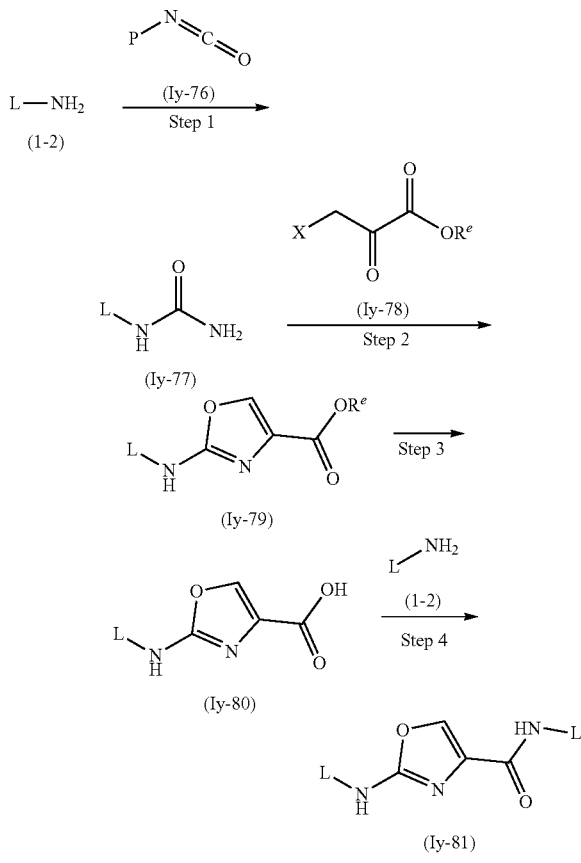

(wherein, L represents $L^1$ or $L^2$, X represents a halogen, $R^e$ represents lower alkyl, and P represents an amine protecting group such as trimethylsilyl, —C(=O)—CCl$_3$, and the like).

(Step 1)

Compound (Iy-77) can be manufactured by reacting compound (I-2) and 1 equivalent to 10 equivalents of compound (Iy-76) in a solvent at a temperature between −20° C. and the boiling point of the solvent used for 5 minutes to 120 hours.

Compound (Iy-76) can be obtained as a commercially available product, or can be obtained by known methods [e.g., Experimental Chemistry Lecture, 4th Edition, Volume 20, p. 473, Maruzen Co., Ltd. (2001) and the like] or methods based thereon.

Examples of the solvent include dichloromethane, toluene, acetonitrile, THF, 1,4-dioxane, and the like, and these are used alone or as a mixture.

(Step 2)

Compound (Iy-79) can be manufactured by reacting compound (Iy-77) and 1 equivalent to 10 equivalents of compound (Iy-78) in a solvent at a temperature between −20° C. and the boiling point of the solvent used for 5 minutes to 120 hours.

Compound (Iy-78) can be obtained as a commercially available product, or can be obtained by known methods [e.g., Experimental Chemistry Lecture, 5th Edition, Volume 15, p. 153, Maruzen Co., Ltd. (2004) and the like] or methods based thereon.

Examples of the solvent include toluene, acetonitrile, ethanol, 1,4-dioxane, DMF, DMA, NMP, and the like, and these are used alone or as a mixture.

(Step 3)

Compound (Iy-80) can be manufactured by using compound (Iy-79) in the same manner as in step 6 of manufacturing method 1.

(Step 4)

Compound (Iy-81) can be manufactured by using compound (Iy-80) and 1 equivalent to 5 equivalents of compound (I-2) in the same manner as in step 2 of manufacturing method 2.

[Manufacturing Method YS10-1]

Among compound (I) in which S is formula (S10), compound (Iy-71) in which $Z^{10}$ is —O— can be manufactured according to the following steps:

[Chemical formula 91]

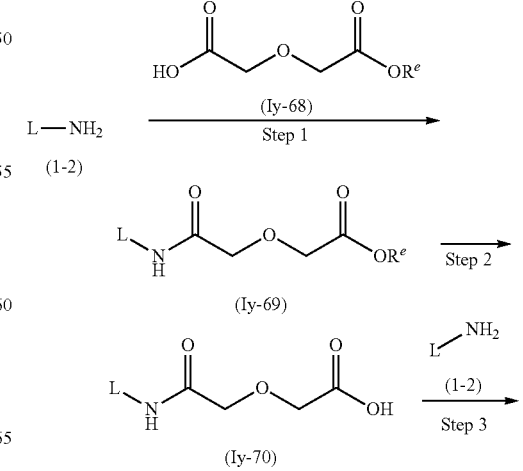

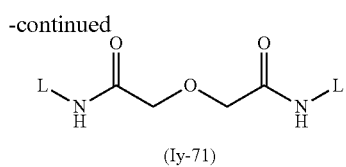

(Iy-71)

(wherein, L represents $L^1$ or $L^2$ and $R^e$ represents lower alkyl).

(Step 1)
Compound (Iy-69) can be manufactured by using compound (I-2) and 1 equivalent to 5 equivalents of compound (Iy-68) in the same manner as in step 2 of manufacturing method 2.

Compound (Iy-68) can be obtained as a commercially available product, or can be obtained by known methods [e.g., Experimental Chemistry Lecture, 5th Edition, Volume 16, p. 1, Maruzen Co., Ltd. (2004) and the like] or methods based thereon.

(Step 2)
Compound (Iy-70) can be manufactured by using compound (Iy-69) in the same manner as in step 6 of manufacturing method 1.

(Step 3)
Compound (Iy-71) can be manufactured by using compound (Iy-70) and 1 equivalent to 5 equivalents of compound (I-2) in the same manner as in step 2 of manufacturing method 2.

[Manufacturing Method YS10-2]

Among compound (I) in which S is formula (S10), compound (I-46t) in which $Z^{10}$ is —NH— can be manufactured according to the following steps:

[Chemical formula 92]

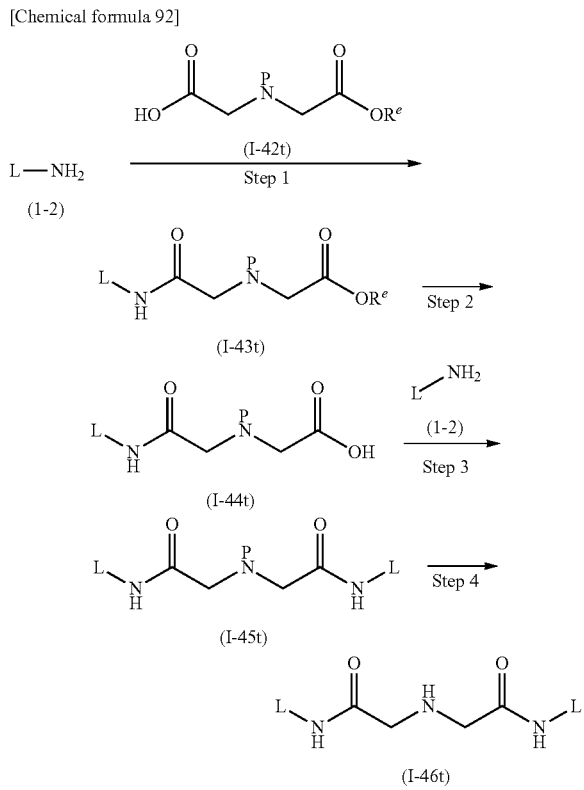

(wherein, L represents $L^1$ or $L^2$, Re represents lower alkyl, and P represents an amine protecting group such as Boc, Cbz, PMB, Fmoc, and the like).

(Step 1)
Compound (I-43t) can be manufactured by using compound (I-2) and 1 equivalent to 5 equivalents of compound (I-42t) in the same manner as in step 2 of manufacturing method 2.

Compound (I-42t) can be obtained as a commercially available product, or can be obtained by known methods [e.g., Experimental Chemistry Lecture, 5th Edition, Volume 16, p. 1, Maruzen Co., Ltd. (2004) and the like] or methods based thereon.

(Step 2)
Compound (I-44t) can be manufactured by using compound (I-43t) in the same manner as in step 6 of manufacturing method 1.

(Step 3)
Compound (I-45t) can be manufactured by using compound (I-44t) and 1 equivalent to 5 equivalents of compound (I-2) in the same manner as in step 2 of manufacturing method 2.

(Step 4)
Compound (I-46t) can be manufactured by using compound (I-45t) in the same manner as in step 4 of manufacturing method 1 when P in compound (I-45t) is, for example, Boc, Cbz, or PMB, and can be manufactured by using compound (I-45t) in the same manner as in step 3 of manufacturing method 2 when P in compound (I-45t) is, for example, Fmoc.

[Manufacturing Method YS11-1]

Among compound (I) in which S is formula (S11), compound (Iy-116a) in which $X^{11b}$ is —C(═O)—NH— can be manufactured according to the following steps:

[Chemical formula 93]

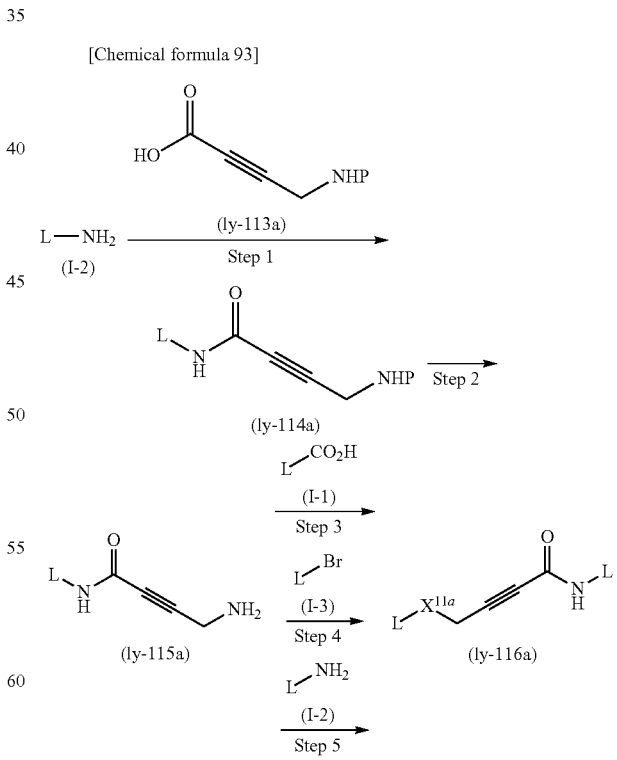

(wherein, $X^{11a}$ is as defined above, L represents $L^1$ or $L^2$, and P represents an amine protecting group such as Boc, Cbz, PMB, and the like).

(Step 1)

Compound (Iy-114a) can be manufactured by using compound (I-2) and 1 equivalent to 5 equivalents of compound (Iy-113a) in the same manner as in step 2 of manufacturing method 2.

Compound (Iy-113a) can be obtained as a commercially available product, or can be obtained by known methods [e.g., Experimental Chemistry Lecture, 5th Edition, Volume 16, p. 1, Maruzen Co., Ltd. (2004) and the like] or methods based thereon.

(Step 2)

Compound (Iy-115a) can be manufactured by using compound (Iy-114a) in the same manner as in step 4 of manufacturing method 1.

(Step 3)

Among compound (Iy-116a), a compound in which $X^{11a}$ is —C(=O)—NH— can be manufactured by using compound (Iy-115a) and 1 equivalent to 5 equivalents of compound (I-1) in the same manner as in step 2 of manufacturing method 2.

(Step 4)

Among compound (Iy-116a), a compound in which $X^{11a}$ is —SO$_2$—NH— can be manufactured by using compound (Iy-115a) and 1 equivalent to 5 equivalents of compound (I-3) in the same manner as in step 4 of manufacturing method 5.

(Step 5)

Among compound (Iy-116a), a compound in which $X^{11a}$ is —NH—C(=O)—NH— can be manufactured by using compound (Iy-115a) and 1 equivalent to 5 equivalents of compound (I-2) in the same manner as in step 9 of manufacturing method 5.

[Manufacturing Method YS11-2]

Among compound (I) in which $L^1$ is (A) and S is formula (S11), under the condition that ring RA is ring RA3 and $X^{11b}$ is —C(=O)—, (i) compound (Iy-118a) in which $X^{11a}$ is —C(=O)—NH—, (ii) compound (Iy-118b) in which $X^{11a}$ is —SO$_2$—NH—, and (iii) compound (Iy-118c) in which $X^{11a}$ is —NH—C(=O)—NH— can be manufactured respectively according to the following steps:

[Chemical formula 94]

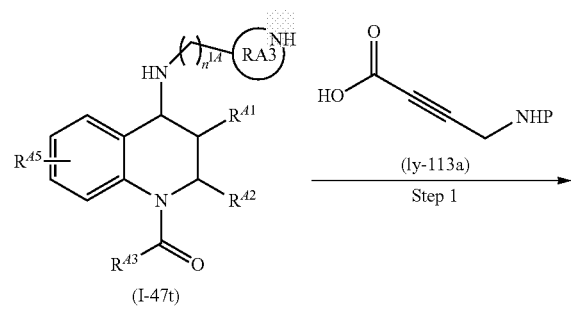

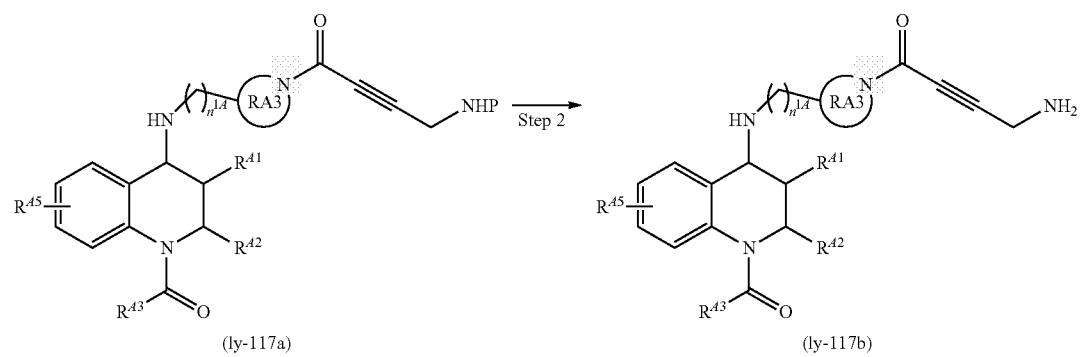

-continued

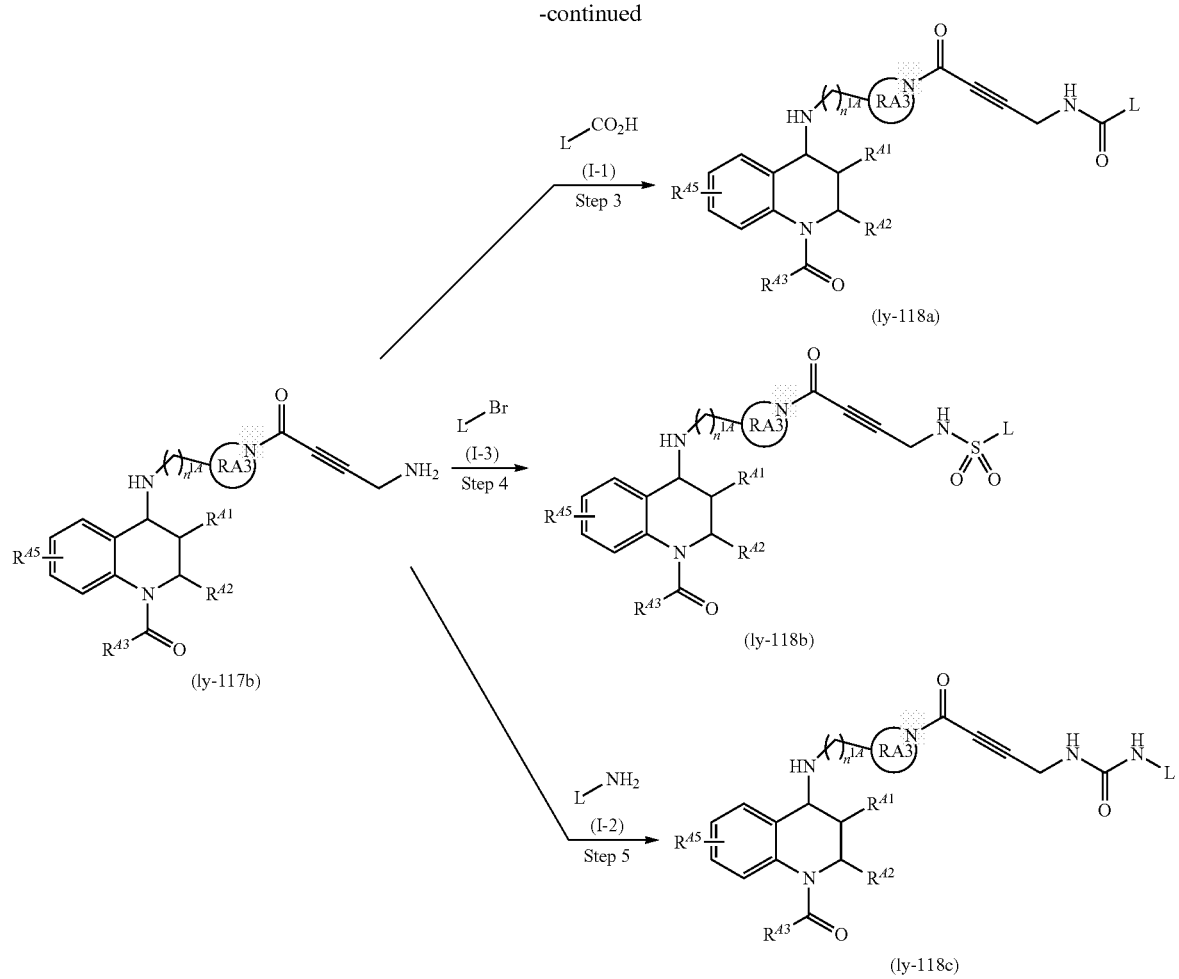

(wherein, $R^{A1}$, $R^{A2}$, $R^{A3}$, $R^{A5}$, $n^{14}$, and ring RA3 are as defined above, L represents $L^2$, and P represents an amine protecting group such as Boc, Cbz, PMB, and the like. In addition, one secondary amine forming the ring RA3 becomes a reaction point with compound (Iy-113a)).

(Step 1)

Compound (Iy-117a) can be manufactured by using compound (I-47t) and 1 equivalent to 5 equivalents of compound (Iy-113a) in the same manner as in step 2 of manufacturing method 2.

As for compound (I-47t), compound (a-32) obtained in step 6 of manufacturing method 1-3 and compound (a-41) obtained in step 6 of manufacturing method 1-4 shall be collectively represented as compound (I-47t).

Compound (Iy-113a) can be obtained as a commercially available product, or can be obtained by known methods [e.g., Experimental Chemistry Lecture, 5th Edition, Volume 16, p. 1, Maruzen Co., Ltd. (2004) and the like] or methods based thereon.

(Step 2)

Compound (Iy-117b) can be manufactured by using compound (I-117a) in the same manner as in step 4 of manufacturing method 1.

(Step 3)

Compound (Iy-118a) can be manufactured by using compound (Iy-117b) and 1 equivalent to 5 equivalents of compound (I-1) in the same manner as in step 2 of manufacturing method 2.

(Step 4)

Compound (Iy-118b) can be manufactured by using compound (Iy-117b) and 1 equivalent to 5 equivalents of compound (I-3) in the same manner as in step 4 of manufacturing method 5.

(Step 5)

Compound (Iy-118c) can be manufactured by using compound (Iy-117b) and 1 equivalent to 5 equivalents of compound (I-2) in the same manner as in step 9 of manufacturing method 5.

[Manufacturing Method YS12-1]

Among compound (I) in which S is formula (S12), under the condition that $Z^{12}a$ is $CH_2$, (i) compound (Iy-67) in which $X^{12}$ is —C(=O)—NH—, (ii) compound (I-48t) in which $X^{12}$ is —$SO_2$—NH—, and (iii) compound (I-49t) in which $X^{12}$ is —NH—C(=O)—NH— can be manufactured respectively according to the following steps:

[Chemical formula 95]

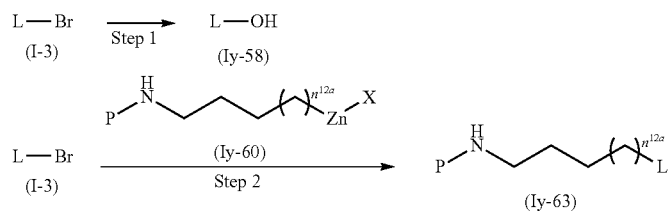

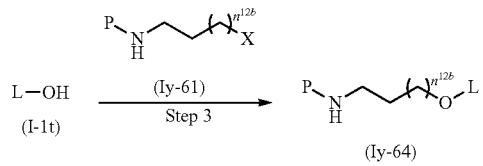

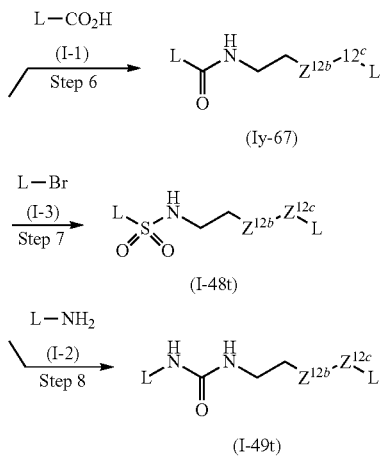

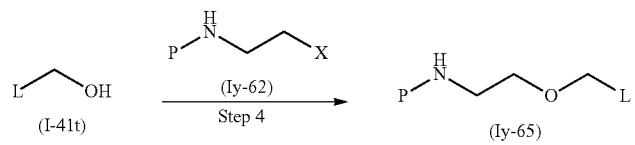

(wherein, $Z^{12b}$ and $Z^{12c}$ are as defined above, $n^{12a}$ and $n^{12b}$ are the same or different and each represents 0 or 1, L represents $L^1$ or $L^2$, X represents a halogen, and P represents an amine protecting group such as Boc, Cbz, PMB, and the like).

(Step 1)

Compound (Iy-58) can be manufactured by (i) reacting compound (I-3) in the presence of 1 equivalent to 5 equivalents of bis(pinacolato)diboron, 0.001 equivalent to 3 equivalents of palladium catalyst, and 0.001 equivalent to 3 equivalents of phosphorus ligand as necessary, and 1 equivalent to a large excess of base in a solvent at a temperature between room temperature and the boiling point of the solvent used for 5 minutes to 120 hours, and then (ii) reacting the obtained compound in the presence of 1 equivalent to a large excess of oxidizing agent in a solvent at a temperature between −20° C. and the boiling point of the solvent used for 5 minutes to 120 hours.

Examples of the palladium catalyst used in (i) include $Pd(dppf)Cl_2$, $Pd_2(dba)_3$, $Pd(PPh_3)_4$, and the like.

Examples of the phosphorus ligand used in (i) include tricyclohexylphosphine and the like.

Examples of the base used in (i) include potassium acetate, potassium carbonate, sodium carbonate, cesium carbonate, potassium phosphate, and the like.

Examples of the solvent used in (i) include chloroform, dichloromethane, DMF, DMA, NMP, DMSO, THF, acetonitrile, 1,4-dioxane, water, and the like, and these can be used alone or as a mixture.

Examples of the oxidizing agent used in (ii) include a hydrogen peroxide solution, sodium perborate, and the like.

Examples of the solvent used in (ii) include THF, 1,4-dioxane, water, and the like, and these can be used alone or as a mixture.

(Step 2)

Compound (Iy-63) can be manufactured by reacting compound (I-3) and 1 equivalent to 10 equivalents of compound (Iy-60) in the presence of 0.001 equivalent to 3 equivalents of palladium catalyst and, as necessary, 0.001 equivalent to 3 equivalents of phosphorus ligand in a solvent at a temperature between −20° C. and the boiling point of the solvent used for 5 minutes to 120 hours.

Compound (Iy-60) can be obtained as a commercially available product, or can be obtained by known methods [e.g., Experimental Chemistry Lecture, 5th Edition, Volume 18, p. 77, Maruzen Co., Ltd. (2004) and the like] or methods based thereon.

Examples of the palladium catalyst include $Pd(dppf)Cl_2$, $Pd_2(dba)_3$, $Pd(PPh_3)_4$, and the like.

Examples of the phosphorus ligand include tricyclohexylphosphine, 2-dicyclohexylphosphino-2',6'-dimethoxybiphenyl (SPhos), and the like.

Examples of the solvent include THF, DMF, DMA, NMP, and the like, and these are used alone or as a mixture.

(Step 3)

Compound (Iy-64) can be manufactured by reacting compound (I-1t) in the presence of 1 equivalent to 5 equivalents of compound (Iy-61) and 1 equivalent to a large excess of base in a solvent at a temperature between −20° C. and the boiling point of the solvent used for 5 minutes to 120 hours.

Examples of the base include sodium hydride, potassium tert-butoxide, triethylamine, N,N-diisopropylethylamine, N-methylmorpholine, DBU, potassium carbonate, cesium carbonate, and the like.

Examples of the solvent include toluene, diethyl ether, THF, DME, 1,4-dioxane, DMF, DMA, NMP, pyridine, acetonitrile, and the like, and these are used alone or as a mixture.

Compound (Iy-61) can be obtained as a commercially available product, or can be obtained by known methods [e.g., Experimental Chemistry Lecture, 5th Edition, Volume 13, p. 374, Maruzen Co., Ltd. (2004) and the like] or methods based thereon.

As for compound (I-1t), compound (ly-58) obtained in step 1 and compound (f-1) obtained in step 1 of manufacturing method Y6 shall be collectively represented as compound (I-1t).

(Step 4)

Compound (Iy-65) can be manufactured by reacting compound (I-41t) and 1 equivalent to 10 equivalents of compound (Iy-62) in the presence of 1 equivalent to 10 equivalents of base in a solvent at a temperature between −20° C. and 150° C. for 5 minutes to 120 hours.

Compound (Iy-62) can be obtained as a commercially available product, or can be obtained by known methods [e.g., Experimental Chemistry Lecture, 5th Edition, Volume 13, p. 374, Maruzen Co., Ltd. (2004) and the like] or methods based thereon.

Examples of the base include sodium hydride, potassium tert-butoxide, triethylamine, N,N-diisopropylethylamine, N-methylmorpholine, DBU, and the like.

Examples of the solvent include toluene, diethyl ether, THF, DME, 1,4-dioxane, DMF, DMA, NMP, pyridine, and the like, and these are used alone or as a mixture.

Compound (I-41t) can be obtained according to step 9 of manufacturing method 17.

(Step 5)

Compound (Iy-66) can be manufactured by using compound (Iy-63), compound (Iy-64), or compound (Iy-65) in the same manner as in step 4 of manufacturing method 1.

(Step 6)

Compound (Iy-67) can be manufactured by using compound (Iy-66) and 1 equivalent to 5 equivalents of compound (I-1) in the same manner as in step 2 of manufacturing method 2.

(Step 7)

Compound (I-48t) can be manufactured by using compound (Iy-66) and 1 equivalent to 5 equivalents of compound (I-3) in the same manner as in step 4 of manufacturing method 5.

(Step 8)

Compound (I-49t) can be manufactured by using compound (Iy-66) and 1 equivalent to 5 equivalents of compound (I-2) in the same manner as in step 9 of manufacturing method 5.

[Manufacturing Method YS12-2]

Among compound (I) in which S is formula (S12), compound (Iy-67a) in which $Z^{12}a$ is $CH_2$ and $X^{12}$ is —NH—C(=O)— can be manufactured according to the following steps:

[Chemical formula 96]

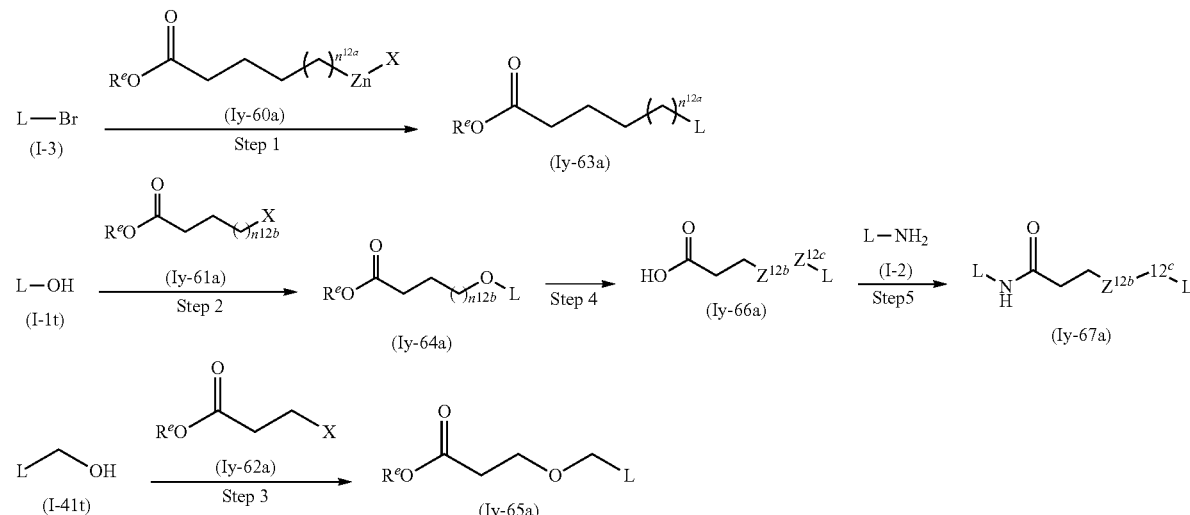

(wherein, $Z^{12b}$ and $Z^{12c}$ are as defined above, $n^{12a}$ and $n^{12b}$ are the same or different and each represents 0 or 1, L represents $L^1$ or $L^2$, X represents a halogen, and Re represents lower alkyl).

(Step 1)

Compound (Iy-63a) can be manufactured by using compound (I-3) and 1 equivalent to 5 equivalents of compound (Iy-60a) in the same manner as in step 2 of manufacturing method YS12-1.

Compound (Iy-60a) can be obtained as a commercially available product, or can be obtained by known methods [e.g., Experimental Chemistry Lecture, 5th Edition, Volume 18, p. 77, Maruzen Co., Ltd. (2004) and the like] or methods based thereon.

(Step 2)

Compound (Iy-64a) can be manufactured by using compound (I-1t) and 1 equivalent to 5 equivalents of compound (Iy-61a) in the same manner as in step 3 of manufacturing method YS12-1.

Compound (Iy-61a) can be obtained as a commercially available product, or can be obtained by known methods [e.g., Experimental Chemistry Lecture, 5th Edition, Volume 13, p. 374, Maruzen Co., Ltd. (2004) and the like] or methods based thereon.

As for compound (I-1t), compound (ly-58) obtained in step 1 of manufacturing method YS12-1 and compound (f-1)

obtained in step 1 of manufacturing method Y6 shall be collectively represented as compound (I-1t).

(Step 3)
Compound (Iy-65a) can be manufactured by using compound (I-41t) and 1 equivalent to 5 equivalents of compound (Iy-62a) in the same manner as in step 4 of manufacturing method YS12-1.

Compound (Iy-62a) can be obtained as a commercially available product, or can be obtained by known methods [e.g., Experimental Chemistry Lecture, 5th Edition, Volume 13, p. 374, Maruzen Co., Ltd. (2004) and the like] or methods based thereon.

Compound (I-41t) can be obtained according to step 9 of manufacturing method 17.

(Step 4)
Compound (Iy-66a) can be manufactured by using compound (Iy-63a), compound (Iy-64a), or compound (Iy-65a) in the same manner as in step 6 of manufacturing method 1.

(Step 5)
Compound (Iy-67a) can be manufactured by using compound (Iy-66a) and 1 equivalent to 5 equivalents of compound (I-2) in the same manner as in step 2 of manufacturing method 2.

[Manufacturing Method YS12-3]
Among compound (I) in which S is formula (S12), compound (I-53t) in which $Z^{12}a$ is NH can be manufactured according to the following steps:

[Chemical formula 97]

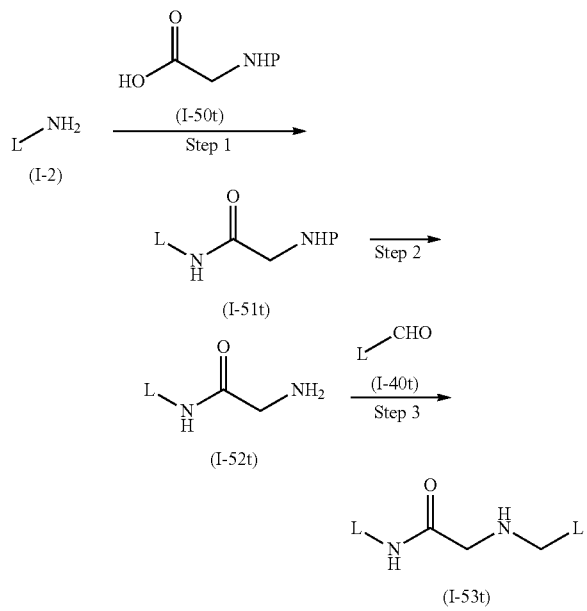

(wherein, L represents $L^1$ or $L^2$, and P represents an amine protecting group such as Boc, Cbz, PMB, and the like).

(Step 1)
Compound (I-51t) can be manufactured by using compound (I-2) and 1 equivalent to 5 equivalents of compound (I-50t) in the same manner as in step 2 of manufacturing method 2.

Compound (I-50t) can be obtained as a commercially available product, or can be obtained by known methods [e.g., Experimental Chemistry Lecture, 5th Edition, Volume 16, p. 175, Maruzen Co., Ltd. (2004) and the like] or methods based thereon.

(Step 2)
Compound (I-52t) can be manufactured by using compound (I-51t) in the same manner as in step 4 of manufacturing method 1.

(Step 3)
Compound (I-53t) can be manufactured by using compound (I-52t) and 1 equivalent to 5 equivalents of compound (I-40t) in the same manner as in step 1 of manufacturing method 1-3.

[Manufacturing Method YS13]
Among compound (I) in which S is formula (S13), (i) compound (Iy-53) in which $n^{13}$ is 0 and (ii) compound (Iy-57) in which $n^{13}$ is $n^{13}a$ can be manufactured respectively according to the following steps:

[Chemical formula 98]

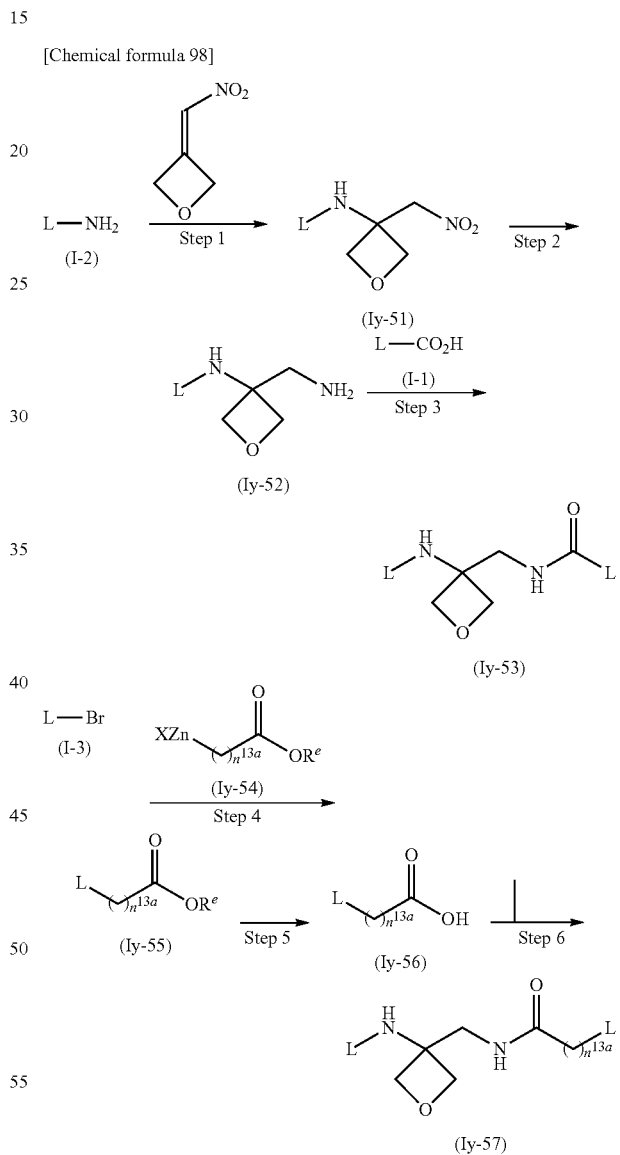

(wherein, $n^{13a}$ represents 1 or 2, L represents $L^1$ or $L^2$, X represents a halogen, and Re represents lower alkyl).

(Step 1)
Compound (Iy-51) can be manufactured by reacting compound (I-2) and 1 equivalent to 10 equivalents of 3-(nitromethylene)oxetane in the presence of a large excess of base in a solvent at a temperature between −20° C. and 150° C. for 5 minutes to 120 hours.

Examples of the base include triethylamine, N,N-diisopropylethylamine, N-methylmorpholine, DBU, and the like.

Examples of the solvent include toluene, diethyl ether, THF, DME, 1,4-dioxane, and the like, and these are used alone or as a mixture.

(Step 2)

Compound (Iy-52) can be manufactured by using compound (Iy-51) in the same manner as in step 8 of manufacturing method 1.

(Step 3)

Compound (Iy-53) can be manufactured by using compound (Iy-52) and 1 equivalent to 5 equivalents of compound (I-1) in the same manner as in step 2 of manufacturing method 2.

(Step 4)

Compound (Iy-55) can be manufactured by using compound (I-3) and 1 equivalent to 5 equivalents of compound (Iy-54) in the same manner as in step 2 of manufacturing method YS12-1.

Compound (Iy-54) can be obtained as a commercially available product, or can be obtained by known methods [e.g., Experimental Chemistry Lecture, 5th Edition, Volume 18, p. 77, Maruzen Co., Ltd. (2004) and the like] or methods based thereon.

(Step 5)

Compound (Iy-56) can be manufactured by using compound (Iy-55) in the same manner as in step 6 of manufacturing method 1.

(Step 6)

Compound (Iy-57) can be manufactured by using compound (Iy-52) and 1 equivalent to 5 equivalents of compound (Iy-56) in the same manner as in step 2 of manufacturing method 2.

[Manufacturing Method YS14]

Among compound (I), compound (Iy-49) in which S is formula (S14) can be manufactured according to the following steps:

[Chemical formula 99]

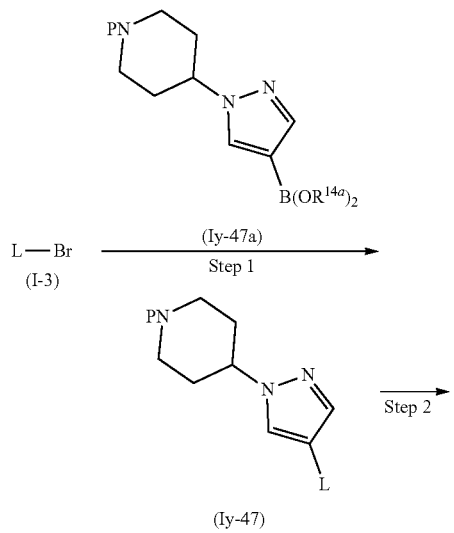

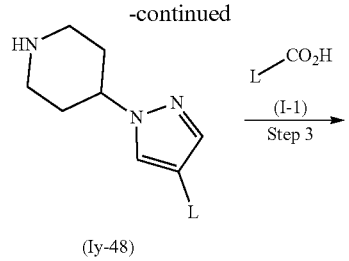

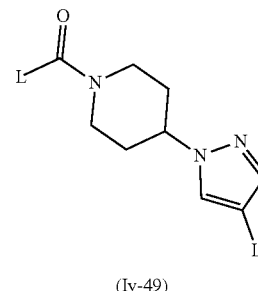

(wherein, L represents $L^1$ or $L^2$, $R^{14a}$ represents a hydrogen atom or lower alkyl, and P represents an amine protecting group such as Boc, Cbz, PMB, and the like).

(Step 1)

Compound (Iy-47) can be manufactured by using compound (I-3) and 1 equivalent to 5 equivalents of compound (Iy-47a) in the same manner as in step 3 of manufacturing method 3.

Compound (Iy-47a) can be obtained as a commercially available product, or can be obtained by known methods [e.g., Experimental Chemistry Lecture, 5th Edition, Volume 18, p. 95, Maruzen Co., Ltd. (2004) and the like] or methods based thereon.

(Step 2)

Compound (Iy-48) can be manufactured by using compound (Iy-47) in the same manner as in step 4 of manufacturing method 1.

(Step 3)

Compound (Iy-49) can be manufactured by using compound (Iy-48) and 1 equivalent to 5 equivalents of compound (I-1) in the same manner as in step 2 of manufacturing method 2.

[Manufacturing Method YS15]

Among compound (I), compound (Iy-46c) in which S is represented by formula (S15) can be manufactured according to the following steps:

[Chemical formula 100]

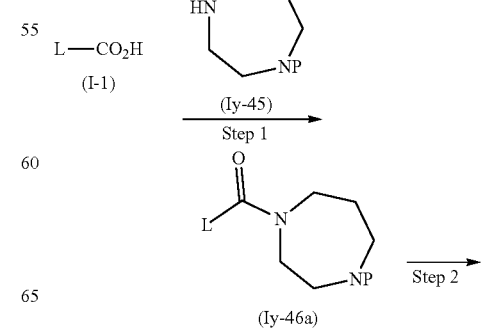

-continued

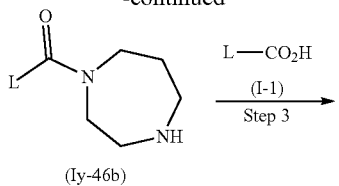

(Iy-46b)

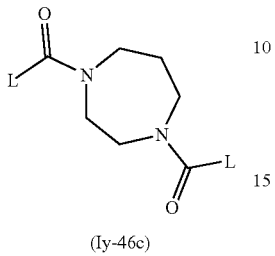

(Iy-46c)

(wherein, L represents $L^1$ or $L^2$ and P represents an amine protecting group such as Boc, Cbz, PMB, and the like).

(Step 1)
Compound (Iy-46a) can be manufactured by using compound (I-1) and 1 equivalent to 5 equivalents of compound (Iy-45) in the same manner as in step 2 of manufacturing method 2.

Compound (Iy-45) can be obtained as a commercially available product, or can be obtained by known methods [e.g., Experimental Chemistry Lecture, 5th Edition, Volume 14, p. 351, Maruzen Co., Ltd. (2004) and the like] or methods based thereon.

(Step 2)
Compound (Iy-46b) can be manufactured by using compound (Iy-46a) in the same manner as in step 4 of manufacturing method 1.

(Step 3)
Compound (Iy-46c) can be manufactured by using compound (Iy-46b) and 1 equivalent to 5 equivalents of compound (I-1) in the same manner as in step 2 of manufacturing method 2.

[Manufacturing Method YS16-1-2]

Among compound (I) in which $L^1$ is $L^E$ and S is formula (S16), under the condition that $Ar^{16}$ is triazolediyl, (i) compound (Iy-14) in which $X^{16}$ is —C(=O)—NH—, (ii) compound (Iy-20) in which $X^{16}$ is —NH—C(=O)—, (iii) compound (Iy-17b) in which $X^{16}$ is —NH—C(=O)—NH—, and (iv) compound (I-60t) in which $X^{16}$ is —CH$_2$—O— can be manufactured respectively according to the following steps:

[Chemical formula 101]

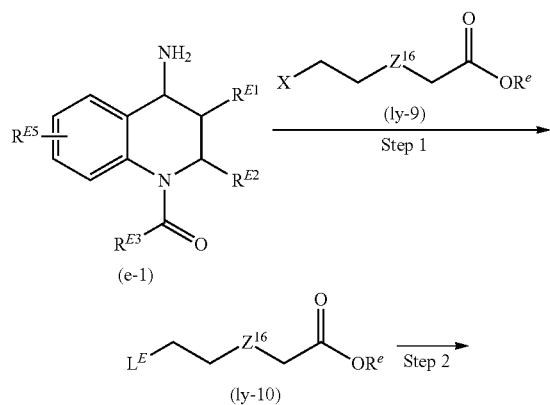

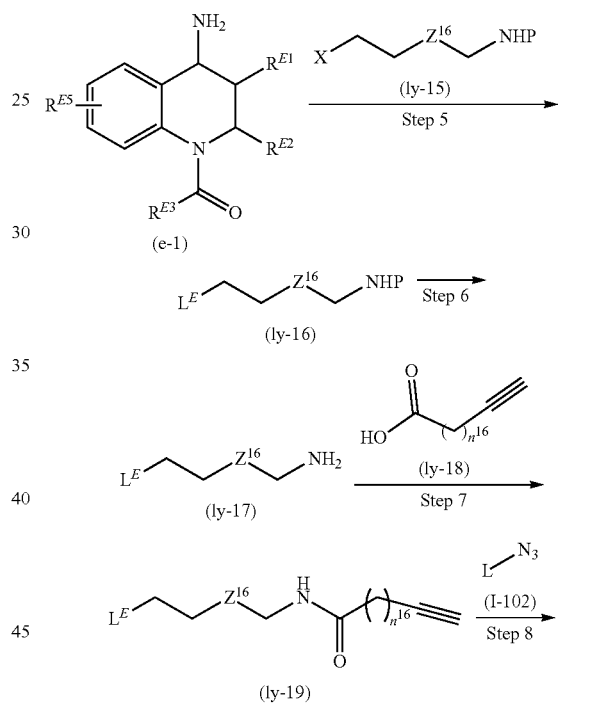

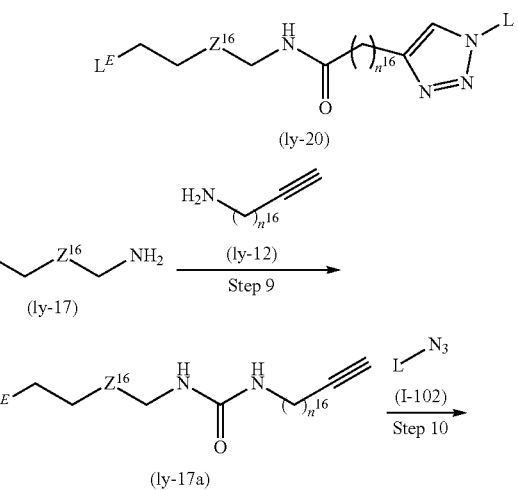

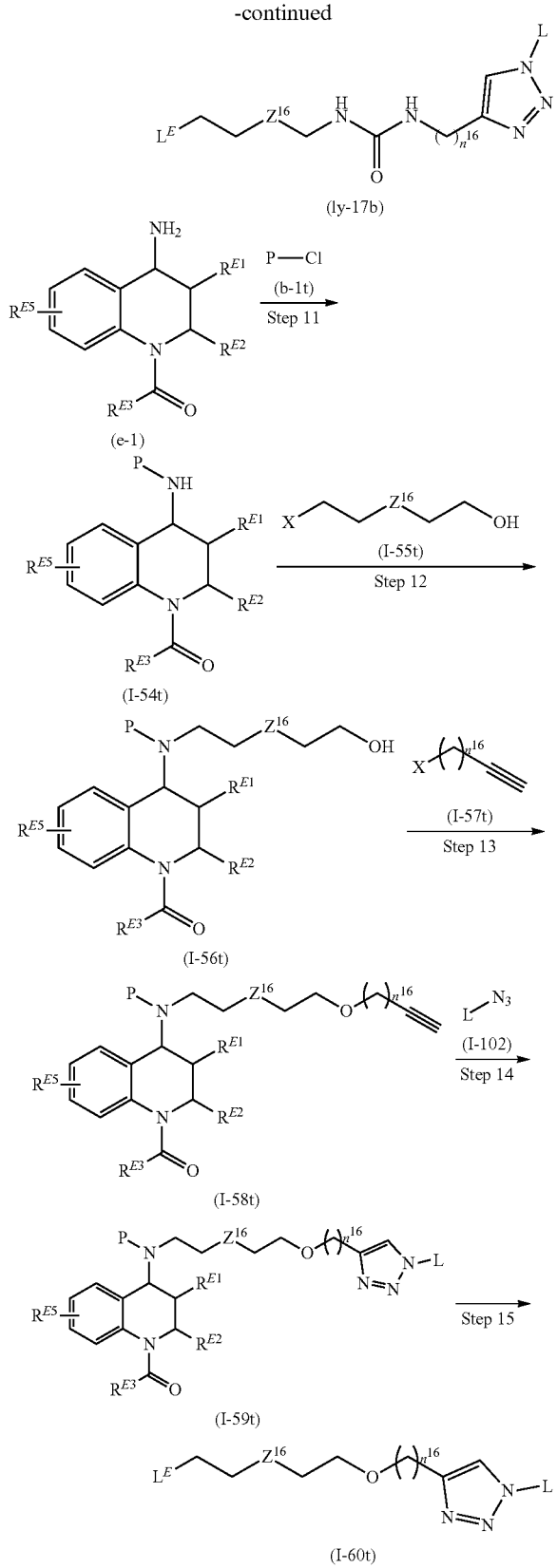

(wherein, $R^{E1}$, $R^{E2}$, $R^{E3}$, $R^{E5}$, $n^{16}$, and $Z^{16}$ are as defined above, $L^E$ is a group represented by formula (E), L represents $L^2$, X represents a halogen, $R^e$ represents lower alkyl, and P represents an amine protecting group such as Boc, Cbz, PMB, 2-nitrobenzenesulfonyl (Ns), and the like).

(Step 1)
Compound (Iy-10) can be manufactured by using compound (e-1) and 1 equivalent to 5 equivalents of compound (Iy-9) in the same manner as in step 1 of manufacturing method 1-2.

Compound (e-1) can be obtained in the same manner as in step 4 of manufacturing method 1.

Compound (Iy-9) can be obtained as a commercially available product, or can be obtained by known methods [e.g., Experimental Chemistry Lecture, 5th Edition, Volume 13, p. 374, Maruzen Co., Ltd. (2004) and the like] or methods based thereon.

(Step 2)
Compound (Iy-11) can be manufactured by using compound (Iy-10) in the same manner as in step 6 of manufacturing method 1.

(Step 3)
Compound (Iy-13) can be manufactured by using compound (Iy-11) and 1 equivalent to 5 equivalents of compound (Iy-12) in the same manner as in step 2 of manufacturing method 2.

Compound (Iy-12) can be obtained as a commercially available product, or can be obtained by known methods [e.g., Experimental Chemistry Lecture, 5th Edition, Volume 14, p. 351, Maruzen Co., Ltd. (2004) and the like] or methods based thereon.

(Step 4)
Compound (Iy-14) can be manufactured by using compound (Iy-13) and 1 equivalent to 5 equivalents of compound (I-102) in the same manner as in step 6 of manufacturing method 17.

(Step 5)
Compound (Iy-16) can be manufactured by using compound (e-1) and 1 equivalent to 5 equivalents of compound (Iy-15) in the same manner as in step 1 of manufacturing method 1-2.

Compound (Iy-15) can be obtained as a commercially available product, or can be obtained by known methods [e.g., Experimental Chemistry Lecture, 5th Edition, Volume 13, p. 374, Maruzen Co., Ltd. (2004) and the like] or methods based thereon.

(Step 6)
Compound (Iy-17) can be manufactured by using compound (Iy-16) in the same manner as in step 4 of manufacturing method 1.

(Step 7)
Compound (Iy-19) can be manufactured by using compound (Iy-17) and 1 equivalent to 5 equivalents of compound (Iy-18) in the same manner as in step 2 of manufacturing method 2.

Compound (Iy-18) can be obtained as a commercially available product, or can be obtained by known methods [e.g., Experimental Chemistry Lecture, 5th Edition, Volume 16, p. 1, Maruzen Co., Ltd. (2004) and the like] or methods based thereon.

(Step 8)
Compound (Iy-20) can be manufactured by using compound (Iy-19) and 1 equivalent to 5 equivalents of compound (I-102) in the same manner as in step 6 of manufacturing method 17.

(Step 9)
Compound (Iy-17a) can be manufactured by using compound (Iy-17) and 1 equivalent to 5 equivalents of compound (Iy-12) in the same manner as in step 9 of manufacturing method 5.

(Step 10)

Compound (Iy-17b) can be manufactured by using compound (Iy-17a) and 1 equivalent to 5 equivalents of compound (I-102) in the same manner as in step 6 of manufacturing method 17.

(Step 11)

Compound (I-54t) can be manufactured by using compound (e-1) and 1 equivalent to 5 equivalents of compound (b-1t) in the same manner as in step 6 of manufacturing method T2.

(Step 12)

Compound (I-56t) can be manufactured by using compound (I-54t) and 1 equivalent to 10 equivalents of compound (I-55t) in the same manner as in step 1 of manufacturing method 1-2.

Compound (I-55t) can be obtained as a commercially available product, or can be obtained by known methods [e.g., Experimental Chemistry Lecture, 5th Edition, Volume 13, p. 374, Maruzen Co., Ltd. (2004) and the like] or methods based thereon.

(Step 13)

Compound (I-58t) can be manufactured by using compound (I-56t) and 1 equivalent to 10 equivalents of compound (I-57t) in the same manner as in step 4 of manufacturing method YS12-1.

Compound (I-57t) can be obtained as a commercially available product, or can be obtained by known methods [e.g., Experimental Chemistry Lecture, 5th Edition, Volume 13, p. 374, Maruzen Co., Ltd. (2004) and the like] or methods based thereon.

(Step 14)

Compound (I-59t) can be manufactured by using compound (I-58t) and 1 equivalent to 5 equivalents of compound (I-102) in the same manner as in step 6 of manufacturing method 17.

(Step 15)

When P in compound (I-59t) is, for example, Ns, compound (I-60t) can be manufactured by reacting compound (I-59t) in the presence of 1 equivalent to 10 equivalents of thiol and 1 equivalent to a large excess of base in a solvent at a temperature between −20° C. and the boiling point of the solvent used for 5 minutes to 120 hours.

Examples of the thiol include thiophenol, mercaptoacetic acid, 2-mercaptoethanol, and the like.

Examples of the base include cesium carbonate, potassium carbonate, sodium carbonate, and the like.

Examples of the solvent include acetonitrile, DMF, DMSO, and the like, and these can be used alone or as a mixture.

[Manufacturing Method YS16-2-2]

Among compound (I) in which S is formula (S16), under the condition that $Ar^{16}$ is pyrazolediyl, (i) compound (Iy-7) in which $X^{16}$ is —C(=O)—NH—, (ii) compound (Iy-27) in which $X^{16}$ is —NH—C(=O)—, and (iii) compound (Iy-7a) in which $X^{16}$ is —NH—C(=O)—NH—; and under the condition that $Ar^{16}$ is oxadiazolediyl, (i) compound (Iy-8) in which $X^{16}$ is —C(=O)—NH—, (ii) compound (Iy-28) in which $X^{16}$ is —NH—C(=O)—, and (iii) compound (Iy-8a) in which $X^{16}$ is —NH—C(=O)—NH— can be manufactured respectively according to the following steps:

[Chemical formula 102]

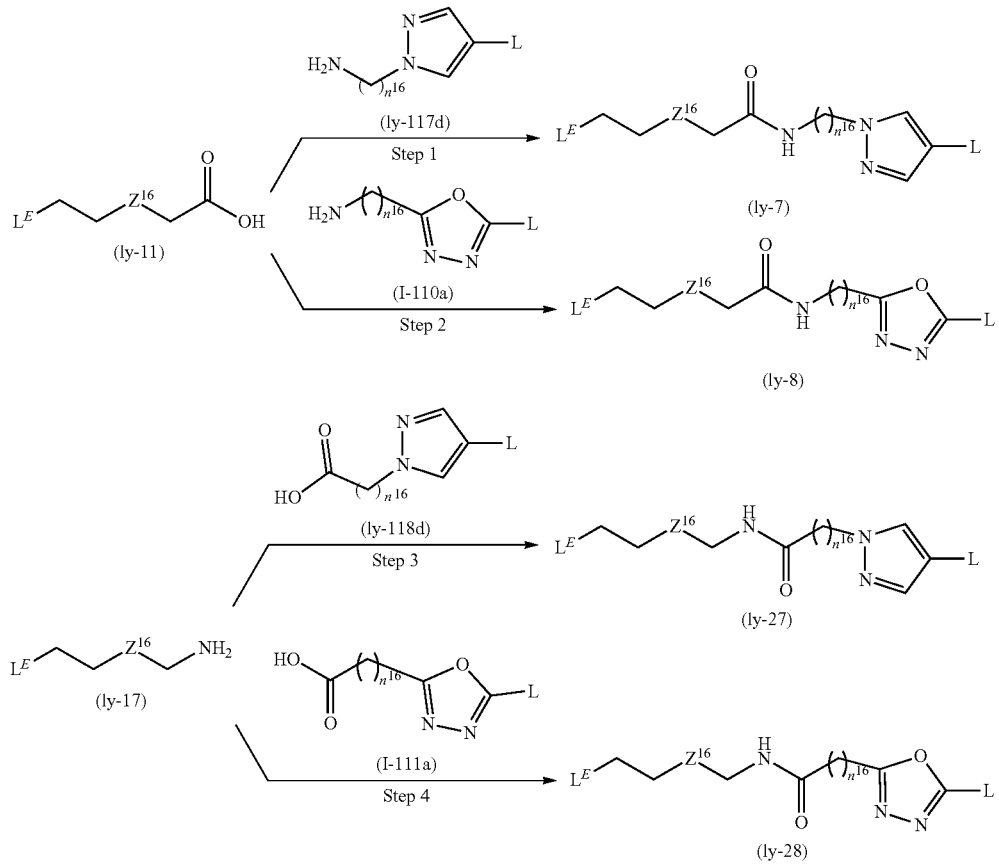

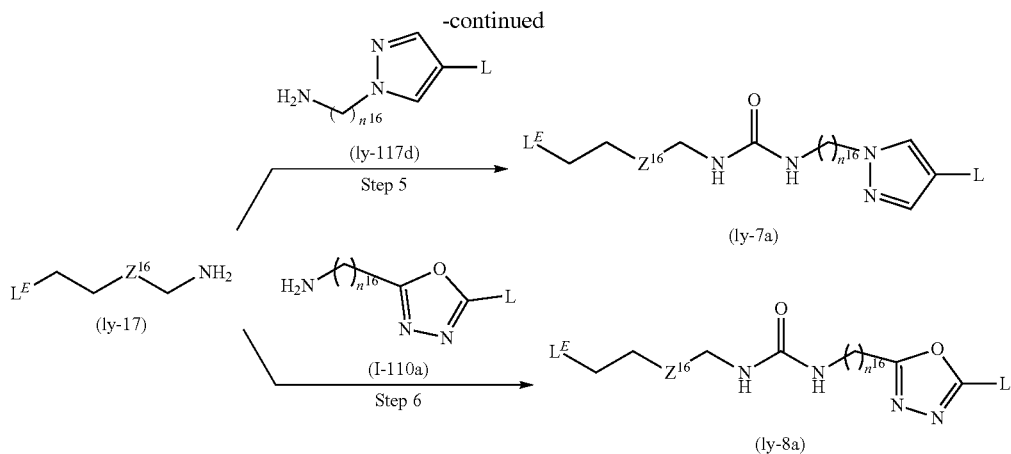

(wherein, $n^{16}$ and $Z^{16}$ are as defined above, $L^E$ is a group represented by formula (E), and L represents $L^2$).

(Step 1)
Compound (Iy-7) can be manufactured by using compound (Iy-11) and 1 equivalent to 5 equivalents of compound (Iy-117d) in the same manner as in step 2 of manufacturing method 2.
Compound (Iy-117d) can be obtained in the same manner as in step 3 of manufacturing method YS6-1.

(Step 2)
Compound (Iy-8) can be manufactured by using compound (Iy-11) and 1 equivalent to 5 equivalents of compound (I-110a) in the same manner as in step 2 of manufacturing method 2.
Compound (I-110a) can be obtained in the same manner as in step 5 of manufacturing method 18.

(Step 3)
Compound (Iy-27) can be manufactured by using compound (Iy-17) and 1 equivalent to 5 equivalents of compound (Iy-118d) in the same manner as in step 2 of manufacturing method 2.
Compound (Iy-118d) can be obtained in the same manner as in step 4 of manufacturing method YS6-1.

(Step 4)
Compound (Iy-28) can be manufactured by using compound (Iy-17) and 1 equivalent to 5 equivalents of compound (I-111a) in the same manner as in step 2 of manufacturing method 2.
Compound (I-111a) can be obtained in the same manner as in step 6 of manufacturing method 18.

(Step 5)
Compound (Iy-7a) can be manufactured by using compound (Iy-17) and 1 equivalent to 5 equivalents of compound (Iy-117d) in the same manner as in step 9 of manufacturing method 5.

(Step 6)
Compound (Iy-8a) can be manufactured by using compound (Iy-17) and 1 equivalent to 5 equivalents of compound (I-110a) in the same manner as in step 9 of manufacturing method 5.

[Manufacturing Method YS17]
Among compound (I) in which $L^1$ is LE and S is formula (S17), (i) compound (I-64t) in which $X^{17}$ is —C(=O)—NH—, (ii) compound (I-68t) in which $X^{17}$ is —NH—C(=O)—, (iii) compound (I-69t) in which $X^{17}$ is —NH—SO$_2$—, and (iv) compound (I-70t) in which $X^{17}$ is —NH—C(=O)—NH— can be manufactured respectively according to the following steps:

[Chemical formula 103]
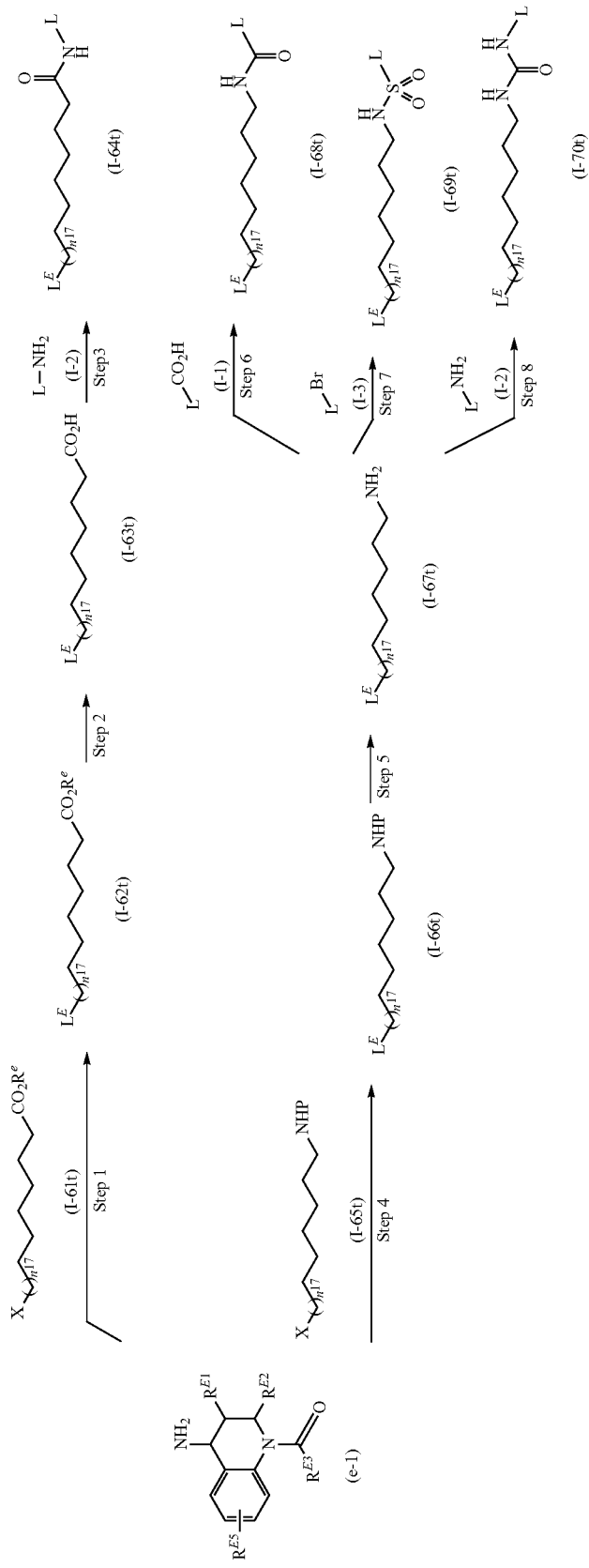

(wherein, $R^{E1}$, $R^{E2}$, $R^{E3}$, $R^{E5}$, and $n^{17}$ are as defined above, $L^E$ is a group represented by formula (E), L represents $L^2$, X represents a halogen, $R^e$ represents lower alkyl, and P represents an amine protecting group such as Boc, Cbz, PMB, and the like).

(Step 1)

Compound (I-62t) can be manufactured by using compound (e-1) and 1 equivalent to 10 equivalents of compound (I-61t) in the same manner as in step 1 of manufacturing method 1-2.

Compound (I-61t) can be obtained as a commercially available product, or can be obtained by known methods [e.g., Experimental Chemistry Lecture, 5th Edition, Volume 13, p. 374, Maruzen Co., Ltd. (2004) and the like] or methods based thereon.

(Step 2)

Compound (I-63t) can be manufactured by using compound (I-62t) in the same manner as in step 6 of manufacturing method 1.

(Step 3)

Compound (I-64t) can be manufactured by using compound (I-63t) and 1 equivalent to 5 equivalents of compound (I-2) in the same manner as in step 2 of manufacturing method 2.

(Step 4)

Compound (I-66t) can be manufactured by using compound (e-1) and 1 equivalent to 10 equivalents of compound (I-65t) in the same manner as in step 1 of manufacturing method 1-2.

Compound (I-65t) can be obtained as a commercially available product, or can be obtained by known methods [e.g., Experimental Chemistry Lecture, 5th Edition, Volume 13, p. 374, Maruzen Co., Ltd. (2004) and the like] or methods based thereon.

(Step 5)

Compound (I-67t) can be manufactured by using compound (I-66t) in the same manner as in step 4 of manufacturing method 1.

(Step 6)

Compound (I-68t) can be manufactured by using compound (I-67t) and 1 equivalent to 5 equivalents of compound (I-1) in the same manner as in step 2 of manufacturing method 2.

(Step 7)

Compound (I-69t) can be manufactured by using compound (I-67t) and 1 equivalent to 5 equivalents of compound (I-3) in the same manner as in step 4 of manufacturing method 5.

(Step 8)

Compound (I-70t) can be manufactured by using compound (I-67t) and 1 equivalent to 5 equivalents of compound (I-2) in the same manner as in step 9 of manufacturing method 5.

[Manufacturing Method YS18]

Compound (I) in which $L^1$ is $L^E$ and S is formula (S18) can be manufactured according to the following steps:

[Chemical formula 104]

(wherein, $R^{E1}$, $R^{E2}$, $R^{E3}$, $R^{E5}$, $n^{18a}$, $n^{18b}$, and $n^{18c}$ are as defined above, $L^E$ is a group represented by formula (E), L represents $L^2$, X represents a halogen, and P represents an amine protecting group such as Boc, Cbz, PMB, and the like).

(Step 1)

Compound (I-72t) can be manufactured by using compound (e-1) and 1 equivalent to 10 equivalents of compound (I-71t) in the same manner as in step 1 of manufacturing method 1-2.

Compound (I-71t) can be obtained as a commercially available product, or can be obtained by known methods [e.g., Experimental Chemistry Lecture, 5th Edition, Volume 13, p. 374, Maruzen Co., Ltd. (2004) and the like] or methods based thereon.

(Step 2)

Compound (I-73t) can be manufactured by using compound (I-72t) in the same manner as in step 4 of manufacturing method 1.

(Step 3)

Compound (I-74t) can be manufactured by using compound (I-73t) and 1 equivalent to 5 equivalents of compound (I-2) in the same manner as in step 9 of manufacturing method 5.

Conversion of various functional groups in the manufacturing methods of compound (I) can be conducted by known methods [e.g., methods described in Comprehensive Organic Transformations, 2nd Edition, R. C. Lark, Vch. Verlagsgesellschaft Mbh (1999) and the like] or methods based thereon.

The intermediates and target compounds in each of the above-mentioned manufacturing methods can be isolated and purified by subjecting them to isolation/purification methods commonly used in synthetic organic chemistry, for example, filtration, extraction, washing, drying, concentration, recrystallization, various chromatography, and the like.

Furthermore, the intermediates can be supplied to the next reactions without any particular purification.

Among compound (I), there are compounds for which there can be stereoisomers such as geometrical isomers, optical isomers, and the like, tautomers, and the like, but the present invention includes all possible isomers including these and mixtures thereof. For example, compound numbers 2c and 2d in Table 2 below are optical isomers, and both of these are included in the scope of compound (I) of the present invention.

A part or all of each atom in compound (I) may be substituted with corresponding isotope atoms, and the present invention also includes the compounds substituted with these isotope atoms. For example, a part or all of hydrogen atoms in compound (I) may be hydrogen atoms having an atomic weight of 2 (deuterium atoms).

A compound obtained by substituting a part or all of each atom in compound (I) with the corresponding isotope atom can be manufactured by a method similar to each of the above-mentioned manufacturing methods by using commercially available building blocks. Furthermore, a compound obtained by substituting a part or all of hydrogen atoms in compound (I) with deuterium atoms can also be synthesized, for example, by 1) a method of deuterating a carboxylic acid and the like by using deuterium peroxide under a basic condition (see the description of U.S. Pat. No. 3849458), 2) a method of deutarating an alcohol, a carboxylic acid, and the like by using an iridium complex as a catalyst and heavy water as a deuterium source [see J. Am. Chem. Soc., Vol. 124, No. 10, 2092 (2002)], 3) a method of deutarating an aliphatic acid by using palladium on carbon as a catalyst and using only deuterium gas as a deuterium source [see LIPIDS, Vol. 9, No. 11, 913 (1974)], 4) a method of deutarating acrylic acid, methyl acrylate, methacrylic acid, methyl methacrylate, and the like by using a metal such as platinum, palladium, rhodium, ruthenium, iridium, and the like as a catalyst and using heavy water or heavy water and deuterium gas as a deuterium source (see Japanese Examined Patent Application Publication No. H5-19536, Japanese Unexamined Patent Application Publication No. S61-277648, and Japanese Unexamined Patent Application Publication No. S61-275241), 5) a method of deuterating acrylic acid, methyl methacrylate, and the like by using a catalyst such as palladium, nickel, copper, copper chromite, and the like, and heavy water as a deuterium source (see Japanese Unexamined Patent Application Publication No. S63-198638), and the like.

When a salt of compound (I) is desired, in the case where compound (I) is obtained in the form of a salt, it should be purified as it is, or in the case where compound (I) is obtained in a free form, it should be dissolved or suspended in a suitable solvent and an acid or a base should be added to form a salt thereof, followed by isolation and purification.

Furthermore, compound (I) and a pharmaceutically acceptable salt thereof may sometimes be present in the form of an adduct with water or various solvents, but these adducts are also included in the present invention.

Compound (I) preferably includes compounds described in the following Tables 1 to 15. In addition, in the Tables, A1, A2, A5, A6, A9, A10, A11, A12, A14, A15, A16, A17, A18, A19, A20, A21, B1, B2, B3, B4, B5, B6, B7, B8, B9, C1, C2, D1, D2, D3, D4, E1, F1, and F2, which are described as $L^1$ or $L^2$, have the following structures, respectively:

[Chemical formula 105]

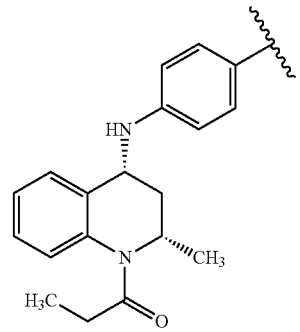

(A1)

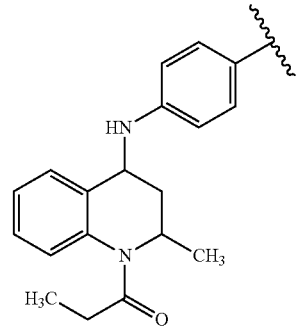

(A2)

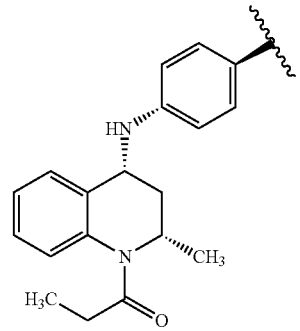

(A5)

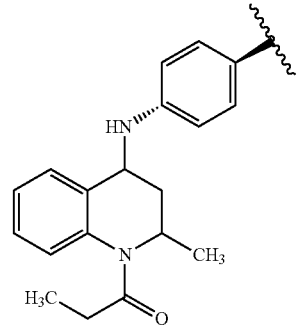

(A6)

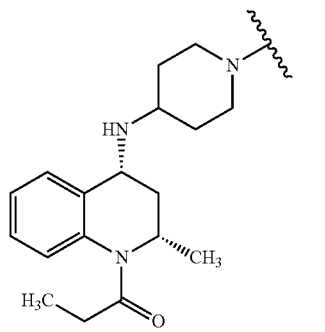
(A9)
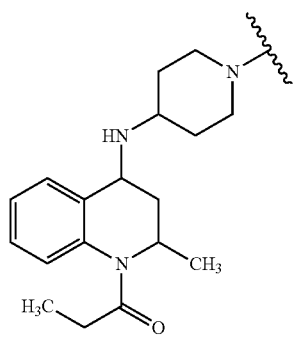
(A10)
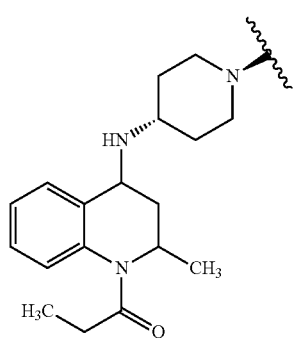
(A11)
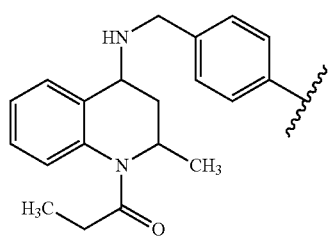
(A12)
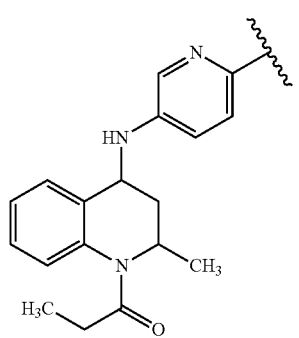
(A14)
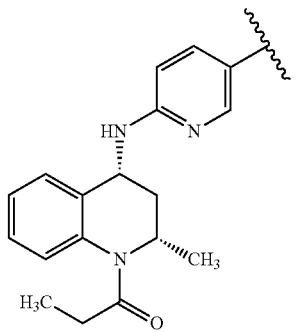
(A15)
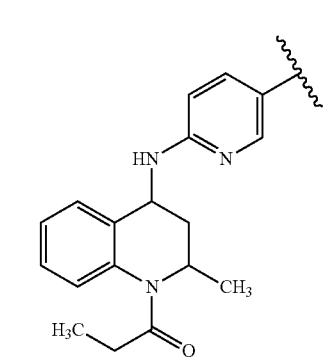
(A16)
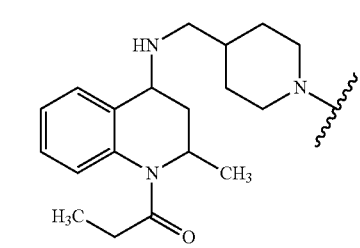
(A17)
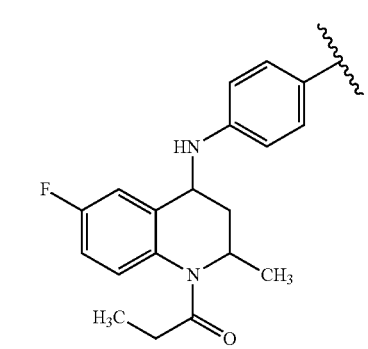
(A18)
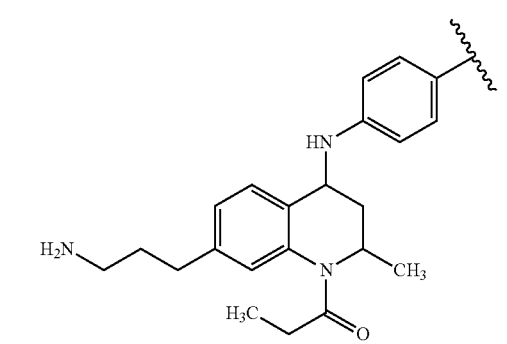
(A19)

(A20) 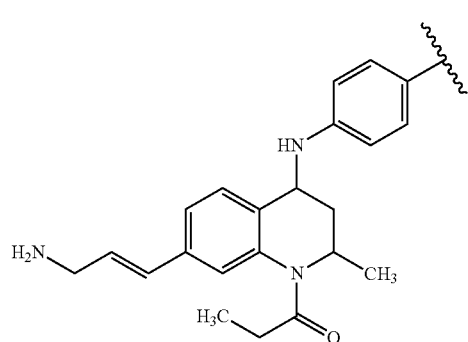
(A21) 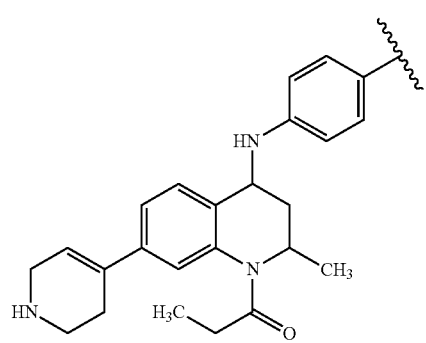
[Chemical formula 106]
(B1) 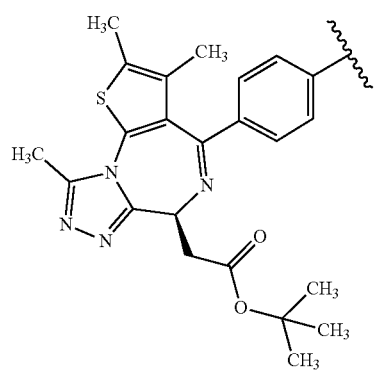
(B2) 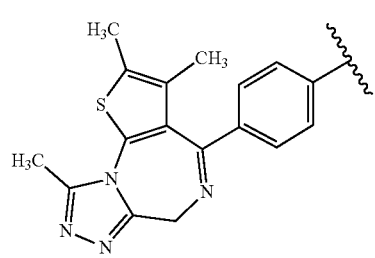
(B3) 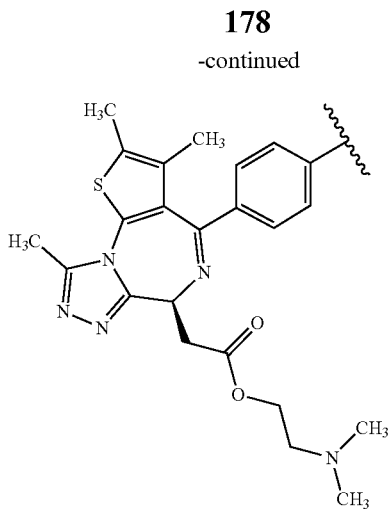
(B4) 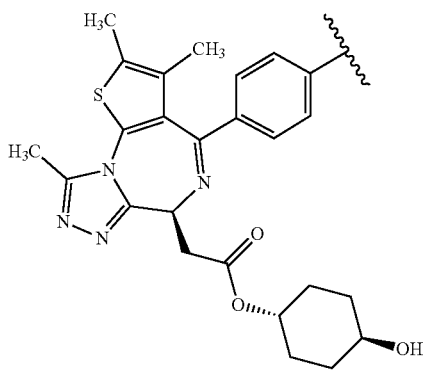
(B5) 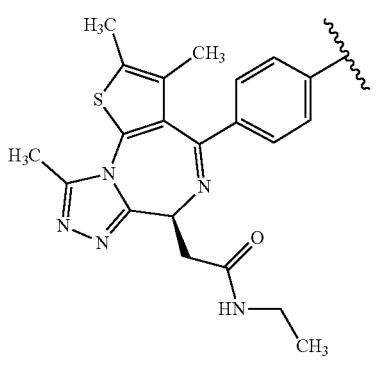
(B6) 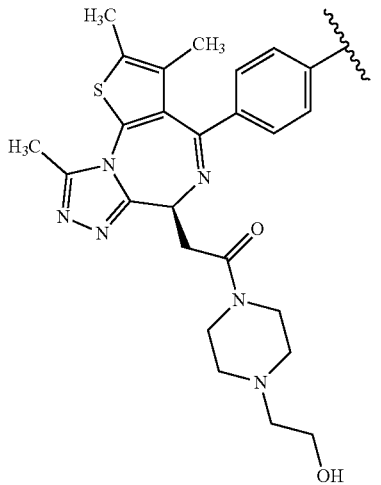

(B7) 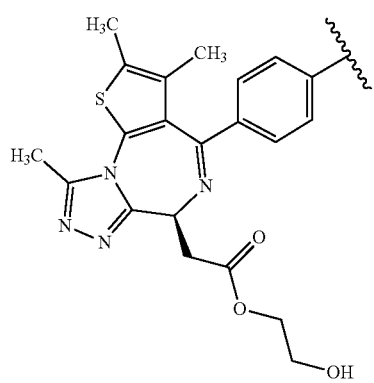
(B8) 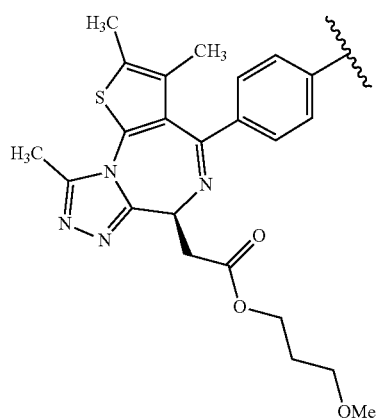
(B9) 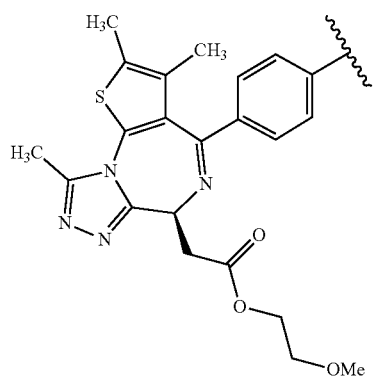
[Chemical formula 107]
(C1) 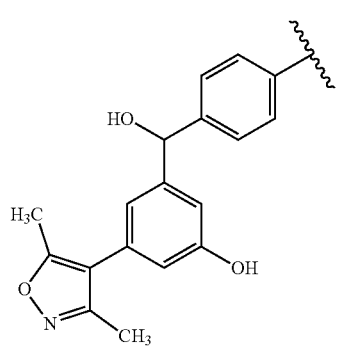
(C2) 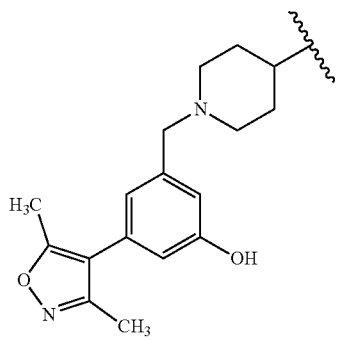
(D1) 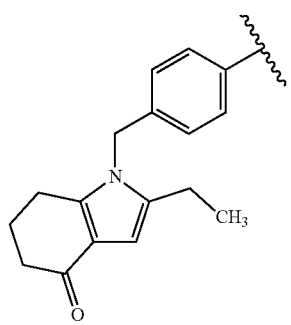
(D2) 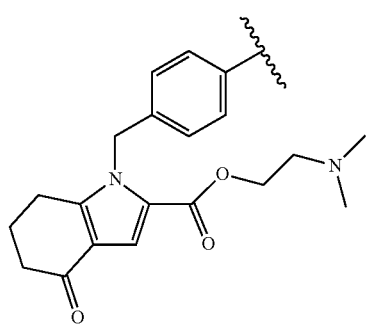
(D3) 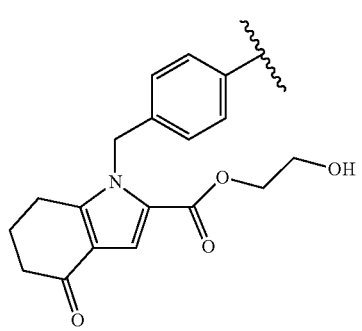
(D4) 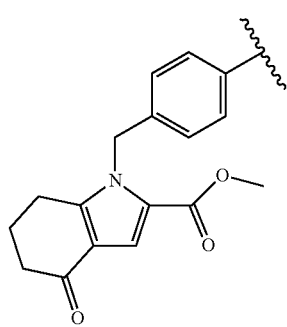

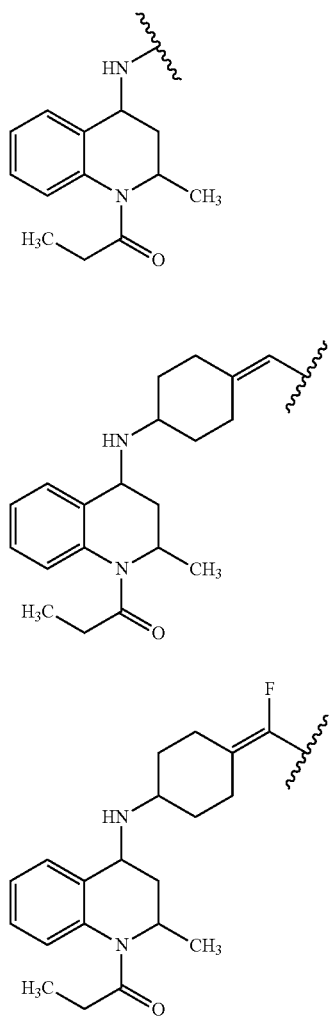

TABLE 1-continued

| Compound No | L¹ | L² | S |
|---|---|---|---|
| 1n | A1 | B1 | (azetidine with acyl and NH-acyl substituents) |
| 1o | A1 | B1 | (-C(O)-NH-CH₂CH₂-NH-C(O)-) |

TABLE 2

| Compound No | L¹ | L² | S |
|---|---|---|---|
| 2a | A2 | A2 | (-NH-C(O)-CH₂-NH-C(O)-) |
| 2b | B1 | B1 | (-NH-C(O)-CH₂-NH-C(O)-) |
| 2c | A2 | A1 | (L-alanine linker, -NH-CH(CH₃)-C(O)-NH-C(O)-) |
| 2d | A2 | A1 | (D-alanine linker) |
| 2e | A2 | A1 | (valine-type linker with gem-dimethyl) |
| 2f | A2 | A1 | (-NH-C(O)-CH₂CH₂-NH-C(O)-) |
| 2g | A1 | A2 | (piperidine-4-carboxamide linker) |

TABLE 2-continued

| Compound No | L¹ | L² | S |
|---|---|---|---|
| 2h | A1 | A2 | (azetidine-3-carboxamide linker) |
| 2i | A1 | A2 | ((S)-pyrrolidine-3-carboxamide linker) |
| 2j | A1 | A2 | (1,3-phenylene bis-amide linker) |

TABLE 3

| Compound No | L¹ | L² | S |
|---|---|---|---|
| 3a | A1 | A1 | (1,2,3-triazole-methyl amide linker) |
| 3b | B1 | B1 | (1,2,3-triazole-methyl amide linker) |
| 3c | A1 | A1 | (1,3,4-oxadiazole-methyl amide linker) |
| 3d | A1 | A1 | (1,2,4-oxadiazole-methyl amide linker) |
| 3e | A1 | A1 | (imidazo[1,2-a]pyrazine linker) |
| 3f | A1 | A1 | (imidazo[1,2-a]pyrazine linker, regioisomer) |

TABLE 3-continued

| Compound No | L¹ | L² | S |
|---|---|---|---|

TABLE 4

| Compound No | L¹ | L² | S |
|---|---|---|---|
| 4a | A2 | A2 | (structure: -NH-C(O)-CH₂CH₂-C(O)-NH-) |
| 4b | A2 | A2 | (structure: -NH-C(O)-CH₂-CH(CH₃)-CH₂-C(O)-NH-) |
| 4c | A2 | A1 | (structure: -NH-SO₂-phenyl-NH-C(O)-) |
| 4d | A1 | A1 | (structure: -SO₂-NH-CH₂CH₂-NH-C(O)-) |
| 4e | A2 | A1 | (structure: -NH-C(O)-CH₂CH₂-S-) |
| 4f | A1 | A1 | (structure: -C(O)-NH-CH₂CH₂-S-) |

TABLE 5

| Compound No | L¹ | L² | S |
|---|---|---|---|
| 5a | A1 | A1 | (structure: -NH-C(O)-oxazole-NH-) |
| 5b | A1 | A1 | (structure: imidazo[1,2-a]pyrazine linker) |
| 5c | A1 | A1 | (structure: imidazo[1,2-a]pyrazine linker) |
| 5d | A1 | A1 | (structure: -NH-C(O)-CH₂-NH-CH₂-C(O)-NH-) |
| 5e | A1 | A1 | (structure: -C(O)-azetidine-NH-CH₂-) |
| 5f | A1 | A1 | (structure: -NH-CH₂CH₂-pyrazole-) |
| 5g | A1 | A1 | (structure: -NH-CH₂-oxadiazole-) |
| 5h | A1 | A1 | (structure: -NH-CH₂-triazole-) |
| 5i | A1 | A1 | (structure: -NH·HCl-CH₂-C(O)-NH-) |
| 5j | A1 | A1 | (structure: -NH-C(O)-triazole-) |
| 5k | A1 | A1 | (structure: tetrahydropyridine-CH₂-C(O)-NH-) |
| 5l | A1 | A1 | (structure: -NH-C(O)-CH₂CH₂-SO₂-) |
| 5m | A1 | A1 | (structure: -NH-C(O)-CH₂CH₂-S(=O)⁺-O⁻) |
| 5n | A1 | A1 | (structure: -O-CH₂CH₂-NH-C(O)-) |

TABLE 5-continued

| Compound No | L¹ | L² | S |
|---|---|---|---|
| 5o | A1 | A1 | (structure) |
| 5p | A1 | A1 | (structure) |
| 5q | A1 | A1 | (structure) |
| 5r | A1 | A1 | (structure) |

TABLE 6

| Compound No | L¹ | L² | S |
|---|---|---|---|
| 6a | A1 | A1 | (structure) |
| 6b | A1 | A1 | (structure) |
| 6c | A1 | A1 | (structure) |
| 6d | A1 | A1 | (structure) |
| 6e | A1 | A1 | (structure) |

TABLE 6-continued

| Compound No | L¹ | L² | S |
|---|---|---|---|
| 6f | A1 | A1 | (structure) |
| 6g | A1 | A1 | (structure) |
| 6h | A1 | A1 | (structure) |
| 6i | A2 | A2 | (structure) |
| 6j | A2 | A2 | (structure) |
| 6k | A1 | A1 | (structure) |
| 6l | A1 | A2 | (structure) |
| 6m | A1 | A2 | (structure) |
| 6n | A2 | A1 | (structure) |
| 6o | A1 | A1 | (structure) |

TABLE 6-continued

| Compound No | L¹ | L² | S |
|---|---|---|---|
| 6p | A1 | A1 | (structure) |
| 6q | A1 | A1 | (structure) |

TABLE 7

| Compound No | L¹ | L² | S |
|---|---|---|---|
| 7a | A1 | A5 | (structure) |
| 7b | A6 | A1 | (structure) |
| 7c | A5 | A1 | (structure) |
| 7d | A6 | A1 | (structure) |
| 7e | A6 | A1 | (structure) |
| 7f | A5 | A1 | (structure) |
| 7g | A1 | A5 | (structure) |

TABLE 7-continued

| Compound No | L¹ | L² | S |
|---|---|---|---|
| 7h | A5 | A1 | (structure) |
| 7i | A6 | A1 | (structure) |
| 7j | A5 | A1 | (structure) |
| 7k | A6 | A1 | (structure) |
| 7l | A6 | A1 | (structure) |
| 7m | A6 | A1 | (structure) |
| 7n | A6 | A1 | (structure) |
| 7o | A5 | A1 | (structure) |
| 7p | A5 | A1 | (structure) |

TABLE 7-continued

| Compound No | L¹ | L² | S |
|---|---|---|---|
| 7q | A5 | A1 | (acetamido-methyl-1,3,4-oxadiazole linker) |
| 7r | A6 | A1 | (bis-amido acetone linker) |

TABLE 8

| Compound No | L¹ | L² | S |
|---|---|---|---|
| 8a | A5 | A1 | (acetamido-ethyl-1,2,3-triazole linker) |
| 8b | A5 | A1 | (bis-amido diglycolyl linker) |
| 8c | A5 | A1 | (azetidine amide linker) |
| 8d | A6 | A1 | (piperidine-pyrazole linker) |
| 8e | A6 | A1 | (acetamido-methyl-thiazole linker) |
| 8f | A6 | A1 | (triazole carboxamide linker) |
| 8g | A1 | A6 | (bis-amido butynyl linker) |
| 8h | A6 | A1 | (tetrahydroimidazo[1,2-a]pyrazine linker) |
| 8i | A6 | A1 | (acetamido-ethyl-thio linker) |
| 8j | A5 | A1 | (urea-glycyl-amide linker) |
| 8k | A6 | A1 | (acetamido-methyl-1,2,4-oxadiazole linker) |
| 8l | A6 | A1 | (acetamido-methyl-1,2,3-triazole linker) |
| 8m | A5 | A1 | (bis-amido butynyl linker) |
| 8n | A6 | A1 | (acetamido-ethyl-urea linker) |
| 8o | A6 | A1 | (acetamido-ethyl-pyrazole linker) |
| 8p | A5 | A1 | (diazabicycloheptane bis-amide linker) |

TABLE 8-continued

| Compound No | L¹ | L² | S |
|---|---|---|---|
| 8q | A6 | A1 | (piperidine-1,4-dicarboxamide linker) |
| 8r | A1 | A5 | (azetidine-1,3-dicarboxamide linker) |

TABLE 9

| Compound No | L¹ | L² | S |
|---|---|---|---|
| 9a | A6 | A1 | (sulfonamide-ethyl-amide linker) |
| 9b | A6 | A1 | (amide-methyl-pyrazole linker) |
| 9c | A6 | A1 | (amide-methyl-urea linker) |
| 9d | A5 | A6 | (amide-propargyl-amide linker) |
| 9h | A5 | A1 | (azetidinyl-urea linker) |

TABLE 10

| Compound No | L¹ | L² | S |
|---|---|---|---|
| 10a | A9 | A1 | (azetidine-1,3-dicarboxamide linker) |
| 10b | A10 | A1 | (amide-methyl-triazole linker) |
| 10c | A9 | A1 | (amide-propargyl-amide linker) |
| 10d | A10 | A1 | (amide-ethyl-pyrazole linker) |
| 10e | A10 | A1 | (azetidine-1,3-dicarboxamide linker) |
| 10f | A11 | A1 | (amide-propargyl-amide linker) |
| 10g | A12 | A1 | (azetidine-1,3-dicarboxamide linker) |
| 10h | A12 | A1 | (amide-methyl-triazole linker) |
| 10j | A1 | A16 | (ethyl-amine-methyl-triazole linker) |
| 10k | A15 | A1 | (glutaramide linker) |
| 10l | A14 | A1 | (succinamide linker) |

TABLE 10-continued

| Compound No | L¹ | L² | S |
|---|---|---|---|
| 10m | A1 | A16 | (structure: acyl-piperidine-4-carboxamide) |
| 10n | A16 | A1 | (structure: amide-C≡C-CH2-NH-acyl, butynediamide) |
| 10o | A16 | A1 | (structure: -NH-CO-CH2-CH2-CO-NH-, β-alanine diamide) |
| 10p | A17 | A1 | (structure: acyl-azetidine-3-carboxamide) |
| 10q | A18 | A18 | (structure: -CO-NH-(CH2)3-NH-CO-) |
| 10r | A18 | A18 | (structure: -CO-NH-(CH2)2-NH-CO-) |
| 10s | A19 | A1 | (structure: -NH-CO-(CH2)3-CO-NH-, glutaramide) |
| 10t | A20 | A1 | (structure: -NH-CO-(CH2)3-CO-NH-, glutaramide) |
| 10u | A21 | A1 | (structure: -NH-CO-(CH2)3-CO-NH-, glutaramide) |

TABLE 11

| Compound No | L¹ | L² | S |
|---|---|---|---|
| 12a | C2 | A1 | (structure: -NH-CO-CH2-[1,3,4-oxadiazole]-) |
| 12b | C2 | A1 | (structure: acyl-azetidine-3-carboxamide) |
| 12c | C2 | A1 | (structure: -NH-CO-(CH2)3-CO-NH-, glutaramide) |
| 12d | E1 | A1 | (structure: -(CH2)3-piperidine-N-C(O)-NH-) |

TABLE 12

| Compound No | L¹ | L² | S |
|---|---|---|---|
| 12e | E1 | A1 | (structure: -CH2CH2-O-CH2CH2-O-CH2-[1,2,3-triazole]-) |
| 12f | E1 | A1 | (structure: -(CH2)4-C(O)-NH-CH2-[1,2,3-triazole]-) |
| 12g | E1 | A1 | (structure: -(CH2)7-C(O)-NH-) |

TABLE 12-continued
| Compound No | L¹ | L² | S |
|---|---|---|---|
| 12h | E1 | A1 | ![structure] |
| 12i | E1 | A1 | ![structure] |
| 12j | E1 | A1 | ![structure] |
TABLE 13
| Compound No | L¹ | L² | S |
|---|---|---|---|
| 13a | B3 | A1 | ![structure] |
| 13b | B3 | A1 | ![structure] |
| 13c | B3 | A1 | ![structure] |
| 13d | B4 | A1 | ![structure] |
| 13e | B5 | A1 | ![structure] |
| 13f | B6 | A1 | ![structure] |
| 13g | B7 | A1 | ![structure] |
| 13h | B8 | A1 | ![structure] |
| 13i | B1 | A2 | ![structure] |
| 13j | B1 | A1 | ![structure] |
TABLE 14
| Compound No | L¹ | L² | S |
|---|---|---|---|
| 14a | B2 | A1 |  |
| 14b | B2 | A1 |  |
| 14c | A6 | B2 |  |

TABLE 14-continued

| Compound No | L¹ | L² | S |
|---|---|---|---|
| 14d | B2 | A1 | (structure: -NH-C(O)-CH₂-O-CH₂-C(O)-NH-) |
| 14e | B2 | B2 | (structure: -NH-C(O)-C≡C-CH₂-NH-C(O)-) |
| 14f | A1 | B2 | (structure: -NH-C(O)-CH₂-NH-C(O)-NH-) |
| 14g | B2 | A1 | (structure: -NH-C(O)-C≡C-CH₂-NH-C(O)-) |
| 14h | B2 | A1 | (structure: -NH-C(O)-CH₂-NH-C(O)-NH-) |
| 14i | A1 | B2 | (structure: -NH-C(O)-C≡C-CH₂-NH-C(O)-) |
| 14j | A1 | B2 | (structure: amide-CH₂-thiophene) |
| 14k | B2 | A1 | (structure: acyl-azetidine-NH-C(O)-) |
| 14l | B2 | A1 | (structure: -NH-C(O)-CH₂-C(O)-CH₂-NH-C(O)-) |
| 14m | B2 | A1 | (structure: -C(O)-NH-CH₂CH₂-NH-C(O)-) |

TABLE 14-continued

| Compound No | L¹ | L² | S |
|---|---|---|---|
| 14n | B2 | A1 | (structure: acyl-NH-CH₂-triazole) |
| 14o | B2 | B2 | (structure: -C(O)-NH-CH₂-C(O)-CH₂-NH-C(O)-) |
| 14p | B2 | B1 | (structure: acyl-piperidine-NH-C(O)-) |
| 14q | A1 | B2 | (structure: acyl-NH-CH₂-triazole) |
| 14r | B2 | A1 | (structure: acyl-imidazopyrazine) |
| 14s | B2 | A1 | (structure: -C(O)-NH-CH₂CH₂-S-) |
| 14t | B2 | A2 | (structure: -NH-C(O)-(CH₂)₃-C(O)-NH-) |

TABLE 15

| Compound No | L¹ | L² | S |
|---|---|---|---|
| 15a | D2 | A1 | (structure: -NH-C(O)-(CH₂)₃-C(O)-NH-) |
| 15b | D2 | A1 | (structure: acyl-NH-CH₂-oxadiazole) |
| 15c | D2 | A1 | (structure: acyl-NH-CH₂CH₂-triazole) |

TABLE 15-continued

| Compound No | L¹ | L² | S |
|---|---|---|---|
| 15d | D2 | A1 | 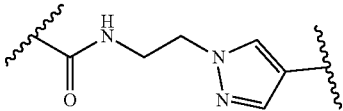 [SMILES: *C(=O)NCCn1cc(*)cn1] |
| 15e | D2 | A1 | 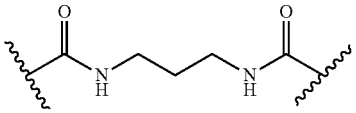 [SMILES: *C(=O)NCCCNC(*)=O] |
| 15f | D1 | A1 | 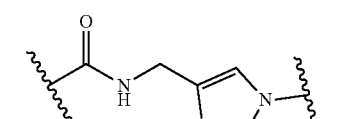 |
| 15g | D4 | A1 | 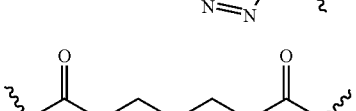 |
| 15h | A1 | D1 |  |
| 15i | D1 | A2 | 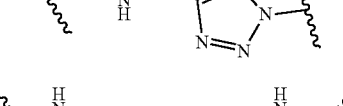 |
| 15j | F1 | A1 | 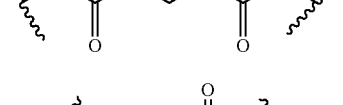 |
| 15k | F2 | A1 | 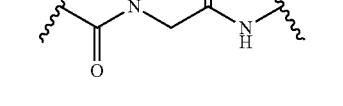 |

Compound (I) or a pharmaceutically acceptable salt thereof can be administered alone, but generally it is desirable to provide it as various pharmaceutical preparations. In addition, these pharmaceutical preparations are used for animals or humans, preferably humans.

The pharmaceutical preparation related to the present invention can contain compound (I) or a pharmaceutically acceptable salt thereof as an active ingredient by itself, or as a mixture with any other active ingredients used for the treatment. Furthermore, those pharmaceutical preparations are manufactured by a well-known method in the technical field of pharmaceutics by mixing the active ingredient with one kind or more pharmaceutically acceptable carriers (e.g., an attenuant, a solvent, a diluent and the like).

The most effective administration route is desirably used for the treatment. For example, it includes an oral or parental administration route such as intravenous injection and the like.

Administration forms include, for example, tablets, injection and the like.

Suitable formulation for the oral administration, for example, such as tablets, can be manufactured using a diluent such as lactose, a disintegrant such as starch, a lubricant such as magnesium stearate, a binder such as hydroxypropylcellulose, and the like.

Suitable formulation for the parenteral administration, for example, such as injection, can be manufactured using an attenuant such as a salt solution, glucose solution or mixed solution of saline and glucose solutions; a solvent or the like.

Dose and frequency of administration of compound (I) or a pharmaceutically acceptable salt thereof differ depending on administration form, age of the patient, body weight or the nature of the symptoms to be treated or severity of them or the like. Generally, they are administered for oral administration at a dosage of 0.01 to 1000 mg per adult, preferably at a dosage of 0.05 to 100 mg once daily or several times a day. In the case of parenteral administrations such as intravenous administration, they are administered at a dosage of 0.001 to 1000 mg per adult, preferably at a dosage of 0.01 to 100 mg once daily or several times a day. However, the dose and frequency of the administration vary depending on the above-mentioned conditions.

According to another embodiment of the present invention, provided is a pharmaceutical composition comprising compound (I) or a pharmaceutically acceptable salt thereof, which pharmaceutical composition may comprise a carrier. The pharmaceutical composition of the present invention is used in administration routes and dosage forms and the like similar to the pharmaceutical preparation mentioned above. Furthermore, the carrier that may be contained in the pharmaceutical composition of the present invention may be an attenuant, solvent, diluent, and the like that are similar to the case of the pharmaceutical preparation mentioned above. Furthermore, the pharmaceutical composition of the present invention is used preferably for inhibiting BET, or for the treatment or prevention of cancers, more preferably for the treatment or prevention of cancers. Here, prevention means that the clinical condition of a disease, the outcome of biological symptoms or the severity of the disease is substantially reduced, or that development of such condition or the biological symptoms is delayed, and the like. The situation is similar to the following prevention.

According to another embodiment of the present invention, provided is a method for the treatment or prevention comprising administering compound (I) of the present invention or a pharmaceutically acceptable salt thereof (preferably a prophylactically or therapeutically safe and effective amount of compound (I) or a pharmaceutically acceptable salt thereof) to a subject (preferably a subject in need thereof). The subject includes, for example, an animal other than a human, but is preferably a human. This is also the same in the following subjects. The method for the treatment or prevention in the present invention is preferably used for inhibiting BET, or for the treatment or prevention of cancers, more preferably is used for the treatment or prevention of cancers.

According to another embodiment of the present invention, provided is compound (I) or a pharmaceutically acceptable salt thereof for use as a medicine.

According to another embodiment of the present invention, provided is compound (I) or a pharmaceutically acceptable salt thereof for use in BET inhibition, or for use in the treatment or prevention of cancer (preferably for use in the treatment or prevention of cancer).

According to another embodiment of the present invention, provided is use of compound (I) or a pharmaceutically acceptable salt thereof for the manufacturing of a drug for inhibiting BET, or for the treatment or prevention of cancer (preferably for the treatment or prevention of cancer).

According to another embodiment of the present invention, provided is use of compound (I) or a pharmaceutically acceptable salt thereof for inhibiting BET, or for the treatment or prevention of cancer (preferably for the treatment or prevention of cancer).

According to another embodiment of the present invention, provided is a medicament comprising compound (I) or a pharmaceutically acceptable salt thereof as an active ingredient.

According to another embodiment of the present invention, provided is a BET inhibitor, or a prophylactic or therapeutic agent for cancer (preferably a prophylactic or therapeutic agent for cancer) comprising compound (I) or a pharmaceutically acceptable salt thereof as an active ingredient.

EXAMPLES

The present invention will be explained by examples more specifically below, but the scope of the present invention is not limited to these examples.

Among compounds (I), the pharmacological action of typical compounds will be specifically described with reference to test examples.

Test Example 1

Inhibitory Effect on Cell Viability

SU-DHL-4 cells (Code No. ACC 495, Deutsche Sammlung von Mikroorganismen and Zellkulturen GmbH) were cultured at 37° C. using a carbon dioxide incubator (95% air, 5% $CO_2$) in RPMI1640 medium (Code No. 11875-093, Thermo Fisher Scientific) in which inactivated fetal bovine serum (FBS: Code No. 10099-148, Thermo Fisher Scientific) in an amount to give a final concentration of 10 vol % and penicillin/streptomycin solution (PS: Code No. 15140-122, Thermo Fisher Scientific) in an amount to give a final concentration of 1 vol % were added. The cells were passaged twice a week at a volume of 20-40 mL so as to maintain a cell concentration of $1\times10^6$ cells/mL or less.

The cultured SU-DHL-4 cells were seeded at 2000 cells/well in a transparent 384-well plate (Code No. 781182, Greiner bio-one). After seeding, the cells were precultured at 37° C. in a carbon dioxide gas incubator for 18 to 25 hours. Next, 1, 0.1 or 0.01 mmol/L DMSO solution of the test compound was prepared and a 9-step dilution series were prepared so that the concentration will be 200 times the final concentration in the RPMI1640 medium containing the above FBS and PS, and 1/200 volume of the dilution series were added to each well. At this time, the final concentration of DMSO was adjusted to be 0.1 vol %. After adding the test compound, the cells were cultured at 37° C. in a carbon dioxide gas incubator for 72 hours. Next, 0.020 mL of Cell Counting Kit-8 (Code No. CK04, DOJINDO) solution diluted 2-fold or 4-fold with phosphate buffered saline (PBS) was added to each well. Color reaction was carried out in a carbon dioxide gas incubator at 37° C. for 2 to 3 hours, and the absorbance at a wavelength of 450 nm was measured using SpectraMax 340PC (Molecular Devices). The inhibition rate of cell viability was calculated by the following formula, and the concentration of the test compound ($IC_{90}$ value) showing a 90% inhibition rate of cell viability was calculated.

Inhibition rate of cell viability (%)=100−(A−B)/(C−B)×100

A: Absorbance of a well containing test compound
B: Absorbance of a well without addition of cells
C: Absorbance of a well without addition of test compound The results are shown in the table below.

TABLE 16

| Compound No. | SU-DHL-4 inhibition rate of cell viability $IC_{90}$ (nmol/L) |
|---|---|
| 1a | 5.21 |
| 1b | 1.78 |
| 1c | 7.85 |
| 1d | 38.0 |
| 1e | 39.8 |
| 1f | 4.78 |
| 1g | 10.6 |
| 1h | 0.27 |
| 1i | 0.54 |
| 1j | 33.1 |
| 1k | 0.55 |
| 1l | 0.04 |
| 1m | 0.53 |
| 1n | 0.49 |
| 1o | 3.18 |
| 2a | 2.12 |
| 2b | 1.52 |
| 2c | 29.1 |
| 2d | 26.6 |
| 2e | 16.3 |
| 2f | 0.23 |
| 2g | 0.63 |
| 2h | 0.03 |
| 2i | 1.84 |
| 2j | 0.36 |
| 3a | 0.04 |
| 3b | 0.18 |
| 3c | 0.11 |
| 3d | 0.11 |
| 3e | 0.12 |
| 3f | 0.33 |
| 4a | 0.45 |
| 4b | 5.87 |
| 4c | 4.03 |
| 4d | 13.0 |
| 4e | 0.34 |
| 4f | 1.19 |
| 5a | 2.15 |
| 5b | 39.56 |
| 5c | 63.60 |
| 5d | 0.67 |
| 5e | 5.93 |
| 5f | 24.73 |
| 5g | 2.53 |
| 5h | 0.12 |
| 5i | 4.49 |
| 5j | 0.08 |
| 5k | 7.48 |
| 5l | 36.95 |
| 5m | 0.59 |
| 5n | 8.83 |
| 5o | 0.14 |
| 5p | 2.68 |
| 5q | 0.11 |
| 5r | 1.78 |
| 6a | 0.89 |
| 6b | 0.10 |
| 6c | 0.83 |
| 6d | 5.08 |
| 6e | 4.31 |
| 6f | 0.11 |
| 6g | 0.31 |

TABLE 16-continued

| Compound No. | SU-DHL-4 inhibition rate of cell viability IC$_{90}$ (nmol/L) |
|---|---|
| 6h | 0.003 |
| 6i | 0.11 |
| 6j | 0.13 |
| 6k | 0.15 |
| 6l | 0.35 |
| 6m | 0.12 |
| 6n | 0.13 |
| 6o | 0.14 |
| 6p | 41.54 |
| 6q | 0.45 |
| 7a | 10.83 |
| 7b | 1.51 |
| 7c | 7.00 |
| 7d | 25.87 |
| 7e | 20.42 |
| 7f | 3.20 |
| 7g | 7.56 |
| 7h | 5.47 |
| 7i | 0.33 |
| 7j | 63.96 |
| 7k | 0.62 |
| 7l | 0.28 |
| 7m | 20.30 |
| 7n | 13.86 |
| 7o | 1.15 |
| 7p | 0.79 |
| 7q | 0.24 |
| 7r | 0.38 |
| 8a | 0.87 |
| 8b | 13.90 |
| 8c | 0.26 |
| 8d | 0.14 |
| 8e | 0.20 |
| 8f | 1.14 |
| 8g | 0.01 |
| 8h | 1.14 |
| 8i | 2.69 |
| 8j | 0.50 |
| 8k | 0.26 |
| 8l | 0.04 |
| 8m | 0.11 |
| 8n | 1.17 |
| 8o | 0.49 |
| 8p | 14.99 |
| 8q | 19.01 |
| 8r | 0.47 |
| 9a | 1.68 |
| 9b | 3.18 |
| 9c | 12.36 |
| 9d | 0.93 |
| 9h | 7.16 |
| 10a | 2.40 |
| 10b | 0.60 |
| 10c | 0.13 |
| 10d | 3.42 |
| 10e | 3.59 |
| 10f | 0.92 |
| 10g | 1.15 |
| 10h | 0.35 |
| 10j | 1.73 |
| 10k | 0.93 |
| 10l | 1.08 |
| 10m | 30.87 |
| 10n | 0.01 |
| 10o | 1.48 |
| 10p | 47.49 |
| 10q | 9.88 |
| 10r | 9.16 |
| 10s | 21.69 |
| 10t | 26.33 |
| 10u | 15.92 |
| 12a | 1.01 |
| 12b | 4.35 |
| 12c | 0.56 |
| 12d | 34.92 |
| 12e | 73.65 |
| 12f | 0.42 |
| 12g | 31.08 |
| 12h | 3.92 |
| 12i | 3.68 |
| 12j | 17.40 |
| 13a | 0.49 |
| 13b | 3.50 |
| 13c | 7.36 |
| 13d | 1.19 |
| 13e | 3.33 |
| 13f | 11.62 |
| 13g | 1.70 |
| 13h | 0.34 |
| 13i | 3.37 |
| 13j | 0.31 |
| 14a | 0.04 |
| 14b | 0.12 |
| 14c | 0.34 |
| 14d | 0.16 |
| 14e | 0.26 |
| 14f | 0.31 |
| 14g | 0.03 |
| 14h | 0.34 |
| 14i | 0.03 |
| 14j | 0.74 |
| 14k | 1.80 |
| 14l | 0.60 |
| 14m | 1.45 |
| 14n | 0.05 |
| 14o | 30.87 |
| 14p | 1.27 |
| 14q | 0.17 |
| 14r | 1.47 |
| 14s | 2.20 |
| 14t | 1.17 |
| 15a | 0.34 |
| 15b | 1.07 |
| 15c | 0.30 |
| 15d | 0.16 |
| 15e | 33.97 |
| 15f | 0.04 |
| 15g | 5.03 |
| 15h | 2.32 |
| L5i | 0.88 |
| 15j | 0.52 |
| 15k | 0.32 |
| Comparative compound 1 | 2557.75 |
| Comparative compound 2 | >10000 |

As described above, compound (I) of the present invention represented by the test compound showed a strong inhibitory effect on cell viability in SU-DHL-4 cells. In addition, the inhibition rate was far stronger than that of the known comparative compounds 1 and 2. Therefore, compound (I) of the present invention was found to be useful for preventing or treating cancer.

Comparative compound 1 is a compound described as example 14 in patent document 2, and comparative compound 2 is a compound described as MT1 in patent document 3. Each comparative compound was synthesized according to the method described in each patent document and used in this test.

Test Example 2

Suppressive Effect on MYC mRNA Expression

SU-DHL-4 cells were cultured at 37° C. using a carbon dioxide gas incubator (95% air, 5% CO$_2$) in RPMI1640 medium in which FBS in an amount to give a final concentration of 10 vol % and PS in an amount to give a final concentration of 1 vol % were added. The cells were passaged twice a week at a volume of 20-40 mL so as to maintain a cell concentration of 1×10$^6$ cells/mL or less.

The cultured SU-DHL-4 cells were seeded at $6\times10^5$ cells/well in a transparent 6-well plate (Code No. 140675, Thermo Fisher Scientific). After seeding, the cells were precultured at 37° C. in a carbon dioxide gas incubator for 18 to 25 hours. Next, a 0.1 mmol/L DMSO solution of the test compound was prepared, diluted so that the concentration will be 200 times the final concentration in the RPMI1640 medium containing the above FBS and PS, and ½₀₀ volume of the diluted solution was added to each well. At this time, the final concentration of DMSO was adjusted to be 0.1 vol %. After adding the test compound, the cells were cultured at 37° C. in a carbon dioxide gas incubator for 6 hours.

Then, the cells were collected by centrifugation and used for extraction of mRNA. mRNA extraction from cells was performed using Maxwell® 16 LEV simplyRNA Purification Kits (Code No. AS1270, Promega). The mRNA recovery protocol was performed according to the manufacturer's recommended protocol attached to the kit.

0.001 mg of the recovered mRNA was converted to cDNA by SuperScript IV VILO Master Mix with ezDNase Enzyme (Code No. 11766050, Thermo Fisher Scientific). The cDNA conversion was performed, according to the manufacturer's recommended protocol attached to the kit, in 0.020 mL of the reaction solution, and GeneAmp® PCR System 9700 (Applied Biosystems) was used. The cDNA-converted sample was diluted 10-fold by adding 0.180 mL of RNase Free Water (Code No. 10977-023, Thermo Fisher Scientific) and used for quantitative real-time polymerase chain reaction (qRT-PCR). For the calibration curve of qRT-PCR, 0.08 mL of RNase Free Water was added to a cDNA sample using DMSO as a test compound for 5-fold dilution. Further, two 5-fold dilutions were prepared stepwise, and these three samples were used as the calibration curve samples.

The following reagents were used for qRT-PCR: TaqMan Gene Expression Assays, Inventoried (Primer probe: Code No. 4331182, Thermo Fisher Scientific, Assay ID: (i) MYC: Hs00153408_m1, (ii) ACTB: Hs01060665_g1, (iii) GAPDH: Hs04420697_g1, (iv) HPRT1: Hs02800695_m1); 2× TaqManR Fast Universal PCR Master Mix, no AmpEraseR UNG (Master Mix: Code No. 4367846, Thermo Fisher Scientific).

Primer probe (0.001 mL), Master Mix (0.010 mL), water (0.004 mL) and the diluted cDNA sample (0.005 mL) were mixed, and qRT-PCR analysis was performed. For qRT-PCR analysis, QuantStudio 7 Flex (Thermo Fisher Scientific) or 7500 Fast Real-Time PCR (Applied Biosystems) was used to measure in Fast mode and analyze. The expression level of the MYC gene was determined by quantifying ACTB, GAPDH, and HPRT1 as housekeeping genes and correcting by the following formula to calculate the suppression rate of (%) of MYC mRNA expression when the test compound was allowed to act at a concentration of 100 nmol/L.

Corrected MYC expression=A/B

A: MYC expression level

B: Geometric mean of expression levels of ACTB, GAPDH and HPRT1

Using the corrected values, the suppression rate of MYC expression for the wells to which the test compound was not added was calculated by the following formula.

Suppression rate of MYC expression (%)=100−C/D×100

C: Corrected MYC expression level in a well containing test compound

D: Corrected MYC expression level in a well to which test compound was not added The results are shown in the table below.

TABLE 17

| Compound No. | Suppression rate of MYC mRNA expression (%) |
|---|---|
| 1a | 96.7 |
| 1b | 98.4 |
| 1c | 97.3 |
| 1k | 98.6 |
| 1l | 98.5 |
| 2d | 80.0 |
| 2f | 98.6 |
| 2h | 98.2 |
| 3a | 98.1 |
| 3e | 98.3 |
| 4a | 98.4 |
| 4d | 98.3 |
| 4e | 98.4 |
| 5d | 97.5 |
| 5h | 97.3 |
| 5j | 96.8 |
| 5q | 97.2 |
| 5r | 96.7 |
| 6h | 97.2 |
| 6k | 97.0 |
| 6m | 97.0 |
| 7h | 97.5 |
| 7o | 97.4 |
| 7p | 97.9 |
| 7q | 97.4 |
| 8g | 96.6 |
| 8j | 97.2 |
| 8r | 96.7 |
| 9d | 98.0 |
| 10b | 96.6 |
| 10g | 97.2 |
| 10k | 97.0 |
| 12a | 98.5 |
| 12b | 97.8 |
| 12c | 97.8 |
| 12f | 97.9 |
| 12h | 96.5 |
| 13a | 97.6 |
| 13d | 97.2 |
| 13h | 97.4 |
| 14a | 97.1 |
| 14d | 97.4 |
| 14e | 96.7 |
| 14f | 97.3 |
| 14p | 97.6 |
| 15a | 97.6 |
| 15d | 96.9 |
| 15f | 97.2 |
| 15k | 97.4 |
| Comparative compound 1 | 61.7 |
| Comparative compound 2 | 57.7 |

As described above, compound (I) of the present invention represented by the test compound strongly suppressed the expression of MYC mRNA. Further, the suppression rate was far stronger than that of the known comparative compounds 1 and 2. Therefore, the compound (I) of the present invention was found to be useful for preventing or treating cancer.

Comparative compound 1 is a compound described as example 14 in patent document 2, and comparative compound 2 is a compound described as MT1 in patent document 3. Each comparative compound was synthesized according to the method described in each patent document and used in this test.

Test Example 3

Antitumor Effect on Subcutaneous Transplant Model in SCID Mouse DLBCL Strain SU-DHL-4

$1 \times 10^7$ cells of DLBCL strain SU-DHL-4 (Code No. ACC 495, Deutsche Sammlung von Mikroorganismen and Zellkulturen GmbH) suspended in a 1:1 mixed solution of PBS and matrigel (CORNING Code No. 354234) were transplanted subcutaneously to the ventral side of a male SCID mouse. Eighteen days after the transplantation, the body weight and the tumor diameter were measured, and the tumor volume was calculated by the following formula, and the mice were divided into two groups (n=5) so that the average tumor volume of each group was equal. E-workbook software (ID Business Solusions) was used for grouping and measurement.

[Tumor volume (mm³)]=[Tumor long diameter (mm)]×[Tumor short diameter (mm)]²×0.5

The test was conducted in two groups, a vehicle administration group and a compound 1a administration group (compound administration group). To the compound 1a administration group, a solution of compound 1a dissolved in 30% DMSO/3% Tween 80/physiological saline so as to give a final concentration of 0.6 mg/mL was administered intravenously (tail vein) at 5 mL/kg (3 mg/kg) 5 times a week for 2 weeks. To the vehicle administration group, 30% DMSO/3% Tween 80/physiological saline was administered intravenously (tail vein) at 5 mL/kg on the same schedule as the compound 1a administration group. After the start of the test, body weight and tumor diameter were measured twice a week. The tumor volume on each measurement day was calculated by the above formula. The tumor growth rate (hereinafter referred to as V/V0) was calculated by dividing the tumor volume V on each measurement day by the tumor volume V0 on the test start day (Day 0). The T/C was calculated by dividing the average value (T) of V/V0 of each group by the average value (C) of the vehicle administration group.

The results are shown in the table below (mean values of n=5 are shown).

TABLE 18

| Measurement day | Tumor volume (mm³) | | V/V0 | |
|---|---|---|---|---|
| | Vehicle administration group | Compound administration group | Vehicle administration group | Compound administration group |
| Day0 | 245.49 | 246.14 | 1.00 | 1.00 |
| Day3 | 396.59 | 284.29 | 1.62 | 1.15 |
| Day7 | 654.80 | 326.25 | 2.68 | 1.29 |
| Day10 | 923.83 | 214.74 | 3.80 | 0.85 |
| Day14 | 1288.10 | 224.55 | 5.30 | 0.89 |
| Day18 | 1951.98 | 325.61 | 8.00 | 1.30 |

| Measurement day | T/C | | Body weight (g) | |
|---|---|---|---|---|
| | Vehicle administration group | Compound administration group | Vehicle administration group | Compound administration group |
| Day0 | 1.00 | 1.00 | 24.14 | 24.56 |
| Day3 | 1.00 | 0.71 | 23.87 | 25.36 |
| Day7 | 1.00 | 0.48 | 23.98 | 25.44 |
| Day10 | 1.00 | 0.22 | 23.66 | 25.14 |
| Day14 | 1.00 | 0.17 | 23.71 | 25.74 |
| Day18 | 1.00 | 0.16 | 23.53 | 26.23 |

As described above, the tumor volume, tumor growth rate and T/C of the compound 1a administration group were smaller than those of the vehicle administration group. On the other hand, no weight loss was observed by the compound 1a administration group. That is, compound 1a showed a strong antitumor effect on SU-DHL-4 subcutaneously transplanted tumor. Therefore, the compound (I) of the present invention represented by the test compound was found to be useful as a therapeutic drug for cancer.

The proton nuclear magnetic resonance spectra ($^1$H NMR) used in the following reference examples and examples were measured at 300 MHz or 400 MHz, and exchangeable protons could not be clearly observed depending on the compound and the measurement conditions. Incidentally, the multiplicity of a signal was indicated with common term, while br indicated that the signal is apparently wide. In addition, ChemBioDraw Ultra version 14.0 was used as necessary for naming each compound synthesized.

Reference Example 1

4-{[(2S,4R)-2-Methyl-1-propionyl-1,2,3,4-tetrahydroquinolin-4-yl]amino}benzoic Acid (Step 1)

Aniline (25.0 g, 268.82 mmol) was dissolved in acetonitrile (200 mL), then acetaldehyde (15 mL, 268.8 mmol), bismuth (III) chloride (8.5 g, 26.9 mmol) and N-vinylformamide (22.67 mL, 322.6 mmol) were added to the solution, and the mixture was stirred at room temperature for 36 hours. A saturated aqueous sodium carbonate solution was added to the reaction mixture, and the mixture was extracted with ethyl acetate. The organic layer was dried over anhydrous sodium sulfate and concentrated under reduced pressure. The obtained residue was purified by silica gel column chromatography (ethyl acetate) to give N-[(2S*,4R*)-2-methyl-1,2,3,4-tetrahydroquinolin-4-yl]formamide (18.0 g).

(Step 2)

N-[(2S*,4R*)-2-Methyl-1,2,3,4-tetrahydroquinolin-4-yl]formamide (18.0 g, 94.7 mmol) obtained in step 1 was dissolved in dichloromethane (100 mL), then pyridine (30.5 mL, 379.0 mmol) and propionyl chloride (8.3 mL, 94.7 mmol) were added to the solution, and the mixture was stirred at 0° C. for 1 hour. Water was added to the reaction mixture, and the mixture was extracted twice with dichloromethane. The organic layer was dried over anhydrous sodium sulfate and concentrated under reduced pressure. The obtained residue was purified by silica gel column chromatography (dichloromethane/methanol=19/1) to give N-[(2S*,4R*)-2-methyl-1-propionyl-1,2,3,4-tetrahydroquinolin-4-yl]formamide (15.0 g).

(Step 3)

N-[(2S*,4R*)-2-Methyl-1-propionyl-1,2,3,4-tetrahydroquinolin-4-yl]formamide (15.0 g, 61.0 mmol) obtained in step 2 was dissolved in methanol (100 mL), then hydrochloric acid (5 mol/L, 18 mL) was added to the solution under ice cooling, and the mixture was stirred at 70° C. for 3 hours. Water was added to the reaction mixture, and the mixture was extracted twice with ethyl acetate. The organic layer was dried over anhydrous sodium sulfate and concentrated under reduced pressure. The obtained residue was purified by silica gel column chromatography (dichloromethane/ methanol=19/1) to give 1-[(2S*,4R*)-4-amino-2-methyl-3,4-dihydroquinolin-1(2H)-yl]propan-1-one (9.0 g, total yield of 3 steps 15%).

(Step 4)

1-[(2S*,4R*)-4-amino-2-methyl-3,4-dihydroquinolin-1(2H)-yl]propan-1-one (5.0 g, 22.9 mmol) obtained in step 3 was dissolved in dichloromethane (100 mL), then [4-(methoxycarbonyl)phenyl]boronic acid (12.3 g, 68.8 mmol), triethylamine (12.9 mL, 91.7 mmol) and copper(II) acetate (6.2 g, 34.4 mmol) were added to the solution, and the mixture was stirred at room temperature for 24 hours under an oxygen atmosphere. The reaction mixture was concentrated under reduced pressure, and the obtained residue was purified by silica gel column chromatography (petroleum ether/ethyl acetate=7/3) to give Methyl 4-{[(2S*,4R*)-2-methyl-1-propionyl-1,2,3,4-tetra hydroquinolin-4-yl]amino}benzoate (2.1 g, 18%).

(Step 5)

Methyl 4-{[(2S*,4R*)-2-methyl-1-propionyl-1,2,3,4-tetrahydroquinolin-4-yl]amino}benzoate (2.1 g, 5.84 mmol) obtained in step 4 was purified by supercritical fluid chromatography (SFC) (Chiralcel OX—H (250×30 mm, 5μ), $CO_2$/methanol=60/40, flow rate 90.0 g/min, retention time (rt)=7.5 min) to give Methyl 4-{[(2S,4R)-2-methyl-1-propionyl-1,2,3,4-tetrahydroquinolin-4-yl]amino}benzoate (750 mg, 36%). SFC (Chiralpak AD-H (250×4.6 mm, 5μ), methanol/$CO_2$=25/75, flow rate 3.0 ml/min): rt=5.38 min (Step 6)

Methyl 4-{[(2S*,4R*)-2-methyl-1-propionyl-1,2,3,4-tetrahydroquinolin-4-yl]amino}benzoate (410 mg, 1.16 mmol) obtained in step 4 was dissolved in methanol (6.0 mL), then aqueous sodium hydroxide solution (4 mol/L, 1.45 mL) was added to the solution, and the mixture was stirred at 50° C. overnight. Hydrochloric acid (1 mol/L) was added to the reaction mixture, and the mixture was extracted twice with chloroform. The organic layer was dried over anhydrous magnesium sulfate and concentrated under reduced pressure to obtain 4-{[(2S*,4R*)-2-methyl-1-propionyl-1,2,3,4-tetrahydroquinolin-4-yl]amino}benzoic acid (390 mg, 99%).

(Step 7)

4-{[(2S,4R)-2-Methyl-1-propionyl-1,2,3,4-tetrahydroquinolin-4-yl]amino}benzoic acid (1.92 g, 100%) was obtained from methyl 4-{[(2S,4R)-2-methyl-1-propionyl-1,2,3,4-tetrahydroquinolin-4-yl]amino}benzoate (2.0 g, 5.67 mmol) obtained in step 5 in the same manner as in step 6.
ESI-MS m/z: 337 (M–H)$^-$, $^1$H-NMR (CDCl$_3$, δ): 1.08-1.23 (m, 6H), 1.23-1.40 (m, 1H), 2.32-2.46 (m, 1H), 2.52-2.77 (m, 2H), 4.21-4.46 (m, 2H), 4.87-5.03 (m, 1H), 6.56-6.66 (m, 2H), 7.09-7.34 (m, 4H), 7.88-7.99 (m, 2H).

Reference Example 2

1-{(2S,4R)-4-[(4-Bromophenyl)amino]-2-methyl-3,4-dihydroquinolin-1(2H)-yl}propan-1-one 1-{(2S*,4R*)-4-[(4-bromophenyl)amino]-2-methyl-3,4-dihydroquinolin-1(2H)-yl}propan-1-one (15.0 g) was obtained from 1-[(2S*,4R*)-4-amino-2-methyl-3,4-dihydroquinolin-1(2H)-yl]propan-1-one (15.0 g, 68.8 mmol) obtained in step 3 of reference example 1 and (4-bromophenyl) boronic acid (13.76 g, 68.81 mmol) in the same manner as in step 4 of reference example 1. The obtained 1-{(2S*,4R*)-4-[(4-bromophenyl)amino]-2-methyl-3,4-dihydroquinolin-1(2H)-yl}propan-1-one (15.0 g) was purified by SFC ((R, R) Whelk-01 (250×30 mm, 5μ), $CO_2$/methanol=80/20, flow rate 100 g/min, rt=10.63 min) to give 1-{(2S,4R)-4-[(4-Bromophenyl)amino]-2-methyl-3,4-dihydroquinolin-1(2H)-yl}propan-1-one (5.4 g, 21%).
ESI-MS (M+H)$^+$: 373, $^1$H NMR (DMSO-d$_6$, δ): 0.99-1.04 (m, 6H), 1.13-1.20 (m, 1H), 2.20-2.25 (m, 1H), 2.55-2.61 (m, 2H), 4.14 (ddd, J=11.98, 7.71, 4.12 Hz, 1H), 4.70-4.75 (m, 1H), 6.28 (d, J=7.63 Hz, 1H), 6.59-6.62 (m, 2H), 7.10 (d, J=7.50 Hz, 1H), 7.16-7.23 (m, 3H), 7.25-7.30 (m, 2H).
SFC ((R, R) Whelk-01 (250×4.6 mm, 5μ), methanol/$CO_2$=25/75, flow rate 3.0 ml/min): rt=7.29 min Reference Example 3

(S)-4-{6-[2-(tert-Butoxy)-2-oxoethyl]-2,3,9-trimethyl-6H-thieno[3,2-f][1,2,4]triazolo[4,3-a][1,4]diazepin-4-yl}benzoic acid tert-Butyl 2-[4-(4-bromophenyl)-2,3,9-trimethyl-6H-thieno[3,2-f][1,2,4]triazolo[4,3-a][1,4]diazepin-6-yl]acetate (5.0 g, 10.0 mmol) synthesized according to the method described in WO2017/030814 was dissolved in a mixed solvent (70 mL) of DMF and water (5:2), then potassium carbonate (2.1 g, 15.0 mmol), palladium acetate (0.67 g, 1.0 mmol) and Bis(diphenylphosphino)propane (0.82 g, 2.0 mmol) were added to the solution, and the mixture was stirred at 100° C. for 16 hours under a carbon monoxide atmosphere. The reaction mixture was filtered through Celite, water was added to the filtrate, and the aqueous layer was washed with ethyl acetate. Citric acid was added to the aqueous layer, and the aqueous layer was extracted twice with ethyl acetate. The organic layer was dried over anhydrous sodium sulfate and concentrated under reduced pressure. The obtained residue was purified by reverse phase column chromatography (acetonitrile/0.1% formic acid aqueous solution=1/1) to give 4-{6-[2-(tert-butoxy)-2-oxoethyl]-2,3,9-trimethyl-6H-thieno[3,2-f][1,2,4]triazolo[4,3-a][1,4]diazepin-4-yl}benzoic acid (2.75 g). The resulting 4-{6-[2-(tert-butoxy)-2-oxoethyl]-2,3,9-trimethyl-6H-thieno[3,2-f][1,2,4]triazolo[4,3-a][1,4]diazepin-4-yl}benzoic acid (2.75 g) was purified by SFC (Chiralpak AD-H (250×30 mm, 5μ), $CO_2$/methanol=70/30, flow rate 90 g/min, rt=3.89 min) to give (S)-4-{6-[2-(tert-butoxy)-2-oxoethyl]-2,3,9-trimethyl-6H-thieno[3,2-f][1,2,4]triazolo[4,3-a][1,4]diazepin-4-yl}benzoic acid (1.68 g, 36%).
ESI-MS (M+H)$^+$: 467, $^1$H NMR (DMSO-d$_6$, δ): 1.43 (s, 9H), 1.60 (d, J=0.61 Hz, 3H), 2.42 (d, J=0.61 Hz, 3H), 2.61 (s, 3H), 3.34-3.40 (m, 2H), 4.46 (dd, J=8.24, 6.41 Hz, 1H), 7.52 (d, J=8.54 Hz, 2H), 7.97 (d, J=8.85 Hz, 2H), 13.14 (brs, 1H).
SFC (Chiralpak AD-H (250×4.6 mm, 5μ), methanol/$CO_2$=25/75, flow rate 3.0 ml/min): rt=3.62 min Reference Example 4

4-(2,3,9-Trimethyl-6H-thieno[3,2-f][1,2,4]triazolo[4,3-a][1,4]diazepin-4-yl)benzoic acid (Step 1)

(tert-Butoxycarbonyl)glycine (79 mg, 0.451 mmol) was dissolved in DMF (1.6 mL), then HATU (184 mg, 0.484 mmol) and N,N-diisopropylethylamine (0.11 mL, 0.645 mmol) were added to the solution and the mixture was stirred at room temperature for 10 minutes. (2-Amino-4,5-dimethylthiophen-3-yl)(4-bromophenyl)methanone (100 mg, 0.322 mmol) synthesized by the method described in WO2017030814 was added to the reaction mixture, and the mixture was stirred at room temperature overnight. A saturated aqueous sodium hydrogen carbonate solution was added to the reaction mixture, and the mixture was extracted twice with ethyl acetate. The organic layer was dried over anhydrous magnesium sulfate and concentrated under reduced pressure. The obtained residue was purified by silica gel column chromatography (heptane/ethyl acetate=100/0-80/20) to give tert-butyl (2-{[3-(4-bromobenzoyl)-4,5-dimethylthiophen-2-yl]amino}-2-oxoethyl)carbamate (110 mg, 73%).

(Step 2)

tert-Butyl (2-{[3-(4-bromo benzoyl)-4,5-dimethylthiophen-2-yl]amino}-2-oxoethyl)carbamate (110 mg, 0.235 mmol) obtained in step 1 was dissolved in dichloromethane (0.79 mL), then trifluoroacetic acid (0.54 mL) was added to the solution, and the mixture was stirred at room temperature overnight. The reaction mixture was concentrated under reduced pressure, the obtained residue (110 mg) was dissolved in toluene (2.0 mL), then pyridine (0.36 mL, 4.49 mmol) and molecular sieves 4A (300 mg) were added to the solution, and the mixture was refluxed overnight. The reaction mixture was suction filtered, and water was added to the obtained filtrate, and the mixture was extracted twice with ethyl acetate. The organic layer was dried over anhydrous magnesium sulfate and concentrated under reduced pressure. The obtained residue was purified by silica gel column chromatography (chloroform/methanol=100/0 to 90/10) to give 5-(4-bromophenyl)-6,7-dimethyl-1,3-dihydro-2H-thieno[2,3-e][1,4]diazepin-2-one (56 mg, 68%).

(Step 3)

5-(4-Bromophenyl)-6,7-dimethyl-1,3-dihydro-2H-thieno[2,3-e][1,4]diazepin-2-one (55 mg, 0.157 mmol) obtained in step 2 was dissolved in THF (1.0 mL), the solution was refrigerated to −78° C., then potassium tert-butoxide (21 mg, 0.189 mmol) was added to the solution, and the mixture was stirred at room temperature for 30 minutes. The reaction mixture was refrigerated to 78° C. and diethylphosphoryl chloride (0.027 mL, 0.189 mmol) was added to the mixture, and the mixture was stirred at 10° C. for 45 minutes. Acetohydrazide (18 mg, 0.236 mmol) and 1-butanol (1.0 mL) were added to the reaction mixture, and the mixture was stirred at 90° C. for 2 hours. The reaction mixture was concentrated under reduced pressure, and the obtained residue was purified by silica gel column chromatography (chloroform/methanol=100/0 to 90/10) to give 4-(4-bromophenyl)-2,3,9-trimethyl-6H-thieno[3,2-f][1,2,4]triazolo[4,3-a][1,4]diazepine (24 mg, 39%).

(Step 4)

4-(4-Bromophenyl)-2,3,9-trimethyl-6H-thieno[3,2-f][1,2,4]triazolo[4,3-a][1,4]diazepine (160 mg, 0.413 mmol) obtained in step 3 was dissolved in a mixed solvent (2.2 mL) of DMF and water (10:1), then palladium acetate (9.3 mg, 0.041 mmol), 1,3-bis(diphenylphosphino)propane (34 mg, 0.083 mmol) and potassium carbonate (120 mg, 0.868 mmol) were added to the solution, and the mixture was stirred at 80° C. overnight under a carbon monoxide atmosphere. Hydrochloric acid (1 mol/L) was added to the reaction mixture, and the mixture was extracted twice with chloroform. The organic layer was dried over anhydrous magnesium sulfate and concentrated under reduced pressure. The obtained residue was slurried with ethyl acetate to give 4-(2,3,9-trimethyl-6H-thieno[3,2-f][1,2,4]triazolo[4,3-a][1,4]diazepin-4-yl)benzoic acid (170 mg, 100%).
ESI-MS m/z: 351 (M−H)$^-$; $^1$H-NMR (DMSO-d$_6$, δ): 2.40 (s, 3H), 2.63 (s, 3H), 2.90 (s, 3H), 4.17-4.20 (m, 1H), 5.26-5.33 (m, 1H), 7.53-7.59 (m, 2H), 7.94-8.02 (m, 2H).

Reference Example 5

4-[(2-Ethyl-4-oxo-4,5,6,7-tetrahydro-1H-indol-1-yl)methyl]benzoic acid (Step 1)

2-(2-Oxobutyl)cyclohexane-1,3-d one (150 mg, 0.823 mmol) synthesized according to the method described in the literature (Eur. J. of Org. Chem. 2016, 5169-5179) was dissolved in toluene (1.2 ml), then methyl 4-(aminomethyl)benzoate hydrochloride (174 mg, 0.864 mmol) and triethylamine (0.23 ml, 1.65 mmol) were added to the solution, and the mixture was stirred at room temperature for 15 minutes and then refluxed for 7 hours. Water was added to the reaction mixture, and the mixture was extracted 3 times with ethyl acetate. The organic layer was dried over anhydrous magnesium sulfate and concentrated under reduced pressure. The obtained residue was purified by silica gel column chromatography (chloroform/methanol=100/0 to 90/10) to give methyl 4-[(2-ethyl-4-oxo-4,5,6,7-tetrahydro-1H-indol-1-yl)methyl]benzoate (120 mg, 47%).

(Step 2)

4-[(2-Ethyl-4-oxo-4,5,6,7-tetrahydro-1H-indol-1-yl)methyl]benzoic acid (170 mg, 77%) was obtained from methyl 4-[(2-ethyl-4-oxo-4,5,6,7-tetrahydro-1H-indol-1-yl)methyl]benzoate (230 mg, 0.739 mmol) obtained in step 1 in the same manner as in step 6 of reference example 1.
ESI-MS m/z: 296 (M−H)$^-$; $^1$H-NMR (CDCl$_3$, δ): 1.20 (t, J=7.4 Hz, 3H), 2.06-2.18 (m, 2H), 2.41 (q, J=7.4 Hz, 2H), 2.45-2.52 (m, 2H), 2.58-2.64 (m, 2H), 5.11 (s, 2H), 6.42 (s, 1H), 6.99 (d, J=8.2 Hz, 2H), 8.06 (d, J=8.2 Hz, 2H).

Reference Example 6

4-{[3-(3,5-Dimethylisoxazol-4-yl)-5-hydroxyphenyl](hydroxy)methyl}benzoic acid (Step 1)

3-Bromo-5-hydroxybenzaldehyde (3.7 g, 18.41 mmol) was dissolved in DMF (100 mL), then tert-butyldimethylchlorosilane (3.33 g, 22.09 mmol) and imidazole (1.38 g, 20.25 mmol) were added to the solution, and the mixture was stirred at room temperature for 2 hours. Water was added to the reaction mixture, and the mixture was extracted twice with ethyl acetate. The organic layer was dried over anhydrous sodium sulfate and concentrated under reduced pressure. The obtained residue was purified by silica gel column chromatography (petroleum ether/ethyl acetate=100/0 to 90/10) to give 3-bromo-5-[(tert-butyldimethylsilyl)oxy]benzaldehyde (4.6 g, 79%).

(Step 2)

3-Bromo-5-[(tert-butyldimethylsilyl)oxy]benzaldehyde (800 mg, 2.54 mmol) obtained in step 1 were mixed with [4-(ethoxycarbonyl)phenyl](iodo)zinc (0.5 mol/L in THF, 30.4 mL, 15.20 mmol), and the mixture was stirred at room temperature for 24 hours. A saturated aqueous ammonium chloride solution was added to the reaction mixture, and the mixture was extracted 3 times with ethyl acetate. The organic layer was dried over anhydrous sodium sulfate and concentrated under reduced pressure. The obtained residue was purified by silica gel column chromatography (petroleum ether/ethyl acetate=95/5 to 50/50) to give ethyl 4-({3-bromo-5-[(tert-butyldimethylsilyloxy]phenyl}(hydroxy)methyl)benzoate (570 mg, 45%).

(Step 3)

Ethyl 4-({3-bromo-5-[(tert-butyldimethylsilyloxy]phenyl}(hydroxy)methyl)benzoate (550 mg, 1.18 mmol)

obtained in step 2 was dissolved in a mixed solvent (24 mL) of 1,4-dioxane and water (5:1), then 3,5-dimethyl-4-(4,4,5,5-tetramethyl-1,3,2-dioxaboran-2-yl)isoxazole (343 mg, 1.54 mmol), potassium carbonate (490 mg, 3.54 mmol) and Pd(dppf)Cl$_2$ (87 mg, 0.12 mmol) were added to the solution, and the mixture was stirred at 80° C. for 16 hours. Ethyl acetate was added to the reaction mixture, the organic layer was dried over anhydrous sodium sulfate, and concentrated under reduced pressure. The obtained residue was purified by thin layer chromatography (petroleum ether/ethyl acetate=67/33) to give ethyl 4-({3-[(tert-butyldimethylsilyl)oxy]-5-(3,5-dimethylisoxazol-4-yl)phenyl}(hydroxy)methyl)benzoate (570 mg, 95%).
(Step 4)
4-{[3-(3,5-Dimethylisoxazol-4-yl)-5-hydroxyphenyl](hydroxy)methyl}benzoic acid (400 mg, 98%) was obtained from ethyl 4-({3-[(tert-butyldimethylsilyl)oxy]-5-(3,5-dimethylisoxazol-4-yl)phenyl}(hydroxy)methyl)benzoate (570 mg, 1.18 mmol) obtained in step 3 in the same manner as in step 6 of reference example 1.
ESI-MS (M+H)$^+$: 340, $^1$H NMR (CD$_3$OD, δ): 2.20 (s, 3H), 2.36 (s, 3H), 5.80 (s, 1H), 6.65-6.61 (t, J=1.6 Hz, 1H), 6.80 (d, J=1.2 Hz, 1H), 6.84 (t, J=1.6 Hz, 1H), 7.51 (d, J=8.4 Hz, 2H), 7.99 (d, J=8.4 Hz, 2H).

Reference Example 7

1-{(2S,4R)-4-[(4-Aminophenyl)amino]-2-methyl-3,4-dihydroquinolin-1(2H)-yl}propan-1-one (Step 1)
1-[(2S*,4R*)-4-Amino-2-methyl-3,4-dihydroquinolin-1(2H)-yl]propan-1-one (10.0 g, 45.87 mmol) obtained in step 3 of reference example 1 was dissolved in DMF (150 mL), then 1-fluoro-4-nitrobenzene (9.7 mL, 91.74 mmol), N,N-diisopropylethylamine (8.0 mL, 45.87 mmol) and potassium carbonate (19 g, 137.61 mmol) were added to the solution, and the mixture was stirred at 100° C. for 48 hours. Water was added to the reaction mixture, and the mixture was extracted with ethyl acetate. The organic layer was washed with saturated brine, dried over anhydrous sodium sulfate, and concentrated under reduced pressure. The obtained residue was purified by silica gel column chromatography (petroleum ether/ethyl acetate=92/8 to 90/10) to give 1-{(2S*,4R*)-2-methyl-4-[(4-nitrophenyl)amino)]-3,4-dihydroquinolin-1(2H)-yl}propan-1-one (4.7 g, 30%).
ESI-MS (M+H)$^+$: 340.
(Step 2)
1-{(2S*,4R*)-2-Methyl-4-[(4-nitrophenyl)amino]-3,4-dihydroquinolin-1(2H)-yl}propan-1-one (2.6 g, 7.66 mmol) obtained in step 1 was dissolved in a mixed solvent (45 mL) of ethanol, water and THF (1:1:1), then iron (2.13 g, 38.3 mmol) and ammonium chloride (0.6 g, 11.50 mmol) were added to the solution, and the mixture was stirred at 70° C. for 2 hours. The reaction mixture was filtered, and water was added to the filtrate, and the mixture was extracted with ethyl acetate. The organic layer was dried over anhydrous sodium sulfate and concentrated under reduced pressure. The obtained residue was purified by silica gel column chromatography (petroleum ether/ethyl acetate=60/40 to 50/50) to give 1-{(2S*,4R*)-4-[(4-aminophenyl)amino]-2-methyl-3,4-dihydroquinolin-1(2H)-yl}propan-1-one (1.65 g, 70%).
ESI-MS (M+H)$^+$: 310: $^1$H-NMR (DMSO-d$_6$, δ): 0.97-1.03 (m, 6H), 1.06-1.08 (m, 1H), 2.18-2.24 (m, 1H), 2.57-2.60 (m, 2H), 3.95-3.99 (m, 1H), 4.29 (brs, 2H), 4.68-4.70 (m, 1H), 5.17 (d, J=8.4 Hz, 1H), 6.41-6.46 (m, 4H), 7.14-7.18 (m, 1H), 7.22-7.28 (m, 3H)
(Step 3)
1-{(2S*,4R*)-4-[(4-Aminophenyl)amino]-2-methyl-3,4-dihydroquinolin-1(2H)-yl}propan-1-one (530 mg) obtained in step 2 was purified by SFC (Chiralcel OJ-H (250×21 mm, 5μ), CO$_2$/methanol=85/15, flow rate 70 g/min, rt=6.36 min) to give 1-{(2S,4R)-4-[(4-aminophenyl)amino]-2-methyl-3,4-dihydroquinolin-1(2H)-yl}propan-1-one (180 mg, 34%).
ESI-MS (M+H)$^+$: 310: $^1$H-NMR (DMSO-d$_6$, δ): 1.12-1.19 (m, 7H), 2.32-2.37 (m, 1H), 2.52-2.67 (m, 2H), 3.49 (brs, 2H), 4.08 (dd, J=12.0, 3.5 Hz, 1H), 4.89-4.90 (m, 1H), 6.53 (d, J=8.5 Hz, 2H), 6.64 (d, J=8.5 Hz, 2H), 7.13 (d, J=7.5 Hz, 1H), 7.18-7.21 (m, 1H), 7.24-7.25 (m, 1H), 7.36 (d, J=7.5 Hz, 1H).
SFC (Chiralcel OJ-H (250×6 mm, 5μ)methanol/CO$_2$=20/80, flow rate 3.0 ml/min): rt=6.51 min Reference Example 8 tert-Butyl (4-formylphenyl)((2S,4R)-2-methyl-1-propionyl-1,2,3,4-tetrahydrquinolin-4-yl)carbamate (Step 1)
Methyl 4-{[(2S,4R)-2-methyl-1-propionyl-1,2,3,4-tetrahydroquinolin-4-yl]amino}benzoate (0.5 g, 1.42 mmol) obtained in step 5 of reference example 1 was dissolved in tetrahydrofuran (10 mL), then DMAP (0.693 g, 5.68 mmol) and di-tert-butyl dicarbonate (1.24 g, 5.68 mmol) were added to the solution, and the mixture was stirred at 70° C. for 16 hours. Water was added to the reaction mixture, and the mixture was extracted with ethyl acetate. The organic layer was dried over anhydrous sodium sulfate and concentrated under reduced pressure. The obtained residue was purified by silica gel column chromatography (petroleum ether/ethyl acetate=4/1) to give methyl 4-((tert-butoxycarbonyl) ((2S,4R)-2-methyl-1-propionyl-1,2,3,4-tetrahydroquinolin-4-yl)amino)benzoate (0.5 g, 77%).
ESI-MS m/z: 453 (M+H)$^+$
(Step 2)
Methyl 4-((tert-butoxycarbonyl) ((2S,4R)-2-methyl-1-propionyl-1,2,3,4-tetrahydroquinolin-4-yl)amino)benzoate (0.50 g, 1.1 mmol) obtained in step 1 was dissolved in methanol (10 mL), then 4 mol/L sodium hydroxide aqueous solution (10 mL) was added to the solution, and the mixture was stirred at 80° C. for 4 hours. The reaction mixture was concentrated under reduced pressure, and an aqueous citric acid solution was added to the obtained aqueous solution until pH approximately 5. The resulting solid was suction filtered to give 4-((tert-butoxycarbonyl)((2S,4R)-2-methyl-1-propionyl-1,2,3,4-tetrahydroquinolin-4-yl)amino)benzoic acid (0.4 g, 83%).
ESI-MS m/z: 439 (M+H)$^+$
(Step 3)
4-((tert-Butoxycarbonyl)((2S,4R)-2-methyl-1-propionyl-1,2,3,4-tetrahydroquinolin-4-yl)amino)benzoic acid (0.40 g, 0.91 mmol) obtained in step 2 was dissolved in dichloromethane (5 mL), then ethyl chloroformate (0.10 mL, 1.1 mmol) and triethylamine (0.38 mL, 2.74 mmol) were added to the solution, and the mixture was stirred at room temperature for 5 hours. Water was added to the reaction mixture, and the mixture was extracted with dichloromethane. The organic layer was dried over anhydrous sodium sulfate and concentrated under reduced pressure. The obtained residue was dissolved in methanol (5 mL), then sodium borohydride (0.069 g, 1.83 mmol) was added to the solution at 0° C., and the mixture was stirred at room temperature for 3 hours. Water was added to the reaction mixture, and the mixture was extracted with dichloromethane. The organic layer was dried over anhydrous sodium sulfate and concentrated under reduced pressure. The obtained residue was purified by silica gel column chromatography (petroleum ether/ethyl acetate=7/3) to give tert-butyl(4-(hydroxymethyl)phenyl) ((2S,4R)-2-methyl-1-propionyl-1,2,3,4-tetrahydroquinolin-4-yl)carbamate (0.28 g, 72%).
ESI-MS m/z: 425 (M+H)$^+$
(Step 4)
tert-Butyl (4-(hydroxymethyl)phenyl)((2S,4R)-2-methyl-1-propionyl-1,2,3,4-tetrahydroquinolin-4-yl)carbamate (0.400 g, 0.94 mmol) obtained in step 3 was dissolved in dichloromethane (5 mL), then DMP (0.480 g, 1.13 mmol) was added to the solution at 0° C., and the mixture was stirred at room temperature for 3 hours. The reaction mixture was diluted with dichloromethane and filtered through Celite. The obtained filtrate was concentrated under reduced pressure, and the obtained residue was purified by silica gel column chromatography (petroleum ether/ethyl acetate=9/1) to give tert-butyl (4-formylphenyl)((2S,4R)-2-methyl-1-propionyl-1,2,3,4-tetrahydroquinolin-4-yl)carbamate (0.26 g, 65%).
ESI-MS m/z: 423 (M+H)$^+$; $^1$H-NMR (DMSO-d$_6$, δ): 0.92-0.99 (m, 6H), 1.34 (s, 9H), 2.10-2.18 (m, 1H), 2.36 (brs, 1H), 2.47-2.48 (m, 1H), 2.51-2.52 (m, 1H), 4.63-4.68 (m, 1H), 4.86 (brs, 1H), 7.34 (brs, 4H), 7.44 (d, J=8.0 Hz, 2H), 7.88-7.90 (m, 2H), 9.97 (s, 1H).

Reference Example 9

1-((2S,4R)-4-(((1r,4R)-4-Aminocyclohexyl)amino)-2-methyl-3,4-dihydroquinolin-1(2H)-yl)propan-1-one dihydrochloride (Step 1)
1-[(2S*,4R*)-4-Amino-2-methyl-3,4-dihydroquinolin-1(2H)-yl]propan-1-one (50.0 g, 230 mmol) obtained in step 3 of reference example 1 was dissolved in methanol (600 mL), then acetic acid (68.80 mL, 1147 mmol), tert-butyl (4-oxocyclohexyl)carbamate (68.4 g, 344 mmol) and sodium borohydride (26.0 g, 689 mmol) were added to the solution, and the mixture was stirred at room temperature for 24 hours. The reaction mixture was concentrated under reduced pressure, and water was added to the obtained residue, and the mixture was extracted twice with ethyl acetate. The organic layer was dried over anhydrous sodium sulfate and concentrated under reduced pressure. The obtained residue was purified by silica gel column chromatography (petroleum ether/ethyl acetate=3/7) to give a crude product of tert-butyl (4-(((2S*,4R*)-2-methyl-1-propionyl-1,2,3,4-tetrahydroquinolin-4-yl)amino)cyclohexyl)carbamate (17 g). The resulting crude product was purified by SFC (Chiralpak IA (250×30 mm, 5μ), CO$_2$/methanol=85/15, flow rate 90.0 g/min, retention time (rt)=6.7 min) to give tert-butyl ((1R,4r)-4-(((2S,4R)-2-methyl-1-propionyl-1,2,3,4-tetrahydroquinolin-4-yl)amino)cyclohexyl)carbamate (6.0 g, 6.2%).
SFC (Chiralpak AD-H (250×4.6 mm, 5μ), methanol/CO$_2$=15/85, Flow rate 3.0 ml/min): rt=6.7 min
ESI-MS m/z: 416.3 (M+H)$^+$
(Step 2)
1-((2S,4R)-4-(((1r,4R)-4-Aminocyclohexyl)amino)-2-methyl-3,4-dihydroquinolin-1(2H)-yl)propan-1-one dihydrochloride (5.0 g, 89%) was obtained from tert-butyl ((1R,4R)-4-(((2S,4R)-2-methyl-1-propionyl-1,2,3,4-tetrahydroquinolin-4-yl)amino)cyclohexyl)carbamate (6.0 g, 14 mmol) obtained in step 1 in the same manner as in step 2 of example 1a.
ESIMS, (M+H)$^+$, m/z: 316.41. $^1$H NMR (DMSO-d$_6$, δ): 0.97 (t, J=7.2 Hz, 3H), 1.04 (d, J=6.4 Hz, 3H), 1.17-1.28 (m, 1H), 1.38-1.54 (m, 1H), 1.58-1.69 (m, 1H), 1.74-1.88 (m, 1H), 2.00-2.17 (m, 3H), 2.21-2.37 (m, 2H), 2.54-2.64 (m, 1H), 2.92-2.97 (m, 2H), 3.21-3.22 (m, 1H), 4.22-4.24 (m, 1H), 4.62-4.74 (m, 1H), 6.52 (brs, 1H), 7.31-7.41 (m, 3H), 7.56 (d, J=7.67 Hz, 1H), 8.18 (brs, 3H), 9.63-9.93 (m, 2H).

Reference Example 10

1-((2S*,4R*)-4-(((1r,4R)-4-Aminocyclohexyl)amino)-2-methyl-3,4-dihydroquinolin-1(2H)-yl)propan-1-one dihydrochloride (Step 1)
The crude product (8.0 g) of tert-butyl (4-(((2S*,4R*)-2-methyl-1-propionyl-1,2,3,4-tetrahydroquinolin-4-yl)amino)cyclohexyl)carbamate obtained in step 1 of reference example 9 was purified by SFC (Chiralpak IA (250×30 mm, 5μ), CO$_2$/methanol=85/15, flow rate 90.0 g/min, retention time (rt)=7.62, 11.0 min) to give tert-butyl ((1R,4r)-4-(((2S*,4R*)-2-methyl-1-propionyl-1,2,3,4-tetrahydroquinolin-4-yl)amino)cyclohexyl)carbamate (3.0 g, total yield of 2 steps 6.7%).
SFC (Chiralpak AD-H (250×4.6 mm, 5μ), Methanol/CO$_2$=15/85, Flow rate 3.0 ml/min): rt=7.62, 11.0 min $^1$H NMR (CDCl$_3$, δ): 0.88-0.91 (m, 1H), 1.07-1.12 (m, 6H), 1.16-1.40 (m, 4H), 1.44 (s, 9H), 2.01-2.06 (m, 4H), 2.24-2.28 (m, 1H), 2.48-2.61 (m, 2H), 2.63-2.66 (m, 1H), 3.46-3.60 (m, 2H), 4.36 (brs, 1H), 4.85 (brs, 1H), 7.09 (d, J=7.0 Hz, 1H), 7.22-7.25 (m, 2H), 7.45-7.47 (m, 1H).
(Step 2)
1-((2S*,4R*)-4-(((1r,4R)-4-Aminocyclohexyl)amino)-2-methyl-3,4-dihydroquinolin-1(2H)-yl)propan-1-one dihydrochloride (2.5 g, 90%) was obtained from tert-butyl ((1R,4r)-4-(((2S*,4R*)-2-methyl-1-propionyl-1,2,3,4-tetrahydroquinolin-4-yl)amino)cyclohexyl)carbamate (3.0 g, 7.23 mmol) obtained in step 1 in the same manner as in step 2 of example 1a.
ESIMS, (M+H)$^+$, m/z: 316.3. $^1$H NMR (DMSO-d$_6$, δ): 0.98 (t, J=7.6 Hz, 3H), 1.04 (d, J=6.4 Hz, 3H), 1.23-1.25 (m, 2H), 1.44-1.51 (m, 2H), 1.61-1.69 (m, 1H), 1.81-1.89 (m, 1H), 2.05-2.14 (m, 3H), 2.25-2.33 (m, 2H), 2.51-2.62 (m, 1H), 2.93-2.98 (m, 2H), 4.18-4.28 (m, 1H), 4.68-4.70 (m, 1H), 7.30-7.41 (m, 3H), 7.57 (d, J=7.6 Hz, 1H), 8.21 (brs, 3H), 9.82-9.88 (m, 2H).

Reference Example 11

(1R,4r)-4-(((2S,4R)-2-Methyl-1-propionyl-1,2,3,4-tetrahydroquinolin-4-yl)amino)cyclohexane-1-carboxylic acid (Step 1)
A crude product of methyl 4-(((2S*,4R*)-2-methyl-1-propionyl-1,2,3,4-tetrahydroquinolin-4-yl)amino)cyclohexane-1-carboxylate was obtained from 1-[(2S*,4R*)-4-amino-2-methyl-3,4-dihydroquinolin-1(2H)-yl]propan-1-one (2.0 g, 9.2 mmol) obtained in step 3 of reference example 1 and methyl 4-oxocyclohexane-1-carboxylate (2.86 g, 18.35 mmol) in the same manner as in step 1 of reference example 9. The crude product was purified by SFC (Chiralpak IA (250×30 mm, 5 μm), CO$_2$/methanol=90/10, flow rate 90.0 g/min) to give methyl (1R,4r)-4-(((2S*,4R*)-

2-methyl-1-propionyl-1,2,3,4-tetrahydroquinolin-4-yl)amino)cyclohexane-1-carboxylate (0.240 g, 7.3%).
SFC (Chiralpak IA (250×4.6 mm, 5 µm), $CO_2$/methanol=90/10, flow rate 3 mL/min, retention time (rt)=8.0 min)
$^1$H NMR (CD$_3$OD, δ): 0.89-1.01 (m, 1H), 1.03-1.10 (m, 6H), 1.21-1.36 (m, 2H), 1.39-1.57 (m, 2H), 1.93-2.14 (m, 4H), 2.15-2.22 (m, 1H), 2.24-2.38 (m, 2H), 2.49-2.60 (m, 1H), 2.62-2.70 (m, 1H), 2.72-2.83 (m, 1H), 3.63-3.70 (m, 3H), 4.76-4.79 (m, 1H), 7.21-7.46 (m, 4H).
(Step 2)
(1R,4r)-4-(((2S*,4R*)-2-Methyl-1-propionyl-1,2,3,4-tetrahydroquinolin-4-yl)amino)cyclohexane-1-carboxylic acid (0.040 g, 83%) was obtained from methyl (1R,4r)-4-(((2S*,4R*)-2-methyl-1-propionyl-1,2,3,4-tetrahydroquinolin-4-yl)amino)cyclohexane-1-carboxylate (0.05 g, 0.14 mmol) obtained in step 1 in the same manner as in step 2 of example 2f.
ESIMS, (M+H)$^+$, m/z: 345.60.
(Step 3)
(1R,4r)-4-(((2S*,4R*)-2-Methyl-1-propionyl-1,2,3,4-tetrahydroquinolin-4-yl)amino)cyclohexane-1-carboxylic acid (250 mg, 0.725 mmol) obtained in step 2 was purified by SFC (Lux Cellulose-2 (250×30 mm, 5 µm), $CO_2$/methanol=75/25, flow rate 90.0 g/min, retention time (rt)=2.3 min) to give (1R,4r)-4-(((2S,4R)-2-methyl-1-propionyl-1,2,3,4-tetrahydroquinolin-4-yl)amino)cyclohexane-1-carboxylic acid (65 mg, 26%).
SFC (Lux Cellulose-2 (250×4.6 mm, 5 µm), $CO_2$/methanol=55/45, flow rate 3.0 mL/min, retention time (rt)=2.3 min) ESIMS, (M+H)$^+$, m/z: 345.35. $^1$H NMR (DMSO-d$_6$, δ): 0.81-0.84 (m, 1H), 0.92-1.01 (m, 6H), 1.03-1.26 (m, 2H), 1.34 (qd, J=12.72, 2.75 Hz, 2H), 1.85-2.02 (m, 4H), 2.09-2.19 (m, 2H), 2.53 (brs, 1H), 2.54-2.62 (m, 2H), 3.45 (dd, J=11.90, 3.97 Hz, 1H), 4.56-4.68 (m, 1H), 7.19-7.25 (m, 3H), 7.47-7.51 (m, 1H).

Reference Example 12

1-((2S,4R)-2-Methyl-4-(piperidin-4-ylamino)-3,4-dihydroquinolin-1(2H)-yl)propan-1-one dihydrochloride (Step 1)
tert-Butyl 4-(((2S*,4R*)-2-methyl-1-propionyl-1,2,3,4-tetrahydroquinolin-4-yl)amino)piperidine-1-carboxylate (2.4 g, 87%) was obtained from 1-[(2S*,4R*)-4-amino-2-methyl-3,4-dihydroquinolin-1(2H)-yl]propan-1-one (1.5 g, 6.9 mmol) obtained in step 3 of reference example 1 and tert-butyl 4-oxopiperidine-1-carboxylate (2.73 g, 13.76 mmol) in the same manner as in step 1 of reference example 9.
ESI-MS m/z: 402 (M+H)$^+$
(Step 2)
1-((2S,4R)-2-Methyl-4-(piperidin-4-ylamino)-3,4-dihydroquinolin-1(2H)-yl)propan-1-one dihydrochloride (1.9 g, 86%) was obtained from tert-butyl 4-(((2S*,4R*)-2-methyl-1-propionyl-1,2,3,4-tetrahydroquinolin-4-yl)amino)piperidine-1-carboxylate (2.4 g, 5.98 mmol) obtained in step 1 in the same manner as in step 2 of example 1a.
ESI-MS m/z: 302.23 (M+H)$^+$; $^1$H-NMR (DMSO-d$_6$, δ): 0.99 (t, J=7.34 Hz, 3H), 1.05 (d, J=6.36 Hz, 3H), 1.20-1.32 (m, 1H), 2.01-2.23 (m, 3H), 2.39 (t, J=15.16 Hz, 2H), 2.55-2.62 (m, 1H), 2.82-3.02 (m, 3H), 3.37-3.39 (m, 2H), 3.64-3.68 (m, 1H), 4.28-4.32 (m, 1H), 4.67-4.70 (m, 1H), 7.30-7.41 (m, 3H), 7.57 (d, J=7.83 Hz, 1H), 9.07-9.09 (m, 1H), 9.30 (d, J=9.29 Hz, 1H), 10.16-10.21 (m, 2H).

Reference Example 13

1-((2S,4R)-2-Methyl-4-(piperidin-4-ylamino)-3,4-dihydroquinolin-1(2H)-yl)propan-1-one dihydrochloride (Step 1)
tert-butyl 4-(((2S*,4R*)-2-methyl-1-propionyl-1,2,3,4-tetrahydroquinolin-4-yl)amino)piperidine-1-carboxylate (3.0 g, 7.47 mmol) obtained in step 1 of reference example 12 was purified by SFC (Chiralpak IG (30×250 mm), 5µ, $CO_2$/methanol=75/25, flow rate 90 g/min, rt=2.4) to give tert-butyl 4-(((2S,4R)-2-methyl-1-propionyl-1,2,3,4-tetrahydroquinolin-4-yl)amino)piperidine-1-carboxylate (0.900 g, 30%).
SFC (Chiralpak IC-3 (150×4.6 mm, 3 µm), methanol/$CO_2$=35/65, flow rate 3.0 ml/min): rt=2.4 min
ESI-MS m/z: 402.35 (M+H)$^+$; $^1$H-NMR (DMSO-d$_6$, δ): 0.98 (t, J=7.3 Hz, 3H), 1.05 (d, J=6.4 Hz, 3H), 1.17-1.25 (m, 1H), 1.38 (s, 9H), 1.52-1.60 (m, 1H), 1.70-1.75 (m, 1H), 2.09-2.23 (m, 3H), 2.54-2.67 (m, 1H), 2.79-2.95 (m, 3H), 3.55-3.61 (m, 1H), 4.03 (d, J=8.8 Hz, 2H), 4.27-4.31 (m, 1H), 4.64-4.72 (m, 1H), 7.35-7.39 (m, 3H), 7.50 (d, J=7.6 Hz, 1H), 9.58 (brs, 1H).
(Step 2)
1-((2S,4R)-2-Methyl-4-(piperidin-4-ylamino)-3,4-dihydroquinolin-1(2H)-yl)propan-1-one dihydrochloride (0.4 g, 53%) was obtained from tert-butyl 4-(((2S,4R)-2-methyl-1-propionyl-1,2,3,4-tetrahydroquinolin-4-yl)amino)piperidine-1-carboxylate (0.800 g, 1.99 mmol) obtained in step 1 in the same manner as in step 2 of example 1a.
ESI-MS m/z: 302 (M+H)$^+$; $^1$H-NMR (DMSO-d$_6$, δ): 0.99 (t, J=7.34 Hz, 3H), 1.05 (d, J=6.14 Hz, 3H), 1.20-1.35 (m, 1H), 1.96-2.25 (m, 3H), 2.39 (t, J=15.13 Hz, 2H), 2.54-2.67 (m, 1H), 2.85-3.04 (m, 3H), 3.32-3.34 (m, 2H), 3.66-3.69 (m, 1H), 4.26-4.32 (m, 1H), 4.68-4.72 (m, 1H), 7.26-7.43 (m, 3H), 7.58 (d, J=7.45 Hz, 1H), 9.08 (d, J=8.99 Hz, 1H), 9.27 (d, J=8.4 Hz, 1H), 10.13-10.18 (m, 2H).

Reference Example 14

1-((2S*,4R*)-4-(((1r,3R)-3-Aminocyclobutyl)amino)-2-methyl-3,4-dihydroquinolin-1(2H)-yl) propan-1-one dihydrochloride (Step 1)
The crude product of tert-butyl (3-(((2S*,4R*)-2-methyl-1-propionyl-1,2,3,4-tetrahydroquinolin-4-yl)amino)cyclobutyl)carbamate was obtained from 1-[(2S*,4R*)-4-amino-2-methyl-3,4-dihydroquinolin-1(2H)-yl]propan-1-one (0.5 g, 2.29 mmol) obtained in step 3 of reference example 1 and tert-butyl(3-oxocyclobutyl)carbamate (0.678 g, 3.66 mmol) in the same manner as in step 1 of reference example 9. The resulting crude product was purified by SFC (Chiralpak IG (30×250 mm), 5 µm, $CO_2$/ethanol=75/25, flow rate 90 g/min) to give tert-butyl ((1R,3r)-3-(((2S*,4R*)-2-methyl-1-propionyl-1,2,3,4-tetrahydroquinolin-4-yl)amino)cyclobutyl)carbamate (120 mg, 13%).
ESI-MS m/z: 388 (M+H)$^+$; $^1$H-NMR (DMSO-d$_6$, δ): 0.79-0.84 (m, 1H), 0.92-0.99 (m, 6H), 1.37 (s, 9H), 1.99-2.04 (m, 3H), 2.06-2.33 (m, 3H), 2.54-2.61 (m, 2H), 3.23-3.25 (m, 1H), 3.46-3.49 (m, 1H), 4.02-4.05 (m, 1H), 4.57-4.63 (m, 1H), 7.14 (d, J=7.2 Hz, 1H), 7.23-7.25 (m, 3H), 7.42-7.47 (m, 1H).

(Step 2)

1-((2S*,4R*)-4-(((1r,3R)-3-Aminocyclobutyl)amino)-2-methyl-3,4-dihydroquinolin-1(2H)-yl)propan-1-one dihydrochloride (0.21 g, 90%) was obtained from tert-butyl ((1R,3r)-3-(((2S*,4R*)-2-methyl-1-propionyl-1,2,3,4-tetrahydroquinolin-4-yl)amino)cyclobutyl)carbamate (0.25 g, 0.64 mmol) obtained in step 1 in the same manner as in step 2 of example 1a.
ESI-MS m/z: 288 (M+H)$^+$; $^1$H-NMR (DMSO-d$_6$, δ): 0.98 (t, J=7.5 Hz, 3H), 1.03 (d, J=6.5 Hz, 3H), 1.10-1.23 (m, 1H), 2.10-2.14 (m, 1H), 2.51-2.60 (m, 3H), 2.74-2.79 (m, 1H), 2.84-2.88 (m, 1H), 2.91-2.99 (m, 1H), 3.91-3.98 (m, 1H), 4.11-4.19 (m, 1H), 4.29-4.34 (m, 1H), 4.62-4.72 (m, 1H), 7.32-7.41 (m, 3H), 7.57 (d, J=8.0 Hz, 1H), 8.42 (brs, 3H), 10.36 (brs, 1H), 10.44 (brs, 1H).

Reference Example 15

4-((((2S*,4R*)-2-Methyl-1-propionyl-1,2,3,4-tetrahydroquinolin-4-yl)amino)methyl)benzoic acid (Step 1)
1-[(2S*,4R*)-4-Amino-2-methyl-3,4-dihydroquinolin-1(2H)-yl]propan-1-one (1.0 g, 4.6 mmol) obtained in step 3 of reference example 1 was dissolved in DMF (3 mL), then methyl 4-(bromomethyl)benzoate (1.56 g, 6.88 mmol) and potassium carbonate (1.89 g, 13.8 mmol) were added to the solution, and the mixture was stirred at 80° C. for 16 hours. The reaction mixture was diluted with water and extracted with ethyl acetate. The organic layer was dried over anhydrous sodium sulfate and concentrated under reduced pressure. The obtained residue was purified by reverse phase column chromatography (acetonitrile/water=1/1) to give methyl 4-((((2S*,4R*)-2-methyl-1-propionyl-1,2,3,4-tetrahydroquinolin-4-yl)amino)methyl)benzoate (1.0 g, 60%).
ESI-MS m/z: 367 (M+H)$^+$
(Step 2)
4-((((2S*,4R*)-2-Methyl-1-propionyl-1,2,3,4-tetrahydroquinolin-4-yl)amino)methyl)benzoic acid (0.6 g, 62%) was obtained from methyl 4-((((2S*,4R*)-2-methyl-1-propionyl-1,2,3,4-tetrahydroquinolin-4-yl)amino)methyl)benzoate (1.0 g, 2.73 mmol) obtained in step 1 in the same manner as in step 2 of example 2f.
ESI-MS m/z: 353.34 (M+H)$^+$ Reference Example 16

1-((2S*,4R*)-4-((5-aminopyridin-2-yl)amino)-2-methyl-3,4-dihydroquinolin-1(2H)-yl)propan-1-one (Step 1)
1-[(2S*,4R*)-4-Amino-2-methyl-3,4-dihydroquinolin-1(2H)-yl]propan-1-one (1.0 g, 4.6 mmol) obtained in step 3 of reference example 1 was dissolved in DMF (5 mL), then 2-fluoro-5-nitropyridine (0.488 g, 3.44 mmol) and potassium carbonate (0.94 g, 6.88 mmol) were added to the solution, and the mixture was stirred at 70° C. for 1 hour. Water was added to the reaction mixture, and the resulting solid was suction filtered to give 1-((2S*,4R*)-2-methyl-4-((5-nitropyridin-2-yl)amino)-3,4-dihydroquinolin-1(2H)-yl)propan-1-one (0.55 g, 71%).
ESI-MS m/z: 341 (M+H)$^+$
(Step 2)
1-((2S*,4R*)-2-Methyl-4-((5-nitropyridin-2-yl)amino)-3,4-dihydroquinolin-1(2H)-yl)propan-1-one (0.55 g, 1.61 mmol) obtained in step 1 was dissolved in a mixed solvent of THF (3 mL), ethanol (3 mL) and water (3 mL), then iron powder (0.452 g, 8.08 mmol) and ammonium chloride (0.128 g, 2.42 mmol) were added to the solution, and the mixture was stirred at 60° C. for 1 hour. The reaction mixture was concentrated under reduced pressure, water was added to the obtained residue, and the mixture was extracted 3 times with ethyl acetate. The organic layer was dried over anhydrous sodium sulfate and concentrated under reduced pressure to give 1-((2S*,4R*)-4-((5-aminopyridin-2-yl)amino)-2-methyl-3,4-dihydroquinolin-1(2H)-yl)propan-1-one (0.45 g, 90%).
ESI-MS m/z: 311 (M+H)$^+$ Reference Example 17

1-((2S,4R)-4-((5-Aminopyridin-2-yl)amino)-2-methyl-3,4-dihydroquinolin-1(2H)-yl)propan-1-one (Step 1)
1-((2S*,4R*)-2-Methyl-4-((5-nitropyridin-2-yl)amino)-3,4-dihydroquinolin-1(2H)-yl)propan-1-one (940 mg, 2.76 mmol) obtained in step 1 of reference example 16 was purified by SFC (CHIRALPAK IB, CO$_2$/methanol=94/6, 30 mL/min, rt=12.38 min) to give 1-((2S,4R)-2-methyl-4-((5-nitropyridin-2-yl)amino)-3,4-dihydroquinolin-1(2H)-yl)propan-1-one (230 mg, 24%).
ESI-MS, (M+H)$^+$, m/z: 341. $^1$H-NMR (CDCl$_3$, δ): 1.10-1.20 (m, 6H), 1.33-1.44 (m, 1H), 2.29-2.43 (m, 1H), 2.53-2.64 (m, 1H), 2.66-2.76 (m, 1H), 4.90-5.04 (m, 1H), 5.69-5.96 (m, 1H), 6.48-6.59 (m, 1H), 7.16-7.25 (m, 3H), 7.29-7.36 (m, 1H), 8.21-8.27 (m, 1H), 9.00-9.04 (m, 1H).
(Step 2)
1-((2S,4R)-2-Methyl-4-((5-nitropyridin-2-yl)amino)-3,4-dihydroquinolin-1(2H)-yl)propan-1-one (90 mg, 0.264 mmol) obtained in step 1 was dissolved in a mixed solvent of ethanol (2 mL) and water (2 mL), then zinc powder (173 mg, 2.64 mmol) and sodium chloride (141 mg, 2.64 mmol) were added to the solution, and the mixture was stirred for 1 hour under reflux. The reaction mixture was cooled to room temperature, filtered through diatomaceous earth, and the filtrate was extracted twice with ethyl acetate. The organic layer was dried over magnesium sulfate and concentrated under reduced pressure. The obtained residue was purified by silica gel column chromatography (heptane/ethyl acetate=4/6 to 0/10) to give 1-((2S,4R)-4-((5-aminopyridin-2-yl)amino)-2-methyl-3,4-dihydroquinolin-1(2H)-yl)propan-1-one (52 mg, 63%).
ESI-MS, (M+H)$^+$, m/z: 311. $^1$H-NMR (CDCl$_3$, δ): 1.12-1.17 (m, 6H), 2.27-2.39 (m, 1H), 2.51-2.61 (m, 1H), 2.62-2.71 (m, 1H), 3.27 (brs, 2H), 4.26 (d, J=9.1 Hz, 1H), 4.46-4.54 (m, 1H), 4.87-4.95 (m, 1H), 6.35 (d, J=8.6 Hz, 1H), 6.98 (dd, J=8.6, 2.7 Hz, 1H), 7.14 (d, J=8.2 Hz, 1H), 7.17-7.22 (m, 1H), 7.24-7.29 (m, 1H), 7.32 (d, J=7.2 Hz, 1H), 7.72 (d, J=3.2 Hz, 1H).

Reference Example 18

1-((2S*,4R*)-2-Methyl-4-((piperidin-4-ylmethyl)amino)-3,4-dihydroquinolin-1(2H)-yl)propan-1-one dihydrochloride (Step 1)
1-[(2S*,4R*)-4-Amino-2-methyl-3,4-dihydroquinolin-1(2H)-yl]propan-1-one (0.26 g, 1.0 mmol) obtained in step 3 of reference example 1 was dissolved in dichloroethane (5 mL), then tert-butyl 4-formylpiperidine-1-carboxylate (0.239 g, 1.12 mmol), acetic acid (0.029 mL, 0.510 mmol) and sodium triacetoxyborohydride (0.433 g, 2.04 mmol)

were added to the solution, and the mixture was stirred at room temperature overnight. Water was added to the reaction mixture, and the mixture was extracted 3 times with ethyl acetate. The organic layer was dried over anhydrous magnesium sulfate and concentrated under reduced pressure. The obtained residue was purified by silica gel column chromatography (petroleum ether/ethyl acetate=7/3) to give tert-butyl 4-((((2S*,4R*)-2-methyl-1-propionyl-1,2,3,4-tetrahydroquinolin-4-yl)amino)methyl)piperidine-1-carboxylate (0.41 g, 98%).
ESI-MS m/z: 416 (M+H)$^+$
(Step 2)
tert-Butyl 4-((((2S*,4R*)-2-methyl-1-propionyl-1,2,3,4-tetrahydroquinolin-4-yl)amino)methyl)piperidine-1-carboxylate (0.41 g, 0.98 mmol) obtained in step 1 was dissolved in ethyl acetate (5 mL), then hydrogen chloride/ethyl acetate solution (4 mol/L, 2.5 mL, 9.9 mmol) was added to the solution, and the mixture was stirred at room temperature for 3 hours. The reaction mixture was suction filtered, and the obtained solid was dissolved in methanol and concentrated under reduced pressure to give 1-((2S*,4R*)-2-methyl-4-((piperidin-4-ylmethyl)amino)-3,4-dihydroquinolin-1(2H)-yl)propan-1-one dihydrochloride (0.43 g, quantitative).
ESI-MS m/z: 316 (M+H)$^+$ Reference Example 19

4-(((2S*,4R*)-6-Fluoro-2-methyl-1-propionyl-1,2,3,4-tetrahydroquinolin-4-yl)amino)benzoic acid (Step 1)
N-((2S*,4R*)-6-Fluoro-2-methyl-1,2,3,4-tetrahydroquinolin-4-yl)formamide (0.3 g, 16%) was obtained from 4-fluoroaniline (1.0 g, 9.0 mmol) in the same manner as in step 1 of reference example 1.
ESI-MS m/z: 209 (M+H)$^+$
(Step 2)
N-((2S*,4R*)-6-Fluoro-2-methyl-1-propionyl-1,2,3,4-tetrahydroquinolin-4-yl)formamide (1.0 g, 79%) was obtained from N-((2S*,4R*)-6-fluoro-2-methyl-1,2,3,4-tetrahydroquinolin-4-yl)formamide (1.0 g, 4.81 mmol) obtained in step 1 in the same manner as in step 2 of reference example 1.
ESI-MS m/z: 265 (M+H)$^+$
(Step 3)
1-((2S*,4R*)-4-Amino-6-fluoro-2-methyl-3,4-dihydroquinolin-1(2H)-yl)propan-1-one (0.5 g, 56%) was obtained from N-((2S*,4R*)-6-fluoro-2-methyl-1-propionyl-1,2,3,4-tetrahydroquinolin-4-yl)formamide (1.0 g, 3.79 mmol) obtained in step 2 in the same manner as in step 3 of reference example 1.
ESI-MS m/z: 237 (M+H)$^+$
(Step 4)
Methyl 4-(((2S*,4R*)-6-fluoro-2-methyl-1-propionyl-1,2,3,4-tetrahydroquinolin-4-yl)amino)benzoate (0.08 g, 10%) was obtained from 1-((2S*,4R*)-4-amino-6-fluoro-2-methyl-3,4-dihydroquinolin-1(2H)-yl)propan-1-one (0.3 g, 1.3 mmol) obtained in step 3 in the same manner as in step 4 of reference example 1.
ESI-MS m/z: 371 (M+H)$^+$
(Step 5)
4-(((2S*,4R*)-6-Fluoro-2-methyl-1-propionyl-1,2,3,4-tetrahydroquinolin-4-yl)amino)benzoic acid (0.65 g, 75%) was obtained from methyl 4-(((2S*,4R*)-6-fluoro-2-methyl-1-propionyl-1,2,3,4-tetrahydroquinolin-4-yl)amino)benzoate (0.9 g, 2.4 mmol) obtained in step 4 in the same manner as in step 6 of reference example 1.
ESI-MS m/z: 357 (M+H)$^+$; $^1$H-NMR (CDCl$_3$, δ): 1.14-1.22 (m, 6H), 1.25-1.34 (m, 1H), 2.32-2.38 (m, 1H), 2.53-2.59 (m, 1H), 2.66-2.73 (m, 1H), 4.24-4.31 (m, 2H), 4.96 (brs, 1H), 6.61 (d, J=8.80 Hz, 2H), 6.93-7.02 (m, 2H), 7.15 (brs, 1H), 7.95 (d, J=8.80 Hz, 2H)

Reference Example 20 tert-Butyl ((E)-3-((2S*,4R*)-4-((4-aminophenyl)amino)-2-methyl-1-propionyl-1,2,3,4-tetrahydroquinolin-7-yl)allyl)carbamate (Step 1)
N-((2S*,4R*)-7-Bromo-2-methyl-1,2,3,4-tetrahydroquinolin-4-yl)formamide (24 g, 62%) was obtained in the same manner as in step 1 of reference example 1 using 3-bromoaniline (25.0 g, 145 mmol).
ESI-MS m/z: 269 (M+H)$^+$
(Step 2)
N-((2S*,4R*)-7-Bromo-2-methyl-1-propionyl-1,2,3,4-tetrahydroquinolin-4-yl)formamide (5.5 g, 19%) was obtained from N-((2S*,4R*)-7-bromo-2-methyl-1,2,3,4-tetrahydroquinolin-4-yl)formamide (24 g, 89 mmol) obtained in step 1 in the same manner as in step 2 of reference example 1.
ESI-MS m/z: 325 (M+H)$^+$
(Step 3)
1-((2S*,4R*)-4-Amino-7-bromo-2-methyl-3,4-dihydroquinolin-1(2H)-yl)propan-1-one (2.0 g, 74%) was obtained from N-((2S*,4R*)-7-bromo-2-methyl-1-propionyl-1,2,3,4-tetrahydroquinolin-4-yl)formamide (3.0 g, 9.2 mmol) obtained in step 2 in the same manner as in step 3 of reference example 1.
ESI-MS m/z: 297 (M+H)$^+$
(Step 4)
1-((2S*,4R*)-7-Bromo-2-methyl-4-((4-nitrophenyl)amino)-3,4-dihydroquinolin-1(2H)-yl)propan-1-one. (0.18 g, 25%) was obtained from 1-((2S*,4R*)-4-amino-7-bromo-2-methyl-3,4-dihydroquinolin-1(2H)-yl)propan-1-one (500 mg, 1.69 mmol) obtained in step 3 and (4-nitrophenyl)boronic acid (422 mg, 2.53 mmol) in the same manner as in Reference example 1 Step 4.
ESI-MS m/z: 418 (M+H)$^+$
(Step 5)
1-((2S*,4R*)-7-Bromo-2-methyl-4-((4-nitrophenyl)amino)-3,4-dihydroquinolin-1(2H)-yl)propan-1-one (0.33 g, 0.79 mmol) obtained in step 4 was dissolved in toluene (5 mL), then tert-butyl (E)-(3-(tributylstannyl)allyl)carbamate (0.422 g, 0.95 mmol) and Pd(PPh$_3$)$_4$ (0.091 g, 0.08 mmol) were added to the solution, and the mixture was stirred at 110° C. for 5 hours under an argon atmosphere. Water was added to the reaction mixture, and the mixture was extracted with ethyl acetate. The organic layer was dried over anhydrous sodium sulfate and concentrated under reduced pressure. The obtained residue was purified by silica gel column chromatography (petroleum ether/ethyl acetate=7/3) to give tert-butyl ((E)-3-((2S*,4R*)-2-methyl-4-((4-nitrophenyl)amino)-1-propionyl-1,2,3,4-tetrahydroquinolin-7-yl)allyl)carbamate (0.3 g, 77%).
ESI-MS m/z: 495 (M+H)$^+$
(Step 6)
tert-Butyl ((E)-3-((2S*,4R*)-4-((4-aminophenyl)amino)-2-methyl-1-propionyl-1,2,3,4-tetrahydroquinolin-7-yl)allyl)carbamate (0.25 g, 88%) was obtained from tert-butyl (E)-(3-((2S*,4R*)-2-methyl-4-((4-nitrophenyl)amino)-1- propionyl-1,2,3,4-tetrahydroquinolin-7-yl)allyl)carbamate (0.3 g, 0.61 mmol) obtained in step 5 in the same manner as in step 2 of reference example 16.
ESI-MS m/z: 465 (M+H)$^+$ Reference Example 21 tert-Butyl 4-((2S*,4R*)-4-((4-aminophenyl)amino)-2-methyl-1-propionyl-1,2,3,4-tetrahydroquinolin-7-yl)-3,6-dihydropyridine-1(2H)-carboxylate (Step 1)

1-((2S*,4R*)-7-Bromo-2-methyl-4-((4-nitrophenyl)amino)-3,4-dihydroquinolin-1(2H)-yl)propan-1-one (0.18 g, 25%) obtained in step 4 of reference example 20 was dissolved in a mixed solvent (6 mL) of 1,2-dimethoxyethane and water (5:1), then tert-butyl 4-(4,4,5,5-tetramethyl-1,3,2-dioxaborolan-2-yl)-3,6-dihydropyridine-1(2H)-carboxylate (0.388 g, 1.25 mmol), lithium chloride (0.052 g, 1.25 mmol), sodium carbonate (0.177 g, 1.67 mmol) and Pd(PPh$_3$)$_4$ (0.096 g, 0.08 mmol) were added to the solution and the mixture was stirred at 100° C. for 2 hours under an argon atmosphere. The reaction mixture was filtered through Celite, and the filtrate was concentrated under reduced pressure. The obtained residue was purified by silica gel column chromatography (petroleum ether/ethyl acetate=7/3) to give tert-butyl 4-((2S*,4R*)-2-methyl-4-((4-nitrophenyl)amino)-1-propionyl-1,2,3,4-tetrahydroquinolin-7-yl)-3,6-dihydropyridine-1(2H)-carboxylate (0.3 g, 68%).
ESI-MS m/z: 521 (M+H)$^+$ (Step 2)

tert-Butyl 4-((2S*,4R*)-4-((4-aminophenyl)amino)-2-methyl-1-propionyl-1,2,3,4-tetrahydroquinolin-7-yl)-3,6-dihydropyridine-1(2H)-carboxylate (0.25 g, 88%) was obtained from tert-butyl 4-((2S*,4R*)-2-methyl-4-((4-nitrophenyl)amino)-1-propionyl-1,2,3,4-tetrahydroquinolin-7-yl)-3,6-dihydropyridine-1(2H)-carboxylate (0.3 g, 0.57 mmol) obtained in step 1 in the same manner as in step 2 of reference example 16.

Reference Example 22

4-(2,3,9-Trimethyl-6H-thieno[3,2-f][1,2,4]triazolo[4,3-a][1,4]diazepin-4-yl)aniline 4-(4-Bromophenyl)-2,3,9-trimethyl-6H-thieno[3,2-f][1,2,4]triazolo[4,3-a][1,4]diazepine (2.0 g, 5.17 mmol) obtained in step 3 of reference example 4 was dissolved in DMSO (30 mL), then copper iodide (0.196 g, 1.03 mmol), 1,2-dimethylethylenediamine (0.136 g, 1.55 mmol) and 28% aqueous ammonia (150 mL) were added to the solution, and the mixture was stirred at 130° C. for 16 hours. A saturated aqueous sodium sulfate solution was added to the reaction mixture, and the mixture was extracted twice with ethyl acetate. The organic layer was dried over anhydrous sodium sulfate and concentrated under reduced pressure. The obtained residue was purified by reverse phase HPLC (10 mmol/L aqueous ammonium bicarbonate solution/acetonitrile) to give 4-(2,3,9-trimethyl-6H-thieno[3,2-f][1,2,4]triazolo[4,3-a][1,4]diazepin-4-yl)aniline (0.850 g, 19%).
ESI-MS m/z: 324 (M+H)$^+$; $^1$H-NMR (DMSO-d$_6$, δ): 1.71 (s, 3H), 2.40 (s, 3H), 2.57 (s, 3H), 4.00 (d, J=12.47 Hz, 1H), 5.09 (d, J=12.72 Hz, 1H), 5.57 (s, 2H), 6.52 (d, J=8.80 Hz, 2H), 7.15 (d, J=8.0 Hz, 2H).

Reference Example 23

1-(4-Aminobenzyl)-2-ethyl-1,5,6,7-tetrahydro-4H-indol-4-one (Step 1)

2-(2-Oxobutyl)cyclohexane-1,3-dione (1.7 g, 9.34 mmol) synthesized according to the method described in the literature (Eur. J. of Org. Chem. 2016, 5169-5179) was dissolved in toluene (20 ml), then tert-butyl (4-(aminomethyl)phenyl)carbamate (2.49 g, 11.21 mmol) was added to the solution, and the mixture was stirred at room temperature for 10 minutes, then refluxed for 4 hours, and concentrated under reduced pressure. The obtained residue was purified by silica gel column chromatography (ethyl acetate/petroleum ether=¼ to ½) to give tert-butyl (4-((2-ethyl-4-oxo-4,5,6,7-tetrahydro-1H-indol-1-yl)methyl)phenyl)carbamate (0.550 g, 16%).
ESI-MS m/z: 369 (M+H)$^+$ (Step 2)

1-(4-Aminobenzyl)-2-ethyl-1,5,6,7-tetrahydro-4H-indol-4-one (0.350 g, 87%) was obtained from tert-butyl (4-((2-ethyl-4-oxo-4,5,6,7-tetrahydro-1H-indol-1-yl)methyl)phenyl)carbamate (0.550 g, 1.49 mmol) obtained in step 1 in the same manner as in step 1 of example 8h.
ESI-MS m/z: 269 (M+H)$^+$ Reference Example 24

1-(3-(3,5-Dimethylisoxazol-4-yl)-5-hydroxybenzyl) piperidine-4-carboxylic acid (Step 1)

Commercially available ethyl 3-bromo-5-hydroxybenzaldehyde (0.25 g, 1.24 mmol) was dissolved in a mixed solvent (3 mL) of 1,4-dioxane and water (2:1), then commercially available 3,5-dimethyl-4-(4,4,5,5-tetramethyl-1,3,2-dioxaborolan-2-yl)isoxazole (0.332 g, 1.49 mmol), tripotassium phosphate (0.791 g, 3.73 mmol) and Pd(dppf)Cl$_2$ (0.09 g, 0.12 mmol) were added to the solution, and the mixture was stirred at 100° C. for 4 hours. The reaction mixture was concentrated under reduced pressure, and the obtained residue was purified by column chromatography (ethyl acetate/petroleum ether=30/70) to give 3-(3,5-dimethylisoxazol-4-yl)-5-hydroxybenzaldehyde (0.17 g, 63%).
ESI-MS m/z: 218 (M+H)$^+$ (Step 2)

Ethyl 1-(3-(3,5-dimethylisoxazol-4-yl)-5-hydroxybenzyl) piperidine-4-carboxylate (0.75 g, 23%) was obtained from 3-(3,5-dimethylisoxazol-4-yl)-5-hydroxybenzaldehyde (2.0 g, 9.22 mmol) obtained in step 1 and commercially available ethyl piperidine-4-carboxylate (1.73 g, 11.06 mmol) in the same manner as in step 1 of example 7d.
ESI-MS m/z: 359 (M+H)$^+$ (Step 3)

1-(3-(3,5-Dimethylisoxazol-4-yl)-5-hydroxybenzyl)piperidine-4-carboxylic acid (0.295 g, 58%) was obtained from ethyl 1-(3-(3,5-dimethylisoxazol-4-yl)-5-hydroxybenzyppiperidine-4-carboxylate (0.55 g, 1.54 mmol) obtained in step 2 in the same manner as in step 2 of example 3d.
ESI-MS m/z: 331 (M+H)$^+$

Reference Example 25

3-((4-Aminopiperidin-1-yl)methyl)-5-(3,5-dimethylisoxazol-4-yl)phenol dihydrochloride

(Step 1)

tert-Butyl (1-(3-(3,5-dimethylisoxazol-4-yl)-5-hydroxybenzyl)piperidin-4-yl)carbamate (0.76 g, 21%) was obtained from 3-(3,5-dimethylisoxazol-4-yl)-5-hydroxybenzaldehyde (2.0 g, 9.22 mmol) obtained in step 1 of reference example 24 and commercially available tert-butyl piperidin-4-ylcarbamate (1.84 g, 9.22 mmol) in the same manner as in step 1 of example 7d.

ESIMS, (M+H)$^+$, m/z: 402.35.

(Step 2)

3-((4-Aminopiperidin-1-yl)ethyl)-5-(3,5-dimethylisoxazol-4-yl)phenol dihydrochloride (0.23 g, 7%) was obtained from tert-butyl (1-(3-(3,5-dimethylisoxazol-4-yl)-5-hydroxybenzyl)piperidin-4-yl)carbamate (0.740 g, 1.84 mmol) obtained in step 1 in the same manner as in step 2 of example 1a.

ESIMS, (M+H)$^+$, m/z: 302.27. $^1$H NMR (DMSO-d$_6$, δ): 1.91-2.07 (m, 4H), 2.25 (s, 3H), 2.43 (s, 3H), 2.73-2.89 (m, 2H), 3.19-3.25 (m, 3H), 3.96-4.11 (m, 2H), 6.81-7.03 (m, 3H), 8.14 (s, 1H), 8.24-8.29 (m, 3H), 9.89 (brs, 1H).

Reference Example 26

(S)-4-(6-(2-(2-(Dimethylamino)ethoxy)-2-oxoethyl)-2,3,9-trimethyl-6H-thieno[3,2-f][1,2,4]triazolo[4,3-a][1,4]diazepin-4-yl)benzoic acid

(Step 1)

(S)-4-{6-[2-(tert-Butoxy)-2-oxoethyl]-2,3,9-trimethyl-6H-thieno[3,2-f][1,2,4]triazolo[4,3-a][1,4]diazepin-4-yl}benzoic acid (1.0 g, 2.14 mmol) obtained in reference example 3 was dissolved in DMF (5 mL), then potassium carbonate (0.88 g, 6.44 mmol) and benzyl bromide (0.55 g, 3.22 mmol) were added to the solution. The mixture was stirred at 100° C. for 2 hours. Water was added to the reaction mixture, and the precipitated solid was collected by filtration and dried under reduced pressure to give benzyl (S)-4-(6-(2-(tert-butoxy)-2-oxoethyl)-2,3,9-trimethyl-6H-thieno[3,2-f][1,2,4]triazolo[4,3-a][1,4]diazepin-4-yl)benzoate (1.1 g, 92%).

ESI-MS m/z: 557 (M+H)$^+$ (Step 2)

Benzyl (S)-4-(6-(2-(tert-butoxy)-2-oxoethyl)-2,3,9-trimethyl-6H-thieno[3,2-f][1,2,4]triazolo[4,3-a][1,4]diazepin-4-yl)benzoate (1.1 g, 1.98 mmol) obtained in step 1 was dissolved in 1,4-dioxane (5 mL), then hydrogen chloride/1,4-dioxane solution (4 mol/L, 5.0 mL, 20 mmol) was added to the solution and the mixture was stirred at room temperature for 2 hours. Water was added to the reaction mixture, and the aqueous layer was extracted twice with ethyl acetate. The organic layer was dried over anhydrous sodium sulfate and concentrated under reduced pressure. The obtained residue was purified by column chromatography (methylene chloride/methanol=95/5) to give (S)-2-(4-(4-((benzyloxy)carbonyl)phenyl)-2,3,9-trimethyl-6H-thieno[3,2-f][1,2,4]triazolo[4,3-a][1,4]diazepin-6-yl)acetic acid (0.8 g, 80%).

ESI-MS m/z: 501 (M+H)$^+$ (Step 3)

A crude product of benzyl (S)-4-(6-(2-(2-(dimethylamino)ethoxy)-2-oxoethyl)-2,3,9-trimethyl-6H-thieno[3,2-f][1,2,4]triazolo[4,3-a][1,4]diazepin-4-yl)benzoate (0.165 g) was obtained from (S)-2-(4-(4-((benzyloxy)carbonyl)phenyl)-2,3,9-trimethyl-6H-thieno[3,2-f][1,2,4]triazolo[4,3-a][1,4]diazepin-6-yl)acetic acid (0.250 g, 0.5 mmol) obtained in step 2 and 2-(dimethylamino)ethan-1-ol (0.044 g, 0.5 mmol) in the same manner as in step 1 of example 1a.

ESI-MS m/z: 572 (M+H)$^+$ (Step 4)

The crude product of benzyl (S)-4-(6-(2-(2-(dimethylamino)ethoxy)-2-oxoethyl)-2,3,9-trimethyl-6H-thieno[3,2-f][1,2,4]triazolo[4,3-a][1,4]diazepin-4-yl)benzoate obtained in step 3 (0.165 g) was dissolved in methanol (5 mL), then palladium on carbon (0.05 g, 10 wt %) was added to the solution, and the mixture was stirred at room temperature for 2 hours under a hydrogen atmosphere. The reaction mixture was filtered through Celite, and the filtrate was concentrated under reduced pressure to obtain a crude product of (S)-4-(6-(2-(2-(dimethylamino)ethoxy)-2-oxoethyl)-2,3,9-trimethyl-6H-thieno[3,2-f][1,2,4]triazolo[4,3-a][1,4]diazepin-4-yl)benzoic acid (0.300 g).

ESI-MS m/z: 482 (M+H)$^+$

Reference Example 27

4-((S)-6-(2-(((1r,4S)-4-Hydroxycyclohexyl)oxy)-2-oxoethyl)-2,3,9-trimethyl-6H-thieno[3,2-f][1,2,4]triazolo[4,3-a][1,4]diazepin-4-yl)benzoic acid

(Step 1)

(S)-2-(4-(4-((Benzyloxy)carbonyl)phenyl)-2,3,9-trimethyl-6H-thieno[3,2-f][1,2,4]triazolo[4,3-a][1,4]diazepin-6-yl)acetic acid (0.250 g, 0.5 mmol) obtained in step 2 of reference example 26 was dissolved in chloroform (5 mL), then p-toluenesulfonic acid (0.019 g, 0.1 mmol) and trans-1,4-cyclohexanediol (0.290 g, 2.5 mmol) were added to the solution and the mixture was stirred at 70° C. for 36 hours. The reaction mixture was concentrated under reduced pressure, and the obtained residue was purified by reverse phase column chromatography (acetonitrile/0.1% formic acid aqueous solution=45/55) to give benzyl 4-((S)-6-(2-(((1r,4S)-4-hydroxycyclohexyl)oxy)-2-oxoethyl)-2,3,9-trimethyl-6H-thieno[3,2-f][1,2,4]triazolo[4,3-a][1,4]diazepin-4-yl)benzoate (0.110 g, 37%).

ESIMS, (M+H)$^+$, m/z: 599.23.

(Step 2)

4-((S)-6-(2-(((1r,4S)-4-Hydroxycyclohexyl)oxy)-2-oxoethyl)-2,3,9-trimethyl-6H-thieno[3,2-f][1,2,4]triazolo[4,3-a][1,4]diazepin-4-yl)benzoic acid (0.115 g, 90%) was obtained from benzyl 4-((S)-6-(2-(((1r,4S)-4-hydroxycyclohexyl)oxy)-2-oxoethyl)-2,3,9-trimethyl-6H-thieno[3,2-f][1,2,4]triazolo[4,3-a][1,4]diazepin-4-yl)benzoate (0.150 g, 0.25 mmol) obtained in step 1 in the same manner as in step 4 of reference example 26.

ESIMS, (M+H)$^+$, m/z: 509.34: $^1$H NMR (DMSO-d$_6$, δ) 1.23-1.32 (m, 2H), 1.37-1.45 (m, 2H), 1.60 (s, 3H), 1.75-1.78 (m, 2H), 1.85-1.91 (m, 2H), 2.42 (s, 3H), 2.61 (s, 3H), 3.17 (d, J=5.38 Hz, 1H), 3.40 (dd, J=8.80, 6.36 Hz, 1H), 3.46-3.55 (m, 1H), 4.49-4.56 (m, 2H), 4.70-4.74 (m, 1H), 7.51 (d, J=8.31 Hz, 2H), 7.97 (d, J=8.4 Hz, 2H), 13.17 (brs, 1H).

Reference Example 28

(S)-4-(6-(2-(Ethylamino)-2-oxoethyl)-2,3,9-trimethyl-6H-thieno[3,2-f][1,2,4]triazolo[4,3-a][1,4]diazepin-4-yl)benzoic acid (Step 1)
Benzyl (S)-4-(6-(2-(ethylamino)-2-oxoethyl)-2,3,9-trimethyl-6H-thieno[3,2-f][1,2,4]triazolo[4,3-a][1,4]diazepin-4-yl)benzoate (0.180 g, 86%) was obtained from (S)-2-(4-(4-((benzyloxy)carbonyl)phenyl)-2,3,9-trimethyl-6H-thieno[3,2-f][1,2,4]triazolo[4,3-a][1,4]diazepin-6-yl)acetic acid (0.200 g, 0.4 mmol) obtained in step 2 of reference example 26 and ethylamine (2 mol/L THF solution, 0.6 ml, 1.2 mmol) in the same manner as in step 3 of example 1b.
ESIMS, (M+H)$^+$, m/z: 528.24.

(Step 2)
(S)-4-(6-(2-(Ethylamino)-2-oxoethyl)-2,3,9-trimethyl-6H-thieno[3,2-f][1,2,4]triazolo[4,3-a][1,4]diazepin-4-yl)benzoic acid (0.135 g, 90%) was obtained from benzyl (S)-4-(6-(2-(ethylamino)-2-oxoethyl)-2,3,9-trimethyl-6H-thieno[3,2-f][1,2,4]triazolo[4,3-a][1,4]diazepin-4-yl)benzoate (0.180 g, 0.34 mmol) obtained in step 1 in the same manner as in step 4 of reference example 26.
ESIMS, (M+H)$^+$, m/z: 438.

Reference Example 29

(S)-4-(6-(2-(4-(2-Hydroxyethyl)piperazin-1-yl)-2-oxoethyl)-2,3,9-trimethyl-6H-thieno[3,2-f][1,2,4]triazolo[4,3-a][1,4]diazepin-4-yl)benzoic acid (Step 1)
A crude product (0.140 g) of benzyl (S)-4-(6-(2-(4-(2-hydroxyethyl)piperazin-1-yl)-2-oxoethyl)-2,3,9-trimethyl-6H-thieno[3,2-f][1,2,4]triazolo[4,3-a][1,4]diazepin-4-yl)benzoate was obtained from (S)-2-(4-(4-((benzyloxy)carbonyl)phenyl)-2,3,9-trimethyl-6H-thieno[3,2-f][1,2,4]triazolo[4,3-a][1,4]diazepin-6-yl)acetic acid (0.150 g, 0.3 mmol) obtained in step 2 of reference example 26, and 2-(piperazin-1-yl)ethan-1-ol (0.039 g, 0.3 mmol) in the same manner as in step 3 of example 1b.
ESIMS, (M+H)$^+$, m/z: 613.27.

(Step 2)
(S)-4-(6-(2-(4-(2-Hydroxyethyl)piperazin-1-yl)-2-oxoethyl)-2,3,9-trimethyl-6H-thieno[3,2-f][1,2,4]triazolo[4,3-a][1,4]diazepin-4-yl)benzoic acid (0.062 g, 80%) was obtained from the crude product (0.140 g) of benzyl (S)-4-(6-(2-(4-(2-hydroxyethyl)piperazin-1-yl)-2-oxoethyl)-2,3,9-trimethyl-6H-thieno[3,2-f][1,2,4]triazolo[4,3-a][1,4]diazepin-4-yl)benzoate obtained in step 1 in the same manner as in step 4 of reference example 26.
ESIMS, (M+H)$^+$, m/z: 523.

Reference Example 30

(S)-4-(6-(2-(3-Methoxypropoxy)-2-oxoethyl)-2,3,9-trimethyl-6H-thieno[3,2-f][1,2,4]triazolo[4,3-a][1,4]diazepin-4-yl)benzoic acid (Step 1)
Benzyl (S)-4-(6-(2-(3-methoxypropoxy)-2-oxoethyl)-2,3,9-trimethyl-6H-thieno[3,2-f][1,2,4]triazolo[4,3-a][1,4]diazepin-4-yl)benzoate (0.192 g, 56%) was obtained from (S)-2-(4-(4-((benzyloxy)carbonyl)phenyl)-2,3,9-trimethyl-6H-thieno[3,2-f][1,2,4]triazolo[4,3-a][1,4]diazepin-6-yl)acetic acid (0.3 g, 0.6 mmol) obtained in step 2 of reference example 26 and 3-methoxypropan-1-ol (0.540 g, 6 mmol) in the same manner as in step 1 of reference example 27.
ESIMS, (M+H)$^+$, m/z: 573.31.

(Step 2)
(S)-4-(6-(2-(3-Methoxypropoxy)-2-oxoethyl)-2,3,9-trimethyl-6H-thieno[3,2-f][1,2,4]triazolo[4,3-a][1,4]diazepin-4-yl)benzoic acid (0.130 g, 80%) was obtained from benzyl (S)-4-(6-(2-(3-methoxypropoxy)-2-oxoethyl)-2,3,9-trimethyl-6H-thieno[3,2-f][1,2,4]triazolo[4,3-a][1,4]diazepin-4-yl)benzoate (0.192 g, 0.33 mmol) obtained in step 1 in the same manner as in step 4 of reference example 26.
ESIMS, (M+H)$^+$, m/z: 483.

Reference Example 31

(S)-4-(6-(2-(2-Methoxyethoxy)-2-oxoethyl)-2,3,9-trimethyl-6H-thieno[3,2-f][1,2,4]triazolo[4,3-a][1,4]diazepin-4-yl)benzoic acid (Step 1)
Benzyl (S)-4-(6-(2-(2-methoxyethoxy)-2-oxoethyl)-2,3,9-trimethyl-6H-thieno[3,2-f][1,2,4]triazolo[4,3-a][1,4]diazepin-4-yl)benzoate (0.2 g, 59%) was obtained from (S)-2-(4-(4-((benzyloxy)carbonyl)phenyl)-2,3,9-trimethyl-6H-thieno[3,2-f][1,2,4]triazolo[4,3-a][1,4]diazepin-6-yl)acetic acid (0.3 g, 0.6 mmol) obtained in step 2 of reference example 26, and 2-methoxyethan-1-ol (0.456 g, 6 mmol) in the same manner as in step 1 of reference example 27.
ESIMS, (M+H)$^+$, m/z: 559.29.

(Step 2)
(S)-4-(6-(2-(2-Methoxyethoxy)-2-oxoethyl)-2,3,9-trimethyl-6H-thieno[3,2-f] [1,2,4]triazolo[4,3-a][1,4]diazepin-4-yl)benzoic acid (0.125 g, 75%) was obtained from benzyl (S)-4-(6-(2-(2-methoxyethoxy)-2-oxoethyl)-2,3,9-trimethyl-6H-thieno[3,2-f][1,2,4]triazolo[4,3-a][1,4]diazepin-4-yl)benzoate (0.2 g, 0.36 mmol) obtained in step 1 in the same manner as in step 4 of reference example 26.
ESIMS, (M+H)$^+$, m/z: 469.

Reference Example 32

4-((2-((2-(Dimethylamino)ethoxy)carbonyl)-4-oxo-4,5,6,7-tetrahydro-1H-indol-1-yl)methyl)benzoic acid (Step 1)
Aluminum chloride (4.73 g, 35.6 mmol) was dissolved in dichloromethane (25 mL), then 1,5,6,7-tetrahydro-4H-indol-4-one (2.0 g, 14.9 mmol) was added to the solution, and the mixture was stirred at −40° C. for 5 minutes. Trichloroacetyl chloride (2.02 mL, 17.8 mmol) was added to the reaction mixture, and the mixture was stirred at −40° C. for 5 minutes and then at room temperature for 16 hours. A saturated aqueous sodium hydrogen carbonate solution was added to the reaction mixture, and the aqueous layer was extracted twice with dichloromethane. The organic layer was dried over anhydrous sodium sulfate and concentrated under reduced pressure. The obtained residue was purified by column chromatography (petroleum ether/ethyl acetate=7/3 to 6/4) to give 2-(2,2,2-trichloroacetyl)-1,5,6,7-tetrahydro-4H-indol-4-one (2.0 g, 48%).
ESIMS, (M+H)$^+$, m/z: 280.03.

(Step 2)
2-(2,2,2-Trichloroacetyl)-1,5,6,7-tetrahydro-4H-indol-4-one (2.0 g, 7.17 mmol) obtained in step 1 was dissolved in methanol (15 mL), then sodium methoxide (0.425 g, 7.88 mmol) was added to the solution, and the mixture was stirred at room temperature for 5 hours. The reaction mixture was diluted with hydrochloric acid (1 mol/L), and the aqueous layer was extracted with dichloromethane. The organic layer was dried over anhydrous sodium sulfate and concentrated under reduced pressure to give methyl 4-oxo-4,5,6,7-tetrahydro-1H-indole-2-carboxylate (1.0 g, 72%).
ESIMS, (M+H)$^+$, m/z: 194.11.
(Step 3)
Methyl 4-oxo-4,5,6,7-tetrahydro-1H-indole-2-carboxylate (1.0 g, 5.18 mmol) obtained in step 2 was dissolved in acetonitrile (10 mL), then potassium carbonate (1.43 g, 10.36 mmol) was added to the solution, and the mixture was stirred at room temperature for 5 minutes. tert-Butyl 4-(bromomethyl)benzoate (1.4 g, 5.18 mmol) was added to the reaction mixture, and the mixture was stirred at 80° C. for 16 hours. The reaction mixture was concentrated under reduced pressure, then water was added, and the aqueous layer was extracted with ethyl acetate. The organic layer was dried over anhydrous sodium sulfate and concentrated under reduced pressure. The obtained residue was purified by column chromatography (ethyl acetate/petroleum ether=¼) to give methyl 1-(4-(tert-butoxycarbonyl)benzyl)-4-oxo-4,5,6,7-tetrahydro-1H-indole-2-carboxylate (1.45 g, 73%).
ESIMS, (M+H)$^+$, m/z: 384.21.
(Step 4)
1-(4-(tert-Butoxycarbonyl)benzyl)-4-oxo-4,5,6,7-tetrahydro-1H-indole-2-carboxylic acid (0.900 g, 64%) was obtained from methyl 1-(4-(tert-butoxycarbonyl)benzyl)-4-oxo-4,5,6,7-tetrahydro-1H-indole-2-carboxylate (1.45 g, 3.78 mmol) obtained in step 3 in the same manner as in step 2 of example 2f.
ESIMS, (M+H)$^+$, m/z: 370.22.
(Step 5)
2-(Dimethylamino)ethyl 1-(4-(tert-butoxycarbonyl)benzyl)-4-oxo-4,5,6,7-tetrahydro-1H-indole-2-carboxylate (0.280 g, 81%) was obtained from 1-(4-(tert-butoxycarbonyl)benzyl)-4-oxo-4,5,6,7-tetrahydro-1H-indole-2-carboxylic acid (0.3 g, 0.81 mmol) obtained in step 4 and 2-(dimethylamino)ethan-1-ol (0.12 mL, 1.22 mmol) in the same manner as in step 1 of example 1a.
ESIMS, (M+H)$^+$, m/z: 441.46.
(Step 6)
4-((2-((2-(Dimethylamino)ethoxy)carbonyl)-4-oxo-4,5,6,7-tetrahydro-1H-indol-1-yl)methyl)benzoic acid (0.150 g, 61%) was obtained from 2-(dimethylamino)ethyl 1-(4-(tert-butoxycarbonyl)benzyl)-4-oxo-4,5,6,7-tetrahydro-1H-indole-2-carboxylate (0.280 g, 0.64 mmol) obtained in step 5 in the same manner as in step 2 of example 1k.
ESIMS, (M+H)$^+$, m/z: 385: $^1$H NMR (DMSO-d$_6$, δ) δ 2.04 (t, J=6.0 Hz, 2H), 2.40 (t, J=6.4 Hz, 2H), 2.45 (s, 6H), 2.75 (t, J=6.0 Hz, 2H), 2.90-2.92 (m, 2H), 4.32 (t, J=5.2 Hz, 2H), 5.69 (s, 2H), 7.12 (d, J=8.4 Hz, 2H), 7.30 (s, 1H), 7.90 (cl, J=8.0 Hz, 2H).

Reference Example 33

4-((2-((2-Hydroxyethoxy)carbonyl)-4-oxo-4,5,6,7-tetrahydro-1H-indol-1-yl)methyl)benzoic acid (Step 1)
The mixture of 2-((tert-butyldimethylsilyl)oxy)ethyl 1-(4-(tert-butoxycarbonyl)benzyl)-4-oxo-4,5,6,7-tetrahydro-1H-indole-2-carboxylate and 2-hydroxyethyl 1-(4-(tert-butoxycarbonyl)benzyl)-4-oxo-4,5,6,7-tetrahydro-1H-indole-2-carboxylate was obtained as a crude product (0.350 g) from 1-(4-(tert-butoxycarbonyl)benzyl)-4-oxo-4,5,6,7-tetrahydro-1H-indole-2-carboxylic acid (0.3 g, 0.81 mmol) obtained in step 4 of reference example 32 and 2-((tert-butyldimethylsilyl)oxy)ethan-1-ol (0.19 mL, 0.97 mmol) in the same manner as in step 1 of example 1a.
ESIMS, (M+H)$^+$, m/z: 528.36.
(Step 2)
A crude product (0.3 g) of 4-((2-((2-hydroxyethoxy)carbonyl)-4-oxo-4,5,6,7-tetrahydro-1H-indol-1-yl)methyl)benzoic acid was obtained from the crude products (0.350 g) of 2-((tert-butyldimethylsilyl)oxy)ethyl 1-(4-(tert-butoxycarbonyl)benzyl)-4-oxo-4,5,6,7-tetrahydro-1H-indole-2-carboxylate and 2-hydroxyethyl 1-(4-(tert-butoxycarbonyl)benzyl)-4-oxo-4,5,6,7-tetrahydro-1H-indole-2-carboxylate obtained in step 5 in the same manner as in step 2 of example 1k.
ESIMS, (M+H)$^+$, m/z: 358.35.

Reference Example 34

4-((2-(Methoxycarbonyl)-4-oxo-4,5,6,7-tetrahydro-1H-indol-1-yl)methyl)benzoic acid 4-((2-(Methoxycarbonyl)-4-oxo-4,5,6,7-tetrahydro-1H-indol-1-yl)methyl)benzoic acid (0.1 g, 81%) was obtained from methyl 1-(4-(tert-butoxycarbonyl)benzyl)-4-oxo-4,5,6,7-tetrahydro-1H-indole-2-carboxylate (0.145 g, 0.37 mmol) obtained in step 3 of reference example 32 in the same manner as in step 2 of example 1k.
ESIMS, (M+H)$^+$, m/z: 328: $^1$H NMR (CDCl$_3$, δ) δ 2.13-2.18 (m, 2H), 2.53 (t, J=6.5 Hz, 2H), 2.69 (t, J=6.10 Hz, 2H), 3.78 (s, 3H), 5.69 (s, 2H), 7.06 (d, J=8.5 Hz, 2H), 7.44 (s, 1H), 8.05 (d, J=8.5 Hz, 2H).

Example 1a

N,N'-(Propane-1,3-diyl)bis(4-{[(2S*,4R*)-2-methyl-1-propionyl-1,2,3,4-tetrahydroquinolin-4-yl]amino}benzamide) (Compound 1a)

(Step 1)
4-{[(2S*,4R*)-2-Methyl-1-propionyl-1,2,3,4-tetrahydroquinolin-4-yl]amino}benzoic acid (200 mg, 0.89 mmol) obtained in step 6 of reference example 1 was dissolved in DMF (6.0 mL), then HATU (337 mg, 0.89 mmol), tert-butyl (3-aminopropyl)carbamate (155 mg, 0.89 mmol) and N,N-diisopropylethylamine (0.21 mL, 1.18 mmol) were added to the solution, and the mixture was stirred at room temperature overnight. A saturated aqueous sodium hydrogen carbonate solution was added to the reaction mixture, and the mixture was extracted twice with ethyl acetate. The organic layer was dried over anhydrous magnesium sulfate and concentrated under reduced pressure. The obtained residue was purified by silica gel column chromatography (chloroform/methanol=100/0 to 90/10) to give tert-butyl[3-(4-{[(2S*,4R*)-2-methyl-1-propionyl-1,2,3,4-tetrahydroquinolin-4-yl]amino}benzamide)propyl]carbamate (330 mg, 75%).
ESIMS, (M+H)$^+$, m/z: 495.
(Step 2)
tert-Butyl [3-(4-{[(2S*,4R*)-2-methyl-1-propionyl-1,2,3,4-tetrahydroquinolin-4-yl]amino}benzamide)propyl]carbamate (330 mg, 0.67 mmol) obtained in step 1 was dissolved in ethyl acetate (20 mL), then hydrogen chloride/1,4-dioxane solution (4 mol/L, 5.0 mL, 20 mmol) was added to the solution. The mixture was stirred at room temperature for 24 hours. The resulting solid was collected by filtration and washed with ethyl acetate to give N-(3-aminopropyl)-4-{[(2S*,4R*)-2-methyl-1-propionyl-1,2,3,4-tetrahydroquinolin-4-yl]amino}benzamide hydrochloride (260 mg, 89%).
ESIMS, (M+H)$^+$, m/z: 395.

(Step 3)

A crude product of compound 1a (360 mg) was obtained from N-(3-aminopropyl)-4-{[(2S*,4R*)-2-methyl-1-propionyl-1,2,3,4-tetrahydroquinolin-4-yl]amino}benzamide hydrochloride (543 mg, 1.38 mmol) obtained in step 2 and 4-{[(2S*,4R*)-2-methyl-1-propionyl-1,2,3,4-tetrahydroquinolin-4-yl]amino}benzoic acid (466 mg, 1.38 mmol) obtained in step 6 of reference example 1 in the same manner as in step 1. The obtained crude product was purified by reverse phase high performance liquid chromatography (reverse phase HPLC) (Column: CHIRALART Cellulose-SB S-5 μm, methyl tert-butyl ether (MtBE)/methanol=80/20, flow rate 1 mL/min, rt=3.9 min) to give compound 1a (34 mg, 3.4%).
ESIMS, (M+H)$^+$, m/z: 715. $^1$H NMR (CDCl$_3$, δ): 1.08-1.20 (m, 12H), 1.21-1.38 (m, 4H), 1.70-1.90 (m, 2H), 2.30-2.44 (m, 2H), 2.50-2.71 (m, 4H), 3.40-3.75 (m, 4H), 4.19-4.29 (m, 2H), 4.88-5.01 (m, 2H), 6.63 (d, J=8.4 Hz, 4H), 7.11-7.31 (m, 8H), 7.76 (d, J=8.7 Hz, 4H).
HPLC (CHIRAL Cellulose-SB (0.46×15 cm, 3 μm), MtBE (0.1% DEA)/methanol=80/20, flow rate 1.0 ml/min): rt=7.9 min Example 1b Di-tert-butyl 2,2'-[(6S,6'S)-({[propane-1,3-diylbis(azanediyl)]bis(carbonyl)}bis(4,1-phenylene))bis(2,3,9-trimethyl-6H-thieno[3,2-f][1,2,4]triazolo[4,3-a][1,4]diazepine-4,6-diyl)]diacetate (Compound 1b)

(Step 1)
(S)-4-{6-[2-(tert-Butoxy)-2-oxoethyl]-2,3,9-trimethyl-6H-thieno[3,2-f][1,2,4]triazolo[4,3-a][1,4]diazepin-4-yl}benzoic acid (800 mg, 1.71 mmol) obtained in reference example 3 was dissolved in DMF (10 mL), then HATU (744 mg, 1.71 mmol), N,N-diisopropylethylamine (5 mL, 28.1 mmol) and benzyl N-(3-aminopropyl)carbamate (464 mg, 2.23 mmol) were added to the solution, and the mixture was stirred at room temperature for 25 hours. The reaction mixture was concentrated under reduced pressure, and the obtained residue was purified by silica gel column chromatography (petroleum ether/ethyl acetate=90/10 to 50/50) to give tert-butyl (S)-2-(4-{4-[(3-{[(benzyloxy)carbonyl]amino}propyl)carbamoyl]phenyl}-2,3,9-trimethyl-6H-thieno[3,2-f][1,2,4]triazolo[4,3-a][1,4]diazepin-6-yl)acetate (910 mg).
ESIMS, (M+H)$^+$, m/z: 657.
(Step 2)
tert-Butyl (S)-2-(4-{4-[(3-{[(benzyloxy)carbonyl]amino}propyl)carbamoyl]phenyl}-2,3,9-trimethyl-6H-thieno[3,2-f][1,2,4]triazolo[4,3-a][1,4]diazepin-6-yl)acetate (900 mg, 1.37 mmol) obtained in step 1 was dissolved in methanol (20 mL), then 10% palladium on carbon (0.20 g, 10 wt %) was added to the solution, and the mixture was stirred at room temperature for 5 hours under a hydrogen atmosphere. The to reaction mixture was suction filtered, and the filtrate was concentrated under reduced pressure to give a crude product (0.72 g) of tert-butyl (S)-2-(4-{4-[(3-aminopropyl)carbamoyl]phenyl}-2,3,9-trimethyl-6H-thieno[3,2-f][1,2,4]triazolo[4,3-a][1,4]diazepin-6-yl)acetate.
ESIMS, (M+H)$^+$, m/z: 523.
(Step 3)
(S)-4-{6-[2-(tert-Butoxy)-2-oxoethyl]-2,3,9-trimethyl-6H-thieno[3,2-f][1,2,4]triazolo[4,3-a][1,4]diazepin-4-yl}benzoic acid (500 mg, 1.07 mmol) obtained in reference example 3 was dissolved in DMF (45 mL), then COMU (2 g, 4.62 mmol) and N,N-diisopropylethylamine (5 mL, 28.0 mmol) were added to the solution, and the mixture was stirred at room temperature for 5 minutes. The crude product (700 mg, 1.34 mmol) of tert-butyl (S)-2-(4-{4-[(3-aminopropyl)carbamoyl]phenyl}-2,3,9-trimethyl-6H-thieno[3,2-f][1,2,4]triazolo[4,3-a][1,4]diazepin-6-yl)acetate obtained in step 2 was added to the reaction mixture, and the mixture was stirred at room temperature for 24 hours. The reaction mixture was concentrated under reduced pressure, and the obtained residue was purified by reverse phase HPLC (0.1% formic acid/acetonitrile=53/47 to 43/57) to give compound 1b (285 mg, total yield of 3 steps 18%).
ESIMS, (M+H)$^+$, m/z: 971. $^1$H NMR (DMSO-d$_6$, δ): 1.58 (s, 18H), 1.75 (s, 6H), 1.70-1.90 (m, 2H), 2.41 (s, 6H), 2.61 (s, 6H), 3.20-3.40 (m, 8H), 4.44 (t, J=7.8 Hz, 2H), 7.48 (d, J=8.4 Hz, 4H), 7.87 (d, J=8.4 Hz, 4H), 8.60 (t, J=5.6 Hz, 2H).

Example 1c

4-{[(2S*,4R*)-2-Methyl-1-propionyl-1,2,3,4-tetrahydroquinolin-4-yl]amino}-N-[1-(4-{[(2S*,4R*)-2-methyl-1-propionyl-1,2,3,4-tetrahydroquinolin-4-yl]amino}benzoyl)piperidin-4-yl]benzamide (Compound 1c)

(Step 1)
tert-Butyl 4-(4-{[(2S*,4R*)-2-methyl-1-propionyl-1,2,3,4-tetrahydroquinolin-4-yl]amino}benzamide)piperidine-1-carboxylate (62 mg, 80%) was obtained from 4-{[(2S*,4R*)-2-methyl-1-propionyl-1,2,3,4-tetrahydroquinolin-4-yl]amino}benzoic acid (50 mg, 0.148 mmol) obtained in step 6 of reference example 1 and tert-butyl 4-aminopiperidine-1-carboxylate (30 mg, 0.148 mmol) in the same manner as in step 1 of example 1a.
ESIMS, (M+H)$^+$, m/z: 521.
(Step 2)
4-{[(2S*,4R*)-2-Methyl-1-propionyl-1,2,3,4-tetrahydroquinolin-4-yl]amino}-N-(piperidin-4-yl)benzamide hydrochloride (55 mg, 92%) was obtained from tert-butyl 4-(4-{[(2S*,4R*)-2-methyl-1-propionyl-1,2,3,4-tetrahydroquinolin-4-yl]amino}benzamide)piperidine-1-carboxylate (66 mg, 0.127 mmol) obtained in step 1 in the same manner as in step 2 of example 1a.
ESIMS, (M+H)$^+$, m/z: 421.
(Step 3)
Compound is (30 mg, 28%) was obtained from 4-{[(2S*,4R*)-2-methyl-1-propionyl-1,2,3,4-tetrahydroquinolin-4-yl]amino}-N-(piperidin-4-yl)benzamide hydrochloride (49 mg, 0.144 mmol) obtained in step 2 in the same manner as in step 3 of example 1a.
ESIMS, (M+H)$^+$, m/z: 741. $^1$H NMR (DMSO-d$_6$, δ): 1.10-1.20 (m, 12H), 1.24-1.36 (m, 2H), 2.03-2.17 (m, 2H), 2.31-2.44 (m, 2H), 2.51-2.75 (m, 4H), 2.93-3.19 (m, 5H), 4.18-4.32 (m, 4H), 4.87-5.02 (m, 2H), 5.91-5.99 (m, 1H), 6.56-6.64 (m, 5H), 7.14-7.35 (m, 11H), 7.58-7.68 (m, 2H).

Example 1d

4-{[3-(3,5-Dimethylisoxazol-4-yl)-5-hydroxyphenyl](hydroxy)methyl}-N-[3-(4-{[(2S*,4R*)-2-methyl-1-propionyl-1,2,3,4-tetrahydroquinolin-4-yl]amino}benzamide)propyl]benzamide (Compound 1d)

N-(3-Aminopropyl)-4-{[(2S*,4R*)-2-methyl-1-propionyl-1,2,3,4-tetrahydroquinolin-4-yl]amino}benzamide hydrochloride (123 mg, 0.32 mmol) obtained in step 2 of example 1a was dissolved in DMF (6.0 mL), then 4-{[3-(3, 5-dimethylisoxazol-4-yl)-5-hydroxyphenyl](hydroxy) methyl}benzoic acid (110 mg, 0.32 mmol) obtained in reference example 6, EDCI (124 mg, 0.65 mmol), HOBt (88 mg, 0.65 mmol) and N,N-diisopropylethylamine (0.23 mL, 1.30 mmol) were added to the solution, and the mixture was stirred at room temperature for 16 hours. Water was added to the reaction mixture, and the mixture was extracted twice with ethyl acetate. The organic layer was dried over anhydrous sodium sulfate and concentrated under reduced pressure. The obtained residue was purified by reverse phase HPLC (10 mmol/L aqueous ammonium bicarbonate solution/acetonitrile=63/37 to 59/41) to give compound 1d (39 mg, 17%).
ESIMS, (M+H)$^+$, m/z: 716. $^1$H NMR (CD$_3$OD, δ): 1.08-1.19 (m, 6H), 1.23-1.38 (m, 1H), 1.80-1.91 (m, 2H), 2.19 (s, 3H), 2.34 (s, 3H), 2.38-2.49 (m, 1H), 2.54-2.72 (m, 2H), 3.29-3.32 (m, 1H), 3.39-3.50 (m, 4H), 4.25 (dd, J=12.3, 4.2 Hz, 1H), 5.79 (s, 1H), 6.61-6.70 (m, 3H), 6.79 (s, 1H), 6.84 (s, 1H), 7.18-7.30 (m, 4H), 7.50 (d, J=8.4 Hz, 2H), 7.66 (d, J=8.7 Hz, 2H), 7.80 (d, J=8.4 Hz, 2H).

Example 1e

4-[(2-Ethyl-4-oxo-4,5,6,7-tetrahydro-1H-indol-1-yl) methyl]-N-[3-(4-{[(2S*,4R*)-2-methyl-1-propionyl-1,2,3,4-tetrahydroquinolin-4-yl]amino}benzamide) propyl]benzamide (Compound 1e)

Compound 1e (15 mg, 24%) was obtained from N-(3-aminopropyl)-4-{[(2S*,4R*)-2-methyl-1-propionyl-1,2,3,4-tetrahydroquinolin-4-yl]amino}benzamide hydrochloride (40 mg, 0.093 mmol) obtained in step 2 of example 1a and 4-[(2-ethyl-4-oxo-4,5,6,7-tetrahydro-1H-indol-1-yl)methyl] benzoic acid (28 mg, 0.093 mmol) obtained in reference example 5 in the same manner as in step 1 of example 1a.
ESIMS, (M+H)$^+$, m/z: 674. $^1$H NMR (CDCl$_3$, δ): 1.10-1.22 (m, 9H), 1.27-1.35 (m, 1H), 1.79-1.89 (m, 2H), 2.06-2.18 (m, 2H), 2.37-2.48 (m, 3H), 2.51-2.72 (m, 6H), 3.44-3.59 (m, 4H), 4.22-4.32 (m, 1H), 4.92-5.04 (m, 1H), 5.11 (s, 2H), 6.40 (s, 1H), 6.60-6.66 (m, 2H), 6.96-7.01 (m, 2H), 7.11-7.17 (m, 1H), 7.19-7.24 (m, 2H), 7.28-7.35 (m, 1H), 7.68-7.72 (m, 2H), 7.72-7.78 (m, 1H), 7.82-7.88 (m, 2H).

Example 1f

4-{[(2S,4R*)-2-Methyl-1-propionyl-1,2,3,4-tetrahydroquinolin-4-yl]amino}-N-{3-[4-(2,3,9-trimethyl-6H-thieno[3,2-f][1,2,4]triazolo[4,3-a][1,4]diazepin-4-yl)benzamide]propyl}benzamide (Compound 1f)

Compound 1f (20 mg, 34%) was obtained from N-(3-aminopropyl)-4-{[(2S*,4R*)-2-methyl-1-propionyl-1,2,3,4-tetrahydroquinolin-4-yl]amino}benzamide hydrochloride (35 mg, 0.081 mmol) obtained in step 2 of example 1a and 4-(2,3,9-trimethyl-6H-thieno[3,2-f][1,2,4]triazolo[4,3-a][1,4]diazepin-4-yl)benzoic acid (29 mg, 0.081 mmol) obtained in reference example 4 in the same manner as in step 1 of example 1a.
ESIMS, (M+H)$^+$, m/z: 729. $^1$H NMR (CDCl$_3$, δ): 1.11-1.21 (m, 6H), 1.28-1.37 (m, 1H), 1.66 (s, 3H), 2.42 (s, 3H), 2.53-2.74 (m, 4H), 3.48-3.61 (m, 4H), 4.11-4.18 (m, 1H), 4.19-4.33 (m, 2H), 4.89-5.01 (m, 1H), 5.47-5.55 (m, 1H), 6.58-6.65 (m, 2H), 6.84-6.91 (m, 1H), 7.14-7.25 (m, 3H), 7.28-7.33 (m, 1H), 7.55-7.61 (m, 2H), 7.68-7.73 (m, 2H), 7.75-7.83 (m, 1H), 7.92-7.96 (m, 2H).

Example 1g

4-{[(2S%4R*)-2-Methyl-1-propionyl-1,2,3,4-tetrahydroquinolin-4-yl]amino}-N-[1-(4-{[(2S*,4R*)-2-methyl-1-propionyl-1,2,3,4-tetrahydroquinolin-4-yl] amino}benzoyl)azetidin-3-yl]benzamide (Compound 1g)

(Step 1)
tert-Butyl 3-(4-{[(2S*,4R*)-2-methyl-1-propionyl-1,2,3,4-tetrahydroquinolin-4-yl]amino}benzamide)azetidine-1-carboxylate (47 mg, 80%) was obtained from 4-{[(2S*,4R*)-2-methyl-1-propionyl-1,2,3,4-tetrahydroquinolin-4-yl]amino}benzoic acid (40 mg, 0.118 mmol) obtained in step 6 of reference example 1 and tert-butyl 4-aminoazetidine-1-carboxylate (20 mg, 0.118 mmol) in the same manner as in step 1 of example 1a.
ESIMS, (M+H)$^+$, m/z: 493.
(Step 2)
N-(Azetidin-3-yl)-4-{[(2S*,4R*)-2-methyl-1-propionyl-1,2,3,4-tetrahydroquinolin-4-yl]amino}benzamide hydrochloride (34 mg, 100%) was obtained from tert-butyl 3-(4-{[(2S*,4R*)-2-methyl-1-propionyl-1,2,3,4-tetrahydroquinolin-4-yl]amino}benzamide)azetidine-1-carboxylate (39 mg, 0.079 mmol) obtained in step 1 in the same manner as in step 2 of example 1a.
ESIMS, (M+H)$^+$, m/z: 393.
(Step 3)
Compound 1g (12 mg, 21%) was obtained from N-(azetidin-3-yl)-4-{[(2S*,4R*)-2-methyl-1-propionyl-1,2,3,4-tetrahydroquinolin-4-yl]amino}benzamide hydrochloride (34 mg, 0.079 mmol) obtained in step 2 in the same manner as in step 3 of example 1a.
ESIMS, (M+H)$^+$, m/z: 713. $^1$H NMR (CDCl$_3$, δ): 1.09-1.19 (m, 12H), 1.23-1.35 (m, 2H), 2.32-2.46 (m, 2H), 2.51-2.72 (m, 4H), 4.16-4.29 (m, 4H), 4.58-4.72 (m, 2H), 4.82-5.03 (m, 3H), 6.49-6.63 (m, 4H), 7.14-7.25 (m, 8H), 7.25-7.33 (m, 2H), 7.43-7.54 (m, 2H), 7.67-7.76 (m, 2H).

Example 1h tert-Butyl 2-[(S)-2,3,9-trimethyl-4-(4-{[3-(4-{[(2S, 4R)-2-methyl-1-propionyl-1,2,3,4-tetrahydroquinolin-4-yl]amino}benzamide)propyl] carbamoyl}phenyl)-6H-thieno[3,2-f][1,2,4]triazolo [4,3-a][1,4]diazepin-6-yl]acetate (Compound 1h)

(Step 1)
tert-Butyl [3-(4-{[(2S,4R)-2-methyl-1-propionyl-1,2,3,4-tetrahydroquinolin-4-yl]amino}benzamide)propyl]carbamate (512 mg, 100%) was obtained from 4-{[(2S,4R)-2-methyl-1-propionyl-1,2,3,4-tetrahydroquinolin-4-yl] amino}benzoic acid (350 mg, 1.03 mmol) obtained in step 7 of reference example 1 in the same manner as in step 1 of example 1a.
ESIMS, (M+H)$^+$, m/z: 495.
(Step 2)
N-(3-Aminopropyl)-4-{[(2S,4R)-2-methyl-1-propionyl-1,2,3,4-tetrahydroquinolin-4-yl]amino}benzamide hydrochloride (279 mg, 100%) was obtained from tert-butyl[3-(4-{[(2S,4R)-2-methyl-1-propionyl-1,2,3,4-tetrahydroquinolin-4-yl]amino}benzamide)propyl] carbamate (320 mg, 0.647 mmol) obtained in step 1 in the same manner as in step 2 of example 1a.
ESIMS, (M+H)$^+$, m/z: 395.

(Step 3)

Compound 1h (35 mg, 36%) was obtained from N-(3-aminopropyl)-4-{[(2S,4R)-2-methyl-1-propionyl-1,2,3,4-tetrahydroquinolin-4-yl]amino}benzamide hydrochloride (50 mg, 0.116 mmol) obtained in step 2 and (S)-4-{6-[2-(tert-Butoxy)-2-oxoethyl]-2,3,9-trimethyl-6H-thieno[3,2-f][1,2,4]triazolo[4,3-a][1,4]diazepin-4-yl}benzoic acid (54 mg, 0.116 mmol) obtained in reference example 3 in the same manner as in step 1 of example 1a.
ESIMS, (M+H)+, m/z: 843. 1H NMR (CDCl3, δ): 1.10-1.18 (m, 6H), 1.25-1.35 (m, 1H), 1.50 (s, 9H), 1.97-2.10 (m, 2H), 2.19 (s, 3H), 2.30-2.46 (m, 4H), 2.52-2.73 (m, 5H), 3.45-3.59 (m, 6H), 4.16-4.28 (m, 1H), 4.37-4.44 (m, 1H), 4.56-4.64 (m, 1H), 4.83-5.01 (m, 1H), 6.51-6.66 (m, 2H), 6.99-7.10 (m, 1H), 7.10-7.23 (m, 3H), 7.50-7.59 (m, 2H), 7.67-7.77 (m, 2H), 7.84-7.98 (m, 3H).

Example 1i tert-Butyl 2-((S)-4-{4-[4-(4-{(S)-6-[2-(tert-butoxy)-2-oxoethyl]-2,3,9-trimethyl-6H-thieno[3,2-f][1,2,4]triazolo[4,3-a][1,4]diazepin-4-yl}benzamide)piperidine-1-carbonyl]phenyl}-2,3,9-trimethyl-6H-thieno[3,2-f][1,2,4]triazolo[4,3-a][1,4]diazepin-6-yl) acetate (Compound 1i)

(Step 1)

tert-Butyl 4-aminopiperidine-1-carboxylate (1.0 g, 5.0 mmol) was dissolved in dichloromethane (15 mL), then N,N-diisopropylethylamine (2.61 mL, 15 mmol) and benzyl chloroformate (0.78 mL, 5.5 mmol) were added to the solution under ice cooling. The mixture was stirred at room temperature for 2 hours. Water was added to the reaction mixture, and the mixture was extracted twice with ethyl acetate. The organic layer was dried over anhydrous sodium sulfate and concentrated under reduced pressure. The obtained residue was purified by silica gel column chromatography (petroleum ether/ethyl acetate=85/15 to 80/20) to give tert-butyl 4-{[(benzyloxy)carbonyl]amino}piperidine-1-carboxylate (1.17 g, 70%).
ESIMS, (M+H)+, m/z: 335.
(Step 2)

Benzylpiperidin-4-ylcarbamate (0.80 g, 85%) was obtained from tert-butyl 4-{[(benzyloxy)carbonyl]amino}piperidine-1-carboxylate (1.17 g, 3.50 mmol) obtained in step 1 in the same manner as in step 2 of example 1a.
ESIMS, (M+H)+, m/z: 235.
(Step 3)

tert-Butyl (S)-2-(4-[4-(4-{[(benzyloxy)carbonyl]amino}piperidine-1-carbonyl)phenyl]-2,3,9-trimethyl-6H-thieno[3,2-f][1,2,4]triazolo[4,3-a][1,4]diazepin-6-yl)acetate (105 mg, 72%) was obtained from benzylpiperidin-4-ylcarbamate (69 mg, 0.25 mmol) obtained in step 2 and (S)-4-{6-[2-(tert-butoxy)-2-oxoethyl]-2,3,9-trimethyl-6H-thieno[3,2-f][1,2,4]triazolo[4,3-a][1,4]diazepin-4-yl}benzoic acid (104 mg, 0.21 mmol) obtained in reference example 3 in the same manner as in step 1 of example 1a.
ESIMS, (M+H)+, m/z: 683.
(Step 4)

tert-Butyl (S)-2-(4-[4-(4-{[(benzyloxy)carbonyl]amino}piperidine-1-carbonyl)phenyl]-2,3,9-trimethyl-6H-thieno[3,2-f][1,2,4]triazolo[4,3-a][1,4]diazepin-6-yl)acetate (105 mg, 0.15 mmol) obtained in step 3 was dissolved in methanol (3.0 mL), then 20% palladium hydroxide (50 mg) was added to the solution, and the mixture was stirred at room temperature for 16 hours under a hydrogen atmosphere. The reaction mixture was filtered through Celite, and the filtrate was concentrated under reduced pressure. The obtained residue was slurry-refined with pentane to give tert-butyl (S)-2-{4-[4-(4-aminopiperidine-1-carbonyl)phenyl]-2,3,9-trimethyl-6H-thieno[3,2-f][1,2,4]triazolo[4,3-a][1,4]diazepin-6-yl}acetate (70 mg, 83%).
ESIMS, (M+H)+, m/z: 549.
(Step 5)

Compound 1i (80 mg, 42%) was obtained from tert-butyl (S)-2-{4-[4-(4-aminopiperidine-1-carbonyl)phenyl]-2,3,9-trimethyl-6H-thieno[3,2-f][1,2,4]triazolo[4,3-a][1,4]diazepin-6-yl}acetate (105 mg, 0.19 mmol) obtained in step 4 and (S)-4-{6-[2-(tert-butoxy)-2-oxoethyl]-2,3,9-trimethyl-6H-thieno[3,2-f][1,2,4]triazolo[4,3-a][1,4]diazepin-4-yl}benzoic acid (89 mg, 0.19 mmol) obtained in reference example 3 in the same manner as in step 1 of example 1a.
ESIMS, (M+H)+, m/z: 997. 1H NMR (DMSO-d6, δ): 1.44 (s, 19H), 1.58 (s, 4H), 1.66 (s, 3H), 1.75 (brs, 1H), 1.91 (brs, 1H), 2.36-2.42 (m, 6H), 2.60-2.64 (m, 6H), 2.95 (brs, 1H), 3.15-3.16 (m, 1H), 3.37 (m, 4H), 3.49-3.51 (m, 1H), 4.08 (brs, 1H), 4.44 (q, J=6.5 Hz, 3H), 7.42 (d, J=8.0 Hz, 2H), 7.49 (t, J=8.5 Hz, 4H), 7.87 (d, J=8.0 Hz, 2H), 8.39 (d, J=7.5 Hz, 1H).

Example 1j

N,N'-[(1r,3r)-Cyclobutane-1,3-diyl]bis(4-{[(2S,4R)-2-methyl-1-propionyl-1,2,3,4-tetrahydroquinolin-4-yl]amino}benzamide) (Compound 1j)

(Step 1)

tert-Butyl[(1R,3r)-3-(4-{[(2S,4R)-2-methyl-1-propionyl-1,2,3,4-tetrahydroquinolin-4-yl]amino}benzamide)cyclobutyl]carbamate (70 mg, 94%) was obtained from 4-{[(2S,4R)-2-methyl-1-propionyl-1,2,3,4-tetrahydroquinolin-4-yl]amino}benzoic acid (50 mg, 0.148 mmol) obtained in step 7 of reference example 1 and tert-butyl[(1r,3r)-3-aminocyclobutyl]carbamate (28 mg, 0.148 mmol) in the same manner as in step 3 of example 1b.
ESIMS, (M+H)+, m/z: 507.
(Step 2)

N-[(1r,3R)-3-Aminocyclobutyl]-4-{[(2S,4R)-2-methyl-1-propionyl-1,2,3,4-tetrahydroquinolin-4-yl]amino}benzamide hydrochloride (60 mg, 98%) was obtained from tert-butyl[(1R,3r)-3-(4-{[(2S,4R)-2-methyl-1-propionyl-1,2,3,4-tetrahydroquinolin-4-yl]amino}benzamide)cyclobutyl]carbamate (70 mg, 0.138 mmol) obtained in step 1 in the same manner as in step 2 of example 1a.
ESIMS, (M+H)+, m/z: 407.
(Step 3)

Compound 1j (25 mg, 28%) was obtained from N-[(1r,3R)-3-aminocyclobutyl]-4-{[(2S,4R)-2-methyl-1-propionyl-1,2,3,4-tetrahydroquinolin-4-yl]amino}benzamide hydrochloride (60 mg, 0.137 mmol) obtained in step 2 and 4-{[(2S,4R)-2-methyl-1-propionyl-1,2,3,4-tetrahydroquinolin-4-yl]amino}benzoic acid (42 mg, 0.124 mmol) obtained in step 7 of reference example 1 as in step 3 of example 1b.
ESIMS, (M+H)+, m/z: 727. 1H NMR (CDCl3, δ): 1.11-1.19 (m, 12H), 1.23-1.37 (m, 2H), 2.31-2.45 (m, 2H), 2.44-2.53 (m, 2H), 2.53-2.75 (m, 4H), 4.16-4.33 (m, 4H), 4.59-4.75 (m, 2H), 4.90-5.02 (m, 2H), 6.24-6.29 (m, 2H), 6.59-6.64 (m, 4H), 7.14-7.32 (m, 10H), 7.63-7.69 (m, 4H).

Example 1k 1,1'-{(2S,2'S,4R,4'R)-{[(2,5-Diazabicyclo[2.2.1]
heptane-2,5-dicarbonyl)bis(4,1-phenylene)]bis
(azanediyl)}bis[2-methyl-3,4-dihydroquinoline-4,1
(2H)-diyl]}bis(propan-1-one) (Compound 1k)

(Step 1)

tert-Butyl 5-(4-{[(2S,4R)-2-methyl-1-propionyl-1,2,3,4-tetrahydroquinolin-4-yl]amino}benzoyl)-2,5-diazabicyclo[2.2.1]heptane-2-carboxylate (38 mg, 49%) was obtained from 4-{[(2S,4R)-2-methyl-1-propionyl-1,2,3,4-tetrahydroquinolin-4-yl]amino}benzoic acid (50 mg, 0.148 mmol) obtained in step 7 of reference example 1 and tert-butyl 2,5-diazabicyclo[2.2.1]heptane-2-carboxylate (35.2 mg, 0.177 mmol) in the same manner as in step 1 of example 1d.
ESIMS, (M+H)$^+$, m/z: 519.

(Step 2)

tert-Butyl 5-(4-{[(2S,4R)-2-methyl-1-propionyl-1,2,3,4-tetrahydroquinolin-4-yl]amino}benzoyl)-2,5-diazabicyclo[2.2.1]heptane-2-carboxylate (38 mg, 0.073 mmol) obtained in step 1 was dissolved in dichloromethane (1 mL), then trifluoroacetic acid (1 mL) was added to the solution, and the mixture was stirred at room temperature for 1 hour. The reaction mixture was concentrated under reduced pressure to give a crude product of 1-[(2S,4R)-4-{[4-(2,5-diazabicyclo[2.2.1]heptane-2-carbonyl)phenyl]amino}-2-methyl-3,4-dihydroquinolin-1(2H)-yl]propan-1-one trifluoroacetate (38 mg).
ESIMS, (M+H)$^+$, m/z: 419.

(Step 3)

Compound 1k (17 mg, 32%) was obtained from the crude product (38 mg) of 1-[(2S,4R)-4-{[4-(2,5-diazabicyclo[2.2.1]heptane-2-carbonyl)phenyl]amino}-2-methyl-3,4-dihydroquinolin-1(2H)-yl]propan-1-one trifluoroacetate obtained in step 2 and 4-{[(2S,4R)-2-methyl-1-propionyl-1,2,3,4-tetrahydroquinolin-4-yl]amino}benzoic acid (50 mg, 0.148 mmol) obtained in step 7 of reference example 1 in the same manner as in step 1 of example 1d.
ESIMS, (M+H)$^+$, m/z: 739. $^1$H-NMR (CDCl$_3$, δ): 1.12-1.19 (m, 12H), 1.26-1.36 (m, 4H), 2.31-2.43 (m, 2H), 2.53-2.72 (m, 4H), 3.67-3.83 (m, 4H), 4.11-4.18 (m, 2H), 4.18-4.27 (m, 2H), 4.90-5.00 (m, 2H), 6.54-6.66 (m, 4H), 7.14-7.33 (m, 9H), 7.39-7.49 (m, 3H).

Example 1l

N,N'-(2-Oxopropane-1,3-diyl)bis(4-{[(2S,4R)-2-methyl-1-propionyl-1,2,3,4-tetrahydroquinolin-4-yl]amino}benzamide) (Compound 1l)

(Step 1)

N,N'-(2-Hydroxypropane-1,3-diyl)bis(4-{[(2S,4R)-2-methyl-1-propionyl-1,2,3,4-tetrahydroquinolin-4-yl]}benzamide) (200 mg, 19%) was obtained from 4-{[(2S,4R)-2-methyl-1-propionyl-1,2,3,4-tetrahydroquinolin-4-yl]amino}benzoic acid (500 mg, 1.47 mmol) obtained in step 7 of reference example 1 and 1,3-diaminopropan-2-ol (66 mg, 0.73 mmol) in the same manner as in step 1 of example 1a.
ESIMS, (M+H)$^+$, m/z: 731.

(Step 2)

N,N'-(2-Hydroxypropane-1,3-diyl)bis(4-{[(2S,4R)-2-methyl-1-propionyl-1,2,3,4-tetrahydroquinolin-4-yl]amino}benzamide) (50 mg, 0.068 mmol) obtained in step 1 was dissolved in dichloromethane (3 mL), then DMP (58 mg, 0.136 mmol) was added to the solution, and the mixture was stirred at 50° C. for 2 hours. Aqueous sodium hydrogen carbonate solution was added to the reaction mixture, and the mixture was extracted with dichloromethane. The organic layer was washed with water and saturated aqueous sodium chloride solution, dried over anhydrous sodium sulfate, and concentrated under reduced pressure. The obtained residue was purified by reverse phase HPLC (acetonitrile/10 mM aqueous ammonium bicarbonate solution=42/58) to give compound 1l (22 mg, 22%).
ESIMS, (M+H)$^+$, m/z: 729. $^1$H-NMR (DMSO-d$_6$, δ): 1.00-1.06 (m, 12H), 1.18-1.25 (m, 2H), 2.22-2.27 (m, 2H), 2.56-2.62 (m, 4H), 4.10 (d, J=5.49 Hz, 4H), 4.29 (t, J=11.60 Hz, 2H), 4.74 (d, J=6.71 Hz, 2H), 6.63-6.68 (m, 6H), 7.10 (d, J=7.63 Hz, 2H), 7.17 (t, J=7.32 Hz, 2H), 7.25-7.32 (m, 4H), 7.67 (d, J=8.54 Hz, 4H), 8.41 (t, J=5.49 Hz, 2H).

Example 1m

4-{[(2S,4R)-2-Methyl-1-propionyl-1,2,3,4-tetrahydroquinolin-4-yl]amino}-N-{1-[4-(2,3,9-trimethyl-6H-thieno[3,2-f][1,2,4]triazolo[4,3-a][1,4]diazepin-4-yl)benzoyl]piperidin-4-yl}benzamide (Compound 1m)

(Step 1)

tert-Butyl {1-[4-(2,3,9-trimethyl-6H-thieno[3,2-f][1,2,4]triazolo[4,3-a][1,4]diazepin-4-yl)benzoyl]piperidin-4-yl}carbamate (200 mg, 88%) was obtained from 4-(2,3,9-trimethyl-6H-thieno[3,2-f][1,2,4]triazolo[4,3-a][1,4]diazepin-4-yl)benzoic acid (150 mg, 0.420 mmol) obtained in reference example 4 and tert-butyl (piperidin-4-yl)carbamate (93 mg, 0.460 mmol) in the same manner as in step 1 of example 1d.
ESIMS, (M+H)$^+$, m/z: 535.

(Step 2)

A crude product (65 mg) of (4-aminopiperidin-1-yl)[4-(2,3,9-trimethyl-6H-thieno[3,2-f][1,2,4]triazolo[4,3-a][1,4]diazepin-4-yl)phenyl]methanone hydrochloride was obtained from tert-butyl {1-[4-(2,3,9-trimethyl-6H-thieno[3,2-f][1,2,4]triazolo[4,3-a][1,4]diazepin-4-yl)benzoyl]piperidin-4-yl}carbamate (110 mg, 0.200 mmol) obtained in step 1 in the same manner as in step 2 of example 1a.
ESIMS, (M+H)$^+$, m/z: 435.

(Step 3)

Compound 1m (25 mg, total yield of 2 steps 9%) was obtained from the crude product (196 mg) of (4-aminopiperidin-1-yl)[4-(2,3,9-trimethyl-6H-thieno[3,2-f][1,2,4]triazolo[4,3-a][1,4]diazepin-4-yl)phenyl]methanone hydrochloride obtained in step 2 and 4-{[(2S,4R)-2-methyl-1-propionyl-1,2,3,4-tetrahydroquinolin-4-yl]amino}benzoic acid (120 mg, 0.350 mmol) obtained in step 7 of reference example 1 in the same manner as in step 1 of example 1d.
ESIMS, (M+H)$^+$, m/z: 755. $^1$H-NMR (DMSO-d$_6$, δ): 0.99-1.05 (m, 6H), 1.17-1.24 (m, 1H), 1.40-1.51 (m, 2H), 1.64 (s, 3H), 1.71 (s, 1H), 1.86 (s, 1H), 2.25 (dd, J=15.72, 7.48 Hz, 1H), 2.41 (s, 3H), 2.51-2.64 (m, 5H), 2.95 (s, 1H), 3.14-3.17 (m, 1H), 3.49-3.50 (m, 1H), 4.03 (d, J=7.63 Hz, 1H), 4.18 (d, J=12.82 Hz, 1H), 4.24-4.29 (m, 1H), 4.42 (s, 1H), 4.74 (d, J=6.10 Hz, 1H), 5.27 (d, J=12.51 Hz, 1H), 6.57 (d, J=7.93 Hz, 1H), 6.64 (d, J=8.54 Hz, 2H), 7.08 (d, J=7.63 Hz, 1H), 7.16 (t, J=7.32 Hz, 1H), 7.20-7.32 (m, 2H), 7.40 (d, J=8.24 Hz, 2H), 7.54 (d, J=7.93 Hz, 2H), 7.63 (d, J=8.85 Hz, 2H), 7.85 (d, J=7.63 Hz, 1H).

Example 1n tert-Butyl 2-[(S)-2,3,9-trimethyl-4-(4-{[1-(4-{[(2S,4R)-2-methyl-1-propionyl-1,2,3,4-tetrahydroquinolin-4-yl]amino}benzoyl)azetidin-3-yl]carbamoyl}phenyl)-6H-thieno[3,2-f][1,2,4]triazolo[4,3-a][1,4]diazepin-6-yl]acetate (Compound 1n)

(Step 1)

tert-Butyl [1-(4-{[(2S,4R)-2-methyl-1-propionyl-1,2,3,4-tetrahydroquinolin-4-yl]amino}benzoyl)azetidin-3-yl]carbamate (170 mg, 81%) was obtained from 4-{[(2S,4R)-2-methyl-1-propionyl-1,2,3,4-tetrahydroquinolin-4-yl]amino}benzoic acid (150 mg, 0.440 mmol) obtained in step 7 of reference example 1 and tert-butyl (azetidin-3-yl)carbamate (76 mg, 0.440 mmol) in the same manner as in step 1 of example 1d.
ESIMS, (M+H)$^+$, m/z: 493.

(Step 2)

tert-Butyl [1-(4-{[(2S,4R)-2-methyl-1-propionyl-1,2,3,4-tetrahydroquinolin-4-yl]amino}benzoyl)azetidin-3-yl]carbamate (170 mg, 0.340 mmol) obtained in step 1 was dissolved in dichloromethane (6 mL), then trifluoroacetic acid (1 mL) was added to the solution, and the mixture was stirred at room temperature for 2 hours. The reaction mixture was concentrated under reduced pressure to give 1-[(2S,4R)-4-{[4-(3-aminoazetidine-1-carbonyl)phenyl]amino}-2-methyl-3,4-dihydroquinolin-1(2H)-yl]propan-1-one trifluoroacetate (150 mg, 89%).
ESIMS, (M+H)$^+$, m/z: 393.

(Step 3)

Compound 1n (69 mg, 39%) was obtained from 1-[(2S,4R)-4-{[4-(3-aminoazetidine-1-carbonyl)phenyl]amino}-2-methyl-3,4-dihydroquinolin-1(2H)-yl]propan-1-one trifluoroacetate (100 mg, 0.190 mmol) obtained in step 2 and (S)-4-{6-[2-(tert-butoxy)-2-oxoethyl]-2,3,9-trimethyl-6H-thieno[3,2-f][1,2,4]triazolo[4,3-a][1,4]diazepin-4-yl}benzoic acid (92 mg, 0.190 mmol) obtained in reference example 3 in the same manner as in step 1 of example 1d.
ESIMS, (M+H)$^+$, m/z: 841. $^1$H-NMR (DMSO-d$_6$, δ): 0.99-1.05 (m, 6H), 1.20-1.25 (m, 1H), 1.44 (s, 9H), 1.59 (s, 3H), 2.19-2.27 (m, 1H), 2.41 (s, 3H), 2.57-2.64 (m, 5H), 3.34-3.36 (m, 2H), 4.15 (s, 1H), 4.23-4.28 (m, 3H), 4.43 (t, J=1.5 Hz, 1H), 4.53-4.75 (m, 3H), 6.65 (d, J=2.5 Hz, 3H), 7.10 (d, J=7.32 Hz, 1H), 7.16-7.19 (m, 1H), 7.25-7.32 (m, 2H), 7.47-7.51 (m, 4H), 7.91 (d, J=8.85 Hz, 2H), 9.12 (d, J=7.02 Hz, 1H).

Example 1o tert-Butyl 2-[(S)-2,3,9-trimethyl-4-(4-{[2-(4-{[(2S,4R)-2-methyl-1-propionyl-1,2,3,4-tetrahydroquinolin-4-yl]amino}benzamide)ethyl]carbamoyl}phenyl)-6H-thieno[3,2-f][1,2,4]triazolo[4,3-a][1,4]diazepin-6-yl]acetate (Compound 1o)

(Step 1)

tert-Butyl (S)-2-(4-{4-[(2-{[(benzyloxy)carbonyl]amino}ethyl)carbamoyl]phenyl}-2,3,9-trimethyl-6H-thieno[3,2-f][1,2,4]triazolo[4,3-a][1,4]diazepin-6-yl)acetate (290 mg, 70%) was obtained from (S)-4-{6-[2-(tert-butoxy)-2-oxoethyl]-2,3,9-trimethyl-6H-thieno[3,2-f][1,2,4]triazolo[4,3-a][1,4]diazepin-4-yl}benzoic acid (300 mg, 0.64 mmol) obtained in reference example 3 and benzyl (2-aminoethyl)carbamate (249 mg, 1.29 mmol) in the same manner as in step 3 of example 1b.
ESIMS, (M+H)$^+$, m/z: 643.

(Step 2)

tert-Butyl (S)-2-(4-{4-[(2-aminoethyl)carbamoyl]phenyl}-2,3,9-trimethyl-6H-thieno[3,2-f][1,2,4]triazolo[4,3-a][1,4]diazepin-6-yl)acetate (200 mg, 87%) was obtained from tert-butyl (S)-2-(4-{4-[(2-{[(benzyloxy)carbonyl]amino}ethyl)carbamoyl]phenyl}-2,3,9-trimethyl-6H-thieno[3,2-f][1,2,4]triazolo[4,3-a][1,4]diazepin-6-yl)acetate (290 mg, 0.45 mmol) obtained in step 1 in the same manner as in step 4 of example 1i.
ESIMS, (M+H)$^+$, m/z: 509.

(Step 3)

Compound 1o (220 mg, 67%) was obtained from tert-butyl (S)-2-(4-{4-[(2-aminoethyl)carbamoyl]phenyl}-2,3,9-trimethyl-6H-thieno[3,2-f][1,2,4]triazolo[4,3-a][1,4]diazepin-6-yl)acetate (200 mg, 0.39 mmol) obtained in step 2 and 4-{[(2S,4R)-2-methyl-1-propionyl-1,2,3,4-tetrahydroquinolin-4-yl]amino}benzoic acid (133 mg, 0.39 mmol) obtained in step 7 of reference example 1 in the same manner as in step 3 of example 1b.
ESIMS, (M+H)$^+$, m/z: 829. $^1$H-NMR (DMSO-d$_6$, δ): 0.99-1.06 (m, 6H), 1.17-1.26 (m, 1H), 1.43 (s, 9H), 1.59 (s, 3H), 2.22-2.28 (m, 1H), 2.41 (s, 3H), 2.57-2.64 (m, 5H), 3.24-3.28 (m, 2H), 3.40 (s, 4H), 4.27 (m, 1H), 4.44 (t, J=7.2 Hz, 1H), 4.73-4.74 (m, 1H), 6.58 (d, J=8.0 Hz, 1H), 6.65 (d, J=8.5 Hz, 2H), 7.08 (d, J=7.5 Hz, 1H), 7.16 (t, J=7.5 Hz, 1H), 7.25-7.32 (m, 2H), 7.48 (d, J=8.0 Hz, 2H), 7.63 (d, J=8.5 Hz, 2H), 7.88 (d, J=8.0 Hz, 2H), 8.21 (brs, 1H), 8.68 (brs, 1H).

Example 2a

4-{[(2S*,4R*)-2-Methyl-1-propionyl-1,2,3,4-tetrahydroquinolin-4-yl]amino}-N-{2-[(4-{[(2S*,4R*)-2-methyl-1-propionyl-1,2,3,4-tetrahydroquinolin-4-yl]amino}phenyl)amino]-2-oxoethyl}benzamide (Compound 2a)

(Step 1)

A crude product (263 mg) of (9H-fluoren-9-yl)methyl{2-[(4-{[(2S*,4R*)-2-methyl-1-propionyl-1,2,3,4-tetrahydroquinolin-4-yl]amino}phenyl)amino]-2-oxoethyl}carbamate was obtained from 1-{(2S*,4R*)-4-[(4-aminophenyl)amino]-2-methyl-3,4-dihydroquinolin-1(2H)-yl}propan-1-one (100 mg, 0.323 mmol obtained in step 2 of reference example 7 and {[(9H-fluoren-9-yl)methoxy]carbonyl}glycine (144 mg, 0.485 mmol) in the same manner as in step 1 of example 1a.
ESIMS, (M+H)$^+$, m/z: 589.

(Step 2)

The crude product (263 mg) of (9H-fluoren-9-yl)methyl{2-[(4-{[(2S*,4R*)-2-methyl-1-propionyl-1,2,3,4-tetrahydroquinolin-4-yl]amino}phenyl)amino]-2-oxoethyl}carbamate obtained in step 1 was dissolved in DMF (1.6 mL), then piperidine (0.160 mL, 1.62 mmol) was added to the solution, and the mixture was stirred at room temperature overnight. Water was added to the reaction mixture, then the reaction mixture was filtered, and the filtrate was extracted twice with ethyl acetate. The organic layer was washed with saturated aqueous sodium chloride solution, dried over anhydrous sodium sulfate, and concentrated under reduced pressure. The obtained residue was purified by silica gel chromatography (chloroform/methanol=10/0 to 9/1) to give 2-amino-N-(4-{[(2S*,4R*)-2-methyl-1-propionyl-1,2,3,4-tetrahydroquinolin-4-yl]amino}phenyl)acetamide (50.7 mg, total yield of 2 steps 43%).
ESIMS, (M+H)$^+$, m/z: 367.

(Step 3)

Compound 2a (3.2 mg, 9%) was obtained from 2-amino-N-(4-{[(2S*,4R*)-2-methyl-1-propionyl-1,2,3,4-tetrahydroquinolin-4-yl]amino}phenyl)acetamide (19.5 mg, 0.053 mmol) obtained in step 2 and 4-{[(2S*,4R*)-2-methyl-1-propionyl-1,2,3,4-tetrahydroquinolin-4-yl]amino}benzoic acid (21.4 mg, 0.063 mmol) obtained in step 6 of reference example 1 in the same manner as in step 1 of example 1a. ESIMS, (M+H)$^+$, m/z: 687 $^1$H-NMR (CDCl$_3$, δ): 1.10-1.20 (m, 12H), 1.24-1.33 (m, 2H), 2.31-2.44 (m, 2H), 2.51-2.73 (m, 4H), 4.10-4.19 (m, 2H), 4.21-4.30 (m, 4H), 4.88-5.00 (m, 2H), 5.32-5.37 (m, 1H), 6.59 (d, J=9.0 Hz, 2H), 6.63 (d, J=8.5 Hz, 2H), 7.13-7.30 (m, 8H), 7.33 (d, J=9.0 Hz, 2H), 7.71 (d, J=9.0 Hz, 2H).

Example 2b tert-Butyl 2-[(S)-4-{4-[2-(4-{(S)-6-[2-(tert-butoxy)-2-oxoethyl]-2,3,9-trimethyl-6H-thieno[3,2-f][1,2,4]triazolo[4,3-a][1,4]diazepin-4-yl}benzamide)acetamide]phenyl}-2,3,9-trimethyl-6H-thieno[3,2,4]triazolo[4,3-a][1,4]diazepin-6-yl]acetate (Compound 2b)

(Step 1)

(S)-4-{6-[2-(tert-Butoxy)-2-oxoethyl]-2,3,9-trimethyl-6H-thieno[3,2-f][1,2,4]triazolo[4,3-a][1,4]diazepin-4-yl}benzoic acid (200 mg, 0.430 mmol) obtained in reference example 3 was dissolved in toluene (10 mL), then DPPA (124 mg, 0.450 mmol) and triethylamine (104 mg, 1.03 mmol) were added to the solution, and the mixture was stirred at room temperature for 3 hours. Water (3 mL) was added to the reaction mixture, and the mixture was stirred at 70° C. for 2 hours. The reaction mixture was cooled to room temperature, diluted with ethyl acetate, dried over anhydrous sodium sulfate, and concentrated under reduced pressure. The obtained residue was purified by reverse phase HPLC (acetonitrile/10 mmol/L aqueous ammonium bicarbonate solution=42/58) to give tert-butyl (S)-2-{4-(4-aminophenyl)-2,3,9-trimethyl-6H-thieno[3,2-f][1,2,4]triazolo[4,3-a][1,4]diazepin-6-yl}acetate (45 mg, 22%).
ESIMS, (M+H)$^+$, m/z: 438.
(Step 2)

tert-Butyl (S)-2-{4-[4-(2-{[(benzyloxy)carbonyl]amino}acetamide)phenyl]-2,3,9-trimethyl-6H-thieno[3,2-f][1,2,4]triazolo[4,3-a][1,4]diazepin-6-yl}acetate (70 mg, 74%) was obtained from tert-butyl (S)-2-{4-(4-aminophenyl)-2,3,9-trimethyl-6H-thieno[3,2-f][1,2,4]triazolo[4,3-a][1,4]diazepin-6-yl}acetate (60 mg, 0.140 mmol) obtained in step 1, and 2-{[(benzyloxy)carbonyl]amino}acetic acid (34.4 mg, 0.160 mmol) in the same manner as in step 1 of example 1a.
ESIMS, (M+H)$^+$, m/z: 629.
(Step 3)
tert-Butyl (S)-2-{4-[4-(2-{[(benzyloxy)carbonyl]amino}acetamide)phenyl]-2,3,9-trimethyl-6H-thieno[3,2-f][1,2,4]triazolo[4,3-a][1,4]diazepin-6-yl}acetate (70 mg, 0.110 mmol) obtained in step 2 was dissolved in methanol (20 mL), then palladium on carbon (70 mg, 10 wt %) was added to the solution, and the mixture was stirred overnight at room temperature under a hydrogen atmosphere. The reaction mixture was filtered, and the filtrate was concentrated under reduced pressure to give tert-butyl (S)-2-{4-[4-(2-aminoacetamide)phenyl]-2,3,9-trimethyl-6H-thieno[3,2-f][1,2,4]triazolo[4,3-a][1,4]diazepin-6-yl}acetate (50 mg, 84%). ESIMS, (M+H)$^+$, m/z: 495.

(Step 4)

Compound 2b (17 mg, 17%) was obtained from tert-butyl (S)-2-{4-[4-(2-aminoacetamide)phenyl]-2,3,9-trimethyl-6H-thieno[3,2-f][1,2,4]triazolo[4,3-a][1,4]diazepin-6-yl}acetate (53 mg, 0.110 mmol) obtained in step 3 and (S)-4-{6-[2-(tert-butoxy)-2-oxoethyl]-2,3,9-trimethyl-6H-thieno[3,2-f][1,2,4]triazolo[4,3-a][1,4]diazepin-4-yl}benzoic acid (50 mg, 0.110 mmol) obtained in reference example 3 in the same manner as in step 1 of example 1a.
ESIMS, (M+H)$^+$, m/z: 943. $^1$H-NMR (CD$_3$OD, δ): 1.53 (s, 18H), 1.73 (d, J=8.8 Hz, 6H), 2.48 (s, 6H), 2.80-2.70 (m, 6H), 3.52-3.40 (m, 4H), 4.22 (s, 2H), 4.64-4.51 (m, 2H), 7.44 (d, J=8.8 Hz, 2H), 7.60 (d, J=8.4 Hz, 2H), 7.67 (d, J=9.2 Hz, 2H), 7.94 (d, J=8.4 Hz, 2H).

Example 2c

4-{[(2S,4R)-2-Methyl-1-propionyl-1,2,3,4-tetrahydroquinolin-4-yl]amino}-N—{(R)-1-[(4-{[(2S*,4R*)-2-methyl-1-propionyl-1,2,3,4-tetrahydroquinolin-4-yl]amino}phenyl)amino]-1-oxopropan-2-yl}benzamide (Compound 2c)

(Step 1)

tert-Butyl {(R)-1-[(4-{[(2S*,4R*)-2-methyl-1-propionyl-1,2,3,4-tetrahydroquinolin-4-yl]amino}phenyl)amino]-1-oxopropan-2-yl}carbamate (160 mg, 68%) was obtained from 1-{(2S*,4R*)-4-[(4-aminophenyl)amino]-2-methyl-3,4-dihydroquinolin-1(2H)-yl}propan-1-one (150 mg, 0.480 mmol) obtained in step 2 of reference example 7, and (tert-butoxycarbonyl)-D-alanine (92 mg, 0.480 mmol) in the same manner as in step 1 of example 1d.
ESIMS, (M+H)$^+$, m/z: 481.
(Step 2)

(R)-2-Amino-N-(4-{[(2S*,4R*)-2-methyl-1-propionyl-1,2,3,4-tetrahydroquinolin-4-yl]amino}phenyl)propanamide hydrochloride (160 mg, 92%) was obtained from tert-butyl {(R)-1-[(4-{[(2S*,4R*)-2-methyl-1-propionyl-1,2,3,4-tetrahydroquinolin-4-yl]amino}phenyl)amino]-1-oxopropan-2-yl}carbamate (200 mg, 0.410 mmol) obtained in step 1 in the same manner as in step 2 of example 1a.
ESIMS, (M+H)$^+$, m/z: 381.
(Step 3)

Compound 2c (86 mg, 32%) was obtained from (R)-2-amino-N-(4-{[(2S*,4R*)-2-methyl-1-propionyl-1,2,3,4-tetrahydroquinolin-4-yl]amino}phenyl)propanamide hydrochloride (160 mg, 0.380 mmol) obtained in step 2 and 4-{[(2S,4R)-2-methyl-1-propionyl-1,2,3,4-tetrahydroquinolin-4-yl]amino}benzoic acid (130 mg, 0.380 mmol) obtained in step 7 of reference example 1 in the same manner as in step 1 of example 1d.
ESIMS, (M+H)$^+$, m/z: 701. $^1$H-NMR (DMSO-d$_6$, δ): 0.98-1.06 (m, 12H), 1.11-1.23 (m, 2H), 1.37 (d, J=7.2 Hz, 3H), 2.20-2.33 (m, 2H), 2.55-2.67 (m, 4H), 4.12 (brs, 1H), 4.26-4.28 (m, 1H), 4.53 (t, J=7.2 Hz, 1H), 4.71-4.73 (m, 2H), 5.86 (d, J=8.0 Hz, 1H), 6.57-6.67 (m, 5H), 7.09-7.18 (m, 4H), 7.23-7.32 (m, 6H), 7.70 (d, J=8.8 Hz, 2H), 8.04 (d, J=7.6 Hz, 1H), 9.59 (s, 1H)

Example 2d

4-{[(2S,4R)-2-Methyl-1-propionyl-1,2,3,4-tetrahydroquinolin-4-yl]amino}-N—{(S)-1-[(4-{[(2S*,4R*)-2-methyl-1-propionyl-1,2,3,4-tetrahydroquinolin-4-yl]amino}phenyl)amino]-1-oxopropan-2-yl}benzamide (Compound 2d)

(Step 1)
tert-Butyl {(S)-1-[(4-{[(2S*,4R*)-2-methyl-1-propionyl-1,2,3,4-tetrahydroquinolin-4-yl]amino}phenyl)amino]-1-oxopropan-2-yl}carbamate (155 mg, 67%) was obtained from 1-{(2S*,4R*)-4-[(4-aminophenyl)amino]-2-methyl-3,4-dihydroquinolin-1(2H)-yl}propan-1-one (150 mg, 0.480 mmol) obtained in step 2 of reference example 7, and (tert-butoxycarbonyl)-L-alanine (92 mg, 0.480 mmol) in the same manner as in step 1 of example 1d.
ESIMS, (M+H)$^+$, m/z: 481.
(Step 2)
(S)-2-Amino-N-(4-{[(2S*,4R*)-2-methyl-1-propionyl-1,2,3,4-tetrahydroquinolin-4-yl]amino}phenyl)propanamide hydrochloride (120 mg, 90%) was obtained from tert-butyl {(S)-1-[(4-{[(2S*,4R*)-2-methyl-1-propionyl-1,2,3,4-tetrahydroquinolin-4-yl]amino}phenyl)amino]-1-oxopropan-2-yl}carbamate (155 mg, 0.320 mmol) obtained in step 1 in the same manner as in step 2 of example 1a.
ESIMS, (M+H)$^+$, m/z: 381.
(Step 3)
Compound 2d (55 mg, 27%) was obtained from (S)-2-amino-N-(4-{[(2S*,4R*)-2-methyl-1-propionyl-1,2,3,4-tetrahydroquinolin-4-yl]amino}phenyl)propanamide hydrochloride (120 mg, 0.310 mmol) obtained in step 2 and 4-{[(2S,4R)-2-methyl-1-propionyl-1,2,3,4-tetrahydroquinolin-4-yl]amino}benzoic acid (106 mg, 0.310 mmol) obtained in step 7 of reference example 1 in the same manner as in step 1 of example 1d.
ESIMS, (M+H)$^+$, m/z: 701. $^1$H-NMR (DMSO-d$_6$, δ): 0.98-1.06 (m, 12H), 1.14-1.24 (m, 2H), 1.35 (d, J=7.6 Hz, 3H), 2.20-2.28 (m, 2H), 2.55-2.64 (m, 4H), 4.08-4.12 (m, 1H), 4.26-4.31 (m, 1H), 4.54 (t, J=7.0 Hz, 1H), 4.71-4.75 (m, 2H), 5.85 (d, J=8.0 Hz, 1H), 6.56-6.60 (m, 3H), 6.66 (d, J=8.8 Hz, 2H), 7.09-7.18 (m, 4H), 7.24-7.32 (m, 6H), 7.71 (d, J=8.0 Hz, 2H), 8.04 (d, J=7.2 Hz, 1H), 9.58 (s, 1H)

Example 2e

N—{(S)-3-Methyl-1-[(4-{[(2S*,4R*)-2-methyl-1-propionyl-1,2,3,4-tetrahydroquinolin-4-yl]amino}phenyl)amino]-1-oxobutan-2-yl}-4-{[(2S,4R)-2-methyl-1-propionyl-1,2,3,4-tetrahydroquinolin-4-yl]amino}benzamide (Compound 2e)

(Step 1)
tert-Butyl {(S)-3-methyl-1-[(4-{[(2S*,4R*)-2-methyl-1-propionyl-1,2,3,4-tetrahydroquinolin-4-yl]amino}phenyl)amino]-1-oxobutan-2-yl}carbamate (160 mg, 67%) was obtained from 1-{(2S*,4R*)-4-[(4-aminophenyl)amino]-2-methyl-3,4-dihydroquinolin-1(2H)-yl}propan-1-one (150 mg, 0.480 mmol) obtained in step 2 of reference example 7 and (tert-butoxycarbonyl)-L-valine (105 mg, 0.480 mmol) in the same manner as in step 1 of example 1d.
ESIMS, (M+H)$^+$, m/z: 509.
(Step 2)
(S)-2-Amino-3-methyl-N-(4-{[(2S*,4R*)-2-methyl-1-propionyl-1,2,3,4-tetrahydroquinolin-4-yl]amino}phenyl)butanamide hydrochloride (125 mg, 92%) was obtained from tert-butyl {(S)-3-methyl-1-[(4-{[(2S*,4R*)-2-methyl-1-propionyl-1,2,3,4-tetrahydroquinolin-4-yl]amino}phenyl)amino]-1-oxobutan-2-yl}carbamate (160 mg, 0.314 mmol) obtained in step 1 in the same manner as in step 2 of example 1a.
ESIMS, (M+H)$^+$, m/z: 409.
(Step 3)
Compound 2e (55 mg, 27%) was obtained from (S)-2-amino-3-methyl-N-(4-{[(2S*,4R*)-2-methyl-1-propionyl-1,2,3,4-tetrahydroquinolin-4-yl]amino}phenyl)butanamide hydrochloride (125 mg, 0.280 mmol) obtained in step 2 and 4-{[(2S,4R)-2-methyl-1-propionyl-1,2,3,4-tetrahydroquinolin-4-yl]amino}benzoic acid (95 mg, 0.280 mmol) obtained in step 7 of reference example 1 in the same manner as in step 1 of example 1d.
ESIMS, (M−H)$^−$, m/z: 727. $^1$H-NMR (DMSO-d$_6$, δ): 0.93-1.06 (m, 18H), 1.11-1.26 (m, 2H), 2.13-2.28 (m, 3H), 2.56-2.63 (m, 4H), 4.11-4.23 (m, 1H), 4.27-4.36 (m, 2H), 4.71-4.75 (m, 2H), 5.86 (d, J=8.0 Hz, 1H), 6.58-6.67 (m, 4H), 7.08-7.18 (m, 4H), 7.25-7.33 (m, 5H), 7.70 (d, J=8.4 Hz, 2H), 7.81 (d, J=8.8 Hz, 1H), 9.70 (s, 1H).

Example 2f

4-{[(2S,4R)-2-Methyl-1-propionyl-1,2,3,4-tetrahydroquinolin-4-yl]amino}-N-{3-[(4-{[(2S*,4R*)-2-methyl-1-propionyl-1,2,3,4-tetrahydroquinolin-4-yl]amino}phenyl)amino]-3-oxopropyl}benzamide (Compound 2f)

(Step 1)
Ethyl 3-(4-{[(2S,4R)-2-methyl-1-propionyl-1,2,3,4-tetrahydroquinolin-4-yl]amino}benzamide)propanoate (150 mg, 77%) was obtained from 4-{[(2S,4R)-2-methyl-1-propionyl-1,2,3,4-tetrahydroquinolin-4-yl]amino}benzoic acid (150 mg, 0.44 mmol) obtained in step 7 of reference example 1 and ethyl 3-aminopropanoate hydrochloride (0.102 g, 0.66 mmol) in the same manner as in step 1 of example 1a.
ESIMS, (M+H)$^+$, m/z: 438.
(Step 2)
Ethyl 3-(4-{[(2S,4R)-2-methyl-1-propionyl-1,2,3,4-tetrahydroquinolin-4-yl]amino}benzamide)propanoate (150 mg, 0.34 mmol) obtained in step 1 was dissolved in a mixed solvent (5.0 mL) of THF and water (4:1), then lithium hydroxide monohydrate (0.029 g, 0.69 mmol) was added to the solution, and the mixture was stirred at room temperature for 3 hours. The reaction mixture was concentrated under reduced pressure, then the obtained residue was diluted with ice water, and an aqueous citric acid solution was added at 0° C. until the diluted residue became acidic. The precipitated solid was collected by filtration and dried under reduced pressure to give a crude product of 3-(4-{[(2S,4R)-2-methyl-1-propionyl-1,2,3,4-tetrahydroquinolin-4-yl)amino]benzamide}propanoic acid (100 mg).
ESIMS, (M+H)$^+$, m/z: 410.
(Step 3)
Compound 2f (65 mg, total yield of 2 steps 27%) was obtained from the crude product (100 mg, 0.24 mmol) of 3-(4-{[(2S,4R)-2-methyl-1-propionyl-1,2,3,4-tetrahydroquinolin-4-yl)amino]benzamide}propanoic acid obtained in step 2 and 1-{(2S*,4R*)-4-[(4-aminophenyl)amino]-2-methyl-3,4-dihydroquinolin-1(2H)-yl}propan-1-one (75.0 mg, 0.24 mmol) obtained in step 2 of reference example 7 in the same manner as in step 1 of example 1a.
ESIMS, (M+H)$^+$, m/z: 701. $^1$H-NMR (DMSO-d$_6$, δ): 1.01-1.05 (m, 12H), 1.13-1.24 (m, 2H), 2.21-2.23 (m, 2H), 2.56-2.62 (m, 6H), 3.48 (q, J=6.5 Hz, 2H), 4.09-4.12 (m, 1H), 4.25-4.26 (m, 1H), 4.72-4.74 (m, 2H), 5.87 (d, J=8.0 Hz, 1H), 6.56-6.65 (m, 5H), 7.09 (d, J=7.5 Hz, 1H), 7.15-7.18 (m, 3H), 7.23-7.31 (m, 6H), 7.63 (d, J=8.5 Hz, 2H), 8.14 (t, J=5.3 Hz, 1H), 9.59 (s, 1H).

Example 2g 1-(4-{[(2S,4R)-2-Methyl-1-propionyl-1,2,3,4-tetrahydroquinolin-4-yl]amino}benzoyl)-N-(4-{[(2S*, 4R*)-2-methyl-1-propionyl-1,2,3,4-tetrahydroquinolin-4-yl]amino}phenyl)piperidine-4-carboxamide (Compound 2g)

(Step 1)

A crude product (0.12 g) of tert-butyl 4-[(4-{[(2S*,4R*)-2-methyl-1-propionyl-1,2,3,4-tetrahydroquinolin-4-yl]amino}phenyl)carbamoyl]piperidine-1-carboxylate was obtained from 1-{(2S*,4R*)-4-[(4-aminophenyl)amino]-2-methyl-3,4-dihydroquinolin-1(2H)-yl}propan-1-one (0.1 g, 0.32 mmol) obtained in step 2 of reference example 7 and 1-(tert-butoxycarbonyl)piperidine-4-carboxylic acid (0.074 g, 0.32 mmol) in the same manner as in step 3 of example 1b.

ESIMS, (M+H)$^+$, m/z: 521.

(Step 2)

A crude product (0.15 g) of N-(4-{[(2S*,4R*)-2-methyl-1-propionyl-1,2,3,4-tetrahydroquinolin-4-yl]amino}phenyl)piperidine-4-carboxamide hydrochloride was obtained from the crude product (0.17 g, 0.32 mmol) of tert-butyl 4-[(4-{[(2S*,4R*)-2-methyl-1-propionyl-1,2,3,4-tetrahydroquinolin-4-yl]amino}phenyl)carbamoyl]piperidine-1-carboxylate obtained in step 1 in the same manner as in step 2 of example 1a.

ESIMS, (M+H)$^+$, m/z: 421.

(Step 3)

Compound 2g (0.032 g, total yield of 3 steps 9%) was obtained from the crude product (0.15 g, 0.32 mmol) of N-(4-{[(2S*,4R*)-2-methyl-1-propionyl-1,2,3,4-tetrahydroquinolin-4-yl]amino}phenyl)piperidine-4-carboxamide hydrochloride obtained in step 2 and 4-{[(2S,4R)-2-methyl-1-propionyl-1,2,3,4-tetrahydroquinolin-4-yl]amino}benzoic acid (0.11 g, 0.32 mmol) obtained in step 7 of reference example 1 in the same manner as in step 1 of example 1a.

ESIMS, (M+H)$^+$, m/z: 741.61. $^1$H-NMR (DMSO-d$_6$, δ): 0.99-1.05 (m, 12H), 1.13-1.24 (m, 2H), 1.55-1.57 (m, 2H), 1.77 (d, J=11.60 Hz, 2H), 2.21-2.25 (m, 2H), 2.53-2.62 (m, 5H), 2.92 (s, 2H), 4.09-4.22 (m, 4H), 4.73 (t, J=7.25 Hz, 2H), 5.87 (d, J=7.93 Hz, 1H), 6.49 (d, J=7.63 Hz, 1H), 6.58 (d, J=8.54 Hz, 2H), 6.66 (d, J=8.24 Hz, 2H), 7.14-7.31 (m, 12H), 9.54 (s, 1H).

Example 2h 1-(4-{[(2S,4R)-2-Methyl-1-propionyl-1,2,3,4-tetrahydroquinolin-4-yl]amino}benzoyl)-N-(4-{[(2S*, 4R*)-2-methyl-1-propionyl-1,2,3,4-tetrahydroquinolin-4-yl]amino}phenyl)azetidine-3-carboxamide (Compound 2h)

(Step 1)

A crude product (0.12 g, 75%) of tert-butyl 3-[(4-{[(2S*,4R*)-2-methyl-1-propionyl-1,2,3,4-tetrahydroquinolin-4-yl]amino}phenyl)carbamoyl]azetidine-1-carboxylate was obtained from 1-{(2S*,4R*)-4-[(4-aminophenyl)amino]-2-methyl-3,4-dihydroquinolin-1(2H)-yl}propan-1-one (0.1 g, 0.32 mmol) obtained in step 2 of reference example 7 and 1-(tert-butoxycarbonyl)azetidine-3-carboxylic acid (0.065 g, 0.32 mmol) in the same manner as in step 3 of example 1b.

ESIMS, (M+H)$^+$, m/z: 493.

(Step 2)

A crude product (0.1 g) of N-(4-{[(2S*,4R*)-2-methyl-1-propionyl-1,2,3,4-tetrahydroquinolin-4-yl]amino}phenyl)azetidine-3-carboxamide hydrochloride was obtained from the crude product (0.12 g, 0.24 mmol) of tert-butyl 3-[(4-{[(2S*,4R*)-2-methyl-1-propionyl-1,2,3,4-tetrahydroquinolin-4-yl]amino}phenyl)carbamoyl]azetidine-1-carboxylate obtained in step 1 in the same manner as in step 2 of example 1a.

ESIMS, (M+H)$^+$, m/z: 393.

(Step 3)

Compound 2h (0.03 g, total yield of 3 steps 18%) was obtained from the crude product (0.1 g, 0.23 mmol) of N-(4-{[(2S*,4R*)-2-methyl-1-propionyl-1,2,3,4-tetrahydroquinolin-4-yl]amino}phenyl)azetidine-3-carboxamide hydrochloride obtained in step 2 and 4-{[(2S,4R)-2-methyl-1-propionyl-1,2,3,4-tetrahydroquinolin-4-yl]amino}benzoic acid (0.078 g, 0.23 mmol) obtained in step 7 of reference example 1 were used in the same manner as in step 3 of example 1b.

ESIMS, (M+H)$^+$, m/z: 713.53. $^1$H-NMR (DMSO-d$_6$, δ): 1.00-1.05 (m, 12H), 1.14-1.22 (m, 2H), 2.21-2.24 (m, 2H), 2.59 (d, J=8.5 Hz, 4H), 3.50 (s, 1H), 4.06-4.12 (m, 3H), 4.26-4.45 (m, 3H), 4.73 (s, 2H), 5.91 (d, J=7.63 Hz, 1H), 6.59-6.67 (m, 5H), 7.01-7.19 (m, 4H), 7.26-7.32 (m, 6H), 7.45 (d, J=8.54 Hz, 2H), 9.70 (s, 1H)

Example 2i (R)-1-(4-{[(2S,4R)-2-Methyl-1-propionyl-1,2,3,4-tetrahydroquinolin-4-yl]amino}benzoyl)-N-(4-{[(2S*,4R*)-2-methyl-1-propionyl-1,2,3,4-tetrahydroquinolin-4-yl]amino}phenyl)pyrrolidine-3-carboxamide (Compound 2i)

(Step 1)

tert-Butyl (R)-3-[(4-{[(2S*,4R*)-2-methyl-1-propionyl-1,2,3,4-tetrahydroquinolin-4-yl]amino}phenyl)carbamoyl]pyrrolidine-1-carboxylate (55 mg, 84%) was obtained from 1-{(2S*,4R*)-4-[(4-aminophenyl)amino]-2-methyl-3,4-dihydroquinolin-1(2H)-yl}propan-1-one (40 mg, 0.129 mmol) obtained in step 2 of reference example 7 and (R)-1-(tert-butoxycarbonyl)pyrrolidine-3-carboxylic acid (28 mg, 0.129 mmol) in the same manner as in step 3 of example 1b.

ESIMS, (M+H)$^+$, m/z: 507.

(Step 2)

(R)—N-(4-{[(2S*,4R*)-2-Methyl-1-propionyl-1,2,3,4-tetrahydroquinolin-4-yl]amino}phenyl)pyrrolidine-3-carboxamide hydrochloride (57 mg, 100%) was obtained from tert-butyl (R)-3-[(4-{[(2S*,4R*)-2-methyl-1-propionyl-1,2,3,4-tetrahydroquinolin-4-yl]amino}phenyl)carbamoyl]pyrrolidine-1-carboxylate (65 mg, 0.128 mmol) obtained in step 1 in the same manner as in step 2 of example 1a.

ESIMS, (M+H)$^+$, m/z: 407.

(Step 3)

Compound 2i (25 mg, 28%) was obtained from (R)—N-(4-{[(2S*,4R*)-2-methyl-1-propionyl-1,2,3,4-tetrahydroquinolin-4-yl]amino}phenyl)pyrrolidine-3-carboxamide hydrochloride (55 mg, 0.124 mmol) obtained in step 2 and 4-{[(2S,4R)-2-methyl-1-propionyl-1,2,3,4-tetrahydroquinolin-4-yl]amino}benzoic acid (42 mg, 0.124 mmol) obtained in step 7 of reference example 1 in the same manner as in step 3 of example 1b.

249

ESIMS, (M+H)$^+$, m/z: 727. $^1$H-NMR (CDCl$_3$, δ): 1.07-1.20 (m, 12H), 1.20-1.33 (m, 2H), 2.32-2.44 (m, 3H), 2.50-2.68 (m, 4H), 2.86-3.14 (m, 1H), 3.36-3.66 (m, 4H), 3.72-3.92 (m, 2H), 4.07-4.25 (m, 2H), 4.82-5.02 (m, 2H), 6.52-6.66 (m, 4H), 7.11-7.49 (m, 13H), 7.99-8.19 (m, 1H).

Example 2j 3-(4-{[(2S,4R)-2-Methyl-1-propionyl-1,2,3,4-tetrahydroquinolin-4-yl]amino}benzamide)-N-(4-{[(2S*, 4R*)-2-methyl-1-propionyl-1,2,3,4-tetrahydroquinolin-4-yl]amino}phenyl)benzamide (Compound 2j)

(Step 1)

A crude product (0.12 g) of methyl 3-(4-{[(2S,4R)-2-methyl-1-propionyl-1,2,3,4-tetrahydroquinolin-4-yl]amino}benzamide)benzoate was obtained from 4-{[(2S,4R)-2-methyl-1-propionyl-1,2,3,4-tetrahydroquinolin-4-yl]amino}benzoic acid (0.1 g, 0.29 mmol) obtained in step 7 of reference example 1 and methyl 3-aminobenzoate (0.045 g, 0.29 mmol) in the same manner as in step 1 of example 1a. ESIMS, (M+H)$^+$, m/z: 472.

(Step 2)

3-(4-{[(2S,4R)-2-Methyl-1-propionyl-1,2,3,4-tetrahydroquinolin-4-yl]amino}benzamide)benzoic acid (0.1 g, 87%) was obtained from the crude product (0.12 g, 0.25 mmol) of methyl 3-(4-{[(2S,4R)-2-methyl-1-propionyl-1,2,3,4-tetrahydroquinolin-4-yl]amino}benzamide)benzoate obtained in step 1 in the same manner as in step 2 of example 2f. ESIMS, (M+H)$^+$, m/z: 458.

(Step 3)

Compound 2j (0.037 g, 19%) was obtained from 3-(4-{[(2S,4R)-2-methyl-1-propionyl-1,2,3,4-tetrahydroquinolin-4-yl]amino}benzamide)benzoic acid (0.1 g, 0.21 mmol) obtained in step 2 and 1-{(2S*,4R*)-4-[(4-aminophenyl)amino]-2-methyl-3,4-dihydroquinolin-1(2H)-yl}propan-1-one (0.068 g, 0.218 mmol) obtained in step 2 of reference example 7 in the same manner as in step 1 of example 1a. ESIMS, (M+H)$^+$, m/z: 749. $^1$H-NMR (DMSO-d$_6$, δ): 0.99-1.07 (m, 12H), 1.56-1.25 (m, 2H), 2.22-2.29 (m, 2H), 2.55-2.66 (m, 4H), 4.10-4.19 (m, 1H), 4.27-4.36 (m, 1H), 4.75 (t, J=6.6 Hz, 2H), 5.95 (d, J=8.0 Hz, 1H), 6.65 (d, J=8.8 Hz, 2H), 6.73 (d, J=8.0 Hz, 3H), 7.12 (d, J=8.8 Hz, 1H), 7.19 (d, J=5.2 Hz, 3H), 7.24-7.33 (m, 4H), 7.41-7.47 (m, 3H), 7.59 (d, J=8.0 Hz, 1H), 7.82 (d, J=8.4 Hz, 2H), 7.96 (d, J=8.8 Hz, 1H), 8.23 (s, 1H), 9.91 (s, 1H), 9.98 (s, 1H).

Example 3a

4-{[(2S,4R)-2-Methyl-1-propionyl-1,2,3,4-tetrahydroquinolin-4-yl]amino}-N-{[1-(4-{[(2S,4R)-2-methyl-1-propionyl-1,2,3,4-tetrahydroquinolin-4-yl]amino}phenyl)-1H-1,2,3-triazol-4-yl]methyl}benzamide (Compound 3a)

(Step 1)

4-{[(2S,4R)-2-Methyl-1-propionyl-1,2,3,4-tetrahydroquinolin-4-yl]amino}-N-(prop-2-yn-1-yl)benzamide (52 mg, 96%) was obtained from 4-{[(2S,4R)-2-methyl-1-propionyl-1,2,3,4-tetrahydroquinolin-4-yl]amino}benzoic acid (50 mg, 0.148 mmol) obtained in step 7 of reference example 1 and propargylamine (0.014 mL, 0.222 mmol) in the same manner as in step 1 of example 1d. ESIMS, (M+H)$^+$, m/z: 376.

(Step 2)

1-{(2S,4R)-4-[(4-aminophenyl)amino]-2-methyl-3,4-dihydroquinolin-1(2H)-yl}propan-1-one (6 mg, 0.019 mmol) obtained in step 3 of reference example 7 was dissolved in acetonitrile, then ADMP (6.6 mg, 0.023 mmol) and DMAP (2.8 mg, 0.023 mmol) were added to the solution, and the mixture was stirred at room temperature for 1 hour. The reaction mixture was concentrated under reduced pressure to give a crude product (15 mg) of 1-{(2S,4R)-4-[(4-azidophenyl)amino]-2-methyl-3,4-dihydroquinolin-1(2H)-yl}propan-1-one.
ESIMS, (M+H)$^+$, m/z: 336.

(Step 3)

A crude product (15 mg) of 1-{(2S,4R)-4-[(4-azidophenyl)amino]-2-methyl-3,4-dihydroquinolin-1(2H)-yl}propan-1-one obtained in step 2 and 4-{[(2S,4R)-2-methyl-1-propionyl-1,2,3,4-tetrahydroquinolin-4-yl]amino}-N-(prop-2-yn-1-yl)benzamide (6.7 mg, 0.018 mmol) obtained in step 1 were dissolved in a mixed solvent (0.6 mL) of ethanol and water (1:1), then sodium L-ascorbate (1.8 mg, 0.0089 mmol) and copper sulfate pentahydrate (4.5 mg, 0.018 mmol) were added to the solution, and the mixture was stirred at 60° C. overnight. The reaction mixture was diluted with ethyl acetate, dried over magnesium sulfate, and concentrated under reduced pressure. The obtained residue was purified by reverse phase HPLC (acetonitrile/0.1% TFA aqueous solution=45/55 to 50/50) to give compound 3a (4 mg, total yield of 2 steps 9%).
ESIMS, (M+H)$^+$, m/z: 711. $^1$H-NMR (CDCl$_3$, δ): 1.12-1.21 (m, 12H), 1.23-1.37 (m, 2H), 2.35-2.45 (m, 2H), 2.54-2.74 (m, 4H), 4.01 (brs, 2H), 4.20-4.28 (m, 2H), 4.76 (d, J=5.9 Hz, 2H), 4.95-4.97 (m, 2H), 6.61 (d, J=8.6 Hz, 2H), 6.70 (d, J=8.6 Hz, 2H), 7.14-7.37 (m, 8H), 7.50 (d, J=8.6 Hz, 2H), 7.68 (d, J=8.6 Hz, 2H), 8.05 (s, 1H).

Example 3b tert-Butyl 2-[(S)-4-(4-{4-[(4-{(S)-6-[2-(tert-butoxy)-2-oxoethyl]-2,3,9-trimethyl-6H-thieno[3,2-f][1,2,4]triazolo[4,3-a][1,4]diazepin-4-yl}benzamide)methyl]-1H-1,2,3-triazol-1-yl}phenyl)-2,3,9-trimethyl-6H-thieno[3,2-f][1,2,4]triazolo[4,3-a][1,4]diazepin-6-yl]acetate (Compound 3b)

(Step 1)

tert-Butyl (S)-2-[4-(4-bromophenyl)-2,3,9-trimethyl-6H-thieno[3,2-f][1,2,4]triazolo[4,3-a][1,4]diazepin-6-yl]acetate (5.0 g, 10.0 mmol) synthesized according to the method described in WO2017/030814 was dissolved in a mixed solvent (2.0 mL) of ethanol and water (3:1), then sodium azide (26 mg, 0.399 mmol), (1R,2R)—N,N'-dimethylcyclohexane-1,2-diamine (0.00473 mL, 0.030 mmol), sodium (R)-ascorbate (2.4 mg, 0.012 mmol) and copper iodide (3.8 mg, 0.02 mmol) were added to the solution, and the mixture was refluxed for 3 hours. A saturated aqueous sodium hydrogen carbonate solution was added to the reaction mixture, and the mixture was extracted twice with ethyl acetate. The organic layer was dried over anhydrous magnesium sulfate and concentrated under reduced pressure. The obtained residue was purified by silica gel column chromatography (heptane/ethyl acetate=100/0 to 60/40) to give tert-butyl (S)-2-[4-(4-azidophenyl)-2,3,9-trimethyl-6H-thieno[3,2-f][1,2,4]triazolo[4,3-a][1,4]diazepin-6-yl]acetate (60 mg, 65%).
ESIMS, (M+H)$^+$, m/z: 464.

(Step 2)

tert-Butyl (S)-2-{2,3,9-trimethyl-4-[4-(prop-2-yn-1-ylcarbamoyl)phenyl]-6H-thieno[3,2-f][1,2,4]triazolo[4,3-a][1,4]diazepin-6-yl}acetate (90 mg, 93%) was obtained from (S)-4-{6-[2-(tert-butoxy)-2-oxoethyl]-2,3,9-trimethyl-6H- thieno[3,2-f][1,2,4]triazolo[4,3-a][1,4]diazepin-4-yl}benzoic acid (90 mg, 0.193 mmol) obtained in reference example 3 and prop-2-yn-1-amine (0.0183 mL, 0.289 mmol) in the same manner as in step 1 of example 1a.
ESIMS, (M+H)$^+$, m/z: 504.
(Step 3)
tert-Butyl (S)-2-[4-(4-azidophenyl)-2,3,9-trimethyl-6H-thieno[3,2-f][1,2,4]triazolo[4,3-a][1,4]diazepin-6-yl]acetate (21 mg, 0.045 mmol) obtained in step 1 and tert-butyl (S)-2-{2,3,9-trimethyl-4-[4-(prop-2-yn-1-ylcarbamoyl)phenyl]-6H-thieno[3,2-f][1,2,4]triazolo[4,3-a][1,4]diazepin-6-yl}acetate (27 mg, 0.054 mmol) obtained in step 2 were dissolved in a mixed solvent (1.5 mL) of s-butanol and water (3:2), then sodium (R)-ascorbate (2.4 mg, 0.012 mmol) and copper(II) sulfate pentahydrate (5.7 mg, 0.023 mmol) were added to the solution, and the mixture was stirred at 50° C. for 6 hours. Water was added to the reaction mixture, and the mixture was extracted twice with chloroform. The organic layer was dried over anhydrous magnesium sulfate and concentrated under reduced pressure. The obtained residue was purified by reverse phase HPLC (aqueous ammonium bicarbonate solution/acetonitrile=50/50-40/60) to give compound 3b (14 mg, 32%).
ESIMS, (M+H)$^+$, m/z: 967. $^1$H-NMR (CDCl$_3$, δ): 1.24-1.27 (m, 3H), 1.48-1.53 (m, 18H), 1.61-1.63 (m, 3H), 2.36-2.48 (m, 6H), 2.63-2.78 (m, 6H), 3.49-3.60 (m, 4H), 4.54-4.64 (m, 2H), 4.75-4.85 (m, 2H), 7.05-7.14 (m, 1H), 7.47-7.56 (m, 2H), 7.59-7.67 (m, 2H), 7.69-7.84 (m, 4H), 8.13 (s, 1H).

Example 3c

4-{[(2S,4R)-2-Methyl-1-propionyl-1,2,3,4-tetrahydroquinolin-4-yl]amino}-N-{[5-(4-{[(2S,4R)-2-methyl-1-propionyl-1,2,3,4-tetrahydroquinolin-4-yl]amino}phenyl)-1,3,4-oxadiazol-2-yl]methyl}benzamide (Compound 3c)

(Step 1)
tert-Butyl {2-[2-(4-{[(2S,4R)-2-methyl-1-propionyl-1,2,3,4-tetrahydroquinolin-4-yl]amino}benzoyl)hydrazinyl]-2-oxoethyl}carbamate (30 mg, 25%) was obtained from 4-{[(2S,4R)-2-methyl-1-propionyl-1,2,3,4-tetrahydroquinolin-4-yl]amino}benzoic acid (80 mg, 0.236 mmol) obtained in step 7 of reference example 1 and tert-butyl (2-hydrazinyl-2-oxoethyl)carbamate (67.1 mg, 0.355 mmol) in the same manner as in step 1 of example 1d.
ESIMS, (M+H)$^+$, m/z: 510.
(Step 2)
tert-Butyl {2-[2-(4-{[(2S,4R)-2-methyl-1-propionyl-1,2,3,4-tetrahydroquinolin-4-yl]amino}benzoyl)hydrazinyl]-2-oxoethyl}carbamate (15 mg, 29 μmol) obtained in step 1 was dissolved in acetonitrile (0.3 mL), then triphenylphosphine (15 mg, 0.059 mmol), carbon tetrachloride (0.011 mL, 0.118 mmol) and triethylamine (0.0082 mL, 0.059 mmol) were added to the solution, and the mixture was stirred at 80° C. for 1 hour. The reaction mixture was concentrated under reduced pressure, and the obtained residue was purified by reverse phase HPLC (acetonitrile/0.1% TFA aqueous solution=40/60 to 50/50) to give tert-butyl {[5-(4-{[(2S,4R)-2-methyl-1-propionyl-1,2,3,4-tetrahydroquinolin-4-yl]amino}phenyl)-1,3,4-oxadiazol-2-yl]methyl}carbamate (10 mg, yield 69%).
ESI-MS, (M+H)$^+$, m/z: 492.
(Step 3)
tert-Butyl {[5-(4-{[(2S,4R)-2-methyl-1-propionyl-1,2,3,4-tetrahydroquinolin-4-yl]amino}phenyl)-1,3,4-oxadiazol-2-yl]methyl}carbamate (10 mg, 0.020 mmol) obtained in step 2 was dissolved in dichloromethane (1 mL), then trifluoroacetic acid (1 mL) was added to the solution, and the mixture was stirred at room temperature for 1 hour. The reaction mixture was concentrated under reduced pressure to give a crude product (8 mg) of 1-[(2S,4R)-4-({4-[5-(aminomethyl)-1,3,4-oxadiazol-2-yl]phenyl}amino)-2-methyl-3,4-dihydroquinolin-1(2H)-yl]propan-1-one trifluoroacetate.
ESI-MS, (M+H)$^+$, m/z: 392.
(Step 4)
Compound 3c (2.3 mg, total yield of 2 steps 16%) was obtained from the crude product (8 mg) of 1-[(2S,4R)-4-({4-[5-(aminomethyl)-1,3,4-oxadiazol-2-yl]phenyl}amino)-2-methyl-3,4-dihydroquinolin-1(2H)-yl]propan-1-one trifluoroacetate obtained in step 3 and 4-{[(2S,4R)-2-methyl-1-propionyl-1,2,3,4-tetrahydroquinolin-4-yl]amino}benzoic acid (10.3 mg, 0.031 mmol) obtained in step 7 of reference example 1 in the same manner as in step 1 of example 1d.
ESI-MS, (M+H)$^+$, m/z: 712. $^1$H-NMR (CDCl$_3$, δ): 1.13-1.19 (m, 12H), 1.25-1.35 (m, 2H), 2.23 (t, J=7.7 Hz, 1H), 2.33-2.43 (m, 2H), 2.54-2.65 (m, 2H), 2.64-2.74 (m, 2H), 4.23-4.30 (m, 2H), 4.91 (d, J=5.4 Hz, 2H), 4.93-5.01 (m, 2H), 5.32-5.37 (m, 1H), 6.63 (d, J=8.6 Hz, 2H), 6.68 (d, J=8.6 Hz, 2H), 7.15-7.34 (m, 8H), 7.71 (d, J=8.6 Hz, 2H), 7.87 (d, J=8.6 Hz, 2H).

Example 3d

4-{[(2S,4R)-2-Methyl-1-propionyl-1,2,3,4-tetrahydroquinolin-4-yl]amino}-N-{[5-(4-{[(2S,4R)-2-methyl-1-propionyl-1,2,3,4-tetrahydroquinolin-4-yl]amino}phenyl)-1,2,4-oxadiazol-3-yl]methyl}benzamide (Compound 3d)

(Step 1)
Methyl 4-{[(2S,4R)-2-methyl-1-propionyl-1,2,3,4-tetrahydroquinolin-4-yl]amino}benzoate (1.9 g, 5.39 mmol) obtained in step 5 of reference example 1 was dissolved in THF (20 mL), then di-tert-butyl dicarbonate (3.53 g, 16.2 mmol) and dimethylaminopyridine (66 mg, 0.539 mmol) were added to the solution, and the mixture was stirred overnight under reflux. The reaction mixture was cooled to room temperature and concentrated under reduced pressure. The obtained residue was purified by silica gel column chromatography (petroleum ether/ethyl acetate=8/2 to 6/4) to give methyl 4-{(tert-butoxycarbonyl)[(2S,4R)-2-methyl-1-propionyl-1,2,3,4-tetrahydroquinolin-4-yl]amino}benzoate (2.09 g, 86%).
ESIMS, (M+H)$^+$, m/z: 453.
(Step 2)
Methyl 4-{(tert-butoxycarbonyl)[(2S,4R)-2-methyl-1-propionyl-1,2,3,4-tetrahydroquinolin-4-yl]amino}benzoate (259 mg, 0.572 mmol) obtained in step 1 was dissolved in methanol (3 mL), then aqueous sodium hydroxide solution (4 mol/L, 3 mL) was added to the solution, and the mixture was stirred for 3 hours under reflux. The reaction mixture was neutralized with hydrochloric acid (5 mol/L), and extracted twice with ethyl acetate. The organic layer was dried over anhydrous magnesium sulfate and concentrated under reduced pressure to give a crude product (270 mg) of 4-{(tert-butoxycarbonyl)[(2S,4R)-2-methyl-1-propionyl-1,2,3,4-tetrahydroquinolin-4-yl]amino}benzoic acid.
ESIMS, (M−H)$^−$, m/z: 437.
(Step 3)
The crude product (270 mg) of 4-{(tert-butoxycarbonyl)[(2S,4R)-2-methyl-1-propionyl-1,2,3,4-tetrahydroquinolin-4-yl]amino}benzoic acid obtained in step 2 was dissolved in DMF (3 mL), then tert-butyl[2-amino-2-(hydroxyimino)

ethyl]carbamate (175 mg, 0.924 mmol), COMU (396 mg, 0.924 mmol) and N,N-diisopropylethylamine (0.209 mL, 1.23 mmol) were added to the solution, and the mixture was stirred at 60° C. overnight, and then at 100° C. for 4 hours. The reaction mixture was concentrated under reduced pressure, and the obtained residue was purified by silica gel column chromatography (petroleum ether/ethyl acetate=8/2 to 6/4) to give tert-butyl[4-(3-{[(tert-butoxycarbonyl)amino]methyl}-1,2,4-oxadiazol-5-yl)phenyl][(2S,4R)-2-methyl-1-propionyl-1,2,3,4-tetrahydroquinolin-4-yl]carbamate (57 mg, total yield of 2 steps 15%).
ESIMS, (M+H)$^+$, m/z: 592.
(Step 4)
tert-Butyl [4-(3-{[(tert-butoxycarbonyl)amino]methyl}-1,2,4-oxadiazol-5-yl)phenyl][(2S,4R)-2-methyl-1-propionyl-1,2,3,4-tetrahydroquinolin-4-yl]carbamate (57 mg, 0.096 mmol) obtained in step 3 was dissolved in dichloromethane (1 mL), then trifluoroacetic acid (1 mL) was added to the solution, and the mixture was stirred at room temperature for 1 hour. The reaction mixture was concentrated under reduced pressure to give a crude product (37 mg) of 1-[(2S,4R)-4-({4-[3-(aminomethyl)-1,2,4-oxadiazol-5-yl]phenyl}amino)-2-methyl-3,4-dihydroquinolin-1(2H)-yl]propan-1-one trifluoroacetate.
ESIMS, (M+H)$^+$, m/z: 392.
(Step 5)
Compound 3d (1.6 mg, total yield of 2 steps 2%) was obtained from the crude product (37 mg, 0.095 mmol) of 1-[(2S,4R)-4-({4-[3-(aminomethyl)-1,2,4-oxadiazol-5-yl]phenyl}amino)-2-methyl-3,4-dihydroquinolin-1(2H)-yl]propan-1-one trifluoroacetate obtained in step 4 and 4-{[(2S,4R)-2-methyl-1-propionyl-1,2,3,4-tetrahydroquinolin-4-yl]amino}benzoic acid (32 mg, 0.095 mmol) obtained in step 7 of reference example 1 in the same manner as in step 1 of example 1d.
ESIMS, (M+H)$^+$, m/z: 712. $^1$H-NMR (CDCl$_3$, δ): 1.11-1.20 (m, 12H), 1.27-1.37 (m, 2H), 2.33-2.44 (m, 2H), 2.54-2.74 (m, 4H), 4.22-4.33 (m, 2H), 4.81 (d, J=5.0 Hz, 2H), 4.96 (s, 2H), 6.63 (d, J=8.6 Hz, 2H), 6.69 (d, J=8.2 Hz, 2H), 7.14-7.34 (m, 8H), 7.72 (d, J=8.6 Hz, 2H), 7.95 (d, J=8.2 Hz, 2H).

Example 3e

1-[(2S,4R)-2-Methyl-4-({4-[3-(4-{[(2S,4R)-2-methyl-1-propionyl-1,2,3,4-tetrahydroquinolin-4-yl]amino}phenyl)-5,6,7,8-tetrahydroimidazo[1,2-a]pyrazine-7-carbonyl]phenyl}amino)-3,4-dihydroquinolin-1(2H)-yl]propan-1-one (Compound 3e)

(Step 1)
tert-Butyl 3-bromo-5,6-dihydroimidazo[1,2-a]pyrazine-7(8H)-carboxylate (80 mg, 0.265 mmol) purchased from J & W PharmLab was dissolved in THF (1.5 ml), then isopropylmagnesium chloride-lithium chloride (1.3 mol/L THF solution, 0.346 ml, 0.450 mmol) was added to the solution at −10° C., and the mixture was stirred at −10° C. for 1 hour. Tributyltin chloride (0.122 ml, 0.450 mmol) was added to the reaction mixture, and the mixture was stirred at 0° C. for 1 hour and then at room temperature for 1 hour. Water was added to the reaction mixture, and the mixture was extracted with ethyl acetate. The organic layer was dried over anhydrous magnesium sulfate and concentrated under reduced pressure to give a crude product (312 mg) of tert-butyl 3-(tributylstannyl)-5,6-dihydroimidazo[1,2-a]pyrazine-7(8H)-carboxylate.
ESIMS, (M+H)$^+$, m/z: 514.

(Step 2)
1-{(2S,4R)-4-[(4-Bromophenyl)amino]-2-methyl-3,4-dihydroquinolin-1(2H)-yl}propan-1-one (39.6 mg, 0.106 mmol) obtained in reference example 2 was dissolved in toluene (2 mL), then the crude product (312 mg) of tert-butyl 3-(tributylstannyl)-5,6-dihydroimidazo[1,2-a]pyrazine-7(8H)-carboxylate obtained in step 1 and Pd(PPh$_3$)$_4$ (12.3 mg, 0.011 mmol) were added to the solution, and the mixture was stirred under reflux for 1 hour. The reaction mixture was concentrated under reduced pressure, and the resulting residue was purified by silica gel column chromatography (chloroform/methanol=99/1 to 97/3) and reverse phase HPLC (0.05% TFA/acetonitrile=53/35 to 43/45) to give tert-butyl 3-(4-{[(2S,4R)-2-methyl-1-propionyl-1,2,3,4-tetrahydroquinolin-4-yl]amino}phenyl)-5,6-dihydroimidazo[1,2-a]pyrazine-7(8H)-carboxylate (28.2 mg, 52%). ESIMS, (M+H)$^+$, m/z: 516.
(Step 3)
1-((2S,4R)-2-Methyl-4-{[4-(5,6,7,8-tetrahydroimidazo[1,2-a]pyrazin-3-yl)phenyl]amino}-3,4-dihydroquinolin-1(2H)-yl)propan-1-one hydrochloride (23.0 mg, 93%) was obtained from tert-butyl 3-(4-{[(2S,4R)-2-methyl-1-propionyl-1,2,3,4-tetrahydroquinolin-4-yl]amino}phenyl)-5,6-dihydroimidazo[1,2-a]pyrazine-7(8H)-carboxylate (28.2 mg, 0.055 mmol) obtained in step 2 in the same manner as in step 2 of example 1a.
ESIMS, (M+H)$^+$, m/z: 416.
(Step 4)
Compound 3e (15.7 mg, 42%) was obtained from 1-((2S,4R)-2-methyl-4-{[4-(5,6,7,8-tetrahydroimidazo[1,2-a]pyrazin-3-yl)phenyl]amino}-3,4-dihydroquinolin-1(2H)-yl)propan-1-one hydrochloride (23.0 mg, 0.051 mmol) obtained in step 3 and 4-{[(2S,4R)-2-methyl-1-propionyl-1,2,3,4-tetrahydroquinolin-4-yl]amino}benzoic acid (17.2 mg, 0.051 mmol) obtained in step 7 of reference example 1 in the same manner as in step 3 of example 1b.
ESIMS, (M+H)$^+$, m/z: 736.6. $^1$H-NMR (DMSO-d$_6$, δ): 0.98-1.06 (m, 12H), 1.17-1.28 (m, 2H), 2.19-2.30 (m, 2H), 2.54-2.69 (m, 4H), 3.85-3.89 (m, 2H), 4.01-4.08 (m, 2H), 4.15-4.30 (m, 2H), 4.70-4.79 (m, 4H), 6.29 (d, J=7.7 Hz, 1H), 6.62 (d, J=7.7 Hz, 1H), 6.70 (dd, J=8.6, 4.5 Hz, 4H), 6.88 (s, 1H), 7.12-7.37 (m, 12H).

Example 3f

1-[(2S,4R)-2-Methyl-4-({4-[2-(4-{[(2S,4R)-2-methyl-1-propionyl-1,2,3,4-tetrahydroquinolin-4-yl]amino}phenyl)-5,6,7,8-tetrahydroimidazo[1,2-a]pyrazine-7-carbonyl]phenyl}amino)-3,4-dihydroquinolin-1(2H)-yl]propan-1-one (Compound 3f)

(Step 1)
1-{(2S,4R)-4-[(4-Bromophenyl)amino]-2-methyl-3,4-dihydroquinolin-1(2H)-yl}propan-1-one (200 mg, 0.536 mmol) obtained in reference example 2 was dissolved in 1,4-dioxane (1 mL), then potassium acetate (105 mg, 1.07 mmol), bis(pinacolato)diboron (163 mg, 0.643 mmol) and PdCl$_2$(dppf)-CH$_2$Cl$_2$ (43.8 mg, 0.054 mmol) were added to the solution, and the mixture was stirred for 2 hours under reflux. Water and ethyl acetate were added to the reaction mixture, the mixture was filtered through diatomaceous earth, and the filtrate was concentrated under reduced pressure. The obtained residue was purified by silica gel column chromatography (heptane/ethyl acetate=90/10 to 60/40) to give 1-((2S,4R)-2-methyl-4-{[4-(4,4,5,5-tetramethyl-1,3,2- dioxaborolan-2-yl)phenyl]amino}-3,4-dihydroquinolin-1 (2H)-yl)propan-1-one (101 mg, 45%).
ESIMS, (M+H)$^+$, m/z: 421.
(Step 2)
1-((2S,4R)-2-Methyl-4-{[4-(4,4,5,5-tetramethyl-1,3,2-dioxaborolan-2-yl)phenyl]amino}-3,4-dihydroquinolin-1 (2H)-yl)propan-1-one (50.0 mg, 0.119 mmol) obtained in step 1 was dissolved in a mixed solvent (3.3 mL) of 1,4-dioxane and water (3:1), then tert-butyl 2-bromo-5,6-dihydroimidazo[1,2-a]pyrazine-7(8H)-carboxylate (53.9 mg, 0.178 mmol) purchased from J&W PharmLab, cesium carbonate (78.0 mg, 0.238 mmol) and Pd(PPh$_3$)$_4$ (20.6 mg, 0.018 mmol) were added to the solution, and the mixture was stirred for 14 hours under reflux. Water and ethyl acetate were added to the reaction mixture, the mixture was filtered through diatomaceous earth, and the filtrate was concentrated under reduced pressure. The obtained residue was purified by silica gel column chromatography (heptane/ethyl acetate=50/50 to 0/100) to give a crude product (87.4 mg) of tert-butyl 2-(4-{[(2S,4R)-2-methyl-1-propionyl-1,2,3,4-tetrahydroquinolin-4-yl]amino}phenyl)-5,6-dihydroimidazo[1,2-a]pyrazine-7(8H)-carboxylate.
ESIMS, (M+H)$^+$, m/z: 516.
(Step 3)
1-((2S,4R)-2-Methyl-4-{[4-(5,6,7,8-tetrahydroimidazo[1,2-a]pyrazin-2-yl)phenyl]amino}-3,4-dihydroquinolin-1 (2H)-yl)propan-1-one hydrochloride (49.4 mg, 92%) was obtained from the crude product (87.4 mg) of tert-butyl 2-(4-{[(2S,4R)-2-methyl-1-propionyl-1,2,3,4-tetrahydroquinolin-4-yl]amino}phenyl)-5,6-dihydroimidazo[1,2-a]pyrazine-7(8H)-carboxylate obtained in step 2 in the same manner as in step 2 of example 1a.
ESIMS, (M+H)$^+$, m/z: 416.
(Step 4)
Compound 3f (11.4 mg, 15%) was obtained from 1-((2S,4R)-2-methyl-4-{[4-(5,6,7,8-tetrahydroimidazo [1,2-a]pyrazin-2-yl)phenyl]amino}-3,4-dihydroquinolin-1(2H)-yl)propan-1-one hydrochloride (42.1 mg, 0.101 mmol) obtained in step 3 and 4-{[(2S,4R)-2-methyl-1-propionyl-1,2,3,4-tetrahydroquinolin-4-yl]amino}benzoic acid (37.7 mg, 0.111 mmol) obtained in step 7 of reference example 1 in the same manner as in step 3 of example 1b.
ESIMS, (M+H)$^+$, m/z: 736. $^1$H-NMR (DMSO-d$_6$, δ): 0.99-1.06 (m, 12H), 1.14-1.28 (m, 2H), 2.19-2.30 (m, 2H), 2.57-2.67 (m, 4H), 3.92 (t, J=5.0 Hz, 2H), 4.05 (t, J=5.0 Hz, 2H), 4.14-4.31 (m, 2H), 4.69-4.79 (m, 4H), 6.02 (d, J=7.7 Hz, 1H), 6.60-6.65 (m, 3H), 6.70 (d, J=8.6 Hz, 2H), 7.13-7.23 (m, 4H), 7.24-7.34 (m, 7H), 7.44 (d, J=8.6 Hz, 2H).

Example 4a

N$^1$,N$^5$-bis(4-{[(2S*,4R*)-2-Methyl-1-propionyl-1,2,3,4-tetrahydroquinolin-4-yl]amino}phenyl)glutaramide (Compound 4a)

(Step 1)
A crude product (0.15 g) of methyl 5-[(4-{[(2S*,4R*)-2-methyl-1-propionyl-1,2,3,4-tetrahydroquinolin-4-yl]amino}phenyl)amino]-5-oxopentanoate was obtained from 1-{(2S*,4R*)-4-[(4-aminophenyl)amino]-2-methyl-3,4-dihydroquinolin-1(2H)-yl}propan-1-one (0.1 g, 0.32 mmol) obtained in step 2 of reference example 7 and 5-methoxy-5-oxopentanoic acid (0.047 g, 0.32 mmol) in the same manner as in step 3 of example 1b.
ESIMS, (M+H)$^+$, m/z: 438.

(Step 2)
A crude product (0.1 g) of 5-[(4-{[(2S*,4R*)-2-methyl-1-propionyl-1,2,3,4-tetrahydroquinolin-4-yl]amino}phenyl)amino]-5-oxopentanoic acid was obtained from the crude product (0.15 g, 0.34 mmol) of methyl 5-[(4-{[(2S*,4R*)-2-methyl-1-propionyl-1,2,3,4-tetrahydroquinolin-4-yl]amino}phenyl)amino]-5-oxopentanoate obtained in step 1 in the same manner as in step 2 of example 2f.
ESIMS, (M+H)$^+$, m/z: 424.
(Step 3)
Compound 4a (0.09 g, total yield of 3 steps 39%) was obtained from the crude product (0.1 g, 0.23 mmol) of 5-[(4-{[(2S*,4R*)-2-methyl-1-propionyl-1,2,3,4-tetrahydroquinolin-4-yl]amino}phenyl)amino]-5-oxopentanoic acid obtained in step 2 and 1-{(2S*,4R*)-4-[(4-aminophenyl)amino]-2-methyl-3,4-dihydroquinolin-1(2H)-yl}propan-1-one (0.073 g, 0.23 mmol) obtained in step 2 of reference example 7 in the same manner as in step 1 of example 1a.
ESIMS, (M+H)$^+$, m/z: 715.54. $^1$H-NMR (DMSO-d$_6$, δ): 0.98-1.04 (m, 12H), 1.11-1.18 (m, 2H), 1.84-1.88 (m, 2H), 2.21-2.29 (m, 6H), 2.59 (t, J=15.25 Hz, 4H), 4.11 (s, 2H), 4.72 (d, J=6.5 Hz, 2H), 5.86 (d, J=7.93 Hz, 2H), 6.58 (d, J=8.5 Hz, 4H), 7.16 (d, J=4.27 Hz, 4H), 7.25-7.31 (m, 8H), 9.52 (s, 2H).

Example 4b

3-Methyl-N$^1$,N$^5$-bis(4-{[(2S*,4R*)-2-methyl-1-propionyl-1,2,3,4-tetrahydroquinolin-4-yl] amino}phenyl)pentanediamide (Compound 4b)

(Step 1)
A crude product (0.1 g, 68%) of methyl 3-methyl-5-[(4-{[(2S*,4R*)-2-methyl-1-propionyl-1,2,3,4-tetrahydroquinolin-4-yl]amino}phenyl)amino]-5-oxopentanoate was obtained from 1-{(2S*,4R*)-4-[(4-aminophenyl)amino]-2-methyl-3,4-dihydroquinolin-1(2H)-yl}propan-1-one (0.1 g, 0.32 mmol) obtained in step 2 of reference example 7 and 5-methoxy-3-methyl-5-oxopentanoic acid (0.052 g, 0.324 mmol) in the same manner as in step 3 of example 1b.
ESIMS, (M+H)$^+$, m/z: 452.
(Step 2)
A crude product (0.09 g, 94%) of 3-methyl-5-[(4-{[(2S*,4R*)-2-methyl-1-propionyl-1,2,3,4-tetrahydroquinolin-4-yl]amino}phenyl)amino]-5-oxopentanoic acid was obtained from the crude product (0.1 g, 0.22 mmol) of methyl 3-methyl-5-[(4-{[(2S*,4R*)-2-methyl-1-propionyl-1,2,3,4-tetrahydroquinolin-4-yl]amino}phenyl)amino]-5-oxopentanoate obtained in step 1 in the same manner as in step 2 of example 2f.
ESIMS, (M+H)$^+$, m/z: 438.
(Step 3)
Compound 4b (0.04 g, 27%) was obtained from the crude product of 3-methyl-5-[(4-{[(2S*,4R*)-2-methyl-1-propionyl-1,2,3,4-tetrahydroquinolin-4-yl]amino}phenyl)amino]-5-oxopentanoic acid (0.09 g, 0.20 mmol) obtained in step 2 and 1-{(2S*,4R*)-4-[(4-aminophenyl)amino]-2-methyl-3,4-dihydroquinolin-1(2H)-yl}propan-1-one (0.064 g, 0.23 mmol) obtained in step 2 of reference example 7 in the same manner as in step 1 of example 1a.
ESIMS, (M+H)$^+$, m/z: 729. $^1$H-NMR (DMSO-d$_6$, δ): 0.94 (d, J=6.41 Hz, 3H), 0.98-1.04 (m, 12H), 1.11-1.15 (m, 2H), 2.12 (dd, J=13.73, 8.54 Hz, 2H), 2.21-2.31 (m, 4H), 2.36-2.45 (m, 1H), 2.51-2.61 (m, 4H), 4.08-4.12 (m, 2H), 4.72 (d, J=6.41 Hz, 2H), 5.86 (d, J=7.93 Hz, 2H), 6.58 (d, J=9.16 Hz, 4H), 7.16 (d, J=4.27 Hz, 4H), 7.23-7.30 (m, 8H), 9.53 (s, 2H).

Example 4c

4-{[(2S,4R)-2-Methyl-1-propionyl-1,2,3,4-tetrahydroquinolin-4-yl]amino}-N-{3-[N-(4-{[(2S*,4R*)-2-methyl-1-propionyl-1,2,3,4-tetrahydroquinolin-4-yl]amino}phenyl)sulfamoyl]phenyl}benzamide (Compound 4c)

(Step 1)

1-{(2S*,4R*)-4-[(4-Aminophenyl)amino]-2-methyl-3,4-dihydroquinolin-1(2H)-yl}propan-1-one (200 mg, 0.536 mmol) obtained in step 2 of reference example 7 was dissolved in dichloromethane (1 mL), then pyridine (0.026 mL, 0.323 mmol) and 3-nitrobenzenesulfonyl chloride (43.0 mg, 0.194 mmol) were added to the solution, and the mixture was stirred at room temperature for 2 hours. Hydrochloric acid (1 mol/L) and ethyl acetate were added to the reaction mixture, the mixture was filtered through diatomaceous earth, and the filtrate was concentrated under reduced pressure. The obtained residue was purified by silica gel column chromatography (heptane/ethyl acetate=80/20 to 40/60) to give N-(4-{[(2S*,4R*)-2-methyl-1-propionyl-1,2,3,4-tetrahydroquinolin-4-yl]amino}phenyl)-3-nitrobenzenesulfonamide (74.4 mg, 93%).

ESIMS, (M−H)+, m/z: 493.

(Step 2)

3-Amino-N-(4-{[(2S*,4R*)-2-methyl-1-propionyl-1,2,3,4-tetrahydroquinolin-4-yl]amino}phenyl)benzenesulfonamide (74.2 mg, quantitative) was obtained from N-(4-{[(2S*,4R*)-2-methyl-1-propionyl-1,2,3,4-tetrahydroquinolin-4-yl]amino}phenyl)-3-nitrobenzenesulfonamide (74.4 mg, 0.150 mmol) obtained in step 1 in the same manner as in step 2 of reference example 7.

ESIMS, (M−H)+, m/z: 463.

(Step 3)

Compound 4c (15.9 mg, 47%) was obtained from 3-amino-N-(4-{[(2S*,4R*)-2-methyl-1-propionyl-1,2,3,4-tetrahydroquinolin-4-yl]amino}phenyl)benzenesulfonamide (20.0 mg, 0.043 mmol) obtained in step 2 and 4-{[(2S,4R)-2-methyl-1-propionyl-1,2,3,4-tetrahydroquinolin-4-yl]amino}benzoic acid (14.6 mg, 0.043 mmol) obtained in step 7 of reference example 1 in the same manner as in step 3 of example 1b.

ESIMS, (M+H)+, m/z: 785. $^1$H-NMR (DMSO-$d_6$, δ): 0.95-1.07 (m, 12H), 1.22-1.28 (m, 2H), 2.14-2.30 (m, 2H), 2.57-2.69 (m, 4H), 4.00-4.08 (m, 1H), 4.29-4.36 (m, 1H), 4.62-4.78 (m, 2H), 5.97 (d, J=8.6 Hz, 1H), 6.48-6.52 (m, 2H), 6.72 (d, J=8.6 Hz, 2H), 6.76-6.80 (m, 3H), 7.07-7.13 (m, 2H), 7.15-7.22 (m, 2H), 7.25-7.32 (m, 4H), 7.45 (t, J=7.9 Hz, 1H), 7.79 (d, J=8.6 Hz, 2H), 7.85 (d, J=9.1 Hz, 1H), 7.93 (d, J=8.2 Hz, 1H), 8.22 (s, 1H), 9.56 (s, 1H), 10.06 (s, 1H).

Example 4d

4-{[(2S,4R)-2-Methyl-1-propionyl-1,2,3,4-tetrahydroquinolin-4-yl]amino}-N-{2-[(4-{[(2S,4R)-2-methyl-1-propionyl-1,2,3,4-tetrahydroquinolin-4-yl]amino}phenyl)sulfonamide]ethyl}benzamide (Compound 4d)

(Step 1)

1-{(2S,4R)-4-[(4-Bromophenyl)amino]-2-methyl-3,4-dihydroquinolin-1(2H)-yl}propan-1-one (200 mg, 0.536 mmol) obtained in reference example 2 was dissolved in 1,4-dioxane (4 mL), then (4-methoxyphenyl)methanethiol (0.112 ml, 0.804 mmol), Pd$_2$(dba)$_3$ (49.1 mg, 0.054 mmol), xantphos (62.0 mg, 0.107 mmol) and N,N-diisopropylethylamine (0.187 ml, 1.072 mmol) were added to the solution, and the mixture was stirred for 15 hours under reflux. The reaction mixture was concentrated under reduced pressure, and the obtained residue was purified by silica gel column chromatography (heptane/ethyl acetate=80/20 to 40/60) to give 1-[(2S,4R)-4-({4-[(4-methoxybenzyl)thio]phenyl}amino)-2-methyl-3,4-dihydroquinolin-1(2H)-yl]propan-1-one (244 mg, quantitative).

ESIMS, (M−H)+, m/z: 445.

(Step 2)

1-[(2S,4R)-4-({4-[(4-Methoxybenzyl)thio]phenyl}amino)-2-methyl-3,4-dihydroquinolin-1(2H)-yl]propan-1-one (127 mg, 0.284 mmol) obtained in step 1 was dissolved in a mixed solvent (0.9 mL) of acetonitrile and water (8:1), then trichloroisocyanuric acid (79.0 mg, 0.341 mmol) was added to the solution at −15° C., and the mixture was stirred for 30 minutes. The reaction mixture was heated to −5° C., then N-(tert-butoxycarbonyl)-1,2-diaminoethane (0.135 ml, 0.853 mmol) was added to the reaction mixture, and the mixture was stirred for 30 minutes. The reaction mixture was heated to 5° C., then N-(tert-butoxycarbonyl)-1,2-diaminoethane (0.090 ml, 0.569 mmol) was added to the reaction mixture, and the mixture was stirred for 30 minutes. Water and saturated aqueous ammonium chloride solution were added to the reaction mixture, and the mixture was extracted with ethyl acetate. The organic layer was washed with saturated aqueous sodium hydrogen carbonate solution, dried over anhydrous magnesium sulfate, and concentrated under reduced pressure. The obtained residue was purified by silica gel column chromatography (heptane/ethyl acetate=70/30 to 20/80) to give tert-butyl {2-[(4-{[(2S,4R)-2-methyl-1-propionyl-1,2,3,4-tetrahydroquinolin-4-yl]amino}phenyl)sulfonamide]ethyl}carbamate (14.4 mg, 10%).

ESIMS, (M−H)+, m/z: 515.

(Step 3)

A crude product (24.7 mg) of N-(2-aminoethyl)-4-{[(2S,4R)-2-methyl-1-propionyl-1,2,3,4-tetrahydroquinolin-4-yl]amino}benzenesulfonamide hydrochloride was obtained from tert-butyl {2-[(4-{[(2S,4R)-2-methyl-1-propionyl-1,2,3,4-tetrahydroquinolin-4-yl]amino}phenyl)sulfonamide]ethyl}carbamate (23.4 mg, 0.045 mmol) obtained in step 2 in the same manner as in step 2 of example 1a.

ESIMS, (M+H)+, m/z: 417.

(Step 4)

Compound 4d (23.9 mg, total yield of 2 steps 72%) was obtained from the crude product (24.7 mg) of N-(2-aminoethyl)-4-{[(2S,4R)-2-methyl-1-propionyl-1,2,3,4-tetrahydroquinolin-4-yl]amino}benzenesulfonamide hydrochloride obtained in step 3 and 4-{[(2S,4R)-2-methyl-1-propionyl-1,2,3,4-tetrahydroquinolin-4-yl]amino}benzoic acid (15.2 mg, 0.045 mmol) obtained in step 7 of reference example 1 in the same manner as in step 3 of example 1b.

ESIMS, (M+H)+, m/z: 737.51. $^1$H-NMR (DMSO-$d_6$, δ): 1.00 (t, J=7.5 Hz, 6H), 1.05 (d, J=6.3 Hz, 6H), 1.18-1.25 (m, 2H), 2.19-2.30 (m, 2H), 2.59 (q, J=7.5 Hz, 4H), 2.80 (t, J=6.3 Hz, 2H), 3.24 (dt, J=6.3, 5.9 Hz, 2H), 4.24-4.32 (m, 2H), 4.69-4.78 (m, 2H), 6.57 (d, J=7.2 Hz, 1H), 6.64 (d, J=9.1 Hz, 2H), 6.73 (d, J=9.1 Hz, 2H), 6.87 (d, J=8.2 Hz, 2H), 7.08 (d, J=7.2 Hz, 2H), 7.16 (q, J=6.3 Hz, 2H), 7.24-7.33 (m, 5H), 7.49 (d, J=8.6 Hz, 2H), 7.59 (d, J=8.6 Hz, 2H), 8.03 (t, J=5.9 Hz, 1H).

Example 4e

N-(4-{[(2S*,4R*)-2-Methyl-1-propionyl-1,2,3,4-tetrahydroquinolin-4-yl]amino}phenyl)-3-[(4-{[(2S,4R)-2-methyl-1-propionyl-1,2,3,4-tetrahydroquinolin-4-yl]amino}phenyl)thio]propanamide
(Compound 4e)

(Step 1)
Methyl 3-[(4-{[(2S,4R)-2-methyl-1-propionyl-1,2,3,4-tetrahydroquinolin-4-yl]amino}phenyl)thio]propanoate (0.12 g, 72%) was obtained from 1-{(2S,4R)-4-[(4-bromophenyl)amino]-2-methyl-3,4-dihydroquinolin-1(2H)-yl}propan-1-one (0.150 g, 0.403 mmol) obtained in reference example 2 and methyl 3-mercaptopropionate (0.13 mL, 1.21 mmol) in the same manner as in step 1 of example 4d.
ESIMS, (M+H)$^+$, m/z: 413.

(Step 2)
A crude product (0.075 g, 86%) of 3-[(4-{[(2S,4R)-2-methyl-1-propionyl-1,2,3,4-tetrahydroquinolin-4-yl]amino}phenyl)thio]propanoic acid was obtained from methyl 3-[(4-{[(2S,4R)-2-methyl-1-propionyl-1,2,3,4-tetrahydroquinolin-4-yl]amino}phenyl)thio]propanoate (0.09 g, 0.22 mmol) obtained in step 1 in the same manner as in step 2 of example 2f.
ESIMS, (M+H)$^+$, m/z: 399.

(Step 3)
Compound 4e (0.04 g, 30%) was obtained from the crude product (0.075 g, 0.19 mmol) of 3-[(4-{[(2S,4R)-2-methyl-1-propionyl-1,2,3,4-tetrahydroquinolin-4-yl]amino}phenyl)thio]propanoic acid obtained in step 2 and 1-{(2S*,4R*)-4-[(4-aminophenyl)amino]-2-methyl-3,4-dihydroquinolin-1(2H)-yl}propan-1-one (0.058 g, 0.19 mmol) obtained in step 2 of reference example 7 in the same manner as in step 3 of example 1b.
ESIMS, (M+H)$^+$, m/z: 690.69. $^1$H-NMR (DMSO-d$_6$, δ): 0.98-1.05 (m, 12H), 1.14-1.19 (m, 2H), 2.20-2.26 (m, 2H), 2.45-2.47 (m, 2H), 2.55-2.61 (m, 4H), 2.97 (t, J=7.2 Hz, 2H), 4.11-4.15 (m, 2H), 4.72 (brs, 2H), 5.84 (d, J=8.0 Hz, 1H), 6.24 (d, J=7.6 Hz, 1H), 6.56-6.65 (m, 4H), 7.13-7.30 (m, 12H), 9.54 (s, 1H).

Example 4f

4-{[(2S,4R)-2-Methyl-1-propionyl-1,2,3,4-tetrahydroquinolin-4-yl]amino}-N-{2-[(4-{[(2S,4R)-2-methyl-1-propionyl-1,2,3,4-tetrahydroquinolin-4-yl]amino}phenyl)thio]ethyl}benzamide (Compound 4f)

(Step 1)
tert-Butyl {2-[(4-{[(2S,4R)-2-methyl-1-propionyl-1,2,3,4-tetrahydroquinolin-4-yl]amino}phenyl)thio]ethyl}carbamate (0.080 g, 42%) was obtained from 1-{(2S,4R)-4-[(4-bromophenyl)amino]-2-methyl-3,4-dihydroquinolin-1(2H)-yl}propan-1-one (0.150 g, 0.403 mmol) obtained in reference example 2 and tert-butyl (2-mercaptoethyl)carbamate (0.214 g, 1.21 mmol) in the same manner as in step 1 of example 4d.
ESIMS, (M+H)$^+$, m/z: 470.

(Step 2)
1-[(2S,4R)-4-({4-[(2-Aminoethyl)thio]phenyl}amino)-2-methyl-3,4-dihydroquinolin-1(2H)-yl]propan-1-one hydrochloride (0.06 g, 87%) was obtained from tert-butyl {2-[(4-{[(2S,4R)-2-methyl-1-propionyl-1,2,3,4-tetrahydroquinolin-4-yl]amino}phenyl)thio]ethyl}carbamate (0.08 g, 0.17 mmol) obtained in step 1 in the same manner as in step 2 of example 1a.
ESIMS, (M+H)$^+$, m/z: 370.

(Step 3)
Compound 4f (0.025 g, 25%) was obtained from 1-[(2S,4R)-4-({4-[(2-aminoethyl)thio]phenyl}amino)-2-methyl-3,4-dihydroquinolin-1(2H)-yl]propan-1-one hydrochloride (0.06 g, 0.15 mmol) obtained in step 2 and 4-{[(2S,4R)-2-methyl-1-propionyl-1,2,3,4-tetrahydroquinolin-4-yl]amino}benzoic acid (0.05 g, 0.15 mmol) obtained in step 7 of reference example 1 in the same manner as in step 3 of example 1b.
ESIMS, (M+H)$^+$, m/z: 690. $^1$H-NMR (DMSO-d$_6$, δ): 1.02-1.05 (m, 12H), 1.14-1.24 (m, 2H), 2.21-2.26 (m, 2H), 2.54-2.63 (m, 4H), 2.85 (t, J=7.0 Hz, 2H), 3.35 (s, 2H), 4.15 (brs, 1H), 4.24-4.27 (m, 1H), 4.73-4.74 (m, 2H), 6.25 (d, J=7.5 Hz, 1H), 6.58 (d, J=7.5 Hz, 1H), 6.62-6.65 (m, 4H), 7.09 (d, J=8.0 Hz, 1H), 7.13-7.19 (m, 3H), 7.22-7.31 (m, 6H), 7.60 (d, J=8.5 Hz, 2H), 8.17 (t, J=5.5 Hz, 1H).

Example 5a

N-(4-(((2S,4R)-2-Methyl-1-propionyl-1,2,3,4-tetrahydroquinolin-4-yl)amino)phenyl)-2-((4-(((2S,4R)-2-methyl-1-propionyl-1,2,3,4-tetrahydroquinolin-4-yl)amino)phenyl)amino)oxazole-4-carboxamide
(Compound 5a)

(Step 1)
1-{(2S,4R)-4-[(4-Aminophenyl)amino]-2-methyl-3,4-dihydroquinolin-1(2H)-yl}propan-1-one (200 mg, 0.646 mmol) obtained in step 3 of reference example 7 and trimethylsilyl isocyanate (0.128 mL, 0.970 mmol) were dissolved in THF (4 mL), and the mixture was stirred for 3 hours under reflux. The reaction mixture was cooled to room temperature, then water was added to the reaction mixture, and the mixture was extracted twice with ethyl acetate. The organic layer was dried over magnesium sulfate and concentrated under reduced pressure. The obtained residue was purified by silica gel column chromatography (chloroform/methanol=10/0 to 9/1) to give 1-(4-(((2S,4R)-2-methyl-1-propionyl-1,2,3,4-tetrahydroquinolin-4-yl)amino)phenyl)urea (185 mg, 81%).
ESI-MS, (M+H)$^+$, m/z: 353.

(Step 2)
1-(4-(((2S,4R)-2-Methyl-1-propionyl-1,2,3,4-tetrahydroquinolin-4-yl)amino)phenyl)urea (180 mg, 0.511 mmol) obtained in step 1 and ethyl 3-bromopyruvate (0.077 mL, 0.613 mmol) were dissolved in ethanol (5 mL), and the mixture was stirred for 4 hours under reflux. The reaction mixture was cooled to room temperature and concentrated under reduced pressure. The obtained residue was purified by silica gel column chromatography (heptane/ethyl acetate=6/4 to 2/8) to give ethyl 2-((4-(((2S,4R)-2-methyl-1-propionyl-1,2,3,4-tetrahydroquinolin-4-yl)amino)phenyl)amino)oxazole-4-carboxylate (150 mg, 65%).
ESI-MS, (M+H)$^+$, m/z: 449.

(Step 3)
Ethyl 2-((4-(((2S,4R)-2-methyl-1-propionyl-1,2,3,4-tetrahydroquinolin-4-yl)amino)phenyl)amino)oxazole-4-carboxylate (40 mg, 0.089 mmol) obtained in step 2 and trimethyltin hydroxide (18 mg, 0.098 mmol) were dissolved in 1,2-dichloroethane (1 mL), and the mixture was stirred at 80° C. overnight. The reaction mixture was cooled to room temperature and filtered through diatomaceous earth. The filtrate was concentrated under reduced pressure to give a crude product (40 mg) of 2-((4-(((2S,4R)-2-methyl-1-propionyl-1,2,3,4-tetrahydroquinolin-4-yl)amino)phenyl)amino)oxazole-4-carboxylic acid.
ESI-MS, (M+H)⁺, m/z: 421.
(Step 4)

A crude product of compound 5a was obtained from the crude product (30 mg) of 2-((4-(((2S,4R)-2-methyl-1-propionyl-1,2,3,4-tetrahydroquinolin-4-yl)amino)phenyl)amino)oxazole-4-carboxylic acid obtained in step 3 and 1-{(2S,4R)-4-[(4-aminophenyl)amino]-2-methyl-3,4-dihydroquinolin-1(2H)-yl}propan-1-one (27 mg, 0.086 mmol) obtained in step 3 of reference example 7 in the same manner as in step 3 of example 1b. The obtained crude product was purified by reverse phase HPLC (10 mmol/L aqueous ammonium bicarbonate solution/acetonitrile=60/40 to 50/50) to give compound 5a (8 mg, total yield of 2 steps 16%).
ESI-MS, (M+H)⁺, m/z: 712. ¹H-NMR (CDCl₃, δ): 1.10-1.18 (m, 12H), 1.22-1.31 (m, 2H), 2.32-2.43 (m, 2H), 2.52-2.71 (m, 4H), 3.79-3.86 (m, 2H), 4.12-4.22 (m, 2H), 4.94 (s, 2H), 6.63 (d, J=9.1 Hz, 2H), 6.66 (d, J=9.1 Hz, 2H), 6.75 (s, 1H), 7.13-7.23 (m, 4H), 7.27-7.35 (m, 5H), 7.47 (d, J=8.6 Hz, 2H), 7.82 (s, 1H), 8.46 (s, 1H).

Example 5b 1-((2S,4R)-2-Methyl-4-((4-((2-(4-(((2S,4R)-2-methyl-1-propionyl-1,2,3,4-tetrahydroquinolin-4-yl)amino)phenyl)-5,6-dihydroimidazo[1,2-a]pyrazin-7(8H)-yl)methyl)phenyl)amino)-3,4-dihydroquinolin-1(2H)-yl)propan-1-one (Compound 5b)

(Step 1)

A saturated aqueous sodium hydrogen carbonate solution was added to 1-((2S,4R)-2-methyl-4-{[4-(5,6,7,8-tetrahydroimidazo[1,2-a]pyrazin-2-yl)phenyl]amino}-3,4-dihydroquinolin-1(2H)-yl)propan-1-one hydrochloride (0.120 g, 0.265 mmol) obtained in step 3 of example 3f, and the organic layer was extracted with ethyl acetate. The organic layer was dried over anhydrous sodium sulfate and concentrated under reduced pressure to give a crude product (0.090 g) of 1-((2S,4R)-2-methyl-4-{[4-(5,6,7,8-tetrahydroimidazo[1,2-a]pyrazin-2-yl)phenyl]amino}-3,4-dihydroquinolin-1(2H)-yl)propan-1-one.
ESIMS, (M+H)⁺, m/z: 430.
(Step 2)

The crude product (0.09 g) of 1-((2S,4R)-2-methyl-4-{[4-(5,6,7,8-tetrahydroimidazo[1,2-a]pyrazin-2-yl)phenyl]amino}-3,4-dihydroquinolin-1(2H)-yl)propan-1-one obtained in step 3 of example 3f was dissolved in methanol (2 mL9, then tert-butyl (4-formylphenyl)((2S,4R)-2-methyl-1-propionyl-1,2,3,4-tetrahydroquinolin-4-yl)carbamate (0.091 g, 0.22 mmol) obtained in reference example 8 and acetic acid (0.08 mL, 1.30 mmol) were added to the solution, and the mixture was stirred at room temperature for 40 minutes. Sodium cyanoborohydride (0.041 g, 0.65 mmol) was added to the reaction mixture, and the mixture was stirred at room temperature for 6 hours. The reaction mixture was diluted with water, and the aqueous layer was extracted with ethyl acetate. The organic layer was dried over anhydrous sodium sulfate and concentrated under reduced pressure to give a crude product (0.120 g) of tert-butyl ((2S,4R)-2-methyl-1-propionyl-1,2,3,4-tetrahydroquinolin-4-yl)(4-((2-(4-(((2S,4R)-2-methyl-1-propionyl-1,2,3,4-tetrahydroquinolin-4-yl)amino)phenyl)-5,6-dihydroimidazo[1,2-a]pyrazin-7(8H)-yl)methyl)phenyl)carbamate.
ESIMS, (M+H)⁺, m/z: 822.

(Step 3)

Compound 5b (0.020 g, yield of 3 steps 10%) was obtained from the crude product (0.140 g, 0.17 mmol) of tert-butyl ((2S,4R)-2-methyl-1-propionyl-1,2,3,4-tetrahydroquinolin-4-yl)(4-((2-(4-(((2S,4R)-2-methyl-1-propionyl-1,2,3,4-tetrahydroquinolin-4-yl)amino)phenyl)-5,6-dihydroimidazo[1,2-a]pyrazin-7(8H)-yl)ethyl)phenyl)carbamate obtained in step 2 in the same manner as in step 2 of example 1a.
ESIMS, (M+H)⁺, m/z: 722. ¹H-NMR (DMSO-d₆, δ) 0.96-1.08 (m, 12H), 1.11-1.28 (m, 2H), 2.18-2.28 (m, 2H), 2.55-2.64 (m, 4H), 2.81 (t, J=5.36 Hz, 2H), 3.52 (d, J=16.93 Hz, 4H), 3.93 (t, J=5.25 Hz, 2H), 4.10-4.20 (m, 2H), 4.68-4.80 (m, 2H), 5.99-6.05 (m, 2H), 6.62 (t, J=8.4 Hz, 4H), 7.08 (d, J=8.34 Hz, 2H), 7.15-7.22 (m, 5H), 7.23-7.32 (m, 4H), 7.42 (d, J=8.4 Hz, 2H).

Example 5c 1,1'-((2S,2'S,4R,4'R)-((((5,6-Dihydroimidazo[1,2-a]pyrazine-3,7(8H)-diyl)bis(methylene))bis(4,1-phenylene))bis(azanediyl))bis(2-methyl-3,4-dihydroquinoline-4,1(2H)-diyl))bis(propan-1-one) (Compound 5c) (Step 1)

Commercially available tert-butyl 3-bromo-5,6-dihydroimidazo[1,2-a]pyrazine-7(8H)-carboxylate (0.644 g, 2.13 mmol) was dissolved in THF (5 mL), then isopropylmagnesium chloride-lithium chloride (1.3 mol/L THF solution, 2.46 mL, 3.20 mmol) was added to the solution at 0° C., and the mixture was stirred at 0° C. for 30 minutes. tert-Butyl (4-formylphenyl)((2S,4R)-2-methyl-1-propionyl-1,2,3,4-tetrahydroquinolin-4-yl)carbamate (0.3 g, 0.71 mmol) obtained in reference example 8 was added to the reaction mixture at 0° C., and the mixture was stirred at 0° C. for 30 minutes. The reaction mixture was diluted with saturated aqueous ammonium chloride solution, and the aqueous layer was extracted with ethyl acetate. The organic layer was dried over anhydrous sodium sulfate and concentrated under reduced pressure. The obtained residue was purified by silica gel column chromatography (petroleum ether/ethyl acetate=1/4) to give tert-butyl 3-((4-((tert-butoxycarbonyl)((2S,4R)-2-methyl-1-propionyl-1,2,3,4-tetrahydroquinolin-4-yl)amino)phenyl)(hydroxy)methyl)-5,6-dihydroimidazo[1,2-a]pyrazine-7(8H)-carboxylate (0.150 g, 32%).
ESIMS, (M+H)⁺, m/z: 646.
(Step 2)

tert-Butyl 3-((4-((tert-butoxycarbonyl)((2S,4R)-2-methyl-1-propionyl-1,2,3,4-tetrahydroquinolin-4-yl)amino)phenyl)(hydroxy)methyl)-5,6-dihydroimidazo[1,2-a]pyrazine-7(8H)-carboxylate (0.100 g, 0.15 mmol) obtained in step 1 was dissolved in trifluoroacetic acid (1 mL), then triethylsilane was added to the solution, and the mixture was stirred at room temperature for 1 hour. The reaction mixture was concentrated under reduced pressure to give a crude product (0.085 g) of 1-((2S,4R)-2-methyl-4-((4-((5,6,7,8-tetrahydroimidazo[1,2-a]pyrazin-3-yl)methyl)phenyl)amino)-3,4-dihydroquinolin-1(2H)-yl)propan-1-one trifluoroacetate.
ESIMS, (M−TFA+H)⁺, m/z: 430.
(Step 3)

A saturated aqueous sodium hydrogen carbonate solution was added to crude product (0.120 g) of 1-((2S,4R)-2-methyl-4-((4-((5,6,7,8-tetrahydroimidazo[1,2-a]pyrazin-3-yl)methyl)phenyl)amino)-3,4-dihydroquinolin-1(2H)-yl)propan-1-one trifluoroacetate obtained in step 2, and the organic layer was extracted with ethyl acetate. The organic layer was dried over anhydrous sodium sulfate and concentrated under reduced pressure to give a crude product (0.090 g) of 1-((2S,4R)-2-methyl-4-((4-((5,6,7,8-tetrahydroimidazo[1,2-a]pyrazin-3-yl)methyl)phenyl)amino)-3,4-dihydroquinolin-1(2H)-yl)propan-1-one.
ESIMS, (M+H)⁺, m/z: 430.

(Step 4)
tert-Butyl ((2S,4R)-2-methyl-1-propionyl-1,2,3,4-tetrahydroquinolin-4-yl)(4-((3-(4-(a2S,4R)-2-methyl-1-propionyl-1,2,3,4-tetrahydroquinolin-4-yl)amino)benzyl)-5,6-dihydroimidazo[1,2-a]pyrazin-7(8H)-yl)methyl)phenyl)carbamate (0.120 g, total yield of 3 steps 68%) was obtained from the crude product (0.090 g) of 1-((2S,4R)-2-methyl-4-((4-((5,6,7,8-tetrahydroimidazo[1,2-a]pyrazin-3-yl)methyl)phenyl)amino)-3,4-dihydroquinolin-1(2H)-yl)propan-1-one obtained in step 3 and tert-butyl (4-formylphenyl)((2S,4R)-2-methyl-1-propionyl-1,2,3,4-tetrahydroquinolin-4-yl)carbamate (0.088 g, 0.21 mmol) obtained in reference example 8 in the same manner as in step 2 of example 5b.
ESIMS, (M+H)⁺, m/z: 836.

(Step 5)
Compound 5c (0.027 g, 26%) was obtained from tert-butyl ((2S,4R)-2-methyl-1-propionyl-1,2,3,4-tetrahydroquinolin-4-yl)(4-((3-(4-(a2S,4R)-2-methyl-1-propionyl-1,2,3,4-tetrahydroquinolin-4-yl)amino)benzyl)-5,6-dihydroimidazo[1,2-a]pyrazin-7(8H)-yl)methyl)phenyl)carbamate (0.120 g, 0.14 mmol) obtained in step 4 in the same manner as in step 2 of example 1a.
ESIMS, (M+H)⁺, m/z: 736; ¹H-NMR (DMSO-d₆, δ) 0.97-1.05 (m, 12H), 1.12-1.22 (m, 2H), 2.18-2.32 (m, 2H), 2.57-2.61 (m, 4H), 2.68-2.78 (m, 2H), 3.45 (s, 2H), 3.50 (s, 2H), 3.61-3.70 (m, 2H), 3.73 (s, 2H), 4.05-4.15 (m, 2H), 4.71-4.73 (m, 2H), 5.93 (d, J=7.6 Hz, 1H), 6.02 (d, J=7.6 Hz, 1H), 6.50 (s, 1H), 6.59 (dd, J=12.99, 8.46 Hz, 4H), 6.90 (d, J=8.4 Hz, 2H), 7.03 (d, J=8.4 Hz, 2H), 7.14-7.19 (m, 4H), 7.22-7.30 (m, 4H).

Example 5d 2,2'-Azanediylbis(N-(4-(((2S,4R)-2-methyl-1-propionyl-1,2,3,4-tetrahydroquinolin-4-yl)amino)phenyl)acetamide) (Compound 5d)

(Step 1)
tert-Butyl N-(((9H-fluoren-9-yl)methoxy)carbonyl)-N-(2-((4-(a2S,4R)-2-methyl-1-propionyl-1,2,3,4-tetrahydroquinolin-4-yl)amino)phenyl)amino)-2-oxoethyl)glycinate (250 mg, 97%) was obtained from 1-{(2S,4R)-4-[(4-aminophenyl)amino]-2-methyl-3,4-dihydroquinolin-1(2H)-yl}propan-1-one (0.112 g, 0.36 mmol) and N-(((9H-fluoren-9-yl)methoxy)carbonyl)-N-(2-(tert-butoxy)-2-oxoethyl)glycine (0.150 g, 0.36 mmol) obtained in reference example 7 in the same manner as in step 3 of example 1b.
ESIMS, (M+H)⁺, m/z: 703.48.

(Step 2)
tert-Butyl N-M9H-fluoren-9-yl)methoxy)carbonyl)-N-(2-((4-(((2S,4R)-2-methyl-1-propionyl-1,2,3,4-tetrahydroquinolin-4-yl)amino)phenyl)amino)-2-oxoethyl)glycinate (240 mg, 0.34 mmol) obtained in step 1 was dissolved in dichloromethane (3 mL), then trifluoroacetic acid (1.5 mL) was added to the solution under ice cooling, and the mixture was stirred for 2 hours. The reaction mixture was concentrated under reduced pressure to give a crude product (0.200 g) of N-(((9H-fluoren-9-yl)ethoxy)carbonyl)-N-(2-((4-(((2S,4R)-2-methyl-1-propionyl-1,2,3,4-tetrahydroquinolin-4-yl)amino)phenyl)amino)-2-oxoethyl)glycine.
ESIMS, (M+H)⁺, m/z: 647.02.

(Step 3)
A crude product (0.200 g) of (9H-fluoren-9-yl)methyl bis(2-((4-(((2S,4R)-2-methyl-1-propionyl-1,2,3,4-tetrahydroquinolin-4-yl)amino)phenyl)amino)-2-oxoethyl)carbamate was obtained from the crude product (0.200 g) of N-(((9H-fluoren-9-yl)methoxy)carbonyl)-N-(2-((4-(((2S,4R)-2-methyl-1-propionyl-1,2,3,4-tetrahydroquinolin-4-yl)amino)phenyl)amino)-2-oxoethyl)glycine obtained in step 2 and 1-{(2S,4R)-4-[(4-aminophenyl)amino]-2-methyl-3,4-dihydroquinolin-1(2H)-yl}propan-1-one (0.095 g, 0.31 mmol) obtained in reference example 7 in the same manner as in step 3 of example 1b.
ESIMS, (M+H)⁺, m/z: 938.60.

(Step 4)
Compound 5d (0.037 g, total yield of 3 steps 19%) was obtained from the crude product (0.250 g) of (9H-fluoren-9-yl)methyl bis(2-((4-(((2S,4R)-2-methyl-1-propionyl-1,2,3,4-tetrahydroquinolin-4-yl)amino)phenyl)amino)-2-oxoethyl)carbamate obtained in step 3 and in the same manner as in step 2 of example 2a.
ESIMS, (M+H)⁺, m/z: 716.21. ¹H-NMR (DMSO-d₆, δ): 0.98-1.04 (m, 12H), 1.13-1.17 (m, 2H), 2.20-2.26 (m, 2H), 2.53-2.61 (m, 4H), 3.29 (s, 4H), 4.10-4.14 (m, 2H), 4.72-4.74 (m, 2H), 5.87 (d, J=7.6 Hz, 2H), 6.60 (d, J=9.2 Hz, 4H), 7.16 (d, J=3.2 Hz, 4H), 7.23-7.35 (m, 8H), 9.63 (s, 2H).

Example 5e 1-((2S,4R)-2-Methyl-4-((4-(((1-(4-(((2S,4R)-2-methyl-1-propionyl-1,2,3,4-tetrahydroquinolin-4-yl)amino)benzoyl)azetidin-3-yl)amino)methyl)phenyl)amino)-3,4-dihydroquinolin-1(2H)-yl)propan-1-one (Compound 5e)

(Step 1)
tert-Butyl [1-(4-{[(2S,4R)-2-methyl-1-propionyl-1,2,3,4-tetrahydroquinolin-4-yl]amino}benzoyl)azetidin-3-yl]carbamate (0.160 g, 0.32 mmol) obtained in step 1 of example in was dissolved in dichloromethane (2 mL), then trifluoroacetic acid (1 mL) was added to the solution, and the mixture was stirred at room temperature for 1 hour. The reaction mixture was concentrated under reduced pressure, then the obtained residue was neutralized with a saturated aqueous sodium hydrogen carbonate solution, and the mixture was extracted with ethyl acetate. The organic layer was washed with saturated brine, dried over anhydrous sodium sulfate, and concentrated under reduced pressure to give 1-[(2S,4R)-4-{[4-(3-aminoazetidine-1-carbonyl)phenyl]amino}-2-methyl-3,4-dihydroquinolin-1(2H)-yl]propan-1-one (0.115 g, 90%).
ESIMS, (M+H)⁺, m/z: 393.66.

(Step 2)
tert-Butyl ((2S,4R)-2-methyl-1-propionyl-1,2,3,4-tetrahydroquinolin-4-yl)(4-(((1-(4-(((2S,4R)-2-methyl-1-propionyl-1,2,3,4-tetrahydroquinolin-4-yl)amino)benzoyl)azetidin-3-yl)amino)methyl)phenyl)carbamate (0.180 g, 76%) was obtained from 1-[(2S,4R)-4-{[4-(3-aminoazetidine-1-carbonyl)phenyl]amino}-2-methyl-3,4-dihydroquinolin-1(2H)-yl]propan-1-one (0.115 g, 0.29 mmol) obtained in step 1 and tert-butyl (4-formylphenyl)((2S,4R)-2-methyl-1-propionyl-1,2,3,4-tetrahydroquinolin-4-yl)carbamate (0.123 g, 0.29 mmol) obtained in reference example 8 in the same manner as in step 2 of example 5b.
ESIMS, (M+H)⁺, m/z: 799.79.

(Step 3)
Compound 5e (0.063 g, 41%) was obtained from tert-butyl ((2S,4R)-2-methyl-1-propionyl-1,2,3,4-tetrahydroquinolin-4-yl)(4-(((1-(4-(((2S,4R)-2-methyl-1-propionyl-1,2,3, 4-tetrahydroquinolin-4-yl)amino)benzoyl)azetidin-3-yl) amino)methyl)phenyl)carbamate (0.180 g, 0.22 mmol) obtained in step 2 in the same manner as in step 1.
ESI-MS m/z: 699.5 (M+H)+: $^1$H-NMR (DMSO-d$_6$, δ): 0.98-1.05 (m, 12H), 1.09-1.25 (m, 2H), 2.18-2.28 (m, 2H), 2.53-2.67 (m, 4H), 3.48-3.57 (m, 3H), 3.65-4.33 (m, 6H), 4.61-4.82 (m, 2H), 5.92 (d, J=7.67 Hz, 1H), 6.57-6.65 (m, 5H), 7.03 (d, J=8.55 Hz, 2H), 7.09-7.19 (m, 4H), 7.22-7.31 (m, 4H), 7.41 (d, J=8.8 Hz, 2H).

Example 5f 1-((2S,4R)-2-Methyl-4-((4-(((2-(4-(4-(((2S,4R)-2-methyl-1-propionyl-1,2,3,4-tetrahydroquinolin-4-yl)amino)phenyl)-1H-pyrazol-1-yl)ethyl)amino)methyl)phenyl)amino)-3,4-dihydroquinolin-1(2H)-yl)propan-1-one (Compound 5f)

tert-Butyl (4-formylphenyl)((2S,4R)-2-methyl-1-propionyl-1,2,3,4-tetrahydroquinolin-4-yl)carbamate (30 mg, 0.071 mmol) obtained in reference example 8 was dissolved in dichloromethane (1.5 mL), then 1-((2S,4R)-4-((4-(1-(2-aminoethyl)-1H-pyrazol-4-yl)phenyl)amino)-2-methyl-3,4-dihydroquinolin-1(2H)-yl)propan-1-one (28.7 mg, 0.071 mmol) obtained in step 2 of example 6q was added to the solution, and the mixture was stirred at room temperature for 10 minutes. Sodium triacetoxyborohydride (75 mg, 0.355 mmol) was added to the reaction mixture, and the mixture was stirred at room temperature for 2 hours. The reaction mixture was diluted with 1 mol/L aqueous sodium hydroxide solution, and the aqueous layer was extracted with chloroform. The organic layer was dried over anhydrous magnesium sulfate and concentrated under reduced pressure. The obtained residue was dissolved in dichloromethane (5 mL), then trifluoroacetic acid (1 mL) was added to the solution, and the mixture was stirred at room temperature for 30 min. The reaction mixture was neutralized with saturated aqueous sodium hydrogen carbonate solution, and the aqueous layer was extracted with chloroform. The organic layer was dried over anhydrous sodium sulfate and concentrated under reduced pressure. The obtained residue was purified by reverse phase HPLC (10 mmol/L aqueous ammonium bicarbonate solution/acetonitrile=50/50-40/60) to give compound 5f (46.3 mg, 92%).
ESIMS, (M+H)+, m/z: 710: $^1$H-NMR (CDCl$_3$, δ) 1.06-1.41 (m, 16H), 2.30-2.41 (m, 4H), 2.50-2.71 (m, 4H), 3.09 (t, J=5.2 Hz, 2H), 3.70 (s, 2H), 3.79 (d, J=7.6 Hz, 1H), 3.90 (d, J=7.6 Hz, $^1$H), 4.09-4.31 (m, 4H), 4.85-5.08 (m, 1H), 6.58 (d, J=8.8 Hz, 2H), 6.63 (d, J=8.8 Hz, 2H), 7.06-7.36 (m, 12H), 7.54 (s, 1H), 7.69 (s, 1H).

Example 5g 1-((2S,4R)-2-Methyl-4-((4-((((5-(4-(((2S,4R)-2-methyl-1-propionyl-1,2,3,4-tetrahydroquinolin-4-yl)amino)phenyl)-1,3,4-oxadiazol-2-yl)methyl)amino)methyl)phenyl)amino)-3,4-dihydroquinolin-1(2H)-yl)propan-1-one (Compound 5g)

(Step 1)
A crude product (468 mg) of tert-butyl (4-(2-((tert-butoxycarbonyl)glycyl)hydrazine-1-carbonyl)phenyl)((2S,4R)-2-methyl-1-propionyl-1,2,3,4-tetrahydroquinolin-4-yl) carbamate was obtained from 4-((tert-butoxycarbonyl)((2S,4R)-2-methyl-1-propionyl-1,2,3,4-tetrahydroquinolin-4-yl)amino)benzoic acid (300 mg, 0.684 mmol) obtained in step 2 of reference example 8 and tert-butyl (2-hydrazinyl-2-oxoethyl)carbamate (259 mg, 1.37 mmol) in the same manner as in step 3 of example 1b.
ESIMS, (M+H)+, m/z: 610.
(Step 2)
A crude product (374 mg) of tert-butyl (4-(5-(((tert-butoxycarbonyl)amino)methyl)-1,3,4-oxadiazol-2-yl)phenyl)((2S,4R)-2-methyl-1-propionyl-1,2,3,4-tetrahydroquinolin-4-yl)carbamate was obtained from the crude product (450 mg) of tert-butyl (4-(2-((tert-butoxycarbonyl)glycyl) hydrazine-1-carbonyl)phenyl)((2S,4R)-2-methyl-1-propionyl-1,2,3,4-tetrahydroquinolin-4-yl)carbamate obtained in step 1 in the same manner as in step 2 of example 3c.
ESIMS, (M+H)+, m/z: 592.
(Step 3)
The crude product (370 mg) of tert-Butyl (4-(5-(((tert-butoxycarbonyl)amino)methyl)-1,3,4-oxadiazol-2-yl)phenyl)((2S,4R)-2-methyl-1-propionyl-1,2,3,4-tetrahydroquinolin-4-yl)carbamate obtained in step 2 was dissolved in dichloromethane (10 mL), then trifluoroacetic acid (2 mL) was added to the solution, and the mixture was stirred at room temperature for 1 hour. The reaction mixture was diluted with ethyl acetate and washed twice with water. The organic layer was dried over anhydrous magnesium sulfate and concentrated under reduced pressure. The obtained residue was purified by column chromatography (chloroform/methanol=100/0 to 80/20) to give 1-((2S,4R)-4-((4-(5-(aminomethyl)-1,3,4-oxadiazol-2-yl)phenyl)amino)-2-methyl-3,4-dihydroquinolin-1(2H)-yl)propan-1-one (250 mg, total yield of 3 steps 97%).
ESIMS, (M+H)+, m/z: 392.
(Step 4)
Compound 5g (42.9 mg, total yield of 2 steps 87%) was obtained from tert-butyl (4-formylphenyl)((2S,4R)-2-methyl-1-propionyl-1,2,3,4-tetrahydroquinolin-4-yl)carbamate (30 mg, 0.071 mmol) obtained in reference example 8 and 1-[(2S,4R)-4-({4-[5-(aminomethyl)-1,3,4-oxadiazol-2-yl]phenyl}amino)-2-methyl-3,4-dihydroquinolin-1(2H)-yl]propan-1-one (27.8 mg, 0.071 mmol) obtained in step 3 in the same manner as in example 5f.
ESIMS, (M−H)−, m/z: 696: $^1$H-NMR (CDCl$_3$, δ) 1.06-1.41 (m, 16H), 2.31-2.46 (m, 2H), 2.52-2.65 (m, 3H), 2.67-2.78 (m, 1H), 3.79 (s, 2H), 4.06 (s, 2H), 4.06-4.17 (m, 1H), 4.21-4.40 (m, 2H), 4.81-5.08 (m, 2H), 6.58 (d, J=8.8 Hz, 2H), 6.68 (d, J=8.8 Hz, 2H), 7.09-7.38 (m, 10H), 7.85 (d, J=8.8 Hz, 2H).

Example 5h 1-((2S,4R)-2-Methyl-4-((4-(((((1-(4-(((2S,4R)-2-methyl-1-propionyl-1,2,3,4-tetrahydroquinolin-4-yl)amino)phenyl)-1H-1,2,3-triazol-4-yl)methyl)amino)methyl)phenyl)amino)-3,4-dihydroquinolin-1(2H)-yl)propan-1-one (Compound 5h)

(Step 1)
tert-Butyl ((2S,4R)-2-methyl-1-propionyl-1,2,3,4-tetrahydroquinolin-4-yl)(4-((prop-2-yn-1-ylamino)methyl)phenyl)carbamate (0.140 g, 85%) was obtained from tert-butyl (4-formylphenyl)((2S,4R)-2-methyl-1-propionyl-1,2,3,4-tetrahydroquinolin-4-yl)carbamate (0.150 g, 0.35 mmol) obtained in reference example 8 and prop-2-yn-1-amine (0.023 g, 0.42 mmol) in the same manner as in step 2 of example 5b. ESIMS, (M+H)+, m/z: 462.39.
(Step 2)
tert-Butyl ((2S,4R)-2-methyl-1-propionyl-1,2,3,4-tetrahydroquinolin-4-yl)(4-(((((1-(4-(((2S,4R)-2-methyl-1-propionyl-1,2,3,4-tetrahydroquinolin-4-yl)amino)phenyl)-1H-

1,2,3-triazol-4-yl)methyl)amino)methyl)phenyl)carbamate (0.130 g, 53%) was obtained from tert-butyl ((2S,4R)-2-methyl-1-propionyl-1,2,3,4-tetrahydroquinolin-4-yl)(4-((prop-2-yn-1-ylamino)methyl)phenyl)carbamate (0.140 g, 0.30 mmol) obtained in step 1 and the crude product (0.102 g) of 1-{(2S,4R)-4-[(4-azidophenyl)amino]-2-methyl-3,4-dihydroquinolin-1(2H)-yl}propan-1-one obtained in step 2 of example 3a in the same manner as in step 3 of example 5j.
ESIMS, (M+H)$^+$, m/z: 797.67.

(Step 3)
Compound 5h (0.040 g, 35%) was obtained from tert-butyl ((2S,4R)-2-methyl-1-propionyl-1,2,3,4-tetrahydroquinolin-4-yl)(4-((((1-(4-(a2S,4R)-2-methyl-1-propionyl-1,2,3,4-tetrahydroquinolin-4-yl)amino)phenyl)-1H-1,2,3-triazol-4-yl)methyl)amino)methyl)phenyl)carbamate (0.130 g, 0.16 mmol) obtained in step 2 in the same manner as in step 2 of example 1a.
ESI-MS m/z: 697.69 (M+H)$^+$: $^1$H-NMR (DMSO-d$_6$, δ): 0.98-1.07 (m, 12H), 1.13-1.26 (m, 2H), 2.21-2.28 (m, 2H), 2.55-2.66 (m, 4H), 3.76 (s, 2H), 3.94 (s, 2H), 4.10-4.19 (m, 1H), 4.21-4.31 (m, 1H), 4.65-4.84 (m, 2H), 6.05 (d, J=7.34 Hz, 1H), 6.50 (d, J=7.82 Hz, 1H), 6.63 (d, J=8.31 Hz, 2H), 6.80 (d, J=8.56 Hz, 2H), 7.13-7.20 (m, 6H), 7.24-7.33 (m, 4H), 7.54 (d, J=8.56 Hz, 2H), 8.44 (s, 1H).

Example 5i 2-((4-(((2S,4R)-2-Methyl-1-propionyl-1,2,3,4-tetrahydroquinolin-4-yl)amino)benzyl)amino)-N-(4-(((2S,4R)-2-methyl-1-propionyl-1,2,3,4-tetrahydroquinolin-4-yl)amino)phenyl)acetamide hydrochloride (Compound 5i)

(Step 1)
A crude product (0.170 g) of tert-butyl (2-((4-(((2S,4R)-2-methyl-1-propionyl-1,2,3,4-tetrahydroquinolin-4-yl)amino)phenyl)amino)-2-oxoethyl)carbamate was obtained from 1-{(2S,4R)-4-[(4-aminophenyl)amino]-2-methyl-3,4-dihydroquinolin-1(2H)-yl}propan-1-one (0.150 g, 0.48 mmol) obtained in reference example 7 and (tert-butoxycarbonyl)glycine (0.084 g, 0.48 mmol) in the same manner as in step 3 of example 1b.
ESIMS, (M+H)$^+$, m/z: 467.28.

(Step 2)
A crude product (0.130 g) of 2-amino-N-(4-(((2S,4R)-2-methyl-1-propionyl-1,2,3,4-tetrahydroquinolin-4-yl)amino)phenyl)acetamide hydrochloride was obtained from the crude product (0.170 g) of tert-butyl (2-((4-(((2S,4R)-2-methyl-1-propionyl-1,2,3,4-tetrahydroquinolin-4-yl)amino)phenyl)amino)-2-oxoethyl)carbamate obtained in step 1 in the same manner as in step 2 of example 1a.
ESIMS, (M+H)$^+$, m/z: 367.25.

(Step 3)
A crude product (0.120 g) of tert-butyl ((2S,4R)-2-methyl-1-propionyl-1,2,3,4-tetrahydroquinolin-4-yl)(4-(((2-((4-(((2S,4R)-2-methyl-1-propionyl-1,2,3,4-tetrahydroquinolin-4-yl)amino)phenyl)amino)-2-oxoethyl)amino)methyl)phenyl)carbamate was obtained from the crude product (0.130 g) of 2-amino-N-(4-(a2S,4R)-2-methyl-1-propionyl-1,2,3,4-tetrahydroquinolin-4-yl)amino)phenyl)acetamide hydrochloride obtained in step 2 and tert-butyl (4-formylphenyl)((2S,4R)-2-methyl-1-propionyl-1,2,3,4-tetrahydroquinolin-4-yl)carbamate (0.136 g, 0.32 mmol) obtained in reference example 8 in the same manner as in step 2 of example 5b.
ESIMS, (M+H)$^+$, m/z: 773.70.

(Step 4)
Compound 5i (0.030 g, total yield of 3 steps 28%) was obtained from the crude product (0.120 g) of tert-butyl ((2S,4R)-2-methyl-1-propionyl-1,2,3,4-tetrahydroquinolin-4-yl)(4-(((2-((4-(((2S,4R)-2-methyl-1-propionyl-1,2,3,4-tetrahydroquinolin-4-yl)amino)phenyl)amino)-2-oxoethyl)amino)methyl)phenyl)carbamate obtained in step 3 in the same manner as in step 2 of example 1a.
ESIMS, (M+H)$^+$, m/z: 673.61. $^1$H-NMR (DMSO-d$_6$, δ): 0.99-1.05 (m, 12H), 1.12-1.20 (m, 1H), 2.20-2.27 (m, 2H), 2.56-2.63 (m, 4H), 3.67-3.78 (m, 2H), 4.03-4.21 (m, 4H), 4.73-4.75 (m, 2H), 5.99-6.05 (m, 1H), 6.29-6.32 (m, 1H), 6.62-6.69 (m, 4H), 7.08-7.18 (m, 4H), 7.22-7.32 (m, 8H), 9.15 (brs, 2H), 10.18 (s, 1H).

Example 5j 1-(4-(((2S,4R)-2-Methyl-1-propionyl-1,2,3,4-tetrahydroquinolin-4-yl)amino)benzyl)-N-(4-(((2S,4R)-2-methyl-1-propionyl-1,2,3,4-tetrahydroquinolin-4-yl)amino)phenyl)-1H-1,2,3-triazole-4-carboxamide (Compound 5j)

(Step 1)
N-(4-(((2S,4R)-2-Methyl-1-propionyl-1,2,3,4-tetrahydroquinolin-4-yl)amino)phenyl)propiolamide (0.140 g, 80%) was obtained from 1-{(2S,4R)-4-[(4-aminophenyl)amino]-2-methyl-3,4-dihydroquinolin-1(2H)-yl}propan-1-one (0.150 g, 0.48 mmol) obtained in reference example 7 and propiolic acid (0.036 g, 0.51 mmol) in the same manner as in step 3 of example 1b.
ESIMS, (M+H)$^+$, m/z: 362.25.

(Step 2)
tert-Butyl (4-(hydroxymethyl)phenyl)((2S,4R)-2-methyl-1-propionyl-1,2,3,4-tetrahydroquinolin-4-yl)carbamate (0.150 g, 0.35 mmol) obtained in step 3 of reference example 8 was dissolved in toluene (3 mL), then DPPA (0.11 mL, 0.53 mmol) and DBU (0.1 mL, 0.70 mmol) were added to the solution, and the mixture was stirred at room temperature for 16 hours. Water (3 mL) was added to the reaction mixture, and the mixture was extracted with ethyl acetate. The organic layer was dried over anhydrous sodium sulfate, and concentrated under reduced pressure to give a crude product (0.180 g) of tert-butyl (4-(azidomethyl)phenyl)((2S,4R)-2-methyl-1-propionyl-1,2,3,4-tetrahydroquinolin-4-yl)carbamate. ESIMS, (M+H)$^+$, m/z: 450.29.

(Step 3)
N-(4-(((2S,4R)-2-Methyl-1-propionyl-1,2,3,4-tetrahydroquinolin-4-yl)amino)phenyl)propiolamide (0.085 g, 0.23 mmol) obtained in step 1 and the crude product (0.180 g) of tert-butyl (4-(azidomethyl)phenyl)((2S,4R)-2-methyl-1-propionyl-1,2,3,4-tetrahydroquinolin-4-yl)carbamate obtained in step 2 were dissolved in t-butanol (2 mL), then sodium L-ascorbate (9 mg, 0.05 mmol), copper sulfate pentahydrate (6 mg, 0.023 mmol) and water (1 mL) were added to the solution, and the mixture was stirred at room temperature for 16 hours. The reaction mixture was diluted with water and extracted with ethyl acetate. The organic layer was dried over anhydrous sodium sulfate and concentrated under reduced pressure. The obtained residue was purified by reverse phase column chromatography (acetonitrile/0.1% formic acid aqueous solution=45/55) to give tert-butyl ((2S,4R)-2-methyl-1-propionyl-1,2,3,4-tetrahydroquinolin-4-yl)(4-((4-((4-(((2S,4R)-2-methyl-1-propionyl-1,2,3,4-tetrahydroquinolin-4-yl)amino)phenyl)carbamoyl)-1H-1,2,3-triazol-1-yl)ethyl)phenyl)carbamate (0.100 g, 52%).
ESIMS, (M+H)$^+$, m/z: 811.58.

(Step 4)

Compound 5j (0.020 g, 23%) was obtained from tert-butyl ((2S,4R)-2-methyl-1-propionyl-1,2,3,4-tetrahydroquinolin-4-yl)(4-((4-((4-(a2S,4R)-2-methyl-1-propionyl-1,2,3,4-tetrahydroquinolin-4-yl)amino)phenyl)carbamoyl)-1H-1,2,3-triazol-1-yl)methyl)phenyl)carbamate (0.1 g, 0.12 mmol) obtained in step 3 in the same manner as in step 2 of example 1a.
ESIMS, (M+H)$^+$, m/z: 711.50. 1H NMR (DMSO-d$_6$, δ): 0.98-1.12 (m, 12H), 1.15-1.17 (m, 2H), 2.20-2.27 (m, 2H), 2.51-2.62 (m, 4H), 4.11-4.17 (m, 2H), 4.71-4.74 (m, 2H), 5.47 (s, 2H), 5.96 (d, J=7.87 Hz, 1H), 6.22 (d, J=7.63 Hz, 1H), 6.60-6.65 (m, 4H), 7.10-7.18 (m, 6H), 7.23-7.30 (m, 4H), 7.48 (d, J=8.82 Hz, 2H), 8.61 (s, 1H), 10.03 (s, 1H).

Example 5k

N-(4-(((2S,4R)-2-Methyl-1-propionyl-1,2,3,4-tetrahydroquinolin-4-yl)amino)phenyl)-2-(4-(4-(((2S,4R)-2-methyl-1-propionyl-1,2,3,4-tetrahydroquinolin-4-yl)amino)phenyl)-3,6-dihydropyridin-1(2H)-yl) acetamide (Compound 5k)

(Step 1)

1-((2S,4R)-4-((4-Bromophenyl)amino)-2-methyl-3,4-dihydroquinolin-1(2H)-yl)propan-1-one (300 mg, 0.804 mmol) obtained in reference example 2 and tert-butyl 4-(4,4,5,5-tetramethyl-1,3,2-dioxaborolan-2-yl)-3,6-dihydropyridine-1(2H)-carboxylate (373 mg, 1.21 mmol) were dissolved in a mixed solvent of 1,4-dioxane (2.5 mL) and water (1.0 mL), then Pd(dppf)Cl$_2$ dichloromethane complex (65.6 mg, 0.080 mmol) and potassium phosphate (512 mg, 2.41 mmol) were added to the solution, and the mixture was stirred at 100° C. overnight. The reaction mixture was cooled to room temperature and filtered through diatomaceous earth. The filtrate was concentrated under reduced pressure, and the obtained residue was purified by silica gel column chromatography (heptane/ethyl acetate=8/2 to 5/5) to give tert-butyl 4-(4-(((2S,4R)-2-methyl-1-propionyl-1,2,3,4-tetrahydroquinolin-4-yl)amino)phenyl)-3,6-dihydropyridine-1(2H)-carboxylate (348 mg, 91%).
ESI-MS, (M+H)$^+$, m/z: 476.

(Step 2)

A crude product (275 mg) of 1-((2S,4R)-2-methyl-4-((4-(1,2,3,6-tetrahydropyridin-4-yl)phenyl)amino)-3,4-dihydroquinolin-1(2H)-yl)propan-1-one trifluoroacetate was obtained from tert-butyl 4-(4-(((2S,4R)-2-methyl-1-propionyl-1,2,3,4-tetrahydroquinolin-4-yl)amino)phenyl)-3,6-dihydropyridine-1(2H)-carboxylate (348 mg, 0.732 mmol) obtained in step 1 in the same manner as in step 2 of example 1k.
ESI-MS, (M+H)$^+$, m/z: 376.

(Step 3)

The crude product (275 mg) of 1-((2S,4R)-2-methyl-4-((4-(1,2,3,6-tetrahydropyridin-4-yl)phenyl)amino)-3,4-dihydroquinolin-1(2H)-yl)propan-1-one trifluoroacetate obtained in step 2 was dissolved in DMF (5 mL), then tert-butyl bromoacetate (0.161 mL, 1.10 mmol) and cesium carbonate (716 mg, 2.2 mmol) were added to the solution, and the mixture was stirred at room temperature overnight. Water was added to the reaction mixture, and the mixture was extracted with ethyl acetate. The organic layer was washed twice with water and once with saturated brine, dried over magnesium sulfate, and concentrated under reduced pressure to give a crude product (421 mg) of tert-butyl 2-(4-(4-(a2S,4R)-2-methyl-1-propionyl-1,2,3,4-tetrahydroquinolin-4-yl)amino)phenyl)-3,6-dihydropyridin-1(2H)-yl)acetate.
ESI-MS, (M+H)$^+$, m/z: 490.

(Step 4)

A crude product (100 mg) of 2-(4-(4-(((2S,4R)-2-methyl-1-propionyl-1,2,3,4-tetrahydroquinolin-4-yl)amino)phenyl)-3,6-dihydropyridin-1(2H)-yl)acetic acid trifluoroacetate was obtained from the crude product (421 mg) of tert-butyl 2-(4-(4-(((2S,4R)-2-methyl-1-propionyl-1,2,3,4-tetrahydroquinolin-4-yl)amino)phenyl)-3,6-dihydropyridin-1(2H)-yl)acetate obtained in step 3 in the same manner as in step 2 of example 1k.
ESI-MS, (M+H)$^+$, m/z: 434.

(Step 5)

A crude product of compound 5k was obtained from the crude product (40 mg) of 2-(4-(4-(((2S,4R)-2-methyl-1-propionyl-1,2,3,4-tetrahydroquinolin-4-yl)amino)phenyl)-3,6-dihydropyridin-1(2H)-yl)acetic acid trifluoroacetate obtained in step 4 and 1-{(2S,4R)-4-[(4-aminophenyl)amino]-2-methyl-3,4-dihydroquinolin-1(2H)-yl}propan-1-one (35 mg, 0.112 mmol) obtained in step 3 of reference example 7 in the same manner as in step 3 of example 1b. The crude product obtained was purified by reverse phase HPLC (10 mmol/L aqueous ammonium bicarbonate solution/acetonitrile=45/55 to 35/65) to give compound 5k (4 mg, total yield of 4 steps 6%).
ESI-MS, (M+H)$^+$, m/z: 725. $^1$H-NMR (CDCl$_3$) δ: 1.11-1.19 (m, 12H), 2.20-2.25 (m, 1H), 2.32-2.42 (m, 2H), 2.51-2.71 (m, 6H), 2.85 (t, J=5.7 Hz, 2H), 3.24 (s, 2H), 3.31 (d, J=2.7 Hz, 2H), 3.78 (d, J=8.2 Hz, 1H), 3.90 (d, J=7.2 Hz, 1H), 4.13-4.24 (m, 2H), 4.89-4.99 (m, 2H), 5.32-5.37 (m, 1H), 5.98 (s, 1H), 6.59-6.64 (m, 4H), 7.13-7.22 (m, 4H), 7.25-7.32 (m, 6H), 7.39 (d, J=9.1 Hz, 2H), 9.03 (s, 1H).

Example 5l

N-(4-(((2S,4R)-2-Methyl-1-propionyl-1,2,3,4-tetrahydroquinolin-4-yl)amino)phenyl)-3-((4-(((2S,4R)-2-methyl-1-propionyl-1,2,3,4-tetrahydroquinolin-4-yl)amino)phenyl)sulfonyl)propanamide (Compound 5l)

(Step 1)

N-(4-(((2S,4R)-2-Methyl-1-propionyl-1,2,3,4-tetrahydroquinolin-4-yl)amino)phenyl)-3-((4-(((2S,4R)-2-methyl-1-propionyl-1,2,3,4-tetrahydroquinolin-4-yl)amino)phenyl)thio)propanamide (0.4 g, 62%) was obtained from 3-[(4-{[(2S,4R)-2-methyl-1-propionyl-1,2,3,4-tetrahydroquinolin-4-yl]amino}phenyl)thio]propanoic acid (0.370 g, 0.93 mmol) obtained in step 2 of example 4e and 1-{(2S,4R)-4-[(4-aminophenyl)amino]-2-methyl-3,4-dihydroquinolin-1(2H)-yl}propan-1-one (0.287 g, 0.93 mmol) obtained in step 3 of reference example 7 in the same manner as in step 3 of example 1b.
ESIMS, (M+H)$^+$, m/z: 690.

(Step 2)

N-(4-(((2S,4R)-2-Methyl-1-propionyl-1,2,3,4-tetrahydroquinolin-4-yl)amino)phenyl)-3-((4-(((2S,4R)-2-methyl-1-propionyl-1,2,3,4-tetrahydroquinolin-4-yl)amino)phenyl)thio)propanamide (0.2 g, 0.29 mmol) obtained in step 1 was dissolved in dichloromethane (4 mL), then meta-chloroperbenzoic acid (60% w/w (water content), 0.167 g, 0.58 mmol) was added to the solution at 0° C., and the mixture was stirred at room temperature for 2 hours. The reaction mixture was diluted with water and the aqueous layer was extracted with dichloromethane. The organic layer was washed with saturated aqueous sodium hydrogen carbonate solution, dried over anhydrous sodium sulfate, and concentrated under reduced pressure. The obtained residue was purified by reverse phase HPLC (10 mmol/L aqueous ammonium bicarbonate solution/acetonitrile=40/60 to 10/90) to give compound 5l (0.027 g, 13%). ESIMS, (M+H)$^+$, m/z: 722: $^1$H-NMR (DMSO-d$_6$, δ) 0.97-1.05 (m, 12H), 1.13-1.21 (m, 2H), 2.19-2.26 (m, 2H), 2.54-2.62 (m, 6H), 3.40 (t, J=7.56 Hz, 2H), 4.08-4.13 (m, 1H), 4.25-4.34 (m, $^1$H), 4.71-4.74 (m, 2H), 5.86 (d, J=7.89 Hz, 1H), 6.57 (d, J=8.99 Hz, 2H), 6.78 (d, J=8.77 Hz, 2H), 7.07 (t, J=8.0 Hz, 2H), 7.14-7.33 (m, 9H), 7.56 (d, J=8.99 Hz, 2H), 9.69 (s, 1H).

Example 5m

N-(4-(((2S,4R)-2-Methyl-1-propionyl-1,2,3,4-tetrahydroquinolin-4-yl)amino)phenyl)-3-((4-(((2S,4R)-2-methyl-1-propionyl-1,2,3,4-tetrahydroquinolin-4-yl)amino)phenyl)sulfinyl)propanamide (Compound 5m)

N-(4-(((2S,4R)-2-Methyl-1-propionyl-1,2,3,4-tetrahydroquinolin-4-yl)amino)phenyl)-3-((4-(a2S,4R)-2-methyl-1-propionyl-1,2,3,4-tetrahydroquinolin-4-yl)amino)phenyl)thio)propanamide (0.150 g, 0.22 mmol) obtained in step 1 of example 5l was dissolved in dichloromethane (2 mL), then meta-chloroperbenzoic acid (60% w/w (containing water), 0.037 g, 0.13 mmol) was added to the solution at 0° C., and the mixture was stirred at room temperature for 2 hours. The reaction mixture was diluted with water and the aqueous layer was extracted with dichloromethane. The organic layer was washed with saturated aqueous sodium hydrogen carbonate solution, dried over anhydrous sodium sulfate, and concentrated under reduced pressure. The obtained residue was purified by reverse phase HPLC (10 mmol/L aqueous ammonium bicarbonate solution/acetonitrile=55/45 to 19/81) to give compound 5m (0.042 g, 27%). ESIMS, (M+H)$^+$, m/z: 706: $^1$H-NMR (DMSO-d$_6$, δ) 0.98-1.05 (m, 12H), 1.10-1.25 (m, 2H), 2.20-2.27 (m, 2H), 2.38-2.45 (m, 1H), 2.53-2.64 (m, 5H), 2.94-3.01 (m, 1H), 3.06-3.13 (m, 1H), 4.07-5.13 (m, 1H), 4.22-4.28 (m, 1H), 4.71-4.76 (m, 2H), 5.85 (d, J=8.0 Hz, 1H), 6.57 (d, J=8.77 Hz, 2H), 6.65 (dd, J=7.2, 2.0 Hz, 1H), 6.80 (d, J=8.4 Hz, 2H), 7.11-7.19 (m, 4H), 7.24-7.32 (m, 6H), 7.38-7.40 (m, 2H), 9.64 (s, 1H).

Example 5n 4-(((2S,4R)-2-Methyl-1-propionyl-1,2,3,4-tetrahydroquinolin-4-yl)amino)-N-(2-(4-(((2S,4R)-2-methyl-1-propionyl-1,2,3,4-tetrahydroquinolin-4-yl)amino)phenoxy)ethyl)benzamide (Compound 5n)

(Step 1)
1-((2S,4R)-4-((4-Bromophenyl)amino)-2-methyl-3,4-dihydroquinolin-1(2H)-yl)propan-1-one (500 mg, 1.34 mmol) obtained in reference example 2 was dissolved in 1,4-dioxane (10 mL), then bis(pinacolato)diboron (395 mg, 1.61 mmol) and potassium acetate (276 mg, 2.82 mmol) were added to the solution, and the mixture was stirred at room temperature for 5 minutes under an argon atmosphere. PdCl$_2$(dppf) dichloromethane complex (49 mg, 0.067 mmol) was added to the mixture, and the mixture was stirred at 100° C. for 16 hr under an argon atmosphere. The reaction mixture was filtered through Celite, and the filtrate was concentrated under reduced pressure. The obtained residue was purified by silica gel column chromatography (hexane/ethyl acetate=100/0 to 70/30) to give 1-((2S,4R)-2-methyl-4-((4-(4,4,5,5-tetramethyl-1,3,2-dioxaborolan-2-yl)phenyl)amino)-3,4-dihydroquinolin-1(2H)-yl)propan-1-one (380 mg, 67%).
ESI-MS m/z: 421 (M+H)$^+$ (Step 2)
1-((2S,4R)-2-Methyl-4-((4-(4,4,5,5-tetramethyl-1,3,2-dioxaborolan-2-yl)phenyl)amino)-3,4-dihydroquinolin-1(2H)-yl)propan-1-one (380 mg, 0.900 mmol) obtained in step 1 was dissolved in THF (5 mL), then 30% aqueous hydrogen peroxide solution (0.51 mL, 4.52 mmol) was added to the solution under ice cooling, and the mixture was stirred at room temperature for 16 hours. Water was added to the reaction mixture, and the mixture was extracted with ethyl acetate. The organic layer was dried over anhydrous sodium sulfate and concentrated under reduced pressure. The obtained residue was purified by silica gel column chromatography (petroleum ether/ethyl acetate=100/0 to 70/30) to give 1-((2S,4R)-4-((4-hydroxyphenyl)amino)-2-methyl-3,4-dihydroquinolin-1(2H)-yl)propan-1-one (190 mg, 68%).
ESI-MS m/z: 311 (M+H)$^+$ (Step 3)
1-((2S,4R)-4-((4-hydroxyphenyl)amino)-2-methyl-3,4-dihydroquinolin-1(2H)-yl)propan-1-one (300 mg, 0.97 mmol) obtained in step 2 was dissolved in acetonitrile (5 mL), then potassium carbonate (400 mg, 2.90 mmol) and tert-butyl (2-bromoethyl)carbamate (431 mg, 1.93 mmol) were added to the solution, and the mixture was stirred at 80° C. for 16 hours. The reaction mixture was filtered through Celite, and the filtrate was concentrated under reduced pressure. The obtained residue was purified by reverse phase silica gel column chromatography (acetonitrile/0.1% formic acid=50/50) to give a crude product (300 mg) of tert-butyl (2-(4-(((2S,4R)-2-methyl-1-propionyl-1,2,3,4-tetrahydroquinolin-4-yl)amino)phenoxy)ethyl)carbamate. 1-((2S,4R)-4-((4-(2-aminoethoxy)phenyl)amino)-2-methyl-3,4-dihydroquinolin-1(2H)-yl)propan-1-one hydrochloride (200 mg, 77%) was obtained from the crude product obtained (0.03 g, 0.07 mmol) in the same manner as in step 2 of example 1a.
ESI-MS m/z: 354 (M+H)$^+$ (Step 4)
Compound 5n (13 mg, 37%) was obtained from 1-((2S,4R)-4-((4-(2-aminoethoxy)phenyl)amino)-2-methyl-3,4-dihydroquinolin-1(2H)-yl)propan-1-one hydrochloride (20 mg, 0.05 mmol) obtained in step 3 and 4-(((2S,4R)-2-methyl-1-propionyl-1,2,3,4-tetrahydroquinolin-4-yl)amino)benzoic acid (14 mg, 0.04 mmol) obtained in reference example 1 in the same manner as in step 3 of example 1b.
ESI-MS m/z: 674 (M+H)$^+$: $^1$H-NMR (DMSO-d$_6$, δ): 0.98-1.06 (m, 12H), 1.11-1.13 (m, 2H), 2.22-2.25 (m, 2H), 2.52-2.64 (m, 4H), 3.52 (q, J=5.90 Hz, 2H), 3.94 (t, J=6.10 Hz, 2H), 4.05 (m, 1H), 4.27 (m, 1H), 4.66-4.80 (m, 2H), 5.64 (d, J=8.0 Hz, 1H), 6.58 (d, J=8.85 Hz, 3H), 6.65 (d, J=8.85 Hz, 2H), 6.75 (d, J=9.16 Hz, 2H), 7.09 (d, J=7.63 Hz, 1H), 7.14-7.17 (m, 3H), 7.23-7.31 (m, 4H), 7.65 (d, J=8.85 Hz, 2H), 8.22 (t, J=5.5 Hz, 1H).

Example 5o 2,2'-Oxybis(N-(4-(((2S,4R)-2-methyl-1-propionyl-1,2,3,4-tetrahydroquinolin-4-yl)amino)phenyl)acetamide) (Compound 5o)

(Step 1)
A crude product (0.15 g) of methyl 2-(2-((4-(((2S,4R)-2-methyl-1-propionyl-1,2,3,4-tetrahydroquinolin-4-yl)amino)

phenyl)amino)-2-oxyethoxy)acetate was obtained from 1-((2S,4R)-4-((4-aminophenyl)amino)-2-methyl-3,4-dihydroquinolin-1(2H)-yl)propan-1-one (270 mg, 0.63 mmol) obtained in reference example 7 in the same manner as in step 3 of example 1b. From the crude product obtained, a crude product (0.13 g) of 2-(2-((4-(((2S,4R)-2-methyl-1-propionyl-1,2,3,4-tetrahydroquinolin-4-yl)amino)phenyl)amino)-2-oxyethoxy)acetic acid was obtained in the same manner as in step 2 of example 2f.
ESI-MS m/z: 426 (M+H)$^+$
(Step 2)
Compound 5o (6 mg, total yield of 2 steps 13%) was obtained from the crude product (0.13 g) of 2-(2-((4-(((2S,4R)-2-methyl-1-propionyl-1,2,3,4-tetrahydroquinolin-4-yl)amino)phenyl)amino)-2-oxyethoxy)acetic acid obtained in step 1 and 1-((2S,4R)-4-((4-aminophenyl)amino)-2-methyl-3,4-dihydroquinolin-1(2H)-yl)propan-1-one (270 mg, 0.63 mmol) obtained in reference example 7 in the same manner as in step 3 of example 1b.
ESI-MS m/z: 717 (M+H)$^+$: $^1$H-NMR (DMSO-d$_6$, δ): 1.01-1.04 (m, 12H), 1.14-1.17 (m, 2H), 2.21-2.25 (m, 2H), 2.56-2.61 (m, 4H), 4.20-4.31 (m, 6H), 4.72-4.74 (m, 2H), 5.96 (d, J=8.0 Hz, 2H), 6.62 (d, J=9.0 Hz, 4H), 7.15-7.18 (m, 4H), 7.24-7.30 (m, 4H), 7.34 (d, J=8.85 Hz, 4H), 9.76 (s, 2H).

Example 5p 4-(((2S,4R)-2-Methyl-1-propionyl-1,2,3,4-tetrahydroquinolin-4-yl)amino)-N-(3-(4-(((2S,4R)-2-methyl-1-propionyl-1,2,3,4-tetrahydroquinolin-4-yl)amino)phenoxy)propyl)benzamide (Compound 5p)

(Step 1)
1-((2S,4R)-4-((4-Hydroxyphenyl)amino)-2-methyl-3,4-dihydroquinolin-1(2H)-yl)propan-1-one (190 mg, 68%) obtained in step 2 of example 5n was dissolved in acetonitrile (5 mL), then potassium carbonate (0.334 g, 2.41 mmol) and tert-butyl (3-bromopropyl)carbamate (0.288 g, 1.21 mmol) were added to the solution, and the mixture was stirred at 80° C. for 16 hours. The reaction mixture was filtered through Celite, and the filtrate was concentrated under reduced pressure. The obtained residue was purified by reverse phase column chromatography (acetonitrile/0.1% formic acid=60/40) to give tert-butyl (3-(4-(((2S,4R)-2-methyl-1-propionyl-1,2,3,4-tetrahydroquinolin-4-yl)amino)phenoxy)propyl)carbamate (0.05 g, 13%).
ESI-MS m/z: 468 (M+H)$^+$
(Step 2)
1-((2S,4R)-4-((4-(3-Aminopropoxy)phenyl)amino)-2-methyl-3,4-dihydroquinolin-1(2H)-yl)propan-1-one hydrochloride (0.04 g, 93%) was obtained from tert-butyl (3-(4-(((2S,4R)-2-methyl-1-propionyl-1,2,3,4-tetrahydroquinolin-4-yl)amino)phenoxy)propyl)carbamate (0.05 g, 0.11 mmol) obtained in step 1 in the same manner as in step 2 of example 1a.
ESI-MS m/z: 368 (M+H)$^+$
(Step 3)
Compound 5p (0.024 g, 35%) was obtained from 1-(2S,4R)-4-((4-(3-aminopropoxy)phenyl)amino)-2-methyl-3,4-dihydroquinolin-1(2H)-yl)propan-1-one hydrochloride (0.04 g, 0.1 mmol) obtained in step 2 and 4-(((2S,4R)-2-methyl-1-propionyl-1,2,3,4-tetrahydroquinolin-4-yl)amino)benzoic acid (30 mg, 0.09 mmol) obtained in reference example 1 in the same manner as in step 3 of example 1b.
ESI-MS m/z: 688 (M+H)$^+$: $^1$H-NMR (DMSO-d$_6$, δ): 0.97-1.08 (m, 12H), 1.10-1.25 (m, 2H), 1.89 (quin, J=6.47 Hz, 2H), 2.20-2.28 (m, 2H), 2.54-2.63 (m, 4H), 3.34-3.37 (m, 2H), 3.88 (t, J=6.25 Hz, 2H), 4.02-4.06 (m, 1H), 4.26-4.28 (m, 1H), 4.71-4.79 (m, 2H), 5.60 (d, J=7.67 Hz, 1H), 6.53 (d, J=7.67 Hz, 1H), 6.58 (d, J=8.99 Hz, 2H), 6.64 (d, J=8.77 Hz, 2H), 6.73 (d, J=8.99 Hz, 2H), 7.09 (d, J=7.2 Hz, 1H), 7.14-7.19 (m, 3H), 7.24-7.31 (m, 4H), 7.63 (d, J=8.77 Hz, 2H), 8.07 (d, J=5.4 Hz, 1H).

Example 5q 1-((2S,4R)-2-Methyl-4-((4-((7-(4-(((2S,4R)-2-methyl-1-propionyl-1,2,3,4-tetrahydroquinolin-4-yl)amino)benzoyl)-5,6,7,8-tetrahydroimidazo[1,2-a]pyrazin-3-yl)methyl)phenyl)amino)-3,4-dihydroquinolin-1(2H)-yl)propan-1-one (Compound 5q)

(Step 1)
tert-Butyl 3-((4-((tert-butoxycarbonyl)((2S,4R)-2-methyl-1-propionyl-1,2,3,4-tetrahydroquinolin-4-yl)amino)phenyl)(hydroxy)methyl)-5,6-dihydroimidazo[1,2-a]pyrazine-7(8H)-carboxylate (0.20 g, 0.31 mmol) obtained in step 1 of example 6a was dissolved in trifluoroacetic acid (2.0 mL), then triethylsilane (0.1 mL, 0.62 mmol) was added to the solution, and the mixture was stirred at room temperature for 3 hours. The reaction mixture was concentrated under reduced pressure to give 1-((2S,4R)-2-methyl-4-((4-((5,6,7,8-tetrahydroimidazo [1,2-a]pyrazin-3-yl)ethyl)phenyl)amino)-3,4-dihydroquinolin-1(2H)-yl)propan-1-one trifluoroacetate (0.2 g, 98%).
ESI-MS m/z: 430 (M+H)$^+$
(Step 2)
Compound 5q (0.1 g, 45%) was obtained from 4-{[(2S,4R)-2-methyl-1-propionyl-1,2,3,4-tetrahydroquinolin-4-yl]amino}benzoic acid (0.1 g, 0.29 mmol) obtained in reference example 1 and 1-((2S,4R)-2-methyl-4-((4-((5,6,7,8-tetrahydroimidazo[1,2-a]pyrazin-3-yl)methyl)phenyl)amino)-3,4-dihydroquinolin-1(2H)-yl)propan-1-one trifluoroacetate (0.19 g, 0.29 mmol) obtained in step 1 in the same manner as in step 3 of example 1b.
ESI-MS m/z: 750 (M+H)$^+$: $^1$H-NMR (DMSO-d$_6$, δ): 0.97-1.06 (m, 12H), 1.11-1.26 (m, 2H), 2.19-2.26 (m, 2H), 2.54-2.64 (m, 4H), 3.73-3.87 (m, 6H), 4.07-4.13 (m, 1H), 4.22-4.27 (m, 1H), 4.65-4.73 (m, 4H), 5.92 (d, J=7.67 Hz, 1H), 6.55-6.60 (m, 4H), 6.68 (d, J=8.55 Hz, 2H), 6.91-6.93 (m, 2H), 7.13-7.21 (m, 4H), 7.22-7.32 (m, 6H).

Example 5r

N,4-Bis(4-(((2S,4R)-2-methyl-1-propionyl-1,2,3,4-tetrahydroquinolin-4-yl)amino)phenyl)butanamide (Compound 5r)

(Step 1)
1-{(2S,4R)-4-[(4-Bromophenyl)amino]-2-methyl-3,4-dihydroquinolin-1(2H)-yl}propan-1-one (55.3 mg, 0.148 mmol) obtained in reference example 2 was dissolved in THF (1.0 mL), then SPhos (24.33 mg, 0.059 mmol), palladium acetate (6.65 mg, 0.030 mmol) and 4-ethoxy-4-oxobutylzinc bromide (0.5 mol/L THF solution, 0.44 mL, 0.22 mmol) were added to the solution, and the mixture was stirred at room temperature for 2 hours. A saturated aqueous ammonium chloride solution and ethyl acetate were added to the reaction mixture, the mixture was filtered through diatomaceous earth, and the filtrate was concentrated under reduced pressure. The obtained residue was purified by silica gel column chromatography (heptane/ethyl acetate=90/10 to 70/30) to give ethyl 4-(4-(((2S,4R)-2-methyl-1-propionyl-1,2,3,4-tetrahydroquinolin-4-yl)amino)phenyl)butanoate (57.5 mg, 95%).
ESIMS, (M+H)+, m/z: 409.
(Step 2)
Ethyl 4-(4-(((2S,4R)-2-methyl-1-propionyl-1,2,3,4-tetrahydroquinolin-4-yl)amino)phenyl)butanoate (53.8 mg, 0.132 mmol) obtained in step 1 was dissolved in ethanol (0.88 mL), then aqueous sodium hydroxide solution (4 mol/L, 0.17 mL, 0.66 mmol) was added to the solution, and the mixture was stirred at room temperature for 1 hour. The reaction mixture was concentrated under reduced pressure, then water was added to the obtained residue, and the mixture was washed with ethyl acetate. Hydrochloric acid (1 mol/L) was added to the aqueous layer, and the mixture was extracted twice with ethyl acetate. The organic layer was dried over anhydrous magnesium sulfate and concentrated under reduced pressure to give 4-(4-(((2S,4R)-2-methyl-1-propionyl-1,2,3,4-tetrahydroquinolin-4-yl)amino)phenyl)butyric acid (42.0 mg, 84%).
ESIMS, (M–H)−, m/z: 379.
(Step 3)
Compound 5r (30.1 mg, 81%) was obtained from 4-(4-(((2S,4R)-2-methyl-1-propionyl-1,2,3,4-tetrahydroquinolin-4-yl)amino)phenyl)butyric acid (21.0 mg, 0.055 mmol) obtained in step 2, and 1-((2S,4R)-4-((4-aminophenyl)amino)-2-methyl-3,4-dihydroquinolin-1(2H)-yl)propan-1-one (13.76 g, 68.81 mmol) obtained in reference example 7 in the same manner as in step 3 of example 1b.
ESIMS, (M+H)+, m/z: 672. $^1$H-NMR (DMSO-$d_6$, δ): 0.98-1.04 (m, 12H), 1.10-1.21 (m, 2H), 1.75-1.83 (m, 2H), 2.19-2.28 (m, 4H), 2.45 (t, J=7.2 Hz, 2H), 2.53-2.62 (m, 4H), 4.06-4.15 (m, 2H), 4.68-4.77 (m, 2H), 5.84 (d, J=6.8 Hz, 2H), 6.57 (d, J=8.2 Hz, 4H), 6.93 (d, J=8.2 Hz, 2H), 7.14-7.18 (m, 4H), 7.23-7.30 (m, 6H), 9.47 (s, 1H).

Example 6a 1-((2S,4R)-4-((4-(3-(Hydroxy(4-(((2S,4R)-2-methyl-1-propionyl-1,2,3,4-tetrahydroquinolin-4-yl)amino)phenyl)methyl)-5,6,7,8-tetrahydroimidazo[1,2-a]pyrazine-7-carbonyl)phenyl)amino)-2-methyl-3,4-dihydroquinolin-1(2H)-yl)propan-1-one (Compound 6a)

(Step 1)
Commercially available tert-butyl 3-bromo-5,6-dihydroimidazo[1,2-a]pyrazine-7(8H)-carboxylate (0.4 g, 1.32 mmol) was dissolved in THF (4 mL), then isopropylmagnesium chloride-lithium chloride (1.3 mol/L THF solution, 1.52 mL, 1.99 mmol) was added to the solution under ice-cooling, and the mixture was stirred for 30 minutes at room temperature. The THF solution (1 mL) of tert-butyl (4-formylphenyl)((2S,4R)-2-methyl-1-propionyl-1,2,3,4-tetrahydroquinolin-4-yl)carbamate (0.558 g, 1.32 mmol) obtained in reference example 8 was added dropwise to the reaction mixture under ice cooling, and the mixture was further stirred at room temperature for 2 hours. Water was added to the reaction mixture, and the mixture was extracted with ethyl acetate. The organic layer was dried over anhydrous sodium sulfate and concentrated under reduced pressure. The obtained residue was purified by reverse phase column chromatography (acetonitrile/0.1% formic acid=40/60) to give tert-butyl 3-((4-((tert-butoxycarbonyl)((2S,4R)-2-methyl-1-propionyl-1,2,3,4-tetrahydroquinolin-4-yl)amino)phenyl)(hydroxy)methyl)-5,6-dihydroimidazo[1,2-a]pyrazine-7(8H)-carboxylate (0.4 g, 46%).
ESI-MS m/z: 646 (M+H)+

(Step 2)
1-((2S,4R)-4-((4-(Hydroxy(5,6,7,8-tetrahydroimidazo[1,2-a]pyrazin-3-yl)ethyl)phenyl)amino)-2-methyl-3,4-dihydroquinolin-1(2H)-yl)propan-1-one hydrochloride (0.110 g, 98%) was obtained from tert-butyl 3-((4-((tert-butoxycarbonyl) ((2S,4R)-2-methyl-1-propionyl-1,2,3,4-tetrahydroquinolin-4-yl)amino)phenyl)(hydroxy)methyl)-5,6-dihydroimidazo[1,2-a]pyrazine-7(8H)-carboxylate (150 mg, 0.23 mmol) obtained in step 1 in the same manner as in step 2 of example 1a.
ESI-MS m/z: 446 (M+H)+
(Step 3)
Compound 6a (0.045 g, 28%) was obtained from 4-{[(2S,4R)-2-methyl-1-propionyl-1,2,3,4-tetrahydroquinolin-4-yl]amino}benzoic acid (0.070 g, 0.21 mmol) obtained in reference example 1 and 1-((2S,4R)-4-((4-(hydroxy(5,6,7,8-tetrahydroimidazo[1,2-a]pyrazin-3-yl)methyl)phenyl)amino)-2-methyl-3,4-dihydroquinolin-1(2H)-yl)propan-1-one hydrochloride (0.107 g, 0.21 mmol) obtained in step 2 in the same manner as in step 3 of example 1b.
ESI-MS m/z: 766 (M+H)+; $^1$H-NMR (DMSO-$d_6$, b): 0.98-1.06 (m, 12H), 1.13-1.26 (m, 2H), 2.19-2.28 (m, 2H), 2.55-2.67 (m, 4H), 3.86-3.94 (m, 4H), 4.15-4.28 (m, 2H), 4.61-4.75 (m, 4H), 5.59 (brs, 2H), 6.02 (d, J=6.58 Hz, 1H), 6.36 (d, J=3.29 Hz, 1H), 6.59-6.63 (m, 3H), 6.69 (d, J=8.77 Hz, 2H), 7.09-7.23 (m, 6H), 7.26-7.32 (m, 6H).

Example 6b

N-(4-(((2S,4R)-2-Methyl-1-propionyl-1,2,3,4-tetrahydroquinolin-4-yl)amino)phenyl)-3-(N-(4-(((2S,4R)-2-methyl-1-propionyl-1,2,3,4-tetrahydroquinolin-4-yl)amino)phenyl)sulfamoyl)propanamide (Compound 6b)

(Step 1)
Methyl 3-(N-(4-(((2S,4R)-2-methyl-1-propionyl-1,2,3,4-tetrahydroquinolin-4-yl)amino)phenyl)sulfamoyl)propanoate (0.12 g, 81%) was obtained from 1-((2S,4R)-4-((4-aminophenyl)amino)-2-methyl-3,4-dihydroquinolin-1(2H)-yl)propan-1-one (100 mg, 0.32 mmol) obtained in reference example 7 and 3-(chlorosulfonyl)propanoate (0.046 mmol, 0.35 mmol) in the same manner as in step 1 of example 6g.
ESI-MS m/z: 460 (M+H)+
(Step 2) 1-((2S,4R)-4-((4-Aminophenyl)amino)-2-methyl-3,4-dihydroquinolin-1(2H)-yl)propan-1-one (0.067 g, 0.21 mmol) obtained in reference example 7 was dissolved in toluene (2 mL), then trimethylaluminum (2 mol/L toluene solution, 0.326 mL, 0.65 mmol) was added to the solution under ice cooling, and the mixture was stirred for 30 minutes at room temperature. Methyl 3-(N-(4-(((2S,4R)-2-methyl-1-propionyl-1,2,3,4-tetrahydroquinolin-4-yl)amino)phenyl) sulfamoyl)propanoate (100 mg, 0.21 mmol) obtained in step 1 was added to the reaction mixture, and the mixture was stirred at 80° C. for 16 hours. Water was added to the reaction mixture, and the mixture was extracted with ethyl acetate. The organic layer was dried over anhydrous sodium sulfate and concentrated under reduced pressure. The obtained residue was purified by reverse phase HPLC (10 mmol/L aqueous ammonium bicarbonate solution/acetonitrile=65/35 to 10/90) to give compound 6b (0.048 g, 30%).
ESI-MS m/z: 737 (M+H)+; $^1$H-NMR (DMSO-$d_6$, δ): 0.97-1.04 (m, 12H), 1.10-1.20 (m, 2H), 2.20-2.26 (m, 2H), 2.54-2.61 (m, 4H), 2.66-2.70 (m, 2H), 3.22 (t, J=7.8 Hz, 2H), 4.09-4.14 (m, 2H), 4.70-4.75 (m, 2H), 5.87 (d, J=8.0 Hz, 1H), 6.05 (d, J=7.6 Hz, 1H), 6.60 (dd, J=16.4, 8.8 Hz, 4H), 6.99 (d, J=8.8 Hz, 2H), 7.15-7.17 (m, 4H), 7.23-7.29 (m, 6H), 9.15 (s, 1H), 9.70 (s, 1H).

Example 6c 4-(((2S,4R)-2-Methyl-1-propionyl-1,2,3,4-tetrahydroquinolin-4-yl)amino)-N-(2-(1-(4-(((2S,4R)-2-methyl-1-propionyl-1,2,3,4-tetrahydroquinolin-4-yl)amino)phenyl)-1H-1,2,3-triazol-4-yl)ethyl)benzamide (Compound 6c)

(Step 1)
N-(But-3-yn-1-yl)-4-(((2S,4R)-2-methyl-1-propionyl-1,2,3,4-tetrahydroquinolin-4-yl)amino)benzamide (38 mg, 66%) was obtained from 4-{[(2S,4R)-2-methyl-1-propionyl-1,2,3,4-tetrahydroquinolin-4-yl]amino}benzoic acid (50 mg, 0.148 mmol) obtained in step 7 of reference example 1 and 3-butyn-1-amine (0.018 µL, 0.222 mmol) in the same manner as in step 3 of example 1b.
ESIMS, (M+H)$^+$, m/z: 390.

(Step 2)
A crude product of compound 6c was obtained from the crude product (30 mg) of 1-{(2S,4R)-4-[(4-azidophenyl)amino]-2-methyl-3,4-dihydroquinolin-1(2H)-yl}propan-1-one obtained in step 2 of example 3a and N-(but-3-yn-1-yl)-4-(((2S,4R)-2-methyl-1-propionyl-1,2,3,4-tetrahydroquinolin-4-yl)amino)benzamide (20 mg, 0.051 mmol) obtained in step 1 of example 6c in the same manner as in step 3 of example 3a. The crude product obtained was purified by reverse phase HPLC (0.05% TFA aqueous solution/acetonitrile=55/45 to 50/50) to give compound 6c (11 mg, total yield of 2 steps 29%).
ESIMS, (M+H)$^+$, m/z: 725. $^1$H-NMR (CDCl$_3$) δ: 1.13-1.20 (m, 12H), 1.24-1.35 (m, 2H), 2.33-2.44 (m, 2H), 2.54-2.74 (m, 4H), 3.07 (t, J=6.1 Hz, 2H), 3.84 (q, J=6.0 Hz, 2H), 4.10-4.27 (m, 4H), 4.96 (s, 2H), 6.61 (d, J=8.6 Hz, 2H), 6.70 (d, J=9.1 Hz, 2H), 7.02 (t, J=5.0 Hz, 1H), 7.15-7.22 (m, 5H), 7.25-7.33 (m, 2H), 7.48 (d, J=8.6 Hz, 2H), 7.69 (d, J=7.2 Hz, 3H).

Example 6d 1-(4-(((2S,4R)-2-Methyl-1-propionyl-1,2,3,4-tetrahydroquinolin-4-yl)amino)benzyl)-N-(4-(((2S,4R)-2-methyl-1-propionyl-1,2,3,4-tetrahydroquinolin-4-yl)amino)phenyl)azetidine-3-carboxamide (Compound 6d)

(Step 1)
tert-Butyl 3-((4-(((2S,4R)-2-methyl-1-propionyl-1,2,3,4-tetrahydroquinolin-4-yl)amino)phenyl)carbamoyl)azetidine-1-carboxylate (55 mg, 49%) was obtained from 1-((2S,4R)-4-((4-aminophenyl)amino)-2-methyl-3,4-dihydroquinolin-1(2H)-yl)propan-1-one (70 mg, 0.23 mmol) obtained in step 3 of reference example 7 in the same manner as in step 3 of example 1b.
ESI-MS m/z: 493 (M+H)$^+$ (Step 2)
tert-Butyl 3-((4-(((2S,4R)-2-methyl-1-propionyl-1,2,3,4-tetrahydroquinolin-4-yl)amino)phenyl)carbamoyl)azetidine-1-carboxylate (0.08 g, 0.162 mmol) obtained in step 1 was dissolved in ethyl acetate (0.8 mL), then 4 mol/L hydrochloric acid (0.61 mL, 2.4 mmol) was added to the solution, and the mixture was stirred at room temperature for 1 hour. The reaction mixture was concentrated under reduced pressure to give N-(4-(((2S,4R)-2-methyl-1-propionyl-1,2,3,4-tetrahydroquinolin-4-yl)amino)phenyl)azetidine-3-carboxamide hydrochloride (43 mg, 67%).
ESI-MS m/z: 393 (M+H)$^+$ (Step 3)
tert-Butyl (4-formylphenyl)((2S,4R)-2-methyl-1-propionyl-1,2,3,4-tetrahydroquinolin-4-yl)carbamate (51 mg, 0.12 mmol) obtained in reference example 8 was dissolved in dichloromethane (1.5 mL), then N-(4-(((2S,4R)-2-methyl-1-propionyl-1,2,3,4-tetrahydroquinolin-4-yl)amino)phenyl)azetidine-3-carboxamide hydrochloride (43 mg, 0.11 mmol) obtained in step 2, and sodium triacetoxyborohydride (38 mg, 0.18 mmol) were added to the solution, and the mixture was stirred at room temperature for 3 hours. Sodium triacetoxyborohydride (38 mg, 0.18 mmol) was added again to the mixture, and the mixture was stirred at room temperature for 3 hours. A 1 mol/L aqueous sodium hydroxide solution was added to the reaction mixture, and the mixture was extracted twice with dichloromethane. The organic layer was dried over anhydrous magnesium sulfate and concentrated under reduced pressure. The obtained residue was purified by silica gel column chromatography (chloroform/methanol=100/0 to 19/1) to give tert-butyl ((2S,4R)-2-methyl-1-propionyl-1,2,3,4-tetrahydroquinolin-4-yl)(4-((3-((4-(((2S,4R)-2-methyl-1-propionyl-1,2,3,4-tetrahydroquinolin-4-yl)amino)phenyl)carbamoyl)azetidin-1-yl)methyl)phenyl)carbamate (29 mg, 30%).
ESI-MS m/z: 799 (M+H)$^+$ (Step 4)
tert-Butyl ((2S,4R)-2-methyl-1-propionyl-1,2,3,4-tetrahydroquinolin-4-yl)(4-((3-((4-(((2S,4R)-2-methyl-1-propionyl-1,2,3,4-tetrahydroquinolin-4-yl)amino)phenyl)carbamoyl)azetidin-1-yl)methyl)phenyl)carbamate (29 mg, 0.0036 mmol) obtained in step 3 was dissolved in ethyl acetate (1 mL), then 4 mol/L hydrochloric acid (0.18 mL, 0.73 mmol) was added to the solution, and the mixture was stirred at room temperature for 1 hour. A saturated aqueous sodium hydrogen carbonate solution was added to the reaction mixture, and the mixture was extracted 3 times with chloroform. The organic layer was dried over anhydrous magnesium sulfate and concentrated under reduced pressure. The obtained residue was purified by reverse phase HPLC (0.05 mmol/L ammonium bicarbonate/acetonitrile=50/50 to 40/60) to give compound 6d (9 mg, 36%).
ESI-MS m/z: 697 (M+H)$^+$; $^1$H-NMR (CDCl$_3$, δ): 1.07-1.19 (m, 12H), 1.19-1.41 (m, 2H), 2.25-2.42 (m, 2H), 2.50-2.72 (m, 4H), 3.03-3.16 (m, 1H), 3.35-3.49 (m, 4H), 3.53 (s, 2H), 3.74-3.87 (m, 2H), 4.07-4.21 (m, 2H), 4.79-5.03 (m, 2H), 6.55-6.62 (m, 4H), 7.06-7.11 (m, 2H), 7.10-7.21 (m, 4H), 7.23-7.32 (m, 4H), 7.32-7.38 (m, 2H), 8.42 (s, 1H).

Example 6e

N-(4-(((2S,4R)-2-Methyl-1-propionyl-1,2,3,4-tetrahydroquinolin-4-yl)amino)phenyl)-3-((4-(((2S,4R)-2-methyl-1-propionyl-1,2,3,4-tetrahydroquinolin-4-yl)amino)phenyl)sulfonamide)propanamide (Compound 6e)

(Step 1)
Ethyl 3-((4-(((2S,4R)-2-methyl-1-propionyl-1,2,3,4-tetrahydroquinolin-4-yl)amino)phenyl)sulfonamide)propanoate (9.3 mg, 7.6%) was obtained from 1-[(2S,4R)-4-({4-[(4-methoxybenzyl)thio]phenyl}amino)-2-methyl-3,4-dihydroquinolin-1(2H)-yl]propan-1-one (116 mg, 0.260 mmol) obtained in step 1 of example 4d, ethyl 3-aminopropanoate hydrochloride (120 mg, 0.779 mmol) and triethylamine (0.109 ml, 0.779 mmol) in the same manner as in step 2 of example 4d.
ESIMS, (M−H)⁻, m/z: 472.
(Step 2)
Compound 6e (8.8 mg, 57%) was obtained from 1-((2S,4R)-4-((4-aminophenyl)amino)-2-methyl-3,4-dihydroquinolin-1(2H)-yl)propan-1-one (13.76 g, 68.81 mmol) obtained in reference example 7 and ethyl 3-((4-(((2S,4R)-2-methyl-1-propionyl-1,2,3,4-tetrahydroquinolin-4-yl)amino)phenyl)sulfonamide)propanoate (10.0 mg, 0.055 mmol) obtained in step 1 in the same manner as in step 2 of example 6b.
ESIMS, (M+H)⁺, m/z: 737. ¹H-NMR (DMSO-d₆, δ): 1.12-1.17 (m, 12H), 1.30-1.34 (m, 2H), 2.31-2.42 (m, 2H), 2.53-2.69 (m, 6H), 3.24 (q, J=6.0 Hz, 2H), 4.09-4.17 (m, 1H), 4.19-4.25 (m, 1H), 4.47 (d, J=6.8 Hz, 1H), 4.88-5.00 (m, 2H), 5.33-5.39 (m, 1H), 6.57 (d, J=9.1 Hz, 2H), 6.62 (d, J=9.1 Hz, 2H), 7.12-7.21 (m, 5H), 7.24-7.26 (m, 2H), 7.28-7.32 (m, 2H), 7.48 (s, 1H), 7.65 (d, J=9.1 Hz, 2H).

Example 6f 1,1'-((2S,2'S,4R,4'R)-(((5,6,7,8-Tetrahydroimidazo[1,2-a]pyrazine-3,7-dicarbonyl)bis(4,1-phenylene))bis(azanediyl))bis(2-methyl-3,4-dihydroquinoline-4,1(2H)-diyl))bis(propan-1-one) (Compound 6f)

(Step 1)
tert-Butyl 3-((4-((tert-butoxycarbonyl)((2S,4R)-2-methyl-1-propionyl-1,2,3,4-tetrahydroquinolin-4-yl)amino)phenyl)(hydroxy)methyl)-5,6-dihydroimidazo[1,2-a]pyrazine-7(8H)-carboxylate (0.20 g, 0.31 mmol) obtained in step 1 of example 6a was dissolved in dichloromethane (5 mL), then Dess-Martin periodinane (0.197 g, 0.46 mmol) was added to the solution under ice cooling, and the mixture was stirred at room temperature for 2 hours. The reaction mixture was filtered through Celite, then saturated aqueous sodium hydrogen carbonate solution was added to the obtained filtrate, and the mixture was extracted 3 times with ethyl acetate. The organic layer was dried over anhydrous magnesium sulfate and concentrated under reduced pressure. The obtained residue was purified by reverse phase HPLC (0.1% formic acid aqueous solution/acetonitrile=45/55) to give tert-butyl 3-(4-((tert-butoxycarbonyl) ((2S,4R)-2-methyl-1-propionyl-1,2,3,4-tetrahydroquinolin-4-yl)amino)benzoyl)-5,6-dihydroimidazo[1,2-a]pyrazine-7(8H)-carboxylate (9 mg, 36%).
ESI-MS m/z: 644 (M+H)⁺
(Step 2)
1-((2S,4R)-2-methyl-4-((4-(5,6,7,8-tetrahydroimidazo[1,2-a]pyrazine-3-carbonyl)phenyl)amino)-3,4-dihydroquinolin-1(2H)-yl)propan-1-one hydrochloride (0.09 g, 94%) was obtained from tert-butyl 3-(4-((tert-butoxycarbonyl) ((2S,4R)-2-methyl-1-propionyl-1,2,3,4-tetrahydroquinolin-4-yl)amino)benzoyl)-5,6-dihydroimidazo[1,2-a]pyrazine-7(8H)-carboxylate (120 mg, 0.19 mmol) obtained in step 1 in the same manner as in step 2 of example 1a.
ESI-MS m/z: 444 (M+H)⁺
(Step 3)
Compound 6f (0.035 g, 26%) was obtained from 4-{[(2S,4R)-2-methyl-1-propionyl-1,2,3,4-tetrahydroquinolin-4-yl]amino}benzoic acid (0.070 g, 0.21 mmol) obtained in reference example 1 and 1-((2S,4R)-2-methyl-4-((4-(5,6,7,8-tetrahydroimidazo[1,2-a]pyrazine-3-carbonyl)phenyl)amino)-3,4-dihydroquinolin-1(2H)-yl)propan-1-one hydrochloride (0.091 g, 0.18 mmol) obtained in step 2 in the same manner as in step 3 of example 1b.
ESI-MS m/z: 764 (M+H)⁺; ¹H-NMR (DMSO-d₆, δ): 1.05-1.07 (m, 12H), 1.21-1.26 (m, 2H), 2.22-2.26 (m, 2H), 2.58-2.64 (m, 4H), 3.93 (s, 2H), 4.21-4.30 (m, 1H), 4.36-4.37 (m, 3H), 4.75-4.81 (m, 4H), 6.64 (d, J=7.63 Hz, 1H), 6.70 (d, J=8.54 Hz, 2H), 6.75 (d, J=8.54 Hz, 2H), 7.02 (d, J=7.63 Hz, 1H), 7.10-7.15 (m, 2H), 7.19 (t, J=7.32 Hz, 2H), 7.26-7.35 (m, 6H), 7.50 (s, 1H), 7.71 (d, J=8.5 Hz, 2H).

Example 6g 4-(((2S,4R)-2-Methyl-1-propionyl-1,2,3,4-tetrahydroquinolin-4-yl)amino)-N-(2-(N-(4-(((2S,4R)-2-methyl-1-propionyl-1,2,3,4-tetrahydroquinolin-4-yl)amino)phenyl)sulfamoyl)ethyl)benzamide (Compound 6g)

(Step 1)
1-((2S,4R)-4-((4-Aminophenyl)amino)-2-methyl-3,4-dihydroquinolin-1(2H)-yl)propan-1-one (100 mg, 0.32 mmol) obtained in reference example 7 was dissolved in pyridine (2 mL), then benzyl (2-(chlorosulfonyl)ethyl)carbamate (0.108 g, 0.38 mmol) was added to the solution under ice cooling, and the mixture was stirred at room temperature for 3 hours. Water was added to the reaction mixture, and the mixture was extracted with ethyl acetate. The organic layer was dried over anhydrous sodium sulfate and concentrated under reduced pressure. n-Pentane was added to the obtained residue and the resulting solid was filtered to give benzyl (2-(N-(4-(((2S,4R)-2-methyl-1-propionyl-1,2,3,4-tetrahydroquinolin-4-yl)amino)phenyl)sulfamoyl)ethyl)carbamate (0.14 g, 79%).
(Step 2)
Benzyl (2-(N-(4-(((2S,4R)-2-methyl-1-propionyl-1,2,3,4-tetrahydroquinolin-4-yl)amino)phenyl)sulfamoyl)ethyl)carbamate (0.16 g, 0.29 mmol) obtained in step 1 was dissolved in methanol (2 mL), then 20% palladium hydroxide/carbon (0.04 g) was added to the solution, and the mixture was stirred at room temperature for 1 hour under a hydrogen atmosphere. The reaction mixture was filtered through Celite, and the filtrate was concentrated under reduced pressure to give 2-amino-N-(4-(((2S,4R)-2-methyl-1-propionyl-1,2,3,4-tetrahydroquinolin-4-yl)amino)phenyl)ethane-1-sulfonamide (0.11 g, 92%).
(Step 3)
Compound 6g (0.066 g, 37%) was obtained from 4-{[(2S,4R)-2-methyl-1-propionyl-1,2,3,4-tetrahydroquinolin-4-yl]amino}benzoic acid (0.070 g, 0.21 mmol) obtained in reference example 1 and 2-amino-N-(4-(((2S,4R)-2-methyl-1-propionyl-1,2,3,4-tetrahydroquinolin-4-yl)amino)phenyl)ethane-1-sulfonamide (0.11 g, 92%) obtained in step 2 in the same manner as in step 3 of example 1b.
ESI-MS m/z: 737 (M+H)⁺; ¹H-NMR (DMSO-d₆, δ): 0.97-1.05 (m, 12H), 1.14-1.21 (m, 2H), 2.22-2.25 (m, 2H), 2.55-2.62 (m, 4H), 3.13-3.16 (m, 2H), 3.56-3.59 (m, 2H), 4.05-4.15 (m, 1H), 4.23-4.30 (m, 1H), 4.71-4.74 (m, 2H), 6.07 (d, J=7.5 Hz, 1H), 6.60-6.65 (m, 5H), 7.00 (d, J=9.0 Hz, 2H), 7.08 (d, J=7.5 Hz, 1H), 7.14-7.19 (m, 3H), 7.24-7.32 (m, 4H), 7.60 (d, J=9.0 Hz, 2H), 8.19 (t, J=5.75 Hz, 1H), 9.14 (brs, 1H).

Example 6h 4-(((2S,4R)-2-Methyl-1-propionyl-1,2,3,4-tetrahydroquinolin-4-yl)amino)-N-(4-((4-((2-methyl-1-propionyl-1,2,3,4-tetrahydroquinolin-4-yl)amino)phenyl)amino)-4-oxobut-2-yn-1-yl)benzamide (Compound 6h)

(Step 1)

tert-Butyl (4-((4-(((2S*,4R*)-2-methyl-1-propionyl-1,2,3,4-tetrahydroquinolin-4-yl)amino)phenyl)amino)-4-oxobut-2-yn-1-yl)carbamate (110 mg, 46%) was obtained from 1-((2S*,4R*)-4-((4-aminophenyl)amino)-2-methyl-3,4-dihydroquinolin-1(2H)-yl)propan-1-one (150 mg, 0.48 mmol) obtained in step 2 of reference example 7, and 4-(tert-butoxycarbonylamino)but-2-ynoic acid (145 mg, 0.72 mmol) in the same manner as in step 1 of example 1a.
ESI-MS, (M+H)$^+$, m/z: 491.

(Step 2)

4-Amino-N-(4-(((2S*,4R*)-2-methyl-1-propionyl-1,2,3,4-tetrahydroquinolin-4-yl)amino)phenyl)but-2-yl)amide trifluoroacetate (80 mg, 90%) was obtained from tert-butyl (4-((4-(((2S*,4R*)-2-methyl-1-propionyl-1,2,3,4-tetrahydroquinolin-4-yl)amino)phenyl)amino)-4-oxobut-2-yn-1-yl)carbamate (90 mg, 0.18 mmol) obtained in step 1 in the same manner as in step 2 of example 1k.
ESI-MS, (M+H)$^+$, m/z: 391.

(Step 3)

4-(((2S,4R)-2-Methyl-1-propionyl-1,2,3,4-tetrahydroquinolin-4-yl)amino)-N-(4-((4-(((2S*,4R*)-2-methyl-1-propionyl-1,2,3,4-tetrahydroquinolin-4-yl)amino)phenyl)amino)-4-oxobut-2-yn-1-yl)benzamide (0.034 g, 30%) was obtained from 4-amino-N-(4-(((2S*,4R*)-2-methyl-1-propionyl-1,2,3,4-tetrahydroquinolin-4-yl)amino)phenyl)but-2-ynamide trifluoroacetate (80 mg, 0.16 mmol) obtained in step 2 and 4-{[(2S,4R)-2-methyl-1-propionyl-1,2,3,4-tetrahydroquinolin-4-yl]amino}benzoic acid (0.53 mg, 0.16 mmol) obtained in step 7 of reference example 1 in the same manner as in step 3 of example 1b.
ESI-MS, (M+H)$^+$, m/z: 711.38.

(Step 4)

4-(((2S,4R)-2-Methyl-1-propionyl-1,2,3,4-tetrahydroquinolin-4-yl)amino)-N-(4-((4-(((2S,4R)-2-methyl-1-propionyl-1,2,3,4-tetrahydroquinolin-4-yl)amino)phenyl)amino)-4-oxobut-2-yn-1-yl)benzamide (14 mg, 0.020 mmol) obtained in step 3 was purified with SFC (CHIRALPAK IB, CO$_2$/methanol=75/25 to 70/30, 30 mL/min, rt=12.72 min) to give 4-(((2S,4R)-2-methyl-1-propionyl-1,2,3,4-tetrahydroquinolin-4-yl)amino)-N-(4-((4-(((2S,4R)-2-methyl-1-propionyl-1,2,3,4-tetrahydroquinolin-4-yl)amino)phenyl)amino)-4-oxobut-2-yn-1-yl)benzamide (4.3 mg, 31%).
ESI-MS, (M+H)$^+$, m/z: 711. $^1$H-NMR (CDCl$_3$) δ: 1.11-1.19 (m, 12H), 1.21-1.35 (m, 2H), 2.30-2.44 (m, 2H), 2.51-2.73 (m, 4H), 3.85 (d, J=7.2 Hz, 1H), 4.11-4.18 (m, 1H), 4.22-4.29 (m, 2H), 4.38 (d, J=5.4 Hz, 2H), 4.95 (s, 2H), 6.30 (t, J=5.4 Hz, 1H), 6.58 (d, J=8.6 Hz, 2H), 6.63 (d, J=8.6 Hz, 2H), 7.13-7.23 (m, 5H), 7.27-7.35 (m, 5H), 7.54 (s, 1H), 7.67 (d, J=9.1 Hz, 2H).

Example 6i

N-(4-(((2S*,4R*)-2-Methyl-1-propionyl-1,2,3,4-tetrahydroquinolin-4-yl)amino)phenyl)-2-(1-(4-(((2S*,4R*)-2-methyl-1-propionyl-1,2,3,4-tetrahydroquinolin-4-yl)amino)phenyl)-1H-1,2,3-triazol-4-yl)acetamide (Compound 6i)

(Step 1)

Commercially available 3-butynoic acid (0.272 g, 3.23 mmol) was dissolved in dichloromethane (5 mL), then oxalyl chloride (1.04 mL, 12.13 mmol) was added to the solution, and the mixture was stirred at room temperature for 1 hour. The reaction mixture was concentrated under reduced pressure, then a dichloromethane solution (2 mL) of 1-((2S*,4R*)-4-((4-aminophenyl)amino)-2-methyl-3,4-dihydroquinolin-1(2H)-yl)propan-1-one (0.5 g, 1.61 mmol) obtained in step 2 of reference example 7 and N,N-diisopropylethylamine (0.847 mL, 4.85 mmol) was added to the resulting residue, and the mixture was stirred at room temperature for 1 hour. The reaction mixture was concentrated under reduced pressure, and the obtained residue was purified by silica gel column chromatography (petroleum ether/ethyl acetate=1/1) to give N-(4-(((2S*,4R*)-2-methyl-1-propionyl-1,2,3,4-tetrahydroquinolin-4-yl)amino)phenyl)but-3-ynamide (0.12 g, 21%).
ESIMS, (M+H)$^+$, m/z: 376.

(Step 2)

1-{(2S*,4R*)-4-[(4-Azidophenyl)amino]-2-methyl-3,4-dihydroquinolin-1(2H)-yl}propan-1-one (0.07 g, 32%) was obtained from 1-{(2S*,4R*)-4-[(4-aminophenyl)amino]-2-methyl-3,4-dihydroquinolin-1(2H)-yl}propan-1-one (0.25 g, 0.80 mmol) obtained in step 2 of reference example 7 in the same manner as in step 2 of example 3a.
ESIMS, (M+H)$^+$, m/z: 336.

(Step 3)

Compound 6i (0.014 g, 7%) was obtained from 1-{(2S*,4R*)-4-[(4-azidophenyl)amino]-2-methyl-3,4-dihydroquinolin-1(2H)-yl}propan-1-one (0.09, 0.26 mmol) obtained in step 2 and N-(4-(((2S*,4R*)-2-methyl-1-propionyl-1,2,3,4-tetrahydroquinolin-4-yl)amino)phenyl)but-3-yl)amide (0.110 g, 0.29 mmol) obtained in step 1 in the same manner as in step 3 of example 3a.
ESIMS, (M+H)$^+$, m/z: 711; $^1$H-NMR (DMSO-d$_6$, δ) 0.98-1.07 (m, 12H), 1.11-1.20 (m, 2H), 2.20-2.33 (m, 2H), 2.55-2.63 (m, 4H), 3.74 (s, 2H), 4.09-4.14 (m, 1H), 4.14-4.28 (m, 1H), 4.73-4.76 (m, 2H), 5.88 (d, J=8.0 Hz, 1H), 6.47 (d, J=7.67 Hz, 1H), 6.60 (d, J=8.8 Hz, 2H), 6.79 (d, J=9.2 Hz, 2H), 7.15-7.21 (m, 4H), 7.23-7.32 (m, 6H), 7.56 (d, J=8.8 Hz, 2H), 8.37 (s, 1H), 9.83 (brs, 1H).

Example 6j

N-(4-(((2S*,4R*)-2-Methyl-1-propionyl-1,2,3,4-tetrahydroquinolin-4-yl)amino)phenyl)-2-(3-(4-(((2S*,4R*)-2-methyl-1-propionyl-1,2,3,4-tetrahydroquinolin-4-yl)amino)phenyl)ureido)acetamide (Compound 6j)

(Step 1)

Commercially available ethyl glycinate hydrochloride (0.112 g, 0.80 mmol) and triphosgene (0.096 g, 0.32 mmol) were dissolved in dichloromethane (10 mL), then a dichloromethane solution (1 mL) of triethylamine (0.5 mL, 3.23 mmol) was added to the solution at −10° C., and the mixture was stirred at 0° C. for 1 hour. A dichloromethane solution (15 mL) of 1-((2S*,4R*)-4-((4-aminophenyl)amino)-2- methyl-3,4-dihydroquinolin-1(2H)-yl)propan-1-one (0.25 g, 0.80 mmol) obtained in step 2 of reference example 7 was added dropwise to the reaction mixture at 0° C., and the mixture was stirred at room temperature for 6 hours. The reaction mixture was diluted with water, the resulting solid was removed by filtration, and the filtrate was extracted with dichloromethane. The organic layer was dried over anhydrous sodium sulfate and concentrated under reduced pressure. The obtained residue was purified by silica gel column chromatography (petroleum ether/ethyl acetate=4/1) to give a crude product (0.26 g) of ethyl ((4-(((2S*,4R*)-2-methyl-1-propionyl-1,2,3,4-tetrahydroquinolin-4-yl)amino)phenyl)carbamoyl)glycinate.
ESIMS, (M+H)$^+$, m/z: 439
(Step 2)
Compound 6j (0.045 g, total yield of 2 steps 14%) was obtained from the crude product (0.14 g) of ethyl ((4-(((2S*,4R*)-2-methyl-1-propionyl-1,2,3,4-tetrahydroquinolin-4-yl)amino)phenyl)carbamoyl)glycinate obtained in step 1 and 1-{(2S*,4R*)-4-[(4-aminophenyl)amino]–2-methyl-3,4-dihydroquinolin-1(2H)-yl}propan-1-one (0.1 g, 0.32 mmol) obtained in step 2 of reference example 7 in the same manner as in step 2 of example 6n.
ESIMS, (M+H)$^+$, m/z: 702; $^1$H-NMR (DMSO-d$_6$, δ) 0.98-1.04 (m, 12H), 1.09-1.19 (m, 2H), 2.19-2.28 (m, 2H), 2.55-2.60 (m, 4H), 3.83 (d, J=5.6 Hz, 2H), 4.05-4.12 (m, 2H), 4.65-4.80 (m, 2H), 5.69 (d, J=8.0 Hz, 1H), 5.87 (d, J=8.0 Hz, 1H), 6.19 (t, J=5.4 Hz, 1H), 6.58 (dd, J=15.6, 8.8 Hz, 4H), 7.10 (d, J=8.4 Hz, 2H), 7.17 (dd, J=7.6, 3.6 Hz, 4H), 7.23-7.30 (m, 6H), 8.31 (s, 1H), 9.61 (s, 1H).

Example 6k

N$^1$,N$^5$-Bis(4-(((2S,4R)-2-methyl-1-propionyl-1,2,3,4-tetrahydroquinolin-4-yl)amino)phenyl)glutaramide
(Compound 6k)

(Step 1)
Methyl 5-[(4-{[(2S,4R)-2-methyl-1-propionyl-1,2,3,4-tetrahydroquinolin-4-yl]amino}phenyl)amino]-5-oxopentanoate (0.450 g, 91%) was obtained from 1-{(2S,4R)-4-[(4-aminophenyl)amino]-2-methyl-3,4-dihydroquinolin-1(2H)-yl}propan-1-one (0.350 g, 1.13 mmol) obtained in step 3 of reference example 7 and 5-methoxy-5-oxopentanoic acid (0.181 g, 1.24 mmol) in the same manner as in step 3 of example 1b.
ESIMS, (M+H)$^+$, m/z: 438.
(Step 2)
5-[(4-{[(2S,4R)-2-Methyl-1-propionyl-1,2,3,4-tetrahydroquinolin-4-yl]amino}phenyl)amino]-5-oxopentanoic acid (0.350 g, 80%) was obtained from methyl 5-[(4-{[(2S,4R)-2-methyl-1-propionyl-1,2,3,4-tetrahydroquinolin-4-yl]amino}phenyl)amino]-5-oxopentanoate (0.450 g, 1.03 mmol) obtained in step 1 in the same manner as in step 2 of example 2f.
ESIMS, (M–H)$^-$, m/z: 422.
(Step 3)
Compound 6k (0.290 g, 49%) was obtained from 5-[(4-{[(2S,4R)-2-methyl-1-propionyl-1,2,3,4-tetrahydroquinolin-4-yl]amino}phenyl)amino]-5-oxopentanoic acid (0.350 g, 0.82 mmol) obtained in step 2 and 1-((2S,4R)-4-((4-aminophenyl)amino)-2-methyl-3,4-dihydroquinolin-1(2H)-yl)propan-1-one (0.255 g, 0.82 mmol) obtained in step 3 of reference example 7 in the same manner as in step 1 of example 1a.
ESIMS, (M+H)$^+$, m/z: 715; $^1$H-NMR (DMSO-d$_6$, δ): 0.98-1.04 (m, 12H), 1.10-1.19 (m, 2H), 1.85 (t, J=7.2 Hz, 2H), 2.20-2.29 (m, 6H), 2.53-2.61 (m, 4H), 4.08-4.14 (m, 2H), 4.72-4.73 (m, 2H), 5.83 (d, J=7.89 Hz, 2H), 6.58 (d, J=8.99 Hz, 4H), 7.15-7.16 (m, 4H), 7.23-7.31 (m, 8H), 9.50 (s, 2H).

Example 6l 4-(((2S,4R)-2-Methyl-1-propionyl-1,2,3,4-tetrahydroquinolin-4-yl)amino)-N-(2-(3-(4-(((2S*,4R*)-2-methyl-1-propionyl-1,2,3,4-tetrahydroquinolin-4-yl)amino)phenyl)ureido)ethyl)benzamide (Compound 6l)
(Step 1)
1-{(2S*,4R*)-4-[(4-Aminophenyl)amino]-2-methyl-3,4-dihydroquinolin-1(2H)-yl}propan-1-one (0.2 g, 0.64 mmol) obtained in step 2 of reference example 7 and commercially available tert-butyl (2-aminoethyl)carbamate (0.135 g, 0.84 mmol) were dissolved in THF (6 mL), then DMAP (0.418 g, 3.43 mmol), N,N-diisopropylethylamine (0.34 mL, 1.94 mmol) and triphosgene were added to the solution at 0° C., and the mixture was stirred at room temperature for 30 minutes and then at 70° C. for 4 hours. The reaction mixture was diluted with water and extracted with ethyl acetate. The organic layer was dried over anhydrous sodium sulfate and concentrated under reduced pressure to give a crude product (0.3 g) of tert-butyl (2-(3-(4-(((2S*,4R*)-2-methyl-1-propionyl-1,2,3,4-tetrahydroquinolin-4-yl)amino)phenyl)ureido)ethyl)carbamate.
ESIMS, (M+H)$^+$, m/z: 496
(Step 2)
A crude product (0.2 g) of 1-(2-aminoethyl)-3-(4-(((2S*,4R*)-2-methyl-1-propionyl-1,2,3,4-tetrahydroquinolin-4-yl)amino)phenyl)urea hydrochloride was obtained from the crude product (0.3 g) of tert-butyl (2-(3-(4-(((2S*,4R*)-2-methyl-1-propionyl-1,2,3,4-tetrahydroquinolin-4-yl)amino)phenyl)ureido)ethyl)carbamate obtained in step 1 in the same manner as in step 2 of example 1a.
ESIMS, (M+H)$^+$, m/z: 396
(Step 3)
Compound 6l (0.04 g, total yield of 3 steps 1.9%) was obtained from the crude product (0.159 g) of 1-(2-aminoethyl)-3-(4-(((2S*,4R*)-2-methyl-1-propionyl-1,2,3,4-tetrahydroquinolin-4-yl)amino)phenyl)urea hydrochloride obtained in step 2 and 4-{[(2S,4R)-2-methyl-1-propionyl-1,2,3,4-tetrahydroquinolin-4-yl]amino}benzoic acid (0.125 g, 0.36 mmol) obtained in step 7 of reference example 1 in the same manner as in step 3 of example 1b.
ESIMS, (M+H)$^+$, m/z: 716; $^1$H-NMR (DMSO-d$_6$, δ) 0.98-1.06 (m, 12H), 1.08-1.20 (m, 2H), 2.20-2.28 (m, 2H), 2.54-2.64 (m, 4H), 3.18-3.23 (m, 4H), 4.04-4.10 (m, 1H), 4.24-4.30 (m, 1H), 4.67-4.77 (m, 2H), 5.67 (d, J=7.6 Hz, 1H), 6.03 (t, J=5.6 Hz, 1H), 6.55 (d, J=8.8 Hz, 3H), 6.65 (d, J=8.8 Hz, 2H), 7.07-7.10 (m, 3H), 7.14-7.19 (m, 3H), 7.23-7.31 (m, 4H), 7.64 (d, J=8.8 Hz, 2H), 8.04 (s, 1H), 8.12 (t, J=5.0 Hz, 1H).

Example 6m 4-(4-(((2S,4R)-2-Methyl-1-propionyl-1,2,3,4-tetrahydroquinolin-4-yl)amino)benzoyl)-N-(4-(((2S*,4R*)-2-methyl-1-propionyl-1,2,3,4-tetrahydroquinolin-4-yl)amino)phenyl)piperazine-1-carboxamide
(Compound 6m)

(Step 1)
1-{(2S*,4R*)-4-[(4-Aminophenyl)amino]-2-methyl-3,4-dihydroquinolin-1(2H)-yl}propan-1-one (0.3 g, 0.97 mmol)

obtained in step 2 of reference example 7 was dissolved in THF (10 mL), then triethylamine (0.4 mL, 2.91 mmol) and commercially available tert-butyl 4-(chlorocarbonyl)piperazine-1-carboxylate (0.24 g, 0.97 mmol) were added to the solution at 0° C., and the mixture was stirred at room temperature for 16 hours. The reaction mixture was diluted with water and extracted with ethyl acetate. The organic layer was dried over anhydrous sodium sulfate and concentrated under reduced pressure to give a crude product (0.15 g) of tert-butyl 4-((4-(((2S*,4R*)-2-methyl-1-propionyl-1,2,3,4-tetrahydroquinolin-4-yl)amino)phenyl)carbamoyl)piperazine-1-carboxylate.
ESIMS, (M+H)$^+$, m/z: 522.
(Step 2)

A crude product (0.2 g) of N-(4-(((2S*,4R*)-2-methyl-1-propionyl-1,2,3,4-tetrahydroquinolin-4-yl)amino)phenyl)piperazine-1-carboxamide hydrochloride was obtained from the crude product (0.3 g) of tert-butyl 4-((4-(((2S*,4R*)-2-methyl-1-propionyl-1,2,3,4-tetrahydroquinolin-4-yl)amino)phenyl)carbamoyl)piperazine-1-carboxylate obtained in step 1 in the same manner as in step 2 of example 1a.
ESIMS, (M+H)$^+$, m/z: 422.
(Step 3)

Compound 6m (0.06 g, total yield of 3 steps 44.1%) was obtained from the crude product (0.2 g) of N-(4-(((2S*,4R*)-2-methyl-1-propionyl-1,2,3,4-tetrahydroquinolin-4-yl)amino)phenyl)piperazine-1-carboxamide hydrochloride obtained in step 2 and 4-{[(2S,4R)-2-methyl-1-propionyl-1,2,3,4-tetrahydroquinolin-4-yl]amino}benzoic acid (0.2 g, 0.43 mmol) obtained in step 7 of reference example 1 in the same manner as in step 1 of example 1a.
ESIMS, (M+H)$^+$, m/z: 742: $^1$H-NMR (DMSO-d$_6$, δ) 0.98-1.06 (m, 12H), 1.09-1.20 (m, 2H), 2.19-2.28 (m, 2H), 2.53-2.64 (m, 4H), 3.43-3.52 (m, 8H), 4.07-4.13 (m, 1H), 4.20-4.26 (m, 1H), 4.72-4.75 (m, 2H), 5.74 (d, J=8.0 Hz, 1H), 6.54 (dd, J=18.0, 7.2 Hz, 3H), 6.67 (d, J=8.8 Hz, 2H), 7.10-7.32 (m, 12H), 8.19 (s, 1H).

Example 6n

N-(4-(((2S*,4R*)-2-Methyl-1-propionyl-1,2,3,4-tetrahydroquinolin-4-yl)amino)phenyl)-2-(4-(4-(((2S,4R)-2-methyl-1-propionyl-1,2,3,4-tetrahydroquinolin-4-yl)amino)phenyl)-1H-pyrazol-1-yl)acetamide (Compound 6n)

(Step 1)
Ethyl 1-{(2S,4R)-4-[(4-bromophenyl)amino]-2-methyl-3,4-dihydroquinolin-1(2H)-yl}propan-1-one (0.212 g, 0.57 mmol) obtained in reference example 2 was dissolved in THF (20 mL), then commercially available ethyl 2-(4-(4,4,5,5-tetramethyl-1,3,2-dioxaborolan-2-yl)-1H-pyrazol-1-yl)acetate (0.2 g, 0.71 mmol), potassium carbonate (0.363 g, 1.71 mmol), and Pd(dppf)Cl$_2$ (0.038 g, 0.05 mmol) were added to the solution, and the mixture was stirred at 80° C. for 16 hour. The reaction mixture was diluted with water, and the aqueous layer was extracted with ethyl acetate. The organic layer was dried over anhydrous sodium sulfate and concentrated under reduced pressure. The obtained residue was purified by column chromatography (methanol/dichloromethane=0/100 to 6/94) to give ethyl 2-(4-(4-(((2S,4R)-2-methyl-1-propionyl-1,2,3,4-tetrahydroquinolin-4-yl)amino)phenyl)-1H-pyrazol-1-yl)acetate (0.130 g, 37%).
ESIMS, (M+H)$^+$, m/z: 447.
(Step 2)

Compound 6n (0.050 g, 24%) was obtained from ethyl 2-(4-(4-(((2S,4R)-2-methyl-1-propionyl-1,2,3,4-tetrahydroquinolin-4-yl)amino)phenyl)-1H-pyrazol-1-yl)acetate (0.076 g, 0.25 mmol) obtained in step 1 and 1-{(2S*,4R*)-4-[(4-aminophenyl)amino]-2-methyl-3,4-dihydroquinolin-1(2H)-yl}propan-1-one (0.110 g, 0.25 mmol) obtained in step 2 of reference example 7 in the same manner as in step 2 of example 6b.
ESIMS, (M+H)$^+$, m/z: 710: $^1$H-NMR (DMSO-d$_6$, δ) 0.98-1.05 (m, 12H), 1.11-1.24 (m, 2H), 2.20-2.28 (m, 2H), 2.54-2.67 (m, 4H), 4.09-4.20 (m, 2H), 4.70-4.75 (m, 2H), 4.90 (m, 2H), 5.92 (d, J=7.67 Hz, 1H), 6.03 (d, J=7.67 Hz, 1H), 6.63 (dd, J=18.85, 8.77 Hz, 4H), 7.15-7.18 (m, 4H), 7.23-7.32 (m, 8H), 7.71 (s, 1H), 7.94 (s, 1H), 9.92 (s, 1H).

Example 6o 1-((2S,4R)-2-Methyl-4-((4-(1-(1-(4-(((2S,4R)-2-methyl-1-propionyl-1,2,3,4-tetrahydroquinolin-4-yl)amino)benzoyl)piperidin-4-yl)-1H-pyrazol-4-yl)phenyl)amino)-3,4-dihydroquinolin-1(2H)-yl)propan-1-one (Compound 6o)

(Step 1)
Ethyl 1-{(2S,4R)-4-[(4-bromophenyl)amino]-2-methyl-3,4-dihydroquinolin-1(2H)-yl}propan-1-one (0.150 g, 0.40 mmol) obtained in reference example 2 was dissolved in 1,4-dioxane (4 mL), then commercially available (1-(1-(tert-butoxycarbonyl)piperidin-4-yl)-1H-pyrazol-4-yl)boronic acid (0.142 g, 0.48 mmol) and cesium carbonate (0.392 g, 1.21 mmol), Pd(PPh$_3$)$_4$ (0.046 g, 0.04 mmol) and water (1 mL) were added to the solution, and the mixture was stirred at 120° C. for 1 hour. The reaction mixture was diluted with water, and the aqueous layer was extracted with ethyl acetate. The organic layer was dried over anhydrous sodium sulfate and concentrated under reduced pressure. The obtained residue was purified by column chromatography (ethyl acetate/petroleum ether=3/7) to give tert-butyl 4-(4-(4-(((2S,4R)-2-methyl-1-propionyl-1,2,3,4-tetrahydroquinolin-4-yl)amino)phenyl)-1H-pyrazol-1-yl)piperidine-1-carboxylate (0.065 g, 30%).
ESIMS, (M+H)$^+$, m/z: 544.
(Step 2)

1-((2S,4R)-2-Methyl-4-((4-(1-(piperidin-4-yl)-1H-pyrazol-4-yl)phenyl)amino)-3,4-dihydroquinolin-1(2H)-yl)propan-1-one hydrochloride (0.050 g, 87%) was obtained from tert-butyl 4-(4-(4-(((2S,4R)-2-methyl-1-propionyl-1,2,3,4-tetrahydroquinolin-4-yl)amino)phenyl)-1H-pyrazol-1-yl)piperidine-1-carboxylate (0.065 g, 0.120 mmol) obtained in step 1 in the same manner as in step 2 of example 1a.
ESIMS, (M+H)$^+$, m/z: 444.
(Step 3)

1-((2S,4R)-2-Methyl-4-((4-(1-(1-(4-(((2S,4R)-2-methyl-1-propionyl-1,2,3,4-tetrahydroquinolin-4-yl)amino)benzoyl)piperidin-4-yl)-1H-pyrazol-4-yl)phenyl)amino)-3,4-dihydroquinolin-1(2H)-yl)propan-1-one (0.035 g, 27%) was obtained from 1-((2S,4R)-2-methyl-4-((4-(1-(piperidin-4-yl)-1H-pyrazol-4-yl)phenyl)amino)-3,4-dihydroquinolin-1(2H)-yl)propan-1-one hydrochloride (0.080 g, 0.17 mmol) obtained in step 2 and 4-(((2S,4R)-2-methyl-1-propionyl-1,2,3,4-tetrahydroquinolin-4-yl)amino)benzoic acid (0.057 g, 0.17 mmol) obtained in step 7 of reference example 1 in the same manner as in step 1 of example 1a.
ESIMS, (M+H)$^+$, m/z: 764: $^1$H-NMR (DMSO-d$_6$, δ) 0.99-1.06 (m, 12H), 1.17-1.25 (m, 2H), 1.86-1.90 (m, 2H), 2.04-2.07 (m, 2H), 2.21-2.33 (m, 2H), 2.55-2.67 (m, 4H), 3.06-3.10 (m, 2H), 4.14-4.23 (m, 4H), 4.40-4.42 (m, 1H), 4.71-4.75 (m, 2H), 6.00 (d, J=7.89 Hz, 1H), 6.49 (d, J=7.67

Hz, 1H), 6.66 (dd, J=11.62, 8.77 Hz, 4H), 7.14-7.21 (m, 4H), 7.23-7.31 (m, 8H), 7.68 (s, 1H), 8.03 (s, 1H).

Example 6p 1,1'-(((2S,2'S,4R,4'R)-(((1,4-Diazepane-1,4-dicarbonyl)bis(4,1-phenylene))bis(azanediyl))bis(2-methyl-3,4-dihydroquinoline-4,1(2H)-diyl))bis(propan-1-one) (Compound 6p)

Compound 6p (0.035 g, 11%) was obtained from 4-(((2S,4R)-2-methyl-1-propionyl-1,2,3,4-tetrahydroquinolin-4-yl)amino)benzoic acid (0.1 g, 0.29 mmol) obtained in step 7 of reference example 1 and 1,4-diazepine (0.015 g, 0.15 mmol) in the same manner as in step 1 of example 1a.
ESIMS, (M+H)$^+$, m/z: 741: $^1$H-NMR (DMSO-$d_6$, δ) 0.98-1.05 (m, 12H), 1.16-1.24 (m, 2H), 1.73-1.75 (m, 2H), 2.18-2.27 (m, 2H), 2.54-2.62 (m, 4H), 3.53-3.62 (m, 8H), 4.18-4.23 (m, 2H), 4.73-4.76 (m, 2H), 6.43 (d, J=7.6 Hz, 2H), 6.63 (d, J=8.4 Hz, 4H), 7.13-7.19 (m, 8H), 7.24-7.31 (m, 4H).

Example 6q 4-(((2S,4R)-2-Methyl-1-propionyl-1,2,3,4-tetrahydroquinolin-4-yl)amino)-N-(2-(4-(4-(((2S,4R)-2-methyl-1-propionyl-1,2,3,4-tetrahydroquinolin-4-yl)amino)phenyl)-1H-pyrazol-1-yl)ethyl)benzamide (Compound 6q)

(Step 1)
A crude product of tert-butyl (2-(4-(4-(((2S,4R)-2-methyl-1-propionyl-1,2,3,4-tetrahydroquinolin-4-yl)amino)phenyl)-1H-pyrazol-1-yl)ethyl)carbamate was obtained from 1-((2S,4R)-4-((4-bromophenyl)amino)-2-methyl-3,4-dihydroquinolin-1(2H)-yl)propan-1-one (600 mg, 1.6 mmol) and tert-butyl (2-(4-(4,4,5,5-tetramethyl-1,3,2-dioxaborolan-2-yl)-1H-pyrazol-1-yl)ethyl)carbamate (650 mg, 1.93 mmol) obtained in reference example 2 in the same manner as in step 1 of example 5k. The crude product obtained was purified by silica gel column chromatography (heptane/ethyl acetate=6/4 to 2/8) to give tert-butyl (2-(4-(4-(((2S,4R)-2-methyl-1-propionyl-1,2,3,4-tetrahydroquinolin-4-yl)amino)phenyl)-1H-pyrazol-1-yl)ethyl)carbamate (640 mg, 79%).
ESI-MS, (M+H)$^+$, m/z: 504.
(Step 2)
A crude product of 1-((2S,4R)-4-((4-(1-(2-aminoethyl)-1H-pyrazol-4-yl)phenyl)amino)-2-methyl-3,4-dihydroquinolin-1(2H)-yl)propan-1-one was obtained from tert-butyl (2-(4-(4-(((2S,4R)-2-methyl-1-propionyl-1,2,3,4-tetrahydroquinolin-4-yl)amino)phenyl)-1H-pyrazol-1-yl)ethyl)carbamate (640 mg, 1.27 mmol) obtained in step 1 in the same manner as in step 2 of example 1k. The crude product obtained was purified by silica gel column chromatography (chloroform/methanol=10/0 to 8/2) to give 1-((2S,4R)-4-((4-(1-(2-aminoethyl)-1H-pyrazol-4-yl)phenyl)amino)-2-methyl-3,4-dihydroquinolin-1(2H)-yl)propan-1-one (440 mg, 86%).
ESI-MS, (M+H)$^+$, m/z: 404.
(Step 3)
A crude product (200 mg) of tert-butyl ((2S,4R)-2-methyl-1-propionyl-1,2,3,4-tetrahydroquinolin-4-yl)(4-((2-(4-(4-(((2S,4R)-2-methyl-1-propionyl-1,2,3,4-tetrahydroquinolin-4-yl)amino)phenyl)-1H-pyrazol-1-yl)ethyl)carbamoyl)phenyl)carbamate was obtained from 1-((2S,4R)-4-((4-(1-(2-aminoethyl)-1H-pyrazol-4-yl)phenyl)amino)-2-methyl-3,4-dihydroquinolin-1(2H)-yl)propan-1-one (100 mg, 0.248 mmol) obtained in step 2 and 4-((tert-butoxycarbonyl)((2S,4R)-2-methyl-1-propionyl-1,2,3,4-tetrahydroquinolin-4-yl)amino)benzoic acid (109 mg, 0.248 mmol) obtained in step 2 of reference example 8 in the same manner as in step 3 of example 1b.
ESIMS, (M+H)$^+$, m/z: 824.
(Step 4)
A crude product of compound 6q was obtained from the crude product (200 mg) of tert-butyl ((2S,4R)-2-methyl-1-propionyl-1,2,3,4-tetrahydroquinolin-4-yl)(4-((2-(4-(4-(((2S,4R)-2-methyl-1-propionyl-1,2,3,4-tetrahydroquinolin-4-yl)amino)phenyl)-1H-pyrazol-1-yl)ethyl)carbamoyl)phenyl)carbamate obtained in step 3 in the same manner as in step 2 of example 1k. The crude product obtained was purified by reverse phase HPLC (0.05% TFA aqueous solution/acetonitrile=5/5 to 3/7) to give compound 6q (18 mg, total yield of 2 steps 10%).
ESI-MS, (M+H)$^+$, m/z: 724. $^1$H-NMR (CDCl$_3$) δ: 1.12-1.18 (m, 12H), 1.21-1.34 (m, 2H), 2.32-2.44 (m, 2H), 2.53-2.62 (m, 2H), 2.62-2.72 (m, 2H), 3.90 (q, J=5.3 Hz, 2H), 4.18-4.26 (m, 2H), 4.39 (t, J=5.4 Hz, 2H), 4.94 (d, J=5.9 Hz, 2H), 6.60 (d, J=8.6 Hz, 2H), 6.64 (d, J=8.6 Hz, 2H), 6.83 (t, J=5.4 Hz, 1H), 7.14-7.22 (m, 5H), 7.27-7.33 (m, 5H), 7.56 (s, 1H), 7.62 (d, J=9.1 Hz, 2H), 7.76 (s, 1H).

Example 7a 3-((1R,4r)-4-(((2S,4R)-2-Methyl-1-propionyl-1,2,3,4-tetrahydroquinolin-4-yl)amino)cyclohexane-1-carboxamide)-N-(4-(((2S,4R)-2-methyl-1-propionyl-1,2,3,4-tetrahydroquinolin-4-yl)amino)phenyl)azetidine-1-carboxamide (Compound 7a)

(Step 1)
tert-Butyl azetidin-3-ylcarbamate (0.218 g, 1.05 mmol) was dissolved in THF (10 mL), then N,N-diisopropylethylamine (0.70 mL, 4.04 mmol) and DMAP (0.049 g, 4.04 mmol) were added to the solution at 0° C., and the mixture was stirred at 0° C. for 5 minutes. Triphosgene (0.12 g, 0.40 mmol) was added to the reaction mixture, and the mixture was stirred at 0° C. for 30 minutes. 1-{(2S,4R)-4-[(4-Aminophenyl)amino]-2-methyl-3,4-dihydroquinolin-1(2H)-yl}propan-1-one (0.25 g, 0.81 mmol) obtained in reference example 7 was added to the mixture, and the mixture was stirred at 65° C. for 3 hours. Water was added to the reaction mixture, and the mixture was extracted 3 times with ethyl acetate. The organic layer was washed with saturated brine, dried over anhydrous sodium sulfate, and concentrated under reduced pressure. The obtained residue was purified by silica gel column chromatography (petroleum ether/ethyl acetate=1/1) to give tert-butyl (1-((4-(((2S,4R)-2-methyl-1-propionyl-1,2,3,4-tetrahydroquinolin-4-yl)amino)phenyl)carbamoyl)azetidin-3-yl)carbamate (0.150 g, 36%).
ESIMS, (M+H)$^+$, m/z: 508.34.
(Step 2)
3-Amino-N-(4-(((2S,4R)-2-methyl-1-propionyl-1,2,3,4-tetrahydroquinolin-4-yl)amino)phenyl)azetidine-1-carboxamide trifluoroacetate (0.085 g, 83%) was obtained from tert-butyl (1-((4-(((2S,4R)-2-methyl-1-propionyl-1,2,3,4-tetrahydroquinolin-4-yl)amino)phenyl)carbamoyl)azetidin-3-yl)carbamate (0.1 g, 0.20 mmol) obtained in step 1 in the same manner as in step 2 of example 1k.
ESIMS, (M+H)$^+$, m/z: 408.36

(Step 3)

Compound 7a (0.035 g, 27%) was obtained from 3-amino-N-(4-(((2S,4R)-2-methyl-1-propionyl-1,2,3,4-tetrahydroquinolin-4-yl)amino)phenyl)azetidine-1-carboxamide trifluoroacetate (0.099 g, 0.19 mmol) obtained in step 2 and (1R,4r)-4-(((2S,4R)-2-methyl-1-propionyl-1,2,3,4-tetrahydroquinolin-4-yl)amino)cyclohexane-1-carboxylic acid (0.06 g, 0.17 mmol) obtained in reference example 11 in the same manner as in step 3 of example 1b.

ESI-MS m/z: 734.40 (M+H)$^+$: $^1$H-NMR (DMSO-d$_6$, δ): 0.81-0.83 (m, 1H), 0.94-1.06 (m, 13H), 1.08-1.18 (m, 2H), 1.33-1.44 (m, 2H), 1.73-1.78 (m, 3H), 1.91-2.17 (m, 4H), 2.19-2.27 (m, 1H), 2.52-2.61 (m, 5H), 3.41-3.50 (m, 1H), 3.69 (dd, J=8.39, 5.34 Hz, 2H), 4.06-4.12 (m, 3H), 4.34-4.42 (m, 1H), 4.59-4.77 (m, 2H), 5.74 (d, J=7.63 Hz, 1H), 6.55 (d, J=9.16 Hz, 2H), 7.13-7.17 (m, 4H), 7.22-7.29 (m, 5H), 7.48-7.50 (m, 1H), 8.05 (s, 1H), 8.35 (d, J=6.71 Hz, 1H).

Example 7b 1-((2S*,4R*)-2-Methyl-4-(((1R,4r)-4-(2-(4-(a2S,4R)-2-methyl-1-propionyl-1,2,3,4-tetrahydroquinolin-4-yl)amino)phenyl)-5,6,7,8-tetrahydroimidazo[1,2-a]pyrazine-7-carbonyl)cyclohexyl)amino)-3,4-dihydroquinolin-1(2H)-yl)propan-1-one (Compound 7b)

Compound 7b (0.037 g, 22%) was obtained from 1-((2S,4R)-2-methyl-4-{[4-(5,6,7,8-tetrahydroimidazo[1,2-a]pyrazin-2-yl)phenyl]amino}-3,4-dihydroquinolin-1(2H)-yl)propan-1-one hydrochloride (0.100 g, 0.22 mmol) obtained in step 3 of example 3f and (1R,4r)-4-(((2S*,4R*)-2-methyl-1-propionyl-1,2,3,4-tetrahydroquinolin-4-yl)amino)cyclohexane-1-carboxylic acid (0.076 g, 0.22 mmol) obtained in step 2 of reference example 11 in the same manner as in step 3 of example 1b.

ESIMS, (M+H)$^+$, m/z: 742: $^1$H-NMR (DMSO-d$_6$, δ) 0.83 (d, J=9.78 Hz, 1H), 0.92-1.08 (m, 12H), 1.14-1.32 (m, 3H), 1.34-1.52 (m, 2H), 1.66-1.81 (m, 2H), 1.90-2.06 (m, 2H), 2.11-2.30 (m, 2H), 2.55-2.75 (m, 6H), 3.41-3.51 (m, 2H), 3.81-4.08 (m, 4H), 4.09-4.22 (m, 1H), 4.56-4.85 (m, 4H), 6.03 (d, J=7.6 Hz, 1H), 6.63 (d, J=8.58 Hz, 2H), 7.15-7.31 (m, 8H), 7.42-7.54 (m, 3H).

Example 7c

N$^1$-((1R,4r)-4-(((2S,4R)-2-Methyl-1-propionyl-1,2,3,4-tetrahydroquinolin-4-yl)amino)cyclohexyl)-N$^3$-(4-(((2S,4R)-2-methyl-1-propionyl-1,2,3,4-tetrahydroquinolin-4-yl)amino)phenyl)azetidine-1,3-dicarboxamide (Compound 7c)

1-((2S,4R)-4-(((1r,4R)-4-aminocyclohexyl)amino)-2-methyl-3,4-dihydroquinolin-1(2H)-yl)propan-1-one dihydrochloride (0.106 g, 0.28 mmol) obtained in reference example 9 was dissolved in DMF (3 mL), then DMAP (0.084 g, 0.69 mmol), triethylamine (0.15 mL, 1.10 mmol) and CDI (0.044 g, 0.28 mmol) were added to the solution, and the mixture was stirred at 85° C. for 1 hour. A DMF solution (1 mL) of crude product (0.140 g) of N-(4-(((2S,4R)-2-methyl-1-propionyl-1,2,3,4-tetrahydroquinolin-4-yl)amino)phenyl)azetidine-3-carboxamide trifluoroacetate obtained in step 1 of example 10e was added to the reaction mixture, and the mixture was stirred at 85° C. for 16 hours. The reaction mixture was diluted with ice water and extracted with ethyl acetate. The organic layer was washed with water and saturated brine, dried over anhydrous sodium sulfate, and concentrated under reduced pressure. The obtained residue was purified by reverse phase HPLC (10 mmol/L aqueous ammonium bicarbonate solution/acetonitrile=60/40 to 10/90) to give compound 7c (0.070 g, 35%).

ESI-MS m/z: 734.51 (M+H)$^+$: $^1$H-NMR (DMSO-d$_6$, δ): 0.81-0.83 (m, 1H), 0.93-1.22 (m, 18H), 1.70-1.77 (m, 3H), 1.87-2.01 (m, 2H), 2.06-2.29 (m, 2H), 2.52-2.62 (m, 4H), 3.34-3.48 (m, 3H), 3.83-3.90 (m, 4H), 4.07-4.17 (m, 1H), 4.58-4.77 (m, 2H), 5.91 (d, J=7.87 Hz, 1H), 6.06 (d, J=7.87 Hz, 1H), 6.59 (d, J=8.82 Hz, 2H), 7.15-7.31 (m, 9H), 7.48-7.50 (m, 1H), 9.63 (s, 1H).

Example 7d

O-((1R,4R)-4-(((2S*,4R*)-2-Methyl-1-propionyl-1,2,3,4-tetrahydroquinolin-4-yl)amino)cyclohexyl)(2-((4-(((2S,4R)-2-methyl-1-propionyl-1,2,3,4-tetrahydroquinolin-4-yl)amino)phenyl)amino)-2-oxoethyl) carbamothioate (Compound 7d)

(Step 1)

1-((2S*,4R*)-4-Amino-2-methyl-3,4-dihydroquinolin-1(2H)-yl)propan-1-one (2.01 g, 9.21 mmol) obtained in step 3 of reference example 1 was dissolved in methanol (20 mL), then 4-hydroxycyclohexan-1-one (1.58 g, 13.8 mmol), sodium cyanoborohydride (1.78 g, 28.3 mmol) and acetic acid (2.64 mL, 46.0 mmol) were added to the solution, and the mixture was stirred at 50° C. for 15 hours. The reaction mixture was neutralized with an aqueous sodium hydroxide solution (4 mol/L), and the aqueous layer was extracted with chloroform. The organic layer was dried over anhydrous sodium sulfate and concentrated under reduced pressure. The obtained residue was purified by reverse phase HPLC (10 mmol/L aqueous ammonium bicarbonate solution/acetonitrile=75/25 to 70/30) to give 1-((2S*,4R*)-4-(((1r,4R)-4-hydroxycyclohexyl)amino)-2-methyl-3,4-dihydroquinolin-1(2H)-yl)propan-1-one (1.30 g, 45%) and 1-((2S*,4R*)-4-(((1s,4S)-4-hydroxycyclohexyl)amino)-2-methyl-3,4-dihydroquinolin-1(2H)-yl)propan-1-one (1.39 g, 48%).

1-((2S*,4R*)-4-(((1r,4R)-4-Hydroxycyclohexyl)amino)-2-methyl-3,4-dihydroquinolin-1(2H)-yl)propan-1-one ESIMS, (M+H)$^+$, m/z: 317; $^1$H-NMR (CDCl$_3$, δ) 0.85-0.98 (m, 2H), 1.01-1.13 (m, 6H), 1.16-1.43 (m, 4H), 1.88-2.09 (m, 4H), 2.18-2.34 (m, 1H), 2.46-2.74 (m, 3H), 3.53 (dd, J=12.4, 4.4 Hz, 1H), 3.61-3.73 (m, 1H), 4.76-4.91 (m, 1H), 7.04-7.16 (m, 1H), 7.18-7.27 (m, 2H), 7.42-7.48 (m, 1H).

1-((2S*,4R*)-4-(((1s,4S)-4-Hydroxycyclohexyl)amino)-2-methyl-3,4-dihydroquinolin-1(2H)-yl)propan-1-one ESIMS, (M+H)$^+$, m/z: 317; $^1$H-NMR (CDCl$_3$, δ) 0.87-1.04 (m, 1H), 1.06-1.14 (m, 6H), 1.58-1.89 (m, 8H), 2.27 (ddd, J=15.4, 8.0, 8.0 Hz, 1H), 2.46-2.65 (m, 2H), 2.76-2.87 (m, 1H), 3.52 (dd, J=12.0, 4.0 Hz, 1H), 3.81-3.98 (m, 1H), 4.78-4.96 (m, 1H), 7.10 (d, J=6.8 Hz, 1H), 7.21-7.33 (m, 2H), 7.48-7.58 (m, 1H).

(Step 2)

tert-Butyl (2-((4-(((2S,4R)-2-methyl-1-propionyl-1,2,3,4-tetrahydroquinolin-4-yl)amino)phenyl)amino)-2-oxoethyl)carbamate (227 mg, 100%) was obtained from 1-{(2S,4R)-4-((4-aminophenyl)amino)-2-methyl-3,4-dihydroquinolin-1(2H)-yl)propan-1-one (150 mg, 0.485 mmol) obtained in step 3 of reference example 7 and commercially available (tert-butoxycarbonyl)glycine (102 mg, 0.582 mmol) in the same manner as in step 3 of example 1b.

ESIMS, (M+H)$^+$, m/z: 467

(Step 3)

2-Amino-N-(4-(((2S,4R)-2-methyl-1-propionyl-1,2,3,4-tetrahydroquinolin-4-yl)amino)phenyl)acetamide hydrochloride (196 mg, 100%) was obtained from tert-butyl (2-((4-(((2S,4R)-2-methyl-1-propionyl-1,2,3,4-tetrahydroquinolin-4-yl)amino)phenyl)amino)-2-oxoethyl)carbamate (227 mg, 0.486 mmol) obtained in step 2 in the same manner as in step 2 of example 1a ESIMS, (M+H)$^+$, m/z: 367
(Step 4)
1-((2S*,4R*)-4-(((1r,4R)-4-Hydroxycyclohexyl)amino)-2-methyl-3,4-dihydroquinolin-1(2H)-yl)propan-1-one (50.8 mg, 0.161 mmol) obtained in step 1 was dissolved in DMF (1 mL), then triethylamine (0.112 mL, 0.803 mmol), DMAP (49.0 mg, 0.401 mmol) and 1,1'-thiocarbonyldiimidazole (28.6 mg, 0.161 mmol) were added to the solution, and the mixture was stirred at room temperature for 1 hour. 2-amino-N-(4-(((2S,4R)-2-methyl-1-propionyl-1,2,3,4-tetrahydroquinolin-4-yl)amino)phenyl)acetamide hydrochloride (70.6 mg, 0.193 mmol) obtained in step 4 was added to the reaction mixture, and the mixture was stirred at 70° C. for 15 hours. The reaction mixture was diluted with saturated aqueous sodium hydrogen carbonate solution, and the aqueous layer was extracted with ethyl acetate. The organic layer was dried over anhydrous sodium sulfate and concentrated under reduced pressure. The obtained residue was purified by reverse phase HPLC (10 mmol/L aqueous ammonium bicarbonate solution/acetonitrile=55/45 to 50/50) to give compound 7d (16.1 mg, 14%). ESIMS, (M+H)$^+$, m/z: 725; $^1$H-NMR (CDCl$_3$, δ) 1.03-1.48 (m, 18H), 1.90-2.43 (m, 6H), 2.47-2.69 (m, 4H), 2.70-2.82 (m, 1H), 3.44-3.61 (m, 1H), 3.77-3.89 (m, 1H), 4.09-4.23 (m, 1H), 4.34 (d, J=5.2 Hz, 2H), 4.78-5.04 (m, 2H), 5.19-5.45 (m, 1H), 6.60 (d, J=9.2 Hz, 2H), 6.94-7.35 (m, 9H), 7.42-7.55 (m, 1H), 7.80 (brs, 1H).

Example 7e (1R,4R)-4-(((2S*,4R*)-2-Methyl-1-propionyl-1,2,3,4-tetrahydroquinolin-4-yl)amino)cyclohexyl (2-((4-(((2S,4R)-2-methyl-1-propionyl-1,2,3,4-tetrahydroquinolin-4-yl)amino)phenyl)amino)-2-oxoethyl)carbamate (Compound 7e)

(Step 1)
Ethyl ((((1R,4r)-4-(((2S,4R)-2-methyl-1-propionyl-1,2,3,4-tetrahydroquinolin-4-yl)amino)cyclohexyl)oxy)carbonyl)glycinate (55.8 mg, 69%) was obtained from 1-((2S*,4R*)-4-(((1r,4R)-4-hydroxycyclohexyl)amino)-2-methyl-3,4-dihydroquinolin-1(2H)-yl)propan-1-one (50.8 mg, 0.161 mmol) obtained in step 1 of example 7d and ethyl glycinate hydrochloride (33.0 mg, 0.237 mmol) in the same manner as in example 7c.
ESIMS, (M+H)$^+$, m/z: 446.
(Step 2)
Ethyl ((((1R,4r)-4-(((2S*,4R*)-2-methyl-1-propionyl-1,2,3,4-tetrahydroquinolin-4-yl)amino)cyclohexyl)oxy)carbonyl)glycinate (55.0 mg, 0.123 mmol) obtained in step 1 was dissolved in THF (1 mL), then potassium trimethylsilanolate (55.3 mg, 0.431 mmol) was added to the solution, and the mixture was stirred at 50° C. for 5.5 hours, and the reaction mixture was concentrated under reduced pressure. The obtained residue was dissolved in DMF (1 mL), then N,N-diisopropylethylamine (0.107 mL, 0.615 mmol), COMU (79.0 mg, 0.185 mmol) and 1-((2S,4R)-4-((4-aminophenyl)amino)-2-methyl-3,4-dihydroquinolin-1(2H)-yl)propan-1-one (38.1 mg, 0.123 mmol) obtained in step 3 of reference example 7 were added to the solution, and the mixture was stirred at room temperature for 15 hours. The reaction mixture was diluted with saturated aqueous sodium hydrogen carbonate solution, and the aqueous layer was extracted with ethyl acetate. The organic layer was dried over anhydrous magnesium sulfate and concentrated under reduced pressure. The obtained residue was purified by reverse phase HPLC (10 mmol/L aqueous ammonium bicarbonate solution/acetonitrile=0/40 to 50/50) to give compound 7e (18.3 mg, 21%).
ESIMS, (M+H)$^+$, m/z: 709; $^1$H-NMR (CDCl$_3$, δ) 0.82-0.99 (m, 2H), 1.03-1.56 (m, 14H), 1.91-2.15 (m, 5H), 2.18-2.42 (m, 2H), 2.45-2.80 (m, 5H), 3.51 (dd, J=12.0, 4.0 Hz, 1H), 3.83 (d, J=3.6 Hz, 1H), 3.97 (d, J=6.0 Hz, 2H), 4.08-4.22 (m, 1H), 4.58-4.75 (m, 1H), 4.78-5.03 (m, 2H), 5.40 (brs, 1H), 6.60 (d, J=9.2 Hz, 2H), 7.01-7.36 (m, 9H), 7.43-7.51 (m, 1H), 7.85 (brs, 1H).

Example 7f 2-((4-(((2S,4R)-2-Methyl-1-propionyl-1,2,3,4-tetrahydroquinolin-4-yl)amino)phenyl)amino)-2-oxoethyl ((1R,4R)-4-(((2S,4R)-2-methyl-1-propionyl-1,2,3,4-tetrahydroquinolin-4-yl)amino)cyclohexyl)carbamate (Compound 7f)

(Step 1)
Methyl glycolate (0.2 g, 2.22 mmol) and pyridine (0.35 mL, 4.44 mmol) were dissolved in dichloromethane (5 mL), then 4-nitrophenyl chloroformate (0.492 g, 2.44 mmol) was added to the solution at 0° C., and the mixture was stirred at room temperature for 2 hours. The reaction mixture was diluted with water and extracted with ethyl acetate. The organic layer was washed with water and saturated brine, dried over anhydrous sodium sulfate, and concentrated under reduced pressure. The obtained residue was purified by silica gel column chromatography (petroleum ether/ethyl acetate=85/15) to give a crude product of methyl 2-(((4-nitrophenoxy)carbonyl)oxy)acetate (0.405 g).
ESIMS, (M+H)$^+$, m/z: 256.17.
(Step 2)
1-((2S,4R)-4-(((1r,4R)-4-aminocyclohexyl)amino)-2-methyl-3,4-dihydroquinolin-1(2H)-yl)propan-1-one dihydrochloride (0.15 g, 0.39 mmol) obtained in reference example 9 and triethylamine (0.27 mL, 1.94 mmol) were dissolved in dichloromethane (2 mL), then the crude product (0.148 g) of methyl 2-(((4-nitrophenoxy)carbonyl)oxy)acetate obtained in step 1 was added to the solution, and the mixture was stirred at room temperature for 2 hours. The reaction mixture was concentrated under reduced pressure, and the obtained residue was purified by reverse phase column chromatography (acetonitrile/water=40/60 to 60/40) to give 3-((1R,4r)-4-(((2S,4R)-2-methyl-1-propionyl-1,2,3,4-tetrahydroquinolin-4-yl)amino)cyclohexyl)oxazolidine-2,4-dione (0.090 g, 58%).
ESIMS, (M+H)$^+$, m/z: 400.27.
(Step 3)
A crude product (0.11 g) of 2-((((1R,4r)-4-(((2S,4R)-2-methyl-1-propionyl-1,2,3,4-tetrahydroquinolin-4-yl)amino)cyclohexyl)carbamoyl)oxy)acetic acid was obtained from 3-((1R,4r)-4-(((2S,4R)-2-methyl-1-propionyl-1,2,3,4-tetrahydroquinolin-4-yl)amino)cyclohexyl)oxazolidine-2,4-dione (0.09 g, 0.21 mmol) obtained in step 2 in the same manner as in step 2 of example 2f.
ESIMS, (M+H)$^+$, m/z: 418.33.

(Step 4)

Compound 7f (0.038 g, 30%) was obtained from the crude product (0.11 g) of 2-((((1R,4r)-4-(((2S,4R)-2-methyl-1-propionyl-1,2,3,4-tetrahydroquinolin-4-yl)amino)cyclohexyl)carbamoyl)oxy)acetic acid obtained in step 3 and 1-{(2S,4R)-4-[(4-aminophenyl)amino]-2-methyl-3,4-dihydroquinolin-1(2H)-yl}propan-1-one (0.055 g, 0.18 mmol) obtained in reference example 7 in the same manner as in step 1 of example 1a.
ESIMS, (M+H)$^+$, m/z: 709.49. $^1$H-NMR (DMSO-d$_5$, δ): 0.80-0.83 (m, 1H), 0.93-1.04 (m, 12H), 1.11-1.24 (m, 5H), 1.80-1.96 (m, 5H), 2.07-2.29 (m, 2H), 2.51-2.62 (m, 5H), 3.20-3.28 (m, 1H), 3.44 (dd, J=11.32, 2.98 Hz, 1H), 4.07-4.17 (m, 1H), 4.46 (s, 2H), 4.64-4.73 (m, 2H), 5.92 (d, J=7.87 Hz, 1H), 6.60 (d, J=8.82 Hz, 2H), 7.15-7.30 (m, 10H), 7.47-7.49 (m, 1H), 9.58 (s, 1H).

Example 7g 2-(((1R,4R)-4-(((2S,4R)-2-Methyl-1-propionyl-1,2,3,4-tetrahydroquinolin-4-yl)amino)cyclohexyl)amino)-N-(4-(((2S,4R)-2-methyl-1-propionyl-1,2,3,4-tetrahydroquinolin-4-yl)amino)phenyl)oxazole-4-carboxamide (Compound 7g)

(Step 1)
1-((2S,4R)-4-(((1r,4R)-4-Aminocyclohexyl)amino)-2-methyl-3,4-dihydroquinolin-1(2H)-yl)propan-1-one dihydrochloride (200 mg, 0.515 mmol) obtained in reference example 9 was dissolved in water (1 mL), then potassium cyanate (45.9 mg, 0.566 mmol) was added to the solution, and the mixture was stirred at 70° C. overnight. The reaction mixture was cooled to room temperature and extracted twice with chloroform. The organic layer was dried over magnesium sulfate and concentrated under reduced pressure to give a crude product (185 mg) of 1-((1R,4r-4-(((2S,4R)-2-methyl-1-propionyl-1,2,3,4-tetrahydroquinolin-4-yl)amino)cyclohexyl)urea.
ESI-MS, (M+H)$^+$, m/z: 359.
(Step 2)
A crude product (100 mg) of ethyl 2-(((1R,4r)-4-(((2S,4R)-2-methyl-1-propionyl-1,2,3,4-tetrahydroquinolin-4-yl)amino)cyclohexyl)amino)oxazole-4-carboxylate was obtained from the crude product (185 mg) of 1-((1R,4r)-4-(((2S,4R)-2-methyl-1-propionyl-1,2,3,4-tetrahydroquinolin-4-yl)amino)cyclohexyl)urea obtained in step 1 in the same manner as in step 2 of example 5a.
ESI-MS, (M+H)$^+$, m/z: 455.
(Step 3)
A crude product (70 mg) of ethyl 2-(((1R,4r)-4-(((2S,4R)-2-methyl-1-propionyl-1,2,3,4-tetrahydroquinolin-4-yl)amino)cyclohexyl)amino)oxazole-4-carboxylate obtained in step 2 was dissolved in THF (1 mL), then potassium trimethylsilanolate (39.5 mg, 0.308 mmol) was added to the solution, and the mixture was stirred at room temperature for 1 hour. The reaction mixture was concentrated under reduced pressure to give a crude product (60 mg) of 2-(((1R,4r)-4-(((2S,4R)-2-methyl-1-propionyl-1,2,3,4-tetrahydroquinolin-4-yl)amino)cyclohexyl)amino)oxazole-4-carboxylic acid.
ESI-MS, (M+H)$^+$, m/z: 427.
(Step 4)
A crude product of compound 7g was obtained from the crude product (60 mg) of 2-(((1R,4r)-4-(((2S,4R)-2-methyl-1-propionyl-1,2,3,4-tetrahydroquinolin-4-yl)amino)cyclohexyl)amino)oxazole-4-carboxylic acid obtained in step 3 and 1-{(2S,4R)-4-[(4-aminophenyl)amino]-2-methyl-3,4-dihydroquinolin-1(2H)-yl}propan-1-one (52.2 mg, 0.169 mmol) obtained in step 3 of reference example 7 in the same manner as in step 3 of example 1b. The crude product obtained was purified by reverse phase HPLC (0.05% aqueous ammonium bicarbonate solution/acetonitrile=55/45 to 50/50) to give compound 7g (4 mg, total yield of 4 steps 4%).
ESI-MS, (M+H)$^+$, m/z: 718. $^1$H-NMR (CDCl$_3$) δ: 1.07-1.18 (m, 12H), 1.22-1.43 (m, 4H), 2.01-2.16 (m, 2H), 2.19-2.43 (m, 4H), 2.48-2.78 (m, 6H), 3.52-3.67 (m, 2H), 3.76-3.85 (m, 1H), 4.12-4.21 (m, 1H), 4.49 (d, J=7.7 Hz, 1H), 4.56 (s, 1H), 4.83-5.00 (m, 2H), 6.63 (m, 3H), 7.08-7.22 (m, 4H), 7.27-7.33 (m, 3H), 7.49 (m, 3H), 7.75 (s, 1H), 8.44 (s, 1H).

Example 7h

N-((3-(((1R,4r)-4-(((2S,4R)-2-Methyl-1-propionyl-1,2,3,4-tetrahydroquinolin-4-yl)amino)cyclohexyl))amino)oxetan-3-yl)methyl)-3-(4-(((2S,4R)-2-methyl-1-propionyl-1,2,3,4-tetrahydroquinolin-4-yl)amino)phenyl)propanamide (Compound 7h)

(Step 1)
1-((2S,4R)-4-(((1r,4R)-4-Aminocyclohexyl)amino)-2-methyl-3,4-dihydroquinolin-1(2H)-yl)propan-1-one dihydrochloride (50 mg, 0.129 mmol) obtained in reference example 9 was suspended in THF (1 mL), then N,N-diisopropylethylamine (0.090 mL, 0.515 mmol) and 3-(nitromethylene)oxetane (16.30 mg, 0.142 mmol) were added to the suspension at 0° C., and the mixture was stirred at room temperature for 5.5 hours. The reaction mixture was diluted with saturated aqueous ammonium chloride solution, and the aqueous layer was extracted with chloroform. The organic layer was dried over anhydrous magnesium sulfate and concentrated under reduced pressure, and the resulting residue was purified by silica gel column chromatography (chloroform/methanol=95/5 to 80/20) to give 1-((2S,4R)-2-methyl-4-(((1r,4R)-4-((3-(nitromethyl)oxetan-3-yl)amino)cyclohexyl)amino)-3,4-dihydroquinolin-1(2H)-yl)propan-1-one (28.9 mg, 52%).
ESIMS, (M+H)$^+$, m/z: 431.
(Step 2)
1-((2S,4R)-4-(((1r,4R)-4-((3-(Aminomethyl)oxetan-3-yl)amino)cyclohexyl)amino)-2-methyl-3,4-dihydroquinolin-1(2H)-yl)propan-1-one (20.9 mg, 80%) was obtained from 1-((2S,4R)-2-methyl-4-(((1r,4R)-4-((3-(nitromethyl)oxetan-3-yl)amino)cyclohexyl)amino)-3,4-dihydroquinolin-1(2H)-yl)propan-1-one (28.0 mg, 0.065 mmol) obtained in step 1 in the same manner as in step 2 of reference example 17.
ESIMS, (M+H)$^+$, m/z: 401.
(Step 3)
Ethyl 1-((2S,4R)-4-((4-bromophenyl)amino)-2-methyl-3,4-dihydroquinolin-1(2H)-yl)propan-1-one (311 mg, 0.833 mmol) obtained in reference example 2 was dissolved in THF (5 mL), then palladium acetate (37.4 mg, 0.167 mmol), SPhos (137 mg, 0.333 mmol) and 3-ethoxy-3-oxopropylzinc bromide (0.50 mol/L THF solution, 3.33 mL, 1.67 mmol) were added to the solution, and the mixture was stirred at room temperature for 22 hours. The reaction mixture was diluted with saturated aqueous ammonium chloride solution, and the aqueous layer was extracted with ethyl acetate. The organic layer was dried over anhydrous magnesium sulfate and concentrated under reduced pressure. The obtained residue was purified by silica gel column chromatography (ethyl acetate/heptane=1/9 to 3/7) to give ethyl 3-(4-(((2S, 4R)-2-methyl-1-propionyl-1,2,3,4-tetrahydroquinolin-4-yl) amino)phenyl)propanoate (95.6 mg, 29%).
ESIMS, (M+H)+, m/z: 395.
(Step 4)

A crude product (90.0 mg) of 3-(4-(((2S,4R)-2-methyl-1-propionyl-1,2,3,4-tetrahydroquinolin-4-yl)amino)phenyl) propanoic acid was obtained from ethyl 3-(4-(((2S,4R)-2-methyl-1-propionyl-1,2,3,4-tetrahydroquinolin-4-yl)amino) phenyl)propanoate (95.0 mg, 0.241 mmol) obtained in step 3 and in the same manner as in step 6 of reference example 1.
ESIMS, (M+H)+, m/z: 367.
(Step 5)

Compound 7h (6.8 mg, 20%) was obtained from 1-((2S, 4R)-4-(((1r,4R)-4-((3-(aminomethyl)oxetan-3-yl)amino)cyclohexyl)amino)-2-methyl-3,4-di hydroquinolin-1 (2H)-yl) propan-1-one (18.4 mg, 0.046 mmol) obtained in step 2 and the crude product (16.3 mg) of 3-(4-(((2S,4R)-2-methyl-1-propionyl-1,2,3,4-tetrahydroquinolin-4-yl)amino)phenyl) propanoic acid obtained in step 4 in the same manner as in step 3 of example 1b.
ESIMS, (M+H)+, m/z: 749; $^1$H-NMR (CDCl$_3$, δ) 1.32-1.40 (m, 16H), 1.70-1.84 (m, 2H), 1.89-2.08 (m, 2H), 2.17-2.69 (m, 10H), 2.88 (t, J=8.0 Hz, 2H), 3.50 (dd, J=12.0, 4.0 Hz, 1H), 3.57-3.69 (m, 3H), 3.71-3.86 (m, 1H), 4.14 (d, J=12.4 Hz, 1H), 4.30 (d, J=6.8 Hz, 1H), 4.32 (d, J=6.8 Hz, 1H), 4.37 (d, J=6.8 Hz, 1H), 4.39 (d, J=6.8 Hz, 1H), 4.76-5.05 (m, 2H), 5.70-5.86 (m, 1H), 6.57 (d, J=8.8 Hz, 2H), 7.03 (d, J=8.8 Hz, 2H), 7.06-7.34 (m, 7H), 7.42-7.49 (m, 1H).

Example 7i 1-((2S*,4R*)-2-Methyl-4-(((1r,4R)-4-(3-(4-(((2S, 4R)-2-methyl-1-propionyl-1,2,3,4-tetrahydroquinolin-4-yl)amino)benzoyl)-5,6,7,8-tetrahydroimidazo [1,2-a]pyrazine-7-carbonyl)cyclohexyl)amino)-3,4-dihydroquinolin-1(2H)-yl)propan-1-one (Compound 7i)

(Step 1)
tert-Butyl 3-(4-((tert-butoxycarbonyl)((2S,4R)-2-methyl-1-propionyl-1,2,3,4-tetrahydroquinolin-4-yl)amino)benzoyl)-5,6-dihydroimidazo[1,2-a]pyrazine-7(8H)-carboxylate (0.140 g, 94%) was obtained from tert-butyl 3-((4-((tert-butoxycarbonyl)((2S,4R)-2-methyl-1-propionyl-1,2,3,4-tetrahydroquinolin-4-yl)amino)phenyl)(hydroxy)methyl)-5,6-dihydroimidazo[1,2-a]pyrazine-7(8H)-carboxylate (0.150 g, 0.23 mmol) obtained in step 1 of example 5c in the same manner as in step 4 of example 7r.
ESIMS, (M+H)+, m/z: 644.
(Step 2)

A crude product (0.105 g) of 1-((2S,4R)-2-methyl-4-((4-(5,6,7,8-tetrahydroimidazo[1,2-a]pyrazine-3-carbonyl)phenyl)amino)-3,4-dihydroquinolin-1(2H)-yl)propan-1-one dihydrochloride was obtained from tert-butyl 3-(4-((tert-butoxycarbonyl)((2S,4R)-2-methyl-1-propionyl-1,2,3,4-tetrahydroquinolin-4-yl)amino)benzoyl)-5,6-dihydroimidazo [1,2-a]pyrazine-7(8H)-carboxylate (0.140 g, 0.22 mmol) obtained in step 1 in the same manner as in step 2 of example 1a.
ESIMS, (M+H)+, m/z: 444.
(Step 3)

Compound 7i (0.030 g, total yield of 2 steps 22%) was obtained from the crude product (0.099 g) of 1-((2S,4R)-2-methyl-4-((4-(5,6,7,8-tetrahydroimidazo[1,2-a]pyrazine-3-carbonyl)phenyl)amino)-3,4-dihydroquinolin-1(2H)-yl)propan-1-one dihydrochloride obtained in step 2 and (1R,4r)-4-(((2S*,4R*)-2-methyl-1-propionyl-1,2,3,4-tetrahydroquinolin-4-yl)amino)cyclohexane-1-carboxylic acid (0.06 g, 0.17 mmol) obtained in step 2 of reference example 11 in the same manner as in step 3 of example 1b.
ESIMS, (M+H)+, m/z: 770; $^1$H-NMR (DMSO-d$_6$, δ) 0.78-0.89 (m, 1H), 0.82-1.07 (m, 12H), 1.12-1.31 (m, 3H), 1.38-1.51 (m, 2H), 1.66-1.77 (m, 3H), 1.92-2.04 (m, 2H), 2.09-2.26 (m, 2H), 2.51-2.66 (m, 6H), 3.47 (d, J=10.07 Hz, 1H), 3.87-4.03 (m, 2H), 4.19-4.26 (m, 1H), 4.32-4.38 (m, 2H), 4.57-4.68 (m, 1H), 4.69-4.94 (m, 3H), 6.75 (d, J=8.54 Hz, 2H), 7.02 (d, J=7.93 Hz, 1H), 7.11 (d, J=7.63 Hz, 1H), 7.16-7.35 (m, 6H), 7.47-7.55 (m, 2H), 7.71 (d, J=8.8 Hz, 2H).

Example 7j 4-(((2S,4R)-2-Methyl-1-propionyl-1,2,3,4-tetrahydroquinolin-4-yl)amino)-N-((3-(((1R,4R)-4-(((2S, 4R)-2-methyl-1-propionyl-1,2,3,4-tetrahydroquinolin-4-yl)amino)cyclohexyl)amino)oxetan-3-yl)ethyl) benzamide (Compound 7j)

1-((2S,4R)-4-(((1r,4R)-4-((3-(Aminomethyl)oxetan-3-yl) amino)cyclohexyl)amino)-2-methyl-3,4-dihydroquinolin-1 (2H)-yl)propan-1-one (20.9 mg, 0.052 mmol) obtained in step 2 of example 7h and 4-((tert-butoxycarbonyl)((2S,4R)-2-methyl-1-propionyl-1,2,3,4-tetrahydroquinolin-4-yl) amino)benzoic acid (16.3 mg, 0.046 mmol) obtained in step 2 of reference example 8 were dissolved in DMF (0.5 mL), then N,N-diisopropylethylamine (0.023 mL, 0.130 mmol) and COMU (33.5 mg, 0.078 mmol) were added to the solution, and the mixture was stirred at room temperature for 17 hours. The reaction mixture was diluted with saturated aqueous sodium hydrogen carbonate solution, and the aqueous layer was extracted with ethyl acetate. The organic layer was dried over anhydrous magnesium sulfate and concentrated under reduced pressure. The obtained residue was dissolved in dichloromethane (0.5 mL), then trifluoroacetic acid (0.5 mL) was added to the solution, and the mixture was stirred at room temperature for 3 hours. The reaction mixture was neutralized with saturated aqueous sodium hydrogen carbonate solution, and the aqueous layer was extracted with chloroform. The organic layer was dried over anhydrous sodium sulfate and concentrated under reduced pressure. The obtained residue was purified by reverse phase HPLC (10 mmol/L aqueous ammonium bicarbonate solution/acetonitrile=60/40 to 55/45) to give compound 5f (4.0 mg, 11%).
ESIMS, (M+H)+, m/z: 721; $^1$H-NMR (CDCl$_3$, δ) 1.03-1.36 (m, 16H), 1.76-2.12 (m, 4H), 2.16-2.43 (m, 2H), 2.45-2.74 (m, 7H), 3.50 (dd, J=12.0, 4.4 Hz, 1H), 3.84 (d, J=4.4 Hz, 2H), 4.16-4.33 (m, 2H), 4.47 (s, 4H), 4.77-5.04 (m, 2H), 6.44-6.53 (m, 1H), 6.62 (d, J=8.4 Hz, 2H), 7.05-7.34 (m, 8H), 7.42-7.51 (m, 1H), 7.65 (d, J=8.4 Hz, 2H).

Example 7k (1R,4R)-4-(((2S*,4R*)-2-Methyl-1-propionyl-1,2,3, 4-tetrahydroquinolin-4-yl)amino)-N-(2-((4-(((2S, 4R)-2-methyl-1-propionyl-1,2,3,4-tetrahydroquinolin-4-yl)amino)phenyl)amino)-2-oxoethyl) cyclohexane-1-carboxamide (Compound 7k)

Compound 7k (0.064 g, 35%) was obtained from 2-amino-N-(4-(((2S,4R)-2-methyl-1-propionyl-1,2,3,4-tetrahydroquinolin-4-yl)amino)phenyl)acetamide hydrochloride (0.105 g, 0.26 mmol) obtained in step 3 of example 7d and (1R,4r)-4-(((2S*,4R*)-2-methyl-1-propionyl-1,2,3,4-tetrahydroquinolin-4-yl)amino)cyclohexane-1-carboxylic acid (0.100 g, 0.26 mmol) obtained in step 2 of reference example 11 in the same manner as in step 3 of example 1b. ESIMS, (M+H)$^+$, m/z: 693; $^1$H-NMR (DMSO-d$_6$, δ) 0.77-0.89 (m, 1H), 0.91-1.20 (m, 16H), 1.33-1.45 (m, 2H), 1.67-1.83 (m, 3H), 1.90-2.05 (m, 2H), 2.08-2.28 (m, 3H), 2.52-2.64 (m, 4H), 3.42-3.51 (m, 1H), 3.78 (d, J=5.70 Hz, 2H), 4.08-4.12 (m, 1H), 4.59-4.78 (m, 2H), 5.88 (d, J=7.89 Hz, 1H), 6.59 (d, J=8.77 Hz, 2H), 7.16 (d, J=3.73 Hz, 2H), 7.22-7.29 (m, 7H), 7.46-7.52 (m, 1H), 7.97 (t, J=5.6 Hz, 1H), 9.53 (s, 1H).

Example 7l 1-((2S*,4R*)-2-Methyl-4-(((1 r,4R)-4-(3-(4-(((2S,4R)-2-methyl-1-propionyl-1,2,3,4-tetrahydroquinolin-4-yl)amino)benzyl)-5,6,7,8-tetrahydroimidazo[1,2-a]pyrazine-7-carbonyl)cyclohexyl)amino)-3,4-dihydroquinolin-1(2H)-yl)propan-1-one (Compound 7l)

Compound 7l (0.023 g, 23%) was obtained from the crude product (0.082 g) of 1-((2S,4R)-2-methyl-4-((4-((5,6,7,8-tetrahydroimidazo[1,2-a]pyrazin-3-yl)methyl)phenyl)amino)-3,4-dihydroquinolin-1(2H)-yl)propan-1-one trifluoroacetate obtained in step 2 of example 5c and 4-{[(2S,4R)-2-methyl-1-propionyl-1,2,3,4-tetrahydroquinolin-4-yl]amino}benzoic acid (0.045 g, 0.13 mmol) obtained in step 7 of reference example 1 in the same manner as in step 3 of example 1b.
ESIMS, (M+H)$^+$, m/z: 756; $^1$H-NMR (DMSO-d$_6$, δ) 0.79-0.88 (m, 1H), 0.99-1.07 (m, 12H), 1.11-1.20 (m, 2H), 1.22-1.30 (m, $^1$H), 1.31-1.47 (m, 2H), 1.61-1.72 (m, 3H), 1.88-2.04 (m, 2H), 2.08-2.28 (m, 2H), 2.53-2.71 (m, 6H), 3.42-3.52 (m, 1H), 3.63-3.80 (m, 4H), 3.81-3.94 (m, 2H), 4.08-4.12 (m, 1H), 4.55-4.72 (m, 4H), 5.95 (d, J=7.87 Hz, 1H), 6.58 (d, J=8.11 Hz, 3H), 6.91 (d, J=8.11 Hz, 2H), 7.15 (brs, 2H), 7.22-7.29 (m, 5H), 7.50 (brs, 1H).

Example 7m 4-(((2S,4R)-2-Methyl-1-propionyl-1,2,3,4-tetrahydroquinolin-4-yl)amino)-N-(3-((1R,4r)-4-(((2S*,4R*)-2-methyl-1-propionyl-1,2,3,4-tetrahydroquinolin-4-yl)amino)cyclohexane-1-carboxamide)propyl)benzamide (Compound 7m)

Compound 7m (0.059 g, 18%) was obtained from N-(3-amino propyl)-4-{[(2S,4R)-2-methyl-1-propionyl-1,2,3,4-tetrahydroquinolin-4-yl]amino}benzamide hydrochloride (0.200 g, 0.46 mmol) obtained in step 2 of example 1h, and (1R,4r)-4-(((2S*,4R*)-2-methyl-1-propionyl-1,2,3,4-tetrahydroquinolin-4-yl)amino)cyclohexane-1-carboxylic acid (0.176 g, 0.46 mmol) obtained in step 2 of reference example 11 in the same manner as in step 3 of example 1b.
ESIMS, (M+H)$^+$, m/z: 721. $^1$H-NMR (DMSO-d$_6$, δ): 0.75-0.87 (m, 1H), 0.90-1.25 (m, 16H), 1.31-1.45 (m, 2H), 1.53-1.63 (m, 2H), 1.72 (d, J=11.68 Hz, 3H), 1.89-2.18 (m, 4H), 2.21-2.29 (m, 1H), 2.52-2.66 (m, 4H), 3.06 (q, J=6.44 Hz, 2H), 3.20 (q, J=6.60 Hz, 2H), 3.40-3.51 (m, 1H), 4.22-4.30 (m, 1H), 4.56-4.79 (m, 2H), 6.56 (d, J=8.0 Hz, 1H), 6.65 (d, J=8.82 Hz, 2H), 7.06-7.11 (m, 1H), 7.13-7.33 (m, 6H), 7.46-7.53 (m, 2H), 7.62 (d, J=8.82 Hz, 2H), 7.73 (t, J=5.60 Hz, 1H), 8.02 (t, J=5.60 Hz, 1H).

Example 7n 4-(((2S,4R)-2-Methyl-1-propionyl-1,2,3,4-tetrahydroquinolin-4-yl)amino)-N-(1-((1R,4R)-4-(((2S*,4R*)-2-methyl-1-propionyl-1,2,3,4-tetrahydroquinolin-4-yl)amino)cyclohexane-1-carbonyl)azetidin-3-yl)benzamide (Compound 7n)

Compound 7n (0.048 g, 32%) was obtained from 1-[(2S,4R)-4-{[4-(3-aminoazetidine-1-carbonyl)phenyl]amino}-2-methyl-3,4-dihydroquinolin-1(2H)-yl]propan-1-one trifluoroacetate (0.106 g, 0.21 mmol) obtained in step 2 of example in and (1R,4r)-4-(((2S*,4R*)-2-methyl-1-propionyl-1,2,3,4-tetrahydroquinolin-4-yl)amino)cyclohexane-1-carboxylic acid (0.08 g, 0.21 mmol) obtained in step 2 of reference example 11 in the same manner as in step 3 of example 1b.
ESIMS, (M+H)$^+$, m/z: 719. $^1$H-NMR (DMSO-d$_6$, δ): 0.76-0.86 (m, 1H), 0.93-1.06 (m, 13H), 1.09-1.26 (m, 3H), 1.29-1.44 (m, 2H), 1.69 (d, J=12.87 Hz, 3H), 1.91-2.04 (m, 2H), 2.08-2.30 (m, 3H), 2.52-2.64 (m, 4H), 3.40-3.50 (m, 1H), 3.81 (dd, J=10.13, 5.36 Hz, 1H), 4.01-4.11 (m, 2H), 4.22-4.32 (m, 1H), 4.39-4.48 (m, 1H), 4.59-4.68 (m, 2H), 4.70-4.78 (m, 1H), 6.62-6.68 (m, 3H), 7.08-7.32 (m, 7H), 7.48-7.50 (m, 1H), 7.67 (d, J=8.82 Hz, 2H), 8.55 (d, J=6.8 Hz, 1H).

Example 7o

N$^1$-((1R,4r)-4-(((2S,4R)-2-Methyl-1-propionyl-1,2,3,4-tetrahydroquinolin-4-yl)amino)cyclohexyl)-N$^5$-(4-(((2S,4R)-2-methyl-1-propionyl-1,2,3,4-tetrahydroquinolin-4-yl)amino)phenyl)glutaramide (Compound 7o)

Compound 7o (0.060 g, 25%) was obtained from 1-(4-(((1r,4r)-4-aminocyclohexyl)amino)-2-methyl-3,4-dihydroquinolin-1(2H)-yl)propan-1-one dihydrochloride (0.127 g, 0.33 mmol) obtained in reference example 9 and 5-((4-(((2S,4R)-2-methyl-1-propionyl-1,2,3,4-tetrahydroquinolin-4-yl)amino)phenyl)amino)-5-oxopentanoic acid (0.140 g, 0.33 mmol) obtained in step 2 of example 6k in the same manner as in step 3 of example 1b.
ESIMS, (M+H)$^+$, m/z: 721.55. $^1$H-NMR (DMSO-d$_6$, δ): 0.79-0.89 (m, 1H), 0.93-1.04 (m, 12H), 1.10-1.19 (m, 5H), 1.75-1.78 (m, 4H), 1.91-1.99 (m, 2H), 2.05-2.26 (m, 6H), 2.53-2.61 (m, 5H), 3.45-3.52 (m, 2H), 3.91-4.15 (m, 1H), 4.61-4.78 (m, 2H), 5.82 (d, J=7.6 Hz, 1H), 6.57 (d, J=9.2 Hz, 2H), 7.15 (d, J=3.6 Hz, 2H), 7.22-7.30 (m, 7H), 7.47-7.49 (m, 1H), 7.64 (d, J=8.0 Hz, 1H), 9.46 (s, 1H).

Example 7p 4-((1R,4r)-4-(((2S,4R)-2-Methyl-1-propionyl-1,2,3,4-tetrahydroquinolin-4-yl)amino)cyclohexane-1-carbonyl)-N-(4-(((2S,4R)-2-methyl-1-propionyl-1,2,3,4-tetrahydroquinolin-4-yl)amino)phenyl)piperazine-1-carboxamide (Compound 7p)

(Step 1)
1-{(2S,4R)-4-[(4-Aminophenyl)amino]-2-methyl-3,4-dihydroquinolin-1(2H)-yl}propan-1-one (70 mg, 0.226 mmol) obtained in reference example 7 was dissolved in THF (3 mL), then triethylamine (0.095 ml, 0.679 mmol) and tert-butyl 4-(chlorocarbonyl)piperazine-1-carboxylate (61.9 mg, 0.249 mmol) were added to the solution, and the mixture was stirred at room temperature overnight. Water and saturated aqueous ammonium chloride solution were added to the reaction mixture, and the mixture was extracted twice with ethyl acetate. The organic layer was dried over anhydrous magnesium sulfate and concentrated under reduced pressure. The obtained residue was purified by silica gel column chromatography (chloroform/methanol=100/0 to 90/10) to give tert-butyl 4-((4-(((2S,4R)-2-methyl-1-propionyl-1,2,3,4-tetrahydroquinolin-4-yl)amino)phenyl)carbamoyl)piperazine-1-carboxylate (156 mg, quantitative).

ESIMS, (M−H)⁻, m/z: 520.80.

(Step 2)

N-(4-(((2S,4R)-2-Methyl-1-propionyl-1,2,3,4-tetrahydroquinolin-4-yl)amino)phenyl)piperazine-1-carboxamide (113.9 mg, quantitative) was obtained from tert-butyl 4-((4-(((2S,4R)-2-methyl-1-propionyl-1,2,3,4-tetrahydroquinolin-4-yl)amino)phenyl)carbamoyl)piperazine-1-carboxylate (118 mg, 0.226 mmol) obtained in step 1 in the same manner as in step 1 of example 8h.

ESIMS, (M+H)⁺, m/z: 422.58.

(Step 3)

Compound 7p (27.2 mg, 63%) was obtained from N-(4-(((2S,4R)-2-methyl-1-propionyl-1,2,3,4-tetrahydroquinolin-4-yl)amino)phenyl)piperazine-1-carboxamide (20 mg, 0.058 mmol) obtained in step 2 and (1R,4r)-4-(((2S,4R)-2-methyl-1-propionyl-1,2,3,4-tetrahydroquinolin-4-yl)amino) cyclohexane-1-carboxylic acid (20 mg, 0.058 mmol) obtained in reference example 11 in the same manner as in step 3 of example 1b.

ESIMS, (M+H)⁺, m/z: 749.04. ¹H-NMR (DMSO-d₅, δ): 0.80-0.86 (m, 1H), 0.93-1.04 (m, 12H), 1.10-1.28 (m, 3H), 1.35-1.47 (m, 2H), 1.69 (d, J=11.8 Hz, 2H), 1.91-2.03 (m, 2H), 2.11-2.28 (m, 2H), 2.53-2.64 (m, 6H), 3.35-3.51 (m, 10H), 4.07-4.14 (m, 1H), 4.60-4.76 (m, 2H), 5.76 (d, J=7.7 Hz, 1H), 6.56 (d, J=8.6 Hz, 2H), 7.11 (d, J=8.6 Hz, 2H), 7.14-7.30 (m, 7H), 7.50 (t, J=3.6 Hz, 1H), 8.21 (s, 1H).

Example 7q (1R,4R)-4-(((2S,4R)-2-Methyl-1-propionyl-1,2,3,4-tetrahydroquinolin-4-yl)amino)-N-((5-(4-(((2S,4R)-2-methyl-1-propionyl-1,2,3,4-tetrahydroquinolin-4-yl)amino)phenyl)-1,3,4-oxadiazol-2-yl)methyl) cyclohexane-1-carboxamide (Compound 7q)

Compound 7q (97.5 mg, 59%) was obtained from (1R,4r)-4-(((2S,4R)-2-methyl-1-propionyl-1,2,3,4-tetrahydroquinolin-4-yl)amino)cyclohexane-1-carboxylic acid (80 mg, 0.232 mmol) obtained in reference example 11 and 1-((2S,4R)-4-((4-(5-(aminomethyl)-1,3,4-oxadiazol-2-yl)phenyl)amino)-2-methyl-3,4-dihydroquinolin-1(2H)-yl)propan-1-one (91 mg, 0.232 mmol) obtained in step 3 of example 5g in the same manner as in step 1 of example 1a.

ESIMS, (M+H)⁺, m/z: 718; ¹H-NMR (CDCl₃, δ) 1.04-1.41 (m, 17H), 1.96-2.80 (m, 12H), 3.56 (dd, J=12.0, 4.0 Hz, 1H), 4.22-4.38 (m, 2H), 4.72 (d, J=5.6 Hz, 2H), 4.79-5.06 (m, 2H), 6.24-6.33 (m, 1H), 6.68 (d, J=8.8 Hz, 2H), 7.05-7.36 (m, 7H), 7.43-7.50 (m, 1H), 7.84 (d, J=8.8 Hz, 2H).

Example 7r 4-(((2S,4R)-2-Methyl-1-propionyl-1,2,3,4-tetrahydroquinolin-4-yl)amino)-N-(3-((1R,4r)-4-(((2S*, 4R*)-2-methyl-1-propionyl-1,2,3,4-tetrahydroquinolin-4-yl)amino)cyclohexane-1-carboxamide)-2-oxopropyl)benzamide (Compound 7r)

(Step 1)

tert-Butyl (4-((3-((tert-butoxycarbonyl)amino)-2-hydroxypropyl)carbamoyl)phenyl)((2S,4R)-2-methyl-1-propionyl-1,2,3,4-tetrahydroquinolin-4-yl)carbamate (324 mg, 93%) was obtained from 4-((tert-butoxycarbonyl)((2S,4R)-2-methyl-1-propionyl-1,2,3,4-tetrahydroquinolin-4-yl) amino)benzoic acid (250 mg, 0.570 mmol) obtained in step 2 of reference example 8 and tert-butyl (3-amino-2-hydroxypropyl)carbamate (130 mg, 0.684 mmol) in the same manner as in step 3 of example 1b.

ESIMS, (M+H)⁺, m/z: 611

(Step 2)

N-(3-Amino-2-hydroxypropyl)-4-(((2S,4R)-2-methyl-1-propionyl-1,2,3,4-tetrahydroquinolin-4-yl)amino)benzamide hydrochloride (216 mg, 100%) was obtained from tert-butyl (4-((3-((tert-butoxycarbonyl)amino)-2-hydroxypropyl)carbamoyl)phenyl)((2S,4R)-2-methyl-1-propionyl-1,2,3,4-tetrahydroquinolin-4-yl)carbamate (322 mg, 0.527 mmol) obtained in step 1 in the same manner as in step 2 of example 1a.

ESIMS, (M+H)⁺, m/z: 411.

(Step 3)

N-(2-Hydroxy-3-((1R,4r-4-(((2S*,4R*)-2-methyl-1-propionyl-1,2,3,4-tetrahydroquinolin-4-yl)amino)cyclohexane-1-carboxamide)propyl)-4-(((2S,4R)-2-methyl-1-propionyl-1,2,3,4-tetrahydroquinolin-4-yl)amino)benzamide (24.1 mg, 22%) was obtained from N-(3-amino-2-hydroxypropyl)-4-(((2S,4R)-2-methyl-1-propionyl-1,2,3,4-tetrahydroquinolin-4-yl)amino)benzamide hydrochloride (60.0 mg, 0.146 mmol) obtained in step 2 and (1R,4r)-4-(((2S*,4R*)-2-methyl-1-propionyl-1,2,3,4-tetrahydroquinolin-4-yl)amino) cyclohexane-1-carboxylic acid (50.3 mg, 0.146 mmol) obtained in step 2 of reference example 11 in the same manner as in step 1 of example 1a.

ESIMS, (M+H)⁺, m/z: 737.

(Step 4)

N-(2-Hydroxy-3-((1R,4r)-4-(((2S*,4R*)-2-methyl-1-propionyl-1,2,3,4-tetrahydroquinolin-4-yl)amino)cyclohexane-1-carboxamide)propyl)-4-(((2S,4R)-2-methyl-1-propionyl-1,2,3,4-tetrahydroquinolin-4-yl)amino)benzamide (11.6 mg, 0.016 mmol) obtained in step 3 was dissolved in dichloromethane (0.2 mL), then DMP (26.7 mg, 0.062 mmol) was added to the solution, and the mixture was stirred at room temperature for 4 hours. The reaction mixture was diluted with saturated sodium thiosulfate and stirred for 5 minutes. Furthermore, a saturated aqueous sodium hydrogen carbonate solution was added to the reaction mixture, and the aqueous layer was extracted with ethyl acetate. The organic layer was dried over anhydrous magnesium sulfate, concentrated under reduced pressure, and the obtained residue was purified by reverse phase HPLC (10 mmol/L ammonium bicarbonate aqueous solution/acetonitrile=65/35 to 55/45) to give compound 7r (4.1 mg, 35%) was obtained.

ESIMS, (M+H)⁺, m/z: 735; ¹H-NMR (CDCl₃, δ) 1.04-1.16 (m, 12H), 1.20-1.49 (m, 4H), 1.93-2.44 (m, 7H), 2.47-2.79 (m, 5H), 3.56 (dd, J=12.4, 4.0 Hz, 1H), 4.19-4.31 (m, 2H), 4.24 (d, J=4.4 Hz, 2H), 4.35 (d, J=4.4 Hz, 2H), 4.76-5.06 (m, 2H), 6.19-6.31 (m, 1H), 6.62 (d, J=8.8 Hz, 2H), 6.68-6.76 (m, 1H), 7.07-7.38 (m, 8H), 7.43-7.51 (m, 1H), 7.68 (d, J=8.8 Hz, 2H).

Example 8a (1R,4r)-4-(((2S,4R)-2-Methyl-1-propionyl-1,2,3,4-tetrahydroquinolin-4-yl)amino)-N-(2-(1-(4-(((2S,4R)-2-methyl-1-propionyl-1,2,3,4-tetrahydroquinolin-4-yl)amino)phenyl)-1H-1,2,3-triazol-4-yl)ethyl)cyclohexane-1-carboxamide (Compound 8a)

(Step 1)
(1R,4r)-N-(But-3-yn-1-yl)-4-(((2S,4R)-2-methyl-1-propionyl-1,2,3,4-tetrahydroquinolin-4-yl)amino)cyclohexane-1-carboxamide (87 mg, 76%) was obtained from (1R,4r)-4-(((2S,4R)-2-methyl-1-propionyl-1,2,3,4-tetrahydroquinolin-4-yl)amino)cyclohexane-1-carboxylic acid (100 mg, 0.290 mmol) obtained in reference example 11 and 3-butyn-1-amine (0.029 mL, 0.348 mmol) in the same manner as in step 3 of example 1b.
ESI-MS, (M+H)$^+$, m/z: 396.

(Step 2)
A crude product of compound 8a was obtained from the crude product (80 mg) of 1-(2S,4R)-4-((4-azidophenyl)amino)-2-methyl-3,4-dihydroquinolin-1(2H)-yl)propan-1-one obtained in step 2 of example 3a and (1R,4r)-N-(but-3-yn-1-yl)-4-(((2S,4R)-2-methyl-1-propionyl-1,2,3,4-tetrahydroquinolin-4-yl)amino)cyclohexane-1-carboxamide (80 mg, 0.202 mmol) obtained in step 1 in the same manner as in step 3 of example 3a. The obtained crude product of compound 8a was purified by reverse phase HPLC (0.05% ammonium bicarbonate aqueous solution/acetonitrile=6/4 to 5/5) to give compound 8a (85 mg, total yield of 2 steps 57%).
ESI-MS, (M+H)$^+$, m/z: 731. $^1$H-NMR (CDCl$_3$), δ: 1.06-1.12 (m, 6H), 1.15-1.20 (m, 6H), 1.47-1.56 (m, 2H), 1.56-1.64 (m, 3H), 1.90-1.97 (m, 2H), 1.98-2.05 (m, 1H), 2.06-2.15 (m, 2H), 2.22-2.34 (m, 1H), 2.34-2.44 (m, 1H), 2.46-2.63 (m, 3H), 2.64-2.75 (m, 2H), 2.97 (t, J=6.1 Hz, 2H), 3.55 (dd, J=11.8, 4.1 Hz, 1H), 3.66 (dd, J=6.0, 3.0 Hz, 2H), 4.11-4.17 (m, 1H), 4.20-4.27 (m, 1H), 4.85 (d, J=7.2 Hz, 1H), 4.97 (d, J=6.8 Hz, 1H), 6.38-6.44 (m, 1H), 6.71 (d, J=8.6 Hz, 2H), 7.07-7.13 (m, 1H), 7.17-7.26 (m, 4H), 7.27-7.33 (m, 2H), 7.43-7.47 (m, 1H), 7.49 (d, J=9.1 Hz, 2H), 7.68 (s, 1H).

Example 8b

N-((1R,4r)-4-(((2S,4R)-2-Methyl-1-propionyl-1,2,3,4-tetrahydroquinolin-4-yl)amino)cyclohexyl)-2-(2-((4-(((2S,4R)-2-methyl-1-propionyl-1,2,3,4-tetrahydroquinolin-4-yl)amino)phenyl)amino)-2-oxyethoxy)acetamide (Compound 8b)

(Step 1)
Methyl 2-(2-((4-(((2S,4R)-2-methyl-1-propionyl-1,2,3,4-tetrahydroquinolin-4-yl)amino)phenyl)amino)-2-oxyethoxy)acetate (140 mg, 99%) was obtained from 1-((2S,4R)-4-((4-aminophenyl)amino)-2-methyl-3,4-dihydroquinolin-1(2H)-yl)propan-1-one (100 mg, 0.323 mmol) obtained in step 3 of reference example 7 and 2-(2-methoxy-2-oxyethoxy)acetic acid (96 mg, 0.646 mmol) in the same manner as in step 3 of example 1b.
ESIMS, (M+H)$^+$, m/z: 440

(Step 2)
Methyl 2-(2-((4-(((2S,4R)-2-methyl-1-propionyl-1,2,3,4-tetrahydroquinolin-4-yl)amino)phenyl)amino)-2-oxyethoxy)acetate (54.0 mg, 0.123 mmol) obtained in step 1 was dissolved in a mixed solvent (1.2 mL) of THF and methanol (1:1), then an aqueous sodium hydroxide solution (4 mol/L, 1.0 mL) was added to the solution, and the mixture was stirred at room temperature overnight. The reaction mixture was neutralized with 6 mol/L hydrochloric acid, and the aqueous layer was extracted with chloroform. The organic layer was dried over anhydrous magnesium sulfate and concentrated under reduced pressure. The obtained residue was dissolved in DMF (1 mL), then N,N-diisopropylethylamine (0.104 mL, 0.611 mmol), COMU (79 mg, 0.183 mmol) and 1-((2S,4R)-4-(((1r,4R)-4-aminocyclohexyl)amino)-2-methyl-3,4-dihydroquinolin-1(2H)-yl)propan-1-one dihydrochloride (47.5 mg, 0.122 mmol) obtained in reference example 9 were added to the solution, and the mixture was stirred at room temperature for 21 hours. The reaction mixture was diluted with saturated aqueous sodium hydrogen carbonate solution, and the aqueous layer was extracted with ethyl acetate. The organic layer was dried over anhydrous sodium sulfate and concentrated under reduced pressure. The obtained residue was purified by reverse phase HPLC (10 mmol/L aqueous ammonium bicarbonate solution/acetonitrile=55/45 to 50/50) to give compound 8b (15.7 mg, 18%).
ESIMS, M+H)$^+$, m/z: 724.03; $^1$H-NMR (CDCl$_3$, δ) 1.04-1.17 (m, 12H), 1.19-1.40 (m, 5H), 1.94-2.19 (m, 4H), 2.17-2.42 (m, 2H), 2.45-2.73 (m, 5H), 3.45-3.59 (m, 1H), 3.76-3.96 (m, 2H), 4.08-4.22 (m, 2H), 4.12 (s, 2H), 4.16 (s, 2H), 4.77-5.06 (m, 2H), 6.15-6.28 (m, 1H), 6.62 (d, J=9.2 Hz, 2H), 7.07-7.35 (m, 8H), 7.37 (d, J=9.2 Hz, 2H), 7.43-7.57 (m, 1H), 8.13 (brs, 1H).

Example 8c 1-((1R,4R)-4-(((2S,4R)-2-Methyl-1-propionyl-1,2,3,4-tetrahydroquinolin-4-yl)amino)cyclohexane-1-carbonyl)-N-(4-(((2S,4R)-2-methyl-1-propionyl-1,2,3,4-tetrahydroquinolin-4-yl)amino)phenyl)azetidine-3-carboxamide (Compound 8c)

Compound 8c (0.028 g, 40%) was obtained from the crude product (0.050 g) of N-(4-(((2S,4R)-2-methyl-1-propionyl-1,2,3,4-tetrahydroquinolin-4-yl)amino)phenyl)azetidine-3-carboxamide trifluoroacetate obtained in step 1 of example 10e and (1R,4r)-4-(((2S,4R)-2-methyl-1-propionyl-1,2,3,4-tetrahydroquinolin-4-yl)amino)cyclohexane-1-carboxylic acid (0.034 g, 0.10 mmol) obtained in reference example 11 in the same manner as in step 3 of example 1b.
ESIMS, (M+H)$^+$, m/z: 719.71. $^1$H-NMR (DMSO-d$_6$, δ): 0.79-0.88 (m, 1H), 0.94-1.25 (m, 15H), 1.31-1.41 (m, 2H), 1.69 (d, J=13.37 Hz, 3H), 1.93-2.03 (m, 2H), 2.10-2.29 (m, 3H), 2.56-2.60 (m, 5H), 3.41-3.47 (m, 2H), 3.85-4.03 (m, 2H), 4.11-4.13 (m, 1H), 4.20-4.32 (m, 2H), 4.59-4.79 (m, 2H), 5.90 (d, J=7.89 Hz, 1H), 6.61 (d, J=8.77 Hz, 2H), 7.17 (d, J=3.73 Hz, 2H), 7.20-7.34 (m, 7H), 7.49-7.51 (m, 1H), 9.69 (s, 1H).

Example 8d 1-((2S*,4R*)-2-Methyl-4-(((1r,4R)-4-(4-(4-(4-((2S,4R)-2-methyl-1-propionyl-1,2,3,4-tetrahydroquinolin-4-yl)amino)phenyl)-1H-pyrazol-1-yl)piperidine-1-carbonyl)cyclohexyl)amino)-3,4-dihydroquinolin-1(2H)-yl)propan-1-one (Compound 8d)

(Step 1)
1-((2S,4R)-4-((4-Bromophenyl)amino)-2-methyl-3,4-dihydroquinolin-1(2H)-yl)propan-1-one (60 mg, 0.161 mmol) obtained in reference example 2 was dissolved in a mixed solvent (1.8 mL) of 1,4-dioxane and water (8:1), then tert-butyl 4-(4-(4,4,5,5-tetramethyl-1,3,2-dioxaborolan-2- yl)-1H-pyrazol-1-yl)piperidine-1-carboxylate (72.8 mg, 0.193 mmol), Pd(PPh$_3$)$_4$ (19 mg, 0.016 mmol) and cesium carbonate (157 mg, 0.482 mmol) were added to the solution, and the mixture was stirred at 120° C. for 1 hour under an argon atmosphere under microwave irradiation. Water was added to the reaction mixture, and the mixture was extracted twice with ethyl acetate. The organic layer was dried over anhydrous magnesium sulfate and concentrated under reduced pressure. The obtained residue was purified by silica gel column chromatography (chloroform/methanol=100/0 to 90/10) to give tert-butyl 4-(4-(4-(((2S,4R)-2-methyl-1-propionyl-1,2,3,4-tetrahydroquinolin-4-yl)amino)phenyl)-1H-pyrazol-1-yl)piperidine-1-carboxylate (0.4 g, 84%).
(Step 2)

tert-Butyl 4-(4-(4-(((2S,4R)-2-methyl-1-propionyl-1,2,3,4-tetrahydroquinolin-4-yl)amino)phenyl)-1H-pyrazol-1-yl)piperidine-1-carboxylate (0.55 g, 0.101 mmol) obtained in step 1 was dissolved in ethyl acetate (0.8 mL), then 4 mol/L hydrochloric acid (0.39 mL, 1.52 mmol) was added to the solution, and the mixture was stirred at room temperature for 3 hours. The reaction mixture was suction filtered, and the obtained solid was washed with ethyl acetate to give a crude product (55 mg) of 1-((2S,4R)-2-methyl-4-((4-(1-(piperidin-4-yl)-1H-pyrazol-4-yl)phenyl)amino)-3,4-dihydroquinolin-1(2H)-yl)propan-1-one hydrochloride.
(Step 3)

Compound 8d (10 mg, 2 step yield 12%) was obtained from the crude product (55 mg) of 1-((2S,4R)-2-methyl-4-((4-(1-(piperidin-4-yl)-1H-pyrazol-4-yl)phenyl)amino)-3,4-dihydroquinolin-1(2H)-yl)propan-1-one hydrochloride obtained in step 2 and (1R,4r)-4-(((2S*,4R*)-2-methyl-1-propionyl-1,2,3,4-tetrahydroquinolin-4-yl)amino)cyclohexane-1-carboxylic acid (0.039 g, 0.115 mmol) obtained in step 2 of reference example 11 in the same manner as in step 3 of example 1b.
ESI-MS m/z: 770 (M+H)+: $^1$H-NMR (CDCl$_3$, δ): 1.05-1.19 (m, 12H), 1.19-1.37 (m, 2H), 1.57-1.75 (m, 4H), 1.80-1.90 (m, 2H), 1.89-2.09 (m, 2H), 2.10-2.44 (m, 6H), 2.45-2.82 (m, 7H), 3.18-3.30 (m, 1H), 3.51-3.63 (m, 1H), 3.81-3.93 (m, 1H), 4.01-4.14 (m, 1H), 4.16-4.27 (m, 1H), 4.31-4.44 (m, 1H), 4.72-5.01 (m, 3H), 6.59-6.67 (m, 2H), 7.06-7.36 (m, 10H), 7.43-7.49 (m, 1H), 7.53-7.58 (m, 1H), 7.66-7.74 (m, 1H).

Example 8e (1R,4R)-4-(((2S*,4R*)-2-Methyl-1-propionyl-1,2,3,4-tetrahydroquinolin-4-yl)amino)-N-((5-(4-(((2S,4R)-2-methyl-1-propionyl-1,2,3,4-tetrahydroquinolin-4-yl)amino)phenyl)thiophen-2-yl)methyl)cyclohexane-1-carboxamide (Compound 8e)

(Step 1)
tert-Butyl ((5-(4-(((2S,4R)-2-methyl-1-propionyl-1,2,3,4-tetrahydroquinolin-4-yl)amino)phenyl)thiophen-2-yl)ethyl)carbamate (22 mg, 23%) was obtained from 1-((2S,4R)-4-((4-bromophenyl)amino)-2-methyl-3,4-dihydroquinolin-1(2H)-yl)propan-1-one (70 mg, 0.188 mmol) obtained in reference example 2 and (5-(((tert-butoxycarbonyl)amino)methyl)thiophen-2-yl)boronic acid (57.9 mg, 0.225 mmol) in the same manner as in step 1 of example 8d.
ESI-MS m/z: 506 (M+H)+
(Step 2)

A crude product (25 mg) of 1-((2S,4R)-4-((4-(5-(aminomethyl)thiophen-2-yl)phenyl)amino)-2-methyl-3,4-dihydroquinolin-1(2H)-yl)propan-1-one hydrochloride was obtained from tert-butyl ((5-(4-(((2S,4R)-2-methyl-1-propionyl-1,2,3,4-tetrahydroquinolin-4-yl)amino)phenyl)thiophen-2-yl)ethyl)carbamate (22 mg, 0.044 mmol) obtained in step 1 in the same manner as in step 2 of example 8d.
ESI-MS m/z: 406 (M+H)+
(Step 3)

Compound 8e (8 mg, total yield of 2 steps 24%) was obtained from the crude product (25 mg) of 1-((2S,4R)-4-((4-(5-(aminomethyl)thiophen-2-yl)phenyl)amino)-2-methyl-3,4-dihydroquinolin-1(2H)-yl)propan-1-one hydrochloride obtained in step 2 and (1R,4r)-4-(((2S*,4R*)-2-methyl-1-propionyl-1,2,3,4-tetrahydroquinolin-4-yl)amino)cyclohexane-1-carboxylic acid (0.019 g, 0.057 mmol) obtained in step 2 of reference example 11 in the same manner as in step 3 of example 1b.
ESI-MS m/z: 732 (M+H)+: $^1$H-NMR (CDCl$_3$, δ): 1.04-1.20 (m, 12H), 1.20-1.39 (m, 2H), 1.48-1.68 (m, 2H), 1.93-2.17 (m, 7H), 2.19-2.44 (m, 2H), 2.45-2.76 (m, 5H), 3.50-3.61 (m, 1H), 3.92-4.01 (m, 1H), 4.15-4.29 (m, 1H), 4.53-4.62 (m, 2H), 4.79-5.01 (m, 2H), 5.77-5.86 (m, 1H), 6.59-6.65 (m, 2H), 6.86 (d, J=3.8 Hz, 1H), 6.97 (d, J=3.8 Hz, 1H), 7.08-7.12 (m, 1H), 7.14-7.23 (m, 2H), 7.23-7.32 (m, 5H), 7.37-7.41 (m, 2H), 7.43-7.48 (m, 1H).

Example 8f 1-(4-(((2S,4R)-2-Methyl-1-propionyl-1,2,3,4-tetrahydroquinolin-4-yl)amino)benzyl)-N-((1R,4R)-4-(((2S,4R)-2-methyl-1-propionyl-1,2,3,4-tetrahydroquinolin-4-yl)amino)cyclohexyl)-1H-1,2,3-triazole-4-carboxamide (Compound 8f)

(Step 1)
tert-Butyl (4-(hydroxymethyl)phenyl)((2S,4R)-2-methyl-1-propionyl-1,2,3,4-tetrahydroquinolin-4-yl)carbamate (90 mg, 0.212) obtained in step 3 of reference example 8 was dissolved in toluene (2 mL), then diphenylphosphoryl azide (0.055 mL, 0.254 mmol) and DBU (0.038 mL, 0.254 mmol) were added to the solution, and the mixture was stirred at room temperature for 3 hours. The reaction mixture was purified by silica gel column chromatography (heptane/ethyl acetate=8/2 to 5/5) to give tert-butyl (4-(azidomethyl)phenyl)((2S,4R)-2-methyl-1-propionyl-1,2,3,4-tetrahydroquinolin-4-yl)carbamate (67 mg, 70%).
(Step 2)

A crude product (40 mg) of 1-(4-((tert-butoxycarbonyl)((2S,4R)-2-methyl-1-propionyl-1,2,3,4-tetrahydroquinolin-4-yl)amino)benzyl)-1H-1,2,3-triazole-4-carboxylic acid was obtained from tert-butyl (4-(azidomethyl)phenyl)((2S,4R)-2-methyl-1-propionyl-1,2,3,4-tetrahydroquinolin-4-yl)carbamate (50 mg, 0.111 mmol) obtained in step 1 and acetylene monocarboxylic acid (0.010 mL, 0.167 mmol) in the same manner as in step 3 of example 3a.
ESI-MS, (M+H)+, m/z: 520.
(Step 3)

A crude product (52 mg) of tert-butyl ((2S,4R)-2-methyl-1-propionyl-1,2,3,4-tetrahydroquinolin-4-yl)(4-((4-(((1R,4R)-4-(((2S*,4R*)-2-methyl-1-propionyl-1,2,3,4-tetrahydroquinolin-4-yl)amino)cyclohexyl)carbamoyl)-1H-1,2,3-triazol-1-yl)ethyl)phenyl)carbamate was obtained from the crude product (40 mg) of 1-(4-((tert-butoxycarbonyl)((2S,4R)-2-methyl-1-propionyl-1,2,3,4-tetrahydroquinolin-4-yl)amino)benzyl)-1H-1,2,3-triazole-4-carboxylic acid obtained in step 2 and 1-((2S*,4R*)-4-(((1r,4R)-4-aminocyclohexyl)amino)-2-methyl-3,4-dihydroquinolin-1(2H)-yl)propan-1-one dihydrochloride (25 mg, 0.064 mmol) obtained in reference example 10 in the same manner as in step 3 of example 1b.
ESI-MS, (M+H)+, m/z: 817.

(Step 4)

A crude product of compound 8f was obtained from the crude product (52 mg) of tert-butyl ((2S,4R)-2-methyl-1-propionyl-1,2,3,4-tetrahydroquinolin-4-yl)(4-((4-(((1R,4R)-4-(((2S*,4R*)-2-methyl-1-propionyl-1,2,3,4-tetrahydroquinolin-4-yl)amino)cyclohexyl)carbamoyl)-1H-1,2,3-triazol-1-yl)methyl)phenyl)carbamate obtained in step 3 in the same manner as in step 2 of example 1k. The crude product obtained was purified by reverse phase HPLC (0.05% aqueous ammonium bicarbonate solution/acetonitrile=55/45 to 45/55) to give compound 8f (13 mg, total yield of 3 steps 28%).
ESI-MS, (M+H)$^+$, m/z: 717. $^1$H-NMR (CDCl$_3$), δ: 1.06-1.12 (m, 6H), 1.12-1.17 (m, 6H), 1.23-1.40 (m, 5H), 1.98-2.05 (m, 1H), 2.07-2.16 (m, 3H), 2.22-2.43 (m, 2H), 2.47-2.74 (m, 5H), 3.54 (dd, J=12.2, 4.1 Hz, 1H), 3.91-3.97 (m, 1H), 3.99 (d, JJ=7.2 Hz, 1H), 4.13-4.22 (m, 1H), 4.82-4.98 (m, 2H), 5.42 (s, 2H), 6.61 (d, J=8.6 Hz, 2H), 6.98 (d, J=8.2 Hz, 1H), 7.07-7.32 (m, 10H), 7.46-7.50 (m, 1H), 7.92 (s, 1H).

Example 8g (1R,4r)-4-(((2S*,4R*)-2-Methyl-1-propionyl-1,2,3,4-tetrahydroquinolin-4-yl)amino)-N-(4-((4-(((2S,4R)-2-methyl-1-propionyl-1,2,3,4-tetrahydroquinolin-4-yl)amino)phenyl)amino)-4-oxobut-2-yn-1-yl)cyclohexane-1-carboxamide (Compound 8g)

(Step 1)

tert-Butyl (4-((4-(((2S,4R)-2-methyl-1-propionyl-1,2,3,4-tetrahydroquinolin-4-yl)amino)phenyl)amino)-4-oxobut-2-yn-1-yl)carbamate (79 mg, 100%) was obtained from 1-((2S,4R)-4-((4-aminophenyl)amino)-2-methyl-3,4-dihydroquinolin-1(2H)-yl)propan-1-one (50 mg, 0.162 mmol) obtained in step 3 of reference example 7 and 4-((tert-butoxycarbonyl)amino)but-2-ynoic acid (32.2 mg, 0.162 mmol) in the same manner as in step 3 of example 1b.
ESI-MS m/z: 491 (M+H)$^+$ (Step 2)

A crude product (79 mg) of 4-amino-N-(4-(((2S,4R)-2-methyl-1-propionyl-1,2,3,4-tetrahydroquinolin-4-yl)amino)phenyl)but-2-ynamide trifluoroacetate was obtained from tert-butyl (4-((4-(((2S,4R)-2-methyl-1-propionyl-1,2,3,4-tetrahydroquinolin-4-yl)amino)phenyl)amino)-4-oxobut-2-yn-1-yl)carbamate (79 mg, 0.161 mmol) obtained in step 1 in the same manner as in step 2 of example 1k.
ESI-MS m/z: 391 (M+H)$^+$ (Step 3)

Compound 8g (25 mg, total yield of 2 steps 22%) was obtained from the crude product (32 mg, 0.094 mmol) of 4-Amino-N-(4-(((2S,4R)-2-methyl-1-propionyl-1,2,3,4-tetrahydroquinolin-4-yl)amino)phenyl)but-2-ynamide trifluoroacetate obtained in step 2 and (1R,4r)-4-(((2S*,4R*)-2-methyl-1-propionyl-1,2,3,4-tetrahydroquinolin-4-yl)amino)cyclohexane-1-carboxylic acid (32 mg, 0.094 mmol) obtained in step 2 of reference example 11 in the same manner as in step 3 of example 1b.
ESI-MS m/z: 717 (M+H)$^+$: $^1$H-NMR (CDCl$_3$, δ): 0.96-1.11 (m, 12H), 1.11-1.23 (m, 2H), 1.40-1.66 (m, 4H), 1.82-2.00 (m, 3H), 2.00-2.13 (m, 3H), 2.13-2.36 (m, 2H), 2.36-2.70 (m, 5H), 3.40-3.52 (m, 1H), 3.86-4.00 (m, 1H), 4.00-4.14 (m, 3H), 4.72-4.88 (m, 2H), 6.37-6.46 (m, 1H), 6.46-6.56 (m, 2H), 6.97-7.15 (m, 3H), 7.15-7.23 (m, 4H), 7.23-7.32 (m, 2H), 7.36-7.43 (m, 1H), 7.96-8.06 (m, 1H).

Example 8h 1-((2S*,4R*)-2-methyl-4-(((1R,4R)-4-(3-(4-(((2S,4R)-2-methyl-1-propionyl-1,2,3,4-tetrahydroquinolin-4-yl)amino)phenyl)-5,6,7,8-tetrahydroimidazo[1,2-a]pyrazine-7-carbonyl)cyclohexyl)amino)-3,4-dihydroquinolin-1(2H)-yl)propan-1-one (Compound 8h)

(Step 1)

tert-Butyl 3-(4-{[(2S,4R)-2-methyl-1-propionyl-1,2,3,4-tetrahydroquinolin-4-yl]amino}phenyl)-5,6-dihydroimidazo[1,2-a]pyrazine-7(8H)-carboxylate (0.325 g, 0.63 mmol) obtained in step 2 of example 3e was dissolved in 1,4-dioxane (15 mL), then hydrogen chloride/1,4-dioxane solution (4 mol/L, 4.0 mL, 16 mmol) was added to the solution at 0° C., and the mixture was stirred at room temperature for 2 hours. The reaction mixture was concentrated under reduced pressure, and the obtained residue was basified with a 10% aqueous sodium hydrogen carbonate solution, and extracted with ethyl acetate. The organic layer was washed with saturated brine, dried over anhydrous sodium sulfate, and concentrated under reduced pressure to give 1-((2S,4R)-2-methyl-4-{[4-(5,6,7,8-tetrahydroimidazo[1,2-a]pyrazin-3-yl)phenyl]amino}-3,4-dihydroquinolin-1(2H)-yl)propan-1-one (0.220 g, 84%).
ESIMS, (M+H)$^+$, m/z: 416.27

(Step 2)

Compound 8h (0.045 g, 30%) was obtained from 1-((2S,4R)-2-methyl-4-{[4-(5,6,7,8-tetrahydroimidazo [1,2-a]pyrazin-3-yl)phenyl]amino}-3,4-dihydroquinolin-1(2H)-yl)propan-1-one (0.084 g, 0.20 mmol) obtained in step 1 and (1R,4r)-4-(((2S*,4R*)-2-methyl-1-propionyl-1,2,3,4-tetrahydroquinolin-4-yl)amino)cyclohexane-1-carboxylic acid obtained in step 2 of reference example 11 in the same manner as in step 3 of example 1b.
ESIMS, (M+H)$^+$, m/z: 742.7. $^1$H-NMR (DMSO-d$_6$, δ): 0.97-1.06 (m, 12H), 1.15-1.23 (m, 1H), 1.41-1.68 (m, 4H), 1.84-1.92 (m, 2H), 2.09-2.34 (m, 4H), 2.54-2.69 (m, 4H), 2.72-2.80 (m, 1H), 2.94 (t, J=9.10 Hz, 1H), 3.90-4.08 (m, 3H), 4.13-4.40 (m, 4H), 4.65-4.78 (m, 2H), 4.86-5.14 (m, 2H), 6.53-6.63 (m, 1H), 6.78 (d, J=8.33 Hz, 2H), 7.12-7.21 (m, 2H), 7.25-7.45 (m, 7H), 7.61 (brs, 1H), 9.13 (brs, 2H).

Example 8i (1R,4R)-4-(((2S*,4R*)-2-Methyl-1-propionyl-1,2,3,4-tetrahydroquinolin-4-yl)amino)-N-(2-((4-(((2S,4R)-2-methyl-1-propionyl-1,2,3,4-tetrahydroquinolin-4-yl)amino)phenyl)thio)ethyl)cyclohexane-1-carboxamide (Compound 8i)

Compound 8i (0.036 g, 30%) was obtained from 1-[(2S,4R)-4-({4-[(2-aminoethyl)thio]phenyl}amino)-2-methyl-3,4-dihydroquinolin-1(2H)-yl]propan-1-one hydrochloride (0.078 g, 0.19 mmol) obtained in step 2 of example 4f and (1R,4r)-4-(((2S*,4R*)-2-methyl-1-propionyl-1,2,3,4-tetrahydroquinolin-4-yl)amino)cyclohexane-1-carboxylic acid (0.06 g, 0.17 mmol) obtained in step 2 of reference example 11 in the same manner as in step 3 of example 1b.
ESIMS, (M+H)$^+$, m/z: 696.68. $^1$H-NMR (DMSO-d$_6$, δ): 0.91-1.22 (m, 15H), 1.31-2.31 (m, 11H), 2.52-2.63 (m, 4H), 2.66-2.76 (m, 2H), 3.08-3.20 (m, 2H), 3.38 (brs, 1H), 4.11-4.19 (m, 1H), 4.54-4.81 (m, 2H), 6.27 (d, J=7.45 Hz, 1H), 6.62 (d, J=8.55 Hz, 2H), 7.08-7.52 (m, 10H), 7.87 (brs, 1H), 9.11 (s, 1H).

Example 8j 2-(3-((1R,4R)-4-(((2S,4R)-2-Methyl-1-propionyl-1, 2,3,4-tetrahydroquinolin-4-yl)amino)cyclohexyl) ureido)-N-(4-(((2S,4R)-2-methyl-1-propionyl-1,2,3, 4-tetrahydroquinolin-4-yl)amino)phenyl)acetamide (Compound 8j)

(Step 1)

1-((2S,4R)-4-(((1r,4R)-4-aminocyclohexyl)amino)-2-methyl-3,4-dihydroquinolin-1(2H)-yl)propan-1-one dihydrochloride (0.250 g, 0.64 mmol) obtained in reference example 9 was dissolved in DMF (5 mL), then triethylamine (0.18 mL, 1.29 mmol), DMAP (0.196 g, 1.61 mmol) and CDI (0.208 g, 0.64 mmol) were added to the solution at room temperature, and the mixture was stirred at 80° C. for 45 minutes. Ethyl glycinate hydrochloride (0.116 g, 0.84 mmol) was added to the reaction mixture at room temperature, and the mixture was stirred at 80° C. for 16 hours. The reaction mixture was diluted with water and extracted with ethyl acetate. The organic layer was washed with water and saturated brine, dried over anhydrous sodium sulfate, and concentrated under reduced pressure. The obtained residue was purified by reverse phase column chromatography (acetonitrile/0.1% formic acid aqueous solution=60/40) to give ethyl (((1R,4r)-4-(((2S,4R)-2-methyl-1-propionyl-1,2,3,4-tetrahydroquinolin-4-yl)amino)cyclohexyl)carbamoyl) glycinate (0.150 g, 52%).

ESIMS, (M+H)$^+$, m/z: 445.56.

(Step 2)

2-(3-((1R,4r)-4-((2S,4R)-2-Methyl-1-propionyl-1,2,3,4-tetrahydroquinolin-4-ylamino)cyclohexyl)ureido)acetic acid (0.110 g, 79%) was obtained from ethyl (((1R,4r)-4-(((2S,4R)-2-methyl-1-propionyl-1,2,3,4-tetrahydroquinolin-4-yl)amino)cyclohexyl)carbamoyl)glycinate (0.150 g, 0.34 mmol) obtained in step 1 in the same manner as in step 2 of example 2f.

ESIMS, (M+H)$^+$, m/z: 417.36.

(Step 3)

2-(3-((1R,4r)-4-((2S,4R)-2-Methyl-1-propionyl-1,2,3,4-tetrahydroquinolin-4-ylamino)cyclohexyl)ureido)acetic acid (0.110 g, 0.26 mmol) obtained in step 2 was dissolved in DMF (5 mL), then DCC (0.076 g, 0.37 mmol) and DMAP (0.096 g, 0.79 mmol) were added to the solution, and the mixture was stirred at room temperature for 30 minutes. 1-{(2S,4R)-4-[(4-Aminophenyl)amino]–2-methyl-3,4-dihydroquinolin-1(2H)-yl}propan-1-one (0.082 g, 0.26 mmol) obtained in reference example 7 was added to the reaction mixture, and the mixture was stirred at room temperature for 16 hours. The reaction mixture was added to ice water and the mixture was stirred for 10 minutes. The resulting solid was collected by filtration and dried under reduced pressure. The obtained solid was purified by reverse phase HPLC (10 mmol/L aqueous ammonium bicarbonate solution/acetonitrile=70/30 to 37/63) to give compound 8j (0.064 g, 34%).

ESI-MS m/z: 708.67 (M+H)$^+$: $^1$H-NMR (DMSO-d$_6$, δ): 0.78-0.86 (m, 1H), 0.93-1.06 (m, 12H), 1.09-1.22 (m, 4H), 1.83-1.99 (m, 4H), 2.07-2.28 (m, 2H), 2.53-2.67 (m, 5H), 3.37-3.38 (m, 1H), 3.43 (dd, J=12.0, 4.0 Hz, 1H), 3.76 (d, J=5.48 Hz, 2H), 4.08-4.14 (m, 1H), 4.60-4.78 (m, 2H), 5.87 (d, J=7.89 Hz, 1H), 5.96 (t, J=5.37 Hz, 1H), 6.09 (d, J=7.02 Hz, 1H), 6.59 (d, J=8.77 Hz, 2H), 7.16 (d, J=3.73 Hz, 2H), 7.19-7.27 (m, 7H), 7.49 (t, J=4.2 Hz, 1H), 9.54 (s, 1H).

Example 8k (1R,4R)-4-(((2S*,4R*)-2-Methyl-1-propionyl-1,2,3, 4-tetrahydroquinolin-4-yl)amino)-N-((5-(4-(((2S, 4R)-2-methyl-1-propionyl-1,2,3,4-tetrahydroquinolin-4-yl)amino)phenyl)-1,2,4-oxadiazol-3-yl)methyl) cyclohexane-1-carboxamide (Compound 8k)

A crude product of compound 8k was obtained from the crude product (11 mg) of 1-((2S,4R)-4-((4-(3-(aminomethyl)-1,2,4-oxadiazol-5-yl)phenyl)amino)-2-methyl-3,4-dihydroquinolin-1(2H)-yl)propan-1-one obtained in step 4 of example 3d and (1R,4R)-4-(((2S*,4R*)-2-methyl-1-propionyl-1,2,3,4-tetrahydroquinolin-4-yl)amino)cyclohexane-1-carboxylic acid obtained in step 2 of reference example 11 (10 mg, 0.029 mmol) in the same manner as in step 3 of example 1b. The crude product of compound 8k was purified by reverse phase HPLC (0.05% TFA aqueous solution/acetonitrile=65/35 to 55/45) to give compound 8k (1 mg, 4%).

ESI-MS, (M+H)$^+$, m/z: 718. $^1$H-NMR (CDCl$_3$), δ: 1.11-1.19 (m, 12H), 1.24-1.52 (m, 2H), 1.66-1.78 (m, 2H), 2.03-2.19 (m, 4H), 2.22-2.45 (m, 5H), 2.50-2.65 (m, 2H), 2.65-2.75 (m, 1H), 2.81-2.89 (m, 1H), 3.34-3.44 (m, 1H), 4.07 (dd, J=13.1, 3.2 Hz, 1H), 4.30 (dd, J=11.6, 4.3 Hz, 1H), 4.61 (d, J=5.4 Hz, 2H), 4.89-5.02 (m, 2H), 6.31-6.36 (m, 1H), 6.68 (d, J=9.1 Hz, 2H), 7.18-7.24 (m, 4H), 7.27-7.35 (m, 2H), 7.38-7.43 (m, 1H), 7.47-7.53 (m, 1H), 7.92 (d, J=8.6 Hz, 2H).

Example 8l (1R,4R)-4-(((2S*,4R*)-2-Methyl-1-propionyl-1,2,3, 4-tetrahydroquinolin-4-yl)amino)-N-((1-(4-(((2S, 4R)-2-methyl-1-propionyl-1,2,3,4-tetrahydroquinolin-4-yl)amino)phenyl)-1H-1,2,3-triazol-4-yl) methyl)cyclohexane-1-carboxamide (compound 8l)

(Step 1)

A crude product (30 mg) of (1R,4r)-4-(((2S*,4R*)-2-methyl-1-propionyl-1,2,3,4-tetrahydroquinolin-4-yl) amino)-N-(prop-2-yn-1-yl)cyclohexane-1-carboxamide was obtained from (1R,4r)-4-(((2S*,4R*)-2-methyl-1-propionyl-1,2,3,4-tetrahydroquinolin-4-yl)amino)cyclohexane-1-carboxylic acid (30 mg, 0.087 mmol) obtained in step 2 of reference example 11 and propargylamine (0.007 μL, 0.105 mmol) in the same manner as in step 3 of example 1b.

ESI-MS, (M+H)$^+$, m/z: 382.

(Step 2)

A crude product of compound 8l was obtained from the crude product (30 mg) of 1-{(2S,4R)-4-[(4-azidophenyl) amino]-2-methyl-3,4-dihydroquinolin-1(2H)-yl}propan-1-one obtained in step 2 of example 3a and the crude product (30 mg) of (1R,4r)-4-(((2S*,4R*)-2-methyl-1-propionyl-1, 2,3,4-tetrahydroquinolin-4-yl)amino)-N-(prop-2-yn-1-yl) cyclohexane-1-carboxamide obtained in step 1 of example 8l in the same manner as in step 3 of 3a. The crude product obtained was purified by reverse phase HPLC (0.05% aqueous ammonium bicarbonate solution/acetonitrile=6/4 to 5/5) to give compound 8l (31 mg, total yield of 2 steps 56%).

ESI-MS, (M+H)$^+$, m/z: 717. $^1$H-NMR (CDCl$_3$) δ: 1.06-1.19 (m, 12H), 1.18-1.36 (m, 3H), 1.49-1.55 (m, 2H), 1.92-2.06 (m, 3H), 2.08-2.17 (m, 2H), 2.21-2.44 (m, 2H), 2.47-2.74 (m, 5H), 3.55 (dd, J=12.2, 4.1 Hz, 1H), 4.11 (d, J=7.2 Hz,

1H), 4.19-4.27 (m, 1H), 4.57 (d, J=5.4 Hz, 2H), 4.80-4.89 (m, 1H), 4.92-5.01 (m, 1H), 6.23 (t, J=5.7 Hz, 1H), 6.71 (d, J=9.1 Hz, 2H), 7.07-7.12 (m, 1H), 7.16-7.20 (m, 1H), 7.21 (d, J=7.2 Hz, 1H), 7.22-7.26 (m, 2H), 7.28-7.33 (m, 2H), 7.44-7.47 (m, 1H), 7.49 (d, J=9.1 Hz, 2H), 7.83 (s, 1H).

Example 8m 4-(((2S,4R)-2-Methyl-1-propionyl-1,2,3,4-tetrahydroquinolin-4-yl)amino)-N-(4-(((1R,4r)-4-(2S,4R)-2-methyl-1-propionyl-1,2,3,4-tetrahydroquinolin-4-yl)amino)cyclohexyl)amino)-4-oxobut-2-yn-1-yl)benzamide (Compound 8m)

(Step 1)
tert-Butyl (4-(((1R,4)-4-(((2S,4R)-2-methyl-1-propionyl-1,2,3,4-tetrahydroquinolin-4-yl)amino)cyclohexyl)amino)-4-oxobut-2-yn-1-yl)carbamate (0.120 g, 72%) was obtained from 1-((2S,4R)-4-(((1r,4R)-4-aminocyclohexyl)amino)-2-methyl-3,4-dihydroquinolin-1(2H)-yl)propan-1-one dihydrochloride (0.120 g, 0.31 mmol) obtained in reference example 9 and 4-((tert-butoxycarbonyl)amino)but-2-ynoic acid (0.062 g, 0.31 mmol) in the same manner as in step 1 of example 1a.
ESIMS, (M+H)$^+$, m/z: 497.33.
(Step 2)
A crude product (0.130 g) of 4-amino-N-((1R,4r)-4-(((2S,4R)-2-methyl-1-propionyl-1,2,3,4-tetrahydroquinolin-4-yl)amino)cyclohexyl)but-2-ynamide trifluoroacetate was obtained from tert-butyl (4-(((1R,4r)-4-(((2S,4R)-2-methyl-1-propionyl-1,2,3,4-tetrahydroquinolin-4-yl)amino)cyclohexyl))amino)-4-oxobut-2-yn-1-yl)carbamate (0.120 g, 0.24 mmol) obtained in step 1 in the same manner as in step 2 of example 1k.
ESIMS, (M+H)$^+$, m/z: 397.44.
(Step 3)
Compound 8m (0.026 g, total yield of 2 steps 15%) was obtained from the crude product (0.126 g) of 4-amino-N-((1R,40-4-(((2S,4R)-2-methyl-1-propionyl-1,2,3,4-tetrahydroquinolin-4-yl)amino)cyclohexyl)but-2-ynamide trifluoroacetate obtained in step 2 and 4-{[(2S,4R)-2-methyl-1-propionyl-1,2,3,4-tetrahydroquinolin-4-yl]amino}benzoic acid (0.060 g, 0.18 mmol) obtained in reference example 1 in the same manner as in step 3 of example 1b.
ESIMS, (M+H)$^+$, m/z: 717.4. $^1$H-NMR (DMSO-d$_6$, δ): 0.79-0.86 (m, 1H), 0.91-1.27 (m, 17H), 1.70-1.80 (m, 2H), 1.84-2.03 (m, 2H), 2.06-2.33 (m, 2H), 2.53-2.68 (m, 5H), 3.39-3.52 (m, 2H), 4.16 (d, J=5.26 Hz, 2H), 4.26-4.32 (m, 1H), 4.57-4.79 (m, 2H), 6.62-6.68 (m, 3H), 7.09 (d, J=7.6 Hz, 1H), 7.14-7.32 (m, 6H), 7.46 (brs, 1H), 7.65 (d, J=8.77 Hz, 2H), 8.48-8.55 (m, 2H).

Example 8n (1R,4R)-4-((2S*,4R*)-2-Methyl-1-propionyl-1,2,3,4-tetrahydroquinolin-4-yl)amino)-N-(2-(3-(4-(((2S,4R)-2-methyl-1-propionyl-1,2,3,4-tetrahydroquinolin-4-yl)amino)phenyl)ureido)ethyl)cyclohexane-1-carboxamide (Compound 8n)
(Step 1)
tert-Butyl (2-(3-(4-(((2S,4R)-2-methyl-1-propionyl-1,2,3,4-tetrahydroquinolin-4-yl)amino)phenyl)ureido)ethyl)carbamate (0.240 g, 60%) was obtained from 1-{(2S,4R)-4-[(4-aminophenyl)amino]-2-methyl-3,4-dihydroquinolin-1(2H)-yl}propan-1-one (0.250 g, 0.81 mmol) obtained in reference example 7 and tert-butyl (2-aminoethyl)carbamate (0.16 mL, 1.05 mmol) in the same manner as in step 1 of example 14h.
ESIMS, (M+H)$^+$, m/z: 496.36.
(Step 2)
1-(2-Aminoethyl)-3-(4-(((2S,4R)-2-methyl-1-propionyl-1,2,3,4-tetrahydroquinolin-4-yl)amino)phenyl)urea hydrochloride (0.210 g, 100%) was obtained from tert-butyl (2-(3-(4-(((2S,4R)-2-methyl-1-propionyl-1,2,3,4-tetrahydroquinolin-4-yl)amino)phenyl)ureido)ethyl)carbamate (0.240 g, 0.48 mmol) obtained in step 1 in the same manner as in step 2 of example 1a.
ESIMS, (M+H)$^+$, m/z: 396.31.
(Step 3)
Compound 8n (0.066 g, 19%) was obtained from 1-(2-aminoethyl)-3-(4-(((2S,4R)-2-methyl-1-propionyl-1,2,3,4-tetrahydroquinolin-4-yl)amino)phenyl)urea hydrochloride (0.210 g, 0.49 mmol) obtained in step 2 and (1R,4r)-4-(((2S*,4R*)-2-methyl-1-propionyl-1,2,3,4-tetrahydroquinolin-4-yl)amino)cyclohexane-1-carboxylic acid (0.167 g, 0.49 mmol) obtained in step 2 of reference example 11 in the same manner as in step 3 of example 1b.
ESIMS, (M+H)$^+$, m/z: 722.67. $^1$H-NMR (DMSO-d$_6$, δ): 0.77-0.89 (m, 1H), 0.92-1.19 (m, 15H), 1.39 (q, J=12.50 Hz, 2H), 1.74 (d, J=12.50 Hz, 3H), 1.90-2.28 (m, 5H), 2.51-2.65 (m, 5H), 3.09 (brs, 4H), 3.46 (dd, J=11.62, 3.29 Hz, 1H), 4.02-4.12 (m, 1H), 4.56-4.78 (m, 2H), 5.68 (d, J=7.67 Hz, 1H), 5.91 (brs, 1H), 6.55 (d, J=8.77 Hz, 2H), 7.08 (d, J=8.77 Hz, 2H), 7.12-7.31 (m, 7H), 7.45-7.53 (m, 1H), 7.75 (brs, 1H), 8.02 (s, 1H).

Example 8o (1R,4r)-4-(((2S*,4R*)-2-Methyl-1-propionyl-1,2,3,4-tetrahydroquinolin-4-yl)amino)-N-(2-(4-(4-(((2S,4R)-2-methyl-1-propionyl-1,2,3,4-tetrahydroquinolin-4-yl)amino)phenyl)-1H-pyrazol-1-yl)ethyl)cyclohexane-1-carboxamide (Compound 8o)

Compound 8o (41.2 mg, 78%) was obtained from (1R,4r)-4-(((2S*,4R*)-2-methyl-1-propionyl-1,2,3,4-tetrahydroquinolin-4-yl)amino)cyclohexane-1-carboxylic acid (25.0 mg, 0.073 mmol) obtained in step 2 of reference example 11 and 1-((2S,4R)-4-((4-(1-(2-aminoethyl)-1H-pyrazol-4-yl)phenyl)amino)-2-methyl-3,4-dihydroquinolin-1(2H)-yl)propan-1-one (29.3 mg, 0.073 mmol) obtained in step 2 of example 6q in the same manner as in step 1 of example 1a.
ESIMS, (M+H)$^+$, m/z: 730; $^1$H-NMR (CDCl$_3$, δ) 1.04-1.34 (m, 18H), 1.86-2.17 (m, 5H), 2.19-2.43 (m, 2H), 2.45-2.75 (m, 5H), 3.54 (dd, J=12.4, 4.4 Hz, 1H), 3.66-3.79 (m, 2H), 3.86-3.96 (m, 1H), 4.11-4.33 (m, 3H), 4.77-5.20 (m, 2H), 6.08-6.24 (m, 1H), 6.65 (d, J=8.8 Hz, 2H), 7.04-7.31 (m, 10H), 7.42-7.48 (m, 1H), 7.51 (s, 1H), 7.73 (s, 1H).

Example 8p 1-((2S,4R)-2-Methyl-4-(((1R,4R)-4-((1R,4R)-5-(4-(((2S,4R)-2-methyl-1-propionyl-1,2,3,4-tetrahydroquinolin-4-yl)amino)benzoyl)-2,5-diazabicyclo[2.2.1]heptane-2-carbonyl)cyclohexyl)amino)-3,4-dihydroquinolin-1(2H)-yl)propan-1-one (compound 8p)

Compound 8p (27.2 mg, 50%) was obtained from (1R,4r)-4-(((2S*,4R*)-2-methyl-1-propionyl-1,2,3,4-tetrahydroquinolin-4-yl)amino)cyclohexane-1-carboxylic acid (25.0 mg, 0.073 mmol) obtained in step 2 of reference example 11 and 1-((2S,4R)-4-((4-(2,5-diazabicyclo[2.2.1]heptane-2-carbonyl)phenyl)amino)-2-methyl-3,4-dihydroquinolin-1(2H)-yl)propan-1-one (30.4 mg, 0.073 mmol) obtained in step 2 of example 1k in the same manner as in step 1 of example 1a.
ESIMS, (M+H)+, m/z: 745; 1H-NMR (CDCl3, δ) 0.84-1.36 (m, 18H), 1.72-2.43 (m, 10H), 2.45-2.82 (m, 5H), 3.37-3.88 (m, 5H), 4.08-4.29 (m, 2H), 4.75-5.10 (m, 3H), 6.52-6.67 (m, 2H), 7.04-7.34 (m, 7H), 7.37-7.51 (m, 3H).

Example 8q 1-((1R,4r)-4-(((2S*,4R*)-2-Methyl-1-propionyl-1,2,3,4-tetrahydroquinolin-4-yl)amino)cyclohexane-1-carbonyl)-N-(4-(((2S,4R)-2-methyl-1-propionyl-1,2,3,4-tetrahydroquinolin-4-yl)amino)phenyl)piperidine-4-carboxamide (Compound 8q)

(Step 1)
tert-Butyl 4-((4-(((2S,4R)-2-methyl-1-propionyl-1,2,3,4-tetrahydroquinolin-4-yl)amino)phenyl)carbamoyl)piperidine-1-carboxylate (0.180 g, 71%) was obtained from 1-{(2S,4R)-4-[(4-aminophenyl)amino]-2-methyl-3,4-dihydroquinolin-1(2H)-yl}propan-1-one (0.150 g, 0.48 mmol) obtained in step 3 of reference example 7 and 1-(tert-butoxycarbonyl)-piperidine-4-carboxylic acid (0.111 g, 0.48 mmol) in the same manner as in step 3 of example 1b.
ESIMS, (M+H)+, m/z: 521.41.
(Step 2)
A crude product (0.160 g) of N-(4-(((2S,4R)-2-methyl-1-propionyl-1,2,3,4-tetrahydroquinolin-4-yl)amino)phenyl)piperidine-4-carboxamide hydrochloride was obtained from tert-butyl 4-((4-(((2S,4R)-2-methyl-1-propionyl-1,2,3,4-tetrahydroquinolin-4-yl)amino)phenyl)carbamoyl)piperidine-1-carboxylate (0.180 g, 0.35 mmol) obtained in step 1 in the same manner as in step 2 of example 1a.
ESIMS, (M+H)+, m/z: 421.32.
(Step 3)
Compound 8q (0.071 g, 27%) was obtained from the crude product (0.160 g) of N-(4-(((2S,4R)-2-methyl-1-propionyl-1,2,3,4-tetrahydroquinolin-4-yl)amino)phenyl)piperidine-4-carboxamide hydrochloride obtained in step 2 and (1R,4r)-4-(((2S*,4R*)-2-methyl-1-propionyl-1,2,3,4-tetrahydroquinolin-4-yl)amino)cyclohexane-1-carboxylic acid (0.121 g, 0.35 mmol) obtained in step 2 of reference example 11 in the same manner as in step 3 of example 1b.
ESIMS, (M+H)+, m/z: 747.54. 1H-NMR (DMSO-d6, δ): 0.74-0.89 (m, 1H), 0.92-1.06 (m, 12H), 1.08-1.29 (m, 3H), 1.32-1.84 (m, 9H), 1.89-2.03 (m, 2H), 2.07-2.29 (m, 2H), 2.52-2.64 (m, 7H), 2.98-3.10 (m, 1H), 3.46 (dd, J=11.51, 3.40 Hz, 1H), 4.00 (d, J=12.72 Hz, 1H), 4.11-4.21 (m, 1H), 4.38-4.47 (m, 1H), 4.58-4.76 (m, 2H), 5.84 (d, J=7.89 Hz, 1H), 6.58 (d, J=8.99 Hz, 2H), 7.16 (d, J=3.73 Hz, 2H), 7.19-7.32 (m, 7H), 7.47-7.54 (m, 1H), 9.51 (s, 1H).

Example 8r 1-(4-(((2S,4R)-2-Methyl-1-propionyl-1,2,3,4-tetrahydroquinolin-4-yl)amino)benzoyl)-N-((1R,4R)-4-(((2S,4R)-2-methyl-1-propionyl-1,2,3,4-tetrahydroquinolin-4-yl)amino)cyclohexyl)azetidine-3-carboxamide (Compound 8r)

(Step 1)
Methyl 1-(4-(((2S,4R)-2-methyl-1-propionyl-1,2,3,4-tetrahydroquinolin-4-yl)amino)benzoyl)azetidine-3-carboxylate (0.360 g, 70%) was obtained from 4-(((2S,4R)-2-methyl-1-propionyl-1,2,3,4-tetrahydroquinolin-4-yl)amino)benzoic acid (0.4 g, 1.18 mmol) obtained in step 7 of reference example 1 and methyl azetidine-3-carboxylate hydrochloride (0.268 g, 1.77 mmol) in the same manner as in step 3 of example 1b.
ESIMS, (M+H)+, m/z: 436.45.
(Step 2)
1-(4-(((2S,4R)-2-methyl-1-propionyl-1,2,3,4-tetrahydroquinolin-4-yl)amino)benzoyl)azetidine-3-carboxylic acid (0.330 g, 95%) was obtained from methyl 1-(4-(((2S,4R)-2-methyl-1-propionyl-1,2,3,4-tetrahydroquinolin-4-yl)amino)benzoyl)azetidine-3-carboxylate (0.360 g, 0.83 mmol) obtained in step 1 in the same manner as in step 2 of example 2f.
ESIMS, (M+H)+, m/z: 422.49.
(Step 3)
Compound 8r (0.033 g, 19%) was obtained from 1-(4-(((2S,4R)-2-methyl-1-propionyl-1,2,3,4-tetrahydroquinolin-4-yl)amino)benzoyl)azetidine-3-carboxylic acid (0.1 g, 0.24 mmol) obtained in step 2 and 1-((2S,4R)-4-(((1r,4R)-4-aminocyclohexyl)amino)-2-methyl-3,4-dihydroquinolin-1(2H)-yl)propan-1-one dihydrochloride (0.090 g, 0.24 mmol) obtained in reference example 9 in the same manner as in step 3 of example 1b.
ESIMS, (M+H)+, m/z: 719.57. 1H-NMR (DMSO-d6, δ): 0.75-0.86 (m, 1H), 0.94-1.06 (m, 12H), 1.11-1.26 (m, 5H), 1.80-1.91 (m, 4H), 2.10-2.26 (m, 2H), 2.51-2.63 (m, 5H), 3.34-3.36 (m, 1H), 3.52-3.54 (m, 2H), 4.22-4.28 (m, 5H), 4.63-4.65 (m, 1H), 4.73-4.75 (m, 1H), 6.63-6.66 (m, 3H), 7.10 (d, J=7.6 Hz, 1H), 7.16-7.32 (m, 6H), 7.43 (d, J=8.77 Hz, 2H), 7.48 (brs, 1H), 7.84-7.86 (m, 1H).

Example 9a 4-(((2S,4R)-2-Methyl-1-propionyl-1,2,3,4-tetrahydroquinolin-4-yl)amino)-N-(2-(N-((1R,4R)-4-(((2S*,4R*)-2-methyl-1-propionyl-1,2,3,4-tetrahydroquinolin-4-yl)amino)cyclohexyl)sulfamoyl)ethyl)benzamide (Compound 9a)

(Step 1)
1-((2S*,4R*)-4-(((1r,4R)-4-Aminocyclohexyl)amino)-2-methyl-3,4-dihydroquinolin-1(2H)-yl)propan-1-one dihydrochloride (0.2 g, 0.51 mmol) obtained in step 2 of reference example 10 was dissolved in dichloromethane (5 mL), then triethylamine (0.29 mL, 2.07 mmol) was added to the solution, and the mixture was stirred at room temperature for 10 minutes. Benzyl (2-(chlorosulfonyl)ethyl)carbamate (0.143 g, 0.51 mmol) was added to the reaction mixture at 0° C., and the mixture was stirred at room temperature for 16 hours. The reaction mixture was diluted with water and extracted with dichloromethane. The organic layer was washed with saturated brine, dried over anhydrous sodium sulfate, and concentrated under reduced pressure. The obtained residue was purified by reverse phase column chromatography (acetonitrile/0.1% formic acid aqueous solution=45/55) to give Benzyl (2-(N-(4-(((2S*,4R*)-2-methyl-1-propionyl-1,2,3,4-tetrahydroquinolin-4-yl)amino)cyclohexyl)sulfamoyl)ethyl)carbamate (0.150 g, 52%).
ESIMS, (M+H)+, m/z: 557.29.
(Step 2)
Benzyl (2-(N-(4-(((2S*,4R*)-2-methyl-1-propionyl-1,2,3,4-tetrahydroquinolin-4-yl)amino)cyclohexyl)sulfamoyl)ethyl)carbamate (0.150 g, 0.27 mmol) obtained in step 1 was dissolved in THF (5 mL), then palladium carbon (0.2 g, 10% wt) was added to the solution, and the mixture was stirred at room temperature for 36 hours under a hydrogen atmosphere. The reaction mixture was filtered, and the filtrate was concentrated under reduced pressure to give 2-amino-N-(4-(a2S*,4R*)-2-methyl-1-propionyl-1,2,3,4-tetrahydroquinolin-4-yl)amino)cyclohexyl)ethane-1-sulfonamide (0.090 g, 80%).

ESIMS, (M+H)⁺, m/z: 423.37.

(Step 3)

Compound 9a (0.045 g, 28%) was obtained from 2-amino-N-(4-(((2S*,4R*)-2-methyl-1-propionyl-1,2,3,4-tetrahydroquinolin-4-yl)amino)cyclohexyl)ethane-1-sulfonamide (0.090 g, 0.21 mmol) obtained in step 2 and 4-{[(2S,4R)-2-methyl-1-propionyl-1,2,3,4-tetrahydroquinolin-4-yl]amino}benzoic acid (0.072 g, 0.21 mmol) obtained in reference example 1 in the same manner as in step 3 of example 1b.

ESIMS, (M+H)⁺, m/z: 743.47. ¹H-NMR (DMSO-d₆, δ): 0.77-0.85 (m, 1H), 0.93-1.06 (m, 12H), 1.09-1.32 (m, 6H), 1.74 (brs, 1H), 1.90-1.97 (m, 4H), 2.10-2.16 (m, 1H), 2.22-2.27 (m, 1H), 2.52-2.64 (m, 4H), 3.06-3.11 (m, 1H), 3.19-3.22 (m, 2H), 3.42 (dd, J=11.74, 3.42 Hz, 1H), 3.54-3.59 (m, 2H), 4.25-4.31 (m, 1H), 4.60-4.76 (m, 2H), 6.60 (d, J=7.83 Hz, 1H), 6.66 (d, J=8.80 Hz, 2H), 7.08 (d, J=7.6 Hz, 1H), 7.13-7.32 (m, 7H), 7.46-7.48 (m, 1H), 7.61 (d, J=8.80 Hz, 2H), 8.15-8.18 (m, 1H).

Example 9b

N-((1R,4R)-4-(((2S*,4R*)-2-Methyl-1-propionyl-1,2,3,4-tetrahydroquinolin-4-yl)amino)cyclohexyl)-2-(4-(4-(((2S,4R)-2-methyl-1-propionyl-1,2,3,4-tetrahydroquinolin-4-yl)amino)phenyl)-1H-pyrazol-1-yl)acetamide (Compound 9b)

(Step 1)

2-(4-(4-(((2S,4R)-2-Methyl-1-propionyl-1,2,3,4-tetrahydroquinolin-4-yl)amino)phenyl)-1H-pyrazol-1-yl)acetic acid (0.140 g, 60%) was obtained from ethyl 2-(4-(4-(((2S,4R)-2-methyl-1-propionyl-1,2,3,4-tetrahydroquinolin-4-yl)amino)phenyl)-1H-pyrazol-1-yl)acetate (0.250 g, 0.56 mmol) obtained in step 1 of example 6n in the same manner as in step 2 of example 2f.

ESIMS, (M+H)⁺, m/z: 419.29.

(Step 2)

Compound 9b (0.031 g, 12%) was obtained from 2-(4-(4-(((2S,4R)-2-methyl-1-propionyl-1,2,3,4-tetrahydroquinolin-4-yl)amino)phenyl)-1H-pyrazol-1-yl)acetic acid (0.150 g, 0.36 mmol) obtained in step 1 and 1-((2S*,4R*)-4-(((1r,4R)-4-aminocyclohexyl)amino)-2-methyl-3,4-dihydroquinolin-1(2H)-yl)propan-1-one dihydrochloride (0.113 g, 0.36 mmol) obtained in step 2 of reference example 10 in the same manner as in step 1 of example 1a.

ESIMS, (M+H)⁺, m/z: 716.51. ¹H-NMR (DMSO-d₆, δ): 0.85-1.05 (m, 13H), 1.11-1.24 (m, 5H), 1.84-2.33 (m, 7H), 2.54-2.67 (m, 4H), 3.35-3.52 (m, 2H), 4.14-4.19 (m, 1H), 4.66-4.75 (m, 4H), 6.03 (d, J=7.67 Hz, 1H), 6.65 (d, J=8.33 Hz, 2H), 7.17-7.30 (m, 9H), 7.48-7.54 (m, 2H), 7.68 (s, 1H), 7.87 (s, 1H), 8.02 (brs, 1H).

Example 9c

N-((1R,4R)-4-(((2S*,4R*)-2-Methyl-1-propionyl-1,2,3,4-tetrahydroquinolin-4-yl)amino)cyclohexyl)-2-(3-(4-(((2S,4R)-2-methyl-1-propionyl-1,2,3,4-tetrahydroquinolin-4-yl)amino)phenyl)ureido)acetamide (Compound 9c)

Compound 9c (0.021 g, 17%) was obtained from ((4-(((2S,4R)-2-methyl-1-propionyl-1,2,3,4-tetrahydroquinolin-4-yl)amino)phenyl)carbamoyl)glycine (0.070 g, 0.17 mmol) obtained in step 2 of example 14h and 1-((2S*,4R*)-4-(((1r,4R)-4-aminocyclohexyl)amino)-2-methyl-3,4-dihydroquinolin-1(2H)-yl)propan-1-one dihydrochloride (0.066 g, 0.17 mmol) obtained in step 2 of reference example 10 in the same manner as in step 3 of example 14f.

ESIMS, (M+H)⁺, m/z: 708.5. ¹H-NMR (DMSO-d₆, δ): 0.76-0.89 (m, 1H), 0.94-1.04 (m, 12H), 1.09-1.23 (m, 6H), 1.72-1.83 (m, 2H), 1.91-2.00 (m, 2H), 2.07-2.26 (m, 2H), 2.54-2.58 (m, 4H), 2.85-3.05 (m, 1H), 3.44-3.52 (m, 2H), 3.65 (d, J=5.38 Hz, 2H), 4.01-4.07 (m, 1H), 4.59-4.79 (m, 2H), 5.68 (d, J=8.0 Hz, 1H), 6.07 (t, J=5.26 Hz, 1H), 6.55 (d, J=8.8 Hz, 2H), 7.08 (d, J=8.8 Hz, 2H), 7.16-7.29 (m, 7H), 7.48-7.50 (m, 1H), 7.75 (d, J=7.83 Hz, 1H), 8.27 (s, 1H).

Example 9d (1R,4R)-4-(((2S*,4R*)-2-Methyl-1-propionyl-1,2,3,4-tetrahydroquinolin-4-yl)amino)-N-(4-(((1R,4R)-4-(((2S,4R)-2-methyl-1-propionyl-1,2,3,4-tetrahydroquinolin-4-yl)amino)cyclohexyl)amino)-4-oxobut-2-yn-1-yl)cyclohexane-1-carboxamide (Compound 9d)

(Step 1)

tert-Butyl (4-(((1R,4r)-4-(((2S,4R)-2-methyl-1-propionyl-1,2,3,4-tetrahydroquinolin-4-yl)amino)cyclohexyl)amino)-4-oxobut-2-yn-1-yl)carbamate (0.100 g, 31%) was obtained from commercially available 4-((tert-butoxycarbonyl)amino)but-2-ynoic acid (0.129 g, 0.65 mmol) and 1-((2S,4R)-4-(((1r,4R)-4-aminocyclohexyl)amino)-2-methyl-3,4-dihydroquinolin-1(2H)-yl)propan-1-one (0.250 g, 0.65 mmol) obtained in reference example 11 in the same manner as in step 1 of example 1a.

ESIMS, (M+H)⁺, m/z: 497.

(Step 2)

4-Amino-N-((1R,4r)-4-(((2S,4R)-2-methyl-1-propionyl-1,2,3,4-tetrahydroquinolin-4-yl)amino)cyclohexyl)but-2-ynamide trifluoroacetate (0.095 g, 93%) was obtained from tert-butyl (4-(((1R,4r)-4-(((2S,4R)-2-methyl-1-propionyl-1,2,3,4-tetrahydroquinolin-4-yl)amino)cyclohexyl))amino)-4-oxobut-2-yn-1-yl)carbamate (0.100 g, 0.20 mmol) obtained in step 1 in the same manner as in step 2 of example 1k.

ESIMS, (M-TFA+H)⁺, m/z: 397.

(Step 3)

Compound 9d (0.030 g, 28%) was obtained from 4-amino-N-((1R,4r)-4-(((2S,4R)-2-methyl-1-propionyl-1,2,3,4-tetrahydroquinolin-4-yl)amino)cyclohexyl)but-2-ynamide trifluoroacetate (0.089 g, 0.17 mmol) obtained in step 2 and (1R,4r)-4-(((2S*,4R*)-2-methyl-1-propionyl-1,2,3,4-tetrahydroquinolin-4-yl)amino)cyclohexane-1-carboxylic acid (0.05 g, 0.14 mmol) obtained in step 2 of reference example 11 in the same manner as in step 3 of example 1b.

ESIMS, (M+H)⁺, m/z: 723; ¹H-NMR (DMSO-d₆, δ) 0.74-0.87 (m, 2H), 0.88-1.02 (m, 12H), 1.03-1.27 (m, 6H), 1.30-1.44 (m, 2H), 1.69-1.81 (m, 6H), 1.86-2.18 (m, 8H), 2.52-2.62 (m, 4H), 3.39-3.58 (m, 3H), 3.98 (t, J=5.2 Hz, 2H), 4.56-4.69 (m, 2H), 7.19-7.28 (m, 6H), 7.46-7.49 (m, 2H), 8.27 (t, J=5.48 Hz, 1H), 8.51 (t, J=8.0 Hz, 1H).

Example 9h 1-(1-((1R,4r)-4-(((2S,4R)-2-Methyl-1-propionyl-1,2,
3,4-tetrahydroquinolin-4-yl)amino)cyclohexane-1-
carbonyl)azetidin-3-yl)-3-(4-(((2S,4R)-2-methyl-1-
propionyl-1,2,3,4-tetrahydroquinolin-4-yl)amino)
phenyl)urea (Compound 9h)

(Step 1)
tert-Butyl (1-((1R,4r)-4-(((2S,4R)-2-methyl-1-propionyl-1,2,3,4-tetrahydroquinolin-4-yl)amino)cyclohexane-1-carbonyl)azetidin-3-yl)carbamate (0.2 g, 55%) was obtained from (1R,4r)-4-(((2S,4R)-2-methyl-1-propionyl-1,2,3,4-tetrahydroquinolin-4-yl)amino)cyclohexane-1-carboxylic acid (0.25 g, 0.73 mmol) obtained in reference example 11 and tert-butyl azetidin-3-ylcarbamate (0.149 g, 0.87 mmol) in the same manner as in step 3 of example 1b.
ESIMS, (M+H)$^+$, m/z: 499.38.
(Step 2)
1-((2S,4R)-4-(((1r,4R)-4-(3-Aminoazetidine-1-carbonyl)cyclohexyl)amino)-2-methyl-3,4-dihydroquinolin-1(2H)-yl)propan-1-one trifluoroacetate (0.18 g, 88%) was obtained from tert-butyl (1-((1R,4r)-4-(((2S,4R)-2-methyl-1-propionyl-1,2,3,4-tetrahydroquinolin-4-yl)amino)cyclohexane-1-carbonyl)azetidin-3-yl)carbamate (0.2 g, 0.40 mmol) obtained in step 1 in the same manner as in step 2 of example 1k.
ESIMS, (M+H)$^+$, m/z: 399.37.
(Step 3)
1-((2S,4R)-4-(((1r,4R)-4-(3-Aminoazetidine-1-carbonyl)cyclohexyl)amino)-2-methyl-3,4-dihydroquinolin-1(2H)-yl)propan-1-one trifluoroacetate (0.08 g, 0.16 mmol) obtained in step 2 was dissolved in DMF (5 mL), then CDI (0.038 g, 0.23 mmol), DMAP (0.047 g, 0.39 mmol) and N,N-diisopropylethylamine (0.13 mL, 0.78 mmol) were added to the solution, and the mixture was stirred at room temperature for 2 hours. 1-((2S,4R)-4-((4-aminophenyl)amino)-2-methyl-3,4-dihydroquinolin-1(2H)-yl)propan-1-one (0.048 g, 0.16 mmol) obtained in reference example 7 was added to the reaction mixture, and the mixture was stirred at room temperature for 16 hours. Ice water was added to the reaction mixture, and the resulting solid was collected by filtration, and dried under reduced pressure. The obtained solid was purified by reverse phase HPLC (10 mmol/L aqueous ammonium bicarbonate solution/acetonitrile=90/10 to 10/90) to give compound 9h (0.054 g, 47%).
ESIMS, (M+H)$^+$, m/z: 734.43. $^1$H-NMR (DMSO-d$_6$, δ): 0.97-1.04 (m, 13H), 1.10-1.17 (m, 2H), 1.40-1.45 (m, 4H), 1.75-1.84 (m, 2H), 2.10-2.25 (m, 5H), 2.54-2.62 (m, 3H), 2.91 (brs, 1H), 3.65-3.68 (m, 1H), 3.98-4.08 (m, 3H), 4.40-4.440 (m, 3H), 4.70-4.73 (m, 2H), 5.75 (d, J=7.63 Hz, 1H), 6.52-6.61 (m, 3H), 7.08 (d, J=8.54 Hz, 2H), 7.15-7.17 (m, 2H), 7.24-7.30 (m, 2H), 7.39-7.41 (m, 4H), 8.09 (s, 1H), 9.03 (brs, 1H).

Example 10a

N-(4-(((2S,4R)-2-Methyl-1-propionyl-1,2,3,4-tetra-
hydroquinolin-4-yl)amino)phenyl)-1-(4-(((2S,4R)-2-
methyl-1-propionyl-1,2,3,4-tetrahydroquinolin-4-yl)
amino)piperidine-1-carbonyl)azetidine-3-
carboxamide (Compound 10a)

Compound 10a (0.0185 g, 8%) was obtained from the crude product (0.080 g) of N-(4-(((2S,4R)-2-methyl-1-propionyl-1,2,3,4-tetrahydroquinolin-4-yl)amino)phenyl)azetidine-3-carboxamide trifluoroacetate obtained in step 1 of example 10e and 1-((2S,4R)-2-Methyl-4-(piperidin-4-ylamino)-3,4-dihydroquinolin-1(2H)-yl)propan-1-one dihydrochloride (0.067 g, 0.17 mmol) obtained in reference example 13 in the same manner as in step 1 of example 14h.
ESIMS, (M+H)$^+$, m/z: 720. $^1$H-NMR (DMSO-d$_6$, δ): 0.79-0.89 (m, 1H), 0.94-1.04 (m, 12H), 1.13-1.24 (m, 4H), 1.85-1.87 (m, 3H), 2.07-2.28 (m, 2H), 2.54-2.62 (m, 3H), 2.77-2.84 (m, 3H), 3.39-3.50 (m, 2H), 3.66 (d, J=9.90 Hz, 2H), 3.98-4.00 (m, 4H), 4.08-4.17 (m, 1H), 4.59-4.77 (m, 2H), 5.91 (d, J=7.93 Hz, 1H), 6.60 (d, J=8.85 Hz, 2H), 7.14-7.32 (m, 9H), 7.47-7.52 (m, 1H), 9.64 (s, 1H).

Example 10b 4-(((2S*,4R*)-2-Methyl-1-propionyl-1,2,3,4-tetrahy-
droquinolin-4-yl)amino)-N-((1-(4-(((2S,4R)-2-
methyl-1-propionyl-1,2,3,4-tetrahydroquinolin-4-yl)
amino)phenyl)-1H-1,2,3-triazol-4-yl)methyl)
piperidine-1-carboxamide (Compound 10b)

(Step 1)
1-((2S*,4R*)-2-Methyl-4-(piperidin-4-ylamino)-3,4-dihydroquinolin-1(2H)-yl)propan-1-one dihydrochloride (1.0 g, 2.68 mmol) obtained in step 2 of reference example 12 was dissolved in methanol (5 mL), then an aqueous ammonia solution (7 mol/L methanol solution, 5 mL) was added to the solution at 0° C., and the mixture was stirred at room temperature for 10 minutes. The reaction mixture was concentrated under reduced pressure, and the obtained residue was purified by reverse phase column chromatography (acetonitrile/0.1% aqueous ammonium bicarbonate solution=18/82) to give 1-((2S*,4R*)-2-methyl-4-(piperidin-4-ylamino)-3,4-dihydroquinolin-1(2H)-yl)propan-1-one (0.55 g, 68%).
(Step 2)
1-((2S*,4R*)-2-Methyl-4-(piperidin-4-ylamino)-3,4-dihydroquinolin-1(2H)-yl)propan-1-one (0.2 g, 0.66 mmol) obtained in step 1 and prop-2-yn-1-amine (0.036 g, 0.66 mmol) were dissolved in THF (10 mL), then N,N-diisopropylethylamine (1.15 mL, 6.64 mmol) and DMAP (0.096 g, 0.79 mmol) were added to the solution, and the mixture was stirred at room temperature for 10 minutes. Triphosgene (0.098 g, 0.33 mmol) was added to the reaction mixture at 0° C., and the mixture was stirred at 50° C. for 24 hours. The reaction mixture was concentrated under reduced pressure, and the obtained residue was purified by reverse phase column chromatography (acetonitrile/0.1% formic acid aqueous solution=40/60) to give 4-(((2S*,4R*)-2-methyl-1-propionyl-1,2,3,4-tetrahydroquinolin-4-yl)amino)-N-(prop-2-yn-1-yl)piperidine-1-carboxamide (0.12 g, 47%).
ESIMS, (M+H)$^+$, m/z: 383.35.
(Step 3)
Compound 10b (0.058 g, 31%) was obtained from 4-(((2S*,4R*)-2-methyl-1-propionyl-1,2,3,4-tetrahydroquinolin-4-yl)amino)-N-(prop-2-yn-1-yl)piperidine-1-carboxamide (0.1 g, 0.26 mmol) obtained in step 2 and the crude product (0.087 g) of 1-((2S,4R)-4-((4-azidophenyl)amino)-2-methyl-3,4-dihydroquinolin-1(2H)-yl)propan-1-one obtained in step 2 of example 3a in the same manner as in step 3 of example 5j.
ESIMS, (M+H)$^+$, m/z: 718.60. $^1$H-NMR (DMSO-d$_6$, δ): 0.82-0.84 (m, 1H), 0.93-1.06 (m, 12H), 1.17-1.23 (m, 3H), 1.83-1.85 (m, 3H), 2.07-2.29 (m, 2H), 2.52-2.66 (m, 4H), 2.78 (t, J=12.04 Hz, 3H), 3.44-3.50 (m, 1H), 3.88-3.91 (m, 2H), 4.26-4.32 (m, 3H), 4.59-4.80 (m, 2H), 6.49 (d, J=7.63

Hz, 1H), 6.78 (d, J=9.06 Hz, 2H), 6.99 (t, J=5.60 Hz, 1H), 7.14-7.33 (m, 7H), 7.48-7.55 (m, 3H), 8.25 (s, 1H).

Example 10c 4-(((2S,4R)-2-Methyl-1-propionyl-1,2,3,4-tetrahydroquinolin-4-yl)amino)-N-(4-(4-(((2S,4R)-2-methyl-1-propionyl-1,2,3,4-tetrahydroquinolin-4-yl)amino)piperidin-1-yl)-4-oxobut-2-yn-1-yl)benzamide (Compound 10c)

(Step 1)
A crude product (0.250 g) of tert-butyl (4-(4-(((2S,4R)-2-methyl-1-propionyl-1,2,3,4-tetrahydroquinolin-4-yl)amino)piperidin-1-yl)-4-oxobut-2-yn-1-yl)carbamate was obtained from 1-((2S,4R)-2-methyl-4-(piperidin-4-ylamino)-3,4-dihydroquinolin-1(2H)-yl)propan-1-one dihydrochloride (0.200 g, 0.53 mmol) obtained in step 2 of reference example 13 and commercially available 4-((tert-butoxycarbonyl)amino)but-2-ynoic acid (0.106 g, 0.53 mmol) in the same manner as in step 1 of example 1a.
ESIMS, (M+H)$^+$, m/z: 483.
(Step 2)
A crude product of 4-amino-1-(4-(((2S,4R)-2-methyl-1-propionyl-1,2,3,4-tetrahydroquinolin-4-yl)amino)piperidin-1-yl)but-2-yn-1-one trifluoroacetate (0.170 g) was obtained from tert-butyl (4-(4-(((2S,4R)-2-methyl-1-propionyl-1,2,3,4-tetrahydroquinolin-4-yl)amino)piperidin-1-yl)-4-oxobut-2-yn-1-yl)carbamate (0.170 g, 0.35 mmol) obtained in step 1 in the same manner as in step 2 of example 1k.
ESIMS, (M−TFA+H)$^+$, m/z: 383.
(Step 3)
Compound 10c (0.047 g, 33%) was obtained from the crude product (0.100 g) of 4-amino-1-(4-(((2S,4R)-2-methyl-1-propionyl-1,2,3,4-tetrahydroquinolin-4-yl)amino)piperidin-1-yl)but-2-yn-1-one trifluoroacetate obtained in step 2 and 4-{[(2S,4R)-2-methyl-1-propionyl-1,2,3,4-tetrahydroquinolin-4-yl]amino}benzoic acid (0.068 g, 0.20 mmol) obtained in step 7 of reference example 1 in the same manner as in step 3 of example 1b.
ESIMS, (M+H)$^+$, m/z: 703; $^1$H-NMR (DMSO-d$_6$, δ) 0.79-0.91 (m, 1H), 0.93-1.06 (m, 12H), 1.20-1.25 (m, 3H), 1.83-1.98 (m, 3H), 2.06-2.17 (m, 1H), 2.19-2.28 (m, 1H), 2.54-2.69 (m, 4H), 2.82-2.95 (m, 2H), 3.18-3.27 (m, 1H), 3.42-3.50 (m, 1H), 4.04-4.14 (m, 2H), 4.17-4.21 (m, 2H), 4.21-4.33 (m, 1H), 4.58-4.67 (m, 1H), 4.69-4.79 (m, 1H), 6.64-6.68 (m, 3H), 7.09 (d, J=7.87 Hz, 1H), 7.13-7.36 (m, 6H), 7.45-7.53 (m, 1H), 7.65 (dd, J=8.8, 3.2 Hz, 2H), 8.56-8.62 (m, 1H).

Example 10d 4-(((2S*,4R*)-2-Methyl-1-propionyl-1,2,3,4-tetrahydroquinolin-4-yl)amino)-N-(2-(4-(4-(((2S,4R)-2-methyl-1-propionyl-1,2,3,4-tetrahydroquinolin-4-yl)amino)phenyl)-1H-pyrazol-1-yl)ethyl)piperidine-1-carboxamide (Compound 10d)

(Step 1)
1-((2S,4R)-4-((4-(1-(2-Aminoethyl)-1H-pyrazol-4-yl)phenyl)amino)-2-methyl-3,4-dihydroquinolin-1(2H)-yl)propan-1-one hydrochloride (0.160 g, 94%) was obtained from tert-butyl (2-(4-(4-(((2S,4R)-2-methyl-1-pupionyl-1,2,3,4-tetrahydro-4-yl)amino)phenyl)-1H-pyrazol-1-yl)ethyl)carbamate (0.180 g, 0.36 mmol) obtained in step 1 of example 6q in the same manner as in step 2 of example 1a.
(Step 2)

Compound 10d (0.023 g, 5%) was obtained from 1-((2S,4R)-4-((4-(1-(2-aminoethyl)-1H-pyrazol-4-yl)phenyl)amino)-2-methyl-3,4-dihydroquinolin-1(2H)-yl)propan-1-one hydrochloride (0.290 g, 0.66 mmol) obtained in step 1 and 1-((2S*,4R*)-2-methyl-4-(piperidin-4-ylamino)-3,4-dihydroquinolin-1(2H)-yl)propan-1-one (0.332 g, 0.86 mmol) obtained in step 2 of reference example 12 in the same manner as in step 1 of example 14h.
ESIMS, (M+H)$^+$, m/z: 731.63. $^1$H-NMR (DMSO-d$_6$, δ): 0.93-1.08 (m, 13H), 1.11-1.32 (m, 5H), 1.79-1.94 (m, 2H), 2.04-2.15 (m, 1H), 2.20-2.30 (m, 1H), 2.53-2.67 (m, 4H), 2.70-2.80 (m, 2H), 2.92-3.02 (m, 1H), 3.36-3.44 (m, 2H), 3.88 (d, J=12.96 Hz, 2H), 4.08-4.20 (m, 3H), 4.59-4.79 (m, 2H), 6.03 (d, J=7.82 Hz, 1H), 6.62-6.67 (m, 3H), 7.16-7.41 (m, 9H), 7.47 (d, J=6.11 Hz, 1H), 7.70 (s, 1H), 7.87 (s, 1H).

Example 10e

N-(4-(((2S*,4R*)-2-Methyl-1-propionyl-1,2,3,4-tetrahydroquinolin-4-yl)amino)phenyl)-1-(4-(((2S,4R)-2-methyl-1-propionyl-1,2,3,4-tetrahydroquinolin-4-yl)amino)piperidine-1-carbonyl)azetidine-3-carboxamide (Compound 10e)

(Step 1)
A crude product (0.250 g) of N-(4-(((2S,4R)-2-methyl-1-propionyl-1,2,3,4-tetrahydroquinolin-4-yl)amino)phenyl)azetidine-3-carboxamide trifluoroacetate was obtained from tert-butyl 3-((4-(((2S,4R)-2-methyl-1-propionyl-1,2,3,4-tetrahydroquinolin-4-yl)amino)phenyl)carbamoyl)azetidine-1-carboxylate (0.290 g, 0.66 mmol) obtained in step 1 of example 6d in the same manner as in step 2 of example 1k.
ESIMS, (M+H)$^+$, m/z: 393.36.
(Step 2)
Compound 10e (0.011 g, 3%) was obtained from the crude product (0.250 g) of N-(4-(((2S,4R)-2-methyl-1-propionyl-1,2,3,4-tetrahydroquinolin-4-yl)amino)phenyl)azetidine-3-carboxamide trifluoroacetate obtained in step 1 and 1-((2S*,4R*)-2-methyl-4-(piperidin-4-ylamino)-3,4-dihydroquinolin-1(2H)-yl)propan-1-one (0.248 g, 0.64 mmol) obtained in step 2 of reference example 12 in the same manner as in step 1 of example 14h.
ESIMS, (M+H)$^+$, m/z: 720.47. $^1$H-NMR (DMSO-d$_6$, δ): 0.78-0.88 (m, 1H), 0.92-1.08 (m, 12H), 1.12-1.27 (m, 3H), 1.79-2.04 (m, 3H), 2.09-2.38 (m, 2H), 2.52-2.62 (m, 4H), 2.80 (t, J=11.6 Hz, 3H), 3.38-3.52 (m, 2H), 3.68 (d, J=10.4 Hz, 2H), 3.96-4.04 (m, 4H), 4.09-4.15 (m, 1H), 4.59-4.68 (m, 2H), 5.91 (d, J=8.0 Hz, 1H), 6.59 (d, J=9.2 Hz, 2H), 7.15-7.19 (m, 2H), 7.23-7.32 (m, 7H), 7.50 (brs, 1H), 9.64 (s, 1H).

Example 10f 4-(((2S,4R)-2-Methyl-1-propionyl-1,2,3,4-tetrahydroquinolin-4-yl)amino)-N-(4-(((1R,3R)-3-(((2S*,4R*)-2-methyl-1-propionyl-1,2,3,4-tetrahydroquinolin-4-yl)amino)cyclobutyl)amino)-4-oxobut-2-yn-1-yl)benzamide (Compound 10f)

(Step 1)
A crude product (0.097 g) of tert-butyl (4-(((1R,3r)-3-(((2S*,4R*)-2-methyl-1-propionyl-1,2,3,4-tetrahydroquinolin-4-yl)amino)cyclobutyl)amino)-4-oxobut-2-yn-1-yl)carbamate was obtained from 1-((2S*,4R*)-4-(((1r,3R)-3-aminocyclobutyl)amino)-2-methyl-3,4-dihydroquinolin-1(2H)-yl)propan-1-one (0.2 g, 0.56 mmol) obtained in step 2 of reference example 14 and 4-((tert-butoxycarbonyl)amino)but-2-ynoic acid (0.110 g, 0.56 mmol) in the same manner as in step 1 of example 1a.
ESIMS, (M+H)$^+$, m/z: 469.40.
(Step 2)
A crude product (0.070 g) of 4-amino-N-((1R,3r)-3-(((2S*,4R*)-2-methyl-1-propionyl-1,2,3,4-tetrahydroquinolin-4-yl)amino)cyclobutyl)but-2-ynamide trifluoroacetic acid was obtained from the crude product (0.090 g) of tert-butyl (4-(((1R,3r)-3-(((2S*,4R*)-2-methyl-1-propionyl-1,2,3,4-tetrahydroquinolin-4-yl)amino)cyclobutyl)amino)-4-oxobut-2-yn-1-yl)carbamate obtained in step 1 in the same manner as in step 2 of example 1k.
ESIMS, (M+H)$^+$, m/z: 369.35.
(Step 3)
Compound 10f (0.021 g, total yield of 3 steps 21%) was obtained from the crude product (0.070 g) of 4-amino-N-((1R,3r)-3-(((2S*,4R*)-2-methyl-1-propionyl-1,2,3,4-tetrahydroquinolin-4-yl)amino)cyclobutyl)but-2-ynamide trifluoroacetate obtained in step 2 and 4-{[(2S,4R)-2-methyl-1-propionyl-1,2,3,4-tetrahydroquinolin-4-yl]amino}benzoic acid (0.049 g, 0.14 mmol) obtained in reference example 1 in the same manner as in step 3 of example 1b.
ESIMS, (M+H)$^+$, m/z: 689.45. $^1$H-NMR (DMSO-d$_6$, δ): 0.75-0.85 (m, 1H), 0.90-1.09 (m, 12H), 1.22 (td, J=12.28, 8.55 Hz, 2H), 2.03-2.31 (m, 7H), 2.54-2.69 (m, 4H), 3.44-3.57 (m, 1H), 4.14-4.33 (m, 4H), 4.52-4.79 (m, 2H), 6.62-6.68 (m, 3H), 7.09 (d, J=7.67 Hz, 1H), 7.14-7.32 (m, 6H), 7.45 (brs, 1H), 7.65 (d, J=8.77 Hz, 2H), 8.54 (t, J=5.48 Hz, 1H), 8.88 (d, J=6.4 Hz, 1H).

Example 10g 1-(4-((((2S*,4R*)-2-Methyl-1-propionyl-1,2,3,4-tetrahydroquinolin-4-yl)amino)methyl)benzoyl)-N-(4-(((2S,4R)-2-methyl-1-propionyl-1,2,3,4-tetrahydroquinolin-4-yl)amino)phenyl)azetidine-3-carboxamide (Compound 10g)

(Step 1)
A crude product (0.30 g) of methyl 1-(4-((((2S*,4R*)-2-methyl-1-propionyl-1,2,3,4-tetrahydroquinolin-4-yl)amino)methyl)benzoyl)azetidine-3-carboxylate was obtained from 4-((((2S*,4R*)-2-methyl-1-propionyl-1,2,3,4-tetrahydroquinolin-4-yl)amino)methyl)benzoic acid (0.25 g, 0.71 mmol) obtained in step 2 of reference example 15 and methyl azetidine-3-carboxylate hydrochloride (0.107 g, 0.71 mmol) in the same manner as in step 3 of example 1b.
ESIMS, (M+H)$^+$, m/z: 450.40.
(Step 2)
1-(4-((((2S*,4R*)-2-Methyl-1-propionyl-1,2,3,4-tetrahydroquinolin-4-yl)amino)methyl)benzoyl)azetidine-3-carboxylic acid (0.12 g, total yield of 2 steps 39%) was obtained from the crude product (0.30 g) of methyl 1-(4-((((2S*,4R*)-2-methyl-1-propionyl-1,2,3,4-tetrahydroquinolin-4-yl)amino)methyl)benzoyl)azetidine-3-carboxylate obtained in step 1 in the same manner as in step 2 of example 2f.
ESIMS, (M+H)$^+$, m/z: 436.40.
(Step 3)
1-(4-((((2S*,4R*)-2-Methyl-1-propionyl-1,2,3,4-tetrahydroquinolin-4-yl)amino)methyl)benzoyl)azetidine-3-carboxylic acid (0.1 g, 0.23 mmol) obtained in step 2 was dissolved in DMF (5 mL), then DCC (0.071 g, 0.34 mmol) and DMAP (0.084 g, 0.69 mmol) were added to the solution, and the mixture was stirred at room temperature for 15 minutes. 1-{(2S,4R)-4-[(4-aminophenyl)amino]-2-methyl-3,4-dihydroquinolin-1(2H)-yl}propan-1-one (0.071 g, 0.23 mmol) obtained in reference example 7 was added to the reaction mixture, and the mixture was stirred at room temperature for 16 hours. Ice water was added to the reaction mixture, and the resulting solid was collected by filtration, and dried under reduced pressure. The obtained solid was purified by reverse phase HPLC (10 mmol/L aqueous ammonium bicarbonate solution/acetonitrile=55/45 to 10/90) to give compound 10 g (0.045 g, 27%).
ESIMS, (M+H)$^+$, m/z: 727.45. $^1$H-NMR (DMSO-d$_6$, δ): 0.86-0.89 (m, 1H), 0.91 (t, J=7.39 Hz, 3H), 0.98-1.04 (m, 9H), 1.14-1.16 (m, 1H), 2.06-2.15 (m, 1H), 2.19-2.28 (m, 1H), 2.47-2.49 (m, 1H), 2.53-2.64 (m, 3H), 2.65-2.70 (m, 1H), 3.34-3.37 (m, 1H), 3.48-3.53 (m, 1H), 3.94-3.97 (m, 2H), 4.10-4.20 (m, 3H), 4.37-4.46 (m, 2H), 4.60-4.76 (m, 2H), 5.92 (d, J=7.87 Hz, 1H), 6.60 (d, J=9.06 Hz, 2H), 7.14-7.16 (m, 2H), 7.23-7.33 (m, 7H), 7.51-7.63 (m, 5H), 9.72 (s, 1H).

Example 10h 4-((((2S*,4R*)-2-Methyl-1-propionyl-1,2,3,4-tetrahydroquinolin-4-yl)amino)methyl)-N-((1-(4-(((2S,4R)-2-methyl-1-propionyl-1,2,3,4-tetrahydroquinolin-4-yl)amino)phenyl)-1H-1,2,3-triazol-4-yl)ethyl)benzamide (Compound 10h)

(Step 1)
4-((((2S*,4R*)-2-Methyl-1-propionyl-1,2,3,4-tetrahydroquinolin-4-yl)amino)methyl)-N-(prop-2-yn-1-yl)benzamide (0.18 g, 65%) was obtained from 4-((((2S*,4R*)-2-methyl-1-propionyl-1,2,3,4-tetrahydroquinolin-4-yl)amino)methyl)benzoic acid (0.25 g, 0.71 mmol) obtained in step 2 of reference example 15 and prop-2-yn-1-amine (0.04 mL, 0.71 mmol) in the same manner as in step 3 of example 1b.
ESIMS, (M+H)$^+$, m/z: 390.37.
(Step 2)
Compound 10h (0.065 g, 20%) was obtained from 4-((((2S*,4R*)-2-methyl-1-propionyl-1,2,3,4-tetrahydroquinolin-4-yl)amino)methyl)-N-(prop-2-yn-1-yl)benzamide (0.174 g, 0.45 mmol) obtained in step 1 and the crude product (0.15 g) of 1-((2S,4R)-4-((4-azidophenyl)amino)-2-methyl-3,4-dihydroquinolin-1(2H)-yl)propan-1-one obtained in step 2 of example 3a in the same manner as in step 3 of example 5j.
ESIMS, (M+H)$^+$, m/z: 725.55. $^1$H-NMR (DMSO-d$_6$, δ): 0.89-0.93 (m, 4H), 0.99-1.06 (m, 9H), 1.20-1.22 (m, 1H), 2.09-2.11 (m, 1H), 2.23-2.25 (m, 1H), 2.47-2.48 (m, 1H), 2.56-2.69 (m, 4H), 3.33-3.37 (m, 1H), 3.90-4.03 (m, 2H), 4.21-4.26 (m, 1H), 4.56-4.61 (m, 3H), 4.74-4.76 (m, 1H), 6.49 (d, J=7.87 Hz, 1H), 6.78 (d, J=9.06 Hz, 2H), 7.14-7.32 (m, 7H), 7.50-7.58 (m, 5H), 7.86 (d, J=8.34 Hz, 2H), 8.40 (s, 1H), 8.98 (t, J=5.60 Hz, 1H).

Example 10j 1-((2S,4R)-2-Methyl-4-((4-((((1-(6-(((2S*,4R*)-2-methyl-1-propionyl-1,2,3,4-tetrahydroquinolin-4-yl)amino)pyridin-3-yl)-1H-1,2,3-triazol-4-yl)methyl)amino)methyl)phenyl)amino)-3,4-dihydroquinoline-1(2H)-yl)propan-1-one (Compound 10j)

(Step 1)
A crude product (0.160 g) of tert-butyl ((2S,4R)-2-methyl-1-propionyl-1,2,3,4-tetrahydroquinolin-4-yl)(4-((prop-2-yn-1-ylamino)methyl)phenyl)carbamate was obtained from tert-butyl (4-formylphenyl)((2S,4R)-2-methyl-1-propionyl-1,2,3,4-tetrahydroquinolin-4-yl)carbamate (0.150 g, 0.35 mmol) obtained in reference example 8 and prop-2-yn-1-amine (0.039 g, 0.71 mmol) in the same manner as in step 1 of example 7b.
ESIMS, (M+H)⁺, m/z: 462.
(Step 2)
1-((2S*,4R*)-4-((5-Azidopyridin-2-yl)amino)-2-methyl-3,4-dihydroquinolin-1(2H)-yl)propan-1-one (0.110 g, 68%) was obtained from 1-((2S*,4R*)-4-((5-aminopyridin-2-yl)amino)-2-methyl-3,4-dihydroquinolin-1(2H)-yl)propan-1-one (0.150 g, 0.48 mmol) obtained in step 2 of reference example 16 in the same manner as in step 2 of example 3a.
ESIMS, (M+H)⁺, m/z: 337.
(Step 3)
tert-Butyl ((2S*,4R*)-2-methyl-1-propionyl-1,2,3,4-tetrahydroquinolin-4-yl)(4-((((1-(6-((2S,4R)-2-methyl-1-propionyl-1,2,3,4-tetrahydroquinolin-4-yl)amino)pyridin-3-yl)-1H-1,2,3-triazol-4-yl)methyl)amino)methyl)phenyl)carbamate (0.1 g, 42%) was obtained from the crude product (0.137 g) of tert-butyl ((2S,4R)-2-methyl-1-propionyl-1,2,3,4-tetrahydroquinolin-4-yl)(4-((prop-2-yn-1-ylamino)methyl)phenyl)carbamate obtained in step and 1-((2S*,4R*)-4-((5-azidopyridin-2-yl)amino)-2-methyl-3,4-dihydroquinolin-1(2H)-yl)propan-1-one (0.100 g, 0.30 mmol) obtained in step 2 in the same manner as in step 3 of example 3a.
ESIMS, (M+H)⁺, m/z: 798.
(Step 4)
Compound 10j (0.026 g, 30%) was obtained from tert-butyl ((2S*,4R*)-2-methyl-1-propionyl-1,2,3,4-tetrahydroquinolin-4-yl)(4-((((1-(6-(((2S,4R)-2-methyl-1-propionyl-1,2,3,4-tetrahydroquinolin-4-yl)amino)pyridin-3-yl)-1H-1,2,3-triazol-4-yl)methyl)amino)methyl)phenyl)carbamate (0.1 g, 0.12 mmol) obtained in step 3 in the same manner as in step 2 of example 1a.
ESIMS, (M+H)⁺, m/z: 698; ¹H-NMR (DMSO-d₆, δ) 0.93-1.08 (m, 12H), 1.09-1.31 (m, 2H), 2.14-2.28 (m, 2H), 2.53-2.70 (m, 4H), 3.60 (s, 2H), 3.77 (s, 2H), 4.01-4.12 (m, 1H), 4.72-4.76 (m, 3H), 5.94 (d, J=7.87 Hz, 1H), 6.59 (d, J=8.58 Hz, 2H), 6.81 (d, J=9.06 Hz, 1H), 7.08 (d, J=8.34 Hz, 2H), 7.14-7.34 (m, 8H), 7.42 (d, J=8.34 Hz, 1H), 7.90 (dd, J=8.94, 2.74 Hz, 1H), 8.36-8.41 (m, 2H).

Example 10k

N¹-(4-(((2S,4R)-2-Methyl-1-propionyl-1,2,3,4-tetrahydroquinolin-4-yl)amino)phenyl)-N⁵-(6-(((2S,4R)-2-methyl-1-propionyl-1,2,3,4-tetrahydroquinolin-4-yl)amino)pyridin-3-yl)glutaramide (Compound 10k)

A crude product of compound 10k was obtained from 1-((2S,4R)-4-((5-aminopyridin-2-yl)amino)-2-methyl-3,4-dihydroquinolin-1(2H)-yl)propan-1-one (50 mg, 0.161 mmol) obtained in reference example 17 and 5-((4-(((2S,4R)-2-methyl-1-propionyl-1,2,3,4-tetrahydroquinolin-4-yl)amino)phenyl)amino)-5-oxopentanoic acid (80 mg, 0.193 mmol) obtained in step 2 of example 6k in the same manner as in step 3 of example 1b. The crude product obtained was purified by reverse phase HPLC (0.05% aqueous ammonium bicarbonate solution/acetonitrile=6/4 to 5/5) to give compound 10k (48 mg, 41%).
ESI-MS, (M+H)⁺, m/z: 716. ¹H-NMR (CDCl₃, δ): 1.11-1.18 (m, 12H), 1.19-1.32 (m, 2H), 2.08-2.17 (m, 2H), 2.29-2.42 (m, 2H), 2.46-2.60 (m, 4H), 2.61-2.71 (m, 2H), 3.50 (d, J=5.4 Hz, 2H), 3.81 (d, J=7.2 Hz, 1H), 4.11-4.19 (m, 1H), 4.54-4.65 (m, 2H), 4.87-4.98 (m, 2H), 6.43 (d, J=9.1 Hz, 1H), 6.60 (d, J=9.1 Hz, 2H), 7.12-7.21 (m, 4H), 7.25-7.33 (m, 6H), 7.45 (s, 1H), 7.79-7.83 (m, 2H), 8.13 (d, J=2.3 Hz, 1H).

Example 10l

N¹-(4-(((2S,4R)-2-Methyl-1-propionyl-1,2,3,4-tetrahydroquinolin-4-yl)amino)phenyl)-N⁵-(5-(((2S*,4R*)-2-methyl-1-propionyl-1,2,3,4-tetrahydroquinolin-4-yl)amino)pyridin-2-yl)glutaramide (compound 10l)

(Step 1)
1-((2S*,4R*)-2-Methyl-4-((6-nitropyridin-3-yl)amino)-3,4-dihydroquinolin-1(2H)-yl)propan-1-one (71.8 mg, 96%) was obtained from 1-((2S*,4R*)-4-amino-2-methyl-3,4-dihydroquinolin-1(2H)-yl)propan-1-one (47.8 mg, 0.219 mmol) obtained in step 3 of reference example 1 and 5-fluoro-2-nitropyridine (62.2 mg, 0.438 mmol) in the same manner as in step 1 of reference example 16.
ESIMS, (M−H)⁻, m/z: 339.
(Step 2)
1-((2S*,4R*)-4-((6-Aminopyridin-3-yl)amino)-2-methyl-3,4-dihydroquinolin-1(2H)-yl)propan-1-one (52.8 mg, 81%) was obtained from 1-((2S*,4R*)-2-methyl-4-((6-nitropyridin-3-yl)amino)-3,4-dihydroquinolin-1(2H)-yl)propan-1-one (71.8 mg, 0.211 mmol) obtained in step 1 in the same manner as in step 2 of reference example 16.
ESIMS, (M+H)⁺, m/z: 311.
(Step 3)
Compound 10l (4.1 mg, 5%) was obtained from 1-((2S*,4R*)-4-((6-aminopyridin-3-yl)amino)-2-methyl-3,4-dihydroquinolin-1(2H)-yl)propan-1-one (32.4 mg, 0.104 mmol) obtained in step 2 and 5-((4-(((2S,4R)-2-methyl-1-propionyl-1,2,3,4-tetrahydroquinolin-4-yl)amino)phenyl)amino)-5-oxopentanoic acid (44.0 mg, 0.104 mmol) obtained in step 2 of example 6k in the same manner as in step 3 of example 1b. ESIMS, (M+H)⁺, m/z: 716; ¹H-NMR (CDCl₃, δ) 1.02-1.08 (m, 14H), 2.13 (t, J=6.8 Hz, 2H), 2.26-2.73 (m, 10H), 3.71-3.88 (m, 2H), 4.07-4.19 (m, 2H), 4.81-5.04 (m, 2H), 6.59 (d, J=8.8 Hz, 2H), 6.99 (dd, J=8.8, 2.8 Hz, 1H), 7.07-7.36 (m, 10H), 7.55 (s, 1H), 7.73 (d, J=2.8 Hz, 1H), 8.03 (d, J=8.8 Hz, 1H), 8.23 (brs, 1H).

Example 10m 1-(4-(((2S,4R)-2-Methyl-1-propionyl-1,2,3,4-tetrahydroquinolin-4-yl)amino)benzoyl)-N-(6-(((2S*,4R*)-2-methyl-1-propionyl-1,2,3,4-tetrahydroquinolin-4-yl)amino)pyridin-3-yl)piperidine-4-carboxamide (compound 10m)

(Step 1)
A crude product (0.130 g) of methyl 1-(4-(((2S,4R)-2-methyl-1-propionyl-1,2,3,4-tetrahydroquinolin-4-yl)amino)benzoyl)piperidine-4-carboxylate was obtained from 4-{[(2S,4R)-2-methyl-1-propionyl-1,2,3,4-tetrahydroquinolin-4-yl]amino}benzoic acid (0.1 g, 0.29 mmol) obtained in reference example 1 and methyl piperidine-4-carboxylate (0.042 g, 0.29 mmol) in the same manner as in step 3 of example 1b.
ESIMS, (M+H)⁺, m/z: 464.33.
(Step 2)
A crude product (0.080 g) of 1-(4-(((2S,4R)-2-methyl-1-propionyl-1,2,3,4-tetrahydroquinolin-4-yl)amino)benzoyl)piperidine-4-carboxylic acid was obtained from the crude product (0.130 g) of methyl 1-(4-(((2S,4R)-2-methyl-1-propionyl-1,2,3,4-tetrahydroquinolin-4-yl)amino)benzoyl)piperidine-4-carboxylate obtained in step 1 in the same manner as in step 2 of example 2f.
ESIMS, (M+H)$^+$, m/z: 450.29.
(Step 3)

Compound 10m (0.034 g, 26%) was obtained from the crude product (0.080 g) of 1-(4-(((2S,4R)-2-methyl-1-propionyl-1,2,3,4-tetrahydroquinolin-4-yl)amino)benzoyl)piperidine-4-carboxylic acid obtained in step 2 and 1-((2S*,4R*)-4-((5-aminopyridin-2-yl)amino)-2-methyl-3,4-dihydroquinolin-1(2H)-yl)propan-1-one (0.055 g, 0.18 mmol) obtained in step 2 of reference example 16 in the same manner as in step 3 of example 1b.
ESIMS, (M+H)$^+$, m/z: 742.60; $^1$H-NMR (DMSO-d$_6$, δ): 0.99-1.06 (s, 12H), 1.17-1.22 (m, 2H), 1.51-1.61 (m, 2H), 1.80 (d, J=11.6 Hz, 2H), 2.14-2.31 (m, 2H), 2.52-2.62 (m, 5H), 2.88-2.99 (m, 2H), 4.05-4.25 (m, 3H), 4.69-4.75 (m, 3H), 6.49 (d, J=7.6 Hz, 1H), 6.59-6.67 (m, 3H), 6.76 (d, J=8.4 Hz, 1H), 7.13-7.30 (m, 10H), 7.67 (dd, J=8.8, 2.4 Hz, 1H), 8.08 (s, 1H), 9.65 (s, 1H).

Example 10n 4-(((2S,4R)-2-Methyl-1-propionyl-1,2,3,4-tetrahydroquinolin-4-yl)amino)-N-(4-((6-(((2S*,4R*)-2-methyl-1-propionyl-1,2,3,4-tetrahydroquinolin-4-yl)amino)pyridin-3-yl)amino)-4-oxobut-2-yn-1-yl)benzamide (Compound 10n)

(Step 1)
tert-Butyl (4-((6-(((2S*,4R*)-2-methyl-1-propionyl-1,2,3,4-tetrahydroquinolin-4-yl)amino)pyridin-3-yl)amino)-4-oxobut-2-yn-1-yl)carbamate (0.165 g, 58%) was obtained from 1-((2S*,4R*)-4-((5-aminopyridin-2-yl)amino)-2-methyl-3,4-dihydroquinolin-1(2H)-yl)propan-1-one (0.18 g, 0.58 mmol) obtained in step 2 of reference example 16 and 4-((tert-butoxycarbonyl)amino)but-2-ynoic acid (0.08 g, 0.40 mmol) in the same manner as in step 1 of example 1a.
ESIMS, (M+H)$^+$, m/z: 492.20.
(Step 2)
A crude product (0.15 g) of 4-amino-N-(6-(((2S*,4R*)-2-methyl-1-propionyl-1,2,3,4-tetrahydroquinolin-4-yl)amino)pyridin-3-yl)but-2-ynamide trifluoroacetate was obtained from tert-butyl (4-((6-(((2S*,4R*)-2-methyl-1-propionyl-1,2,3,4-tetrahydroquinolin-4-yl)amino)pyridin-3-yl)amino)-4-oxobut-2-yn-1-yl)carbamate (0.15 g, 0.30 mmol) obtained in step 1 in the same manner as in step 2 of example 1k.
ESIMS, (MH)$^-$, m/z: 390.17.
(Step 3)
Compound 10n (0.05 g, total yield of 2 steps 23%) was obtained from the crude product (0.15 g) of 4-amino-N-(6-(((2S,4R)-2-methyl-1-propionyl-1,2,3,4-tetrahydroquinolin-4-yl)amino)pyridin-3-yl)but-2-ynamide trifluoroacetate obtained in step 2 and 4-{[(2S,4R)-2-methyl-1-propionyl-1,2,3,4-tetrahydroquinolin-4-yl]amino}benzoic acid (0.07 g, 0.20 mmol) obtained in reference example 1 in the same manner as in step 3 of example 1b.
ESI-MS m/z: 712.43 (M+H)$^+$; $^1$H-NMR (DMSO-d$_6$, δ): 0.98-1.06 (m, 12H), 1.16-1.26 (m, 2H), 2.15-2.30 (m, 2H), 2.52-2.65 (m, 4H), 4.23-4.32 (m, 3H), 4.69-4.75 (m, 3H), 6.63-6.69 (m, 4H), 7.09-7.20 (m, 5H), 7.24-7.32 (m, 4H), 7.67 (d, J=8.77 Hz, 3H), 8.12 (d, J=2.41 Hz, 1H), 8.60 (t, J=5.48 Hz, 1H), 10.47 (brs, 1H).

Example 10o 4-(((2S,4R)-2-Methyl-1-propionyl-1,2,3,4-tetrahydroquinolin-4-yl)amino)-N-(3-((6-(((2S*,4R*)-2-methyl-1-propionyl-1,2,3,4-tetrahydroquinolin-4-yl)amino)pyridin-3-yl)amino)-3-oxopropyl)benzamide (Compound 10o)

Compound 10o (10 mg, 31%) was obtained from the crude product (19 mg) of 3-(4-(((2S,4R)-2-methyl-1-propionyl-1,2,3,4-tetrahydroquinolin-4-yl)amino)benzamide)propanoic acid obtained in step 2 of example 2f and 1-(2S*,4R*)-(4-((5-aminopyridin-2-yl)amino)-2-methyl-3,4-dihydroquinolin-1(2H)-yl)propan-1-one (16 mg, 0.051 mmol) obtained in step 2 of reference example 16 in the same manner as in step 3 of example 1b. ESI-MS m/z: 702 (M+H)±: $^1$H-NMR (CDCl$_3$, δ): 1.10-1.21 (m, 12H), 1.23-1.34 (m, 2H), 2.28-2.45 (m, 2H), 2.48-2.75 (m, 6H), 3.71-3.84 (m, 2H), 4.16-4.29 (m, 2H), 4.54-4.68 (m, 2H), 4.85-5.07 (m, 2H), 6.37-6.46 (m, 1H), 6.55-6.65 (m, 2H), 6.86-6.99 (m, 1H), 7.11-7.23 (m, 5H), 7.23-7.34 (m, 3H), 7.59-7.72 (m, 2H), 7.72-7.86 (m, 1H), 8.14-8.19 (m, 1H), 8.22-8.32 (m, 1H).

Example 10p 1-(4-((((2S*,4R*)-2-Methyl-1-propionyl-1,2,3,4-tetrahydroquinolin-4-yl)amino)methyl)piperidine-1-carbonyl)-N-(4-(((2S,4R)-2-methyl-1-propionyl-1,2,3,4-tetrahydroquinolin-4-yl)amino)phenyl)azetidine-3-carboxamide (Compound 10p)

(Step 1)
tert-Butyl 3-((4-(((2S,4R)-2-methyl-1-propionyl-1,2,3,4-tetrahydroquinolin-4-yl)amino)phenyl)carbamoyl)azetidine-1-carboxylate (80 mg, 0.16 mmol) obtained in step 1 of example 6 was dissolved in ethyl acetate (0.8 mL), then 4 mol/L hydrochloric acid (0.61 mL, 2.4 mmol) was added to the solution, and the mixture was stirred at room temperature for 1 hour. A saturated aqueous sodium hydrogen carbonate solution was added to the reaction mixture, and the mixture was extracted with chloroform. The organic layer was dried over anhydrous magnesium sulfate and concentrated under reduced pressure to give a crude product (55 mg) of N-(4-(((2S,4R)-2-methyl-1-propionyl-1,2,3,4-tetrahydroquinolin-4-yl)amino)phenyl)azetidine-3-carboxamide.
ESI-MS m/z: 393 (M+H)$^+$
(Step 2)
The crude product (51 mg) of N-(4-(((2S,4R)-2-Methyl-1-propionyl-1,2,3,4-tetrahydroquinolin-4-yl)amino)phenyl)azetidine-3-carboxamide obtained in step 1 was dissolved in dichloromethane (1.3 mL), then triphosgene (19 mg, 0.064 mmol) and N,N-diisopropylethylamine (0.067 ml, 0.39 mmol) were added to the solution, and the mixture was stirred at 0° C. for 2 hours. The 1-((2S*,4R*)-2-methyl-4-((piperidin-4-ylmethyl)amino)-3,4-dihydroquinolin-1(2H)-yl)propan-1-one dihydrochloride (0.05 g, 0.129 mmol) obtained in step 2 of reference example 18 was added to the reaction mixture, and the mixture was further stirred at 0° C. for 2 hours. Water was added to the reaction mixture, and the mixture was extracted 3 times with chloroform. The organic layer was dried over anhydrous magnesium sulfate and concentrated under reduced pressure. The obtained residue was purified by silica gel column chromatography (chloroform/methanol=19/1) to give compound 10p (38 mg, yield of 2 steps 50%). ESI-MS m/z: 734 (M+H)$^+$: $^1$H-NMR (CDCl$_3$, δ): 1.00-1.19 (m, 12H), 1.19-1.37 (m, 2H), 1.74-

2.07 (m, 3H), 2.21-2.43 (m, 4H), 2.43-2.90 (m, 10H), 3.29-3.45 (m, 2H), 3.76-4.01 (m, 3H), 4.10-4.33 (m, 4H), 4.70-5.03 (m, 2H), 6.57-6.68 (m, 2H), 6.94-6.98 (m, 1H), 7.08-7.31 (m, 6H), 7.31-7.38 (m, 2H), 7.41-7.48 (m, 1H), 7.48-7.52 (m, 1H).

Example 10q

N,N'-(Propane-1,3-diyl)bis(4-(((2S,4R)-6-fluoro-2-methyl-1-propionyl-1,2,3,4-tetrahydroquinolin-4-yl)amino)benzamide) (Compound 10q)

Compound 10q (0.065 g, 41%) was obtained from 4-((6-fluoro-2-methyl-1-propionyl-1,2,3,4-tetrahydroquinolin-4-yl)amino)benzoic acid (0.1 g, 0.28 mmol) obtained in step 5 of reference example 19 and commercially available propane-1,3-diamine (0.0104 g, 0.14 mmol) in the same manner as in step 3 of example 1b.
ESIMS, (M+H)$^+$, m/z: 751; $^1$H-NMR (DMSO-d$_6$, δ) 0.99-1.05 (m, 12H), 1.16-1.24 (m, 2H), 1.70 (quin, J=6.74 Hz, 2H), 2.21-2.27 (m, 2H), 2.54-2.64 (m, 4H), 3.24-3.27 (m, 4H), 4.27-4.33 (m, 2H), 4.73-4.74 (m, 2H), 6.56 (d, J=7.89 Hz, 2H), 6.69 (d, J=8.77 Hz, 4H), 6.83 (dd, J=9.10, 2.74 Hz, 2H), 7.07-7.13 (m, 2H), 7.38 (dd, J=8.55, 5.04 Hz, 2H), 7.66 (d, J=8.55 Hz, 4H), 8.10 (t, J=5.8 Hz, 2H).

Example 10r

N,N'-(Ethane-1,2-diyl)bis(4-(((2S,4R)-6-fluoro-2-methyl-1-propionyl-1,2,3,4-tetrahydroquinolin-4-yl)amino)benzamide) (Compound 10r)

Compound 10r (0.062 g, 40%) was obtained from 4-((6-fluoro-2-methyl-1-propionyl-1,2,3,4-tetrahydroquinolin-4-yl)amino)benzoic acid (0.1 g, 0.28 mmol) obtained in step 5 of reference example 19 and commercially available ethane-1,2-diamine (0.0084 g, 0.14 mmol) in the same manner as in step 3 of example 1b.
ESIMS, (M+H)$^+$, m/z: 737: $^1$H-NMR (DMSO-d$_6$, δ) 0.99-1.05 (m, 12H), 1.15-1.24 (m, 2H), 2.20-2.26 (m, 2H), 2.54-2.64 (m, 4H), 3.36-3.37 (m, 4H), 4.27-4.33 (m, 2H), 4.73-4.74 (m, 2H), 6.56 (d, J=7.67 Hz, 2H), 6.68 (d, J=8.77 Hz, 4H), 6.82 (dd, J=9.10, 2.74 Hz, 2H), 7.10 (td, J=8.60, 2.96 Hz, 2H), 7.38 (dd, J=8.77, 5.04 Hz, 2H), 7.65 (d, J=8.77 Hz, 4H), 8.20 (brs, 2H).

Example 10s

N$^1$-(4-(((2S*,4R*)-7-(3-Aminopropyl)-2-methyl-1-propionyl-1,2,3,4-tetrahydroquinolin-4-yl)amino)phenyl)-N$^5$-(4-(((2S,4R)-2-methyl-1-propionyl-1,2,3,4-tetrahydroquinolin-4-yl)amino)phenyl)glutaramide (Compound 10s)

Compound 10s (0.054 g, 37%) was obtained from N$^1$-(4-(((2S*,4R*)-7-((E)-3-aminoprop-1-en-1-yl)-2-methyl-1-propionyl-1,2,3,4-tetrahydroquinolin-4-yl)amino)phenyl)-N$^5$-(4-(((2S,4R)-2-methyl-1-propionyl-1,2,3,4-tetrahydroquinolin-4-yl)amino)phenyl)glutaramide (0.150 g, 0.19 mmol) obtained in step 2 of example 10t in the same manner as in step 2 of example 1b.
ESI-MS m/z: 772.62 (M+H)$^+$: $^1$H-NMR (DMSO-d$_6$, δ): 0.98-1.04 (m, 12H), 1.09-1.19 (m, 2H), 1.63 (dq, J=14.63, 7.25 Hz, 2H), 1.84-1.89 (m, 2H), 2.21-2.29 (m, 6H), 2.53-2.60 (m, 8H), 2.89-2.97 (m, 1H), 4.05-4.14 (m, 2H), 4.68-4.73 (m, 2H), 5.81 (dd, J=17.98, 7.89 Hz, 2H), 6.58 (dd, J=8.77, 4.17 Hz, 4H), 6.97-7.17 (m, 5H), 7.23-7.31 (m, 6H), 9.51 (s, 2H).

Example 10t

N$^1$-(4-(((2S*,4R*)-7-((E)-3-Aminoprop-1-en-1-yl)-2-methyl-1-propionyl-1,2,3,4-tetrahydroquinolin-4-yl)amino)phenyl)-N$^5$-(4-(((2S,4R)-2-methyl-1-propionyl-1,2,3,4-tetrahydroquinolin-4-yl)amino)phenyl)glutaramide (Compound 10t)

(Step 1)
tert-Butyl ((E)-3-((2S*,4R*)-2-methyl-4-((4-(5-((4-(((2S,4R)-2-methyl-1-propionyl-1,2,3,4-tetrahydroquinolin-4-yl)amino)phenyl)amino)-5-oxopentanamide)phenyl)amino)-1-propionyl-1,2,3,4-tetrahydroquinolin-7-yl)allyl)carbamate (0.190 g, 77%) was obtained from tert-butyl ((E)-3-((2S*,4R*-4-((4-aminophenyl)amino)-2-methyl-1-propionyl-1,2,3,4-tetrahydroquinolin-7-yl)allyl)carbamate (0.131 g, 0.28 mmol) obtained in step 6 of reference example 20 and 5-((4-(((2S,4R)-2-methyl-1-propionyl-1,2,3,4-tetrahydroquinolin-4-yl)amino)phenyl)amino)-5-oxopentanoic acid (0.120 g, 0.28 mmol) obtained in step 2 of example 6k in the same manner as in step 3 of example 1b.
ESIMS, (M+H)$^+$, m/z: 870.90.
(Step 2)
Compound 10t (0.036 g, 21%) was obtained from tert-butyl ((E)-3-((2S*,4R*)-2-methyl-4-((4-(5-((4-(((2S,4R)-2-methyl-1-propionyl-1,2,3,4-tetrahydroquinolin-4-yl)amino)phenyl)amino)-5-oxopentanamide)phenyl)amino)-1-propionyl-1,2,3,4-tetrahydroquinolin-7-yl)allyl)carbamate (0.190 g, 0.22 mmol) obtained in step 1 in the same manner as in step 2 of example 1a.
ESI-MS m/z: 770.64 (M+H)$^+$: $^1$H-NMR (DMSO-d$_6$, δ): 0.98-1.06 (m, 12H), 1.11-1.20 (m, 2H), 1.83-1.89 (m, 2H), 2.20-2.33 (m, 6H), 2.53-2.67 (m, 4H), 3.57-3.63 (m, 2H), 4.09-4.15 (m, 2H), 4.64-4.78 (m, 2H), 6.27 (dt, J=15.89, 6.52 Hz, 2H), 6.59 (d, J=7.89 Hz, 4H), 6.70-6.74 (m, 1H), 7.17 (d, J=3.51 Hz, 3H), 7.23-7.32 (m, 7H), 7.39 (s, 1H), 8.02 (brs, 3H), 9.53 (s, 2H).

Example 10u

N$^1$-(4-(((2S,4R)-2-Methyl-1-propionyl-1,2,3,4-tetrahydroquinolin-4-yl)amino)phenyl)-N$^5$-(4-(((2S*,4R*)-2-methyl-1-propionyl-7-(1,2,3,6-tetrahydropyridin-4-yl)-1,2,3,4-tetrahydroquinolin-4-yl)amino)phenyl)glutaramide (compound 10u)

(Step 1)
tert-Butyl 4-((2S*,4R*)-2-methyl-4-((4-(5-((4-(((2S,4R)-2-methyl-1-propionyl-1,2,3,4-tetrahydroquinolin-4-yl)amino)phenyl)amino)-5-oxopentanamide)phenyl)amino)-1-propionyl-1,2,3,4-tetrahydroquinolin-7-yl)-3,6-dihydropyridine-1(2H)-carboxylate (0.080 g, 36%) was obtained from tert-butyl 4-((2S*,4R*)-4-((4-aminophenyl)amino)-2-methyl-1-propionyl-1,2,3,4-tetrahydroquinolin-7-yl)-3,6-dihydropyridine-1(2H)-carboxylate (0.121 g, 0.25 mmol) obtained in step 2 of reference example 21 and 5-((4-(((2S,4R)-2-methyl-1-propionyl-1,2,3,4-tetrahydroquinolin-4-yl)amino)phenyl)amino)-5-oxopentanoic acid (0.105 g, 0.25 mmol) obtained in step 2 of example 6k in the same manner as in step 3 of example 1b.
ESIMS, (M+H)$^+$, m/z: 896.76.

(Step 2)

Compound 10u (0.036 g, 21%) was obtained from tert-butyl 4-((2S*,4R*)-2-methyl-4-((4-(5-((4-(((2S,4R)-2-methyl-1-propionyl-1,2,3,4-tetrahydroquinolin-4-yl)amino)phenyl)amino)-5-oxopentanamide)phenyl)amino)-1-propionyl-1,2,3,4-tetrahydroquinolin-7-yl)-3,6-dihydropyridine-1(2H)-carboxylate (0.08 g, 0.09 mmol) obtained in step 1 in the same manner as in step 2 of example 1a.
ESI-MS m/z: 796.57 (M+H)$^+$; $^1$H-NMR (DMSO-d$_6$, δ): 0.98-1.05 (m, 12H), 1.10-1.19 (m, 2H), 1.83-1.87 (m, 2H), 2.22-2.29 (m, 6H), 233-2.37 (m, 1H), 2.51-2.62 (m, 6H), 2.94 (t, J=5.59 Hz, 2H), 3.37 (d, J=18.85 Hz, 2H), 4.08-4.13 (m, 2H), 4.68-4.78 (m, 2H), 5.81-5.84 (m, 2H), 6.20 (brs, 1H), 6.57-6.59 (m, 4H), 7.10 (d, J=7.89 Hz, 1H), 7.16 (d, J=3.51 Hz, 2H), 7.21-7.31 (m, 8H), 9.50 (s, 2H).

Example 12a 1-(3-(3,5-Dimethylisoxazol-4-yl)-5-hydroxybenzyl)-N-((5-(4-(((2S,4R)-2-methyl-1-propionyl-1,2,3,4-tetrahydroquinolin-4-yl)amino)phenyl)-1,3,4-oxadiazol-2-yl)methyl)piperidine-4-carboxamide (Compound 12a)

(Step 1)
tert-Butyl {[5-(4-{[(2S,4R)-2-methyl-1-propionyl-1,2,3,4-tetrahydroquinolin-4-yl]amino}phenyl)-1,3,4-oxadiazol-2-yl]methyl}carbamate (0.2 g, 0.41 mmol) obtained in step 2 of example 3c was dissolved in ethyl acetate (3 mL), then hydrogen chloride/ethyl acetate solution (4 mol/L, 2 mL, 8 mmol) was added to the solution, and the mixture was stirred at room temperature for 2 hours. The resulting solid was collected by filtration and washed with ethyl acetate to give 1-[(2S,4R)-4-({4-[5-(aminomethyl)-1,3,4-oxadiazol-2-yl]phenyl}amino)-2-methyl-3,4-dihydroquinolin-1(2H)-yl]propan-1-one hydrochloride (0.150 g, 86%).
ESIMS, (M+H)$^+$, m/z: 392.35.
(Step 2)
Compound 12a (0.021 g, 12%) was obtained from 1-[(2S,4R)-4-({4-[5-(aminomethyl)-1,3,4-oxadiazol-2-yl]phenyl}amino)-2-methyl-3,4-dihydroquinolin-1(2H)-yl]propan-1-one hydrochloride (0.113 g, 0.27 mmol) obtained in step 1 and 1-(3-(3,5-dimethylisoxazol-4-yl)-5-hydroxybenzyl)piperidine-4-carboxylic acid (0.08 g, 0.24 mmol) obtained in reference example 24 in the same manner as in step 3 of example 1b. ESI-MS, (M+H)$^+$, m/z: 704.35. $^1$H-NMR (DMSO-d$_6$, δ): 1.01-1.06 (m, 6H), 1.22-1.27 (m, 1H), 1.62-1.71 (m, 4H), 1.86-2.00 (m, 2H), 2.18-2.28 (m, 5H), 2.38 (s, 3H), 2.57-2.64 (m, 2H), 2.80-2.88 (m, 2H), 3.35-3.46 (m, 2H), 4.29-4.34 (m, 1H), 4.50 (d, J=5.80 Hz, 2H), 4.72-4.75 (m, 1H), 6.61-6.80 (m, 5H), 6.88 (d, J=7.63 Hz, 1H), 7.10 (d, J=7.63 Hz, 1H), 7.18 (td, J=7.48, 1.22 Hz, 1H), 7.26-7.33 (m, 2H), 7.67 (d, J=8.85 Hz, 1H), 8.56 (brs, 1H), 9.53 (brs, 1H).

Example 12b 1-(1-(3-(3,5-Dimethylisoxazol-4-yl)-5-hydroxybenzyl)piperidine-4-carbonyl)-N-(4-(((2S,4R)-2-methyl-1-propionyl-1,2,3,4-tetrahydroquinolin-4-yl)amino)phenyl)azetidine-3-carboxamide (Compound 12b)

Compound 12b (0.046 g, 21%) was obtained from the crude product (0.168 g) of N-(4-(((2S,4R)-2-methyl-1-propionyl-1,2,3,4-tetrahydroquinolin-4-yl)amino)phenyl)azetidine-3-carboxamide trifluoroacetate obtained in step 1 of example 10e and 1-(3-(3,5-dimethylisoxazol-4-yl)-5-hydroxybenzyppiperidine-4-carboxylic acid (0.1 g, 0.30 mmol) obtained in step 3 of reference example 24 in the same manner as in step 1 of example 1a.
ESI-MS, (M+H)$^+$, m/z: 705.39. $^1$H-NMR (DMSO-d$_6$, δ): 0.98-1.04 (m, 6H), 1.13-1.16 (m, 1H), 1.52-1.58 (m, 4H), 1.92-1.97 (m, 2H), 2.20-2.26 (m, 5H), 2.38 (s, 3H), 2.56-2.62 (m, 2H), 2.82-2.85 (m, 2H), 3.41 (s, 3H), 3.87 (dd, J=9.54, 5.62 Hz, 1H), 3.94-3.99 (m, 1H), 4.08-4.15 (m, 1H), 4.20-4.23 (m, 1H), 4.29 (t, J=8.07 Hz, 1H), 4.72-4.73 (m, 1H), 5.93 (d, J=7.83 Hz, 1H), 6.58-6.61 (m, 3H), 6.68 (s, 1H), 6.74 (s, 1H), 7.15-7.16 (m, 2H), 7.25-7.32 (m, 4H), 9.51 (brs, 1H), 9.71 (s, 1H).

Example 12c

N$^1$-(1-(3-(3,5-Dimethylisoxazol-4-yl)-5-hydroxybenzyl)piperidin-4-yl)-N$^5$-(4-(((2S,4R)-2-methyl-1-propionyl-1,2,3,4-tetrahydroquinolin-4-yl)amino)phenyl)glutaramide (Compound 12c)

Compound 12c (0.036 g, 21%) was obtained from 3-((4-aminopiperidin-1-yl)methyl)-5-(3,5-dimethylisoxazol-4-yl)phenol dihydrochloride (0.079 g, 0.24 mmol) obtained in step 2 of reference example 25 and 5-((4-(((2S,4R)-2-methyl-1-propionyl-1,2,3,4-tetrahydroquinolin-4-yl)amino)phenyl)amino)-5-oxopentanoic acid (0.1 g, 0.24 mmol) obtained in step 2 of example 6k in the same manner as in step 3 of example 1b. ESI-MS, (M+H)$^+$, m/z: 707.41. $^1$H-NMR (DMSO-d$_6$, δ): 0.98-1.04 (m, 6H), 1.13-1.15 (m, 1H), 1.35-1.38 (m, 2H), 1.69-1.78 (m, 4H), 1.99 (t, J=10.46 Hz, 2H), 2.08 (t, J=7.41 Hz, 2H), 2.18-2.23 (m, 6H), 2.38 (s, 3H), 2.53-2.63 (m, 2H), 2.73-2.80 (m, 2H), 3.40 (s, 2H), 3.49-3.58 (m, 1H), 4.06-4.14 (m, 1H), 4.67-4.77 (m, 1H), 5.85 (d, J=7.85 Hz, 1H), 6.56-6.61 (m, 3H), 6.69 (d, J=16.80 Hz, 2H), 7.16 (dd, J=4.90, 1.20 Hz, 2H), 7.23-7.30 (m, 4H), 7.72 (d, J=7.63 Hz, 1H), 9.22-9.80 (m, 2H).

Example 12d

N-(4-(((2S,4R)-2-Methyl-1-propionyl-1,2,3,4-tetrahydroquinolin-4-yl)amino)phenyl)-4-(3-(((25%4R*)-2-methyl-1-propionyl-1,2,3,4-tetrahydroquinolin-4-yl)amino)propyl)piperidine-1-carboxamide (Compound 12d)

(Step 1)
tert-Butyl 4-(3-((N-((2S*,4R*)-2-methyl-1-propionyl-1,2,3,4-tetrahydroquinolin-4-yl)-2-nitrophenyl)sulfonamide)propyl)piperidine-1-carboxylate (0.34 g, 73%) was obtained from N-((2S*,4R*)-2-methyl-1-propionyl-1,2,3,4-tetrahydroquinolin-4-yl)-2-nitrobenzenesulfonamide (0.3 g, 0.74 mmol) obtained in step 1 of example 12e and tert-butyl 4-(3-bromopropyl)piperidine-1-carboxylate (0.339 g, 1.11 mmol) in the same manner as in step 2 of example 12e.
ESIMS, (M+H)$^+$, m/z: 629.70.
(Step 2)
N-((2S*,4R*)-2-Methyl-1-propionyl-1,2,3,4-tetrahydroquinolin-4-yl)-2-nitro-N-(3-(piperidin-4-yl))propyl)benzenesulfonamide hydrochloride (0.25 g, 82%) was obtained from tert-butyl 4-(3-((N-((2S*,4R*)-2-methyl-1-propionyl-1,2,3,4-tetrahydroquinolin-4-yl)-2-nitrophenyl)sulfonamide)propyl)piperidine-1-carboxylate (0.34 g, 0.54 mmol) obtained in step 1 in the same manner as in step 2 of example 1a.
ESIMS, (M+H)$^+$, m/z: 529.36.

(Step 3)

N-((2S*,4R*)-2-Methyl-1-propionyl-1,2,3,4-tetrahydroquinolin-4-yl)-2-nitro-N-(3-(piperidin-4-yl))propyl)benzenesulfonamide hydrochloride (0.24 g, 0.42 mmol) obtained in step 2 and 1-{(2S,4R)-4-[(4-aminophenyl)amino]-2-methyl-3,4-dihydroquinolin-1(2H)-yl}propan-1-one (0.131 g, 0.42 mmol) obtained in reference example 7 were dissolved in THF (5 mL), then N,N-diisopropylethylamine (0.37 mL, 2.12 mmol) and DMAP (0.129 g, 1.06 mmol) were added to the solution, and the mixture was stirred at room temperature for 10 minutes. Triphosgene (0.083 g, 0.42 mmol) was added to the reaction mixture at 0° C., and the mixture was stirred at room temperature for 2 hours. The reaction mixture was concentrated under reduced pressure, and the obtained residue was purified by silica gel column chromatography (petroleum ether/ethyl acetate=1/1) to give a crude product (0.2 g) of 4-(3-((N-((2S*,4R*)-2-methyl-1-propionyl-1,2,3,4-tetrahydroquinolin-4-yl)-2-nitrophenyl)sulfonamide)propyl)-N-(4-(((2S,4R)-2-methyl-1-propionyl-1,2,3,4-tetrahydroquinolin-4-yl)amino)phenyl)piperidine-1-carboxamide.
ESIMS, (M+H)+, m/z: 864.39.
(Step 4)

Compound 12d (0.028 g, total yield of 2 steps 10%) was obtained from the crude product (0.2 g) of 4-(3-((N-((2S*,4R*)-2-methyl-1-propionyl-1,2,3,4-tetrahydroquinolin-4-yl)-2-nitrophenyl)sulfonamide)propyl)-N-(4-(((2S,4R)-2-methyl-1-propionyl-1,2,3,4-tetrahydroquinolin-4-yl)amino)phenyl)piperidine-1-carboxamide obtained in step 3 in the same manner as in step 5 of example 12e.
ESI-MS, (M+H)+, m/z: 679.51. $^1$H-NMR (DMSO-d$_6$, δ): 0.81-0.83 (m, 1H), 0.93-1.06 (m, 14H), 1.09-1.18 (m, 1H), 1.27-1.34 (m, 2H), 1.37-1.47 (m, 1H), 1.48-1.58 (m, 2H), 1.61-1.70 (m, 2H), 1.85-2.01 (m, 1H), 2.07-2.17 (m, 1H), 2.20-2.29 (m, 1H), 2.54-2.64 (m, 5H), 2.65-2.76 (m, 3H), 3.24-3.29 (m, 1H), 4.08-4.09 (m, 3H), 4.59-4.66 (m, 1H), 4.68-4.77 (m, 1H), 5.72 (d, J=7.63 Hz, 1H), 6.55 (d, J=8.85 Hz, 2H), 7.10 (d, J=8.85 Hz, 2H), 7.13-7.29 (m, 7H), 7.44-7.47 (m, 1H), 8.05 (s, 1H).

Example 12e 1-((2S*, 4R*)-2-Methyl-4-((2-(2-((1-(4-(((2S,4R)-2-methyl-1-propionyl-1,2,3,4-tetrahydroquinolin-4-yl)amino)phenyl)-1H-1,2,3-triazol-4-yl)methoxy)ethoxy)ethyl)amino)-3,4-dihydroquinolin-1(2H)-yl)propan-1-one (Compound 12e)

(Step 1)

1-((2S*, 4R*)-4-amino-2-methyl-3,4-dihydroquinolin-1(2H)-yl)propan-1-one (0.5 g, 2.29 mmol) obtained in step 3 of reference example 1 was dissolved in pyridine (10 mL), then 2-nitrobenzenesulfonyl chloride (0.609 g, 2.75 mmol) was added to the solution, and the mixture was stirred at room temperature for 2 hours. The reaction mixture was concentrated under reduced pressure, and the obtained residue was purified by reverse phase column chromatography (acetonitrile/0.1% formic acid aqueous solution=10/90) to give N-((2S*,4R*)-2-methyl-1-propionyl-1,2,3,4-tetrahydroquinolin-4-yl)-2-nitrobenzenesulfonamide (0.25 g, 27%).
ESIMS, (M+H)+, m/z: 404.19.
(Step 2)

N-((2S*,4R*)-2-Methyl-1-propionyl-1,2,3,4-tetrahydroquinolin-4-yl)-2-nitrobenzenesulfonamide (0.5 g, 1.24 mmol) obtained in step 1 was dissolved in DMF (5 mL), then potassium carbonate (0.513 g, 3.72 mmol) and 2-(2-bromoethoxy)ethan-1-ol (0.41 mL, 3.72 mmol) were added to the solution, and the mixture was stirred at 80° C. for 16 hours. The reaction mixture was diluted with ice water and extracted with ethyl acetate. The organic layer was dried over anhydrous sodium sulfate and concentrated under reduced pressure. The obtained residue was purified by reverse phase column chromatography (acetonitrile/0.1% formic acid aqueous solution=20/80) to give N-(2-(2-hydroxyethoxy)ethyl)-N-((2S*,4R*)-2-methyl-1-propionyl-1,2,3,4-tetrahydroquinolin-4-yl)-2-nitrobenzenesulfonamide (0.25 g, 41%).
ESIMS, (M+H)+, m/z: 492.29.
(Step 3)

N-(2-(2-Hydroxyethoxy)ethyl)-N-((2S*,4R*)-2-methyl-1-propionyl-1,2,3,4-tetrahydroquinolin-4-yl)-2-nitrobenzenesulfonamide (0.18 g, 0.37 mmol) obtained in step 2 was dissolved in 1,4-dioxane (3 mL), then propargyl bromide (0.218 g, 1.83 mmol), 40% sodium hydroxide aqueous solution (3.0 mL) and tetrabutylammonium hydrogensulfate (0.024 g, 0.07 mmol) were added to the solution at 10° C., and the mixture was stirred at room temperature for 2 hours. The reaction mixture was filtered through Celite, and the filtrate was washed with ethyl acetate. Citric acid was added to the aqueous layer, and the mixture was extracted with ethyl acetate. The organic layer was dried over anhydrous sodium sulfate and concentrated under reduced pressure. The obtained residue was purified by reverse phase column chromatography (acetonitrile/0.1% formic acid aqueous solution=20/80) to give N-((2S*,4R*)-2-methyl-1-propionyl-1,2,3,4-tetrahydroquinolin-4-yl)-2-nitro-N-(2-(2-(prop-2-yn-1-yloxy)ethoxy)ethyl)benzenesulfonamide (0.15 g, 77%).
ESIMS, (M+H)+, m/z: 530.23.
(Step 4)

A crude product (0.15 g) of N-((2S*,4R*)-2-methyl-1-propionyl-1,2,3,4-tetrahydroquinolin-4-yl)-N-(2-(2-((1-(4-(((2S,4R)-2-methyl-1-propionyl-1,2,3,4-tetrahydroquinolin-4-yl)amino)phenyl)-1H-1,2,3-triazol-4-yl)methoxy)ethoxy)ethyl)-2-nitrobenzenesulfonamide was obtained from N-((2S*,4R*)-2-methyl-1-propionyl-1,2,3,4-tetrahydroquinolin-4-yl)-2-nitro-N-(2-(2-(prop-2-yn-1-yloxy)ethoxy)ethyl)benzenesulfonamide (0.15 g, 0.28 mmol) obtained in step 3 and the crude product (0.094 g) of 1-((2S,4R)-4-((4-azidophenyl)amino)-2-methyl-3,4-dihydroquinolin-1(2H)-yl)propan-1-one obtained in step 2 of example 3a in the same manner as in step 3 of example 5j.
ESIMS, (M+H)+, m/z: 865.36.
(Step 5)

The crude product (0.15 g) of N-((2S*,4R*)-2-methyl-1-propionyl-1,2,3,4-tetrahydroquinolin-4-yl)-N-(2-(2-((1-(4-(((2S,4R)-2-methyl-1-propionyl-1,2,3,4-tetrahydroquinolin-4-yl)amino)phenyl)-1H-1,2,3-triazol-4-yl)ethoxy)ethoxy)ethyl)-2-nitrobenzenesulfonamide obtained in step 4 was dissolved in DMF (3 mL), then potassium carbonate (0.047 g, 0.35 mmol) and benzenethiol (0.022 g, 0.21 mmol) were added to the solution, and the mixture was stirred at room temperature for 3 hours. The reaction mixture was diluted with ice water and extracted with ethyl acetate. The organic layer was washed with saturated brine, dried over anhydrous sodium sulfate, and concentrated under reduced pressure. The obtained residue was purified by reverse phase HPLC (10 mmol/L ammonium bicarbonate/acetonitrile=75/25 to 30/70) to give compound 12e (0.035 g, yield of 2 steps 18%).
ESIMS, (M+H)+, m/z: 680.41. $^1$H-NMR (DMSO-d$_6$, δ): 0.45-0.66 (m, 1H), 0.91-1.07 (m, 12H), 1.18-1.26 (m, 1H), 2.05-2.15 (m, 2H), 2.20-2.30 (m, 1H), 2.48-2.49 (m, 1H), 2.57-2.64 (m, 4H), 2.79-2.80 (m, 1H), 2.86-2.88 (m, 1H), 3.54-3.64 (m, 6H), 4.21-4.32 (m, 1H), 4.60 (s, 3H), 4.71-4.80 (m, 1H), 6.50 (d, J=7.87 Hz, 1H), 6.78 (d, J=8.82 Hz, 2H), 7.14-7.21 (m, 5H), 7.26-7.33 (m, 2H), 7.42-7.44 (m, 1H), 7.53 (d, J=9.06 Hz, 2H), 8.52 (s, 1H).

Example 12f 5-(((2S*,4R*)-2-Methyl-1-propionyl-1,2,3,4-tetrahydroquinolin-4-yl)amino)-N-((1-(4-(((2S,4R)-2-methyl-1-propionyl-1,2,3,4-tetrahydroquinolin-4-yl)amino)phenyl)-1H-1,2,3-triazol-4-yl)methyl)pentanamide (Compound 12f)

(Step 1)
Methyl 5-((N-((2S*,4R*)-2-methyl-1-propionyl-1,2,3,4-tetrahydroquinolin-4-yl)-2-nitrophenyl)sulfonamide)pentanoate (0.25 g, 65%) was obtained from N-((2S*,4R*)-2-methyl-1-propionyl-1,2,3,4-tetrahydroquinolin-4-yl)-2-nitrobenzenesulfonamide (0.3 g, 0.74 mmol) obtained in step 1 of example 12e and 5-bromopentanoate (0.21 mL, 1.49 mmol) in the same manner as in step 2 of example 12e.
ESIMS, (M+H)$^+$, m/z: 518.31.
(Step 2)
5-((N-((2S*,4R*)-2-Methyl-1-propionyl-1,2,3,4-tetrahydroquinolin-4-yl)-2-nitrophenyl)sulfonamide)pentanoic acid (0.2 g, 82%) was obtained from methyl 5-((N-((2S*,4R*)-2-methyl-1-propionyl-1,2,3,4-tetrahydroquinolin-4-yl)-2-nitrophenyl)sulfonamide)pentanoate (0.25 g, 0.48 mmol) obtained in step 1 in the same manner as in step 2 of example 2f.
ESIMS, (M+H)$^+$, m/z: 504.31.
(Step 3)
5-((N-((2S*,4R*)-2-Methyl-1-propionyl-1,2,3,4-tetrahydroquinolin-4-yl)-2-nitrophenyl)sulfonamide)-N-(prop-2-yn-1-yl)pentanamide (0.18 g, 83%) was obtained from 5-((N-((2S*,4R*)-2-methyl-1-propionyl-1,2,3,4-tetrahydroquinolin-4-yl)-2-nitrophenyl)sulfonamide)pentanoic acid (0.2 g, 0.40 mmol) obtained in step 2 and propargylamine (0.03 mL, 0.60 mmol) in the same manner as in step 1 of example 1a.
ESIMS, (M+H)$^+$, m/z: 541.24.
(Step 4)
5-((N-((2S*,4R*)-2-Methyl-1-propionyl-1,2,3,4-tetrahydroquinolin-4-yl)-2-nitrophenyl)sulfonamide)-N-((1-(4-(((2S,4R)-2-methyl-1-propionyl-1,2,3,4-tetrahydroquinolin-4-yl)amino)phenyl)-1H-1,2,3-triazol-4-yl)methyl)pentanamide (0.25 g, 86%) was obtained from 5-((N-((2S*,4R*)-2-methyl-1-propionyl-1,2,3,4-tetrahydroquinolin-4-yl)-2-nitrophenyl)sulfonamide)-N-(prop-2-yn-1-yl)pentanamide (0.18 g, 0.33 mmol) obtained in step 3 and the crude product (0.111 g, 0.33 mmol) of 1-((2,4R)-4-((4-azidophenyl)amino)-2-methyl-3,4-dihydroquinolin-1(2H)-yl)propan-1-one obtained in step 2 of example 3a in the same manner as in step 3 of example 5j.
ESIMS, (M+H)$^+$, m/z: 876.45.
(Step 5)
Compound 12f (0.060 g, 30%) was obtained from 5-((N-((2S*,4R*)-2-methyl-1-propionyl-1,2,3,4-tetrahydroquinolin-4-yl)-2-nitrophenyl)sulfonamide)-N-((1-(4-(((2S,4R)-2-methyl-1-propionyl-1,2,3,4-tetrahydroquinolin-4-yl)amino)phenyl)-1H-1,2,3-triazol-4-yl)methyl)pentanamide (0.25 g, 0.30 mmol) obtained in step 4 in the same manner as in step 5 of example 12e.
ESIMS, (M+H)$^+$, m/z: 691.43. $^1$H-NMR (DMSO-d$_6$, δ): 0.79-0.81 (m, 1H), 0.92-1.06 (m, 12H), 1.20-1.22 (m, 1H), 1.44-1.52 (m, 2H), 1.57-1.63 (m, 2H), 1.82-1.89 (m, 1H), 2.09-2.17 (m, 3H), 2.21-2.29 (m, 1H), 2.48-2.49 (m, 1H), 2.56-2.65 (m, 4H), 2.66-2.74 (m, 1H), 3.25-3.29 (m, 1H), 4.23-4.27 (m, 1H), 4.35 (d, J=5.49 Hz, 2H), 4.56-4.64 (m, 1H), 4.71-4.79 (m, 1H), 6.49 (d, J=7.93 Hz, 1H), 6.77 (d, J=8.85 Hz, 2H), 7.14-7.22 (m, 5H), 7.26-7.32 (m, 2H), 7.42-7.43 (m, 1H), 7.53 (d, J=8.85 Hz, 2H), 8.30-8.32 (m, 2H).

Example 12g 9-(((2S*,4R*)-2-Methyl-1-propionyl-1,2,3,4-tetrahydroquinolin-4-yl)amino)-N-(4-(((2S,4R)-2-methyl-1-propionyl-1,2,3,4-tetrahydroquinolin-4-yl)amino)phenyl)nonanamide (Compound 12g)

(Step 1)
1-((2S*,4R*)-4-Amino-2-methyl-3,4-dihydroquinolin-1(2H)-yl)propan-1-one (0.25 g, 1.15 mmol) obtained in step 3 of reference example 1 was dissolved in DMF (4 mL), then potassium carbonate (0.316 g, 2.29 mmol) and ethyl 9-bromononanoate (0.302 g, 1.15 mmol) were added, and the mixture was stirred at 100° C. for 16 hours. The reaction mixture was diluted with water and extracted with ethyl acetate. The organic layer was dried over anhydrous sodium sulfate and concentrated under reduced pressure. The obtained residue was purified by silica gel column chromatography (petroleum ether/ethyl acetate=80/20) to give ethyl 9-(((2S*,4R*)-2-methyl-1-propionyl-1,2,3,4-tetrahydroquinolin-4-yl)amino)nonanoate (0.3 g, 65%).
ESIMS, (M+H)$^+$, m/z: 403.36.
(Step 2)
9-(((2S*,4R*)-2-Methyl-1-propionyl-1,2,3,4-tetrahydroquinolin-4-yl)amino)nonanoic acid (0.17 g, 73%) was obtained from ethyl 9-(((2S*,4R*)-2-methyl-1-propionyl-1,2,3,4-tetrahydroquinolin-4-yl)amino)nonanoate (0.25 g, 0.62 mmol) obtained in step 1 in the same manner as in step 2 of example 2f.
ESIMS, (M+H)$^+$, m/z: 375.36.
(Step 3)
Compound 12g (0.063 g, 25%) was obtained from 9-(((2S%4R*)-2-methyl-1-propionyl-1,2,3,4-tetrahydroquinolin-4-yl)amino)nonanoic acid (0.14 g, 0.37 mmol) obtained in step 2 and 1-{(2S,4R)-4-[(4-aminophenyl)amino]-2-methyl-3,4-dihydroquinolin-1(2H)-yl}propan-1-one (0.115 g, 0.37 mmol) obtained in step 3 of reference example 7 in the same manner as in step 3 of example 1b.
ESIMS, (M+H)$^+$, m/z: 666.52. $^1$H-NMR (DMSO-d$_6$, δ): 0.83-0.90 (m, 1H), 0.92-1.04 (m, 12H), 1.13-1.16 (m, 1H), 1.30-1.35 (m, 8H), 1.53-1.58 (m, 4H), 2.13-2.23 (m, 4H), 2.51-2.67 (m, 5H), 3.32-3.38 (m, 1H), 4.10-4.15 (m, 1H), 4.64-4.71 (m, 2H), 5.85 (d, J=7.87 Hz, 1H), 6.57 (d, J=8.82 Hz, 2H), 7.16 (d, J=3.81 Hz, 2H), 7.23-7.30 (m, 7H), 7.42-7.44 (m, 1H), 9.47 (s, 1H).

Example 12h 8-(((2S&, 4R*)-2-Methyl-1-propionyl-1,2,3,4-tetrahydroquinolin-4-yl)amino)-N-(4-(((2S,4R)-2-methyl-1-propionyl-1,2,3,4-tetrahydroquinolin-4-yl)amino)phenyl)octanamide (Compound 12h)

(Step 1)
1-((2S*,4R*)-4-Amino-2-methyl-3,4-dihydroquinolin-1(2H)-yl)propan-1-one (0.450 g, 2.06 mmol) obtained in step 3 of reference example 1 was dissolved in DMF (3 mL), then methyl 8-bromooctanoate (0.733 g, 3.09 mmol) and potassium carbonate (0.854 g, 6.19 mmol) were added to the solution, and the mixture was stirred at 100° C. for 16 hours.

The reaction mixture was diluted with water and extracted with ethyl acetate. The organic layer was washed with saturated brine, dried over anhydrous sodium sulfate, and concentrated under reduced pressure. The obtained residue was purified by silica gel column chromatography (petroleum ether/ethyl acetate=85/15) to give methyl 8-(((2S*,4R*)-2-methyl-1-propionyl-1,2,3,4-tetrahydroquinolin-4-yl)amino)octanoate (0.234 g, 30%).
ESIMS, (M+H)$^+$, m/z: 375.29.
(Step 2)

A crude product (0.135 g) of methyl 8-((tert-butoxycarbonyl)((2S*,4R*)-2-methyl-1-propionyl-1,2,3,4-tetrahydroquinolin-4-yl)amino)octanoate was obtained from methyl 8-(((2S*,4R*)-2-methyl-1-propionyl-1,2,3,4-tetrahydroquinolin-4-yl)amino)octanoate (0.234 g, 0.62 mmol) obtained in step 1 in the same manner as in step 1 of example 3d.
ESIMS, (M+H)$^+$, m/z: 475.34.
(Step 3)

A crude product (0.140 g) of 8-((tert-butoxycarbonyl)((2S*,4R*)-2-methyl-1-propionyl-1,2,3,4-tetrahydroquinolin-4-yl)amino)octanoic acid was obtained from the crude product (0.150 g) of methyl 8-((tert-butoxycarbonyl)((2S*,4R*)-2-methyl-1-propionyl-1,2,3,4-tetrahydroquinolin-4-yl)amino)octanoate obtained in step 2 in the same manner as in step 2 of example 2f.
ESIMS, (M+H)$^+$, m/z: 461.38.
(Step 4)

A crude product (0.150 g) of tert-butyl ((2S*,4R*)-2-methyl-1-propionyl-1,2,3,4-tetrahydroquinolin-4-yl)(8-((4-(((2S,4R)-2-methyl-1-propionyl-1,2,3,4-tetrahydroquinolin-4-yl)amino)phenyl)amino)-8-oxooctyl)carbamate was obtained from the crude product (0.150 g) of 8-((tert-butoxycarbonyl)((2S*,4R*)-2-methyl-1-propionyl-1,2,3,4-tetrahydroquinolin-4-yl)amino)octanoic acid obtained in step 3 and 1-((2S,4R)-4-((4-aminophenyl)amino)-2-methyl-3,4-dihydroquinolin-1(2H)-yl)propan-1-one (0.087 g, 0.28 mmol) obtained in reference example 7 in the same manner as in step 3 of example 1b.
ESIMS, (M+H)$^+$, m/z: 752.65.
(Step 5)

Compound 12h (0.030 g, total yield of 4 steps 8.5%) was obtained from the crude product (0.130 g) of tert-butyl ((2S*,4R*)-2-methyl-1-propionyl-1,2,3,4-tetrahydroquinolin-4-yl)(8-((4-(((2S,4R)-2-methyl-1-propionyl-1,2,3,4-tetrahydroquinolin-4-yl)amino)phenyl)amino)-8-oxooctyl)carbamate obtained in step 4 in the same manner as in step 2 of example 1a.
ESI-MS m/z: 652.52 (M+H)$^+$; $^1$H-NMR (DMSO-d$_6$, δ): 0.79-0.84 (m, 1H), 0.92-1.04 (m, 12H), 1.13-1.18 (m, 1H), 1.25-1.40 (m, 6H), 1.42-1.61 (m, 4H), 2.11-2.26 (m, 4H), 2.44-2.49 (m, 1H), 2.53-2.63 (m, 4H), 2.68-2.72 (m, 1H), 3.28 (dd, J=12.28, 3.73 Hz, 2H), 4.08-4.12 (m, 1H), 4.58-4.77 (m, 2H), 5.86 (d, J=7.89 Hz, 1H), 6.57 (d, J=8.99 Hz, 2H), 7.16 (d, J=3.95 Hz, 2H), 7.22-7.30 (m, 7H), 7.44-7.47 (m, 1H), 9.48 (s, 1H).

Example 12i 4-(((2S*,4R*)-2-Methyl-1-propionyl-1,2,3,4-tetrahydroquinolin-4-yl)amino)-N-(2-(4-(4-(((2S,4R)-2-methyl-1-propionyl-1,2,3,4-tetrahydroquinolin-4-yl)amino)phenyl)-1H-pyrazol-1-yl)ethyl)butanamide (Compound 12i)

(Step 1)

Methyl 4-(((2S*,4R*)-2-methyl-1-propionyl-1,2,3,4-tetrahydroquinolin-4-yl)amino)butanoate (273 mg, 62%) was obtained from 1-((2S*,4R*)-4-amino-2-methyl-3,4-dihydroquinolin-1(2H)-yl)propan-1-one (300 mg, 1.374 mmol) obtained in step 3 of reference example 1 and methyl 4-bromobutanoate (0.207 mL, 1.649 mmol) in the same manner as in step 1 of reference example 15.
ESIMS, (M+H)$^+$, m/z: 319.
(Step 2)

Methyl 4-((tert-butoxycarbonyl)((2S*,4R*)-2-methyl-1-propionyl-1,2,3,4-tetrahydroquinolin-4-yl)amino)butanoate (70.5 mg, 54%) was obtained from Methyl 4-(((2S*,4R*)-2-methyl-1-propionyl-1,2,3,4-tetrahydroquinolin-4-yl)amino)butanoate (100 mg, 0.314 mmol) obtained in step 1 in the same manner as in step 1 of reference example 8.
ESIMS, (M+H)$^+$, m/z: 419.
(Step 3)

Methyl 4-((tert-butoxycarbonyl)((2S*,4R*)-2-methyl-1-propionyl-1,2,3,4-tetrahydroquinolin-4-yl)amino)butanoate (180 mg, 0.430 mmol) obtained in step 2 was dissolved in THF (2 mL), then potassium trimethylsilanolate (110 mg, 0.860 mmol) was added to the solution, and the mixture was stirred at room temperature for 17.5 hours. The reaction mixture was concentrated under reduced pressure to give a crude product (263 mg) of 4-((tert-butoxycarbonyl)((2S*,4R*)-2-methyl-1-propionyl-1,2,3,4-tetrahydroquinolin-4-yl)amino)butyric acid.
ESIMS, (M+H)$^+$, m/z: 405.
(Step 4)

tert-Butyl ((2S*,4R*)-2-methyl-1-propionyl-1,2,3,4-tetrahydroquinolin-4-yl)(4-((2-(4-(4-(((2S,4R)-2-methyl-1-propionyl-1,2,3,4-tetrahydroquinolin-4-yl)amino)phenyl)-1H-pyrazol-1-yl)ethyl)amino)-4-oxobutyl)carbamate (44.5 mg, 79%) was obtained from the crude product (29.0 mg) of 4-((tert-butoxycarbonyl) ((2S*,4R*)-2-methyl-1-propionyl-1,2,3,4-tetrahydroquinolin-4-yl)amino)butyric acid obtained in step 3 and 1-((2S,4R)-4-((4-(1-(2-aminoethyl)-1H-pyrazol-4-yl)phenyl)amino)-2-methyl-3,4-dihydroquinolin-1(2H)-ylpropan-1-one (31.8 mg, 0.079 mmol) obtained in step 2 of example 6q in the same manner as in step 3 of example 1b. ESIMS, (M+H)$^+$, m/z: 790.
(Step 5)

Compound 12i (25.5 mg, 66%) was obtained from tert-butyl ((2S*,4R*)-2-methyl-1-propionyl-1,2,3,4-tetrahydroquinolin-4-yl)(4-((2-(4-(4-(((2S,4R)-2-methyl-1-propionyl-1,2,3,4-tetrahydroquinolin-4-yl)amino)phenyl)-1H-pyrazol-1-yl)ethyl)amino)-4-oxobutyl)carbamate (44.5 mg, 0.056 mmol) obtained in step 4 in the same manner as in step 2 of example 1k.
ESIMS, (M+H)$^+$, m/z: 690; $^1$H-NMR (CDCl$_3$, δ) 0.82-0.96 (m, 2H), 1.04-1.12 (m, 6H), 1.15-1.18 (m, 6H), 1.22-1.36 (m, 1H), 1.84-1.93 (m, 2H), 2.18-2.92 (m, 10H), 3.38 (dd, J=12.0, 4.0 Hz, 1H), 3.74-3.81 (m, 2H), 3.84-3.98 (m, 1H), 4.18-4.33 (m, 3H), 4.72-5.03 (m, 2H), 6.49-6.57 (m, 1H), 6.64 (d, J=8.8 Hz, 2H), 7.07-7.33 (m, 9H), 7.37-7.43 (m, 1H), 7.53 (s, 1H), 7.68 (s, 1H).

Example 12j 5-(((2S*,4R*)-2-Methyl-1-propionyl-1,2,3,4-tetrahydroquinolin-4-yl)amino)-N-((5-(4-(((2S,4R)-2-methyl-1-propionyl-1,2,3,4-tetrahydroquinolin-4-yl)amino)phenyl)-1,3,4-oxadiazol-2-yl)ethyl)pentane amide (Compound 12j)

(Step 1)

Methyl 5-(((2S*,4R*)-2-methyl-1-propionyl-1,2,3,4-tetrahydroquinolin-4-yl)amino)pentanoate (273 mg, 61%) was obtained from 1-((2S*,4R*)-4-amino-2-methyl-3,4-dihydroquinolin-1(2H)-yl)propan-1-one (300 mg, 1.374 mmol) obtained in step 3 of reference example 1 and methyl 5-bromopentanoate (0.288 mL, 2.020 mmol) in the same manner as in step 1 of example 12i.
ESIMS, (M+H)$^+$, m/z: 333.
(Step 2)
Methyl 5-((tert-butoxycarbonyl)((2S*,4R*)-2-methyl-1-propionyl-1,2,3,4-tetrahydroquinolin-4-yl)amino)pentanoate (33.4 mg, 61%) was obtained from methyl 5-(((2S*,4R*)-2-methyl-1-propionyl-1,2,3,4-tetrahydroquinolin-4-yl)amino)pentanoate (42.3 mg, 0.127 mmol) obtained in step 1 in the same manner as in step 2 of example 12i.
ESIMS, (M+H)$^+$, m/z: 433.
(Step 3)
5-((tert-Butoxycarbonyl)((2S*,4R*)-2-methyl-1-propionyl-1,2,3,4-tetrahydroquinolin-4-yl)amino)pentanoate (20.6 mg, 0.048 mmol) obtained in step 2 was dissolved in THF (0.4 mL), then potassium trimethylsilanolate (110 mg, 0.860 mmol) was added to the solution, and the mixture was stirred at room temperature for 21 hours. The reaction mixture was concentrated under reduced pressure, and the obtained residue was dissolved in DMF (0.5 mL), then N,N-diisopropylethylamine (0.042 mL, 0.240 mmol), COMU (30.8 mg, 0.072 mmol) and 1-((2S,4R)-4-((4-(5-(aminomethyl)-1,3,4-oxadiazol-2-yl)phenyl)amino)-2-methyl-3,4-dihydroquinolin-1(2H)-yl)propan-1-one (18.8 mg, 0.048 mmol) obtained in step 3 of example 5g were added to the solution, and the mixture was stirred at room temperature for 17 hours. The reaction mixture was neutralized with saturated aqueous sodium hydrogen carbonate solution, and the aqueous layer was extracted with chloroform. The organic layer was dried over anhydrous sodium sulfate and concentrated under reduced pressure. Compound 12j (9.8 mg, 30%) was obtained from the obtained residue in the same manner as in step 2 of example 1k.
ESIMS, (M+H)$^+$, m/z: 692; $^1$H-NMR (CDCl$_3$, δ) 0.99-1.45 (m, 16H), 1.76-1.92 (m, 2H), 2.18-3.04 (m, 11H), 3.42 (dd, J=12.4, 4.0 Hz, 1H), 4.22-4.43 (m, 2H), 4.73 (d, J=5.6 Hz, 2H), 4.77-5.05 (m, 2H), 6.51-6.60 (m, 1H), 6.67 (d, J=9.2 Hz, 2H), 7.06-7.13 (m, 1H), 7.16-7.35 (m, 6H), 7.39-7.47 (m, 1H), 7.84 (d, J=9.2 Hz, 2H).

Example 13a 2-(Dimethylamino)ethyl 2-((S)-2,3,9-trimethyl-4-(4-((2-((4-(((2S,4R)-2-methyl-1-propionyl-1,2,3,4-tetrahydroquinolin-4-yl)amino)phenyl)thio)ethyl)carbamoyl)phenyl)-6H-thieno[3,2-f][1,2,4]triazolo[4,3-a][1,4]diazepin-6-yl)acetate (Compound 13a)

Compound 13a (0.038 g, 26%) was obtained from 1-[(2S,4R)-4-({4-[(2-aminoethyl)thio]phenyl}amino)-2-methyl-3,4-dihydroquinolin-1(2H)-yl]propan-1-one hydrochloride (0.070 g, 0.17 mmol) obtained in step 2 of example 4f and (S)-4-(6-(2-(2-(dimethylamino)ethoxy)-2-oxoethyl)-2,3,9-trimethyl-6H-thieno[3,24][1,2,4]triazolo[4,3-a][1,4]diazepin-4-yl)benzoic acid (0.083 g, 0.17 mmol) obtained in reference example 26 in the same manner as in step 3 of example 1b.
ESIMS, (M+H)$^+$, m/z: 833.51. $^1$H-NMR (DMSO-d$_6$, δ): 0.98-1.05 (m, 6H), 1.13-1.19 (m, 1H), 1.58 (s, 3H), 2.15 (s, 6H), 2.18-2.28 (m, 1H), 2.41 (s, 3H), 2.48-2.49 (m, 2H), 2.54-2.65 (m, 5H), 2.86-2.93 (m, 2H), 3.38-3.46 (m, 4H), 4.09-4.20 (m, 3H), 4.48-4.55 (m, 1H), 4.67-4.78 (m, 1H), 6.26 (d, J=7.63 Hz, 1H), 6.63 (d, J=8.82 Hz, 2H), 7.12-7.31 (m, 6H), 7.48 (d, J=8.34 Hz, 2H), 7.84 (d, J=8.58 Hz, 2H), 8.69 (t, J=5.6 Hz, 1H).

Example 13b 2-(Dimethylamino)ethyl 2-((S)-2,3,9-trimethyl-4-(4-(3-(4-(((2S,4R)-2-methyl-1-propionyl-1,2,3,4-tetrahydroquinolin-4-yl)amino)benzamide)azetidine-1-carbonyl)phenyl)-6H-thieno[3,2-f][1,2,4]triazolo[4,3-a][1,4]diazepin-6-yl)acetate (Compound 13b)

(Step 1)
A crude product (0.070 g) of 2-(dimethylamino)ethyl (S)-2-(4-(4-(3-((tert-butoxycarbonyl)amino)azetidine-1-carbonyl)phenyl)-2,3,9-trimethyl-6H-thieno[3,2-f][1,2,4]triazolo[4,3-a][1,4]diazepin-6-yl)acetate was obtained from (S)-4-(6-(2-(2-(dimethylamino)ethoxy)-2-oxoethyl)-2,3,9-trimethyl-6H-thieno[3,2-f][1,2,4]triazolo[4,3-a][1,4]diazepin-4-yl)benzoic acid (0.1 g, 0.21 mmol) obtained in reference example 26 and tert-butyl azetidin-3-ylcarbamate hydrochloride (0.043 g, 0.21 mmol) in the same manner as in step 3 of example 1b. ESIMS, (M+H)$^+$, m/z: 636.43.
(Step 2)
A crude product (0.06 g) of 2-(dimethylamino)ethyl (S)-2-(4-(4-(3-aminoazetidine-1-carbonyl)phenyl)-2,3,9-trimethyl-6H-thieno[3,2-f][1,2,4]triazolo[4,3-a][1,4]diazepin-6-yl)acetate trifluoroacetate was obtained from the crude product (0.070 g) of 2-(dimethylamino)ethyl (S)-2-(4-(4-(3-((tert-butoxycarbonyl)amino)azetidine-1-carbonyl)phenyl)-2,3,9-trimethyl-6H-thieno[3,2-f][1,2,4]triazolo[4,3-a][1,4]diazepin-6-yl)acetate obtained in step 1 in the same manner as in step 2 of example 1k.
ESIMS, (M+H)$^+$, m/z: 536.42.
(Step 3)
Compound 13b (0.027 g, total yield of 3 steps 15%) was obtained from the crude product (0.06 g) of 2-(dimethylamino)ethyl (S)-2-(4-(4-(3-aminoazetidine-1-carbonyl)phenyl)-2,3,9-trimethyl-6H-thieno[3,2-f][1,2,4]triazolo[4,3-a][1,4]diazepin-6-yl)acetate trifluoroacetate obtained in step 2 and 4-{[(2S,4R)-2-methyl-1-propionyl-1,2,3,4-tetrahydroquinolin-4-yl]amino}benzoic acid (0.031 g, 0.09 mmol) obtained in reference example 1 in the same manner as in step 3 of example 1b. ESIMS, (M+H)$^+$, m/z: 856.3. $^1$H-NMR (DMSO-d$_6$, b): 1.00 (t, J=7.32 Hz, 3H), 1.05 (d, J=6.41 Hz, 3H), 1.20-1.24 (m, 2H), 1.61 (s, 3H), 2.14 (s, 6H), 2.15-2.30 (m, 1H), 2.42 (s, 3H), 2.56-2.64 (m, 6H), 3.36-3.51 (m, 2H), 4.03-4.11 (m, 1H), 4.13-4.21 (m, 3H), 4.24-4.35 (m, 2H), 4.47-4.53 (m, 1H), 4.54-4.61 (m, 1H), 4.67-4.81 (m, 2H), 6.62-6.67 (m, 3H), 7.08 (d, J=7.5 Hz, 1H), 7.16 (t, J=7.48 Hz, 1H), 7.25-7.32 (m, 2H), 7.50 (d, J=8.24 Hz, 2H), 7.66 (t, J=9.16 Hz, 4H), 8.59 (d, 3=6.5 Hz, 1H).

Example 13c 2-(Dimethylamino)ethyl 2-((S)-2,3,9-trimethyl-4-(4-((3-(4-(((2S,4R)-2-methyl-1-propionyl-1,2,3,4-tetrahydroquinolin-4-yl)amino)benzamide)propyl)carbamoyl)phenyl)-6H-thieno[3,2-f][1,2,4]triazolo[4,3-a][1,4]diazepin-6-yl)acetate (Compound 13c)

Compound 13c (0.035 g, 17%) was obtained from (S)-4-(6-(2-(2-(dimethylamino)ethoxy)-2-oxoethyl)-2,3,9-trimethyl-6H-thieno[3,2-f][1,2,4]triazolo[4,3-a][1,4]diazepin-4-yl)benzoic acid (0.118 g, 0.24 mmol) obtained in reference example 26 and N-(3-aminopropyl)-4-{[(2S,4R)-2-methyl- 1-propionyl-1,2,3,4-tetrahydroquinolin-4-yl] amino}benzamide hydrochloride (0.105 g, 0.24 mmol) obtained in step 2 of example 1h in the same manner as in step 3 of example 1b.
ESI-MS m/z: 858.49 (M+H)⁺; ¹H-NMR (DMSO-d₆, δ): 1.01 (t, J=7.32 Hz, 3H), 1.06 (d, J=6.41 Hz, 3H), 1.13-1.27 (m, 1H), 1.60 (s, 3H), 1.73-1.76 (m, 2H), 2.16 (s, 6H), 2.20-2.33 (m, 1H), 2.42 (s, 3H), 2.52-2.56 (m, 2H), 2.58-2.65 (m, 5H), 3.26-3.45 (m, 4H), 3.44-3.47 (m, 2H), 4.17-4.20 (m, 2H), 4.21-4.31 (m, 1H), 4.51-4.55 (m, 1H), 4.68-4.79 (m, 1H), 6.58 (d, J=7.93 Hz, 1H), 6.66 (d, J=8.85 Hz, 2H), 7.10 (d, J=7.5 Hz, 1H), 7.17 (td, J=7.32, 0.92 Hz, 1H), 7.27 (t, J=7.0 Hz, 1H), 7.31 (d, J=7.0 Hz, 1H), 7.50 (d, J=8.54 Hz, 2H), 7.64 (d, J=8.85 Hz, 2H), 7.88 (d, J=8.54 Hz, 2H), 8.11 (t, J=5.65 Hz, 1H), 8.62 (t, J=6.0 Hz, 1H).

Example 13d

4-Hydroxycyclohexyl 2-((S)-2,3,9-trimethyl-4-(4-((3-(4-(((2S,4R)-2-methyl-1-propionyl-1,2,3,4-tetrahydroquinolin-4-yl)amino)benzamide)propyl)carbamoyl)phenyl)-6H-thieno[3,2-f][1,2,4]triazolo[4,3-a][1,4]diazepin-6-yl)acetate (Compound 13d)

Compound 13d (0.027 g, 14%) was obtained from 4-((S)-6-(2-(((1r,4S)-4-hydroxycyclohexyl)oxy)-2-oxoethyl)-2,3,9-trimethyl-6H-thieno[3,2-f][1,2,4]triazolo[4,3-a][1,4]diazepin-4-yl)benzoic acid (0.115 g, 0.22 mmol) obtained in step 2 of reference example 27 and N-(3-aminopropyl)-4-{[(2S,4R)-2-methyl-1-propionyl-1,2,3,4-tetrahydroquinolin-4-yl] amino}benzamide hydrochloride (0.097 g, 0.22 mmol) obtained in step 2 of example 1h in the same manner as in step 1 of example 1a.
ESI-MS m/z: 885.53 (M+H)⁺; ¹H-NMR (DMSO-d₆, δ): 1.01 (t, J=7.4 Hz, 3H), 1.05 (d, J=6.4 Hz, 3H), 1.17-1.32 (m, 3H), 1.37-1.45 (m, 2H), 1.59 (s, 3H), 1.72-1.78 (m, 4H), 1.88-1.91 (m, 2H), 2.22-2.28 (m, 1H), 2.41 (s, 3H), 2.54-2.63 (m, 5H), 3.25-3.27 (m, 2H), 3.34-3.35 (m, 2H), 3.40 (d, J=7.23 Hz, 2H), 3.50 (dt, J=8.22, 4.22 Hz, 1H), 4.23-4.29 (m, 1H), 4.48-4.53 (m, 2H), 4.70-4.75 (m, 2H), 6.54 (d, J=7.67 Hz, 1H), 6.65 (d, J=8.77 Hz, 2H), 7.10 (d, J=7.6 Hz, 1H), 7.16 (t, J=7.0 Hz, 1H), 7.25-7.31 (m, 2H), 7.47 (d, J=8.33 Hz, 2H), 7.63 (d, J=8.77 Hz, 2H), 7.87 (d, J=8.33 Hz, 2H), 8.07 (t, J=5.59 Hz, 1H), 8.58 (t, J=6.8 Hz, 1H).

Example 13e 4-((S)-6-(2-(Ethylamino)-2-oxoethyl)-2,3,9-trimethyl-6H-thieno[3,2-f][1,2,4]triazolo[4,3-a][1,4]diazepin-4-yl)-N-(3-(4-(((2S,4R)-2-methyl-1-propionyl-1,2,3,4-tetrahydroquinolin-4-yl)amino)benzamide) propyl)benzamide (Compound 13e)

Compound 13e (0.040 g, 16%) was obtained from (S)-4-(6-(2-(ethylamino)-2-oxoethyl)-2,3,9-trimethyl-6H-thieno[3,2-f][1,2,4]triazolo[4,3-a][1,4]diazepin-4-yl)benzoic acid (0.135 g, 0.31 mmol) obtained in reference example 28 and N-(3-aminopropyl)-4-{[(2S,4R)-2-methyl-1-propionyl-1,2,3,4-tetrahydroquinolin-4-yl]amino}benzamide hydrochloride (0.133 g, 0.31 mmol) obtained in step 2 of example 1h in the same manner as in step 3 of example 1b.
ESI-MS m/z: 814.50 (M+H)⁺; ¹H-NMR (DMSO-d₆, δ): 0.99-1.09 (m, 9H), 1.17-1.25 (m, 1H), 1.59 (s, 3H), 1.74 (quintet, J=6.8 Hz, 2H), 2.22-2.28 (m, 1H), 2.45 (s, 3H), 2.54-2.67 (m, 4H), 3.07-3.29 (m, 9H), 4.25-4.29 (m, 1H), 4.50-4.54 (m, 1H), 4.72-4.75 (m, 1H), 6.54 (d, J=7.89 Hz, 1H), 6.65 (d, J=8.77 Hz, 2H), 7.10 (d, J=7.6 Hz, 1H), 7.16 (t, J=7.4 Hz, 1H), 7.24-7.31 (m, 2H), 7.48 (d, J=8.4 Hz, 2H), 7.63 (d, J=8.4 Hz, 2H), 7.87 (d, J=8.55 Hz, 2H), 8.07 (t, J=5.37 Hz, 1H), 8.18 (t, J=5.26 Hz, 1H), 8.58 (t, J=5.8 Hz, 1H).

Example 13f 4-((S)-6-(2-(4-(2-Hydroxyethyl)piperazin-1-yl)-2-oxoethyl)-2,3,9-trimethyl-6H-thieno[3,2-f][1,2,4] triazolo[4,3-a][1,4]diazepin-4-yl)-N-(3-(4-(((2S,4R)-2-methyl-1-propionyl-1,2,3,4-tetrahydroquinolin-4-yl)amino)benzamide)propyl)benzamide (Compound 13f)

Compound 13f (0.040 g, 23%) was obtained from (S)-4-(6-(2-(4-(2-hydroxyethyl)piperazin-1-yl)-2-oxoethyl)-2,3,9-trimethyl-6H-thieno[3,2-f][1,2,4]triazolo[4,3-a][1,4]diazepin-4-yl)benzoic acid (0.1 g, 0.19 mmol) obtained in step 2 of reference example 29 and N-(3-aminopropyl)-4-{[(2S,4R)-2-methyl-1-propionyl-1,2,3,4-tetrahydroquinolin-4-yl] amino}benzamide hydrochloride (0.082 g, 0.19 mmol) obtained in step 2 of example 1h in the same manner as in step 1 of example 1a.
ESI-MS m/z: 899.60 (M+H)⁺; ¹H-NMR (DMSO-d₆, δ): 1.01 (t, J=7.2 Hz, 3H), 1.05 (d, J=6.5 Hz, 3H), 1.13-1.27 (m, 1H), 1.60 (s, 3H), 1.72-1.75 (m, 2H), 2.19-2.31 (m, 1H), 2.37-2.39 (m, 2H), 2.41-2.44 (m, 5H), 2.57-2.63 (m, 5H), 3.27-3.31 (m, 6H), 3.41-3.42 (m, 2H), 3.51-3.55 (m, 3H), 3.64-3.66 (m, 3H), 4.21-4.28 (m, 1H), 4.45 (t, J=5.2 Hz, 1H), 4.59 (t, J=5.2 Hz, 1H), 4.68-4.72 (m, 1H), 6.58 (d, J=8.0 Hz, 1H), 6.65 (d, J=8.54 Hz, 2H), 7.09 (d, J=7.5 Hz, 1H), 7.16 (t, J=8.0 Hz, 1H), 7.25-7.28 (m, 1H), 7.31 (d, J=7.0 Hz, 1H), 7.50 (d, J=8.24 Hz, 2H), 7.63 (d, J=8.85 Hz, 2H), 7.87 (d, J=8.5 Hz, 2H), 8.10 (t, J=5.7 Hz, 1H), 8.61 (t, J=5.5 Hz, 1H).

Example 13g

2-Hydroxyethyl 2-((S)-2,3,9-trimethyl-4-(4-((3-(4-(((2S,4R)-2-methyl-1-propionyl-1,2,3,4-tetrahydroquinolin-4-yl)amino)benzamide)propyl)carbamoyl) phenyl)-6H-thieno[3,2-f][1,2,4]triazolo[4,3-a][1,4] diazepin-6-yl)acetate (Compound 13g)

(Step 1)
2-Methoxyethyl 2-((S)-2,3,9-trimethyl-4-(4-((3-(4-(((2S,4R)-2-methyl-1-propionyl-1,2,3,4-tetrahydroquinolin-4-yl)amino)benzamide)propyl)carbamoyl)phenyl)-6H-thieno[3,2-f][1,2,4]triazolo[4,3-a][1,4]diazepin-6-yl)acetate (0.075 g, 33%) was obtained from N-(3-aminopropyl)-4-{[(2S,4R)-2-methyl-1-propionyl-1,2,3,4-tetrahydroquinolin-4-yl] amino}benzamide hydrochloride (0.125 g, 0.27 mmol) obtained in step 2 of example 1h and (S)-4-(6-(2-(2-methoxyethoxy)-2-oxoethyl)-2,3,9-trimethyl-6H-thieno[3,2-f][1,2,4]triazolo[4,3-a][1,4]diazepin-4-yl)benzoic acid (0.114 g, 0.27 mmol) obtained in step 2 of reference example 31 in the same manner as in step 3 of example 1b.
ESI-MS m/z: 844 (M+H)⁺
(Step 2)
2-Methoxyethyl 2-((S)-2,3,9-trimethyl-4-(4-((3-(4-(((2S,4R)-2-methyl-1-propionyl-1,2,3,4-tetrahydroquinolin-4-yl)amino)benzamide)propyl)carbamoyl)phenyl)-6H-thieno[3,2-f][1,2,4]triazolo[4,3-a][1,4]diazepin-6-yl)acetate (0.19 g, 0.22 mmol) obtained in step 1 was dissolved in dichloromethane (5 mL), then boron tribromide (0.1 mL, 1.1 mmol) was added to the solution under ice cooling, and the mixture was stirred at room temperature for 1 hour. Methanol and water were sequentially added to the reaction mixture, and the mixture was extracted with dichloromethane. The organic layer was dried over anhydrous sodium sulfate and concentrated under reduced pressure. The obtained residue was purified by reverse phase HPLC (10 mmol/L aqueous ammonium bicarbonate solution/acetonitrile=65/35 to 30/70) to give compound 13g (50 mg, 27%). ESI-MS m/z: 831 (M+H)+; 1H-NMR (DMSO-d6, δ): 0.92-1.06 (m, 6H), 1.17-1.25 (m, 1H), 1.59 (s, 3H), 1.71-1.77 (m, 2H), 2.22-2.33 (m, 1H), 2.41 (s, 3H), 2.55-2.67 (m, 5H), 3.24-3.27 (m, 2H), 3.33-3.34 (m, 2H), 3.40-3.52 (m, 2H), 3.60 (q, J=5.33 Hz, 2H), 4.11 (t, J=4.8 Hz, 2H), 4.23-4.29 (m, 1H), 4.53 (dd, J=7.78, 6.47 Hz, 1H), 4.71-4.78 (m, 1H), 4.81 (t, J=5.59 Hz, 1H), 6.54 (d, J=7.67 Hz, 1H), 6.65 (d, J=8.77 Hz, 2H), 7.09 (s, 1H), 7.16 (td, J=7.29, 1.21 Hz, 1H), 7.24-7.31 (m, 2H), 7.49 (d, J=8.33 Hz, 2H), 7.63 (d, J=8.55 Hz, 2H), 7.87 (d, J=8.55 Hz, 2H), 8.07 (t, J=5.59 Hz, 1H), 8.58 (t, J=4.8 Hz, 1H).

Example 13h

3-Methoxypropyl 2-((S)-2,3,9-trimethyl-4-(4-((3-(4-(((2S,4R)-2-methyl-1-propionyl-1,2,3,4-tetrahydroquinolin-4-yl)amino)benzamide)propyl)carbamoyl)phenyl)-6H-thieno[3,2-f][1,2,4]triazolo[4,3-a][1,4]diazepin-6-yl)acetate (Compound 13h)

Compound 13h (0.045 g, 19%) was obtained from N-(3-aminopropyl)-4-{[(2S,4R)-2-methyl-1-propionyl-1,2,3,4-tetrahydroquinolin-4-yl]amino}benzamide hydrochloride (0.116 g, 0.27 mmol) obtained in step 2 of example 1 h and (S)-4-(6-(2-(3-methoxypropoxy)-2-oxoethyl)-2,3,9-trimethyl-6H-thieno[3,2-f][1,2,4]triazolo[4,3-a][1,4]diazepin-4-yl)benzoic acid (0.13 g, 0.27 mmol) obtained in reference example 30 in the same manner as in step 3 of example 1b.
ESI-MS m/z: 859 (M+H)+; 1H-NMR (DMSO-d6, δ): 1.01 (t, J=7.32 Hz, 3H), 1.05 (d, J=6.41 Hz, 3H), 1.20-1.23 (m, 1H), 1.60 (s, 3H), 1.74 (quin, J=6.87 Hz, 2H), 1.82 (quin, J=6.33 Hz, 2H), 2.22-2.27 (m, 1H), 2.41 (d, J=0.61 Hz, 3H), 2.57-2.62 (m, 5H), 3.20 (s, 3H), 3.23-3.28 (m, 4H), 3.36 (t, J=6.26 Hz, 2H), 3.39-3.52 (m, 2H), 4.11-4.18 (m, 2H), 4.24-4.28 (m, 1H), 4.52 (dd, J=7.93, 6.41 Hz, 1H), 4.69-4.79 (m, 1H), 6.57 (d, J=7.5 Hz, 1H), 6.65 (d, J=8.85 Hz, 2H), 7.09 (d, J=7.63 Hz, 1H), 7.16 (td, J=7.40, 1.07 Hz, 1H), 7.25-7.32 (m, 2H), 7.48 (d, J=8.5 Hz, 2H), 7.63 (d, J=8.85 Hz, 2H), 7.87 (d, J=8.54 Hz, 2H), 8.10 (t, J=5.65 Hz, 1H), 8.61 (t, J=5.8 Hz, 1H).

Example 13i tert-Butyl 2-((S)-2,3,9-trimethyl-4-(4-((3-((4-(((2S*,4R*)-2-methyl-1-propionyl-1,2,3,4-tetrahydroquinolin-4-yl)amino)phenyl)amino)-3-oxopropyl)carbamoyl)phenyl)-6H-thieno[3,2-f][1,2,4]triazolo[4,3-a][1,4]diazepin-6-yl)acetate (Compound 13i)

(Step 1)
A crude product (0.180 g) of tert-butyl (3-((4-(((2S*,4R*)-2-methyl-1-propionyl-1,2,3,4-tetrahydroquinolin-4-yl)amino)phenyl)amino)-3-oxopropyl)carbamate was obtained from 1-((2S*,4R*)-4-((4-aminophenyl)amino)-2-methyl-3,4-dihydroquinolin-1(2H)-yl)propan-1-one (0.100 g, 0.32 mmol) obtained in step 2 of reference example 7 and commercially available 3-((tert-butoxycarbonyl)amino)propanoic acid (0.061 g, 0.32 mmol) in the same manner as in step 3 of example 1b. ESIMS, (M+H)+, m/z: 479.

(Step 2)
3-Amino-N-(4-(((2S*,4R*)-2-methyl-1-propionyl-1,2,3,4-tetrahydroquinolin-4-yl)amino)phenyl)propanamide hydrochloride (0.180 g, total yield of 2 steps 93%) was obtained from the crude product (0.240 g) of tert-butyl (3-((4-(((2S*,4R*)-2-methyl-1-propionyl-1,2,3,4-tetrahydroquinolin-4-yl)amino)phenyl)amino)-3-oxopropyl)carbamate obtained in step 1 in the same manner as in step 2 of example 1a.
ESIMS, (M+H)+, m/z: 381.
(Step 3)
Compound 13i (0.025 g, 10%) was obtained from 3-amino-N-(4-(((2S*,4R*)-2-methyl-1-propionyl-1,2,3,4-tetrahydroquinolin-4-yl)amino)phenyl)propanamide hydrochloride (0.130 g, 0.31 mmol) obtained in step 2 and (S)-4-{6-[2-(tert-butoxy)-2-oxoethyl]-2,3,9-trimethyl-6H-thieno[3,2-f][1,2,4]triazolo[4,3-a][1,4]diazepin-4-yl}benzoic acid (0.145 g, 0.31 mmol) obtained in reference example 3 in the same manner as in step 1 of example 1a.
ESIMS, (M+H)+, m/z: 829; 1H-NMR (DMSO-d6, δ) 0.92-1.04 (m, 6H), 1.10-1.21 (m, 1H), 1.43 (s, 9H), 1.59 (s, 3H), 2.20-2.33 (m, 1H), 2.41 (s, 3H), 2.52-2.67 (m, 7H), 3.34-3.38 (m, 2H), 3.50-3.55 (m, 2H), 4.07-4.13 (m, 1H), 4.42-4.45 (m, 1H), 4.70-4.73 (m, 1H), 5.84 (d, J=7.6 Hz, 1H), 6.57 (d, J=8.8 Hz, 2H), 7.16 (d, J=3.73 Hz, 2H), 7.23-7.30 (m, 4H), 7.48 (d, J=8.33 Hz, 2H), 7.87 (d, J=8.4 Hz, 2H), 8.63-8.64 (m, 1H), 9.58 (s, 1H).

Example 13j tert-Butyl 2-((S)-2,3,9-trimethyl-4-(4-(4-(4-(((2S,4R)-2-methyl-1-propionyl-1,2,3,4-tetrahydroquinolin-4-yl)amino)benzamide)piperidine-1-carbonyl)phenyl)-6H-thieno[3,2-f][1,2,4]triazolo[4,3-a][1,4]diazepin-6-yl)acetate (Compound 13j)

(Step 1)
tert-Butyl (S)-2-(4-(4-(4-((benzyloxy)carbonyl)amino)piperidine-1-carbonyl)phenyl)-2,3,9-trimethyl-6H-thieno[3,2-f][1,2,4]triazolo[4,3-a][1,4]diazepin-6-yl)acetate (0.12 g, 69%) was obtained from (S)-4-(6-(2-(tert-butoxy)-2-oxoethyl)-2,3,9-trimethyl-6H-thieno[3,2-f][1,2,4]triazolo[4,3-a][1,4]diazepin-4-yl)benzoic acid (0.12 g, 0.257 mmol) obtained in reference example 3 and commercially available benzylpiperidin-4-ylcarbamate hydrochloride (0.07 g, 0.25 mmol) in the same manner as in step 3 of example 1b.
ESIMS, (M+H)+, m/z: 683.
(Step 2)
tert-Butyl (S)-2-(4-(4-(4-((benzyloxy)carbonyl)amino)piperidine-1-carbonyl)phenyl)-2,3,9-trimethyl-6H-thieno[3,2-f][1,2,4]triazolo[4,3-a][1,4]diazepin-6-yl)acetate (0.12 g, 0.17 mmol) obtained in step 1 was dissolved in methanol (5 mL), then 20% palladium hydroxide (0.06 g) was added to the solution, and the mixture was stirred at room temperature for 16 hours under a hydrogen atmosphere. The reaction mixture was filtered through Celite, and the filtrate was concentrated under reduced pressure to give tert-butyl (S)-2-(4-(4-(4-aminopiperidine-1-carbonyl)phenyl)-2,3,9-trimethyl-6H-thieno[3,2-f][1,2,4]triazolo[4,3-a][1,4]diazepin-6-yl)acetate (0.09 g, 94%).
ESIMS, (M+H)+, m/z: 549.
(Step 3)
Compound 13j (0.033 g, 14%) was obtained from tert-butyl (S)-2-(4-(4-(4-aminopiperidine-1-carbonyl)phenyl)-2,3,9-trimethyl-6H-thieno[3,2-f][1,2,4]triazolo[4,3-a][1,4]diazepin-6-yl)acetate (0.046 g, 0.136 mmol) obtained in step 2 and 4-{[(2S,4R)-2-methyl-1-propionyl-1,2,3,4-tetrahydroquinolin-4-yl]amino}benzoic acid (0.075 g, 0.136 mmol) obtained in step 7 of reference example 1 in the same manner as in step 3 of example 1b.
ESIMS, (M+H)⁺, m/z: 869: ¹H-NMR (DMSO-d₆, δ) 0.95 (t, J=7.48 Hz, 3H), 1.03 (d, J=7.0 Hz, 2H), 1.17-1.24 (m, 2H), 1.43 (s, 9H), 1.49-1.53 (m, 1H), 1.66-1.70 (m, 4H), 1.86 (m, 1H), 2.22-2.27 (m, 1H), 2.43 (s, 3H), 2.56-2.63 (m, 5H), 2.93 (m, 1H), 3.12-3.16 (m, 1H), 3.38-3.40 (m, 2H), 3.48 (m, 1H), 4.01 (m, 1H), 4.21-4.32 (m, 1H), 4.42-4.46 (m, 2H), 4.73-4.74 (m, 1H), 4.73-4.75 (m, 1H), 6.57 (d, J=7.93 Hz, 1H), 6.64 (d, J=8.85 Hz, 2H), 7.08 (d, J=7.63 Hz, 1H), 7.16 (t, J=7.48 Hz, 1H), 7.25-7.32 (m, 2H), 7.41 (d, J=8.54 Hz, 2H), 7.50 (d, J=8.0 Hz, 2H), 7.63 (d, J=8.85 Hz, 2H), 7.85 (d, J=7.63 Hz, 1H)

Example 14a 2-(4-(4-(((2S,4R)-2-Methyl-1-propionyl-1,2,3,4-tetrahydroquinolin-4-yl)amino)phenyl)-1H-pyrazol-1-yl)-N-(4-(2,3,9-trimethyl-6H-thieno[3,2-f][1,2,4]triazolo[4,3-a][1,4]diazepin-4-yl)phenyl)acetamide (Compound 14a)

Compound 14a (0.029 g, 10%) was obtained from 4-(2,3,9-trimethyl-6H-thieno[3,2-f][1,2,4]triazolo[4,3-a][1,4]diazepin-4-yl)aniline (0.123 g, 0.38 mmol) obtained in reference example 22 and ethyl 2-(4-(4-(((2S,4R)-2-methyl-1-propionyl-1,2,3,4-tetrahydroquinolin-4-yl)amino)phenyl)-1H-pyrazol-1-yl)acetate (0.170 g, 0.38 mmol) obtained in step 1 of example 6n in the same manner as in step 2 of example 6b.
ESI-MS m/z: 724.43 (M+H)⁺: ¹H-NMR (DMSO-d₆, δ): 0.99-1.06 (m, 6H), 1.13-1.24 (m, 1H), 1.63 (s, 3H), 2.18-2.31 (m, 1H), 2.40 (s, 3H), 2.54-2.64 (m, 5H), 4.09-4.19 (m, 2H), 4.68-4.80 (m, ¹H), 5.00 (s, 2H), 5.20 (d, J=12.8 Hz, 1H), 6.04 (d, J=7.67 Hz, 1H), 6.66 (d, J=8.55 Hz, 2H), 7.17-7.20 (m, 2H), 7.22-7.35 (m, 4H), 7.43 (d, J=8.55 Hz, 2H), 7.64 (d, J=8.99 Hz, 2H), 7.72 (s, 1H), 7.95 (s, 1H), 10.51 (s, 1H).

Example 14b

N-(2-(4-(4-(((2S,4R)-2-Methyl-1-propionyl-1,2,3,4-tetrahydroquinolin-4-yl)amino)phenyl)-1H-pyrazol-1-yl)ethyl)-4-(2,3,9-trimethyl-6H-thieno[3,2-f][1,2,4]triazolo[4,3-a][1,4]diazepin-4-yl)benzamide (Compound 14b)

Compound 14b (0.031 g, 20%) was obtained from 1-((2S,4R)-4-((4-(1-(2-aminoethyl)-1H-pyrazol-4-yl)phenyl)amino)-2-methyl-3,4-dihydroquinolin-1(2H)-yl)propan-1-one hydrochloride (0.112 g, 0.25 mmol) obtained in step 1 of example 10d and 4-(2,3,9-trimethyl-6H-thieno[3,2-f][1,2,4]triazolo[4,3-a][1,4]diazepin-4-yl)benzoic acid (0.075 g, 0.21 mmol) obtained in reference example 4 in the same manner as in step 1 of example 1a.
ESI-MS m/z: 738.43 (M+H)⁺: ¹H-NMR (DMSO-d₆, δ): 0.98-1.05 (m, 6H), 1.13-1.21 (m, 1H), 1.56 (s, 3H), 2.19-2.28 (m, 1H), 2.38 (s, 3H), 2.54-2.67 (m, 5H), 3.66 (q, J=5.85 Hz, 2H), 4.12-4.18 (m, 2H), 4.27 (t, J=6.25 Hz, 2H), 4.66-4.81 (m, 1H), 5.28 (d, J=12.50 Hz, 1H), 6.03 (d, J=7.67 Hz, 1H), 6.62 (d, J=8.77 Hz, 2H), 7.16 (d, J=3.73 Hz, 2H), 7.25-7.31 (m, 4H), 7.52 (d, J=8.11 Hz, 2H), 7.70 (s, 1H), 7.84 (d, J=8.33 Hz, 2H), 7.91 (s, 1H), 8.71 (t, J=5.6 Hz, 1H).
[1307]

Example 14c

N-(4-(((1R,4r)-4-(((2S*,4R*)-2-Methyl-1-propionyl-1,2,3,4-tetrahydroquinolin-4-yl)amino)cyclohexyl)amino)-4-oxobut-2-yn-1-yl)-4-(2,3,9-trimethyl-6H-thieno[3,2-f][1,2,4]triazolo[4,3-a][1,4]diazepin-4-yl)benzamide (Compound 14c)

(Step 1)
A crude product (0.048 g) of tert-butyl (4-(((1R,4R)-4-(((2S*,4R*)-2-methyl-1-propionyl-1,2,3,4-tetrahydroquinolin-4-yl)amino))cyclohexyl)amino)-4-oxobut-2-yn-1-yl)carbamate was obtained from 1-((2S*,4R*)-4-(((1r,4R)-4-aminocyclohexyl)amino)-2-methyl-3,4-dihydroquinolin-1(2H)-yl)propan-1-one dihydrochloride (0.02 g, 0.051 mmol) obtained in reference example 10 in the same manner as in step 1 of example 9d. ESIMS, (M+H)⁺, m/z: 497.
(Step 2)
A crude product (34 mg) of 4-amino-N-((1R,4r)-4-(((2S*,4R*)-2-methyl-1-propionyl-1,2,3,4-tetrahydroquinolin-4-yl)amino)cyclohexyl)but-2-ynamide trifluoroacetate was obtained from the crude product (0.048 g) of tert-butyl (4-(((1R,4r)-4-(((2S*,4R*)-2-methyl-1-propionyl-1,2,3,4-tetrahydroquinolin-4-yl)amino))cyclohexyl)amino)-4-oxobut-2-yn-1-yl)carbamate obtained in step 1 in the same manner as in step 2 of example 1k.
ESIMS, (M+H)⁺, m/z: 397.
(Step 3)
Compound 14c (25 mg, total yield of 3 steps 66%) was obtained from the crude product (34 mg) of 4-amino-N-((1R,4r)-4-(((2S*,4R*)-2-methyl-1-propionyl-1,2,3,4-tetrahydroquinolin-4-yl)amino)cyclohexyl)but-2-ynamide trifluoroacetate obtained in step 2 and 4-(2,3-dimethyl-6H-thieno[3,2-f][1,2,4]triazolo[4,3-a][1,4]diazepin-4-yl)benzoic acid (24 mg, 0.071 mmol) obtained in reference example 4 in the same manner as in step 3 of example 1b.
ESI-MS m/z: 731 (M+H)+: ¹H-NMR (CDCl₃, δ): 1.05-1.15 (m, 6H), 1.19-1.41 (m, 3H), 1.60 (s, 3H), 1.91-2.11 (m, 7H), 2.21-2.33 (m, 1H), 2.42 (s, 3H), 2.46-2.64 (m, 2H), 2.64-2.74 (m, 4H), 3.52-3.62 (m, 1H), 3.66-3.81 (m, 1H), 4.13 (d, J=12.6 Hz, 1H), 4.26-4.33 (m, 2H), 4.77-4.95 (m, 1H), 5.52 (d, J=12.6 Hz, 1H), 6.52-6.63 (m, 1H), 7.09-7.13 (m, 1H), 7.21-7.35 (m, 2H), 7.44-7.54 (m, 3H), 7.75-7.84 (m, 3H).

Example 14d

N-(4-(((2S,4R)-2-Methyl-1-propionyl-1,2,3,4-tetrahydroquinolin-4-yl)amino)phenyl)-2-(2-oxo-2-((4-(2,3,9-trimethyl-6H-thieno[3,2-f][1,2,4]triazolo[4,3-a][1,4]diazepin-4-yl)phenyl)amino)ethoxy)acetamide (Compound 14d)

(Step 1)
Methyl 2-(2-((4-(((2S,4R)-2-methyl-1-propionyl-1,2,3,4-tetrahydroquinolin-4-yl)amino)phenyl)amino)-2-oxyethoxy)acetate (0.130 g, 46%) was obtained from 1-{(2S,4R)-4-[(4-aminophenyl)amino]-2-methyl-3,4-dihydroquinolin-1(2H)-yl}propan-1-one (0.2 g, 0.65 mmol) obtained in reference example 7 and 2-(2-methoxy-2-oxyethoxy)acetic acid (0.143 g, 0.97 mmol) in the same manner as in step 3 of example 1b.
ESIMS, (M+H)⁺, m/z: 440.25.
(Step 2)
Compound 14d (0.025 g, 11%) was obtained from 4-(2,3,9-trimethyl-6H-thieno[3,2-f][1,2,4]triazolo[4,3-a][1,4]diazepin-4-yl)aniline (0.095 g, 0.29 mmol) obtained in reference example 22 and methyl 2-(2-((4-(((2S,4R)-2-methyl- 1-propionyl-1,2,3,4-tetrahydroquinolin-4-yl)amino)phenyl) amino)-2-oxyethoxy)acetate (0.13 g, 0.29 mmol) obtained in step 1 in the same manner as in step 2 of example 6b.
ESI-MS m/z: 731.45 (M+H)$^+$: $^1$H-NMR (DMSO-d$_6$, δ): 0.99-1.05 (m, 6H), 1.12-1.19 (m, 1H), 1.63 (s, 3H), 2.21-2.26 (m, 1H), 2.40 (s, 3H), 2.55-2.62 (m, 5H), 4.10-4.15 (m, 2H), 4.20 (s, 2H), 4.25 (s, 2H), 4.68-4.78 (m, 1H), 5.22 (d, J=13.0 Hz, 1H), 5.96 (d, J=8.0 Hz, 1H), 6.62 (d, J=9.0 Hz, 2H), 7.16-7.18 (m, 2H), 7.24-7.30 (m, 1H), 7.35 (d, J=9.0 Hz, 2H), 7.43 (d, J=8.5 Hz, 2H), 7.71 (d, J=9.0 Hz, 2H), 9.72 (s, 1H), 10.33 (s, 1H).

Example 14e

N-(4-Oxo-4-((4-(2,3,9-trimethyl-6H-thieno[3,2-f][1,2,4]triazolo[4,3-a][1,4]diazepin-4-yl)phenyl)amino)but-2-yn-1-yl)-4-(2,3,9-trimethyl-6H-thieno[3,2-f][1,2,4]triazolo[4,3-a][1,4]diazepin-4-yl)benzamide (Compound 14e)

(Step 1)
tert-Butyl (4-oxo-4-((4-(2,3,9-trimethyl-6H-thieno[3,2-f][1,2,4]triazolo[4,3-a][1,4]diazepin-4-yl)phenyl)amino)but-2-yn-1-yl)carbamate (0.06 g, 25%) was obtained from 4-(2,3,9-trimethyl-6H-thieno[3,2-f][1,2,4]triazolo[4,3-a][1,4]diazepin-4-yl)aniline (0.150 g, 0.46 mmol) obtained in reference example 22 and 4-((tert-butoxycarbonyl)amino)but-2-ynoic acid (0.097 g, 0.49 mmol) in the same manner as in step 1 of example 1a.
ESI-MS (M+H)$^+$: 505.29
(Step 2)
A crude product (0.05 g) of 4-amino-N-(4-(2,3,9-trimethyl-6H-thieno[3,2-f][1,2,4]triazolo[4,3-a][1,4]diazepin-4-yl)phenyl)but-2-ynamide trifluoroacetate was obtained from tert-butyl (4-oxo-4-((4-(2,3,9-trimethyl-6H-thieno[3,2-f][1,2,4]triazolo[4,3-a][1,4]diazepin-4-yl)phenyl)amino)but-2-yn-1-yl)carbamate (0.05 g, 0.1 mmol) obtained in step 1 in the same manner as in step 2 of example 1k.
ESI-MS (M+H)$^+$: 405.22
(Step 3)
Compound 14e (0.033 g, 40%) was obtained from the crude product (0.120 g) of 4-amino-N-(4-(2,3,9-trimethyl-6H-thieno[3,2-f][1,2,4]triazolo[4,3-a][1,4]diazepin-4-yl)phenyl)but-2-ynamide trifluoroacetate obtained in step 2 and 4-(2,3,9-trimethyl-6H-thieno[3,2-f][1,2,4]triazolo[4,3-a][1,4]diazepin-4-yl)benzoic acid (0.04 g, 0.11 mmol) obtained in reference example 4 in the same manner as in step 3 of example 1b.
ESI-MS m/z: 739.63 (M+H)$^+$: $^1$H-NMR (DMSO-d$_6$, δ): 1.58 (s, 3H), 1.62 (s, 3H), 2.40 (s, 6H), 2.59 (s, 3H), 2.61 (s, 3H), 4.09-4.20 (m, 2H), 4.32 (d, J=5.6 Hz, 2H), 5.19-5.30 (m, 2H), 7.42 (d, J=8.58 Hz, 2H), 7.56 (d, J=8.4 Hz, 2H), 7.63 (d, J=8.8 Hz, 2H), 7.91 (d, J=8.4 Hz, 2H), 9.20 (t, J=5.4 Hz, 1H), 10.92 (s, 1H).

Example 14f

N-(4-(((2S,4R)-2-Methyl-1-propionyl-1,2,3,4-tetrahydroquinolin-4-yl)amino)phenyl)-2-(3-(4-(2,3,9-trimethyl-6H-thieno[3,2-f][1,2,4]triazolo[4,3-a][1,4]diazepin-4-yl)phenyl)ureido)acetamide (Compound 14f)

(Step 1)
Ethyl glycinate hydrochloride (0.086 g, 0.62 mmol) and triphosgene (0.073 g, 0.25 mmol) were dissolved in dichloromethane (5 mL), then triethylamine (0.34 mL, 2.47 mmol) was added to the solution at −10° C., and the mixture was stirred at −10° C. for 1 hour. 4-(2,3,9-trimethyl-6H-thieno[3,2-f][1,2,4]triazolo[4,3-a][1,4]diazepin-4-yl)aniline (0.2 g, 0.62 mmol) obtained in reference example 22 was added to the reaction mixture at −10° C., and the mixture was stirred at room temperature for 48 hours. Ice water was added to the reaction mixture, and the mixture was extracted twice with dichloromethane. The organic layer was washed with saturated brine, dried over anhydrous sodium sulfate, and concentrated under reduced pressure. The obtained residue was purified by reverse phase column chromatography (acetonitrile/0.1% formic acid aqueous solution=1/1) to give ethyl ((4-(2,3,9-trimethyl-6H-thieno[3,2-f][1,2,4]triazolo[4,3-a][1,4]diazepin-4-yl))phenyl)carbamoyl)glycinate (0.1 g, 36%).
ESIMS, (M+H)$^+$, m/z: 453.27.
(Step 2)
((4-(2,3,9-Trimethyl-6H-thieno[3,2-f][1,2,4]triazolo[4,3-a][1,4]diazepin-4-yl)phenyl)carbamoyl)glycine (0.080 g, 86%) was obtained from ethyl ((4-(2,3,9-trimethyl-6H-thieno[3,2-f][1,2,4]triazolo[4,3-a][1,4]diazepin-4-yl))phenyl)carbamoyl)glycinate (0.1 g, 0.22 mmol) obtained in step 1 in the same manner as in step 2 of example 2f.
ESIMS, (M+H)$^+$, m/z: 425.31
(Step 3)
((4-(2,3,9-Trimethyl-6H-thieno[3,2-f][1,2,4]triazolo[4,3-a][1,4]diazepin-4-yl)phenyl)carbamoyl)glycine (0.08 g, 0.19 mmol) obtained in step 2 and 1-{(2S,4R)-4-[(4-aminophenyl)amino]-2-methyl-3,4-dihydroquinolin-1(2H)-yl}propan-1-one (0.047 g, 0.15 mmol) obtained in reference example 7 were dissolved in DMF (2 mL), then DMAP (7 mg, 0.057 mmol) was added to the solution, and the mixture was stirred at room temperature for 5 minutes. DCC (0.054 g, 0.26 mmol) was added to the reaction mixture, and the mixture was stirred at room temperature for 16 hours. Ice water was added to the reaction mixture, then the resulting solid was collected by filtration, and dried under reduced pressure. The obtained solid was purified by reverse phase HPLC (10 mmol/L aqueous ammonium bicarbonate solution/acetonitrile=60/40 to 10/90) to give compound 14f (0.030 g, 22%).
ESI-MS m/z: 716.39 (M+H)$^+$: $^1$H-NMR (DMSO-d$_6$, δ): 1.00 (t, J=7.4 Hz, 3H), 1.03 (d, J=6.0 Hz, 3H), 1.11-1.19 (m, 1H), 1.66 (s, 3H), 2.20-2.26 (m, 1H), 2.40 (s, 3H), 2.53-2.63 (m, 5H), 3.88 (d, J=5.26 Hz, 2H), 4.06-4.15 (m, 2H), 4.70-4.76 (m, 1H), 5.18 (d, J=12.72 Hz, 1H), 5.88 (d, J=7.89 Hz, 1H), 6.51 (t, J=5.26 Hz, 1H), 6.60 (d, J=8.77 Hz, 2H), 7.16 (d, J=3.51 Hz, 2H), 7.23-7.35 (m, 6H), 7.42-7.45 (m, 2H), 9.10 (s, 1H), 9.65 (s, 1H).

Example 14g 4-(((2S,4R)-2-Methyl-1-propionyl-1,2,3,4-tetrahydroquinolin-4-yl)amino)-N-(4-oxo-4-((4-(2,3,9-trimethyl-6H-thieno[3,2-f][1,2,4]triazolo[4,3-a][1,4]diazepin-4-yl)phenyl)amino)but-2-yn-1-yl)benzamide (Compound 14g)

Compound 14g (0.016 g, 25%) was obtained from the crude product (0.05 g) of 4-amino-N-(4-(2,3,9-trimethyl-6H-thieno[3,2-f][1,2,4]triazolo[4,3-a][1,4]diazepin-4-yl)phenyl)but-2-ynamide trifluoroacetate obtained in step 2 of example 14e and 4-{[(2S,4R)-2-methyl-1-propionyl-1,2,3,4-tetrahydroquinolin-4-yl]amino}benzoic acid (0.03 g, 0.09 mmol) obtained in reference example 1 in the same manner as in step 3 of example 1b.

ESI-MS m/z: 725.36 (M+H)+: $^1$H-NMR (DMSO-d$_6$, δ): 1.01 (t, J=7.32 Hz, 3H), 1.05 (d, J=6.41 Hz, 3H), 1.21-1.25 (m, 1H), 1.62 (s, 3H), 2.22-2.27 (m, 1H), 2.39 (s, 3H), 2.58-2.64 (m, 5H), 4.10 (d, J=12.51 Hz, 1H), 4.25-4.32 (m, 3H), 4.73-4.75 (m, 1H), 5.21 (d, J=12.82 Hz, 1H), 6.66-6.69 (m, 3H), 7.09 (d, J=7.63 Hz, 1H), 7.17 (t, J=7.5 Hz, 1H), 7.26-7.32 (m, 2H), 7.41 (d, J=8.54 Hz, 2H), 7.62 (d, J=8.5 Hz, 2H), 7.67 (d, J=8.85 Hz, 2H), 8.63 (t, J=5.5 Hz, 1H), 10.90 (s, 1H)

Example 14h 2-(3-(4-(((2S,4R)-2-Methyl-1-propionyl-1,2,3,4-tetrahydroquinolin-4-yl)amino)phenyl)ureido)-N-(4-(2,3,9-trimethyl-6H-thieno[3,2-f][1,2,4]triazolo[4,3-a][1,4]diazepin-4-yl)phenyl)acetamide (Compound 14h)

(Step 1)

1-{(2S,4R)-4-[(4-Aminophenyl)amino]-2-methyl-3,4-dihydroquinolin-1(2H)-yl}propan-1-one (0.1 g, 0.32 mmol) obtained in reference example 7 and ethyl glycinate hydrochloride (0.058 g, 0.42 mmol) were dissolved in THF (5 mL), then N,N-diisopropylethylamine (0.28 mL, 1.61 mmol) and DMAP (0.209 g, 1.71 mmol) were added to the solution at 0° C., and the mixture was stirred at 0° C. for 5 minutes. Triphosgene (0.048 g, 0.16 mmol) was added to the reaction mixture at 0° C., the mixture was stirred at 0° C. for 0.5 hour, and then stirred under reflux for 16 hours. Ice water was added to the reaction mixture, and the mixture was extracted twice with ethyl acetate. The organic layer was washed with saturated brine, dried over anhydrous sodium sulfate, and concentrated under reduced pressure. The obtained residue was purified by reverse phase column chromatography (acetonitrile/0.1% formic acid aqueous solution=40/60 to 50/50) to give ethyl ((4-(((2S,4R)-2-methyl-1-propionyl-1,2,3,4-tetrahydroquinolin-4-yl)amino)phenyl)carbamoyl)glycinate (0.065 g, 46%).
ESIMS, (M+H)+, m/z: 439.24.

(Step 2)

((4-(((2S,4R)-2-Methyl-1-propionyl-1,2,3,4-tetrahydroquinolin-4-yl)amino)phenyl)carbamoyl)glycine (0.050 g, 83%) was obtained from ethyl ((4-(((2S,4R)-2-methyl-1-propionyl-1,2,3,4-tetrahydroquinolin-4-yl)amino)phenyl)carbamoyl)glycinate (0.065 g, 0.15 mmol) obtained in step 1 in the same manner as in step 2 of example 2f.
ESIMS, (M+H)+, m/z: 411.23

(Step 3)

((4-(((2S,4R)-2-Methyl-1-propionyl-1,2,3,4-tetrahydroquinolin-4-yl)amino)phenyl)carbamoyl)glycine (0.05 g, 0.12 mmol) obtained in step 2 and 4-(2,3,9-trimethyl-6H-thieno[3,2-f][1,2,4]triazolo[4,3-a][1,4]diazepin-4-yl)aniline (0.039 g, 0.12 mmol) obtained in reference example 22 were dissolved in dichloromethane (2 mL), then DMAP (0.004 g, 0.04) and DCC (0.035 g, 0.17 mmol) were added to the solution, and the mixture was stirred at room temperature for 16 hours. Ice water was added to the reaction mixture, and the mixture was extracted twice with dichloromethane. The organic layer was washed with saturated brine, dried over anhydrous sodium sulfate, and concentrated under reduced pressure. The obtained residue was purified by reverse phase HPLC (10 mmol/L aqueous ammonium bicarbonate solution/acetonitrile=70/30 to 10/90) to give compound 14h (0.015 g, 17%).
ESI-MS m/z: 716.43 (M+H)+: $^1$H-NMR (DMSO-d$_6$, δ): 0.98-1.04 (m, 6H), 1.13-1.15 (m, 1H), 1.63 (s, 3H), 2.22-2.26 (m, 1H), 2.40 (s, 3H), 2.54-2.59 (m, 5H), 3.90 (d, J=5.48 Hz, 2H), 4.09-4.12 (m, 2H), 4.66-4.75 (m, 1H), 5.20 (d, J=12.50 Hz, 1H), 5.70 (d, J=7.6 Hz, 1H), 6.23 (t, J=5.6 Hz, 1H), 6.56 (d, J=6.8 Hz, 2H), 7.10 (d, J=8.77 Hz, 2H), 7.16-7.19 (m, 2H), 7.23-7.29 (m, 2H), 7.41 (d, J=8.55 Hz, 2H), 7.63 (d, J=8.99 Hz, 2H), 8.31 (s, 1H), 10.17 (s, 1H).

Example 14i

N-(4-((4-(((2S,4R)-2-Methyl-1-propionyl-1,2,3,4-tetrahydroquinolin-4-yl)amino)phenyl)amino)-4-oxobut-2-yn-1-yl)-4-(2,3,9-trimethyl-6H-thieno[3,2-f][1,2,4]triazolo[4,3-a][1,4]diazepin-4-yl)benzamide (Compound 14i)

(Step 1)

tert-Butyl (4-((4-(((2S,4R)-2-methyl-1-propionyl-1,2,3,4-tetrahydroquinolin-4-yl)amino)phenyl)amino)-4-oxobut-2-yn-1-yl)carbamate (0.180 g, 76%) was obtained from 1-{(2S,4R)-4-[(4-aminophenyl)amino]-2-methyl-3,4-dihydroquinolin-1(2H)-yl}propan-1-one (0.150 g, 0.48 mmol) obtained in reference example 7 and 4-((tert-butoxycarbonyl)amino)but-2-ynoic acid (0.097 g, 0.48 mmol) in the same manner as in step 1 of example 1a.
ESIMS, (M+H)+, m/z: 491.29.

(Step 2)

4-Amino-N-(4-(((2S,4R)-2-methyl-1-propionyl-1,2,3,4-tetrahydroquinolin-4-yl)amino)phenyl)but-2-ynamide trifluoroacetate (0.180 g, 97%) was obtained from tert-butyl (4-((4-(((2S,4R)-2-methyl-1-propionyl-1,2,3,4-tetrahydroquinolin-4-yl)amino)phenyl)amino)-4-oxobut-2-yn-1-yl)carbamate (0.180 g, 0.37 mmol) obtained in step 1 in the same manner as in step 2 of example 1k.
ESIMS, (M+H)+, m/z: 391.22.

(Step 3)

Compound 14i (0.035 g, 16%) was obtained from 4-amino-N-(4-(((2S,4R)-2-methyl-1-propionyl-1,2,3,4-tetrahydroquinolin-4-yl)amino)phenyl)but-2-ynamide trifluoroacetate (0.150 g, 0.30 mmol) obtained in step 2 and 4-(2,3,9-trimethyl-6H-thieno[3,2-f][1,2,4]triazolo[4,3-a][1,4]diazepin-4-yl)benzoic acid (0.094 g, 0.27 mmol) obtained in reference example 4 in the same manner as in step 3 of example 1b.
ESI-MS m/z: 725.43 (M+H)+: $^1$H-NMR (DMSO-d$_6$, δ): 0.99 (t, J=7.2 Hz, 3H), 1.03 (d, J=6.5 Hz, 3H), 1.14-1.16 (m, 1H), 1.58 (s, 3H), 2.22-2.25 (m, 1H), 2.40 (s, 3H), 2.54-2.61 (m, 2H), 2.63 (s, 3H), 4.09-4.12 (m, 1H), 4.18 (d, J=12.82 Hz, 1H), 4.29 (d, J=5.49 Hz, 2H), 4.67-4.77 (m, 1H), 5.29 (d, J=12.51 Hz, 1H), 6.01 (d, J=7.63 Hz, 1H), 6.58 (d, J=8.85 Hz, 2H), 7.12-7.17 (m, 2H), 7.23-7.31 (m, 4H), 7.56 (d, J=8.24 Hz, 2H), 7.92 (d, J=8.54 Hz, 2H), 9.18 (t, J=5.49 Hz, 1H), 10.33 (s, 1H).

Example 14j 4-(((2S,4R)-2-Methyl-1-propionyl-1,2,3,4-tetrahydroquinolin-4-yl)amino)-N-((5-(4-(2,3,9-trimethyl-6H-thieno[3,2-f][1,2,4]triazolo[4,3-a][1,4]diazepin-4-yl)phenyl)thiophen-2-yl)methyl)benzamide (Compound 14j)

(Step 1)

4-(4-Bromophenyl)-2,3,9-trimethyl-6H-thieno[3,2-f][1,2,4]triazolo[4,3-a][1,4]diazepine (0.150 g, 0.39 mmol) obtained in step 3 of reference example 4 was dissolved in a mixed solvent (5 mL) of 1,4-dioxane and water (4:1), then (5-(((tert-butoxycarbonyl)amino)methyl)thiophen-2-yl)boronic acid (0.109 g, 0.43 mmol), cesium carbonate (0.379 g, 1.16 mmol) and Pd(PPh$_3$)$_4$ (0.045 g, 0.04 mmol) were added to the solution, and the mixture was stirred at 120° C. for 1 hour under an argon atmosphere under microwave irradiation. The reaction mixture was diluted with ice water and extracted with ethyl acetate. The organic layer was washed with water and saturated brine, dried over anhydrous sodium sulfate, and concentrated under reduced pressure. The obtained residue was washed with diethyl ether to give a crude product (0.160 g) of tert-butyl ((5-(4-(2,3,9-trimethyl-6H-thieno[3,2-f][1,2,4]triazolo[4,3-a][1,4]diazepin-4-yl)phenyl)thiophen-2-yl)methyl)carbamate.

ESIMS, (M+H)$^+$, m/z: 520.25.

(Step 2)

A crude product (0.160 g) of (5-(4-(2,3,9-trimethyl-6H-thieno[3,2-f][1,2,4]triazolo[4,3-a][1,4]diazepin-4-yl)phenyl)thiophen-2-yl)methanamine hydrochloride was obtained from the crude product (0.160 g) of tert-butyl ((5-(4-(2,3,9-trimethyl-6H-thieno[3,2-f][1,2,4]triazolo[4,3-a][1,4]diazepin-4-yl)phenyl)thiophen-2-yl)methyl)carbamate obtained in step 1 in the same manner as in step 2 of example 1a.

ESIMS, (M+H)$^+$, m/z: 420.82

(Step 3)

Compound 14j (0.055 g, total yield of 3 steps 19%) was obtained from the crude product (0.144 g) of (5-(4-(2,3,9-trimethyl-6H-thieno[3,2-f][1,2,4]triazolo[4,3-a][1,4]diazepin-4-yl)phenyl)thiophen-2-yl)methanamine hydrochloride obtained in step 2 and 4-{[(2S,4R)-2-methyl-1-propionyl-1,2,3,4-tetrahydroquinolin-4-yl]amino}benzoic acid (0.107 g, 0.32 mmol) obtained in reference example 1 in the same manner as in step 3 of example 1b.

ESI-MS m/z: 740.36 (M+H)$^+$; $^1$H-NMR (DMSO-d$_6$, δ): 1.01 (t, J=7.2 Hz, 3H), 1.05 (d, J=6.4 Hz, 3H), 1.17-1.25 (m, 1H), 1.65 (s, 3H), 2.21-2.27 (m, 1H), 2.40 (s, 3H), 2.54-2.67 (m, 5H), 4.13 (d, J=12.50 Hz, 1H), 4.25-4.31 (m, 1H), 4.58 (d, J=5.70 Hz, 2H), 4.71-4.77 (m, 1H), 5.25 (d, J=12.50 Hz, 1H), 6.59 (d, J=7.89 Hz, 1H), 6.66 (d, J=8.77 Hz, 2H), 7.01 (d, J=3.51 Hz, 1H), 7.09 (d, J=7.6 Hz, 1H), 7.16 (td, J=7.34, 1.32 Hz, 1H), 7.24-7.31 (m, 2H), 7.41-7.47 (m, 3H), 7.66 (dd, J=16.99, 8.66 Hz, 4H), 8.73 (t, J=6.0 Hz, 1H).

Example 14k 4-(((2S,4R)-2-Methyl-1-propionyl-1,2,3,4-tetrahydroquinolin-4-yl)amino)-N-(1-(4-(2,3,9-trimethyl-6H-thieno[3,2-f][1,2,4]triazolo[4,3-a][1,4]diazepin-4-yl)benzoyl)azetidin-3-yl)benzamide (compound 14k)

Compound 14k (0.050 g, 20%) was obtained from 1-[(2S,4R)-4-{[4-(3-aminoazetidine-1-carbonyl)phenyl]amino}-2-methyl-3,4-dihydroquinolin-1(2H)-yl]propan-1-one trifluoroacetate (0.180 g, 0.35 mmol) obtained in step 2 of example in and 4-(2,3,9-trimethyl-6H-thieno[3,2-f][1,2,4]triazolo[4,3-a][1,4]diazepin-4-yl)benzoic acid (0.125 g, 0.35 mmol) obtained in step 4 of reference example 4 in the same manner as in step 1 of example 1a.

ESIMS, (M+H)$^+$, m/z: 727; $^1$H-NMR (DMSO-d$_6$, δ): 0.98-1.06 (m, 6H), 1.19-1.23 (m, 1H), 1.60 (s, 3H), 2.23-2.25 (m, 1H), 2.40 (s, 3H), 2.54-2.67 (m, 5H), 4.04-4.07 (m, 1H), 4.16-4.20 (m, 2H), 4.28-4.34 (m, 2H), 4.57 (q, J=8.48 Hz, 1H), 4.69-4.74 (m, 2H), 5.28 (d, J=12.72 Hz, 1H), 6.63-6.67 (m, 3H), 7.08 (d, J=7.58 Hz, 1H), 7.16 (t, J=7.34 Hz, 1H), 7.25-7.32 (m, 2H), 7.54 (d, J=8.31 Hz, 2H), 7.66 (t, J=8.44 Hz, 4H), 8.61 (d, J=6.85 Hz, 1H).

Example 14l 4-(((2S,4R)-2-Methyl-1-propionyl-1,2,3,4-tetrahydroquinolin-4-yl)amino)-N-(2-oxo-3-(4-(2,3,9-trimethyl-6H-thieno[3,2-f][1,2,4]triazolo[4,3-a][1,4]diazepin-4-yl)benzamide)propyl)benzamide (compound 14l)

(Step 1)

N-(2-Hydroxy-3-(4-(((2S,4R)-2-methyl-1-propionyl-1,2,3,4-tetrahydroquinolin-4-yl)amino)benzamide)propyl)-4-(2,3,9-trimethyl-6H-thieno[3,2-f][1,2,4]triazolo[4,3-a][1,4]diazepin-4-yl)benzamide (0.150 g, 59%) was obtained from the crude product (0.152 g) of N-(3-amino-2-hydroxypropyl)-4-(((2S,4R)-2-methyl-1-propionyl-1,2,3,4-tetrahydroquinolin-4-yl)amino)benzamide hydrochloride obtained in step 2 of example 7r and 4-(2,3,9-trimethyl-6H-thieno[3,2-f][1,2,4]triazolo[4,3-a][1,4]diazepin-4-yl)benzoic acid (0.120 g, 0.34 mmol) obtained in reference example 3 in the same manner as in step 3 of example 1b.

ESIMS, (M+H)$^+$, m/z: 745.

(Step 2)

Compound 14l (0.040 g, 26%) was obtained from N-(2-hydroxy-3-(4-(((2S,4R)-2-methyl-1-propionyl-1,2,3,4-tetrahydroquinolin-4-yl)amino)benzamide)propyl)-4-(2,3,9-trimethyl-6H-thieno[3,2-f][1,2,4]triazolo[4,3-a][1,4]diazepin-4-yl)benzamide (0.150 g, 0.20 mmol) obtained in step 1 in the same manner as in step 4 of example 7r.

ESIMS, (M+H)$^+$, m/z: 743; $^1$H-NMR (DMSO-d$_6$, δ) 0.99-1.06 (m, 6H), 1.21-1.26 (m, 1H), 1.59 (s, 3H), 2.22-2.33 (m, 1H), 2.40 (s, 3H), 2.55-2.67 (m, 5H), 4.12 (d, J=5.70 Hz, 2H), 4.16-4.20 (m, 3H), 4.27-4.30 (m, 1H), 4.70-4.78 (m, 1H), 5.29 (d, J=8.4 Hz, 1H), 6.62 (d, J=7.67 Hz, 1H), 6.68 (d, J=8.77 Hz, 2H), 7.10 (d, J=7.6 Hz, 1H), 7.17 (td, J=7.34, 1.32 Hz, 1H), 7.25-7.32 (m, 2H), 7.55 (d, J=8.33 Hz, 2H), 7.67 (d, J=8.77 Hz, 2H), 7.90 (d, J=8.55 Hz, 2H), 8.43 (t, J=5.59 Hz, 1H), 8.88 (t, J=5.59 Hz, 1H).

Example 14m 4-(((2S,4R)-2-Methyl-1-propionyl-1,2,3,4-tetrahydroquinolin-4-yl)amino)-N-(3-oxo-3-((4-(2,3,9-trimethyl-6H-thieno[3,2-f][1,2,4]triazolo[4,3-a][1,4]diazepin-4-yl)phenyl)amino)propyl)benzamide (Compound 14m)

(Step 1)

tert-Butyl (3-oxo-3-((4-(2,3,9-trimethyl-6H-thieno[3,2-f][1,2,4]triazolo[4,3-a][1,4]diazepin-4-yl)phenyl)amino)propyl)carbamate (0.11 g, 72%) was obtained from 4-(2,3,9-trimethyl-6H-thieno[3,2-f][1,2,4]triazolo[4,3-a][1,4]diazepin-4-yl)aniline obtained in reference example 22 and commercially available 3-((tert-butoxycarbonyl)amino)propanoic acid (0.058 g, 0.30 mmol) in the same manner as in step 3 of example 1b.

ESIMS, (M+H)$^+$, m/z: 495.

(Step 2)

3-Amino-N-(4-(2,3,9-trimethyl-6H-thieno[3,2-f][1,2,4]triazolo[4,3-a][1,4]diazepin-4-yl)phenyl)propanamide hydrochloride (0.09 g, 95%) was obtained from tert-butyl (3-oxo-3-((4-(2,3,9-trimethyl-6H-thieno[3,2-f][1,2,4]triazolo[4,3-a][1,4]diazepin-4-yl)phenyl)amino)propyl)carbamate (0.11 g, 0.22 mmol) obtained in step 1 in the same manner as in step 2 of example 1a.

ESIMS, (M−(HCl)+H)$^+$, m/z: 395.

(Step 3)

Compound 14m (0.055 g, 37%) was obtained from 3-amino-N-(4-(2,3,9-trimethyl-6H-thieno[3,2-f][1,2,4]triazolo[4,3-a][1,4]diazepin-4-yl)phenyl)propanamide hydrochloride (0.09 g, 0.20 mmol) obtained in step 2 and 1-{(2S,4R)-4-[(4-aminophenyl)amino]-2-methyl-3,4-dihydroquinolin-1(2H)-yl}propan-1-one (0.07 g, 0.20 mmol) obtained in step 7 of reference example 1 based on the manner in step 3 of example 1b. ESIMS, (M+H)$^+$, m/z: 715; $^1$H-NMR (DMSO-d$_6$, δ) 0.99-1.05 (m, 6H), 1.16-1.25 (m, 1H), 1.63 (s, 3H), 2.21-2.29 (m, 1H), 2.40 (m, 3H), 2.60-2.70 (m, 7H), 3.48-3.52 (m, 2H), 4.09 (d, J=12.8 Hz, 1H), 4.23-4.29 (m, 1H), 4.71-4.76 (m, 1H), 5.20 (d, J=12.4 Hz, 1H), 6.54 (d, J=8.0 Hz, 1H), 6.64 (d, J=8.8 Hz, 2H), 7.09 (d, J=7.2 Hz, 1H), 7.16 (t, J=7.6 Hz, 1H), 7.24-7.31 (m, 2H), 7.39 (d, J=8.4 Hz, 2H), 7.63 (dd, J=8.55, 6.80 Hz, 4H), 8.14 (t, J=5.4 Hz, 1H), 10.14 (brs, 1H).

Example 14n

N-((1-(4-(((2S,4R)-2-Methyl-1-propionyl-1,2,3,4-tetrahydroquinolin-4-yl)amino)phenyl)-1H-1,2,3-triazol-4-yl)ethyl)-4-(2,3,9-trimethyl-6H-thieno[3,2-f][1,2,4]triazolo[4,3-a][1,4]diazepin-4-yl)benzamide (Compound 14n)

(Step 1)

N-(Prop-2-yn-1-yl)-4-(2,3,9-trimethyl-6H-thieno[3,2-f][1,2,4]triazolo[4,3-a][1,4]diazepin-4-yl)benzamide (0.1 g, 90%) was obtained from 4-(2,3,9-trimethyl-6H-thieno[3,2-f][1,2,4]triazolo[4,3-a][1,4]diazepin-4-yl)benzoic acid (0.1 g, 0.28 mmol) obtained in step 4 of reference example 4 and commercially available prop-2-yn-1-amine (0.019 mL, 0.31 mmol) in the same manner as in step 1 of example 1a. ESIMS, (M+H)$^+$, m/z: 390.

(Step 2)

Compound 14n (0.038 g, 19%) was obtained from N-(prop-2-yn-1-yl)-4-(2,3,9-trimethyl-6H-thieno[3,2-f][1,2,4]triazolo[4,3-a][1,4]diazepin-4-yl)benzamide (0.1 g, 0.25 mmol) obtained in step 1 and the crude product (0.086 g) of 1-{(2S,4R)-4-[(4-azidophenyl)amino]-2-methyl-3,4-dihydroquinolin-1(2H)-yl}propan-1-one obtained in step 2 of example 3a in the same manner as in step 3 of example 3a. ESIMS, (M+H)$^+$, m/z: 725; $^1$H-NMR (DMSO-d$_6$, δ): 0.99-1.06 (m, 6H), 1.08-1.25 (m, 1H), 1.57 (s, 3H), 2.22-2.27 (m, 1H), 2.39 (s, 3H), 2.64-2.67 (m, 5H), 4.17 (d, J=12.5 Hz, 1H), 4.22-4.28 (m, 1H), 4.57 (d, J=5.2 Hz, 2H), 4.72-4.78 (m, 1H), 5.28 (d, J=12.4 Hz, 1H), 6.47 (d, J=7.6 Hz, 1H), 6.78 (d, J=8.8 Hz, 2H), 7.14-7.20 (m, 2H), 7.25-7.32 (m, 2H), 7.52-7.56 (m, 4H), 7.92 (d, J=8.4 Hz, 2H), 8.41 (s, 1H), 9.11 (t, J=5.6 Hz, 1H).

Example 14o

N,N'-(2-Oxopropane-1,3-diyl)bis(4-(2,3,9-trimethyl-6H-thieno[3,2-f][1,2,4]triazolo[4,3-a][1,4]diazepin-4-yl)benzamide) (Compound 14o)

(Step 1)

4-(2,3,9-Trimethyl-6H-thieno[3,2-f][1,2,4]triazolo[4,3-a][1,4]diazepin-4-yl)benzoic acid (0.2 g, 0.56 mmol) obtained in step 4 of reference example 4 was dissolved in DMF (5 mL), then benzotriazol-1-yloxy)tripyrrolidinophosphonium hexafluorophosphate (PyBOP) (0.88 g, 1.70 mmol) and N,N-diisopropylethylamine (0.50 mL, 2.84 mmol) were added to the solution, and the mixture was stirred at room temperature for 15 minutes. Commercially available 1,3-diaminopropan-2-ol (0.025 g, 0.28 mmol) was added to the reaction mixture, and the mixture was stirred at room temperature for 2 hours. The reaction mixture was concentrated under reduced pressure, and the obtained residue was purified by reverse phase HPLC (water/acetonitrile=7/3) to give N,N'-(2-hydroxypropane-1,3-diyl)bis(4-(2,3,9-trimethyl-6H-thieno[3,2-f][1,2,4]triazolo[4,3-a][1,4]diazepin-4-yl)benzamide) (0.12 g, 28%).
ESIMS, (M+H)$^+$, m/z: 759.

(Step 2)

Compound 14o (0.1 g, 9%) was obtained from N,N'-(2-hydroxypropane-1,3-diyl)bis(4-(2,3,9-trimethyl-6H-thieno[3,2-f][1,2,4]triazolo[4,3-a][1,4]diazepin-4-yl)benzamide) (0.12 g, 0.15 mmol) obtained in step 1 in the same manner as in step 4 of example 7r.
ESIMS, (M+H)$^+$, m/z: 725; $^1$H-NMR (DMSO-d$_6$, δ): 1.58 (s, 6H), 2.40 (s, 6H), 2.61 (m, 6H), 4.17-4.23 (m, 6H), 5.29 (d, J=13.0 Hz, 2H), 7.56 (cl, J=8.5 Hz, 4H), 7.90 (d, J=8.54 Hz, 4H), 8.94 (t, J=5.80 Hz, 2H).

Example 14p tert-Butyl (S)-2-(2,3,9-trimethyl-4-(4-((1-(4-(2,3,9-trimethyl-6H-thieno[3,2-f][1,2,4]triazolo[4,3-a][1,4]diazepin-4-yl)benzoyl)piperidin-4-yl)carbamoyl)phenyl)-6H-thieno[3,2-f][1,2,4]triazolo[4,3-a][1,4]diazepin-6-yl)acetate (Compound 14p)

(Step 1)

A crude product (0.14 g) of tert-butyl 1-(4-(2,3,9-trimethyl-6H-thieno[3,2-f][1,2,4]triazolo[4,3-a][1,4]diazepin-4-yl)benzoyl)piperidin-4-ylcarbamate was obtained from 4-(2,3,9-trimethyl-6H-thieno[3,2-f][1,2,4]triazolo[4,3-a][1,4]diazepin-4-yl)benzoic acid (0.1 g, 0.28 mmol) obtained in step 4 of reference example 4 and commercially available tert-butyl piperidin-4-ylcarbamate (0.059 g, 0.29 mmol) in the same manner as in step 3 of example 1b.
ESIMS, (M+H)$^+$, m/z: 535.

(Step 2)

A crude product (0.12 g) of (4-aminopiperidin-1-yl)(4-(2,3,9-trimethyl-6H-thieno[3,2-f][1,2,4]triazolo[4,3-a][1,4]diazepin-4-yl)phenyl)methanone hydrochloride was obtained from the crude product (0.14 g) of tert-butyl 1-(4-(2,3,9-trimethyl-6H-thieno[3,2-f][1,2,4]triazolo[4,3-a][1,4]diazepin-4-yl)benzoyl)piperidin-4-ylcarbamate obtained in step 1 in the same manner as in step 2 of example 1a.
ESIMS, (M+H)$^+$, m/z: 435.

(Step 3)

Compound 14p (0.043 g, total yield of 3 steps 26%) was obtained from the crude product (0.12 g, 0.25 mmol) of (4-aminopiperidin-1-yl)(4-(2,3,9-trimethyl-6H-thieno[3,2-f][1,2,4]triazolo[4,3-a][1,4]diazepin-4-yl)phenyl)methanone hydrochloride obtained in step 2 and (S)-4-{6-[2-(tert-butoxy)-2-oxoethyl]-2,3,9-trimethyl-6H-thieno[3,2-f][1,2,4]triazolo[4,3-a][1,4]diazepin-4-yl}benzoic acid (0.118 g, 0.25 mmol) obtained in reference example 3 in the same manner as in step 3 of example 1b.
ESIMS, (M+H)$^+$, m/z: 883; $^1$H-NMR (DMSO-d$_6$, δ): 1.44-1.64 (m, 17H), 1.77-1.90 (m, 2H), 2.40 (s, 3H), 2.41 (s, 3H), 2.61 (s, 3H), 2.63 (s, 3H), 2.96-3.18 (m, 2H), 3.32-3.39 (m, 2H), 3.51 (s, $^1$H), 4.08 (brs, 1H), 4.18 (d, J=12.72 Hz, 1H), 4.43 (t, J=7.23 Hz, 2H), 5.27 (d, J=12.72 Hz, 1H), 7.41 (d, J=8.33 Hz, 2H), 7.48 (d, J=8.33 Hz, 2H), 7.54 (d, J=8.11 Hz, 2H), 7.87 (d, J=8.33 Hz, 2H), 8.38 (d, J=7.45 Hz, 1H).

Example 14q 4-(((2S,4R)-2-Methyl-1-propionyl-1,2,3,4-tetrahydroquinolin-4-yl)amino)-N-((1-(4-(2,3,9-trimethyl-6H-thieno[3,2-f][1,2,4]triazolo[4,3-a][1,4]diazepin-4-yl)phenyl)-1H-1,2,3-triazol-4-yl)ethyl)benzamide (Compound 14q)

(Step 1)

A crude product (0.5 g) of 4-(4-azidophenyl)-2,3,9-trimethyl-6H-thieno[3,2-f][1,2,4]triazolo[4,3-a][1,4]diazepine was obtained from 4-(2,3,9-trimethyl-6H-thieno[3,2-f][1,2,4]triazolo[4,3-a][1,4]diazepin-4-yl)aniline (0.3 g, 0.92 mmol) obtained in reference example 22 in the same manner as in step 2 of example 3a.

(Step 2)

Compound 14q (0.035 g, total yield of 2 steps 6%) was obtained from the crude product (0.418 g) of 4-(4-azidophenyl)-2,3,9-trimethyl-6H-thieno[3,2-f][1,2,4]triazolo[4,3-a][1,4]diazepine obtained in step 1 and 4-(((2S,4R)-2-methyl-1-propionyl-1,2,3,4-tetrahydroquinolin-4-yl)amino)-N-(prop-2-yn-1-yl)benzamide (0.3 g, 0.8 mmol) obtained in step 2 of example 15h in the same manner as in step 3 of example 3a.

ESIMS, (M+H)$^+$, m/z: 725: $^1$H-NMR (DMSO-$d_6$, δ) 0.99-1.06 (m, 6H), 1.64 (s, 3H), 2.22-2.27 (m, 1H), 2.41 (s, 3H), 2.55-2.64 (m, 5H), 2.94 (s, 1H), 4.18 (d, J=12.4 Hz, 1H), 4.22-4.31 (m, 1H), 4.56 (d, J=5.2 Hz, 2H), 4.65-4.80 (m, 1H), 5.28 (d, J=12.4 Hz, 1H), 6.58 (d, J=7.89 Hz, 1H), 6.66 (d, J=8.77 Hz, 2H), 7.09 (d, J=7.67 Hz, 1H), 7.16 (t, J=7.4 Hz, 1H), 7.25-7.31 (m, 2H), 7.66 (dd, J=18.96, 8.66 Hz, 4H), 7.98 (d, J=8.77 Hz, 2H), 8.62 (t, J=5.26 Hz, 1H), 8.68 (s, 1H).

Example 14r 1-((2S,4R)-2-Methyl-4-((4-(7-(4-(2,3,9-trimethyl-6H-thieno[3,2-f][1,2,4]triazolo[4,3-a][1,4]diazepin-4-yl)benzoyl)-5,6,7,8-tetrahydroimidazo[1,2-a]pyrazin-2-yl)phenyl)amino)-3,4-dihydroquinolin-1(2H)-yl)propan-1-one (Compound 14r)

Compound 14r (0.03 g, 13%) was obtained from 1-((2S,4R)-2-methyl-4-{[4-(5,6,7,8-tetrahydroimidazo[1,2-a]pyrazin-2-yl)phenyl]amino}-3,4-dihydroquinolin-1(2H)-yl)propan-1-one hydrochloride (0.14 g, 0.309 mmol) obtained in step 3 of example 3f and 4-(2,3,9-trimethyl-6H-thieno[3,2-f][1,2,4]triazolo[4,3-a][1,4]diazepin-4-yl)benzoic acid (0.23 g, 0.30 mmol) obtained in reference example 4 in the same manner, as in step 3 of example 1b.

ESIMS, (M+H)$^+$, m/z: 750. $^1$H-NMR (DMSO-$d_6$, δ): 0.99-1.05 (m, 6H), 1.13-1.22 (m, 1H), 1.65 (s, 3H), 2.22-2.27 (m, 1H), 2.41 (s, 3H), 2.61 (s, 6H), 3.70 (s, 1H), 4.03 (s, 2H), 4.17-4.21 (m, 2H), 4.55-4.85 (m, 3H), 5.29 (d, J=12.72 Hz, 1H), 6.00 (d, J=7.6 Hz, 1H), 6.62 (d, J=7.89 Hz, 2H), 7.17-7.18 (m, 2H), 7.24-7.31 (m, 3H), 7.44 (s, 2H), 7.50-7.58 (m, 4H).

Example 14s

N-(2-((4-(((2S,4R)-2-Methyl-1-propionyl-1,2,3,4-tetrahydroquinolin-4-yl)amino)phenyl)thio)ethyl)-4-(2,3,9-trimethyl-6H-thieno[3,2-f][1,2,4]triazolo[4,3-a][1,4]diazepin-4-yl)benzamide (Compound 14s)

(Step 1)

1-{(2S,4R)-4-[(4-Bromophenyl)amino]-2-methyl-3,4-dihydroquinolin-1(2H)-yl}propan-1-one (0.1 g, 0.26 mmol) obtained in reference example 2 was dissolved in 1,4-dioxane (6 mL), then xantphos (0.062 g, 0.107 mmol), N,N-diisopropylethylamine (0.14 mL, 0.806 mmol), Pd$_2$(dba)$_3$ (0.05 g, 0.053 mmol) and tert-butyl (2-mercaptoethyl)carbamate (0.137 mL, 0.80 mmol) were added to the solution, and the mixture was stirred at 90° C. for 90 minutes. The reaction mixture was filtered through Celite, and the filtrate was concentrated under reduced pressure. The obtained residue was purified by silica gel column chromatography (methanol/dichloromethane=1/9) to give a crude product (0.18 g) of tert-butyl (2-((4-(((2S,4R)-2-methyl-1-propionyl-1,2,3,4-tetrahydroquinolin-4-yl)amino)phenyl)thio)ethyl)carbamate.

ESIMS, (M+H)$^+$, m/z: 470.

(Step 2)

A crude product (0.16 g) of 1-((2S,4R)-4-((4-((2-aminoethyl)thio)phenyl)amino)-2-methyl-3,4-dihydroquinolin-1(2H)-yl)propan-1-one hydrochloride was obtained from the crude product (0.18 g) of tert-butyl (2-((4-(((2S,4R)-2-methyl-1-propionyl-1,2,3,4-tetrahydroquinolin-4-yl)amino)phenyl)thio)ethyl)carbamate obtained in step 1 in the same manner as in step 2 of example 1a.

ESIMS, (M–HCl+H)$^+$, m/z: 370.

(Step 3)

Compound 13s (0.03 g, 16%) was obtained from the crude product (0.12 g, 0.29 mmol) of 1-((2S,4R)-4-((4-((2-aminoethyl)thio)phenyl)amino)-2-methyl-3,4-dihydroquinolin-1(2H)-yl)propan-1-one hydrochloride obtained in step 2 and 4-(2,3,9-trimethyl-6H-thieno[3,2-f][1,2,4]triazolo[4,3-a][1,4]diazepin-4-yl)benzoic acid (0.105 g, 0.29 mmol) obtained in reference example 4 in the same manner as in step 3 of example 1b.

ESIMS (M+H)$^+$, m/z: 704: $^1$H-NMR (DMSO-$d_6$, δ): 0.98-1.05 (m, 6H), 1.16-1.19 (m, 1H), 1.57 (m, 3H), 2.20-2.26 (m, 1H), 2.39 (s, 3H), 2.55-2.63 (m, 5H), 2.90 (t, J=7.2 Hz, 2H), 3.39 (q, J=6.0 Hz, 2H), 4.17 (d, J=12.8 Hz, 2H), 4.73 (d, J=8.4 Hz, 1H), 5.28 (d, J=12.4 Hz, 1H), 6.23 (d, J=7.6 Hz, 1H), 6.63 (d, J=8.4 Hz, 2H), 7.13-7.19 (m, 2H), 7.22-7.30 (m, 4H), 7.52 (d, J=8.4 Hz, 2H), 7.83 (d, J=8.4 Hz, 2H), 8.65 (t, J=5.6 Hz, 1H).

Example 14t

N$^1$-(4-(((2S*,4R*)-2-Methyl-1-propionyl-1,2,3,4-tetrahydroquinolin-4-yl)amino)phenyl)-N$^5$-(4-(2,3,9-trimethyl-6H-thieno[3,2-f][1,2,4]triazolo[4,3-a][1,4]diazepin-4-yl)phenyl)glutaramide (Compound 14t)

Compound 14t (0.04 g, 15%) was obtained from 5-[(4-{[(2S*,4R*)-2-methyl-1-propionyl-1,2,3,4-tetrahydroquinolin-4-yl]amino}phenyl)amino]-5-oxopentanoic acid (0.15 g, 0.35 mmol) obtained in step 2 of example 4a and 4-(2,3,9-trimethyl-6H-thieno[3,2-f][1,2,4]triazolo[4,3-a][1,4]diazepin-4-yl)aniline (0.114 g, 0.35 mmol) obtained in reference example 22 in the same manner as in step 1 of example 1a.

ESIMS, (M+H)$^+$, m/z: 729: $^1$H-NMR (DMSO-$d_6$, δ): 0.98-1.04 (m, 6H), 1.10-1.16 (m, 1H), 1.63 (s, 3H), 1.86-1.89 (m,

2H), 2.20-2.33 (m, 3H), 2.36-2.40 (m, 5H), 2.53-2.61 (m, 5H), 4.09 (dd, J=12.06, 3.95 Hz, 2H), 4.66-4.79 (m, 1H), 5.20 (d, J=11.4 Hz, 1H), 5.83 (d, J=8.0 Hz, 1H), 6.58 (d, J=9.2 Hz, 2H), 7.16 (d, J=3.2 Hz, 2H), 7.23-7.30 (m, 4H), 7.39 (d, J=8.4 Hz, 2H), 7.64 (d, J=8.8 Hz, 2H), 9.51 (s, 1H), 10.09 (s, 1H).

Example 15a 2-(Dimethylamino)ethyl 1-(4-(5-((4-(((2S,4R)-2-methyl-1-propionyl-1,2,3,4-tetrahydroquinolin-4-yl)amino)phenyl)amino)-5-oxopentanamide)benzyl)-4-oxo-4,5,6,7-tetrahydro-1H-indole-2-carboxylate (Compound 15a)

(Step 1)
A crude product (2.0 g) of methyl 1-(4-((tert-butoxycarbonyl)amino)benzyl)-4-oxo-4,5,6,7-tetrahydro-1H-indole-2-carboxylate was obtained from methyl 4-oxo-4,5,6,7-tetrahydro-1H-indole-2-carboxylate (1.80 g, 9.33 mmol) obtained in step 2 of reference example 32 and tert-butyl (4-(bromomethyl)phenyl)carbamate (2.66 g, 9.33 mmol) in the same manner as in step 3 of reference example 32.
ESIMS, (M+H)$^+$, m/z: 399.26.
(Step 2)
A crude product (1.5 g) of 1-(4-((tert-butoxycarbonyl)amino)benzyl)-4-oxo-4,5,6,7-tetrahydro-1H-indole-2-carboxylic acid was obtained from the crude product (2.0 g) of methyl 1-(4-((tert-butoxycarbonyl)amino)benzyl)-4-oxo-4,5,6,7-tetrahydro-1H-indole-2-carboxylate obtained in step 1 in the same manner as in step 2 of example 2f.
ESIMS, (M+H)$^+$, m/z: 385.26.
(Step 3)
A crude product (1.1 g) of 2-(dimethylamino)ethyl 1-(4-((tert-butoxycarbonyl)amino)benzyl)-4-oxo-4,5,6,7-tetrahydro-1H-indole-2-carboxylate was obtained from the crude product (1.5 g) of 1-(4-((tert-butoxycarbonyl)amino)benzyl)-4-oxo-4,5,6,7-tetrahydro-1H-indole-2-carboxylic acid obtained in step 2 in the same manner as in step 5 of reference example 32.
ESIMS, (M+H)$^+$, m/z: 456.37.
(Step 4)
A crude product (0.8 g) of 2-(dimethylamino)ethyl 1-(4-aminobenzyl)-4-oxo-4,5,6,7-tetrahydro-1H-indole-2-carboxylate hydrochloride was obtained from the crude product (1.1 g) of 2-(dimethylamino)ethyl 1-(4-((tert-butoxycarbonyl)amino)benzyl)-4-oxo-4,5,6,7-tetrahydro-1H-indole-2-carboxylate obtained in step 3 in the same manner as in step 2 of example 1a.
ESIMS, (M+H)$^+$, m/z: 356.24.
(Step 5)
Compound 15a (0.054 g, total yield of 5 steps 6%) was obtained from the crude product (0.100 g) of 2-(dimethylamino)ethyl 1-(4-aminobenzyl)-4-oxo-4,5,6,7-tetrahydro-1H-indole-2-carboxylate hydrochloride obtained in step and 5-((4-(((2S,4R)-2-methyl-1-propionyl-1,2,3,4-tetrahydroquinolin-4-yl)amino)phenyl)amino)-5-oxopentanoic acid (0.108 g, 0.25 mmol) obtained in step 2 of example 6k in the same manner as in step 3 of example 1b.
ESI-MS m/z: 761.57 (M+H)$^+$: $^1$H-NMR (DMSO-d$_6$, δ): 0.96-1.06 (m, 6H), 1.14 (td, J=12.04, 9.06 Hz, 1H), 1.86 (quin, J=7.27 Hz, 2H), 1.98-2.06 (m, 2H), 2.17 (s, 6H), 2.19-2.40 (m, 7H), 2.52-2.62 (m, 4H), 2.77 (t, J=6.08 Hz, 2H), 4.05-4.15 (m, 1H), 4.23 (t, J=5.60 Hz, 2H), 4.67-4.78 (m, 1H), 5.55 (s, 2H), 5.85 (d, J=7.87 Hz, 2H), 6.57 (d, J=9.06 Hz, 2H), 6.98 (d, J=8.58 Hz, 2H), 7.11 (s, 1H), 7.13-7.18 (m, 2H), 7.20-7.32 (m, 4H), 7.54 (d, J=8.58 Hz, 2H), 9.51 (s, 1H), 9.91 (s, 1H).

Example 15b 2-(Dimethylamino)ethyl 1-(4-(((5-(4-(((2S,4R)-2-methyl-1-propionyl-1,2,3,4-tetrahydroquinolin-4-yl)amino)phenyl)-1,3,4-oxadiazol-2-yl)ethyl)carbamoyl)benzyl)-4-oxo-4,5,6,7-tetrahydro-1H-indole-2-carboxylate (Compound 15b)

Compound 15b (0.050 g, 19%) was obtained from 1-[(2S,4R)-4-({4-[5-(aminomethyl)-1,3,4-oxadiazol-2-yl]phenyl}amino)-2-methyl-3,4-dihydroquinolin-1(2H)-yl]propan-1-one hydrochloride (0.150 g, 0.35 mmol) obtained in step 1 of example 12a and 4-((2-((2-(dimethylamino)ethoxy)carbonyl)-4-oxo-4,5,6,7-tetrahydro-1H-indol-1-yl)methyl)benzoic acid (0.135 g, 0.35 mmol) obtained in reference example 32 in the same manner as in step 3 of example 1b.
ESI-MS m/z: 758.44 (M+H)$^+$; $^1$H-NMR (DMSO-d$_6$, δ): 0.99-1.06 (m, 6H), 1.22-1.24 (m, 1H), 2.02-2.05 (m, 2H), 2.16 (s, 6H), 2.17-2.27 (m, 1H), 2.36-2.42 (m, 2H), 2.56-2.68 (m, 4H), 2.71-2.78 (m, 2H), 4.21 (t, J=5.6 Hz, 2H), 4.26-4.32 (m, 1H), 4.70-4.75 (m, 3H), 5.67 (s, 2H), 6.77-6.86 (m, 3H), 7.09-7.19 (m, 5H), 7.25-7.32 (m, 2H), 7.67 (d, J=8.77 Hz, 2H), 7.84 (d, J=8.33 Hz, 2H), 9.16 (t, J=5.6 Hz, 1H).

Example 15c 2-(Dimethylamino)ethyl 1-(4-((2-(1-(4-(((2S,4R)-2-methyl-1-propionyl-1,2,3,4-tetrahydroquinolin-4-yl)amino)phenyl)-1H-1,2,3-triazol-4-yl)ethyl)carbamoyl)benzyl)-4-oxo-4,5,6,7-tetrahydro-1H-indole-2-carboxylate (Compound 15c)

(Step 1)
A crude product (0.280 g) of 2-(dimethylamino)ethyl 1-(4-(but-3-yn-1-ylcarbamoyl)benzyl)-4-oxo-4,5,6,7-tetrahydro-1H-indole-2-carboxylate was obtained from 4-((2-((2-(dimethylamino)ethoxy)carbonyl)-4-oxo-4,5,6,7-tetrahydro-1H-indol-1-yl)methyl)benzoic acid (0.250 g, 0.65 mmol) obtained in reference example 32 and but-3-yn-1-amine hydrochloride (0.068 g, 0.65 mmol) in the same manner as in step 1 of example 1a.
ESIMS, (M+H)$^+$, m/z: 436.33.
(Step 2)
The crude product (0.150 g, 0.34 mmol) of 2-(dimethylamino)ethyl 1-(4-(but-3-yn-1-ylcarbamoyl)benzyl)-4-oxo-4,5,6,7-tetrahydro-1H-indole-2-carboxylate obtained in step 1 was dissolved in t-butanol (5 mL), then the crude product (0.114 g) of 1-{(2S,4R)-4-[(4-azidophenyl)amino]-2-methyl-3,4-dihydroquinolin-1(2H)-yl}propan-1-one obtained in step 2 of example 3a, sodium L-ascorbate (0.027 g, 0.14 mmol), copper sulfate pentahydrate (0.017 g, 0.07 mmol) and water (2 mL) were added to the solution at room temperature, and the mixture was stirred at 60° C. for 16 hours. The reaction mixture was concentrated under reduced pressure, the obtained residue was diluted with water, and the mixture was stirred for 15 minutes. The resulting solid was collected by filtration and dried under reduced pressure. The obtained solid was purified by reverse phase HPLC (10 mmol/L aqueous ammonium bicarbonate solution/acetonitrile=60/40) to give compound 15c (0.055 g, 21%).
ESIMS, (M+H)$^+$, m/z: 771.46 $^1$H-NMR (DMSO-d$_6$, δ): 1.00-1.07 (m, 6H), 1.17-1.26 (m, 1H), 2.01-2.04 (m, 2H), 2.15 (s, 6H), 2.20-2.32 (m, 1H), 2.39 (t, J=6.03 Hz, 2H), 2.55-2.69 (m, 4H), 2.74 (t, J=5.92 Hz, 2H), 2.93 (t, J=7.13 Hz, 2H), 3.57 (q, J=6.2 Hz, 2H), 4.17-4.29 (m, 3H), 4.69-4.80 (m, 1H), 5.66 (s, 2H), 6.46 (d, J=7.67 Hz, 1H), 6.78 (d, J=8.55 Hz, 2H), 7.08 (d, J=8.11 Hz, 2H), 7.14-7.21 (m, 3H), 7.26-7.32 (m, 2H), 7.51 (d, J=8.55 Hz, 2H), 7.77 (d, J=7.89 Hz, 2H), 8.34 (s, 1H), 8.56 (t, J=5.6 Hz, 1H).

Example 15d 2-(Dimethylamino)ethyl 1-(4-((2-(4-(4-(((2S,4R)-2-methyl-1-propionyl-1,2,3,4-tetrahydroquinolin-4-yl)amino)phenyl)-1H-pyrazol-1-yl)ethyl)carbamoyl)benzyl)-4-oxo-4,5,6,7-tetrahydro-1H-indole-2-carboxylate (Compound 15d)

Compound 15d (0.062 g, 26%) was obtained from 4-((2-((2-(dimethylamino)ethoxy)carbonyl)-4-oxo-4,5,6,7-tetrahydro-1H-indol-1-yl)methyl)benzoic acid (0.120 g, 0.31 mmol) obtained in step 6 of reference example 32 and 1-((2S,4R)-4-((4-(1-(2-aminoethyl-1H-pyrazol-4-yl)phenyl)amino)-2-methyl-3,4-dihydroquinolin-1(2H)-yl)propan-1-one hydrochloride (0.137 g, 0.31 mmol) obtained in step 1 of example 10d in the same manner as in step 3 of example 1b.
ESI-MS m/z: 770.45 (M+H)$^+$; $^1$H-NMR (DMSO-d$_6$, δ): 0.97-1.07 (m, 6H), 1.11-1.22 (m, 1H), 1.98-2.06 (m, 2H), 2.15 (s, 6H), 2.21-2.28 (m, 1H), 2.33-2.40 (m, 2H), 2.45-2.48 (m, 2H), 2.55-2.65 (m, 2H), 2.74 (t, J=5.8 Hz, 2H), 3.66 (q, J=6.08 Hz, 2H), 4.15-4.26 (m, 5H), 4.70-4.78 (m, 1H), 5.65 (s, 2H), 6.02 (d, J=7.6 Hz, 1H), 6.62 (d, J=8.8 Hz, 2H), 7.07 (d, J=8.34 Hz, 2H), 7.14-7.17 (m, 3H), 7.21-7.24 (m, 4H), 7.69 (s, 1H), 7.75 (d, J=8.4 Hz, 2H), 7.90 (s, 1H), 8.56 (t, J=5.6 Hz, 1H).

Example 15e 2-(Dimethylamino)ethyl 1-(4-((3-(4-(((2S,4R)-2-methyl-1-propionyl-1,2,3,4-tetrahydroquinolin-4-yl)amino)benzamide)propyl)carbamoyl)benzyl)-4-oxo-4,5,6,7-tetrahydro-1H-indole-2-carboxylate (Compound 15e)

Compound 15e (0.060 g, 20%) was obtained from 4-((2-((2-(dimethylamino)ethoxy)carbonyl)-4-oxo-4,5,6,7-tetrahydro-1H-indol-1-yl)ethyl)benzoic acid (0.1 g, 0.19 mmol) obtained in step 6 of reference example 32 and N-(3-aminopropyl)-4-{[(2S,4R)-2-methyl-1-propionyl-1,2,3,4-tetrahydroquinolin-4-yl]amino}benzamide hydrochloride (0.082 g, 0.19 mmol) obtained in step 2 of example 1h in the same manner as in step 3 of example 1b.
ESI-MS m/z: 761.54 (M+H)$^+$; $^1$H-NMR (DMSO-d$_6$, δ): 1.01 (t, J=7.2 Hz, 3H), 1.05 (d, J=6.4 Hz, 3H), 1.17-1.25 (m, 1H), 1.71 (quin, J=6.80 Hz, 2H), 2.03 (quin, J=6.80 Hz, 2H), 2.16 (s, 6H), 2.22-2.28 (m, 1H), 2.39 (t, J=6.25 Hz, 2H), 2.52-2.63 (m, 4H), 2.75 (t, J=5.92 Hz, 2H), 3.24-3.27 (m, 4H), 4.19-4.29 (m, 3H), 4.69-4.79 (m, 1H), 5.66 (s, 2H), 6.54 (d, J=7.67 Hz, 1H), 6.65 (d, J=8.77 Hz, 2H), 7.08-7.11 (m, 3H), 7.15-7.18 (m, 2H), 7.25-7.31 (m, 2H), 7.63 (d, J=8.77 Hz, 2H), 7.78 (d, J=8.33 Hz, 2H), 8.06 (t, J=5.70 Hz, 1H), 8.41 (t, J=5.6 Hz, 1H).

Example 15f 4-((2-Ethyl-4-oxo-4,5,6,7-tetrahydro-1H-indol-1-yl)methyl)-N-((1-(4-(((2S,4R)-2-methyl-1-propionyl-1,2,3,4-tetrahydroquinolin-4-yl)amino)phenyl)-1H-1,2,3-triazol-4-yl)methyl)benzamide (Compound 15f)

(Step 1)

4-((2-Ethyl-4-oxo-4,5,6,7-tetrahydro-1H-indol-1-yl)methyl)-N-(prop-2-yn-1-yl)benzamide (0.105 g, 94%) was obtained from 4-[(2-ethyl-4-oxo-4,5,6,7-tetrahydro-1H-indol-1-yl)methyl]benzoic acid (0.1 g, 0.33 mmol) obtained in step 2 of reference example 5 and commercially available propargylamine (0.023 mL, 0.37 mmol) in the same manner as in step 1 of example 1a.
ESIMS, (M+H)$^+$, m/z: 335.

(Step 2)

Compound 15f (0.085 g, 42%) was obtained from 4-((2-ethyl-4-oxo-4,5,6,7-tetrahydro-1H-indol-1-yl)methyl)-N-(prop-2-yn-1-yl)benzamide (0.105 g, 0.31 mmol) obtained in step 1 and the crude product (0.105 g) of 1-{(2S,4R)-4-[(4-azidophenyl)amino]-2-methyl-3,4-dihydroquinolin-1(2H)-yl}propan-1-one obtained in step 2 of example 3a in the same manner as in step 3 of example 3a.
ESIMS, (M+H)$^+$, m/z: 670; $^1$H-NMR (DMSO-d$_6$, δ): 0.99-1.10 (m, 9H), 1.14-1.25 (m, 1H), 1.97-2.02 (m, 2H), 2.21-2.33 (m, 3H), 2.38-2.45 (m, 2H), 2.55-2.67 (m, 4H), 4.22-4.28 (m, 1H), 4.57 (d, J=5.2 Hz, 2H), 4.72-4.78 (m, 1H), 5.28 (s, 2H), 6.12 (s, 1H), 6.47 (d, J=7.6 Hz, 1H), 6.78 (d, J=8.8 Hz, 2H), 7.04 (d, J=8.4 Hz, 2H), 7.14-7.20 (m, 2H), 7.25-7.32 (m, 2H), 7.54 (d, J=8.8 Hz, 2H), 7.85 (d, J=8.0 Hz, 2H), 8.37 (s, 1H), 8.98 (t, J=5.8 Hz, 1H)

Example 15g

Methyl 1-(4-((3-(4-(((2S,4R)-2-methyl-1-propionyl-1,2,3,4-tetrahydroquinolin-4-yl)amino)benzamide)propyl)carbamoyl)benzyl)-4-oxo-4,5,6,7-tetrahydro-1H-indole-2-carboxylate (Compound 15g)

Compound 15g (0.075 g, 35%) was obtained from 4-((2-(methoxycarbonyl)-4-oxo-4,5,6,7-tetrahydro-1H-indol-1-yl)methyl)benzoic acid (0.1 g, 0.30 mmol) obtained in reference example 34 and N-(3-aminopropyl)-4-{[(2S,4R)-2-methyl-1-propionyl-1,2,3,4-tetrahydroquinolin-4-yl]amino}benzamide hydrochloride (0.144 g, 0.33 mmol) obtained in step 2 of example 1h in the same manner as in step 3 of example 1b.
ESIMS, (M+H)$^+$, m/z: 704; $^1$H-NMR (DMSO-d$_6$, δ) 0.99-1.06 (m, 6H), 1.20-1.25 (m, 1H), 1.71 (t, J=7.0 Hz, 2H), 2.03 (t, J=7.0 Hz, 2H), 2.22-2.28 (m, 1H), 2.40 (t, J=6.25 Hz, 2H), 2.54-2.63 (m, 2H), 2.75 (t, J=6.03 Hz, 2H), 3.25-3.26 (m, 4H), 3.71 (s, 3H), 4.21-4.31 (m, 1H), 4.66-4.79 (m, 1H), 5.67 (s, 2H), 6.54 (d, J=7.89 Hz, 1H), 6.65 (d, J=8.77 Hz, 2H), 7.09 (t, J=7.2 Hz, 3H), 7.15-7.18 (m, 2H), 7.25-7.31 (m, 2H), 7.63 (d, J=8.77 Hz, 2H), 7.78 (d, J=8.4 Hz, 2H), 8.06 (t, J=5.48 Hz, 1H), 8.45 (t, J=5.48 Hz, 1H).

Example 15h

N-((1-(4-((2-Ethyl-4-oxo-4,5,6,7-tetrahydro-1H-indol-1-yl)methyl)phenyl)-1H-1,2,3-triazol-4-yl)methyl)-4-(((2S,4R)-2-methyl-1-propionyl-1,2,3,4-tetrahydroquinolin-4-yl)amino)benzamide (Compound 15h)

(Step 1)

A crude product (0.18 g) of 1-(4-azidobenzyl)-2-ethyl-1,5,6,7-tetrahydro-4H-indol-4-one was obtained from 1-(4-aminobenzyl)-2-ethyl-1,5,6,7-tetrahydro-4H-indol-4-one (0.2 g, 0.74 mmol) obtained in step 2 of reference example 23 in the same manner as in step 2 of example 3a.
ESIMS, (M+H)$^+$, m/z: 295.

(Step 2)

4-(((2S,4R)-2-Methyl-1-propionyl-1,2,3,4-tetrahydroquinolin-4-yl)amino)-N-(prop-2-yn-1-yl)benzamide (0.15 g, 68%) was obtained from 4-(((2S,4R)-2-methyl-1-propionyl-1,2,3,4-tetrahydroquinolin-4-yl)amino)benzoic acid (0.2 g, 0.59 mmol) obtained in step 7 of reference example 1 in the same manner as in step 2 of example 3b.
ESIMS, (M+H)$^+$, m/z: 376.

(Step 3)

Compound 15h (0.03 g, total yield of 2 steps 6.1%) was obtained from the crude product (0.18 g) of 1-(4-azidobenzyl)-2-ethyl-1,5,6,7-tetrahydro-4H-indol-4-one obtained in step 1 and 4-(((2S,4R)-2-methyl-1-propionyl-1,2,3,4-tetrahydroquinolin-4-yl)amino)-N-(prop-2-yn-1-yl)benzamide (0.23 g, 0.61 mmol) obtained in step 2 in the same manner as in step 3 of example 3a.
ESIMS, (M+H)$^+$, m/z: 670; $^1$H-NMR (DMSO-d$_6$, δ) 0.99-1.12 (m, 9H), 1.20-1.22 (m, 1H), 1.99-2.02 (m, 2H), 2.23-2.32 (m, 3H), 2.44 (q, J=7.6 Hz, 2H), 2.56-2.63 (m, 2H), 2.68 (t, J=6.2 Hz, 2H), 4.21-4.32 (m, 1H), 4.54 (d, J=5.6 Hz, 2H), 4.65-4.80 (m, 1H), 5.23 (s, 2H), 6.14 (s, 1H), 6.58 (d, J=7.89 Hz, 1H), 6.66 (d, J=8.77 Hz, 2H), 7.09 (d, J=7.67 Hz, 1H), 7.16 (dd, J=12.4, 8.0 Hz, 3H), 7.24-7.31 (m, 2H), 7.68 (dd, J=18.96, 8.66 Hz, 2H), 7.86 (d, J=12.4 Hz, 2H), 8.56 (s, 1H), 8.61 (t, J=5.26 Hz, 1H).

Example 15i

N$^1$-(4-((2-Ethyl-4-oxo-4,5,6,7-tetrahydro-1H-indol-1-yl)methyl)phenyl)-N$^5$-(4-(((2S,4R))-2-methyl-1-propionyl-1,2,3,4-tetrahydroquinolin-4-yl)amino)phenyl)glutaramide (Compound 15i)

Compound 15i (0.027 g, 8%) was obtained from 5-[(4-{[(2S*,4R*)-2-methyl-1-propionyl-1,2,3,4-tetrahydroquinolin-4-yl]amino}phenyl)amino]-5-oxopentanoic acid (0.1 g, 0.23 mmol) obtained in step 2 of example 4a and 1-(4-aminobenzyl)-2-ethyl-1,5,6,7-tetrahydro-4H-indol-4-one (0.071 g, 0.23 mmol) obtained in reference example 23 in the same manner as in step 3 of example 1b.
ESIMS, (M+H)$^+$, m/z: 674; $^1$H-NMR (DMSO-d$_6$, δ) 0.98-1.11 (m, 9H), 1.13-1.19 (m, 1H), 1.86 (quin, J=3.8 Hz, 2H), 2.00 (quin, J=6.0 Hz, 2H), 2.20-2.35 (m, 7H), 2.42 (q, J=7.6 Hz, 2H), 2.53-2.61 (m, 2H), 2.67 (t, J=6.03 Hz, 2H), 4.07-4.13 (m, 1H), 4.67-4.79 (m, 1H), 5.06 (s, 2H), 5.83 (d, J=7.89 Hz, 1H), 6.09 (s, 1H), 6.58 (d, J=8.77 Hz, 2H), 6.91 (d, J=8.55 Hz, 2H), 7.16 (d, J=3.51 Hz, 2H), 7.23-7.30 (m, 4H), 7.55 (d, J=8.55 Hz, 2H), 9.50 (s, 1H), 9.90 (s, 1H).

Example 15j 2-(4-(((2S*,4R*)-2-Methyl-1-propionyl-1,2,3,4-tetrahydroquinolin-4-yl)amino)cyclohexylidene)-N-(2-((4-(((2S,4R)-2-methyl-1-propionyl-1,2,3,4-tetrahydroquinolin-4-yl)amino)phenyl)amino)-2-oxoethyl)acetamide (Compound 15j)

(Step 1)

4-(((2S*,4R*)-2-Methyl-1-propionyl-1,2,3,4-tetrahydroquinolin-4-yl)amino)cyclohexan-1-one (418 mg, 60%) was obtained from 1-((2S*,4R*)-4-(((1s,4S)-4-hydroxycyclohexyl)amino)-2-methyl-3,4-dihydroquinolin-1(2H)-yl)propan-1-one (70.3 mg, 2.22 mmol) obtained in step 1 of example 7d in the same manner as in step 4 of example 7r.
ESIMS, (M+H)$^+$, m/z: 315.

(Step 2)

Triethyl phosphonoacetate (48.1 mg, 0.215 mmol) was dissolved in THF (0.22 mL), then sodium hydride (60% w/w mineral oil mixture), 8.6 mg, 0.215 mmol) was added to the solution, and the mixture was stirred at 0° C. for 30 minutes. A THF solution (3 mL) of 4-(((2S*,4R*)-2-methyl-1-propionyl-1,2,3,4-tetrahydroquinolin-4-yl)amino)cyclohexan-1-one (45.0 mg, 0.143 mmol) obtained in step 1 was added to the reaction mixture, and the mixture was stirred at room temperature for 30 minutes. A saturated aqueous ammonium chloride solution was added to the reaction mixture, and the aqueous layer was extracted with ethyl acetate. The organic layer was dried over anhydrous sodium sulfate and concentrated under reduced pressure. The obtained residue was purified by silica gel column chromatography (heptane/ethyl acetate=7/3 to 1/1) to give ethyl 2-(4-(((2S*,4R*)-2-methyl-1-propionyl-1,2,3,4-tetrahydroquinolin-4-yl)amino)cyclohexylidene)acetate (38.9 mg, 71%).
ESIMS, (M+H)$^+$, m/z: 385.

(Step 3)

Compound 15j (29.1 mg, 42%) was obtained from ethyl 2-(4-(((2S*,4R*)-2-methyl-1-propionyl-1,2,3,4-tetrahydroquinolin-4-yl)amino)cyclohexylidene)acetate (38 mg, 0.099 mmol) obtained in step 2 and 2-amino-N-(4-(((2S,4R)-2-methyl-1-propionyl-1,2,3,4-tetrahydroquinolin-4-yl)amino)phenyl)acetamide hydrochloride (80.0 mg, 0.198 mmol) obtained in step 3 of example 7d in the same manner as in step 2 of example 8b.
ESIMS, (M+H)$^+$, m/z: 705; $^1$H-NMR (CDCl$_3$, δ) 1.07-1.43 (m, 17H), 1.94-2.13 (m, 2H), 2.15-2.43 (m, 5H), 2.46-2.72 (m, 4H), 2.89-3.04 (m, 1H), 3.54 (dd, J=12.0, 4.0 Hz, 1H), 3.63-3.74 (m, 1H), 3.79-3.86 (m, 1H), 4.08 (d, J=5.6 Hz, 2H), 4.12-4.20 (m, 1H), 4.78-5.02 (m, 2H), 5.64 (s, 1H), 6.18-6.32 (m, 1H), 6.59 (d, J=8.4 Hz, 2H), 7.04-7.34 (m, 9H), 7.43-7.56 (m, 1H), 7.97-8.12 (m, 1H).

Example 15k

2-Fluoro-2-(4-(((2S*,4R*)-2-methyl-1-propionyl-1,2,3,4-tetrahydroquinolin-4-yl)amino)cyclohexylidene)-N-(2-((4-(((2S,4R)-2-methyl-1-propionyl-1,2,3,4-tetrahydroquinolin-4-yl)amino)phenyl)amino)-2-oxoethyl)acetamide (Compound 15k)

(Step 1)

Ethyl 2-fluoro-2-(4-(((2S*,4R*)-2-methyl-1-propionyl-1,2,3,4-tetrahydroquinolin-4-yl)amino)cyclohexylidene)acetate (66.7 mg, 95%) was obtained from 4-(((2S*,4R*)-2-methyl-1-propionyl-1,2,3,4-tetrahydroquinolin-4-yl)amino)cyclohexan-1-one (55.0 mg, 0.175 mmol) obtained in step 1 of example 15j and triethyl 2-fluoro-2-phosphonoacetate (63.6 mg, 0.262 mmol) in the same manner as in step 2 of example 15j.

ESIMS, (M+H)$^+$, m/z: 403.

(Step 2)

Compound 15k (16.4 mg, 71%) was obtained from ethyl 2-fluoro-2-(4-(((2S*,4R*)-2-methyl-1-propionyl-1,2,3,4-tetrahydroquinolin-4-yl)amino)cyclohexylidene)acetate (13 mg, 0.032 mmol) obtained in step 1 and 2-amino-N-(4-(((2S,4R)-2-methyl-1-propionyl-1,2,3,4-tetrahydroquinolin-4-yl)amino)phenyl)acetamide hydrochloride (26 mg, 0.064 mmol) obtained in step 3 of example 7d in the same manner as in step 2 of example 8b.

ESIMS, (M+H)$^+$, m/z: 723; $^1$H-NMR (CDCl$_3$, δ) 1.03-1.49 (m, 16H), 1.94-2.14 (m, 3H), 2.20-2.44 (m, 3H), 2.46-2.72 (m, 4H), 2.78-3.01 (m, 2H), 3.54 (dd, J=12.4, 4.0 Hz, 1H), 3.69 (d, J=14.8 Hz, 1H), 3.84 (d, J=6.4 Hz, 2H), 4.07-4.22 (m, 1H), 4.12 (d, J=5.2 Hz, 2H), 4.78-5.21 (m, 1H), 6.60 (d, J=8.8 Hz, 2H), 6.96-7.34 (m, 10H), 7.44-7.57 (m, 1H), 7.76-7.86 (m, 1H).

The invention claimed is:

1. A compound of the formula I or a pharmaceutically acceptable salt thereof:

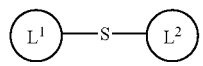
(I)

wherein, L$^1$ and L$^2$ are the same or different and each represents a group represented by a member selected from the group consisting of:

(A)
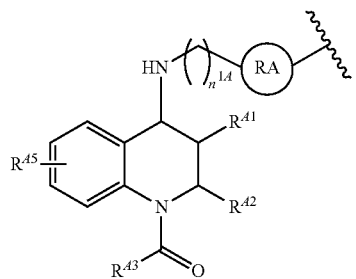

(B)
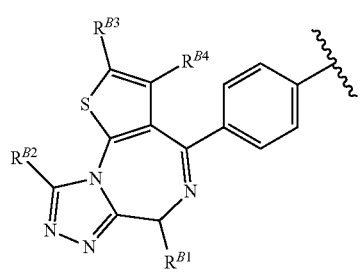

(C)
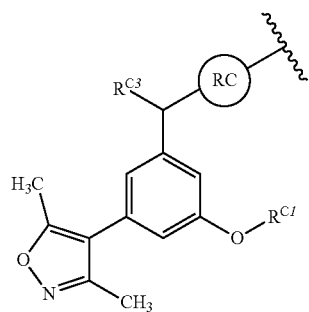

(D)
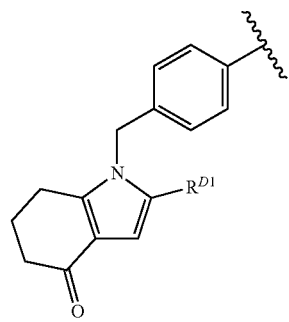

(E)
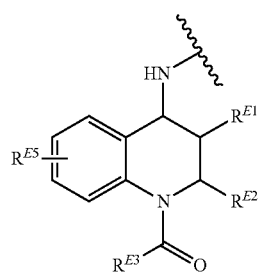

(F)
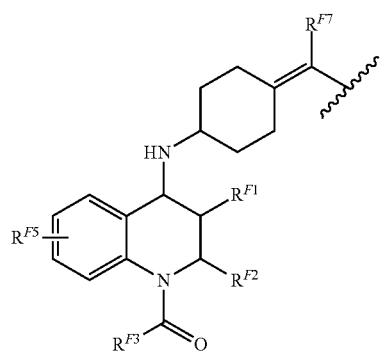

wherein,
at least one of L$^1$ and L$^2$ is a member selected from formula (A),
the wavy line represents a bonding site to S,
R$^{A1}$, R$^{A2}$, and R$^{A3}$ are the same or different and each represents a hydrogen atom or lower alkyl,
R$^{A5}$ represents
a hydrogen atom,
a halogen,
lower alkyl optionally substituted with one or more substituents selected from the group consisting of a halogen, hydroxy, methoxy, ethoxy, nitro, cyano, carboxy, methoxycarbonyl, ethoxycarbonyl, amino, methylamino, ethylamino, dimethylamino, diethylamino, carbamoyl, methylcarbamoyl, ethylcarbamoyl, dimethylcarbamoyl, diethylcarbamoyl, cyclopropyl, cyclobutyl, cyclopentyl, cyclohexyl, phenyl, furyl, thiophenyl, pyrrolyl, pyrazolyl, imidazolyl, oxazolyl, thiazolyl, triazolyl, oxadiazolyl, tetrazolyl, pyridyl, pyridazinyl, pyrimidinyl, and pyrazinyl, lower alkenyl optionally substituted with one or more substituents selected from the group consisting of a halogen, hydroxy, methoxy, ethoxy, nitro, cyano, carboxy, methoxycarbonyl, ethoxycarbonyl, amino, methylamino, ethylamino, dimethylamino, diethylamino, carbamoyl, methylcarbamoyl, ethylcarbamoyl, dimethylcarbamoyl, diethylcarbamoyl, cyclopropyl, cyclobutyl, cyclopentyl, cyclohexyl, phenyl, furyl, thiophenyl, pyrrolyl, pyrazolyl, imidazolyl, oxazolyl, thiazolyl, triazolyl, oxadiazolyl, tetrazolyl, pyridyl, pyridazinyl, pyrimidinyl, and pyrazinyl, tetrahydropyridinyl optionally substituted with one or more substituents selected from the group consisting of a halogen, methyl, ethyl, hydroxy, methoxy, ethoxy, nitro, cyano, carboxy, methoxycarbonyl, ethoxycarbonyl, amino, methylamino, ethylamino, dimethylamino, diethylamino, carbamoyl, methylcarbamoyl, ethylcarbamoyl, dimethylcarbamoyl, and diethylcarbamoyl, dihydro-1H-pyrrolyl optionally substituted with one or more substituents selected from the group consisting of a halogen, methyl, ethyl, hydroxy, methoxy, ethoxy, nitro, cyano, carboxy, methoxycarbonyl, ethoxycarbonyl, amino, methylamino, ethylamino, dimethylamino, diethylamino, carbamoyl, methylcarbamoyl, ethylcarbamoyl, dimethylcarbamoyl, and diethylcarbamoyl, or tetrahydro-1H-azepinyl optionally substituted with one or more substituents selected from the group consisting of a halogen, methyl, ethyl, hydroxy, methoxy, ethoxy, nitro, cyano, carboxy, methoxycarbonyl, ethoxycarbonyl, amino, methylamino, ethylamino, dimethylamino, diethylamino, carbamoyl, methylcarbamoyl, ethylcarbamoyl, dimethylcarbamoyl, and diethylcarbamoyl, ring RA represents phenylene, cycloalkylene, pyridiylene, piperidinylene, azetidinylene, pyrrolidinylene, or homopiperidinylene $n^{1A}$ represents 0 or 1, $R^{B1}$ represents
a hydrogen atom,
lower alkoxy carbonylmethylene, optionally substituted with one or more substituents selected from the group consisting of a halogen, hydroxy, methoxy, ethoxy, nitro, cyano, carboxy, methoxycarbonyl, ethoxycarbonyl, amino, methylamino, ethylamino, dimethylamino, diethylamino, carbamoyl, methylcarbamoyl, ethylcarbamoyl, dimethylcarbamoyl, diethylcarbamoyl, cyclopropyl, cyclobutyl, cyclopentyl, cyclohexyl, phenyl, furyl, thiophenyl, pyrrolyl, pyrazolyl, imidazolyl, oxazolyl, thiazolyl, triazolyl, oxadiazolyl, tetrazolyl, pyridyl, pyridazinyl, pyrimidinyl, and pyrazinyl,
cycloalkyloxy carbonylmethylene, optionally substituted with one or more substituents selected from the group consisting of a halogen, methyl, ethyl, hydroxy, methoxy, ethoxy, nitro, cyano, carboxy, methoxycarbonyl, ethoxycarbonyl, amino, methylamino, ethylamino, dimethylamino, diethylamino, carbamoyl, methylcarbamoyl, ethylcarbamoyl, dimethylcarbamoyl, and diethylcarbamoyl, or —CH$_2$CONR$^{B5}$R$^{B6}$ wherein, R$^{B5}$ and R$^{B6}$ are the same or different and each represents a hydrogen atom, or lower alkyl or they represent a nitrogen-containing aliphatic heterocyclic group together with an adjacent nitrogen atom optionally substituted with one or more substituents selected from the group consisting of a halogen, methyl, ethyl, hydroxy, methoxy, ethoxy, nitro, cyano, carboxy, methoxycarbonyl, ethoxycarbonyl, amino, methylamino, ethylamino, dimethylamino, diethylamino, carbamoyl, methylcarbamoyl, ethylcarbamoyl, dimethylcarbamoyl, diethylcarbamoyl, hydroxymethyl, hydroxyethyl, and hydroxypropyl $R^{B2}$ represents lower alkyl optionally substituted with one or more substituents selected from the group consisting of a halogen, hydroxy, methoxy, ethoxy, nitro, cyano, carboxy, methoxycarbonyl, ethoxycarbonyl, amino, methylamino, ethylamino, dimethylamino, diethylamino, carbamoyl, methylcarbamoyl, ethylcarbamoyl, dimethylcarbamoyl, diethylcarbamoyl, cyclopropyl, cyclobutyl, cyclopentyl, cyclohexyl, phenyl, furyl, thiophenyl, pyrrolyl, pyrazolyl, imidazolyl, oxazolyl, thiazolyl, triazolyl, oxadiazolyl, tetrazolyl, pyridyl, pyridazinyl, pyrimidinyl, and pyrazinyl, $R^{B3}$ and $R^{B4}$ are the same or different and each represents a halogen or lower alkyl optionally substituted with one or more substituents selected from the group consisting of a halogen, hydroxy, methoxy, ethoxy, nitro, cyano, carboxy, methoxycarbonyl, ethoxycarbonyl, amino, methylamino, ethylamino, dimethylamino, diethylamino, carbamoyl, methylcarbamoyl, ethylcarbamoyl, dimethylcarbamoyl, diethylcarbamoyl, cyclopropyl, cyclobutyl, cyclopentyl, cyclohexyl, phenyl, furyl, thiophenyl, pyrrolyl, pyrazolyl, imidazolyl, oxazolyl, thiazolyl, triazolyl, oxadiazolyl, tetrazolyl, pyridyl, pyridazinyl, pyrimidinyl, and pyrazinyl, $R^{C1}$ represents a hydrogen atom, lower alkyl, or lower alkanoyl, $R^{C3}$ represents a hydrogen atom or hydroxy, ring RC represents phenylene, piperidinylene, azetidinylene, pyrrolidinylene, or homopiperidinylene $R^{D1}$ represents
lower alkyl optionally substituted with one or more substituents selected from the group consisting of a halogen, hydroxy, methoxy, ethoxy, nitro, cyano, carboxy, methoxycarbonyl, ethoxycarbonyl, amino, methylamino, ethylamino, dimethylamino, diethylamino, carbamoyl, methylcarbamoyl, ethylcarbamoyl, dimethylcarbamoyl, diethylcarbamoyl, cyclopropyl, cyclobutyl, cyclopentyl, cyclohexyl, phenyl, furyl, thiophenyl, pyrrolyl, pyrazolyl, imidazolyl, oxazolyl, thiazolyl, triazolyl, oxadiazolyl, tetrazolyl, pyridyl, pyridazinyl, pyrimidinyl, and pyrazinyl, or
lower alkoxycarbonyl optionally substituted with one or more substituents selected from the group consisting of a halogen, hydroxy, methoxy, ethoxy, nitro, cyano, carboxy, methoxycarbonyl, ethoxycarbonyl, amino, methylamino, ethylamino, dimethylamino, diethylamino, carbamoyl, methylcarbamoyl, ethylcarbamoyl, dimethylcarbamoyl, diethylcarbamoyl, cyclopropyl, cyclobutyl, cyclopentyl, cyclohexyl, phenyl, furyl, thiophenyl, pyrrolyl, pyrazolyl, imidazolyl, oxazolyl, thiazolyl, triazolyl, oxadiazolyl, tetrazolyl, pyridyl, pyridazinyl, pyrimidinyl, and pyrazinyl, $R^{E1}$ and $R^{F1}$ have the same definition as $R^{A1}$, $R^{E2}$ and $R^{F2}$ have the same definition as $R^{A2}$, $R^{E3}$ and $R^{F3}$ have the same definition as $R^{A3}$, $R^{E5}$ and $R^{F5}$ have the same definition as $R^{A5}$, and $R^{F7}$ represents a hydrogen atom or a halogen);

S represents a member selected from group consisting of

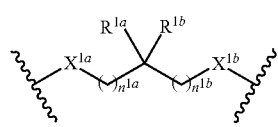 (S1)

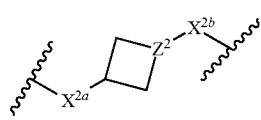 (S2)

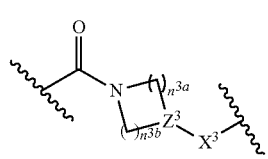 (S3)

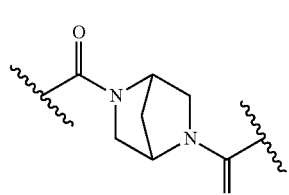 (S4)

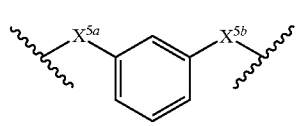 (S5)

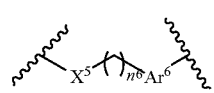 (S6)

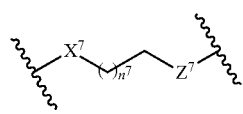 (S7)

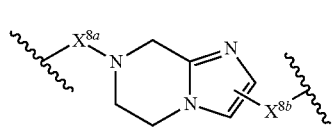 (S8)

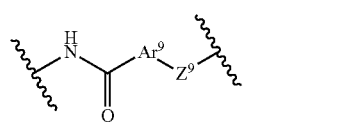 (S9)

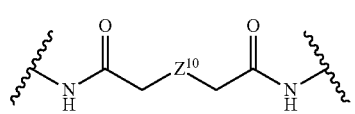 (S10)

-continued

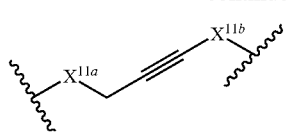 (S11)

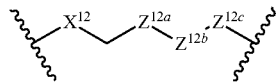 (S12)

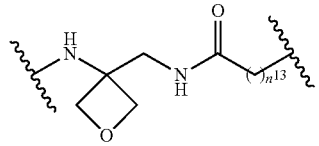 (S13)

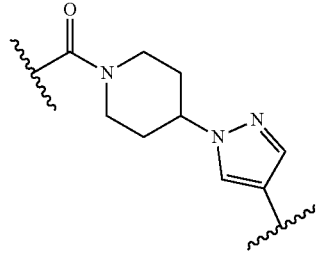 (S14)

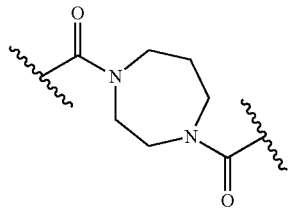 (S15)

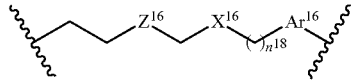 (S16)

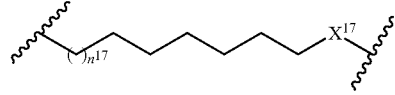 (S17)

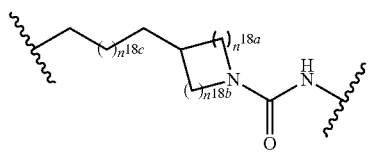 (S18)

wherein, the wavy line represents a bonding site to $L^1$ or $L^2$, $n^{1a}$ and $n^{1b}$ are the same or different and each represents 0 or 1, $X^{1a}$ and $X^{1b}$ are the same or different and each represents —C(=O)—NH—, —NH—C(=O)—, —SO$_2$—NH—, —NH—SO$_2$—, —O—C(=S)—NH—, —O—C(=O)—NH—, —NH—C(=O)—O—, or —NH—C(=O)—NH— except for the cases where (i) $X^{1a}$ is —NH—SO$_2$—, and $X^{1b}$ is —SO$_2$—NH—, (ii) $n^{1a}$ and $n^{1b}$ are 0, $X^{1a}$ is —C(=O)—NH—, —SO$_2$—NH—, —O—C(=S)—NH—, —O—C(=O)—NH—, or —NH—C(=O)—NH—, and $X^{1b}$ is —NH—C(=O)—, —NH—SO$_2$—, —NH—C(=O)—O—, or —NH—C(=O)—NH—, and (iii) $X^{1a}$ is —O—C(=S)—NH—, —O—C(=O)—NH—, —NH—C(=O)—O—, or —NH—C(=O)—NH— and $X^{1a}$ is —O—C(=S)—NH—, —O—C(=O)—NH—, —NH—C(=O)—O—, or —NH—C(=O)—NH—, $R^{1a}$ represents a hydrogen atom and $R^{1b}$ represents a hydrogen atom or lower alkyl, or $R^{1a}$ and $R^{1b}$ together represent carbonyl, $X^{2a}$ represents —C(=O)—NH—, —NH—C(=O)—, —SO$_2$—NH—, or —NH—SO$_2$—, $X^{2b}$ represents —C(=O)—NH—, —NH—C(=O)—, —SO$_2$—NH—, —NH—SO$_2$—, or —CH$_2$-except for the case where $X^{2a}$ is —NH—SO$_2$- and $X^{2b}$ is —SO$_2$—NH—, $Z^2$ represents CH or N except for the cases where (i) $Z^2$ is N and $X^{2b}$ is —NH—C(=O)—, —SO$_2$—NH—, or —NH—SO$_2$— and (ii) $Z^2$ is CH and $X^{2b}$ is —CH$_2$—, $n^{3a}$ and $n^{3b}$ are the same or different and each represents 1 or 2, $X^3$ represents —C(=O)—NH—, —NH—C(=O)—, —SO$_2$—NH—, —NH—SO$_2$—, —NH—C(=O)—NH—, or —NH—CH$_2$—, $Z^3$ represents CH or N except for the cases where (i) $Z^3$ is N and $X^3$ is —NH—C(=O)—, —SO$_2$—NH—, —NH—SO$_2$—, —NH—C(=O)—NH—, or —NH—CH$_2$— and (ii) $Z^3$ is N and $n^{3a}$ or $n^{3b}$ is 1, $X^{5a}$ and $X^{5b}$ are the same or different and each represents —C(=O)—NH—, —NH—C(=O)—, —SO$_2$—NH—, or —NH—SO$_2$— except for the case where $X^{5a}$ is —NH—SO$_2$— and $X^{5b}$ is —SO$_2$—NH—, $n^6$ represents 1 or 2, $Ar^6$ represents triazolediyl, oxadiazolediyl, pyrazolediyl, thiophenediyl, or tetrahydropyridinediyl, $X^6$ represents —C(=O)—NH—, —NH—C(=O)—, —SO$_2$—NH—, —NH—SO$_2$—, —CH$_2$—NH— or —NH—C(=O)—NH— except for the cases where (i) $Ar^6$ is oxadiazolediyl, pyrazolediyl, thiophenediyl, or tetrahydropyridinediyl and $X^6$ is —NH—SO$_2$— and (ii) $n^6$ is 1, $Ar^6$ is pyrazolediyl or tetrahydropyridinediyl, and $X^6$ is —C(=O)—NH—, —SO$_2$—NH—, —CH$_2$—NH—, or —NH—C(=O)—NH—, $X^7$ represents —C(=O)—NH—, —NH—C(=O)—, —SO$_2$—NH—, or —NH—C(=O)—NH—, $n^7$ represents 1, 2, or 3, $Z^7$ represents S, SO, or SO$_2$, $X^{8a}$ represents —C(=O)—, —CH$_2$—, or —NH—C(=O)—, $X^{8b}$ represents a bond, —C(=O)—, —CH$_2$—, or —CH(OH)—, $Ar^9$ represents triazolediyl or oxazolediyl, $Z^9$ represents CH$_2$ or NH except for the cases where (i) $Ar^9$ is triazolediyl and $Z^9$ is NH and (ii) $Ar^9$ is oxazolediyl and $Z^9$ is CH$_2$, $Z^{10}$ represents O or NH, $X^{11a}$ represents —C(=O)—NH—, —SO$_2$—NH—, or —NH—C(=O)—NH—, $X^{11b}$ represents —C(=O)—NH— or —C(=O)—, $X^{12}$ represents —C(=O)—NH—, —NH—C(=O)—, —SO$_2$—NH—, or —NH—C(=O)—NH—, $Z^{12a}$ represents CH$_2$ or NH except for the case where $X^{12}$ is —C(=O)—NH—, —SO$_2$—NH—, or —NH—C(=O)—NH— and $Z^{12a}$ is NH, $Z^{12b}$ represents CH$_2$ or 0 except for the case where $Z^{12a}$ is NH and $Z^{12b}$ is O, $Z^{12c}$ represents a bond, CH$_2$, or O except for the cases where (i) $Z^{12b}$ is 0 and $Z^{12c}$ is O and (ii) $Z^{12a}$ is NH and $Z^{12c}$ is CH$_2$ or O, $n^{13}$ represents 0, 1 or 2, $n^{16}$ represents 1 or 2, $Z^{16}$ represents a bond, CH$_2$, or O, $X^{16}$ represents —CH$_2$—O—, —C(=O)—NH—, —NH—C(=O)—, or —NH—C(=O)—NH— except for the case where $Z^{16}$ is O and $X^{16}$ is —NH—C(=O)— or —NH—C(=O)—NH—, $Ar^{16}$ represents triazolediyl, oxadiazolediyl or pyrazolediyl except for the cases where (i) $X^{16}$ is —CH$_2$—O— and $Ar^{16}$ is oxadiazolediyl or pyrazolediyl and (ii) $n^{16}$ is 1, $X^{16}$ is —C(=O)—NH— or —NH—C(=O)—NH—, and $Ar^{16}$ is pyrazolediyl, $n^{17}$ represents 1 or 2, $X^{17}$ represents —C(=O)—NH—, —NH—C(=O)—, —NH—SO$_2$—, or —NH—C(=O)—NH—, and $n^{18a}$, $n^{18b}$, and $n^{18c}$ are the same or different and each represents 1 or 2.

2. The compound of claim 1 or a pharmaceutically acceptable salt thereof, wherein $L^1$ is a member selected from formula (A), (B), (C), (D), or (F), $L^2$ is a member selected from formula (A), (B), (C), or (D), and S is a member selected from formula (S1) provided that at least one of L1 and L2 is a member selected from formula (A).

3. The compound of claim 1 or a pharmaceutically acceptable salt thereof, wherein $L^1$ and $L^2$ are independently a member selected from formula (A), and S is a member selected from formula (S2).

4. The compound of claim 1 or a pharmaceutically acceptable salt thereof, wherein $L^1$ represents a member selected from formula (A), (B), or (C), $L^2$ is a member selected from formula (A) or (B), and S is a member selected from formula (S3) provided that at least one of $L^1$ and $L^2$ is a member selected from formula (A).

5. The compound according to claim 1 or a pharmaceutically acceptable salt thereof, wherein $L^1$ and $L^2$ are independently a member selected from formula (A), and S is a member selected from formula (S4) or (S5).

6. The compound of claim 1 or a pharmaceutically acceptable salt thereof, wherein $L^1$ is a member selected from formula (A), (B), (C), or (D), $L^2$ is a member selected from formula (A), (B), or (D), and S is a member selected from formula (S6), provided that at least one of $L^1$ and $L^2$ is a member selected from formula (A).

7. The compound of claim 1 or a pharmaceutically acceptable salt thereof, wherein $L^1$ is a member selected from formula (A) or (B), $L^2$ is a member selected from formula (A), and S is a member selected from formula (S7).

8. The compound of claim 1 or a pharmaceutically acceptable salt thereof, wherein $L^1$ is a member selected from formula (A) or (B), $L^2$ is a member selected from formula (A), and S is a member-selected from formula (S8).

9. The compound of claim 1 or a pharmaceutically acceptable salt thereof, wherein $L^1$ and $L^2$ are independently a member selected from formula (A), and S is a member selected from formula (S9).

10. The compound of claim 1 or a pharmaceutically acceptable salt thereof, wherein $L^1$ is a member selected from formula (A) or (B), $L^2$ is a member selected from formula (A), and S is a member selected from formula (S10).

11. The compound of claim 1 or a pharmaceutically acceptable salt thereof, wherein $L^1$ is a member selected from formula (A) or (B), $L^2$ is a member selected from formula (A) or (B), and S is a member selected from formula (S11), provided that at least one of $L^1$ and $L^2$ is a member selected from formula (A).

12. The compound of claim 1 or a pharmaceutically acceptable salt thereof; wherein $L^1$ and $L^2$ are independently a member selected from (A), and S is a member selected from formula (S12), (S13), (S14), or (S15).

13. The compound of claim 1 or a pharmaceutically acceptable salt thereof, wherein $L^1$ is a member selected from formula (E), $L^2$ is a member selected from formula (A), and S is a member selected from formula (S16), (S17), or (S18).

14. The compound to claim 1 or a pharmaceutically acceptable salt thereof, wherein formula (A) is a member selected from:

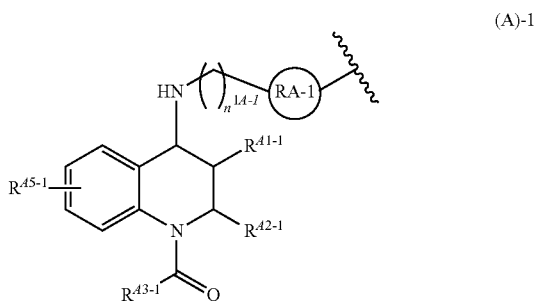

(A)-1 wherein,
the wavy line represents the bonding site to 5,
$R^{A1-1}$ represents a hydrogen atom,
$R^{A2-1}$ and $R^{A3-1}$ are the same or different and each represents alkyl having 1 to 5 carbon atoms,
$R^{A5-1}$ represents
a hydrogen atom,
a fluorine atom,
alkyl having 1 to 5 carbon atoms optionally substituted with one or more substituents selected from the group consisting of a halogen, hydroxy, methoxy, ethoxy, nitro, cyano, carboxy, methoxycarbonyl, ethoxycarbonyl, amino, methylamino, ethylamino, dimethylamino, diethylamino, carbamoyl, methylcarbamoyl, ethylcarbamoyl, dimethylcarbamoyl, diethylcarbamoyl, cyclopropyl, cyclobutyl, cyclopentyl, cyclohexyl, phenyl, furyl, thiophenyl, pyrrolyl, pyrazolyl, imidazolyl, oxazolyl, thiazolyl, triazolyl, oxadiazolyl, tetrazolyl, pyridyl, pyridazinyl, pyrimidinyl, and pyrazinyl,
alkenyl having 2 to 6 carbon atoms optionally substituted with one or more substituents selected from the group consisting of a halogen, hydroxy, methoxy, ethoxy, nitro, cyano, carboxy, methoxycarbonyl, ethoxycarbonyl, amino, methylamino, ethylamino, dimethylamino, diethylamino, carbamoyl, methylcarbamoyl, ethylcarbamoyl, dimethylcarbamoyl, di ethylcarbamoyl, cyclopropyl, cyclobutyl, cyclopentyl, cyclohexyl, phenyl, furyl, thiophenyl, pyrrolyl, pyrazolyl, imidazolyl, oxazolyl, thiazolyl, triazolyl, oxadiazolyl, tetrazolyl, pyridyl, pyridazinyl, pyrimidinyl, and pyrazinyl, or
tetrahydropyridinyl optionally substituted with one or more substituents selected from the group consisting of a halogen, methyl, ethyl, hydroxy, methoxy, ethoxy, nitro, cyano, carboxy, methoxycarbonyl, ethoxycarbonyl, amino, methylamino, ethylamino, dimethylamino, diethylamino, carbamoyl, methylcarbamoyl, ethylcarbamoyl, dimethylcarbamoyl, and diethylcarbamoyl,
ring RA-1 represents, phenylene, cycloalkylene, pyridiylene, or piperidinylene, and
$n^{1A-1}$ represents 0 or 1.

15. The compound of claim 1, or a pharmaceutically acceptable salt thereof, wherein S is a member selected from

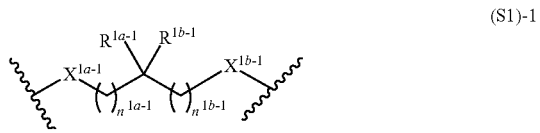

(S1)-1 wherein,
the wavy line represents the bonding site to $L^1$ or $L^2$,
$n^{1a-1}$ and $n^{1b-1}$ are the same or different and each represents 0 or 1,
$X^{1a-1}$ and $X^{1b-1}$ are the same or different and each represents —C(=O)—NH—, —NH—C(=O)—, —SO$_2$—NH—, —NH—SO$_2$—, —O—C(=S)—NH—, —O—C(=O)—NH—, —NH—C(=O)—O—, or —NH—C(=O)—NH—except for the cases where (i) $X^{1a-1}$ is —NH—SO$_2$— and $X^{1b-1}$ is —SO$_2$—NH—, (ii) $n^{1a-1}$ and $n^{1b-1}$ are 0, $X^{1a-1}$ is —C(=O)—NH—, —SO$_2$—NH—, —O—C(=S)—NH—, —O—C(=O)—NH—, or —NH—C(=O)—NH—, and $X^{1b-1}$ is —NH—C(=O)—, —NH—SO$_2$—, —NH—C(=O)—O—, or —NH—C(=O)—NH—, and (iii) $X^{1a-1}$ is —O—C(=S)—NH—, —O—C(=O)—NH—, —NH—C(=O)—O—, or —NH—C(=O)—NH— and $X^{1b-1}$ is —O—C(=S)—NH—, —O—C(=O)—NH—, —NH—C(=O)—O—, or —NH—C(=O)—NH—, and
$R^{1a-1}$ represents a hydrogen atom and $R^{1b-1}$ represents a hydrogen atom or an alkyl having 1 to 5 carbon atoms, or $R^{1a-1}$ and $R^{1b-1}$ together represent carbonyl.

16. The compound of claim 1, or a pharmaceutically acceptable salt thereof, wherein S is a member selected from:

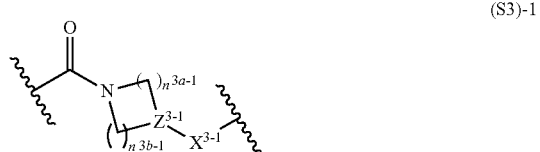

(S3)-1 wherein,
the wavy line represents the bonding site to $L^1$ or $L^2$,
$n^{3a-1}$ and $n^{3b-1}$ are the same or different and each represents 1 or 2,
$X^{3-1}$ represents —C(=O)—NH—, —NH—C(=O)—, —NH—C(=O)—NH—, or —NH—CH$_2$—, and
$Z^{3-1}$ represents CH or N except for the cases where (i) $Z^{3-1}$ is N and $X^{3-1}$ is —NH—C(=O)—, —NH—C(=O)—NH—, or —NH—CH$_2$— and (ii) $Z^{3-1}$ is N and $n^{3a-1}$ or $n^{3b-1}$ is 1.

17. The compound of claim 1, or a pharmaceutically acceptable salt thereof, wherein S is a member selected from:

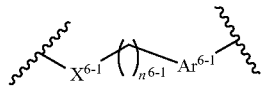

(S6)-1 wherein,
the wavy line represents the bonding site to $L^1$ or $L^2$,
$n^{6-1}$ represents 1 or 2,
$Ar^{6-1}$ represents triazolediyl, oxadiazolediyl, pyrazolediyl, thiophenediyl, or tetrahydropyridinediyl, and
$X^{6-1}$ represents —C(=O)—NH—, —NH—C(=O)—, or —CH$_2$—NH— except for the case where (i) $n^{6-1}$ is 1, $Ar^{6-1}$ is pyrazolediyl or tetrahydropyridinediyl, and $X^{6-1}$ is —C(=O)—NH— or —CH$_2$—NH—.

18. A pharmaceutical composition comprising the compound of claim 1 or a pharmaceutically acceptable salt thereof and a pharmaceutically acceptable carrier.

19. A method of treating a subject with DLBCL (diffuse large B-cell lymphoma) which comprises administering the compound of claim 1 or a pharmaceutically acceptable salt thereof.

* * * * *